US008513235B2

(12) United States Patent
Nakao et al.

(10) Patent No.: US 8,513,235 B2
(45) Date of Patent: Aug. 20, 2013

(54) HOMOCYSTEINE SYNTHASE INHIBITOR

(75) Inventors: Akira Nakao, Osaka (JP); Hiroko Suzuki, Osaka (JP); Ryo Tatsumi, Osaka (JP); Maki Seki, Osaka (JP); Minoru Tanaka, Osaka (JP); Tomofumi Setsuta, Osaka (JP); Hiroshi Iwasaki, Osaka (JP)

(73) Assignee: Mitsubishi Tanabe Pharma Corporation, Osaka-shi (JP)

( * ) Notice: Subject to any disclaimer, the term of this patent is extended or adjusted under 35 U.S.C. 154(b) by 307 days.

(21) Appl. No.: 12/937,187

(22) PCT Filed: Apr. 10, 2009

(86) PCT No.: PCT/JP2009/057397
§ 371 (c)(1),
(2), (4) Date: Oct. 8, 2010

(87) PCT Pub. No.: WO2009/125853
PCT Pub. Date: Oct. 15, 2009

(65) Prior Publication Data
US 2011/0034440 A1 Feb. 10, 2011

(30) Foreign Application Priority Data

Apr. 10, 2008 (JP) ................................. 2008-102924

(51) Int. Cl.
| C07C 237/10 | (2006.01) |
| C07C 237/12 | (2006.01) |
| C07C 255/60 | (2006.01) |
| C07D 209/44 | (2006.01) |
| C07D 271/06 | (2006.01) |
| C07D 295/22 | (2006.01) |
| C07D 295/32 | (2006.01) |
| C07D 401/12 | (2006.01) |
| C07D 403/12 | (2006.01) |
| C07D 405/12 | (2006.01) |
| C07D 409/12 | (2006.01) |
| C07D 413/12 | (2006.01) |
| C07D 413/14 | (2006.01) |
| C07D 487/04 | (2006.01) |
| A61K 31/55 | (2006.01) |
| A61K 31/4035 | (2006.01) |
| A61K 31/165 | (2006.01) |
| A61K 31/495 | (2006.01) |
| A61K 31/4245 | (2006.01) |
| A61K 31/454 | (2006.01) |
| A61K 31/4196 | (2006.01) |
| A61K 31/422 | (2006.01) |
| A61K 31/427 | (2006.01) |
| A61K 31/416 | (2006.01) |
| A61K 31/501 | (2006.01) |
| A61P 9/10 | (2006.01) |

(52) U.S. Cl.
USPC ............ 514/214.02; 514/252.06; 514/255.01; 514/323; 514/364; 514/365; 514/374; 514/383; 514/406; 514/416; 514/616; 540/579; 544/238; 544/382; 546/200; 548/131; 548/144; 548/204; 548/235; 548/266.4; 548/361.1; 548/482; 564/168

(58) Field of Classification Search
None
See application file for complete search history.

(56) References Cited

U.S. PATENT DOCUMENTS

| 6,353,003 | B1 | 3/2002 | Anderson |
| 7,196,093 | B2 | 3/2007 | Yuan |
| 7,507,858 | B2 | 3/2009 | Belvedere et al. |
| 7,517,887 | B2 | 4/2009 | Yuan |
| 7,678,785 | B2 | 3/2010 | Carr et al. |
| 2004/0204429 | A1 | 10/2004 | Yuan |
| 2005/0182075 | A1 | 8/2005 | Yuan |
| 2007/0129386 | A1 | 6/2007 | Yuan |
| 2007/0155726 | A1 | 7/2007 | Arnaiz et al. |
| 2007/0160663 | A1 | 7/2007 | Deboeck et al. |

(Continued)

FOREIGN PATENT DOCUMENTS

| JP | 49-76939 A | 7/1974 |
| JP | 09-319025 A | 12/1997 |

(Continued)

OTHER PUBLICATIONS

CerebralInfarction, 2012, http://www.pyroenergen.com/articles11/prevent-cerebral-infarction.htm.*
MyocardialInfarction, 2012, http://www.disease-symptoms.com/can-myocardial-infarction-be-prevented.*

(Continued)

Primary Examiner — Sun Jae Loewe
(74) Attorney, Agent, or Firm — Leydig, Voit and Mayer, Ltd.

(57) ABSTRACT

The invention provides a homocysteine synthase inhibitor useful for the prophylaxis or treatment of diseases involving homocysteine synthase. The homocysteine synthase inhibitor is a compound of the formula (I)

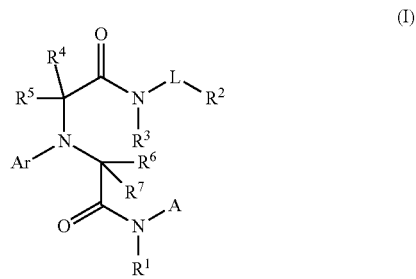

wherein each symbol is as defined herein, or a pharmacologically acceptable salt thereof, or a solvate thereof.

14 Claims, No Drawings

(56) References Cited

U.S. PATENT DOCUMENTS

| | | |
|---|---|---|
| 2007/0207172 A1 | 9/2007 | Yuan |
| 2008/0045497 A1 | 2/2008 | Carr et al. |
| 2008/0096920 A1 | 4/2008 | Belvedere et al. |
| 2008/0171049 A1 | 7/2008 | Yuan |
| 2008/0194594 A1 | 8/2008 | Yuan |
| 2008/0306126 A1 | 12/2008 | Fonseca et al. |
| 2012/0196824 A1 | 8/2012 | Nakao et al. |

FOREIGN PATENT DOCUMENTS

| | | |
|---|---|---|
| JP | 2000-131839 A | 5/2000 |
| JP | 2002-518296 A | 6/2002 |
| JP | 2003-095959 A | 4/2003 |
| JP | 2008-506776 A | 3/2008 |
| WO | WO 2005/009334 A2 | 2/2005 |
| WO | WO 2006/020004 A2 | 2/2006 |
| WO | WO 2006/044573 A2 | 4/2006 |
| WO | WO 2007/116458 A2 | 10/2007 |
| WO | WO 2008/012524 A1 | 1/2008 |

OTHER PUBLICATIONS

Dirksen et al., Cardiovascular Research 74, 2007, 343-355.*
Yao et al., caplus an 2006:1014779.*
ClinicalTrial, 2011, http://www.nature.com/news/2011/110928/full/477526a.html.*
Chawla et al., "Challenges in Polymorphism of Pharmaceuticals", CRIPS vol. 5, No. 1, Jan.-Mar. 2004.*
Newman et al., "Solid-state analysis of the active pharmaceutical ingredient in drug products", DDT vol. 8, No. 19, Oct. 2003, p. 898-905.*
Japanese Patent Office, International Search Report in International Patent Application No. PCT/JP2009/057397 (Jun. 23, 2009).
International Bureau of WIPO, International Preliminary Report on Patentability in International Patent Application No. PCT/JP2009/057397 (Oct. 12, 2010).
Araki et al., *Japanese Journal of Stroke*, 12(2): 111-115 (1990).
Langeinrich et al., *Atherosclerosis*, 171(2): 181-192 (2003).
Japanese Patent Office, International Search Report in International Patent Application No. PCT/JP2010/067800 (Jan. 11, 2011).
European Patent Office, Supplementary European Search Report in European Patent Application No. 09 72 9804 (Dec. 15, 2011).
Boers et al., *The New England Journal of Medicine*, 313(12): 709-715 (1985).
Brattstrom et al., *European Journal of Clinical Investigation*, 22: 214-221 (1992).
Brattstrom et al., *Stroke*, 15: 1012-1016 (1984).
Clarke et al., *JAMA*, 288(16): 2015-2022 (2002).
Coull et al., *Stroke*, 21: 572-576 (1990).
McCully, Kilmer, *Am. J. Pathol.*, 56: 111-128 (1969).
Perry et al., *The Lancet*, 346: 1395-1398 (1995).
Verhoef et al., *Stroke*, 25: 1924-1930 (1994).
Yoo et al., *Stroke*, 29: 2478-2483 (1998).

* cited by examiner

HOMOCYSTEINE SYNTHASE INHIBITOR

TECHNICAL FIELD

The present invention relates to a novel amide derivative. More particularly, the present invention relates to a homocysteine synthase inhibitor comprising an amide derivative or a pharmacologically acceptable salt thereof, or a solvate thereof as an active ingredient.

BACKGROUND ART

Homocysteine is a sulfur amino acid, and is an important intermediate for the metabolism of an essential amino acid, methionine. Homocysteine is maintained at an extremely low concentration in the cell, and redundant homocysteine is extracellularly released, i.e., into the blood. Thirty years ago, Dr. McCully reported that homocysteine causes vascular pathology such as arteriosclerosis and myocardial infarction (non-patent document 1). Thereafter, clinical tests verified that patients having arteriosclerosis in the peripheral vessel or cerebral vessel show high homocysteine values (non-patent document 2). In almost any clinical tests thereafter, a correlation between increased homocysteine value and cerebral infarction has been reported (non-patent documents 3-8). In a large scale test, it was reported that when the blood homocysteine value increases by 25% (3 µM in absolute value), the risk of coronary artery disease increases by 10%, and the risk of cerebral infarction increases by 20% (non-patent document 9), and it is now suggested that homocysteine is an independent risk factor.

At present, as a homocysteine-decreasing therapy, only an ingestion of a coenzyme of metabolic enzyme, i.e., vitamin B6, vitamin B12, folic acid, has been tried. Ingestion of these vitamins decreases the blood homocysteine value to some extent (non-patent document 10). Moreover, improvement in the vascular endothelial function and regression of carotid plaque by a vitamin therapy have been reported (non-patent documents 11-13).

However, in a large scale test aiming to examine an influence of vitamin therapy on the recurrence of cerebral infarction or myocardial infarction (The Vitamin Intervention for Stroke Prevention (VISP)), a recurrence preventive effect was not observed. The cause thereof is suggested to be the absence of a sufficient decrease in homocysteine by a vitamin therapy (non-patent document 14). This report has also clarified that the risk of recurrence of cerebral infarction can be decreased by 10% and the risk of myocardial infarction can be decreased by 26%, when the baseline of homocysteine value is lower by 3 µM. If the homocysteine value could be certainly decreased than the vitamin therapy, the onset of these events is expected to be suppressed significantly.

The enzyme that synthesizes homocysteine in the body is S-Adenosyl-L-homocysteine Hydrolase (hereinafter sometimes to be referred to as "SAHH") alone. This enzyme controls a reaction to hydrolyze S-Adenosyl-L-homocysteine (hereinafter sometimes to be referred to as "SAH") into Adenosine (hereinafter sometimes to be referred to as "Ado") and Homocysteine (hereinafter sometimes to be referred to as "Hcy") and a reversible reaction to conversely synthesize SAH from Adenosine and Homocysteine.

On the other hand, as a compound showing an SAHH inhibitory action, an adenine derivative (patent document 1) and a nitroprusside compound (patent document 2) have been reported. However, they have completely different structures from the structure of the present invention.

In addition, patent documents 3-7 report amide compounds. However, these reports do not disclose the present invention, and an SAHH inhibitory action is not reported (patent documents 3-7).

PRIOR ART DOCUMENTS

Patent Documents patent document 1: WO2005/009334
patent document 2: JP-A-2003-95959
patent document 3: JP-A-9-319025
patent document 4: JP-A-2000-131839
patent document 5: JP-A-49-76939
patent document 6: WO2008/012524
patent document 7: WO2006/020004

Non-Patent Documents non-patent document 1: Am J Pathol 1969; 56: 111-128
non-patent document 2: N Eng J Med 1985; 313: 709-715
non-patent document 3: Stroke. 1984; 15: 1012-1016
non-patent document 4: Eur J Cli Invest. 1992; 22: 214-221
non-patent document 5: Stroke. 1990; 21: 572-576
non-patent document 6: Lancet 1995; 346: 1395-1398
non-patent document 7: Stroke. 1994; 25: 1924-1930
non-patent document 8: Stroke. 1998; 29: 2478-2483
non-patent document 9: JAMA 2002; 288: 2015-22
non-patent document 10: J Nutr 1996; 126 (suppl) 1276S-1280S
non-patent document 11: Circulation 1999; 99: 1156-1160
non-patent document 12: Eur J Clin Invest 1995; 25: 176-181
non-patent document 13: Lancet 1998; 351; 263
non-patent document 14: JAMA 2004; 291: 565-575

SUMMARY OF THE INVENTION

Problems to be Solved by the Invention

The present invention aims to provide a homocysteine synthase inhibitor useful for the prophylaxis or treatment of a disease relating to a homocysteine synthase.

Means of Solving the Problems

The present inventors have conducted intensive studies in an attempt to solve the above-mentioned problems and found that a particular amide derivative can achieve a desired object, which resulted in the completion of the present invention.

Effect of the Invention

The amide derivative of the present invention shows a homocysteine synthase inhibitory action, and can be a medicament effective for the prophylaxis or treatment of a disease involving the enzyme.

EMBODIMENT OF THE INVENTION

The present invention relates to the following amide derivative, a pharmacologically acceptable salt thereof, a solvate thereof and use thereof.

(1) An amide derivative represented by the following formula (I)

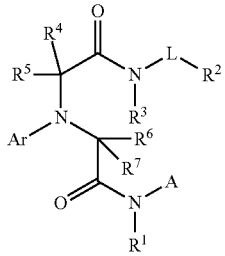

wherein $R^1$ is a hydrogen atom or a $C_1$-$C_3$ alkyl group, $R^2$ is an optionally substituted heterocyclic group (said heterocyclic group contains at least one nitrogen atom in the ring), or —$N(R^{2a})(R^{2b})$, $R^{2a}$ and $R^{2b}$ are independently selected and each is a hydrogen atom, a $C_1$-$C_6$ alkyl group, a haloalkyl group or an optionally substituted aryl group, $R^3$ is a hydrogen atom, $R^4$, $R^5$, $R^6$, $R^7$ are independently selected and each is a hydrogen atom or a $C_1$-$C_4$ alkyl group, L is a linker represented by the following formula

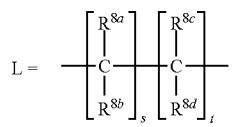

wherein s is an integer of 0-2, t is an integer of 0-2, $R^{8a}$, $R^{8b}$, $R^{8c}$ and $R^{8d}$ are independently selected and each is a hydrogen atom or a $C_1$-$C_3$ alkyl group, Ar is a substituent represented by any of the following formulas (II)-(IV),

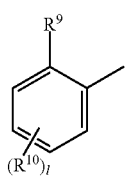

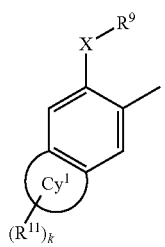

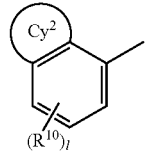

wherein l is an integer of 0-4, k is an integer of 0-4, $Cy^1$ and $Cy^2$ are independently selected and each is a carbocyclic group, a heterocyclic group or a heteroaryl group, X is a bond, an oxygen atom or a sulfur atom, $R^9$ is a halogen atom or $R^{12}$, wherein $R^{12}$ is a hydrogen atom, an optionally substituted $C_1$-$C_6$ alkyl group, an optionally substituted $C_2$-$C_6$ alkenyl group, an optionally substituted $C_2$-$C_6$ alkynyl group, an optionally substituted $C_3$-$C_8$ cycloalkyl group, an optionally substituted heterocyclic group, an optionally substituted aryl group, an optionally substituted heteroaryl group, or an optionally substituted arylalkyl group, $R^{10}$ is a halogen atom, a cyano group, an optionally substituted $C_1$-$C_6$ alkyl group,

—$CF_3$,

—O—$R^{13}$ (wherein $R^{13}$ is a hydrogen atom, a $C_1$-$C_4$ alkyl group or —$CF_3$), —CO—$R^{14}$ (wherein $R^{14}$ is a hydroxy group, a $C_1$-$C_6$ alkyl group, a $C_1$-$C_6$ alkoxy group, or an optionally substituted amino group), an optionally substituted amino group, an optionally substituted aryl group, an optionally substituted heteroaryl group, an optionally substituted heterocyclic group, or an —$S(O)_m$—$C_1$-$C_6$ alkyl group wherein m is an integer of 0-2, $R^{11}$ is a halogen atom, an optionally substituted $C_1$-$C_4$ alkyl group or $CF_3$, A is an optionally substituted aryl group, an optionally substituted aryl-$C_1$-$C_4$ alkyl group, an optionally substituted heteroaryl-$C_1$-$C_4$ alkyl group, a $C_3$-$C_6$ alkynyl group, an optionally substituted $C_3$-$C_8$ cycloalkyl group, or a group represented by any of the following formulas (V)-(VIII)

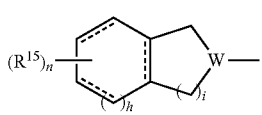

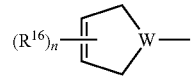

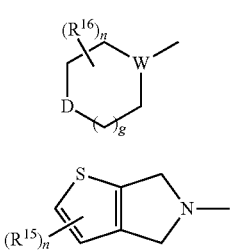 (VII)

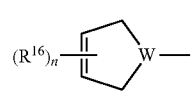 (VI)

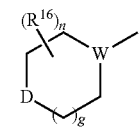 (VII)

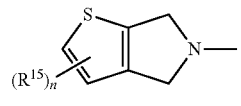 (VIII)

wherein
--- is a single bond or a double bond,
n is an integer of 0-2,
g is an integer of 0-2,
h is an integer of 0-1,
i is an integer of 1-2,
$R^{15}$ is a $C_1$-$C_4$ alkyl group, a $C_1$-$C_4$ alkoxy group, a cyano group or a halogen atom,
$R^{16}$ is a $C_1$-$C_4$ alkyl group,
W is =CH— or =N—, and
D is an oxygen atom, a sulfur atom, =N-(E)u-$R^{17}$ wherein u is an integer of 0-1, E is —$SO_2$— or —CO—, $R^{17}$ is a hydrogen atom, a $C_1$-$C_4$ alkyl group, an aryl group, a $C_1$-$C_4$ alkylamino group, a $C_1$-$C_6$ alkoxy group, an arylamino group or an aryloxy group, or =CH—$R^{17}$ wherein $R^{17}$ is as defined above, or a pharmacologically acceptable salt thereof, or a solvate thereof.

(2) The amide derivative of the aforementioned (1), which is represented by the following formula (IX)

(IX)

the formula (IX) shows that $R^1$ is a $C_1$-$C_3$ alkyl group, $R^3$ is a hydrogen atom, $R^4$, $R^5$, $R^6$ and $R^7$ are each a hydrogen atom in the formula (I), and other symbols are as defined above, or a pharmacologically acceptable salt thereof, or a solvate thereof.

(3) The amide derivative of the aforementioned (1) or (2) wherein $R^1$ is a $C_1$-$C_3$ alkyl group or a pharmacologically acceptable salt thereof, or a solvate thereof.

(4) The amide derivative of any of the aforementioned (1)-(3), wherein A is selected from the groups represented by the following formulas (V)-(VIII)

(V)

wherein
--- is a single bond or a double bond,
n is an integer of 0-2,
g is an integer of 0-2,
h is an integer of 0-1,
i is an integer of 1-2,
$R^{15}$ is a $C_1$-$C_4$ alkyl group, a $C_1$-$C_4$ alkoxy group, a cyano group or a halogen atom,
$R^{16}$ is a $C_1$-$C_4$ alkyl group,
W is =CH— or =N—,
D is an oxygen atom, a sulfur atom, =N-(E)u-$R^{17}$ wherein u is an integer of 0-1, E is —$SO_2$— or —CO—, $R^{17}$ is a hydrogen atom, a $C_1$-$C_4$ alkyl group, an aryl group, a $C_1$-$C_4$ alkylamino group, a $C_1$-$C_6$ alkoxy group, an arylamino group or an aryloxy group, or =CH—$R^{17}$ wherein $R^{17}$ is as defined above, or a pharmacologically acceptable salt thereof, or a solvate thereof.

(5) The amide derivative of any of the aforementioned (1)-(4), wherein A is a group represented by the following formula (V)

(V)

wherein
--- is a single bond or a double bond,
n is an integer of 0-2,
h is an integer of 0-1,
i is an integer of 1-2,
$R^{15}$ is a $C_1$-$C_4$ alkyl group, a $C_1$-$C_4$ alkoxy group, a cyano group or a halogen atom,
W is =CH— or =N—,
or a pharmacologically acceptable salt thereof, or a solvate thereof.

(6) The amide derivative of any of the aforementioned (1)-(5), wherein L is a linker represented by the following formula $$L = -\left[\begin{array}{c} R^{8a} \\ | \\ C \\ | \\ R^{8b} \end{array}\right]_s \left[\begin{array}{c} R^{8c} \\ | \\ C \\ | \\ R^{8d} \end{array}\right]_t-$$

wherein $R^{8a}$, $R^{8b}$, $R^{8c}$ and $R^{8d}$ are each a hydrogen atom, and other symbols are as defined above,
or a pharmacologically acceptable salt thereof, or a solvate thereof.

(7) The amide derivative of any of the aforementioned (1)-(6), wherein $R^{10}$ is
a halogen atom,
a cyano group,
—CO—$R^{14}$ wherein $R^{14}$ is as defined above,
an optionally substituted aryl group,
an optionally substituted heteroaryl group, or
an optionally substituted heterocyclic group,
or a pharmacologically acceptable salt thereof, or a solvate thereof.

(8) The amide derivative of any of the aforementioned (1)-(7), wherein $R^{10}$ is a heteroaryl group having a substituent, or a heterocyclic group having a substituent, or a pharmacologically acceptable salt thereof, or a solvate thereof.

(9) The amide derivative of any of the aforementioned (1)-(8), wherein the heteroaryl group for $R^{10}$ is selected from a furyl group, a thienyl group, a pyrazolyl group, a 1,2,4-triazolyl group, a tetrazolyl group, an oxazolyl group, a thiazolyl group, an isoxazolyl group, a 1,2,4-oxadiazolyl group, a 1,3,4-oxadiazolyl group, a 1,3,4-thiadiazolyl group, a pyridyl group, a pyrazinyl group and a pyrimidyl group, or a pharmacologically acceptable salt thereof, or a solvate thereof.

(10) The amide derivative of any of the aforementioned (1)-(9), wherein $R^{10}$ is a heteroaryl group having a substituent, and the substituent is a group selected from a halogen atom, a cyano group, a $C_1$-$C_4$ alkyl group, a $C_1$-$C_4$ alkoxy group, a —$CH_2OH$ group, a —$CF_3$ group, a —$CHF_2$ group, a —$CH_2F$ group, a —$OCF_3$ group, a —$OCHF_2$ group, a —$OCH_2F$ group, a —$CONH_2$ group, a —$CONHCH_3$ group and a —$CON(CH_3)_2$ group, or a pharmacologically acceptable salt thereof, or a solvate thereof.

(11) The amide derivative of any of the aforementioned (1)-(10), wherein $R^{12}$ is
an optionally substituted $C_1$-$C_6$ alkyl group,
an optionally substituted $C_2$-$C_6$ alkenyl group,
an optionally substituted $C_2$-$C_6$ alkynyl group,
an optionally substituted $C_3$-$C_8$ cycloalkyl group,
an optionally substituted aryl group, or
an optionally substituted heteroaryl group,
or a pharmacologically acceptable salt thereof, or a solvate thereof.

(12) The amide derivative of any of the aforementioned (1)-(11), wherein A is an isoindolyl group optionally substituted at $R^{15}$, or a pharmacologically acceptable salt thereof, or a solvate thereof.

(13) The amide derivative of any of the aforementioned (1)-(12), wherein $R^2$ is —$N(R^{2a})(R^{2b})$ wherein $R^{2a}$ and $R^{2b}$ are as defined above, or a pharmacologically acceptable salt thereof, or a solvate thereof.

(14) The amide derivative of any of the aforementioned (1)-(13), wherein Ar is a group represented by the aforementioned formula (II), or a pharmacologically acceptable salt thereof, or a solvate thereof.

(15) The amide derivative of any of the aforementioned (1)-(13), wherein Ar is a group represented by the aforementioned formula (III), or a pharmacologically acceptable salt thereof, or a solvate thereof.

(16) The amide derivative of any of the aforementioned (1)-(13), wherein Ar is a group represented by the aforementioned formula (IV), or a pharmacologically acceptable salt thereof, or a solvate thereof.

(17) The amide derivative of any of the aforementioned (1)-(15), wherein $R^9$ is a $C_1$-$C_6$ alkyl group, or a pharmacologically acceptable salt thereof, or a solvate thereof.

(18) The amide derivative of any of the aforementioned (1)-(13), (15) and (17), wherein X is a bond, or a pharmacologically acceptable salt thereof, or a solvate thereof.

(19) The amide derivative of any of the aforementioned (1)-(13), (15), (17) and (18), wherein $Cy^1$ is a 8- to 12-membered fused ring heterocyclic group, or 5-membered ring heteroaryl, or a pharmacologically acceptable salt thereof, or a solvate thereof.

(20) An amide derivative selected from the following compounds, or a pharmacologically acceptable salt thereof, or a solvate thereof:

$N^2$-(5-acetyl-2-methylphenyl)-$N^2$-{2-[1,3-dihydro-2H-isoindol-2-yl(methyl)amino]-2-oxoethyl}-$N^1$-[2-(isopropylamino)ethyl]glycinamide (compound of Example 56), $N^2$-(5-acetyl-2-methylphenyl)-$N^2$-{2-[1,3-dihydro-2H-isoindol-2-yl(methyl)amino]-2-oxoethyl}-$N^1$-[2-(ethylamino)ethyl]glycinamide (compound of Example 57), $N^2$-{2-[1,3-dihydro-2H-isoindol-2-yl(methyl)amino]-2-oxoethyl}-$N^2$-[2-methyl-4-(5-methyl-1,2,4-oxadiazol-3-yl)phenyl]-$N^1$-[2-(isopropylamino)ethyl]glycinamide (compound of Example 64), $N^2$-{2-[1,3-dihydro-2H-isoindol-2-yl(methyl)amino]-2-oxoethyl}-$N^2$-[2-methyl-4-(5-methyl-1,2,4-oxadiazol-3-yl)phenyl]-$N^1$-[2-(ethylamino)ethyl]glycinamide (compound of Example 65), $N^2$-{2-[(5-fluoro-1,3-dihydro-2H-isoindol-2-yl)(methyl)amino]-2-oxoethyl}-$N^2$-[2-methyl-4-(5-methyl-1,2,4-oxadiazol-3-yl)phenyl]-$N^1$-[2-(ethylamino)ethyl]glycinamide (compound of Example 204), $N^2$-(5-cyano-2-methylphenyl)-$N^2$-{2-[1,3-dihydro-2H-isoindol-2-yl(methyl)amino]-2-oxoethyl}-$N^1$-[2-(isopropylamino)ethyl]glycinamide (compound of Example 1), $N^2$-(5-cyano-2-methylphenyl)-$N^2$-{2-[1,3-dihydro-2H-isoindol-2-yl(methyl)amino]-2-oxoethyl}-$N^1$-[2-(ethylamino)ethyl]glycinamide (compound of Example 2), $N^2$-{2-[1,3-dihydro-2H-isoindol-2-yl(methyl)amino]-2-oxoethyl}-$N^2$-[2-methyl-5-(5-methyl-1,2,4-oxadiazol-3-yl)phenyl]-$N^1$-[2-(isopropylamino)ethyl]glycinamide (compound of Example 15), $N^2$-{2-[1,3-dihydro-2H-isoindol-2-yl(methyl)amino]-2-oxoethyl}-$N^2$-[2-methyl-5-(5-methyl-1,2,4-oxadiazol-3-yl)phenyl]-$N^1$-[2-(ethylamino)ethyl]glycinamide (compound of Example 16), $N^2$-{2-[(4-fluoro-1,3-dihydro-2H-isoindol-2-yl)(methyl)amino]-2-oxoethyl}-$N^2$-[2-methyl-5-(5-methyl-1,2,4-oxadiazol-3-yl)phenyl]-$N^1$-[2-(ethylamino)ethyl]glycinamide (compound of Example 19), $N^2$-{2-[(5-fluoro-1,3-dihydro-2H-isoindol-2-yl)(methyl)amino]-2-oxoethyl}-$N^2$-[2-methyl-5-(5-methyl-1,2,4-oxadiazol-3-yl)phenyl]-$N^1$-[2-(ethylamino)ethyl]glycinamide (compound of Example 20), $N^2$-{2-[(5-fluoro-1,3-dihydro-2H-isoindol-2-yl)(methyl)amino]-2-oxoethyl}-$N^2$-[2-methyl-5-(5-methyl-1,2,4-oxadiazol-3-yl)phenyl]-$N^1$-[2-(isopropylamino)ethyl]glycinamide (compound of Example 21), $N^2$-{2-[(5-methoxy-1,3-dihydro-2H-isoindol-2-yl)(methyl)amino]-2-oxoethyl}-$N^2$-[2-methyl-5-(5-methyl-1,2,4-oxadiazol-3-yl)phenyl]-$N^1$-[2-(ethylamino)ethyl]glycinamide (compound of Example 24), $N^2$-{2-[2,3-dihydro-1H-inden-2-yl(methyl)amino]-2-oxoethyl}-$N^2$-[2-methyl-5-(5-methyl-1,2,4-oxadiazol-3-yl)phenyl]-$N^1$-[2-(ethylamino)ethyl]glycinamide (compound of Example 26), N²-{2-[1,3-dihydro-2H-isoindol-2-yl(methyl)amino]-2-oxoethyl}-N²-[2-methyl-5-(3-methyl-1,2,4-oxadiazol-5-yl)phenyl]-N¹-[2-(isopropylamino)ethyl]glycinamide (compound of Example 84), N²-{2-[1,3-dihydro-2H-isoindol-2-yl(methyl)amino]-2-oxoethyl}-N²-[2-methyl-5-(3-methyl-1,2,4-oxadiazol-5-yl)phenyl]-N¹-[2-(ethylamino)ethyl]glycinamide (compound of Example 85), N²-{2-[(5-fluoro-1,3-dihydro-2H-isoindol-2-yl)(methyl)amino]-2-oxoethyl}-N²-[2-methyl-5-(3-methyl-1,2,4-oxadiazol-5-yl)phenyl]-N¹-[2-(ethylamino)ethyl]glycinamide (compound of Example 87), N²-{2-[1,3-dihydro-2H-isoindol-2-yl(methyl)amino]-2-oxoethyl}-N²-[2-methyl-5-(4-methyl-5-oxo-4,5-dihydro-1,3,4-oxadiazol-2-yl)phenyl]-N¹-[2-(isopropylamino)ethyl]glycinamide (compound of Example 88), N²-{2-[1,3-dihydro-2H-isoindol-2-yl(methyl)amino]-2-oxoethyl}-N²-[2-methyl-5-(4-methyl-5-oxo-4,5-dihydro-1,3,4-oxadiazol-2-yl)phenyl]-N¹-[2-(ethylamino)ethyl]glycinamide (compound of Example 89), N²-{2-[1,3-dihydro-2H-isoindol-2-yl(methyl)amino]-2-oxoethyl}-N²-[5-(4-ethyl-5-oxo-4,5-dihydro-1,3,4-oxadiazol-2-yl)-2-methylphenyl]-N¹-[2-(ethylamino)ethyl]glycinamide (compound of Example 92), N²-{2-[1,3-dihydro-2H-isoindol-2-yl(methyl)amino]-2-oxoethyl}-N²-(2-methyl-5-pyrimidin-2-ylphenyl)-N¹-[2-(ethylamino)ethyl]glycinamide (compound of Example 129), N²-{2-[1,3-dihydro-2H-isoindol-2-yl(methyl)amino]-2-oxoethyl}-N²-(1-ethyl-7-methyl-2-oxo-1,2,3,4-tetrahydroquinolin-6-yl)-N¹-[2-(isopropylamino)ethyl]glycinamide (compound of Example 176), N²-{2-[1,3-dihydro-2H-isoindol-2-yl(methyl)amino]-2-oxoethyl}-N²-(1-ethyl-7-methyl-2-oxo-1,2,3,4-tetrahydroquinolin-6-yl)-N¹-[2-(ethylamino)ethyl]glycinamide (compound of Example 177), N²-{2-[1,3-dihydro-2H-isoindol-2-yl(methyl)amino]-2-oxoethyl}-N²-(3,6-dimethyl-1,2-benzisoxazol-5-yl)-N¹-[2-(isopropylamino)ethyl]glycinamide (compound of Example 180), N²-{2-[1,3-dihydro-2H-isoindol-2-yl(methyl)amino]-2-oxoethyl}-N²-(3,6-dimethyl-1,2-benzisoxazol-5-yl)-N¹-[2-(ethylamino)ethyl]glycinamide (compound of Example 181), N²-{2-[1,3-dihydro-2H-isoindol-2-yl(methyl)amino]-2-oxoethyl}-N²-(3,5-dimethyl-1,2-benzisoxazol-6-yl)-N¹-[2-(isopropylamino)ethyl]glycinamide (compound of Example 184), N²-{2-[1,3-dihydro-2H-isoindol-2-yl(methyl)amino]-2-oxoethyl}-N²-(3,5-dimethyl-1,2-benzisoxazol-6-yl)-N¹-[2-(ethylamino)ethyl]glycinamide (compound of Example 185), N²-{2-[1,3-dihydro-2H-isoindol-2-yl(methyl)amino]-2-oxoethyl}-N²-(3,6-dimethyl-1,3-benzoxazol-2 (3H)-on-5-yl)-N¹-[2-(isopropylamino)ethyl]glycinamide (compound of Example 190), N²-{2-[1,3-dihydro-2H-isoindol-2-yl(methyl)amino]-2-oxoethyl}-N²-(3,6-dimethyl-1,3-benzoxazol-2 (3H)-on-5-yl)-N¹-[2-(ethylamino)ethyl]glycinamide (compound of Example 191), N²-{2-[1,3-dihydro-2H-isoindol-2-yl(methyl)amino]-2-oxoethyl}-N²-(3,5-dimethyl-1,3-benzoxazol-2 (3H)-on-6-yl)-N¹-[2-(isopropylamino)ethyl]glycinamide (compound of Example 192), N²-{2-[1,3-dihydro-2H-isoindol-2-yl(methyl)amino]-2-oxoethyl}-N²-(3,5-dimethyl-1,3-benzoxazol-2 (3H)-on-6-yl)-N¹-[2-(ethylamino)ethyl]glycinamide (compound of Example 193), N²-{2-[(4-fluoro-1,3-dihydro-2H-isoindol-2-yl)(methyl)amino]-2-oxoethyl}-N²-[2-methyl-4-(5-methyl-1,2,4-oxadiazol-3-yl)phenyl]-N¹-[2-(ethylamino)ethyl]glycinamide (compound of Example 205), N²-(4-acetyl-2-methylphenyl)-N²-{2-[1,3-dihydro-2H-isoindol-2-yl(methyl)amino]-2-oxoethyl}-N¹-[2-(ethylamino)ethyl]glycinamide (compound of Example 210), N²-(4-acetyl-2-methylphenyl)-N²-{2-[(5-fluoro-1,3-dihydro-2H-isoindol-2-yl)(methyl)amino]-2-oxoethyl}-N¹-[2-(ethylamino)ethyl]glycinamide (compound of Example 211), N²-{2-[1,3-dihydro-2H-isoindol-2-yl(methyl)amino]-2-oxoethyl}-N²-(6-methyl-3-oxo-2,3-dihydro-1H-inden-5-yl)-N¹-[2-(ethylamino)ethyl]glycinamide (compound of Example 214), N²-{2-[(5-fluoro-1,3-dihydro-2H-isoindol-2-yl)(methyl)amino]-2-oxoethyl}-N²-(6-methyl-3-oxo-2,3-dihydro-1H-inden-5-yl)-N¹-[2-(ethylamino)ethyl]glycinamide (compound of Example 215), N²-{2-[(4-fluoro-1,3-dihydro-2H-isoindol-2-yl)(methyl)amino]-2-oxoethyl}-N²-(6-methyl-3-oxo-2,3-dihydro-1H-inden-5-yl)-N¹-[2-(ethylamino)ethyl]glycinamide (compound of Example 216), N²-{2-[1,3-dihydro-2H-isoindol-2-yl(methyl)amino]-2-oxoethyl}-N²-[2-methyl-4-(3-methyl-1,2,4-oxadiazol-5-yl)phenyl]-N¹-[2-(ethylamino)ethyl]glycinamide (compound of Example 229), and N²-{2-[(5-fluoro-1,3-dihydro-2H-isoindol-2-yl)(methyl)amino]-2-oxoethyl}-N²-[2-methyl-4-(3-methyl-1,2,4-oxadiazol-5-yl)phenyl]-N¹-[2-(ethylamino)ethyl]glycinamide (compound of Example 231).

(21) A homocysteine synthase inhibitor comprising the amide derivative of the aforementioned (1) to the aforementioned (20), or a pharmacologically acceptable salt thereof, or a solvate thereof as an active ingredient.

(22) A medicament for the treatment or prophylaxis of hyperhomocysteinemia, comprising the amide derivative of the aforementioned (1) to the aforementioned (20), or a pharmacologically acceptable salt thereof, or a solvate thereof as an active ingredient.

(23) Use of the amide derivative of the aforementioned (1) to the aforementioned (20), or a pharmacologically acceptable salt thereof, or a solvate thereof for the production of a homocysteine synthase inhibitor.

(24) A method for the prophylaxis or treatment of a disease relating to a homocysteine synthase, comprising administering an effective amount of the amide derivative of the aforementioned (1) to the aforementioned (20), or a pharmacologically acceptable salt thereof, or a solvate thereof.

In the following, the amide derivative represented by the above-mentioned formula (I) is sometimes referred to as compound (I), and compound (I) or a pharmacologically acceptable salt thereof, or a solvate thereof is sometimes referred to as the compound of the present invention.

The symbols and definitions of the terms used in the present invention are explained in detail in the following.

In the formula (III), $Cy^1$ is a carbocyclic group, a heterocyclic group or a heteroaryl group, preferably a $C_5$-$C_7$ cycloalkyl ring, a 5- to 7-membered heterocyclic ring, a benzene ring or a 5- to 7-membered heteroaryl ring, more preferably a cyclopentane ring, a cyclohexane ring, a dioxolane ring, a dioxane ring, a pyrrolidine ring, an imidazolidine ring, a piperidine ring, a piperazine ring, an oxazolidine ring, a thiazolidine ring, a pyrrole ring, an oxazole ring, a thiazole ring, an isoxazole ring, a pyrazole ring, a morpholine ring, an azepane ring, a benzene ring, a pyridine ring, a pyrazine ring, a pyrimidine ring, a pyridazine ring or a dihydropyridine ring, and particularly preferably an oxazole ring, a thiazole ring, an isoxazole ring or a pyrazole ring.

Examples of the formula (III) include a benzoisoxazole ring, a tetrahydroquinoline ring, a benzoxazolidine ring, a benzothiazolidine ring, an indazole ring, a naphthalene ring, an indane ring, a tetrahydronaphthalene ring, a 6,7,8,9-tetrahydro-5H-benzo[7]annulene ring, a 1,3-benzodioxole ring, a 1-indanone ring, a 1-tetralone ring and a 1-benzosuberone ring.

In the formula (IV), $Cy^2$ is a carbocyclic group, a heterocyclic group or a heteroaryl group, preferably a $C_5$-$C_7$ cycloalkyl ring, a 5- to 7-membered heterocyclic ring, a benzene ring or a 5- to 7-membered heteroaryl ring, and more preferably a cyclopentane ring, a cyclohexane ring, a tetrahydrofuran ring or a benzene ring.

Examples of the formula (IV) include a dihydrobenzofuran ring, a naphthalene ring, an indane ring and a tetrahydronaphthalene ring.

In the formula (I), A is an optionally substituted aryl group, an optionally substituted aryl-$C_1$-$C_4$ alkyl group, an optionally substituted heteroaryl-$C_1$-$C_4$ alkyl group, a $C_3$-$C_6$ alkynyl group, an optionally substituted $C_3$-$C_8$ cycloalkyl group, or any group selected from the formulas (V)-(VIII).

Examples of the following formula (V)

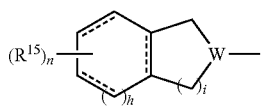

which is A include an indane ring, an isoindoline ring, an octahydro-1H-isoindole ring and an octahydrocyclopenta[c]pyrrole ring.

Examples of the following formula (VI)

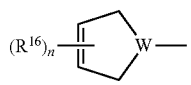

is which is A include a cyclopentene ring and a 2,5-dihydro-1H-pyrrole ring.

Examples of the following formula (VII)

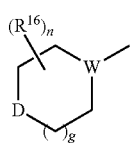

which is A include a morpholine ring, a 1-piperidine ring, a 4-piperidine ring, a piperazine ring, a thiomorpholine ring, an azepane ring, a cyclopentane ring, a cyclohexane ring and a cycloheptane ring.

Examples of the following formula (VIII)

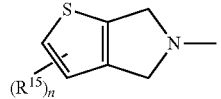

which is A include a 5,6-dihydro-4H-thieno[2,3-c]pyrrole ring.

In the present specification, the "alkyl group" preferably has a carbon number of 1 to 6, and may be a linear or branched chain. Examples of the group include methyl, ethyl, normal (hereinafter to be indicated as n-) propyl, isopropyl, n-butyl, isobutyl, tertiary (hereinafter to be indicated as t-) butyl, n-pentyl, n-hexyl and the like.

As the "$C_1$-$C_3$ alkyl group" for $R^1$, preferred is methyl or ethyl, and more preferred is methyl.

As the "$C_1$-$C_6$ alkyl group" for $R^{2a}$ or $R^{2b}$, preferred is methyl, ethyl, n-propyl, isopropyl, n-butyl, isobutyl or t-butyl, and more preferred is methyl, ethyl or isopropyl.

As the "$C_1$-$C_4$ alkyl group" for $R^4$, $R^5$, $R^6$ or $R^7$, preferred is methyl.

As the "$C_1$-$C_3$ alkyl group" for $R^{8a}$, $R^{8b}$, $R^{8c}$ or $R^{8d}$, preferred is methyl.

As the "$C_1$-$C_6$ alkyl group" for $R^{10}$, preferred is methyl, ethyl, n-propyl, isopropyl, n-butyl, isobutyl or t-butyl, and more preferred is methyl.

As the "$C_1$-$C_4$ alkyl group" for $R^{11}$, preferred is methyl, ethyl, n-propyl or isopropyl, and more preferred is methyl or ethyl.

As the "$C_1$-$C_6$ alkyl group" for $R^{12}$, preferred is methyl, ethyl, n-propyl or isopropyl, and more preferred is methyl or ethyl.

As the "$C_1$-$C_4$ alkyl group" for $R^{13}$, preferred is methyl, ethyl, n-propyl or isopropyl, and more preferred is methyl.

As the "$C_1$-$C_6$ alkyl group" for $R^{14}$, preferred is methyl, ethyl, n-propyl or isopropyl, and more preferred is methyl or ethyl.

As the "$C_1$-$C_4$ alkyl group" for $R^{15}$, preferred is methyl or ethyl, and more preferred is methyl.

As the "$C_1$-$C_4$ alkyl group" for $R^{16}$, preferred is methyl, ethyl, n-propyl or isopropyl, and more preferred is methyl.

As the "$C_1$-$C_6$ alkyl group" for $R^{17}$, preferred is a methyl group, an ethyl group, an isopropyl or t-butyl, and more preferred is methyl or ethyl.

The substituent of the "optionally substituted $C_1$-$C_6$ alkyl group" for $R^{10}$ includes a halogen atom, a hydroxy group, a cyano group, a $C_3$-$C_7$ cycloalkyl group, a 5- to 7-membered heterocyclic group, an aryl group and a $C_1$-$C_4$ alkoxy group, with preference given to a halogen atom, a hydroxy group, a $C_3$-$C_6$ cycloalkyl group and a $C_1$-$C_4$ alkoxy group.

The substituent of the "optionally substituted $C_1$-$C_4$ alkyl group" for $R^{11}$ includes a halogen atom, a hydroxy group and a cyano group, with preference given to fluorine.

The substituent of the "optionally substituted $C_1$-$C_6$ alkyl group" for $R^{12}$ includes a halogen atom, a cyano group, a $C_3$-$C_7$ cycloalkyl group, a 5- to 7-membered heterocyclic group, a hydroxy group and a $C_1$-$C_4$ alkoxy group, with preference given to a halogen atom, a $C_3$-$C_6$ cycloalkyl group and a $C_1$-$C_4$ alkoxy group.

In the present specification, the "haloalkyl group" is a linear or branched chain alkyl group having one or more, preferably 1 to 3, halogen atoms, and a carbon number of 1 to 6, preferably 1 to 4. Examples thereof include trifluoromethyl, fluoroethyl, difluoroethyl, trifluoroethyl, trifluoro-n- propyl, trifluoroisopropyl, trifluoro-n-butyl, trifluoroisobutyl, trifluoro-t-butyl, trifluoro-n-pentyl, trifluoro-n-hexyl and the like.

As the "haloalkyl group" for $R^{2a}$ or $R^{2b}$, preferred is fluoroethyl, difluoroethyl or trifluoroethyl, and more preferred is 2-fluoroethyl, 2,2-difluoroethyl or trifluoroethyl.

In the present specification, the "alkenyl group" preferably has a carbon number of 2 to 6, may be linear or branched chain, and has at least one carbon double bond. Examples thereof include an ethenyl group, a propenyl group, a butenyl group and the like.

As the "$C_2$-$C_6$ alkenyl group" for $R^{12}$, an ethenyl group, 1-propenyl group, a 2-propenyl group, a 1-butenyl group, a 2-butenyl group, a 3-butenyl group and the like are preferable, and an ethenyl group, a 1-propenyl group and a 2-propenyl group are more preferable.

The substituent of the "optionally substituted $C_2$-$C_6$ alkenyl group" for $R^{12}$ includes a halogen atom, a cyano group, a $C_3$-$C_7$ cycloalkyl group, a 5- to 7-membered heterocyclic group, an aryl group, a hydroxy group and a $C_1$-$C_4$ alkoxy group, with preference given to a halogen atom, a $C_3$-$C_6$ cycloalkyl group and a $C_1$-$C_4$ alkoxy group.

In the present specification, the "alkynyl group" preferably has a carbon number of 2 to 6, may be linear or branched chain, and has at least one carbon triple bond. Examples thereof include an ethynyl group, a propynyl group, a butynyl group and the like.

As the "$C_2$-$C_6$ alkynyl group" for $R^{12}$, preferred is an ethynyl group, a 1-propynyl group, a 2-propynyl group, a 1-butynyl group, a 2-butynyl group or a 3-butynyl group, and more preferred is an ethynyl group, a 1-propynyl group, a 2-propynyl group or a 2-butynyl group.

As the "$C_3$-$C_6$ alkynyl group" for A, preferred is a 2-propynyl group, a 1-methyl-2-propynyl group, a 2-butynyl group, a 3-butynyl group or a 1-methyl-2-butynyl group, and more preferred is a 2-propynyl group or a 2-butynyl group.

The substituent of the "optionally substituted $C_2$-$C_6$ alkynyl group" for $R^{12}$ includes a halogen atom, a cyano group, a $C_3$-$C_7$ cycloalkyl group, a 5- to 7-membered heterocyclic group, an aryl group, a hydroxy group and a $C_1$-$C_4$ alkoxy group, with preference given to a halogen atom, a $C_3$-$C_8$ cycloalkyl group and a $C_1$-$C_4$ alkoxy group.

In the present specification, the "cycloalkyl group" is alicyclic hydrocarbon containing only a saturated structure, and includes monocyclic hydrocarbon, fused polycyclic hydrocarbon, and crosslinked hydrocarbon. The carbon number is preferably 3 to 8, and examples of the cycloalkyl group include a cyclopropyl group, a cyclobutyl group, a cyclopentyl group, a cyclohexyl group, a cycloheptyl group, a cyclooctyl group and the like.

As the "$C_3$-$C_8$ cycloalkyl group" for $R^{12}$, preferred is cyclopropyl, cyclobutyl, cyclopentyl, cyclohexyl, cycloheptyl or cyclooctyl, and more preferred is cyclopentyl or cyclohexyl.

As the "$C_3$-$C_8$ cycloalkyl group" for A, preferred is cyclopropyl, cyclobutyl, cyclopentyl, cyclohexyl or cycloheptyl, and more preferred is cyclohexyl.

The substituent of the "optionally substituted $C_3$-$C_8$ cycloalkyl group" for $R^{12}$ include an aryl group, a heteroaryl group, a halogen atom, a cyano group, a $C_1$-$C_4$ alkyl group, a $C_3$-$C_7$ cycloalkyl group, a $C_1$-$C_4$ alkoxy group, a —$CF_3$ group and a —$OCF_3$ group, with preference given to a halogen atom, a $C_1$-$C_4$ alkyl group and a $C_1$-$C_4$ alkoxy group.

The substituent of the "optionally substituted $C_3$-$C_8$ cycloalkyl group" for A include an aryl group, a heteroaryl group, a halogen atom, a cyano group, a $C_1$-$C_4$ alkyl group, a hydroxyl group, a $C_3$-$C_7$ cycloalkyl group, a $C_1$-$C_4$ alkoxy group, a —$CF_3$ group and a —$OCF_3$ group, with preference given to an aryl group, a halogen atom, a $C_1$-$C_4$ alkyl group and a $C_1$-$C_4$ alkoxy group.

The "aryl group" in the present specification is a cyclic hydrocarbon having aromatic property, which is monocyclic hydrocarbon or polycyclic hydrocarbon having a carbon number of 6 to 10, and may be condensed or fused with a cycloalkyl group, a heterocyclic group and a heteroaryl group. For example, a phenyl group, a 1-naphthyl group, a 2-naphthyl group, a 5-indanyl group, a 5-benzofuranyl group, a 6-benzofuranyl group, a 5-benzothienyl group, a 6-benzothienyl group, a 5-benzimidazolyl group, a 5-benzoxazolyl group, a 6-benzoxazolyl group, a 5-benzothiazolyl group, a 6-benzothiazolyl group, a 5-benzoisoxazolyl group, a 6-benzoisoxazolyl group, a 5-indolyl group, a 6-indolyl group, a 1H-indazol-5-yl group, a 1H-indazol-6-yl group, a 6-quinolinyl group, a 7-quinolinyl group, a 6-isoquinolinyl group, 7-isoquinolinyl group, a 6-phthalazinyl group, a 7-phthalazinyl group, a 6-quinoxalinyl group, a 7-quinoxalinyl group, a 6-quinazolinyl group, a 7-quinazolinyl group, a 6-cinnolinyl group, a 7-cinnolinyl group and the like can be mentioned.

As the aryl group for $R^{2a}$ or $R^{2b}$, preferred is a phenyl group.

As the aryl group for $R^{10}$, preferred is a phenyl group.

As the "aryl group" for $R^{12}$, preferred is a phenyl group.

As the aryl group for $R^{17}$, preferred is a phenyl group, a 1-naphthyl group or a 2-naphthyl group.

As the aryl group for A, preferred is a phenyl group, a 1-naphthyl group, a 2-naphthyl group or a 5-indanyl group, and particularly preferred is a phenyl group.

Examples of the substituent of the "optionally substituted aryl group" for $R^{2a}$ or $R^{2b}$ include a halogen atom, a cyano group, a hydroxy group, a $C_1$-$C_4$ alkyl group, a $C_1$-$C_4$ alkoxy group, a —$CF_3$ group and a —$OCF_3$ group.

Examples of the substituent of the "optionally substituted aryl group" for $R^{10}$ include a halogen atom, a cyano group, a $C_1$-$C_4$ alkyl group, a $C_1$-$C_4$ alkoxy group, a —$CH_2OH$ group, a —$CF_3$ group, a —$CHF_2$ group, a —$CH_2F$ group, a —$OCF_3$ group, a —$OCHF_2$ group, a —$OCH_2F$ group, a —$CONH_2$ group, a —$CONHCH_3$ group and a —$CON(CH_3)_2$ group, and preferable examples include a halogen atom and a cyano group.

Examples of the substituent of the "optionally substituted aryl group" for $R^{12}$ include a halogen atom, a cyano group, a hydroxy group, a $C_1$-$C_4$ alkyl group, a $C_1$-$C_4$ alkoxy group, a —$CF_3$ group, a —$OCF_3$ group and a benzyloxy group.

Examples of the substituent of the "optionally substituted aryl group" for A include a halogen atom, a cyano group, a $C_1$-$C_4$ alkyl group, a $C_1$-$C_4$ alkoxy group, a —$CF_3$ group and a —$OCF_3$ group, with preference given to a halogen atom.

In the present specification, the "carbocyclic group" is alicyclic hydrocarbon containing only a saturated structure, alicyclic hydrocarbon containing a partially unsaturated structure, or cyclic hydrocarbon having aromatic property, and includes monocyclic hydrocarbon, fused polycyclic hydrocarbon and crosslinked hydrocarbon. The carbon number is preferably 3 to 10, and they may be condensed or fused with a cycloalkyl group, a heterocyclic group or a heteroaryl group. Furthermore, the carbon atom on the aforementioned cycloalkyl group may be partially substituted by an oxo group or a thioxo group, and the carbon atom or hetero atom on the aforementioned heterocyclic group may be partially substituted by an oxo group or a thioxo group. Examples of the carbocyclic group include the substituents recited for the aforementioned cycloalkyl group and aryl group, as well as a cycloalkenyl group.

As the "carbocyclic group" for $Cy^1$, preferred is a $C_5$-$C_7$ cycloalkyl ring or a benzene ring, and more preferred is a cyclopentane ring, a cyclohexane ring or a benzene ring.

As the "carbocyclic group" for $Cy^2$, preferred is a $C_5$-$C_7$ cycloalkyl ring or a benzene ring, and more preferred is a cyclopentane ring, a cyclohexane ring or a benzene ring.

The "heterocyclic group" in the present specification is a cyclic compound having at least one hetero atom (nitrogen, oxygen or sulfur) and a carbon atom, and a completely saturated or partially unsaturated structure. The heterocyclic group of present specification includes a 3- to 8-membered monocyclic compound, a 8- to 12-membered fused ring compound or heterocyclic spiro compound condensed, fused or bonded with other heterocyclic group, a heteroaryl group, a cycloalkyl group or an aryl group. The carbon atom or hetero atom on the heterocyclic group may be partially substituted by an oxo group or a thioxo group. The monocyclic hetero ring is preferably a 4- to 7-membered ring, and the fused heterocycle is preferably a 8- to 10-membered ring.

Examples of the heterocyclic group include a tetrahydrofuranyl group, a tetrahydropyranyl group, a dioxolanyl group, a dioxanyl group, a pyrrolidinyl group, a piperidinyl group, a dihydropyridinyl group, a tetrahydropyridinyl group, a piperazinyl group, an azepanyl group, an azocanyl group, a morpholinyl group, a thiomorpholinyl group, an oxazolidinyl group, a thiazolidinyl group, a tetrahydrothienyl group, a tetrahydrothiopyranyl group, a dihydrooxadiazolyl group, a dihydrotriazolyl group, a dihydrobenzofuranyl group, a chromanyl group, an indolinyl group, an isoindolinyl group, a tetrahydroquinolinyl group, a tetrahydroisoquinolinyl group and the like.

Examples of the "heterocyclic group" for $Cy^1$ include a 3- to 8-membered monocyclic compound having a completely saturated or partially unsaturated structure, or a 8- to 12-membered fused ring compound condensed with other heterocyclic group, heteroaryl group, cycloalkyl group or aryl group.

Specific examples of the 3- to 8-membered monocyclic compound include a dioxolanyl group (particularly preferably 1,3-dioxolanyl), a pyrrolidinyl group, a piperidinyl group, an oxazolidinyl group and the like.

Specific examples of the 8- to 12-membered fused ring compound include 5,6,7,8-tetrahydro-4H-pyrazolo[1,5-a]azepine, 4,5,6,7-tetrahydro-pyrazolo[1,5-a]pyridine, 5,6-dihydro-4H-pyrazolo[1,2-b]pyrazole, 5,6-dihydro-4H-pyrrolo[1,2-b]pyrazole, 6,7,8,9-tetrahydro-5H-imidazolo[1,2-a]azepine, 5,6,7,8-tetrahydro-imidazolo[1,2-a]pyridine, 6,7-dihydro-5H-pyrrolo[1,2-a]imidazole and the like. Of these, preferably 5,6,7,8-tetrahydro-4H-pyrazolo[1,5-a]azepine, 4,5,6,7-tetrahydro-pyrazolo[1,5-a]pyridine, and 5,6-dihydro-4H-pyrrolo[1,2-b]pyrazole.

Examples of the "heterocyclic group" for $Cy^2$ include a 3- to 8-membered monocyclic compound having a completely saturated or partially unsaturated structure, and a 8- to 12-membered fused ring compound condensed with other heterocyclic group, heteroaryl group, cycloalkyl group or aryl group.

Specific examples of the 3- to 8-membered monocyclic compound include tetrahydrofuran.

Specific examples of the 8- to 12-membered fused ring compound include 5,6,7,8-tetrahydro-4H-pyrazolo[1,5-a]azepine, 4,5,6,7-tetrahydro-pyrazolo[1,5-a]pyridine, 5,6-dihydro-4H-pyrazolo[1,2-b]pyrazole, 6,7,8,9-tetrahydro-5H-imidazolo[1,2-a]azepine, 5,6,7,8-tetrahydro-imidazolo[1,2-a]pyridine, 6,7-dihydro-5H-pyrrolo[1,2-a]imidazole and the like.

The "heterocyclic group" for $R^2$ contains at least one nitrogen atom as a hetero atom, preferably a pyrrolidinyl group, a piperidinyl group, a piperazinyl group, a morpholinyl group, a thiomorpholinyl group or a thiazolidinyl group, and more preferably a 1-pyrrolidinyl group, a 2-pyrrolidinyl group, a 3-pyrrolidinyl group, a 1-piperidinyl group, a 2-piperidinyl group or a 4-morpholinyl group.

As the "heterocyclic group" for $R^{10}$, preferred is a dihydrooxadiazolyl group, a dihydrotriazolyl group or a pyrrolidinyl group, and more preferred is a 1,2,4-dihydrooxadiazolyl group, a 1,3,4-dihydrooxadiazolyl group or a pyrrolidinyl group.

As the "heterocyclic group" for $R^{12}$, preferred is a tetrahydrofuranyl group, a tetrahydropyranyl group, a pyrrolidinyl group, a piperidinyl group, a tetrahydrothienyl group or a tetrahydrothiopyranyl group, and more preferred is a 3-tetrahydrofuranyl group or a 4-tetrahydropyranyl group.

The substituent of the "optionally substituted heterocyclic group" for $R^2$ include a halogen atom, a cyano group, a hydroxy group, a $C_1$-$C_4$ alkyl group, a hydroxy $C_1$-$C_4$ alkyl group, a $C_3$-$C_7$ cycloalkyl group, a $C_1$-$C_4$ alkoxy group, a —$CF_3$ group and a —$OCF_3$ group, with preference given to a hydroxy group.

The substituent of the "optionally substituted heterocyclic group" for $R^{10}$ include an aryl group, a heteroaryl group, a halogen atom, a cyano group, a $C_1$-$C_4$ alkyl group, a $C_3$-$C_7$ cycloalkyl group, a $C_1$-$C_4$ alkoxy group, a —$CF_3$ group, a —$OCF_3$ group, a —$CONH_2$ group, a —$CONHCH_3$ group and a —$CON(CH_3)_2$ group, with preference given to a $C_1$-$C_4$ alkyl group and a —$CONH_2$ group.

Examples of the substituent of the "optionally substituted heterocyclic group" for $R^{12}$ include an aryl group, a heteroaryl group, a halogen atom, a cyano group, a $C_1$-$C_4$ alkyl group, a $C_3$-$C_7$ cycloalkyl group, a $C_1$-$C_4$ alkoxy group, a —$CF_3$ group, a —$OCF_3$ group, a $C_1$-$C_4$ acyl group, a formyl group, a $C_1$-$C_4$ alkylsulfonyl group and an arylsulfonyl group.

The "heteroaryl group" in the present specification is an aromatic ring compound having at least one hetero atom (nitrogen, oxygen or sulfur) and a carbon atom, and includes a 5- or 6-membered monocyclic compound, and a 8- to 12-membered fused ring compound condensed or fused with other heterocyclic group, heteroaryl group, cycloalkyl group or aryl group. Examples of the heteroaryl group include a furyl group, a thienyl group, a pyrrolyl group, an imidazolyl group, a pyrazolyl group, a triazolyl group, a tetrazolyl group, an oxazolyl group, a thiazolyl group, an isoxazolyl group, an isothiazolyl group, an oxadiazolyl group, a thiadiazolyl group, a furazanyl group, a pyridyl group, a pyrazinyl group, a pyrimidyl group, a pyridazinyl group, a triazinyl group, an indolizinyl group, an isoindolyl group, an indolyl group, an indazolyl group, a benzimidazolyl group, a purinyl group, a quinolyl group, an isoquinolyl group, a phthalazinyl group, a quinoxalinyl group, a quinazolinyl group, a cinnolinyl group, a benzofuranyl group, a benzothienyl group, a benzoxazolyl group, a benzothiazolyl group, a benzoisoxazolyl group, a benzoisothiazolyl group and the like.

Preferable examples of the "heteroaryl group" for $Cy^1$ or $Cy^2$ include a pyrrolyl group, an oxazolyl group, a thiazolyl group, an isoxazolyl group, a pyrazolyl group, a pyridyl group, a pyrazinyl group, a pyrimidyl group, a pyridazinyl group and the like, and more preferable examples include an oxazolyl group, a thiazolyl group, an isoxazolyl group, a pyrazolyl group and the like.

As the "heteroaryl group" for $R^{10}$, preferred is a furyl group, a thienyl group, a pyrazolyl group, a triazolyl group, a tetrazolyl group, an oxazolyl group, an isoxazolyl group, a thiazolyl group, an oxadiazolyl group, a thiadiazolyl group, a pyridyl group, a pyrazinyl group, a pyrimidyl group or a pyridazinyl group, and more preferred is a furyl group, a thienyl group, a pyrazolyl group, a 1,2,4-triazolyl group, a tetrazolyl group, an oxazolyl group, a thiazolyl group, an isoxazolyl group, a 1,2,4-oxadiazolyl group, a 1,3,4-oxadiazolyl group, a 1,3,4-thiadiazolyl group, a pyridyl group, a pyrazinyl group or a pyrimidyl group, particularly preferably a 1,2,4-oxadiazolyl group, a 1,3,4-oxadiazolyl group or a 1,3,4-thiadiazolyl group.

As the "heteroaryl group" for $R^{12}$, preferred is a thienyl group or a pyrimidyl group, and more preferred is a 2-thienyl group.

Examples of the substituent of the "optionally substituted heteroaryl group" for $R^{10}$ include a halogen atom, a cyano group, a $C_1$-$C_4$ alkyl group (e.g., methyl group, ethyl group, t-butyl group), a $C_1$-$C_4$ alkoxy group, a —$CHF_2$ group, a —$CF_3$ group, an —$OCF_3$ group, a —$CONH_2$ group, a —$CONHCH_3$ group, a —$CON(CH_3)_2$ group, an amino group and a hydroxy-$C_{1-4}$ alkyl group (e.g., hydroxymethyl group).

Preferable examples of the substituent of the "optionally substituted heteroaryl group" for $R^{10}$ include a halogen atom, a cyano group, a $C_1$-$C_4$ alkyl group, a $C_1$-$C_4$ alkoxy group, a —$CF_3$ group, an —$OCF_3$ group, a —$CONH_2$ group, a —$CONHCH_3$ group and a —$CON(CH_3)_2$ group, more preferably a $C_1$-$C_4$ alkyl group, a $C_1$-$C_4$ alkoxy group, a —$CF_3$ group, an —$OCF_3$ group can be mentioned, with further preference given to a $C_1$-$C_4$ alkyl group (preferably, methyl group, ethyl group).

Examples of the substituent of the "optionally substituted heteroaryl group" for $R^{12}$ include a halogen atom, a cyano group, a $C_1$-$C_4$ alkyl group, a $C_1$-$C_4$ alkoxy group, a —$CF_3$ group and an —$OCF_3$ group.

The "arylalkyl group" in the present specification has an aryl moiety which is as defined above. The alkyl moiety preferably has a carbon number of 1 to 4 and may be linear or branched chain. Examples thereof include benzyl, phenethyl, 3-phenylpropyl, 1-naphthylmethyl, 2-(1-naphthyl)ethyl, 2-(2-naphthyl)ethyl, 3-(2-naphthyl)propyl and the like.

As the "arylalkyl group" for $R^{12}$, preferred is a benzyl group or a phenethyl group, and more preferred is a benzyl group.

As the "aryl-$C_1$-$C_4$ alkyl group" for A, preferred is a benzyl group, a phenethyl group or a 3-phenylpropyl group, and more preferred is a benzyl group or a phenethyl group.

Examples of the substituent of the "optionally substituted arylalkyl group" for $R^{12}$ include a halogen atom, a cyano group, a $C_1$-$C_4$ alkyl group, a $C_1$-$C_4$ alkoxy group, a —$CF_3$ group and an —$OCF_3$ group, and the aryl moiety of the arylalkyl group may be substituted.

Examples of the substituent of the "optionally substituted aryl-$C_1$-$C_4$ alkyl group" for A include a halogen atom, a cyano group, a $C_1$-$C_4$ alkyl group, a $C_1$-$C_4$ alkoxy group, a —$CF_3$ group and an —$OCF_3$ group, and the aryl moiety of the arylalkyl group may be substituted.

The "heteroarylalkyl group" in the present specification has a heteroaryl moiety which is as defined above. The alkyl moiety preferably has a carbon number of 1 to 4 and may be linear or branched chain. Examples thereof include pyridylmethyl, pyridylethyl, furylmethyl, thienylmethyl, furylethyl, thienylethyl and the like.

As the "heteroaryl-$C_1$-$C_4$ alkyl group" for A, preferred is pyridylethyl, furylethyl or thienylethyl, and more preferred is 2-(2-furyl)ethyl or 2-(2-thienyl)ethyl.

Examples of the substituent of the "optionally substituted heteroaryl-$C_1$-$C_4$ alkyl group" for A include a halogen atom, a cyano group, a $C_1$-$C_4$ alkyl group, a $C_1$-$C_4$ alkoxy group, a $CF_3$ group and an $OCF_3$ group. The heteroaryl moiety of the heteroarylalkyl group may be substituted.

The "alkoxy group" in the present specification is a monovalent group resulting from removal of a hydrogen atom from the hydroxyl group of alcohols, which has a carbon number of 1 to 6 and may be linear or branched chain. Examples thereof include methoxy, ethoxy, propoxy, butoxy, pentyloxy, hexyloxy and the like.

As the "$C_1$-$C_6$ alkoxy group" for $R^{14}$, preferred is a methoxy group, an ethoxy group, a propoxy group, an isopropoxy group or a t-butoxy group, and more preferred is a methoxy group or an ethoxy group.

As the "$C_1$-$C_4$ alkoxy group" for $R^{15}$, preferred is a methoxy group or an ethoxy group, and more preferred is a methoxy group.

As the "$C_1$-$C_6$ alkoxy group" for $R^{17}$, preferred is a methoxy group, an ethoxy group or a t-butoxy group, and more preferred is a methoxy group.

Examples of the "halogen atom" in the present specification include fluorine, chlorine, bromine and iodine. Preferred is fluorine, chlorine or bromine, and particularly preferred is fluorine or chlorine.

As the halogen atom for $R^9$, preferred is fluorine or chlorine.

As the halogen atom for $R^{15}$, preferred is fluorine or chlorine.

As the halogen atom for $R^{10}$, preferred is fluorine, chlorine or bromine.

As the halogen atom for $R^{11}$, preferred is fluorine or chlorine.

The "alkylamino group" in the present specification is one wherein 1 or 2 hydrogen atoms of the amino group are substituted by an alkyl group, and the alkyl moiety preferably has a carbon number of 1 to 4 and may be linear or branched chain. Examples of the alkylamino group include methylamino, ethylamino, isopropylamino, dimethylamino, diethylamino and the like.

As the "$C_1$-$C_4$ alkylamino group" for $R^{17}$, preferred is methylamino, dimethylamino, ethylamino or isopropylamino.

The "arylamino group" in the present specification is one wherein 1 or 2 hydrogen atoms of the amino group are substituted by an aryl group, and the aryl moiety is similar to that mentioned above. Examples thereof include a phenylamino group.

As the "arylamino group" for $R^{17}$, preferred is a phenylamino group.

Examples of the "aryloxy group" in the present specification include a phenoxy group and a naphthyloxy group.

Preferable examples of the "aryloxy group" for $R^{17}$ include a phenoxy group.

In the present specification, examples of the substituent of the "optionally substituted amino group" for $R^{10}$ include a $C_1$-$C_4$ alkyl group, a $C_1$-$C_4$ alkylsulfonyl group, a $C_1$-$C_4$ acyl group, a $C_1$-$C_4$ alkoxycarbonyl group, a $C_1$-$C_4$ alkylaminocarbonyl group and the like.

Examples of the substituent of the "optionally substituted amino group" for $R^{14}$ include a $C_1$-$C_4$ alkyl group, a $C_1$-$C_4$ alkylsulfonyl group, a $C_1$-$C_4$ alkyl-amino group, a $C_1$-$C_4$ alkylcarbonyl group, a $C_1$-$C_4$ alkoxycarbonyl group and the like. Particularly preferred is a methyl group, a methylsulfonyl group, a methylamino group, a methylcarbonyl group, a methoxycarbonyl group and the like.

In the present specification, examples of the "ring" formed by $R^1$ and A include a pyrrolidine ring, a piperidine ring, a piperazine ring and the like.

In the above-mentioned formulas (II) and (IV), l is preferably an integer of 0, 1 or 2, more preferably an integer of 1.

In the above-mentioned formula (III), k is preferably an integer of 0, 1 or 2, and X is preferably a bond or an oxygen atom.

In the above-mentioned formulas (V)-(VIII), n is preferably an integer of 0, 1 or 2, more preferably an integer of 0 or 1.

In the above-mentioned formula (VII), g is preferably an integer of 1.

In the above-mentioned formula (V), h is preferably an integer of 1.

In the above-mentioned formula (V), i is preferably an integer of 1 or 2.

In the above-mentioned formulas (V)-(VII), W is preferably =CH— or =N—.

In the above-mentioned formula (VII), D is preferably =N-(E)u-R$^{17}$ wherein E is preferably —SO$_2$— or —CO—, u is preferably an integer of 1, and R$^{17}$ is preferably a C$_1$-C$_4$ alkyl group or a C$_1$-C$_6$ alkoxy group.

Examples of the pharmacologically acceptable salt of compound (I) include salts with mineral acid such as hydrochloric acid, sulfuric acid, hydrobromic acid, phosphoric acid and the like; salts with organic acid such as methanesulfonic acid, p-toluenesulfonic acid, acetic acid, oxalic acid, citric acid, malic acid, fumaric acid and the like; salts with alkali metal such as sodium, potassium and the like; salts with alkaline earth metal such as magnesium and the like; salts with amine such as ammonia, ethanolamine, 2-amino-2-methyl-1-propanol and the like. Besides these, the kind of the salt is not particularly limited as long as it is pharmacologically acceptable.

Examples of the solvate of compound (I) include a solvate with water, ethanol, ethyl acetate and the like. Besides these, the kind of the solvate is not particularly limited as long as it is pharmacologically acceptable.

In the present specification, the "homocysteine synthase inhibition" refers to reversible inhibition of the SAHH activity, which includes competitive inhibition, noncompetitive inhibition and uncompetitive inhibition.

The enzyme inhibition includes reversible inhibition that inhibits the reaction that should inherently proceed by reversible binding, and irreversible inhibition that prevents binding of a substrate by a strong binding such as covalent bond and the like with an amino acid residue near the deficient site.

The reversible inhibition includes 3 types.

The first is a competitive inhibition, wherein enzyme-inhibitor complex (EI) is formed between enzyme (E) and inhibitor (I) to antagonize the binding of the substrate to an enzyme. That is, a competitive inhibitor is bound to an enzyme substrate binding site instead of a substrate and reversibly inhibits enzyme activity. Therefore, even when a competitive inhibitor is present, the inhibitory activity disappears by sufficiently increasing the substrate concentration. The inhibitory constant Ki is defined to be [E][I]/[EI].

The second reversible inhibition is a noncompetitive inhibition, where an inhibitor does not influence free enzymes and the substrate-enzyme binding stage. It reversibly binds only to enzyme-substrate complex (ES) to show an inhibitory action. Therefore, an increased substrate concentration does not influence the inhibition intensity. In this case, the inhibitory constants Ki is [ES][I]/[ESI]. [ESI] is a concentration of enzyme-substrate-inhibitor complex.

The third reversible inhibition is an uncompetitive inhibition, wherein the inhibitor reversibly binds a free enzyme and enzyme-substrate complex to show an inhibitory action. An uncompetitive inhibitor binds an enzyme at a moiety different from the substrate binding site, and achieves inhibition by changing the molecular structure of the enzyme. In this case, two inhibitory constants Ki of Ki$^{EI}$=[E][I]/[EI] and Ki$^{ESI}$=[ES][I]/[ESI] are present.

These inhibitory modes can be determined by Lineweaver-Burk Plotplot.

In the present specification, the "disease relating to homocysteine synthase" refers to a disease whose symptoms are expected to be prevented or improved by reversible inhibition of the homocysteine synthase activity. For example, hyperhomocysteinemia, complications thereof and the like can be mentioned.

Now the production methods of the compound of the present invention are explained.

A compound represented by the formula (I), or a salt thereof can be synthesized by adopting various known synthesis methods, while utilizing the characteristics of basic skeleton or the kind of the substituent. Representative production methods are shown below as examples, which are not to be construed as limitative. Depending on the kind of the functional group, conversion of the functional group to a suitable protecting group, namely, a group easily convertible to the functional group, in the stage of a starting material or intermediate, may be effective for production techniques. In this case, the protecting group can be removed as necessary to give a desired compound. Examples of such functional group include a hydroxyl group, a carboxyl group, an amino group and the like. Examples of the protecting group include those described in Greene and Wutt, "Protective Groups in Organic Synthesis (third edition)", and they may be used as appropriate according to the reaction conditions.

In the present specification, the "room temperature" is generally 0-30° C.

[Production Method 1]

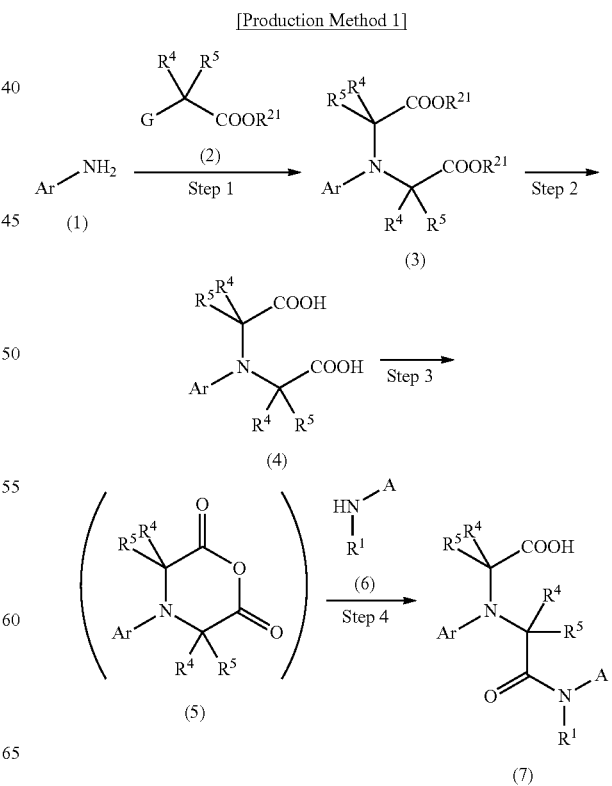

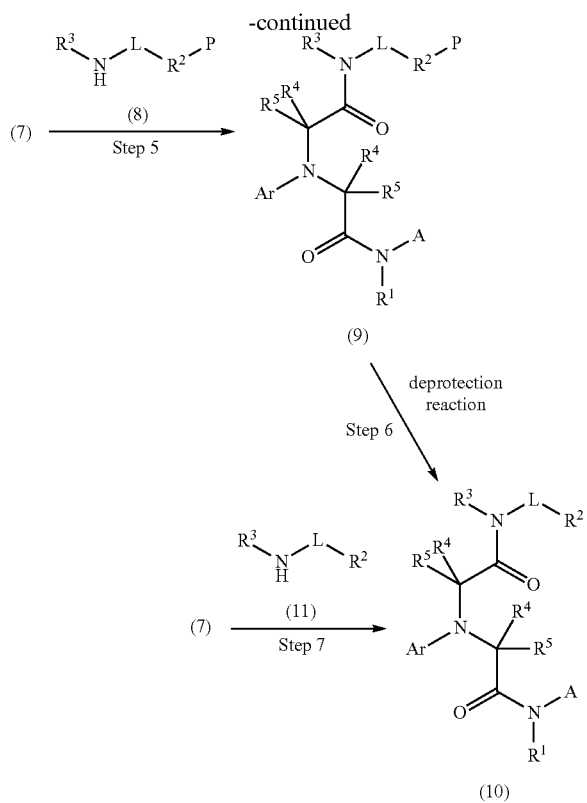

wherein Ar, $R^1$, $R^2$, $R^3$, $R^4$, $R^5$, A, L are as defined above. G is a halogen atom, P is an amino-protecting group, and $R^{21}$ is a $C_{1-4}$ alkyl group. When the nitrogen atom contained in $R^2$ is a primary or secondary amine, the reaction is preferably carried out using compound (8) wherein the nitrogen atom is protected, and after completion of the reaction, the resulting compound is subjected to a deprotection operation.

Step 1 (Alkylation Reaction)

This step is performed under warming in an inert solvent or without a solvent, in the presence of compound (1), 2 or more equivalents of compound (2) and 2 or more equivalents of a base. Examples of the base include alkali metal carbonates such as potassium carbonate, sodium carbonate, cesium carbonate and the like, alkali metal phosphates such as dipotassium hydrogenphosphate, disodium hydrogenphosphate, trisodium phosphate, tripotassium phosphate and the like, amines such as triethylamine, N,N-diisopropylethylamine, N-methylmorpholine, pyridine, 2,6-lutidine, N,N-dimethylaminopyridine, 1,8-diazabicyclo[5.4.0]undec-7-ene (hereinafter to be referred to as DBU) and the like, and the like. The amount of the base to be used is 2 or more equivalents, preferably 2 to 20 equivalents, relative to compound (1). The halogen atom of compound (2) is chlorine, bromine, iodine, fluorine or the like, and the amount thereof to be used is 2 or more equivalents, preferably 2 to 20 equivalents, relative to compound (1). The reaction can be carried out using the "inert solvent" include ethers such as tetrahydrofuran, 1,4-dioxane and the like, halogenated hydrocarbons such as chloroform, carbon tetrachloride, 1,2-dichloroethane and the like, hydrocarbons such as hexane, benzene, toluene, xylene and the like, nitriles such as acetonitrile and the like, amides such as N,N-dimethylformamide, N-methylpyrrolidone, N,N-dimethylacetamide and the like, sulfoxides such as dimethyl sulfoxide and the like, and the like. These solvents may be mixed at an appropriate ratio. Alternatively, the reaction can be carried out without a solvent. The reaction temperature is generally 40 to 200° C., preferably 50 to 150° C.

Step 2 (Hydrolysis of Ester)

This step is generally performed in the presence of an acid or base, in a water-containing solvent. Examples of the acid include formic acid, hydrochloric acid, acetic acid, sulfuric acid, hydrobromic acid, trifluoroacetic acid and the like. Examples of the base include alkali metal carbonates such as potassium carbonate, sodium carbonate and the like, alkali metal hydroxides such as potassium hydroxide, lithium hydroxide, sodium hydroxide and the like, and the like. The amount of the acid or base to be used is generally excess amount relative to compound (3). The preferable amount of the acid to be used is 2 to 100 equivalents relative to compound (3), and the preferable amount of the base to be used is 2 to 10 equivalents relative to compound (3). Examples of the water-containing solvent include a mixed solvent of water and one or more kinds of solvents selected from alcohols such as methanol, ethanol and the like, ethers such as tetrahydrofuran, 1,4-dioxane and the like, dimethyl sulfoxide and acetone and the like, and the like. When $R^{21}$ is a tert-butyl group, acid decomposition may be carried out besides the above-mentioned reaction in a water-containing solvent. Examples of the acid include formic acid, hydrochloric acid, acetic acid, sulfuric acid, hydrobromic acid, trifluoroacetic acid, methanesulfonic acid, p-toluenesulfonic acid and the like. In this case, the solvents may be mixed at an appropriate ratio. Examples of the solvent include halogenated hydrocarbons such as chloroform, dichloromethane, dichloroethane and the like, and the like. The amount of the acid to be used is generally excess amount relative to compound (3), preferably 2 to 200 equivalents relative to compound (3). The reaction temperature is generally −20 to 150° C., preferably −10 to 100° C.

Step 3 (Acid Anhydration Reaction)

This step is generally performed using a dehydrating-condensing agent in an inert solvent. Examples of the "inert solvent" include ethers such as tetrahydrofuran, 1,4-dioxane, diethyl ether and the like, halogenated hydrocarbons such as chloroform, dichloromethane and the like, nitriles such as acetonitrile and the like, amides such as N,N-dimethylformamide, N,N-dimethylacetamide, N-methylpyrrolidone and the like, sulfoxides such as dimethyl sulfoxide and the like, and the like. Of these, acetonitrile, dichloromethane, tetrahydrofuran, N,N-dimethylformamide and the like are preferable.

The reaction temperature is generally about −20° C. to 50° C., preferably at room temperature. The reaction time is generally about 30 min to about 24 hr. Examples of the dehydrating-condensing agent include dicyclohexylcarbodiimide (hereinafter to be referred to as DCC), N-(3-dimethylaminopropyl)-N'-ethylcarbodiimide hydrochloride (hereinafter to be referred to as WSC) and the like. Of these, WSC is preferable.

The amount of the condensing agent to be used is generally 1 to 3 equivalents relative to compound (4). In Step 3 and Step 4 (Amidation Reaction), a partitioning operation may be performed on the way. When the water-soluble condensing agent such as WSC and the like is used for the reaction, the condensing agent can be separated into an aqueous layer and the resultant product (5) can be separated into an organic layer by a partitioning operation. Therefore, a large excess amount of the condensing agent can be used. When the condensing agent cannot be separated by the partitioning operation, or when compound (6) is directly added to the reaction system without an extraction operation, 1 to 1.2 equivalents of the condensing agent is preferably added thereto.

Step 4 (Amidation Reaction)

This step is performed by removing the dehydrating-condensing agent by subjected the reaction mixture of Step 3 to a partitioning operation, concentrating the extraction solvent, dissolving again an "inert solvent" (described in Step 3). Alternatively this step is performed by directly using the reaction mixture without the extraction operation of the reaction mixture of Step 3. The amine of compound (6) is used in the form of a free form or a salt such as hydrochloride and the like. When the amine of compound (6) is used in the form of a salt, examples of the neutralizing agent include tertiary amines such as organic bases (e.g., DBU, N,N-diisopropylethylamine, triethylamine, 4-dimethylaminopyridine, N-methylmorpholine, pyridine, 2,6-lutidine and the like), inorganic bases such as alkali metal carbonates (e.g., sodium carbonate, sodium hydrogen carbonate, potassium carbonate, potassium hydrogen carbonate, cesium carbonate and the like), and the like, and the like. Of these, an organic base is preferable.

Step 5 (Amidation Reaction)

Examples of the method in this step include the following method i) a method using a dehydrating-condensing agent, ii) a method using a reactive derivative in carboxyl group, and the like.

i) Method Using a Dehydrating-Condensing Agent

Compound (7) is reacted with about 1 to 5 equivalents of compound (8) and about 1 to 2 equivalents of a dehydrating-condensing agent in an inert solvent. Examples of the "dehydrating-condensing agent" include DCC, WSC and the like. Of these, WSC is preferable. Examples of the "inert solvent" include the solvents described in Step 3, and the like. These solvents may be used in a mixture of two or more kinds thereof mixed at an appropriate ratio. Of these, acetonitrile, dichloromethane, tetrahydrofuran, N,N-dimethylformamide and the like are preferable. The reaction temperature is generally −20° C. to 50° C., preferably −20° C. to room temperature. The reaction time is generally about 1 hr to about 72 hr, preferably about 1 hr to about 24 hr. Where necessary, this reaction may be carried out in the presence of about 1 to 2 equivalents of 1-hydroxybenzotriazole (hereinafter to be referred to as HOBt) or 1-hydroxy-7-azabenzotriazole (hereinafter to be referred to as HOAt). In addition, where necessary, this reaction may be carried out in the presence of a base. Examples of the "base" include tertiary amines such as DBU, N,N-diisopropylethylamine, triethylamine, 4-dimethylaminopyridine, pyridine, 2,6-lutidine and the like, alkali metal or alkaline earth metal carbonates (e.g., sodium carbonate, potassium carbonate, cesium carbonate and the like), alkali metal or alkaline earth metal hydrogencarbonates (e.g., sodium hydrogen carbonate, potassium hydrogen carbonate and the like). Of these, triethylamine, N,N-diisopropylethylamine, 4-dimethylaminopyridine and the like are preferable.

ii) Method Using a Reactive Derivative in Carboxyl Group

The reactive derivative of compound (7) is reacted with about 1 to 5 equivalents (preferably 1 to 3 equivalents) of compound (8) in an inert solvent. Examples of the reactive derivative of the "reactive derivative of compound (7)" include acid halides (e.g., acid chloride, acid bromide), mixed anhydrides (e.g., anhydrides with a $C_{1-6}$ alkyl-carboxylic acid or $C_{1-6}$ alkyl carbonates, and the like), activated esters (e.g., esters with phenol optionally having substituent(s), HOBt, HOAt or N-hydroxysuccinimide, and the like). Examples of the "substituent" of the "phenol optionally having substituent(s)" include a halogen atom, a nitro group and the like. The number of substituents is 1 to 5. Specific examples of the "phenol optionally having substituent(s)" include phenol, pentachlorophenol, pentafluorophenol, p-nitrophenol and the like. The reactive derivative is preferably acid halide. Examples of the "inert solvent" include the solvents described in Step 1. These solvents may be used in a mixture of two or more kinds thereof mixed at an appropriate ratio. Of these, tetrahydrofuran, dichloromethane, acetonitrile and the like are preferable. The reaction temperature is generally −20° C. to 50° C., preferably at room temperature. The reaction time is generally about 1 hr to 72 hr, preferably about 1 hr to 24 hr. Where necessary, this reaction may be carried out in the presence of about 1 to 10 equivalents, preferably about 1 to 3 equivalents, of a base. Examples of the "base" include those exemplified for the aforementioned i) the "method using a dehydrating-condensing agent".

Step 6 (Deprotection Reaction of Amino Group)

This step and a protection reaction of an amino group are performed according to a known method, for example, the method described in Protective Groups in Organic Synthesis third edition, (1999) or the like. Examples of the amino-protecting group include formyl, $C_{1-6}$ alkyl-carbonyl optionally substituted by halogen atom(s) (e.g., acetyl, propionyl, trifluoroacetyl and the like), $C_{1-6}$ alkoxy-carbonyl optionally substituted by halogen atom(s) (e.g., methoxycarbonyl, ethoxycarbonyl, tert-butoxycarbonyl and the like), benzoyl, $C_{7-10}$ aralkyl-carbonyl (e.g., benzylcarbonyl and the like), $C_{7-10}$ aralkyloxy-carbonyl (e.g., benzyloxycarbonyl and the like), trityl, silyl (e.g., trimethylsilyl, tert-butyldimethylsilyl and the like), $C_{2-6}$ alkenyl (e.g., 2-propenyl and the like), substituted benzenesulfonyl (e.g., 2-nitrobenzenesulfonyl) and the like. The amino-protecting group is preferably tert-butoxycarbonyl, trifluoroacetyl, benzyloxycarbonyl, 2-nitrobenzenesulfonyl or the like. The protecting group of compound (8) is preferably tert-butoxycarbonyl, trifluoroacetyl, benzyloxycarbonyl, 2-nitrobenzenesulfonyl or the like.

Step 7 (Amidation Reaction)

This step can be performed in the same manner as in Step 5. The object compound (10) can be obtained by reacting compound (7) with compound (11) under conditions explained in Step 5.

[Production Method 2]

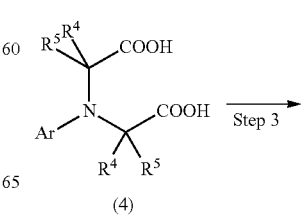

(4)

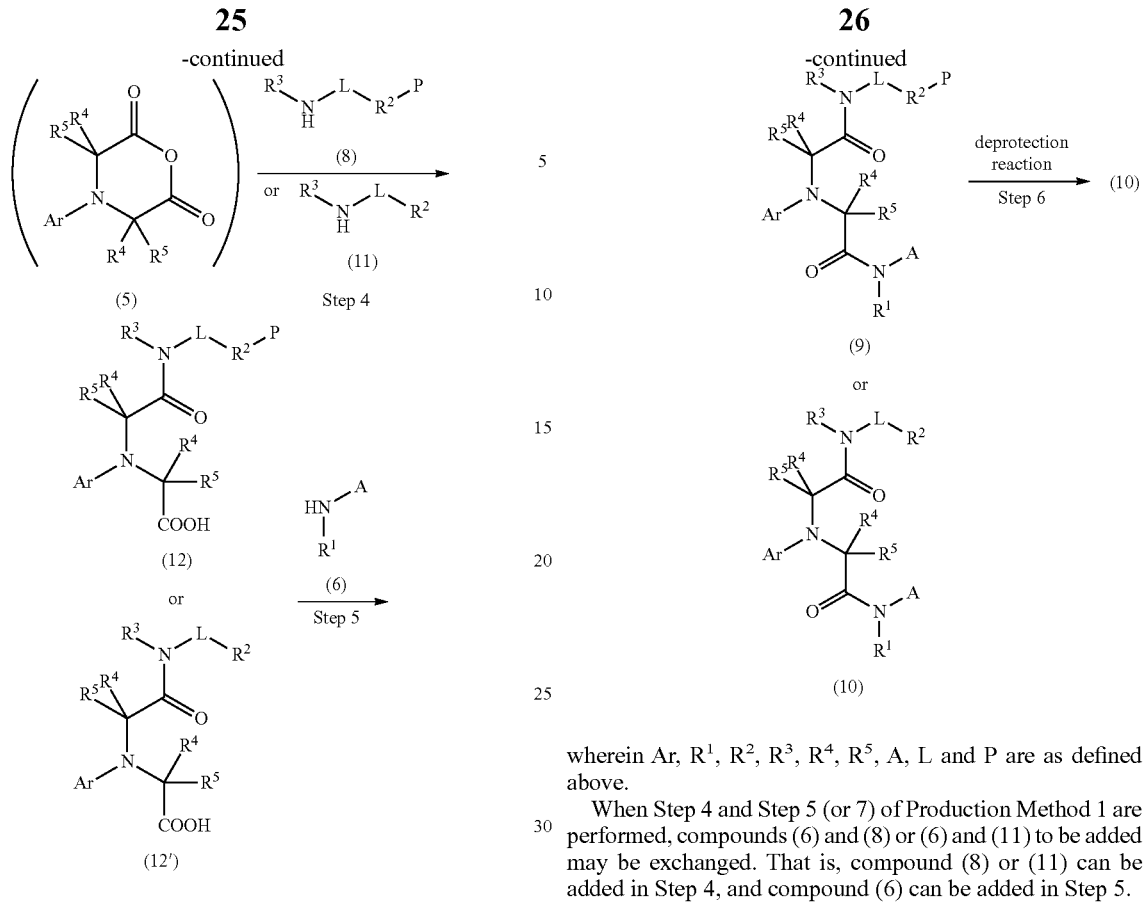
wherein Ar, $R^1$, $R^2$, $R^3$, $R^4$, $R^5$, A, L and P are as defined above.
When Step 4 and Step 5 (or 7) of Production Method 1 are performed, compounds (6) and (8) or (6) and (11) to be added may be exchanged. That is, compound (8) or (11) can be added in Step 4, and compound (6) can be added in Step 5.
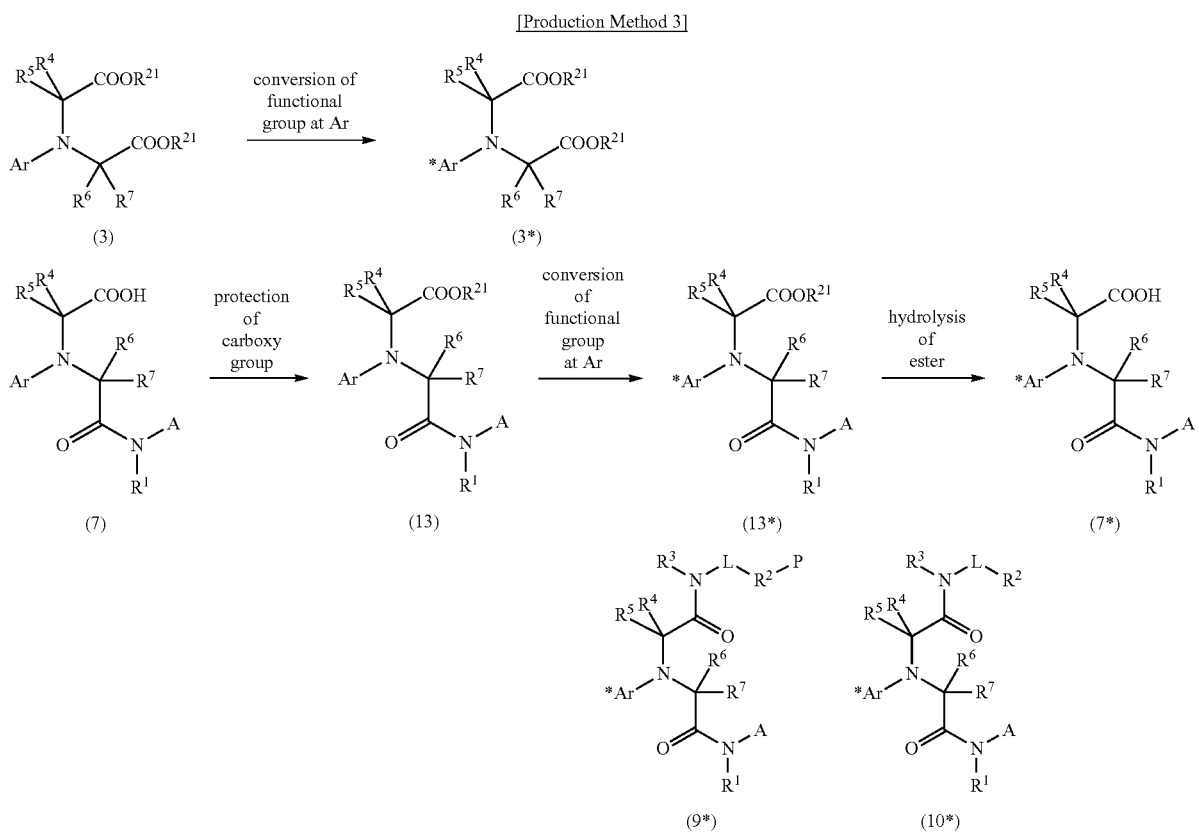

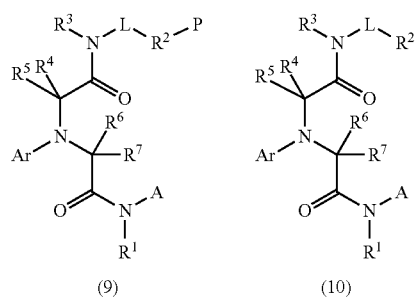

(9)  (10)

conversion of functional group at Ar conversion of functional group at A

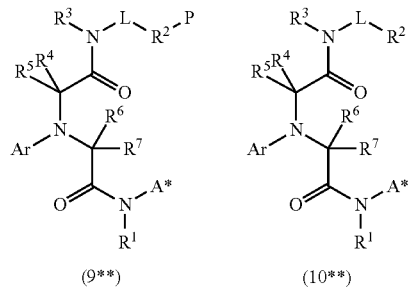

(9)  (10)

wherein Ar, $R^1$, $R^2$, $R^3$, $R^4$, $R^5$, $R^6$, $R^7$, $R^{21}$, A, L and P are as defined above, and *Ar and A* mean substituent conversion.

Regarding Ar and A mentioned in Production Method 1, the conversion of the functional groups contained therein can be carried out by appropriately steps. The conversion method of the functional group is described in the below-mentioned "production method of starting material compounds". Compound (3*) can be synthesized by subjecting the diester compound of compound (3) to conversion of the functional group in Ar. Compound (7) is led to Compound (7*) by protecting the carboxyl group of the monocarboxylic acid compound of compound (7), converting the functional group in Ar of the resulting compound (13), and subjecting the resulting compound (13*) to ester hydrolysis. Compound (9) and (10) can be synthesized by converting the functional group in Ar of compounds (9) and (10). Alternatively, Compounds (9) and (10) can be synthesized by converting the functional group in A of compounds (9*), (10*).

[Production Method 4]

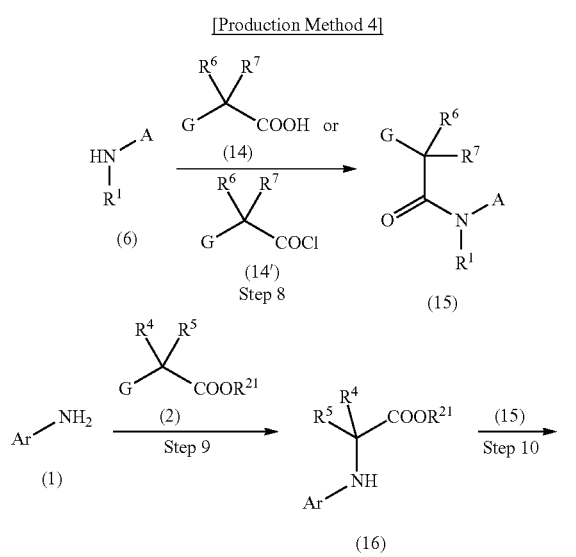

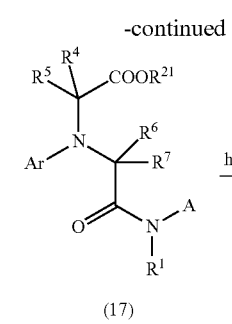

(17)

ester hydrolysis
Step 11

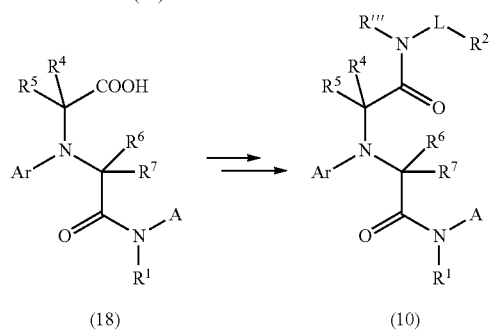

(18)  (10)

wherein $R^1$, $R^2$, $R^3$, $R^4$, $R^5$, $R^6$, $R^7$, $R^{21}$, Ar, A, L and G are as defined above.

Step 8 (Amidation Reaction)

In this step, compound (6) is subjected to an amidation reaction with compound (14) or (14') to give compound (15). This step can be carried out in the same manner as in Step 5 or 7.

Step 9 (Alkylation Reaction)

In this step, compound (1) and compound (2) are subjected to an alkylation reaction to give compound (16). This reaction can be carried out in the same manner as in Step 1. When the reaction is carried out using 1 equivalent or more of compound (2), the amount of compound (2) to be used is preferably below 2 equivalents, more preferably 1 to 1.2 equivalents, since compound (3) may be produced as a by-product.

Step 10 (Alkylation Reaction)

In this step, compounds (16) and (15) are subjected to an alkylation reaction to give compound (17). This reaction can be carried out in the same manner as in Step 1. The amount of compound (15) to be used is 1 equivalent or more, preferably 1 to 10 equivalents, relative to compound (16).

Step 11 (Hydrolysis of Ester)

This reaction can be carried out in the same manner as in Step 2. The steps after compound (18) obtained in this step are the same as those in the method shown in [Production Method 1].

[Production Method 5]

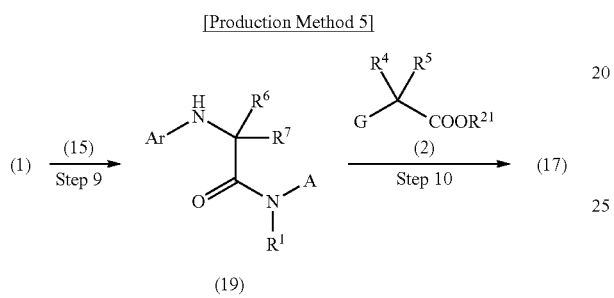

wherein $R^1$, $R^4$, $R^5$, $R^6$, $R^7$, $R^{21}$, Ar, A and G are as defined above.

Step 9 and Step 10 shown in Production Method 4 can be performed by changing the order. That is, compound (17) can be obtained by reacting compound (1) with compound (15), and then reacting the resulting compound (19) with compound (2).

[Production Method 6]

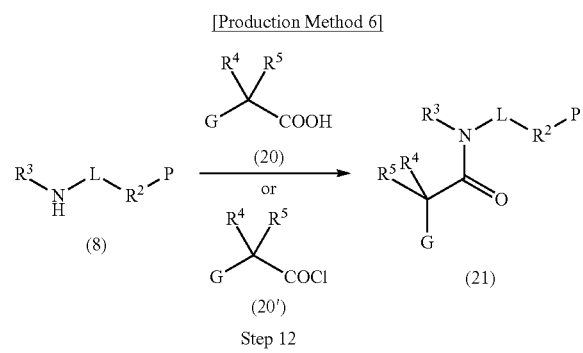

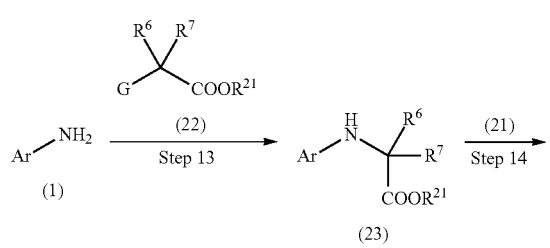

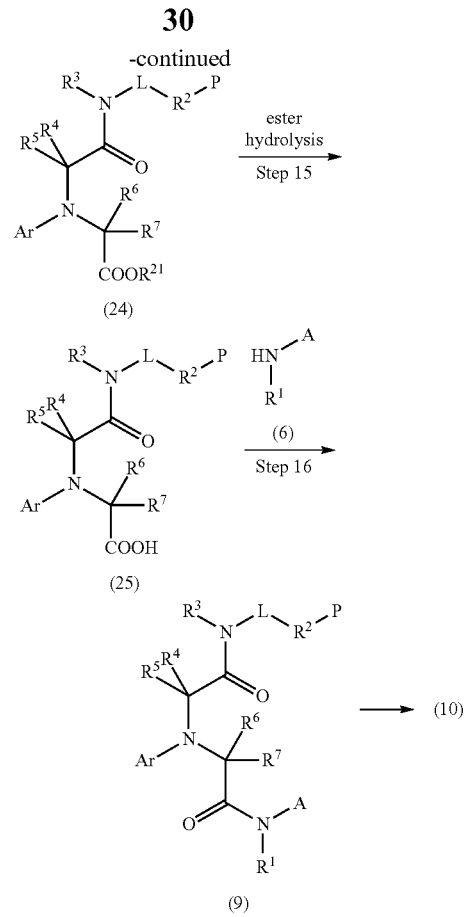

wherein $R^1$, $R^2$, $R^3$, $R^4$, $R^5$, $R^6$, $R^7$, $R^{21}$, Ar, L and G are as defined above.

Step 12 (Amidation Reaction)

In this step, compound (8) is subjected to an amidation reaction with compound (20) or (20') to give compound (21). This step can be carried out in the same manner as in Step 5 or 7.

Step 13 (Alkylation Reaction)

In this step, compound (1) and compound (22) are subjected to an alkylation reaction to give compound (23). This step can be carried out in the same manner as in Step 9. The amount of compound (22) to be used is preferably below 2 equivalents, more preferably 1 to 1.2 equivalents.

Step 14 (Alkylation Reaction)

In this step, compound (23) and (21) are subjected to an alkylation reaction to give compound (24). This step can be carried out in the same manner as in Step 10. The amount of compound (21) to be used is 1 equivalent or more, preferably 1 to 10 equivalents, relative to compound (23).

Step 15 (Hydrolysis of Ester)

This reaction can be carried out in the same manner as in Step 2.

Step 16 (Amidation Reaction)

In this step, compound (25) with and compound (6) are subjected to an amidation reaction to give compound (9). This step can be carried out in the same manner as in Step 5. The steps after compound (9) are the same as those in [Production Method 1].

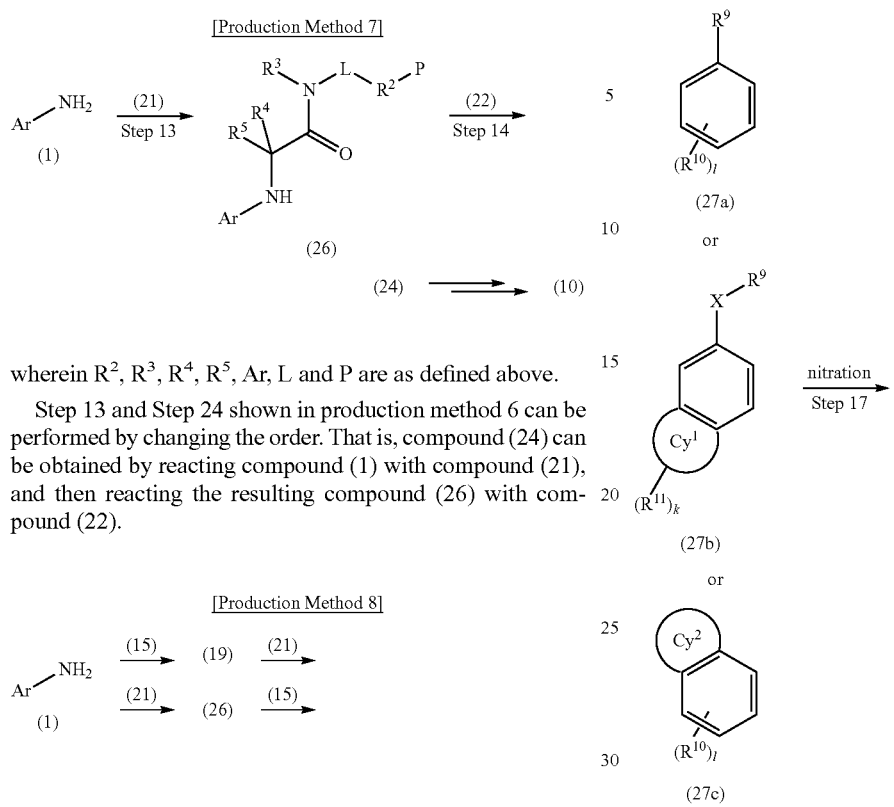

wherein $R^2$, $R^3$, $R^4$, $R^5$, Ar, L and P are as defined above.

Step 13 and Step 24 shown in production method 6 can be performed by changing the order. That is, compound (24) can be obtained by reacting compound (1) with compound (21), and then reacting the resulting compound (26) with compound (22).

wherein $R^1$, $R^2$, $R^3$, $R^4$, $R^5$, $R^6$, $R^7$, Ar, A, L and P are as defined above.

Compound (1), compound (15) and compound (21) can be successively subjected to an alkylation reaction to give compound (9). In this case, the order of compounds (15) and (21) to be reacted may be exchanged. The alkylation reaction can be performed in the same manner as in the methods described in Steps 9, 10, 13 and 14.

The production methods of the starting material compounds used in the above-mentioned production are shown below.

[Production Method 1 of Compound (1)]

A general production method of compound (1) wherein Ar is (II), (III) or (IV), from among the compounds of the formula (I), includes, for examples, nitrating compound (27a), (27b) or (27c) by a known method to give compound (28a), (28b) or (28c) (Step 17), and reducing the nitro group to give compound (29a), (29b) or (29c) (Step 18).

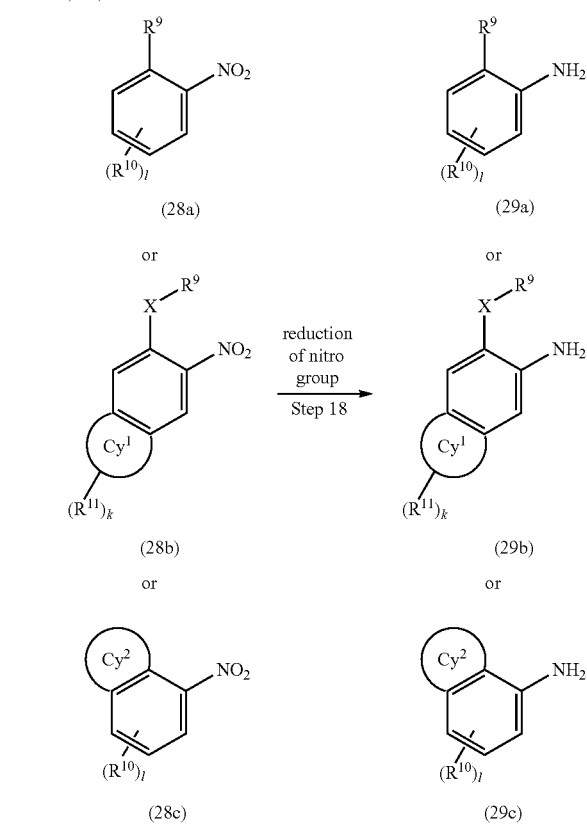

wherein $R^9$, $R^{10}$, $R^{11}$, k, l, X, $Cy^1$ and $Cy^2$ are as defined above.

Step 17 (Nitration Reaction)

In this step, compounds (27a), (27b) and (27c) are converted to compounds (28a), (28b) and (28c) by a nitration reaction, and they can be synthesized by a known method. For example, mixed acid method using conc. sulfuric acid-nitric acid, a method using nitric acid in an acetic acid solvent, a method using nitrite salt (e.g., sodium nitrite, nitrous acid tetrafluoroborate etc.) and nitrate salt (e.g., sodium nitrate etc.) in an acetic acid, trifluoroacetic acid or sulfuric acid solvent and the like can be mentioned.

Step 18 (Reduction of Nitro Group)

In this step, a nitro group is reduced and converted to an amino group, and it can be synthesized according to a known method, for example, the method described in Comprehensive Organic Transformations $3^{rd}$ edition page 821-828 VCH Publishers Inc. 1999, and the like, or a method analogous thereto. For example, it can be synthesized according to a hydrogenation reaction using palladium carbon, Raney-nickel and the like as a catalyst in an inert solvent, under a hydrogen atmosphere, or in the presence of a hydrogen source (e.g., ammonium formate, hydrazine etc.), a reaction using iron, tin chloride and the like under acidic conditions, a reaction using hydrazine and a catalytic amount of ferric chloride in the presence of activated carbon, and the like.

[Production Method 2 of compound (1)]

A general production method of compound (1) wherein Ar is (II), (III) or (IV), from among the compounds of the formula (I), includes, for example, inducing carboxylic acid of compound (30a), (30b) or (30c) to compound (31a), (31b) or (31c) by a rearrangement reaction and performing deprotection to give compound (29a), (29b) or (29c).

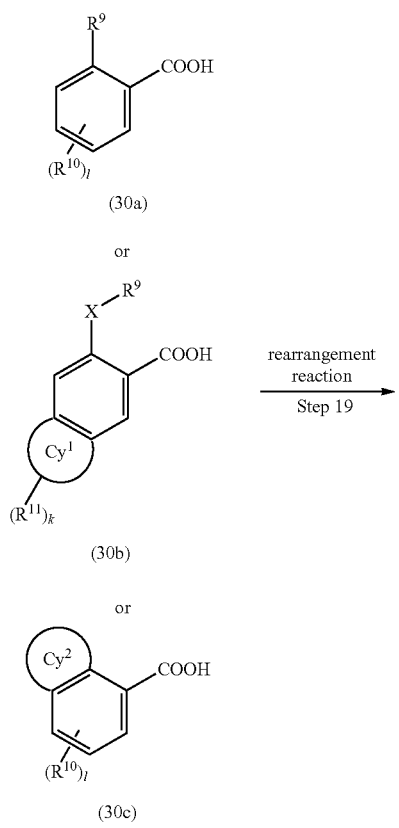

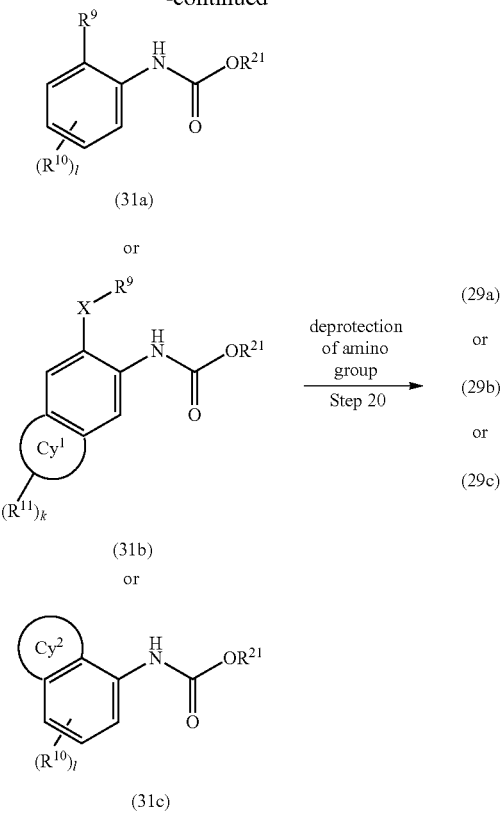

wherein $R^9$, $R^{10}$, $R^{11}$, $R^{21}$, k, l, X, $Cy^1$ and $Cy^2$ are as defined above.

Step 19 (Rearrangement Reaction)

In this step, carboxylic acid is converted to an amino group protected by a carbamate group by a rearrangement reaction, and the synthesis can be performed according to a known method, for example, the method described in Comprehensive Organic Transformations $3^{rd}$ edition page 867-869 VCH Publishers Inc. 1999, and the like, or a method analogous thereto. For example, a method including converting carboxylic acid to an aminocarbonyl group and leading same to an amino group by Hofmann rearrangement, Curtius rearrangement including converting carboxylic acid to acid azide, converting same to an amino group, or converting same to a carbamate group by using diphenylphosphoryl azide (hereinafter to be referred to as DPPA), and the like can be mentioned. In the Curtius rearrangement reaction using DPAA, by using tert-butanol as a solvent to be used, an amino group can be obtained with protection by a tert-butoxycarbonyl group which is a general protecting group for an amino group ($R^{21}$=tert-butyl).

Step 20 (Deprotection Reaction)

In this step, deprotection of carbamate group, which is an amino-protecting group, can be performed according to a known method, for example, the method described in "Protective Groups in Organic Synthesis (third edition) page 503-550".

[Production Method 3 of Compound (1)]

A general production method of compound (1) wherein Ar is (III) and X is an oxygen atom or a sulfur atom, from among the compounds of the formula (I), includes, for example, reacting compound (32b) and compound (33) under basic conditions (Step 21) to give compound (34), and reducing the nitro group to convert same to an amino group to give compound (35) (Step 22).

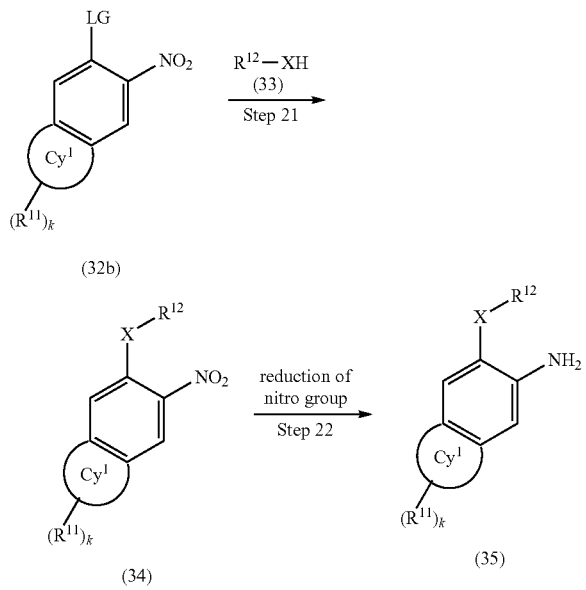

(32b)

(34)

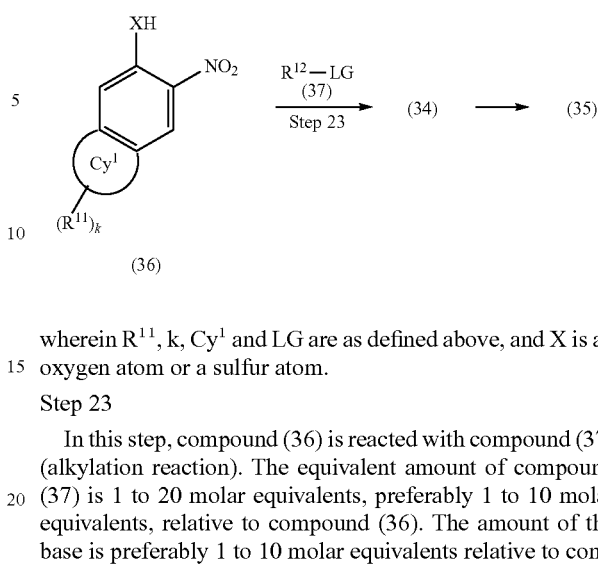

(36)

wherein $R^{11}$, k, $Cy^1$ and LG are as defined above, and X is an oxygen atom or a sulfur atom.

Step 23

In this step, compound (36) is reacted with compound (37) (alkylation reaction). The equivalent amount of compound (37) is 1 to 20 molar equivalents, preferably 1 to 10 molar equivalents, relative to compound (36). The amount of the base is preferably 1 to 10 molar equivalents relative to compound (36). The base and solvent to be used are similar to those described in Step 21.

[Production Method 5 of Compound (1)]

A general production method of compound (1) wherein Ar is (III) and X is an oxygen atom or a sulfur atom, from among the compounds of the formula (I), includes, for example, preferentially reacting compound (37) under basic conditions with a functional, XH group contained in compound (38) (Step 24) to give compound (35).

wherein $R^{11}$, $R^{12}$, k and $Cy^1$ are as defined above, X is an oxygen atom or a sulfur atom, LG is a leaving group (e.g., a halogen atom or —$OSO_2R^{22}$), and $R^{22}$ is a $C_{1-4}$ alkyl group, a $C_{1-4}$ haloalkyl group or an aryl group.

Step 21

This step is generally performed in an inert solvent in the presence of a base. The equivalent amount of compound (33) is 1 to 100 molar equivalents, preferably 1 to 10 molar equivalents, relative to compound (32b). As the base, alkali metal carbonates such as potassium carbonate, sodium carbonate, cesium carbonate and the like, alkali metal alkoxides such as sodium methoxide, sodium ethoxide, potassium tertiary butoxide and the like, alkali metal hydroxides such as potassium hydroxide, sodium hydroxide, lithium hydroxide and the like, metal hydrides such as potassium hydride, sodium hydride and the like, amines such as triethylamine, N,N-diisopropylethylamine, N-methylmorpholine, pyridine, 4-dimethylaminopyridine, DBU and the like, and the like can be used. The amount of the base to be used is preferably 1 to 10 molar equivalents relative to compound (33). The reaction can be generally performed at −50° C.-200° C., preferably −20° C. to 150° C. As the inert solvent, ethers such as diethyl ether, tetrahydrofuran, 1,4-dioxane and the like, halogenated hydrocarbons such as chloroform, dichloromethane, dichloroethane and the like, hydrocarbons such as hexane, benzene, toluene and the like, amides such as N,N-dimethylformamide, N-methylpyrrolidone and the like, sulfoxides such as dimethyl sulfoxide and the like, nitriles such as acetonitrile and the like, and the like can be used. These solvents may be mixed at an appropriate rate and used.

Step 22 (Reduction of Nitro Group)

In this step, the nitro group is reduced to an amino group, which can be performed in the same manner as in Step 18.

[Production Method 4 of Compound (1)]

A general production method of compound (1) wherein Ar is (III) and X is an oxygen atom or a sulfur atom, from among the compounds of the formula (I), includes, for example, reacting compound (36) with compound (37) under basic conditions to give compound (34) (Step 23), and thereafter obtaining compound (35) by the method of Step 22.

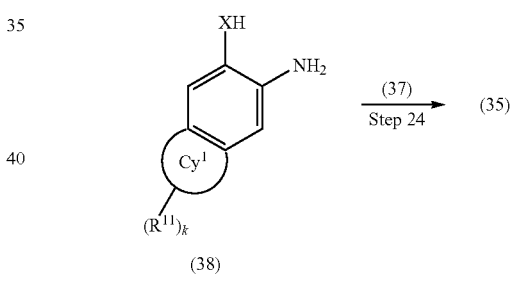

(38)

wherein $R^{11}$, k and $Cy^1$ are as defined above, and X is an oxygen atom or a sulfur atom.

Step 24

In this step, compound (35) is synthesized by reacting a functional XH group wherein X is an oxygen or sulfur atom contained in compound (38) with compound (37). The equivalent amount of compound (37) is 1 to 2 equivalents, preferably 1-1.5 equivalents, relative to compound (38). The reaction solvent and base are similar to those described in Step 21.

[Production Method 6 of Compound (1)]

A general production method of compound (1) wherein Ar is (III) and X is an oxygen atom or sulfur atom, from among the compounds of the formula (I), includes, for example, reacting compound (39) with compound (37) under basic conditions to give compound (40) (Step 25), hydrolyzing ester (Step 26), and converting the carboxyl group to an amino group by a rearrangement reaction to give compound (35) (Steps 27 and 28).

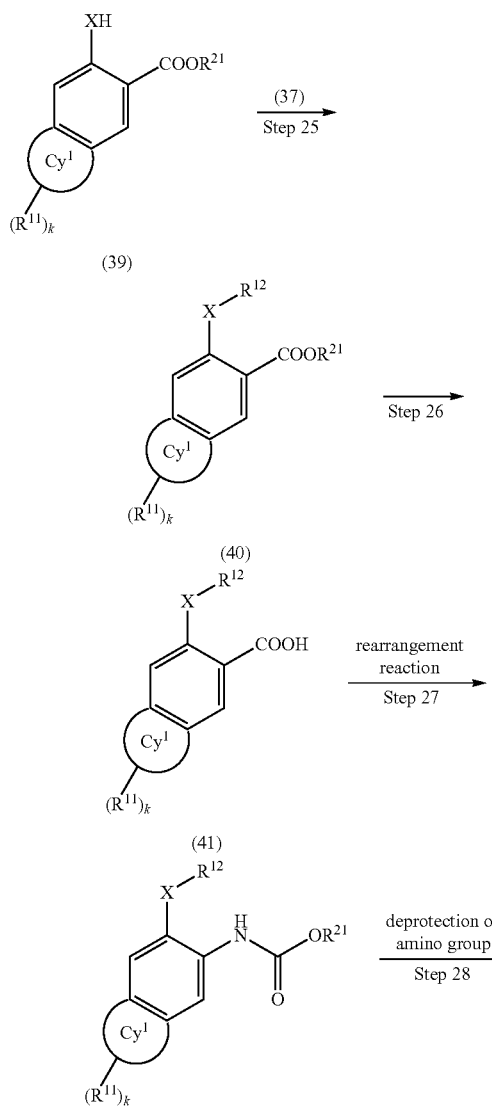

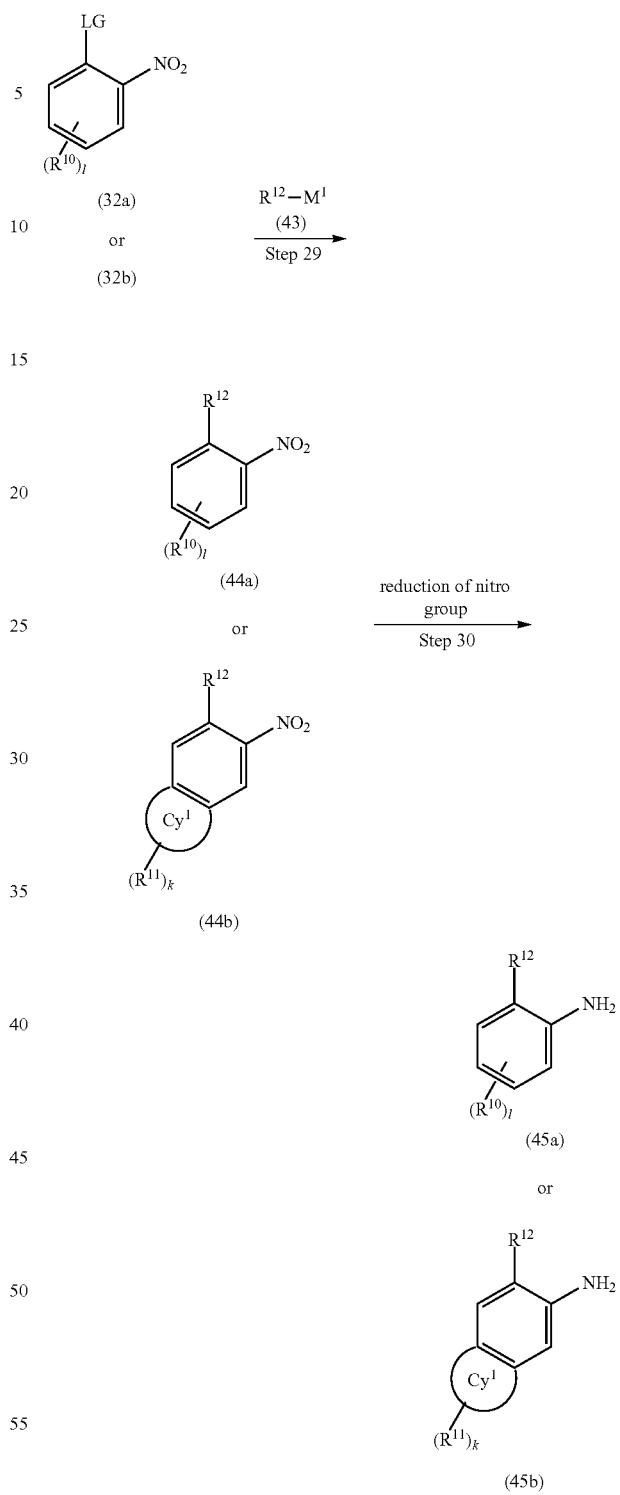

wherein. $R^{11}$, $R^{12}$, $R^{21}$, k and $Cy^1$ are as defined above, and X is an oxygen atom or a sulfur atom.

Step 25

This step can be performed in the same manner as in Step 23.

Step 26

This step is ester hydrolysis which can be performed in the same manner as in Step 2.

Step 27, 28

In this step, carboxylic acid is converted to an amino group by a rearrangement reaction, which can be performed in the same manner as in Steps 19 and 20.

[Production Method 7 of Compound (1)]

A general production method of compound (1) wherein Ar is (II) or (III), $R^9$ is $R^{12}$, and X is a "bond", from among the compounds of the formula (I), includes, for example, cross-coupling reaction of compound (32a) or (32b) with compound (43) to give compound (44a) or (44b) (Step 29), and reducing the nitro group to give compound (45a) or (45b) (Step 30).

wherein $R^{10}$, $R^{11}$, $R^{12}$, k, l, $Cy^1$ and LG are as defined above, and $M^1$ is an atom group (e.g., groups of atoms bound by boron, tin etc. and the like) permitting a cross-coupling reaction.

Step 29

In this step, compound (44a) or (44b) is produced by subjecting compound (32a) or (32b) and compound (43) to a cross-coupling reaction (e.g., Suzuki coupling reaction, Stille coupling reaction, etc.) in the presence of a metal catalyst. This reaction can be generally performed in an inert solvent in the presence of a metal catalyst. In this case, a base may be added. Examples of the metal catalyst include zero-valent palladium, divalent palladium, zero-valent nickel and the like. Here, examples of the zero-valent palladium catalyst include tetrakis(triphenylphosphine)palladium, tris(dibenzylideneacetone)dipalladium and the like. Examples of the divalent palladium catalyst include palladium acetate, dichlorobis(triphenylphosphine)palladium, dichlorobis(tricyclohexylphosphine)palladium and the like. Examples of the zero-valent nickel catalyst include 1,1'-bis(diphenylphosphino)ferrocene nickel and the like. Monodentate ligand such as triphenylphosphine, tris(ortho-tolyl)phosphine and the like, didentate ligand such as diphenylphosphinopropane, diphenylphosphinobutane and the like and the like may be added. Examples of the base include alkali metal hydrogen carbonates such as sodium hydrogen carbonate and the like, alkali metal carbonates such as sodium carbonate, potassium carbonate, cesium carbonate and the like, alkali metal phosphates such as tripotassium phosphate and the like and the like. When $M^1$ in compound (43) is an atom group bound by tin, a base is not necessarily used. The amount of the metal catalyst to be used is, for example, 0.001 to 1 equivalent, preferably 0.01 to 0.5 equivalent, relative to compound (32a) or (32b). The amount of the base to be used is 1 to 20 equivalents, preferably 1 to 10 equivalents, relative to compound (32a) or (32b). The reaction temperature can be generally from room temperature to the refluxing temperature of the solvent. As the inert solvent, alcohols such as methanol, ethanol, isopropanol, tert-butanol and the like, ethers such as tetrahydrofuran, 1,4-dioxane and the like, esters such as ethyl acetate and the like, halogenated hydrocarbons such as dichloromethane, chloroform, dichloroethane, carbon tetrachloride and the like, hydrocarbons such as hexane, benzene, toluene, xylene and the like, amides such as N,N-dimethylformamide, N-methylpyrrolidone, N,N-dimethylacetamide and the like, nitriles such as acetonitrile and the like, sulfoxides such as dimethyl sulfoxide and the like, water and the like can be used. These may be mixed at an appropriate rate and used. In addition, when $M^1$ in compound (43) is an atom group containing tin, the reaction is preferably performed in a non-aqueous solvent. The amount of compound (43) to be used is, for example, 1 to 10 equivalents, preferably 1 to 3 equivalents, relative to compound (32a) or (32b).

Step 30

In this step, a reduction reaction of the nitro group can be performed in the same manner as in Step 18.

[Production Method 8 of Compound (1)]

A general production method of compound (1) wherein Ar is (II) or (III), $R^9$ is $R^{12}$, and X is "bond", from among the compounds of the formula (I), includes, for example, cross-coupling reaction of compound (46a) or (46b) with compound (43) to give compound (45a) or (45b) (Step 31).

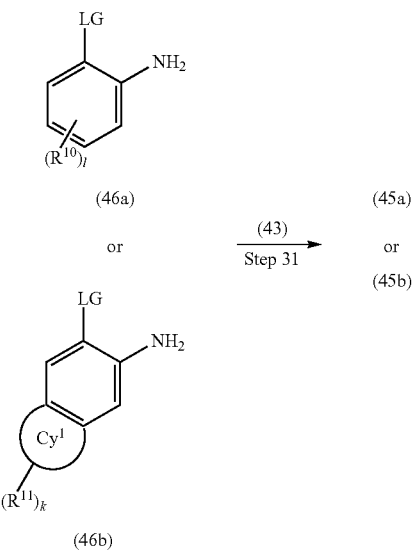

wherein $R^{10}$, $R^{11}$, k, l, $Cy^1$ and LG are as defined above.

Step 31

In this step, a cross-coupling reaction can be performed in the same manner as in Step 29.

In addition, the reaction can also be performed with protection of the amino group of compound (46a) or (46b), and deprotection after cross-coupling can afford compound (45a) or (45b). The amino-protecting group and deprotection method are as mentioned above.

[Production Method 9 of Compound (1)]

A general production method of compound (1) wherein Ar is (II) or (III), $R^9$ is $R^{12}$, and X is a "bond", from among the compounds of the formula (I), includes, for example, cross-coupling reaction of compound (47a) or (47b) with compound (43) to give compound (48a) or (48b) (Step 32), hydrolysis of ester (Step 33) and a rearrangement reaction of carboxylic acid to an amino group to give compound (45a) or (45b) (Steps 34 and 35).

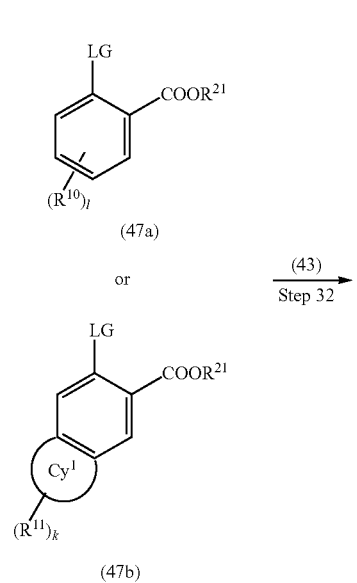

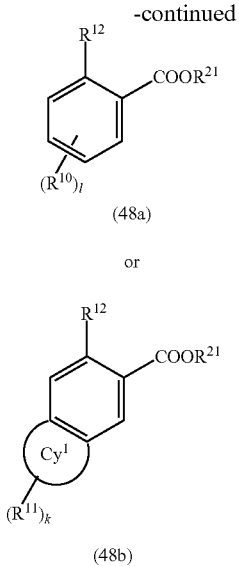

(48a)

or

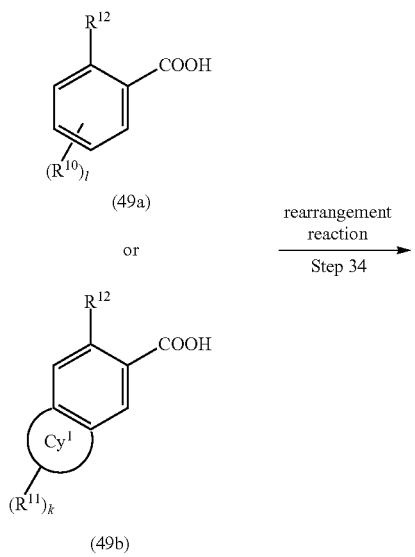

(48b)

Step 33 →

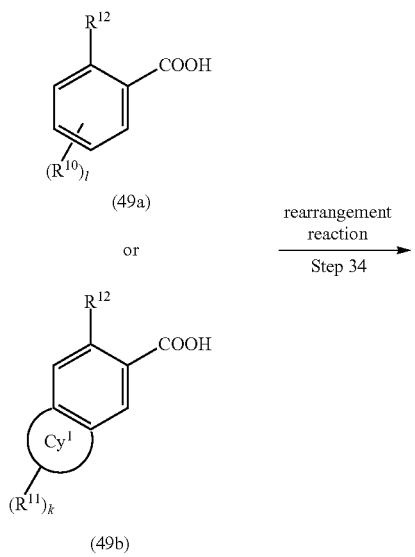

(49a)

or (49b)

rearrangement reaction
Step 34 →

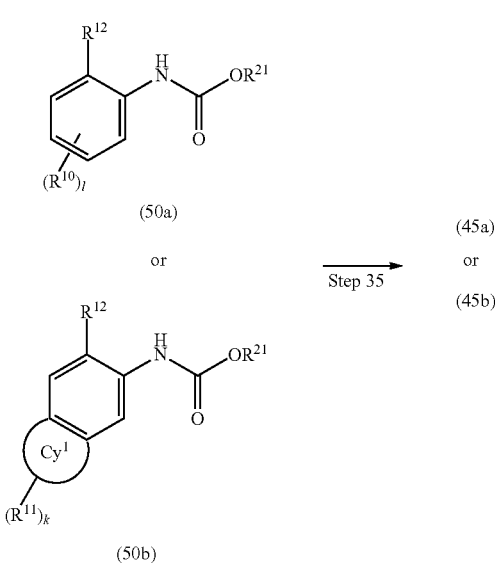

(50a)

or (50b)

Step 35 →

(45a)
or
(45b)

wherein $R^{10}$, $R^{11}$, $R^{12}$, $R^{21}$, k, l, $Cy^1$ and LG are as defined above.

Step 32

In this step, a cross-coupling reaction can be performed in the same manner as in Step 29.

Step 33

In this step, an ester hydrolysis can be performed in the same manner as in Step 2.

Step 34, 35

In this step, the carboxylic acid is converted to an amino group by a rearrangement reaction, which can be performed in the same manner as in Steps 19 and 20.

[Production Method 10 of Compound (1)]

A general production method of compound (1) wherein Ar is (III), from among the compounds of the formula (I), is shown below. A production method when Ar is (III), particularly the formula (III-1) or (III-2) shown below, is described in the following.

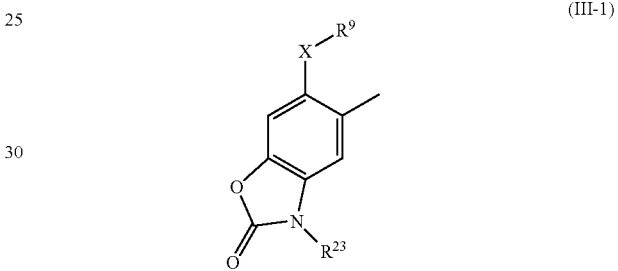

(III-1)

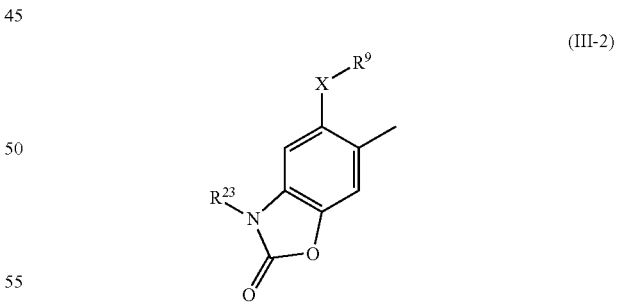

(III-2)

wherein $R^9$ and X are as defined above, and $R^{23}$ is an optionally substituted $C_{1-4}$ alkyl group.

The ortho-aminophenol derivative shown by compound (51a) or (51b) is cyclized by a known method to give a 1,3-benzoxazol-2-one derivative (Step 36). Substituent $R^{23}$ is introduced by an alkylation reaction (Step 37), which is followed by nitration (Step 38), and reduction of the nitro group to give compound (56a) or (56b) (Step 39).

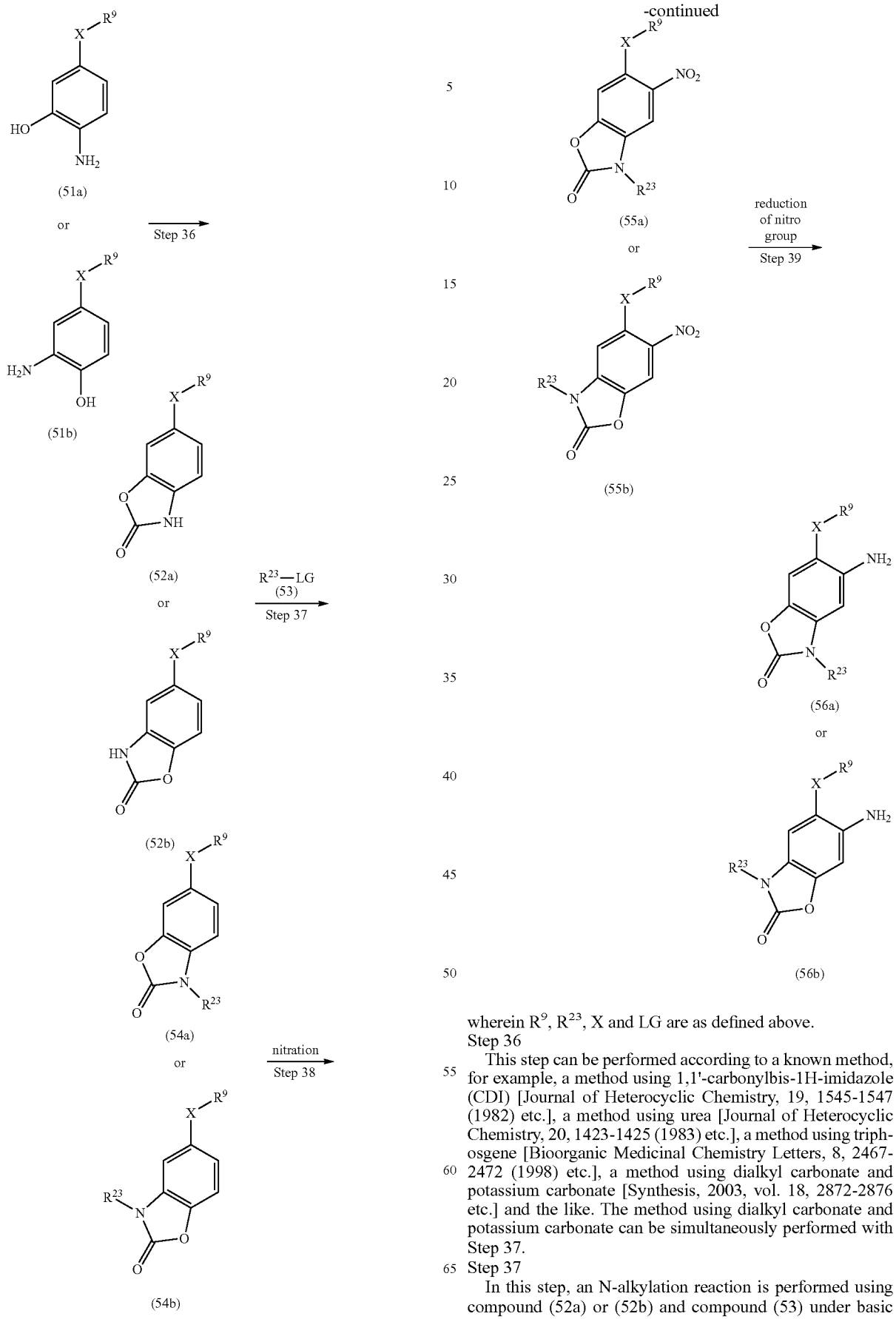

wherein $R^9$, $R^{23}$, X and LG are as defined above.

Step 36

This step can be performed according to a known method, for example, a method using 1,1'-carbonylbis-1H-imidazole (CDI) [Journal of Heterocyclic Chemistry, 19, 1545-1547 (1982) etc.], a method using urea [Journal of Heterocyclic Chemistry, 20, 1423-1425 (1983) etc.], a method using triphosgene [Bioorganic Medicinal Chemistry Letters, 8, 2467-2472 (1998) etc.], a method using dialkyl carbonate and potassium carbonate [Synthesis, 2003, vol. 18, 2872-2876 etc.] and the like. The method using dialkyl carbonate and potassium carbonate can be simultaneously performed with Step 37.

Step 37

In this step, an N-alkylation reaction is performed using compound (52a) or (52b) and compound (53) under basic conditions in an inert solvent. As the base, metal hydrides such as sodium hydride and the like, and the like are preferable. As the solvent, amides such as N,N-dimethylformamide, N-methylpyrrolidone and the like, sulfoxides such as dimethyl sulfoxide and the like, ethers such as tetrahydrofuran, 1,4-dioxane and the like are preferable. These solvents may be mixed at an appropriate rate and used. The reaction temperature is generally −20° C. to 150° C., preferably −10° C. to 100° C.

Step 38

In this step, nitration can be performed in the same manner as in Step 17.

Step 39

In this step, reduction of the nitro group to amine can be performed in the same manner as in Step 18.

[Production Method 11 of Compound (1)]

A general production method of compound (1) wherein Ar is (III), from among the compounds of the formula (I), is shown below. A production method when Ar is (III), particularly (III-3) or (III-4), is described in the following.

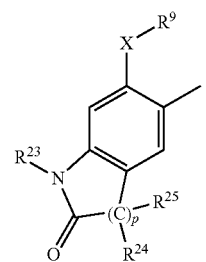
(III-3)

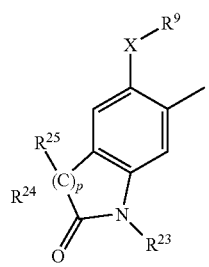
(III-4)

wherein $R^9$, $R^{23}$ and X are as defined above, $R^{24}$ and $R^{25}$ are independently selected and each is hydrogen or an optionally substituted $C_{1-4}$ alkyl group, and p is an integer of 1 to 3.

Compound (57a) or (57b) and compound (58) are subjected to an amidation reaction to give compound (59a) or (59b) (Step 41), and the resulting compound is cyclized by an intramolecular Friedel-Crafts reaction to give compound (60a) or (60b) (Step 42). The object compound (63a) or (63b) can be synthesized by the nitration reaction (Step 43), N-alkylation reaction (Step 44), and reduction reaction of the nitro group (Step 45).

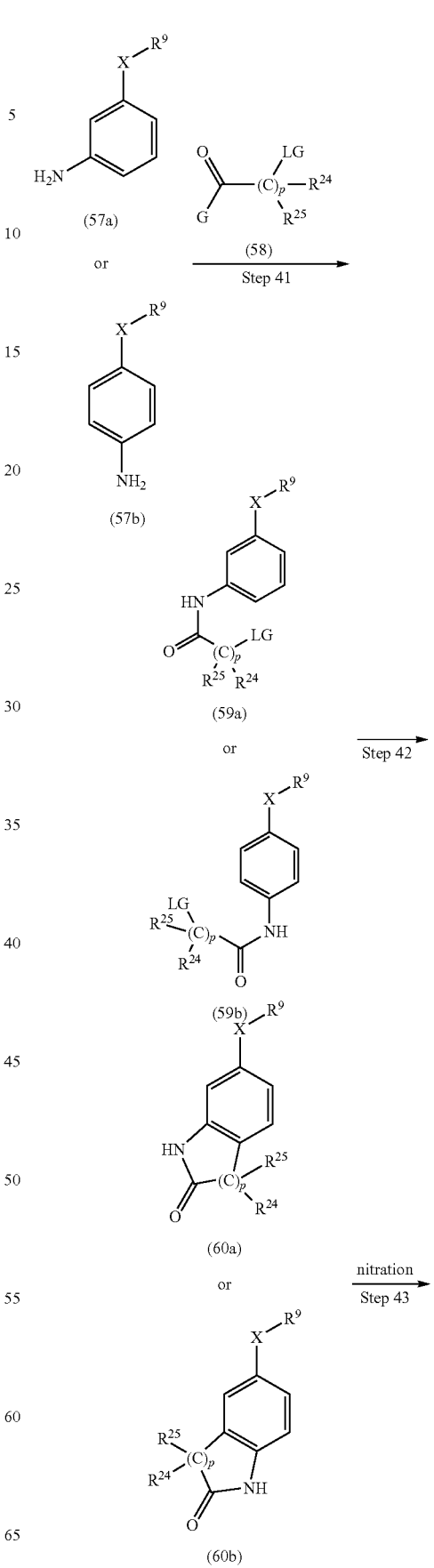

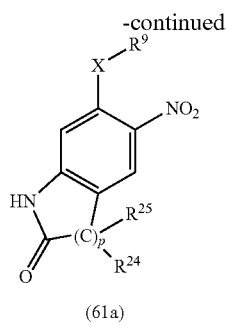

(61a)

or

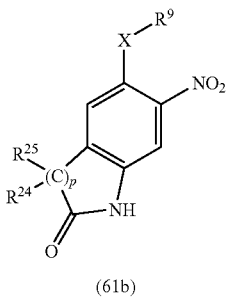

(61b)

$\xrightarrow[\text{Step 44}]{(53)}$

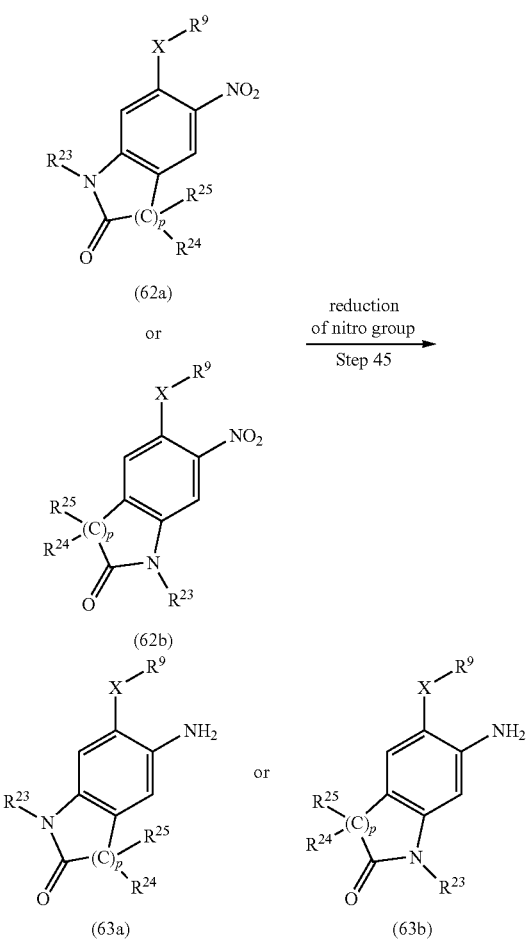

wherein $R^9$, $R^{23}$, $R^{24}$, $R^{25}$, p, G, X and LG are as defined above.

Step 41, Step 42

These steps can be performed according to a known method, for example, the methods described in Berichte der Deutschen Chemischen Geselschaft, 60, 858-867 (1927), Journal of Medicinal Chemistry, 2000, 43, 3718-3735, Journal of Medicinal Chemistry, 2004, 47, 3546-3560 and the like. Step 41 can be performed by an amidation reaction of compound (57a) or (57b) with compound (58) and in the same manner as in Step 5. Step 42 is an intramolecular Friedel-Crafts reaction and the synthesis can be performed by, for example, mixing and reacting compound (59a) or (59b) with aluminum chloride under warming. The reaction temperature is generally 80° C.-250° C.

Step 43

In this step, nitration can be performed in the same manner as in Step 17.

Step 44

In this step, an N-alkylation reaction can be performed in the same manner as in Step 37.

Step 45

In this step, a reduction reaction of the nitro group can be performed in the same manner as in Step 18.

[Production Method 12 of Compound (1)]

A production method of compound (1) when Ar is (III), particularly (III-3a) or (III-4a), from among the compounds of the formula (I), is described in the following.

wherein $R^9$, $R^{23}$ and X are as defined above.

Compound (64a) or (64b) and malonic acid are subjected to a Knoevenagel reaction, or Horner-Emmons reaction with ethyl diethylphosphonoacetate and the like to give compound (65a) or (65b) (Step 46), and an intramolecular cyclization reaction by a simultaneous reduction reaction of the nitro group and the double bond is performed to give compound (66a) or (66b) (Step 47). Hereafter, the object compound (67a) or (67b) can be synthesized by the method described in Steps 43-45 of [Production Method 11 of compound (1)].

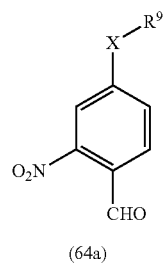

(64a)

or

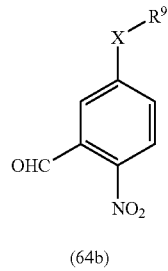

(64b)

→ Step 46

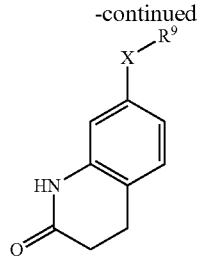

(66a)

or

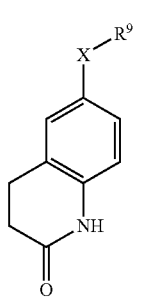

(66b)

⇒

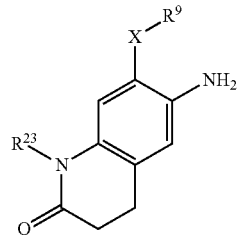

(67a)

or

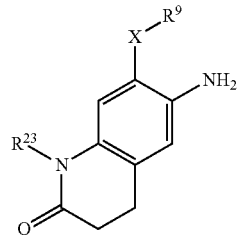

(67b)

wherein $R^9$, $R^{23}$ and X are as defined above, and $R^{26}$ is hydrogen or a $C_{1-4}$ alkyl group.

Steps 46, 47

These steps can be performed according to a known method, for example, the methods described in Berichte der Deutschen Chemischen Geselschaft, 13, 1680-1684 (1880), Journal of Medicinal Chemistry, 1987, 30, 295-303, Journal of Medicinal Chemistry, 2000, 43, 3718-3735, and the like.

Step 46 can be performed by i) Knoevenagel reaction, ii) Horner-Emmons reaction, and the like.

The synthesis method by i) includes reacting compound (64a) or (64b) with malonic acid in the presence of a catalytic amount of a base in an inert solvent. As the base, pyridine,

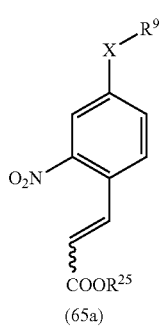

(65a)

or

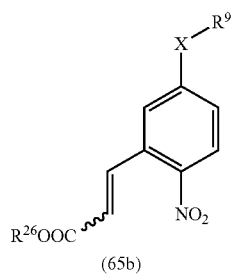

(65b)

→ Step 47 piperidine and the like are preferable. As the inert solvent, ethanol, acetic acid and the like are preferable. The reaction is generally performed at 0° C.-120° C., preferably 60° C.-100° C.

The synthesis method by ii) includes reacting compound (64a) or (64b) with ethyl or methyl diethylphosphonoacetate or the like under basic conditions in an inert solvent. As the base, alkali metal carbonates such as sodium carbonate, potassium carbonate and the like, alkali metal alkoxides such as sodium methoxide, potassium tertiary butoxide and the like, alkali metal hydroxides such as potassium hydroxide, sodium hydroxide and the like, metal hydrides such as potassium hydride, sodium hydride and the like, alkali metal amides such as potassium hexamethyldisilasane, lithium hexamethyldisilasane, lithium diisopropylamide and the like, amines such as triethylamine, N,N-diisopropylethylamine, N-methylmorpholine, pyridine, 4-dimethylaminopyridine, DBU and the like, and the like can be used. The amount of the ethyl or methyl diethylphosphonoacetateto be used is 1 to 10 equivalents, preferably 1 to 1.5 equivalents, relative to compound (64a) or (64b). The amount of the base to be used is preferably 1 to 1.5 equivalents relative to compound (64a) or (64b). The reaction can be generally performed at −80° C. to 150° C., preferably 0° C. to 100° C. As the inert solvent, ethers such as tetrahydrofuran, 1,4-dioxane and the like, hydrocarbons such as hexane, benzene, toluene and the like, amides such as N,N-dimethylformamide, N-methylpyrrolidone and the like, sulfoxides such as dimethyl sulfoxide and the like, nitriles such as acetonitrile and the like, and the like can be used. These solvents may be mixed at an appropriate rate and used.

Step 47 is an intramolecular cyclization reaction based on reduction of the nitro group and a double bond, which can be performed, for example, under a hydrogen atmosphere, using palladium-carbon as a catalyst in an inert solvent (ethanol, methanol, tetrahydrofuran etc.) at normal pressure or under pressurization at room temperature or under warming.

[Production Method 13 of Compound (1)]

A production method of compound (1) when Ar is (III), from among the compounds of the formula (I), is shown below. When Ar is (III), particularly (III-3a), compound (74) can be obtained by performing a Friedel-Crafts reaction of compound (68) with chloroacetic acid chloride to introduce a chloroacetyl group (Step 48), reacting compound (69) with pyridine (Step 49) to give a carboxylic acid form (71) by alkali decomposition (Step 50), which is followed by conversion of carboxylic acid to ester (Step 51), N-alkylation reaction (Step 52), and ester hydrolysis. Hereafter, the object compound (67a) can be obtained by the method shown in [Production Method 2 of Compound (1)]. The N-alkylation reaction of Step 52 can also be performed prior to Step 48.

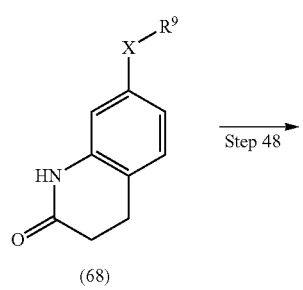

(68)

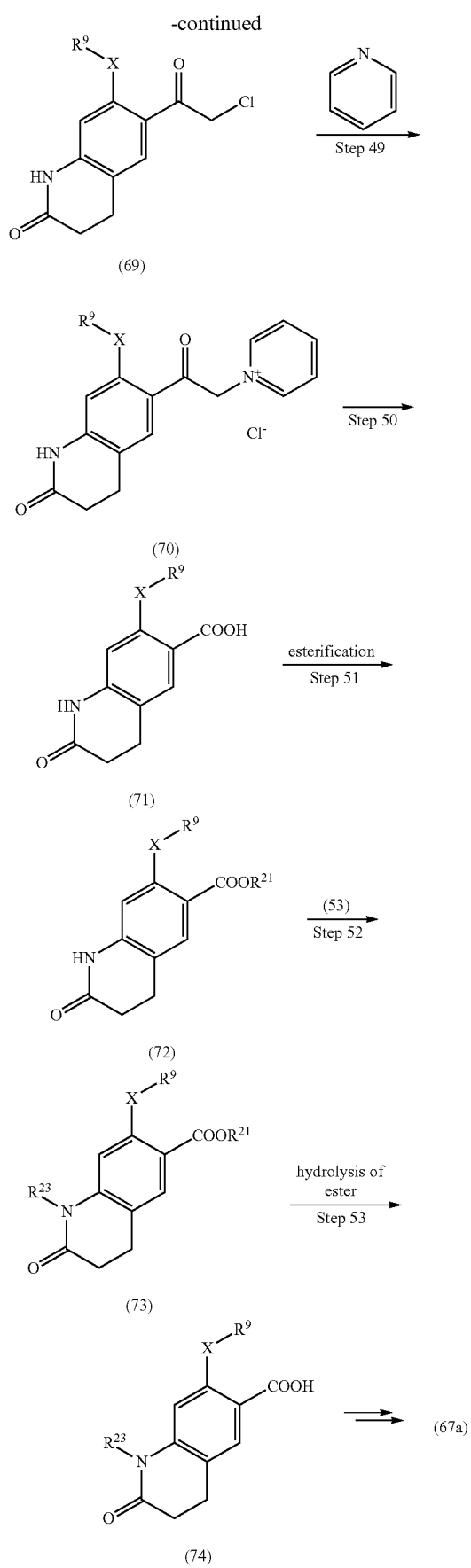

wherein R⁹, R²¹, R²³ and X are as defined above.

Steps 48, 49 and 50

These steps can be performed according to a known method, for example, the methods described in Journal of Medicinal Chemistry, 1992, 35, 620-628, Chemical & Pharmaceutical Bulletin, 1986, 34, 682-693, and the like, or a method analogous thereto.

For example, Step 48 is a reaction of compound (68) with chloroacetyl chloride in the presence of aluminum chloride in an inert solvent. The amount of chloroacetyl chloride is generally 1 to 10 equivalents, preferably 1 to 3 equivalents, relative to compound (68). The amount of aluminum chloride is generally 1 to 50 equivalents, preferably 1 to 10 equivalents, relative to compound (68). As the inert solvent, carbon disulfide and dichloromethane can be generally used. The reaction temperature is generally 0° C.-100° C., preferably from 0° C. to the refluxing temperature of the solvent. The reaction time is generally 1 hr to 24 hr, preferably 1 to 5 hr.

Step 49 can be performed by heating compound (69) in a pyridine solvent. The reaction is generally performed at 70° C.-100° C., and the reaction time is generally 1 to 5 hr.

Step 50 can be performed by treating compound (70) in the presence of alkali metal hydroxides such as sodium hydroxide, potassium hydroxide and the like in a solvent such as water and the like. The amount of the alkali metal hydroxides to be used is generally 1 to 100 equivalents, preferably 1 to 20 equivalents, relative to compound (70). The reaction is generally performed at 50° C.-100° C. The reaction time is generally 1 to 10 hr.

Step 51

In this step, an esterification reaction of carboxylic acid can be performed by a known method, for example, the method described in Protective Groups in Organic Synthesis (third edition) page 373-433.

Step 52

In this step, an N-alkylation reaction can be performed in the same manner as in Step 37.

Step 53

In this step, an ester hydrolysis can be performed in the same manner as in Step 2.

[Production Method 14 of Compound (1)]

A general production method of compound (1) wherein Ar is (III), particularly (III-5a) or (III-6b), from among the compounds of the formula (I), is shown below.

(III-5a)

(III-6a)

wherein R⁹, R²³ and X are as defined above.

A known compound (75a) or (75b), or compound (75a) or (75b) synthesized by the method described in the aforementioned "Production Methods 1, 3 and 7 of compound (1)" is acetylated to protect an amino group (Step 54), and compound (78a) or (78b) is synthesized by a Friedel-Crafts reaction (Step 55). Then, ketone is led to oxime (Step 56), which is subjected to a ring-closure reaction to give compound (80a) or (80b) (Step 57). The object compound (81a) or (81b) can be obtained by deprotection of the amino group (Step 58).

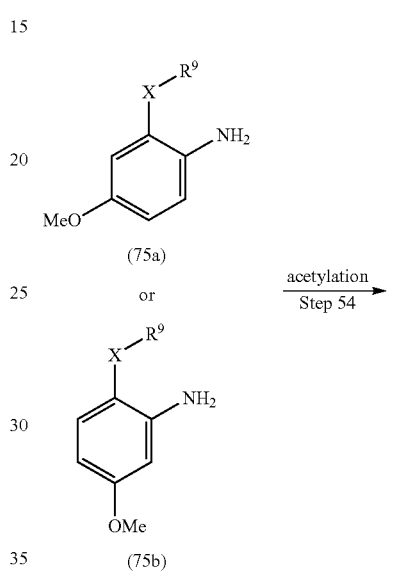

(75a)

or (75b)

acetylation
Step 54

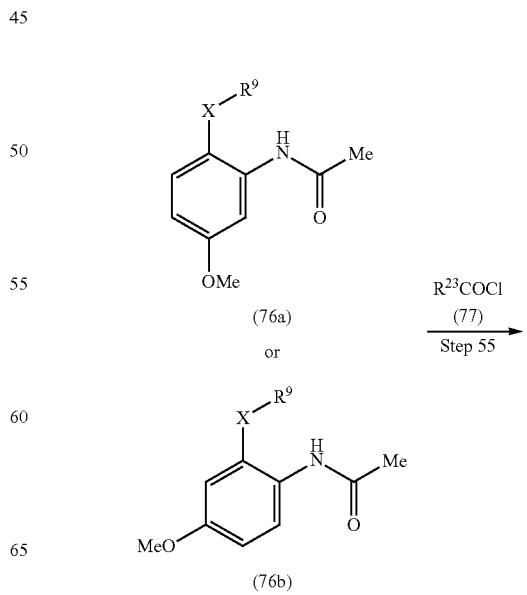

(76a)

or (76b)

R²³COCl
(77)
Step 55

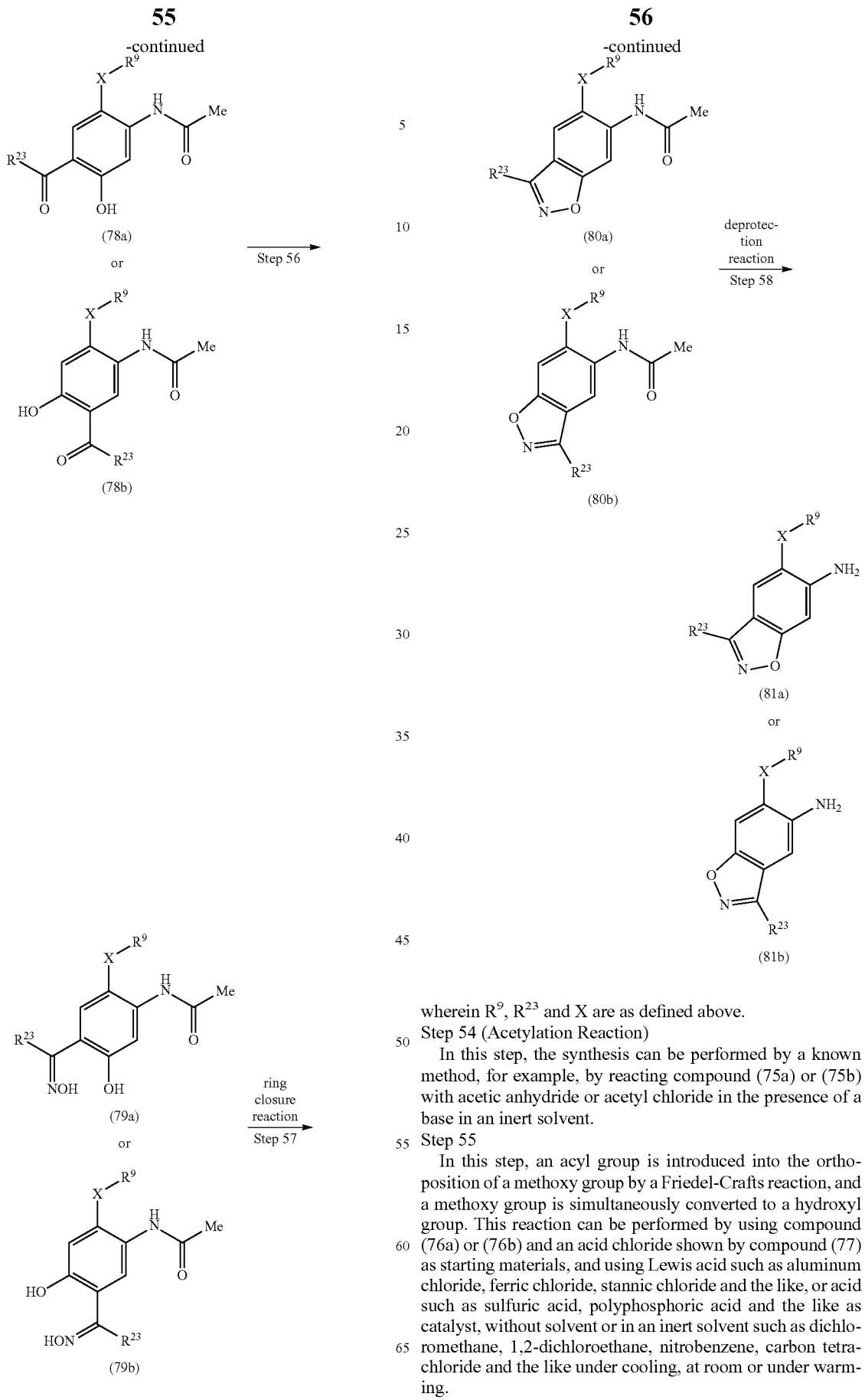

wherein $R^9$, $R^{23}$ and X are as defined above.

Step 54 (Acetylation Reaction)

In this step, the synthesis can be performed by a known method, for example, by reacting compound (75a) or (75b) with acetic anhydride or acetyl chloride in the presence of a base in an inert solvent.

Step 55

In this step, an acyl group is introduced into the ortho-position of a methoxy group by a Friedel-Crafts reaction, and a methoxy group is simultaneously converted to a hydroxyl group. This reaction can be performed by using compound (76a) or (76b) and an acid chloride shown by compound (77) as starting materials, and using Lewis acid such as aluminum chloride, ferric chloride, stannic chloride and the like, or acid such as sulfuric acid, polyphosphoric acid and the like as catalyst, without solvent or in an inert solvent such as dichloromethane, 1,2-dichloroethane, nitrobenzene, carbon tetrachloride and the like under cooling, at room or under warming.

Step 56 (Oximation Reaction)

This step can be performed by a known method, for example, in the presence of compound (78a) or (78b), hydroxylamine hydrochloride and a base (e.g., sodium acetate, potassium carbonate, sodium carbonate, sodium hydroxide, potassium hydroxide, triethylamine, pyridine etc.) to neutralize hydrochloric acid of hydroxylamine hydrochloride in an inert solvent (e.g., ethanol, methanol, water or a mixture thereof) under cooling, at room temperature to under warming.

Step 57 (Ring-Closure Reaction)

This step can be performed by a method according to a known method, for example, the intramolecular Mitsunobu reaction described in Synthetic Communications, 27 (1997) 22, 3839-3846, and the like, the method described in Journal of Medicinal Chemistry, 1995, 38, 2802-2808 and the like, that is, a method including acylating a hydroxyl group contained in the oxime group, reacting the compound in the presence of a base (e.g., sodium hydride, potassium tert-butoxide, sodium hydroxide, potassium carbonate, pyridine etc.) in an inert solvent at room temperature or under warming, and subjecting same to a ring-closure reaction, or the method described in Tetrahedron Letters, Vol. 33, No. 8, p 993-996 (1992) and the like, that is, a method including reacting compound (79a) or (79b) with N,N-dimethylformamide dimethylacetal without a solvent or in an inert solvent (e.g., toluene, 1,4-dioxane etc.) with warming (preferably 70° C.-120° C.), and the like.

Step 58

In this step, deprotection of the amino group can be performed in the same manner as in Step 6. For example, an acetyl group can be deprotected by warming compound (80a) or (80b) in diluted hydrochloric acid.

[Production Method 15 of Compound (1)]

A general production method of compound (1) wherein Ar is (III), particularly (III-5b) or (III-6b), from among the compounds of the formula (I), is shown below.

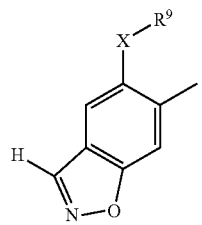
(III-5b)

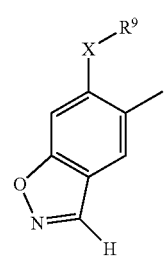
(III-6b)

wherein $R^9$ and X are as defined above.

The methoxy group of the aforementioned compound (76a) or (76b) is deprotected and converted to a hydroxyl group (Step 59), and compound (83a) or (83b) is synthesized by Duff reaction or an improved method thereof (Step 60).

The steps thereafter can be performed in the same manner as in Steps 56-58 of the aforementioned [Production Method 14 of compound (1)], whereby the object compound (84a) or (84b) can be obtained.

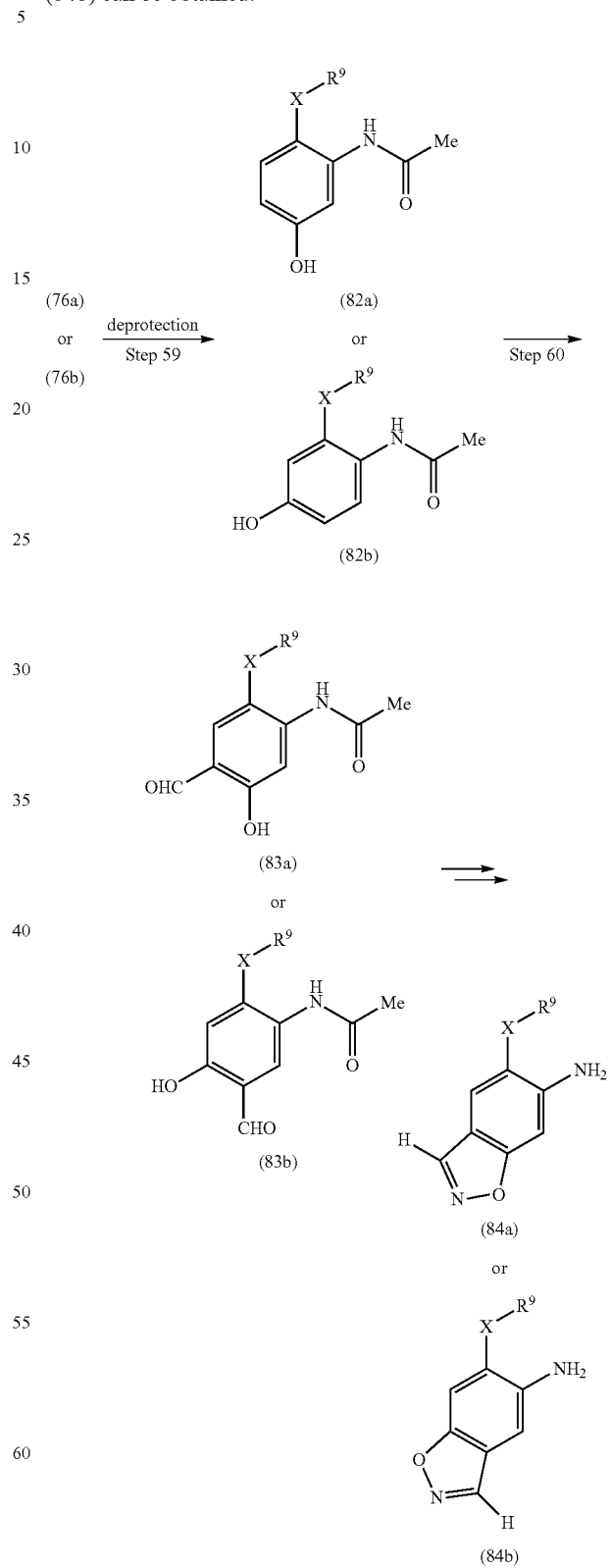

wherein $R^9$ and X are as defined above.

Step 59

This step is a conversion reaction of a methoxy group to a hydroxyl group, which can be performed according to the method described in the section of protection and deprotection of phenol in Protective Groups in Organic Synthesis (third edition) p 249-257, or a method analogous thereto. In addition, compound (82a) or (82b) can also be synthesized by using a compound containing, as a hydroxyl-protecting group, a protecting group other than a methoxy group as starting material.

Step 60

This step is a formylation reaction by a Duff reaction, which can be performed by a known method, for example, the methods described in Chemical & Pharmaceutical Bulletin, 31, 1751-1753 (1983), Synthesis, (1998) 7, 1029-1032, and the like, or a method analogous thereto. For example, the synthesis includes reacting compound (82a) or (82b) with hexamethylenetetramine in a acidic solvent (e.g., trifluoroacetic acid, methanesulfonic acid, polyphosphoric acid etc.) at room temperature or under warming.

[Production Method 16 of Compound (1)]

A general production method of compound (1) wherein Ar is (III), particularly (III-6c), from among the compounds of the formula (I), is shown below.

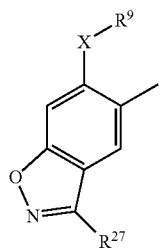

(III-6c)

wherein $R^9$ and X are as defined above, and $R^{27}$ is hydrogen or an optionally substituted $C_{1-4}$ alkyl group.

Compound (85) is acylated by a Friedel-Crafts reaction or formylated by a Duff reaction (Step 61), followed by oximation (Step 62) and a ring-closure reaction (Step 63) to synthesize compound (88), and compound (89) is obtained by nitration (Step 64). The object compound (90) can be obtained by reducing the nitro group according to a method similar to those described in [Production Methods 1, 3 and 7 of compound (1)].

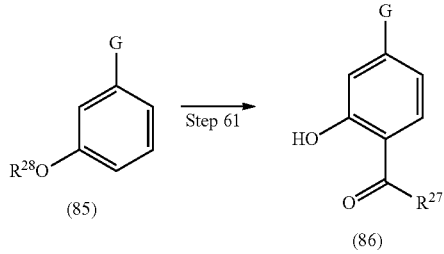

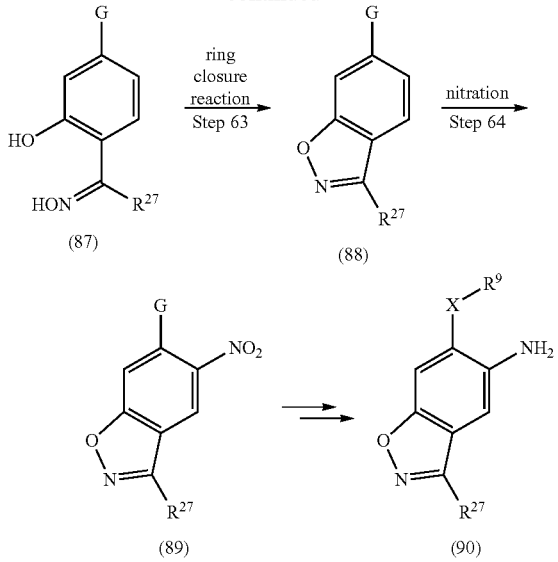

wherein $R^9$, $R^{27}$, G and X are as defined above, and $R^{28}$ is hydrogen or a methyl group.

Step 61

This step can be performed in the same manner as in the aforementioned Step 55 or Step 60.

Step 62

This step can be performed in the same manner as in the aforementioned Step 56.

Step 63

This step can be performed in the same manner as in the aforementioned Step 57.

Step 64 (Nitration)

This step can be performed in the same manner as in the aforementioned Step 17, and can be synthesized, for example, according to the methods described in Journal of the American Chemical Society, vol. 126 (2004) No. 26, 8195-8205, U.S. Pat. No. 5,484,763 and the like, or a method analogous thereto.

[Production Method 17 of Compound (1)]

A general production method of compound (1) wherein Ar is (III), from among the compounds of the formula (I), is shown below. A production method of compound (1) when Ar is (III), particularly (III-7), and $R^9$ is $R^{12}$, is described in the following.

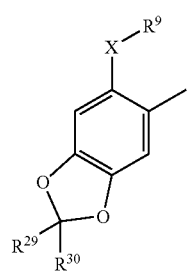

(III-7)

wherein $R^9$ is as defined above, $R^{29}$ and $R^{30}$ are independently selected and each is hydrogen or $R^{11}$, and $R^{11}$ is as defined above.

The object compound (93) can be obtained by leading compound (91) to compound (92) by a nitration reaction (Step 65), and reducing a nitro group in the same manner as in [Production Method 1 of compound (1)].

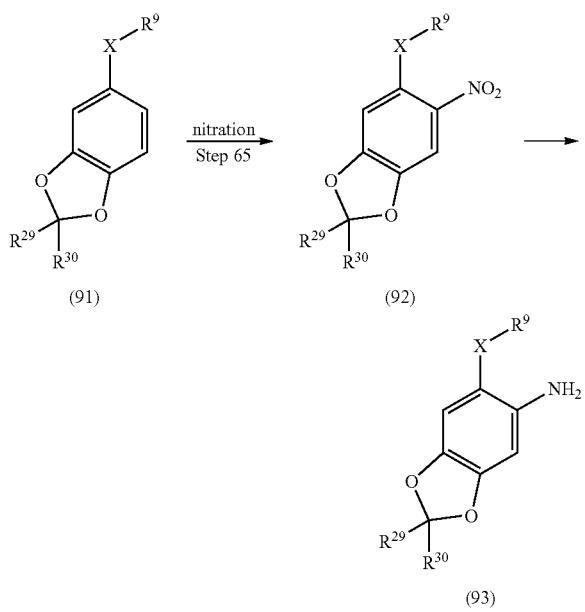

wherein $R^9$, $R^{29}$, $R^{30}$ and X are as defined above.

Step 65

In this step, nitration can be performed in the same manner as in Step 17.

[Production Method 18 of Compound (1)]

A general production method of compound (1) wherein Ar is (III), particularly (III-7), and X is a sulfur atom, from among the compounds of the formula (I), is shown below.

The object compound (97) can be obtained by reacting a known compound (94) or a compound (94) easily synthesizable by a known compound with compound (95) (Step 66) to lead to compound (96), and reducing the nitro group in the same manner as in Step 18.

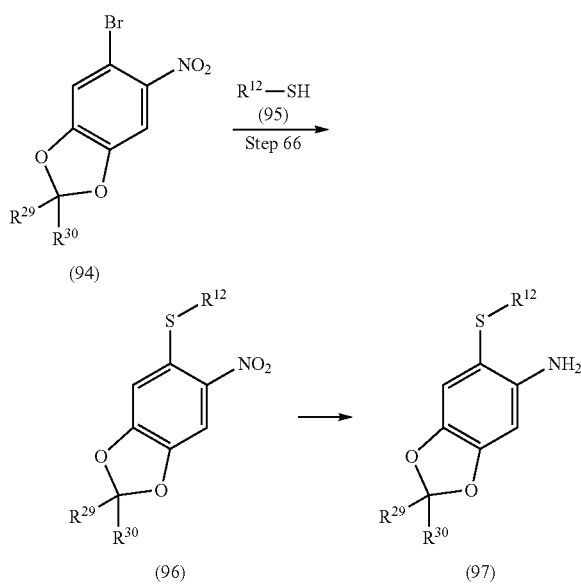

wherein $R^{12}$, $R^{29}$ and $R^{30}$ are as defined above.

Step 66

This step can be performed in the same manner as in Step 21, for example, according to the method described in Chemical & Pharmaceutical Bulletin, 42, 500-511 (1994) and the like, or a method analogous thereto. Compound (96) can be obtained by reacting, for example, compound (94) with compound (95) under basic conditions in an inert solvent at room temperature to under heating. As the base, sodium methoxide, potassium tert-butoxide, sodium hydride and the like can be used. As the inert solvent, sulfoxides such as dimethyl sulfoxide and the like, amides such as N,N-dimethylformamide and the like, and the like can be used.

[Production Method 19 of Compound (1)]

A general production method of compound (1) wherein Ar is (III), particularly (III-7), and X is an oxygen atom, from among the compounds of the formula (I), is shown below.

The object compound (100) can be obtained by subjecting a known compound (98) or a compound (98) easily synthesizable by a known method to an alkylation reaction to lead to compound (99) (Step 67), and reducing the nitro group in the same manner as in Step 18.

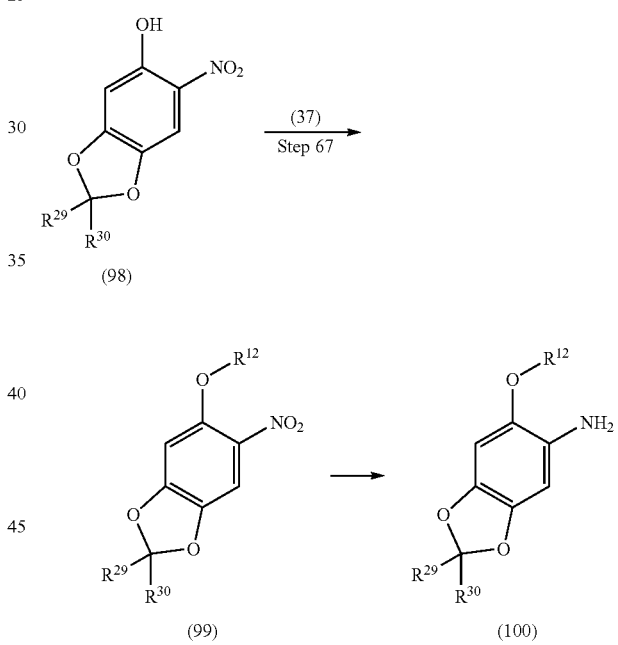

wherein $R^{12}$, $R^{29}$ and $R^{30}$ are as defined above.

Step 67

This step can be performed in the same manner as in Step 23.

[Production Method 20 of Compound (1)]

A general production method of compound (1) wherein Ar is (III), particularly (III-7), X is an oxygen atom, and $R^{12}$ is particularly an optionally substituted aryl group, from among the compounds of the formula (I), is shown below.

The object compound (104) can be obtained by subjecting a known compound (101) or a compound (101) easily synthesizable by a known method to an Ullmann reaction to lead to compound (103) (Step 68), and hereafter in the same manner as in [Production method 6 of compound (1)].

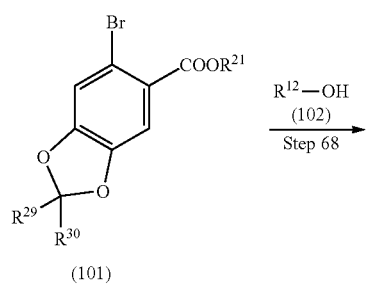

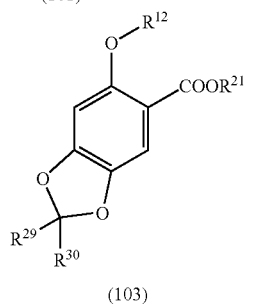

wherein $R^{21}$, $R^{29}$ and $R^{30}$ are as defined above, and $R^{12}$ is an optionally substituted aryl group.

Step 68

This step can be performed by the method described in Chemical & Pharmaceutical Bulletin, 14, 78-82 (1966) and the like, or a method analogous thereto. For example, the synthesis can be performed by warming (preferably 120° C. to 150° C.) compound (101) and compound (102) in the presence of potassium carbonate, copper and pyridine.

[Production Method 21 of Compound (1)]

A general production method of compound (1) wherein Ar is (III), particularly (III-8), X is an oxygen atom, and $R^9$ is $R^{12}$, from among the compounds of the formula (I), is shown below.

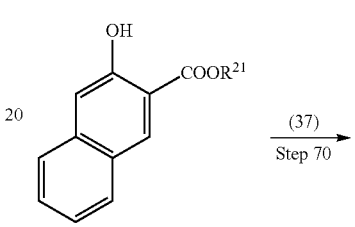

wherein $R^9$ and X are as defined above.

The object compound can be synthesized by subjecting a known compound (116) to an alkylation reaction.

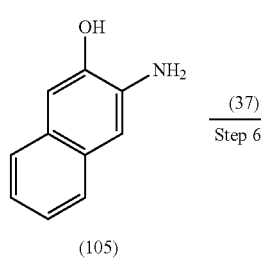

wherein $R^{12}$ is as defined above.

Step 69

This step can be performed in the same manner as in Step 24.

[Production Method 22 of Compound (1)]

A general production method of compound (1) wherein Ar is (III), particularly (III-8), X is an oxygen atom, and $R^9$ is $R^{12}$, from among the compounds of the formula (I), is shown below.

The object compound (106) can be synthesized by leading a known compound (107) to compound (108) by alkylation, and thereafter in the same manner as in [Production Method 6 of compound (1)].

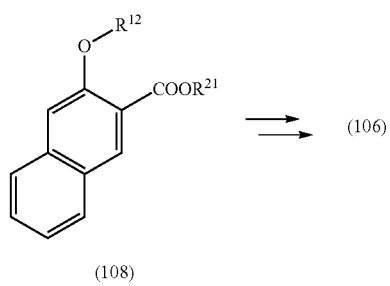

wherein $R^{12}$ and $R^{21}$ are as defined above.

Step 70

This step can be performed in the same manner as in Step 25.

[Production Method 23 of Compound (1)]

A general production method of compound (1) wherein Ar is (III), particularly (III-8), X is a "bond", and $R^9$ is a halogen atom, from among the compounds of the formula (I), is shown below.

The object compound (111) can be synthesized by diazotizing a known compound (109) and halogenating the compound to give compound (110) (Step 71), and thereafter in the same manner as in [Production Method 2 of compound (1)].

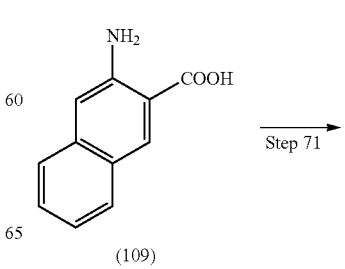

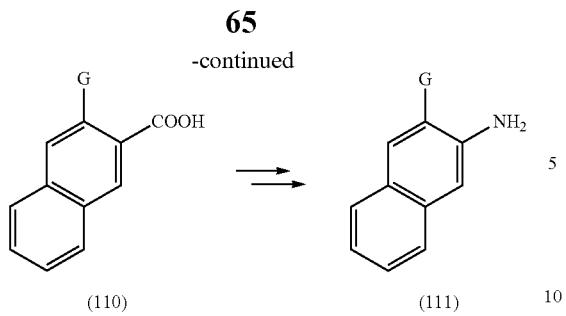

(110)    (111)

wherein G is as defined above.
Step 75

In this step, an amino group is converted to a diazonium salt with sodium nitrite by a known method such as to Sandmeyer reaction and Schiemann reaction, and converted to a halogen atom. In the Sandmeyer reaction, chlorine, bromine and an iodine atom can be introduced using copper chloride, copper bromide and copper iodide, and in the Schiemann reaction, a fluorine atom can be introduced by converting to a diazonium fluoroborate, followed by thermal decomposition. For example, when G is a fluorine atom, the method described in Bioorganic Medicinal Chemistry Letters, 12, 1651-1655 (2002) can be performed.

[Production Method 24 of Compound (1)]

A general production method of compound (1) wherein Ar is (III), particularly (III-8), X is a "bond", and $R^9$ is $R^{12}$, from among the compounds of the formula (I), is shown below.

The object compound (114) can be synthesized by subjecting a known compound (112) to a Stille coupling reaction to introduce $R^{12}$ moiety (Step 72), and thereafter treating in the same manner as in [Production Method 9 of compound (1)]. When compound (43) is an alkenyltin derivative, conversion to an alkyl group can be achieved by subjecting the double bond site contained in $R^{12}$ to a reduction reaction in an appropriate step.

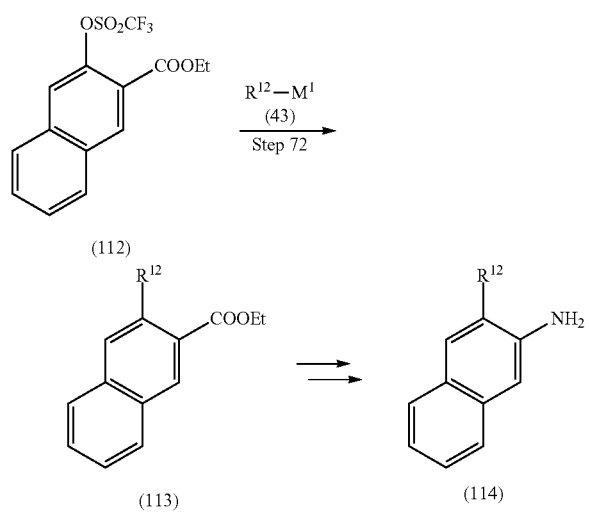

wherein $R^{12}$ and $M^1$ are as defined above.
Step 72

This step can be performed by, for example, using the compound (123) described in Bioorganic Medicinal Chemistry, 10, 779-801 (2002), and the method described therein, or a method analogous thereto. For example, compound (112) and a known compound (43) or a compound (43) easily synthesizable by a known method can be treated according to the method described in Journal of the American Chemical Society, 1987, 109, 5478-5486.

[Production Method 25 of Compound (1)]

A general production method of compound (1) wherein Ar is (III), particularly (III-9), from among the compounds of the formula (I), is shown below.

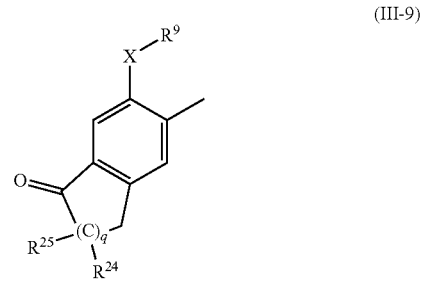

(III-9)

wherein $R^9$, $R^{24}$, $R^{25}$ and X are as defined above, and q is an integer of 1 to 3.

Compound (120) is obtained by converting a known compound (115) or a compound (115) easily synthesizable by a known method to compound (117) by a Friedel-Crafts reaction (Step 73), and by nitration of the ortho-position of substituent —$XR^9$ (Step 74), reduction of the nitro group (Step 75) and acetylation (Step 76). The object compound (123) is obtained by reducing ketone (Step 77), synthesizing compound (122) by an intramolecular Friedel-Crafts cyclization reaction (Step 78), and performing deacetylation (Step 79).

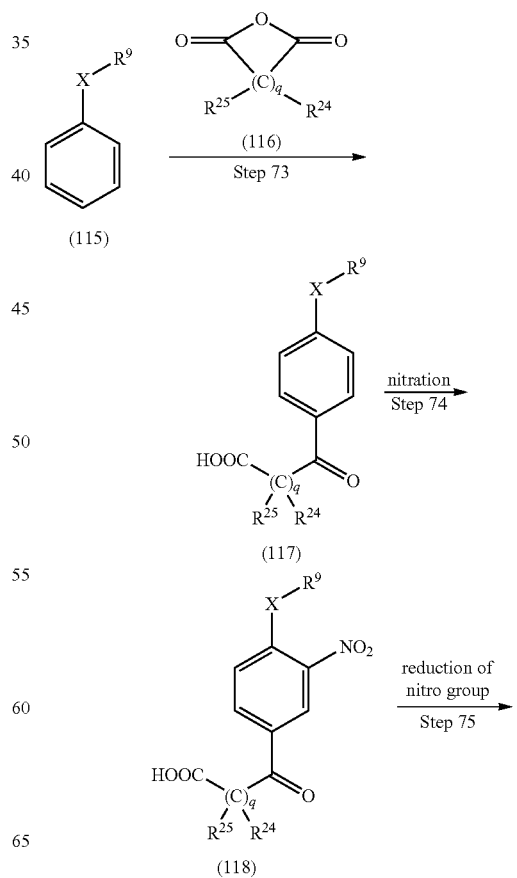

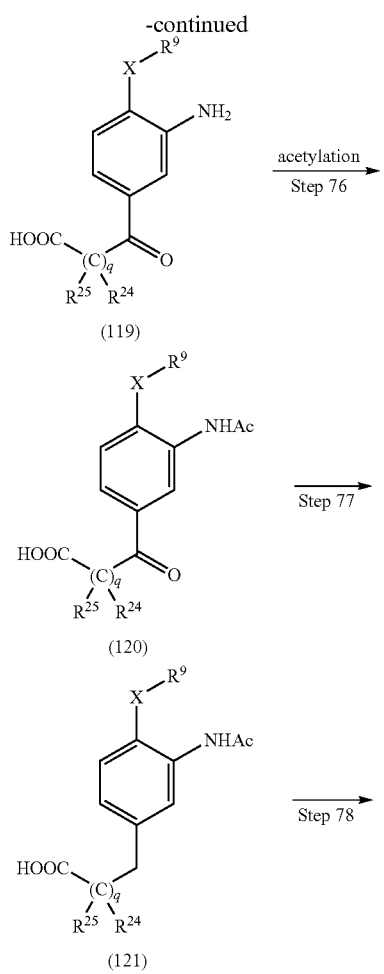

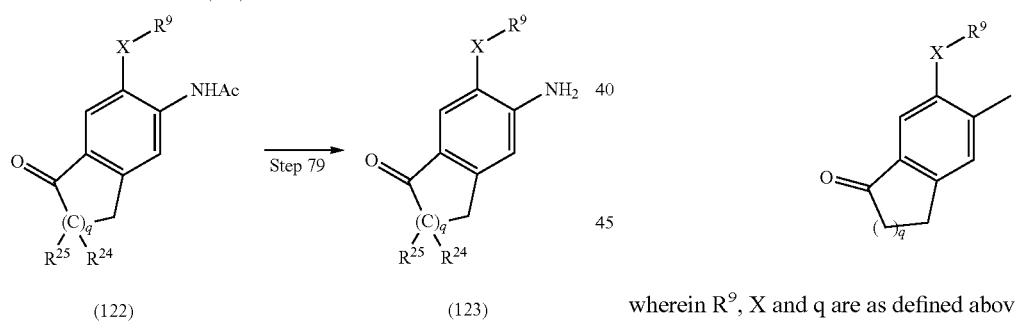

wherein $R^9$, $R^{24}$, $R^{25}$, X and q are as defined above.

Step 73

This step is a Friedel-Crafts reaction and the synthesis can be performed by, for example, the method described in Organic Synthesis collective volume II, p 81-82, or a method analogous thereto. For example, synthesis is performed by warming a mixture of compound (115) and compound (116) in the presence of aluminum chloride.

Step 74

In this step, nitration can be performed in the same manner as in Step 17.

Step 75

In this step, a reduction reaction of the nitro group can be performed in the same manner as in Step 18.

Step 76

This step is an acetylation reaction which can be performed in the same manner as in Step 54. In addition, this step can be simultaneously performed with Step 75. That is, the acetylation can be performed by reducing the nitro group in Step 75 under a hydrogen atmosphere and using palladium-carbon as a catalyst, and adding acetic anhydride to a solvent during the conversion reaction to an amino group.

Step 77

In this step, a reduction reaction of ketone can be performed, for example, under a hydrogen atmosphere using palladium-carbon as a catalyst in a solvent (for example, acetic acid) at room temperature or under warming.

Step 78

In this step, an intramolecular Friedel-Crafts cyclization reaction can be performed by a known method, for example, the method described in Journal of Organic Chemistry, 1962, 27, 70-76 and the like, the method described in Synthetic Communications, vol. 34, No. 20, 3751-3762 (2004) and the like, or a method analogous thereto. For example, a method including converting carboxylic acid contained in compound (121) to acid chloride and the like, and reacting same in the presence of aluminum chloride in an inert solvent (e.g., nitrobenzene etc.), a method including reacting same in the presence of trifluoroacetic anhydride in dichloromethane, a method including reacting same in the presence of diphosphorus pentaoxide in methanesulfonic acid, and the like can be performed.

Step 79

This step can be performed in the same manner as in Step 58.

[Production Method 26 of Compound (1)]

A general production method of compound (1) wherein Ar is (III), particularly (III-9), and $R^{24}$ and $R^{25}$ are hydrogen, from among the compounds of the formula (I), is shown below.

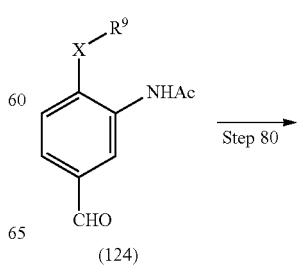

wherein $R^9$, X and q are as defined above.

Compound (126) is obtained by subjecting a known compound (124) or a compound (124) easily synthesizable by a known method to Wittig reaction and the like to lead to compound (125), and reducing the double bond site. Thereafter, the object compound (138) can be synthesized in the same manner as in [Production Method 27 of compound (1)].

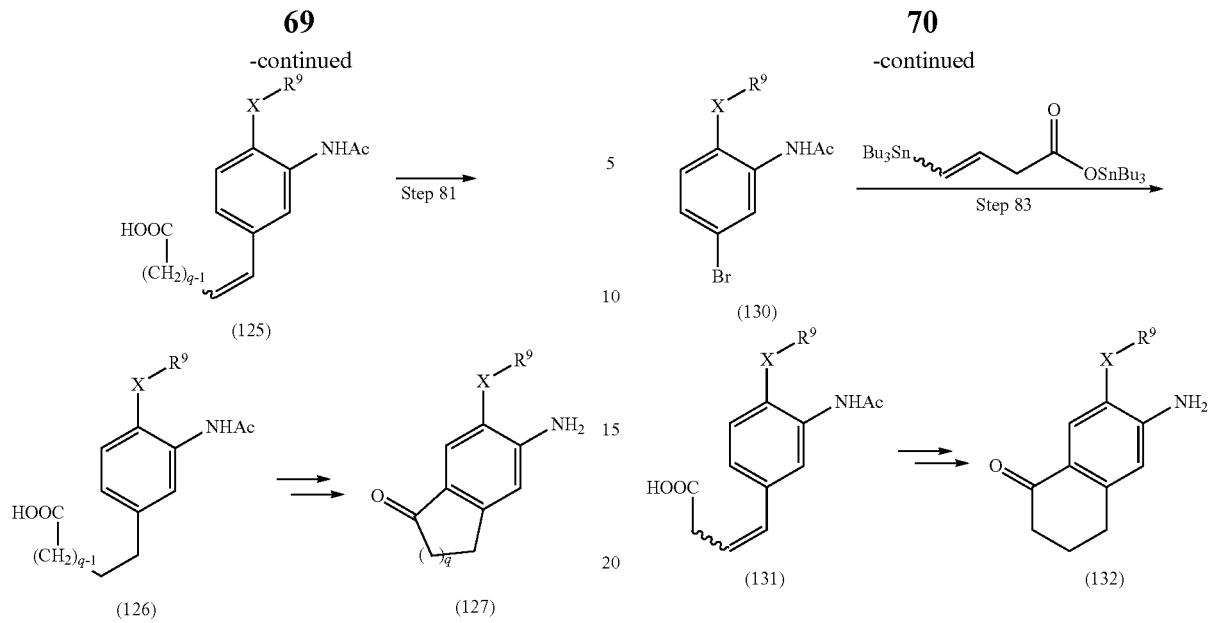

wherein $R^9$, X and q are as defined above.

Step 80

In this step, compound (125) can be synthesized by a method shown in i) of Step 46 when q is 1, that is, Knoevenagel reaction and the like, and compound (125) can be synthesized by Wittig reaction using (2-carboxyethyl)triphenylphosphonium bromide and the like when q is 2, and (3-carboxypropyl)triphenylphosphonium bromide and the like when q is 3.

Step 81

In this step, a reduction reaction of a double bond can be performed, for example, under a hydrogen atmosphere using palladium-carbon as a catalyst in an inert solvent (e.g., ethanol, methanol, tetrahydrofuran etc.) under normal pressure or under pressurization conditions at room temperature or under warming.

[Production Method 27 of Compound (1)]

A general production method of compound (1) wherein Ar is (III), particularly (III-9), $R^{24}$ and $R^{25}$ are hydrogen, and q is 2, from among the compounds of the formula (I), is shown below.

Compound (131) can be synthesized by acetylating an amino group of compound (129) easily synthesizable from known compound (128) according to the method of "Production Methods 1, 3 and 7 of compound (1)" and the like, and subjecting the compound to Stille coupling reaction with an alkenyltin derivative. Thereafter, the object compound (132) can be synthesized in the same manner as in [Production Method 27 of compound (1)].

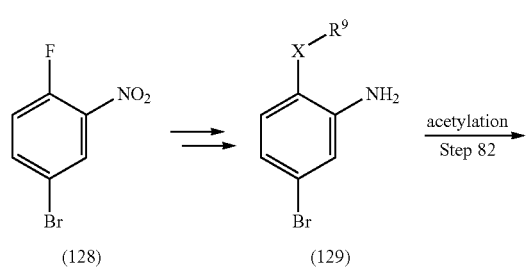

wherein $R^9$ and X are as defined above.

Step 82

This step can be performed in the same manner as in Step 54.

Step 83

This step is a Stille coupling reaction, and compound (131) can be synthesized by reacting compound (130) and an alkenyltin derivative described in Synthetic Communications, vol. 34, No. 20, pp 3751-3762, (2004) and the like using, for example, triphenylphosphinepalladium(0) as a catalyst in toluene under warming, which is followed by a treatment with hydrochloric acid, silica gel or the like.

[Production Method 28 of Compound (1)]

A general production method of compound (1) wherein Ar is (III), particularly (III-10), from among the compounds of the formula (I), is shown below.

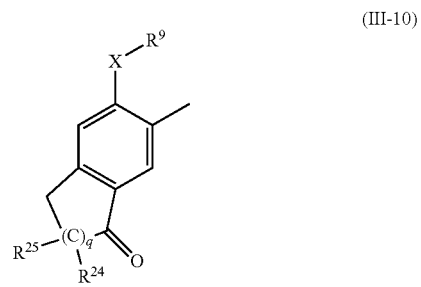

wherein $R^9$, $R^{24}$, $R^{25}$, X and q are as defined above.

Of the compounds (123) easily synthesizable by "Production methods 27, 28 and 29 of compound (1)" and the like, particularly, the amino group of a compound (133) wherein X is a "bond" and $R^9$ is hydrogen is converted to a diazonium salt, converted to a halogen atom or a hydroxyl group (Step 84), and nitrated to synthesize compound (135a) or (135b) (Step 85). Thereafter, the object compound (136) can be synthesized according to the introduction method of substituent-$XR^9$ and the reduction method of the nitro group described in [Production Methods 1, 3, 4 and 7 of compound (1)] and the like.

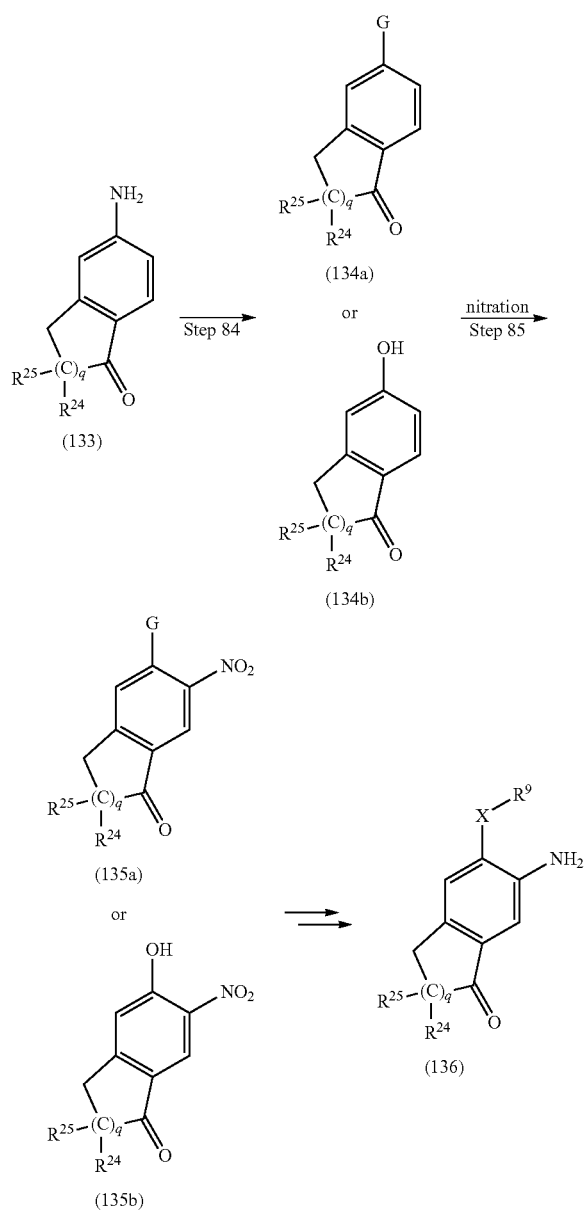

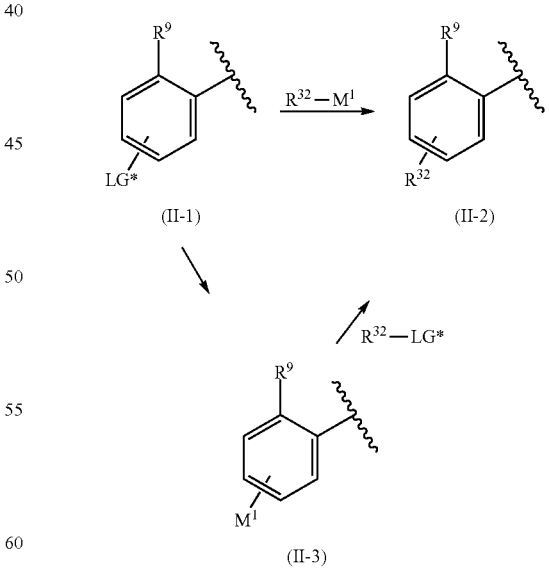

wherein $R^9$, $R^{24}$, $R^{25}$, X, G and q are as defined above.

Step 84

Synthesis in this step can be performed by a known method, for example, the methods described in Journal of Organic Chemistry, 1962, 27, 70-76, Bioorganic Medicinal Chemistry, 13, 3309-3320, (2005) and the like, or a method analogous thereto.

Step 85

This step is a nitration reaction which can be performed in the same manner as in Step 17 and, for example, synthesis can be performed according to the method described in U.S. Pat. No. 5,034,311.

[Production Method 29 of Compound (1)]

Introduction and conversion methods of substituent $R^{10}$ of a compound of the formula (I) wherein Ar is (II) or (IV) are shown below. A compound wherein a substituent of $R^{10}$ is hydrogen, a halogen atom, an alkyl group, a hydroxyl group, trifluoromethyl, a carbonyl group, a carboxyl group, an amino group, a cyano group, sulfide, sulfoxide, a sulfone group and the like can be synthesized using a known compound as a starting compound, or according to a known method, for example, the method described in Comprehensive Organic Transformations $2^{nd}$ Edition VCH Publishers Inc. 1999 and the like, or a method analogous thereto. For example, when the substituent is a halogen atom (chlorine, bromine, iodine etc.), an alkyl group, an alkenyl group, an alkynyl group, a cyano group, an aryl group, a heteroaryl group, a heterocycle group, and the like can be introduced by a cross-coupling reaction using a derivative of boron, tin and the like, and a transition metal catalyst. In addition, hydrolysis of a cyano group results in the conversion to a carboxyl group (carboxylic acid). Furthermore, conversion to an amino group can be performed by subjecting a carboxyl group to a rearrangement reaction, conversion to an aminocarbonyl group (amide) can be performed by amidation, and conversion to aldehyde can be performed by a reduction reaction. Moreover, conversion to a cyano group can be performed by subjecting an aminocarbonyl group to a dehydration reaction, and conversion to a heteroaryl group, a heterocyclic group and the like can be performed by a ring formation reaction using an aminocarbonyl group or a cyano group. In addition, conversion to a hydroxyalkyl group and further to an alkyl group can be performed by reducing a carboxyl group and a carbonyl group. Moreover, an amino group can be converted to an alkylamino group by alkylation, to a carbonylamino group or a sulfonylamino group by amidation, and to a halogen atom, a phenolic hydroxyl group or a cyano group via a diazonium salt. Furthermore, a cross-coupling reaction can also be performed after conversion of a phenolic hydroxyl group to an alkoxy group by an alkylation reaction with alkyl halide or by a Mitsunobu reaction with alkyl alcohol, and conversion of a phenolic hydroxyl group to a trifluoromethylsulfonyloxy group.

Examples of the introduction and conversion methods of the substituent $R^{10}$ include the following production methods.

wherein $R^9$ and $M^1$ are as defined above, LG* is chlorine, bromine, iodine or a triflate group, and $R^{32}$ is an aryl group, a heteroaryl group and the like.

(II-2) wherein $R^{10}$ is an aryl group, a heteroaryl group or a heterocycle group can be synthesized by a cross-coupling reaction (e.g., Suzuki coupling reaction, Stills coupling reaction etc.) using (II-1) having a halogen atom permitting a cross-coupling reaction such as chlorine, bromine, iodine and the like or a triflate group as a substituent, and compound $R^{32}$-$M^1$ which is an atom group (e.g., boron, tin, magnesium etc.) permitting a cross-coupling reaction. The reaction conditions and the like are the same as those in Step 29 of [Production Method 7 of compound (1)].

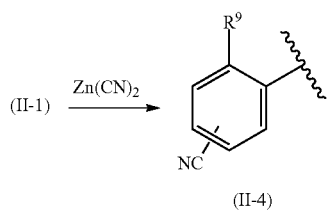

wherein $R^9$ is as defined above.

In addition, (II-4) wherein $R^{10}$ is a cyano group can be synthesized by warming (II-1) and zinc cyanide in the presence of a transition metal catalyst (e.g., tetrakistriphenylphosphinepalladium (0) etc.)

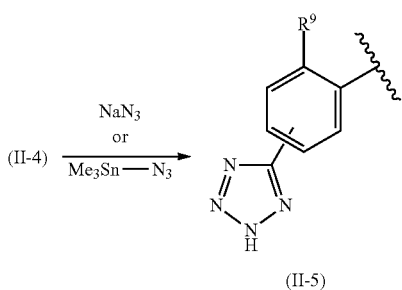

wherein $R^9$ is as defined above.

In addition, (II-4) can be converted to (II-5) wherein $R^{10}$ is a tetrazole group by using, for example, sodium azide, trimethyltin azide and the like.

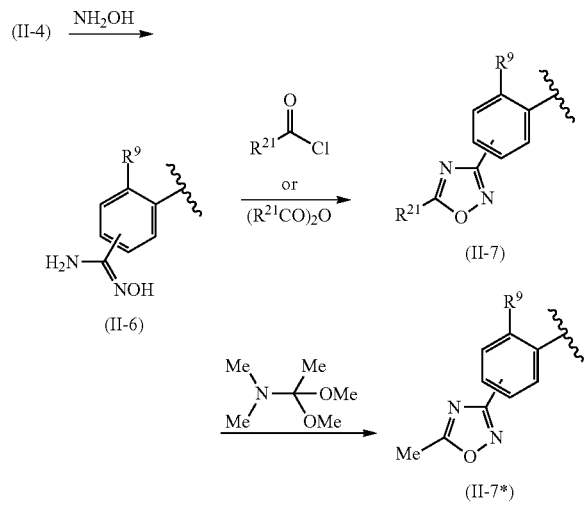

wherein $R^9$ and $R^{21}$ are as defined above.

In addition, (II-4) can be converted to (II-7) wherein $R^{10}$ is a 1,2,4-oxadiazol-3-yl group by reacting (II-4) with hydroxy- lamine or a salt thereof for conversion to (II-6), acylating the hydroxyl group, and performing a dehydrating reaction. In addition, (II-6) can also be converted to (II-7*) wherein $R^{10}$ is a 5-methyl-1,2,4-oxadiazol-3-yl group by reaction with N,N-dimethylacetamide dimethylacetal under warming.

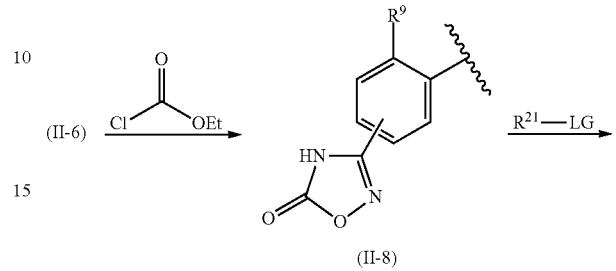

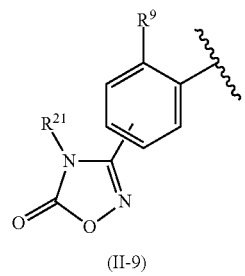

wherein $R^9$, $R^{21}$ and LG are as defined above.

In addition, (II-6) can be converted to (II-8) by reacting (II-6) with ethyl chloroformate and the like under basic conditions, and can be further converted to (II-9) by an alkylation.

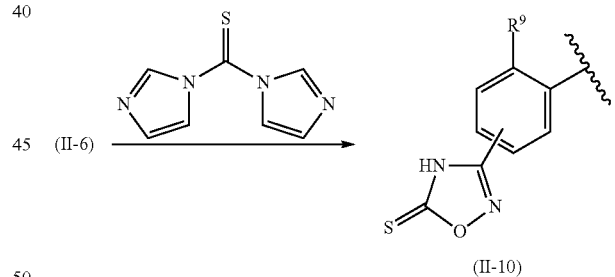

wherein $R^9$ is as defined above.

In addition, (II-6) can be converted to (II-10) by reacting (II-6) with 1,1'-thiocarbonyldiimidazole and the like.

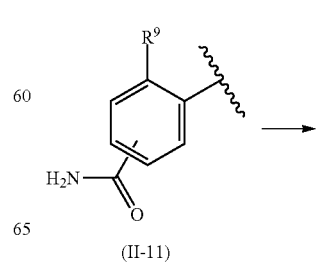

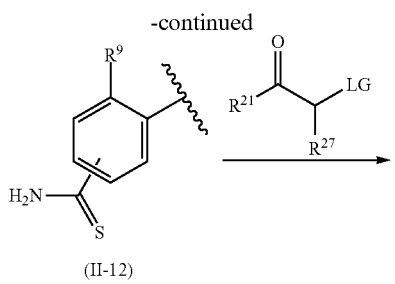

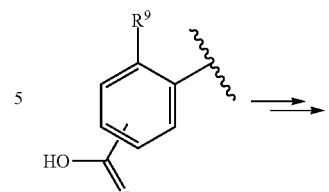

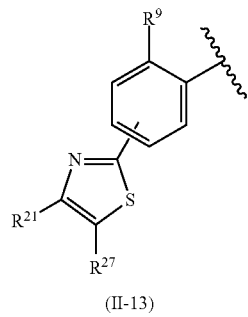

wherein R⁹, R²¹, R²⁷ and LG are as defined above.

In addition, (II-11) can be converted to an aminocarbonothioyl group to give (II-12), which can then be converted to (II-13) wherein R¹⁰ is a thiazole group.

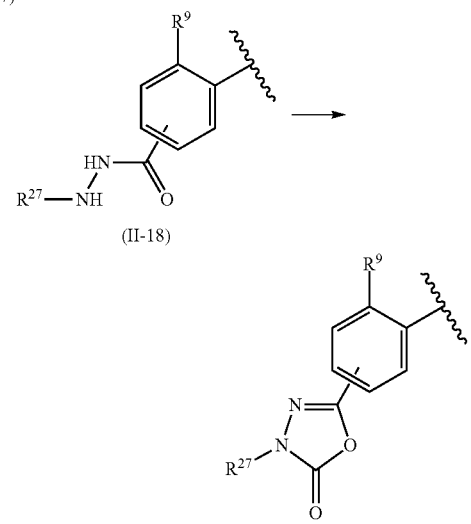

wherein R⁹ and R²⁷ are as defined above.

In addition, (II-17) can be converted to (II-19) wherein R¹⁰ is a 2-oxo-1,3,4-oxadiazole group by condensing (II-17) with a hydrazine derivative to give (II-18), which is then cyclized using triphosgene and the like.

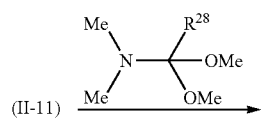

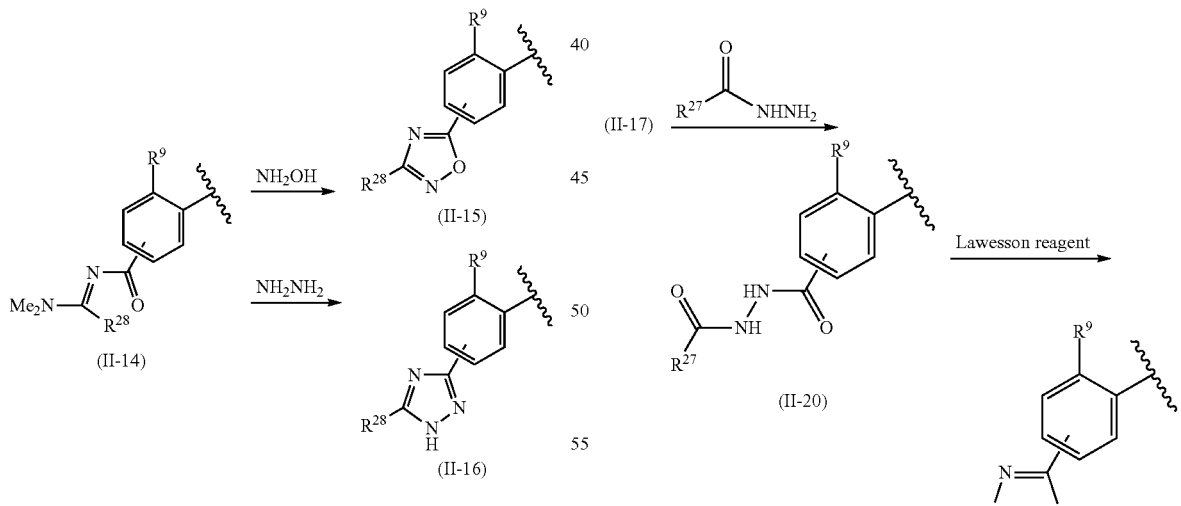

wherein R⁹ and R²⁸ are as defined above.

In addition, (II-11) can be converted to (II-15) wherein R¹⁰ is a 1,2,4-oxadiazol-5-yl group by reacting (II-11) with N,N-dimethylformamide dimethyl acetal or N,N-dimethylacetamide dimethyl acetal to give (II-14), which is then reacted with hydroxylamine or a salt thereof, and can be converted to (II-16) wherein R¹⁰ is a 1,2,4-triazol-3-yl group by a reaction with hydrazine or hydrazinium salt.

wherein R⁹ and R²⁷ are as defined above.

In addition, (II-17) can be converted to (II-21) wherein R¹⁰ is a 1,3,4-thiadiazole group by converting (II-17) to (II-20), and treating (II-20) with a Lawesson reagent and the like.

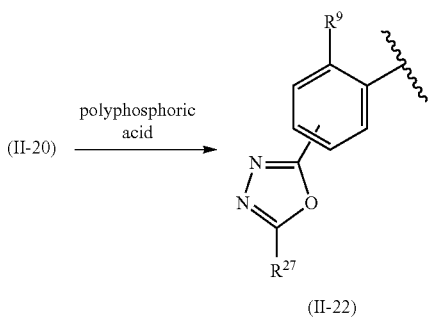

wherein $R^9$ and $R^{27}$ are as defined above.

In addition, (II-20) can be converted to (II-22) wherein $R^{10}$ is a 1,3,4-oxadiazole group using polyphosphoric acid and the like.

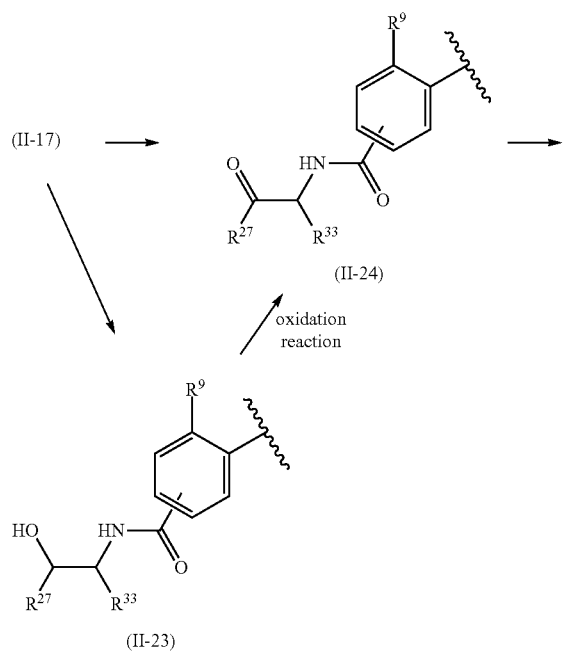

wherein $R^9$ and $R^{27}$ are as defined above, and $R^{33}$ is hydrogen or a $C_{1-4}$ alkyl group.

In addition, (II-17) can be converted to (II-25) wherein $R^{10}$ is an oxazole group by converting compound (II-17) to (II-24) directly or via (II-23), and then using phosphorus oxychloride, a Burgess reagent and the like.

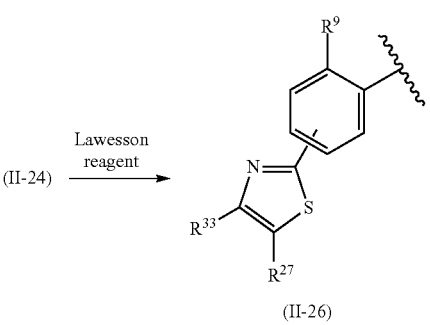

wherein $R^9$, $R^{27}$ and $R^{33}$ are as defined above.

In addition, (II-24) can be converted to (II-26) wherein $R^{10}$ is a thiazole group by using a Lawesson reagent and the like.

[Production Method 1 of Compound (6)]

An example of a general production method of starting compound (6) for introducing $—N(A)(R^1)$ which is a partial structure of the formula (I) is shown below. A is an optionally substituted aryl group, an optionally substituted aryl-$C_1$-$C_4$ alkyl group, an optionally substituted heteroaryl-$C_1$-$C_4$ alkyl group, a $C_3$-$C_6$ alkynyl group, an optionally substituted $C_3$-$C_8$ cycloalkyl group, or a group represented by (V), (VI), (VII) or (VIII).

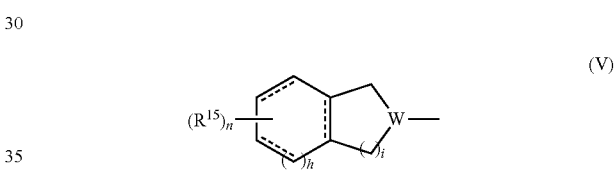

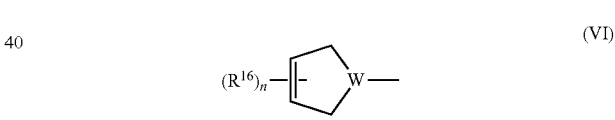

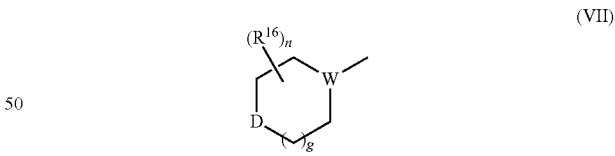

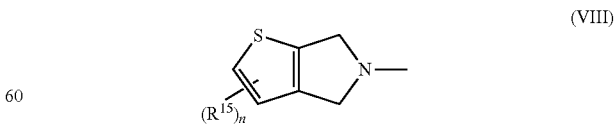

wherein $R^{15}$, $R^{16}$, W, D, h, i, g and n are as defined above.

Production methods of compounds (6a), (6b) and (6c), which are compounds (6) wherein W for A is CH and $R^1$ is a $C_1$-$C_3$ alkyl group, are shown below.

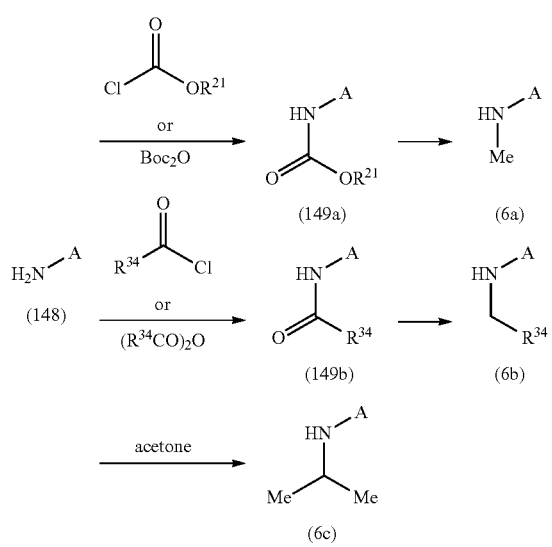

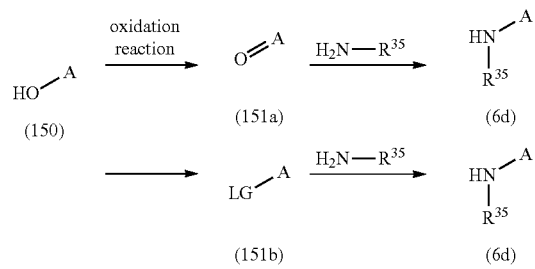

wherein A and $R^{21}$ are as defined above, and $R^{34}$ is methyl or an ethyl group.

Compound (6a) and (6b) can be obtained by converting compound (148) to an alkylcarbamate form (149a) and an amide form (149b), and converting them to an alkyl group by a reduction reaction (e.g., reduction reaction using lithium aluminum hydride etc.). Compound (6c) wherein an isopropyl group is substituted can be synthesized by subjecting compound (148) to a reductive amination reaction with acetone.

[Production Method 2 of Compound (6)]

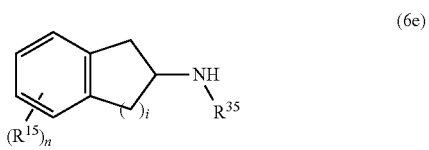

wherein A and LG are as defined above, and $R^{35}$ is a $C_1$-$C_3$ alkyl group.

A production method of compound (6d), which is compound (6) wherein $R^1$ is a $C_1$-$C_3$ alkyl group, is shown below. In compound (6d), when A is (V)-(VII), then W is =CH—.

Compound (6d) can be obtained by leading an alcohol form of compound (150) to a ketone or aldehyde form (151a) by an oxidation reaction, and then performing a reductive amination reaction. Compound (6d) can be obtained by converting compound (150) to a halogen atom (e.g., chlorine, bromine, iodine etc.) or a leaving group such as methanesulfonyloxy, paratoluenesulfonyloxy, trifluoromethanesulfonyloxy group and the like, and then performing an alkylation reaction.

[Production Method 3 of Compound (6)]

A production method of compound (6e) wherein the formula A is particularly (V), especially W is =CH—, $R^1$ is a $C_{1-3}$ alkyl group, h is 1, and the dotted line shows a double bond, is shown below.

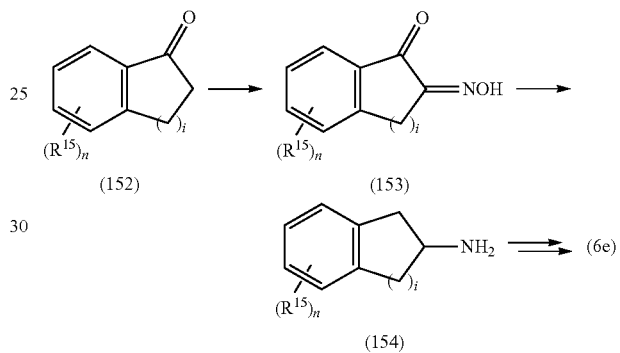

wherein $R^{15}$, $R^{35}$, i and n are as defined above.

wherein $R^{15}$, i and n are as defined above.

As a production method of compound (6e), for example, compound (6e) can be produced using compound (152) as a starting material and according to the methods described in Organic Reactions, Vol. VII, Wiley, 1966, 327-377, Journal of Medicinal Chemistry, 1982, 25, 1442-1446, Journal of Medicinal Chemistry, 2001, 44, 4716-4732, Tetrahedron Letters, Vol. 36, No. 25, 4337-4340, 1995 and the like, or a method analogous thereto. For example, compound (152) is treated with alkyl nitrite to convert the α-position of ketone to oxyimino to give compound (153), subjecting the compound to a hydrogenation reaction under pressure using a palladium catalyst to give compound (154), and thereafter performing the method of [Production Method 1 of compound (6)].

[Production Method 4 of Compound (6)]

Production methods of compound (6e*) wherein the formula A is particularly (V), especially W is =CH—, h is 1, the dotted line shows a double bond, and $R^1$ is a methyl group, and (6e**) wherein $R^1$ is an ethyl group or a propyl group, are shown below.

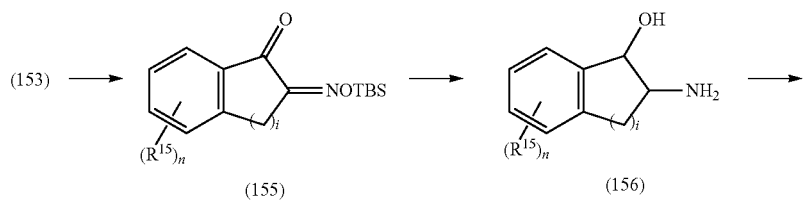

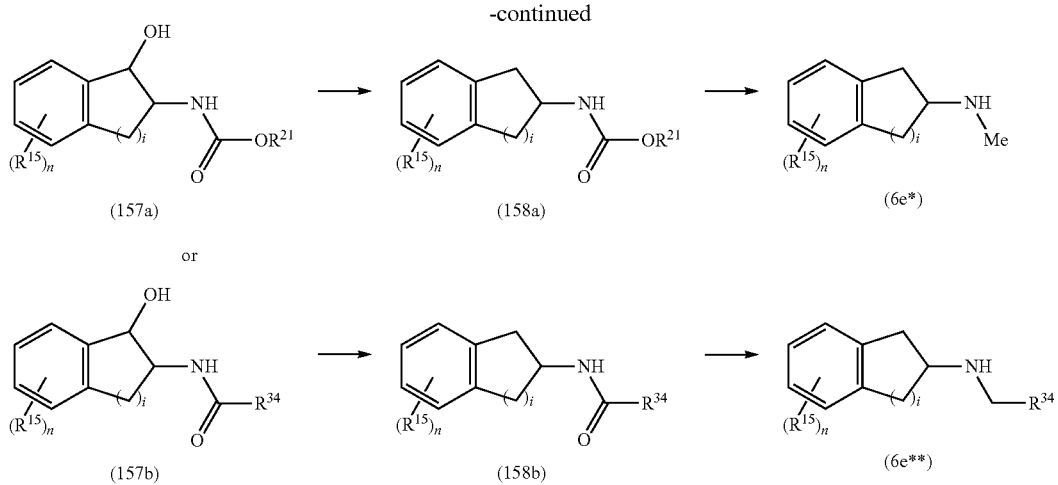

wherein $R^{15}$, $R^{21}$, $R^{34}$, i and n are as defined above.

Compounds (6e*) and (6e**) can be produced by protecting the hydroxyl group of compound (153) with a tert-butyldimethylsilyl group (TBS), performing a reduction reaction with boron to lead to compound (156), converting the amino group to a carbamate form or an amide form, reducing the hydroxyl group with triethylsilane and the like in the presence of a Lewis acid to lead to compound (158a) or (158b), and thereafter following the [Production Method 3 of compound (6)].

[Production Method 5 of Compound (6)]

When A of compound (6) is (V), (VI), (VII), or (VIII), W is $=N-$, and $R^1$ is a $C_{1-3}$ alkyl group, compound (6) is tri-substituted hydrazine (6f). An example of a general production method of tri-substituted hydrazine (6f) is shown below.

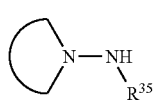

(6f)

wherein $R^{35}$ is as defined above.

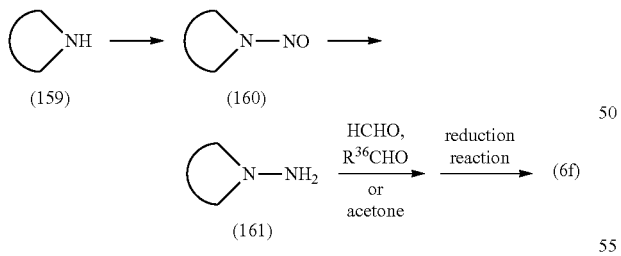

wherein $R^{35}$ is as defined above.

Secondary amine is indicated as (159) for convenience. Compound (6f) can be synthesized by reacting (159) with sodium nitrite under acidic conditions to give a nitroso form (160), reducing the nitroso group with lithium aluminum hydride, zinc, titanium trichloride or the like to give compound (161), converting the amino group to imine, and introducing the $R^{35}$ group by a reduction reaction.

[Production Method 6 of Compound (6)]

Examples of the synthesis methods of compounds (6g), (6h) and (6i) when $R^1$ is a $C_1$-$C_3$ alkyl group, A is (V), W is $=N-$, i is 1, h is 1, and the dotted line shows a double bond, or A is (VI) and W is $=N-$ or A is (VIII) are shown below.

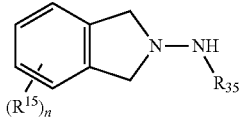

(6g)

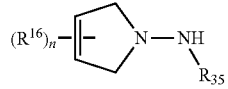

(6h)

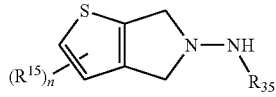

(6i)

wherein $R^{15}$, $R^{16}$, $R^{35}$ and n are as defined above.

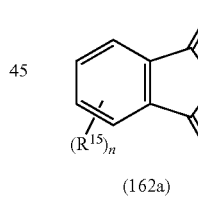

(162a)

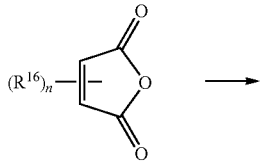

(162b)

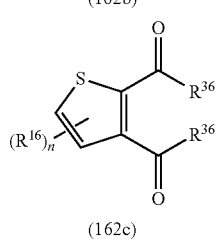

(162c)

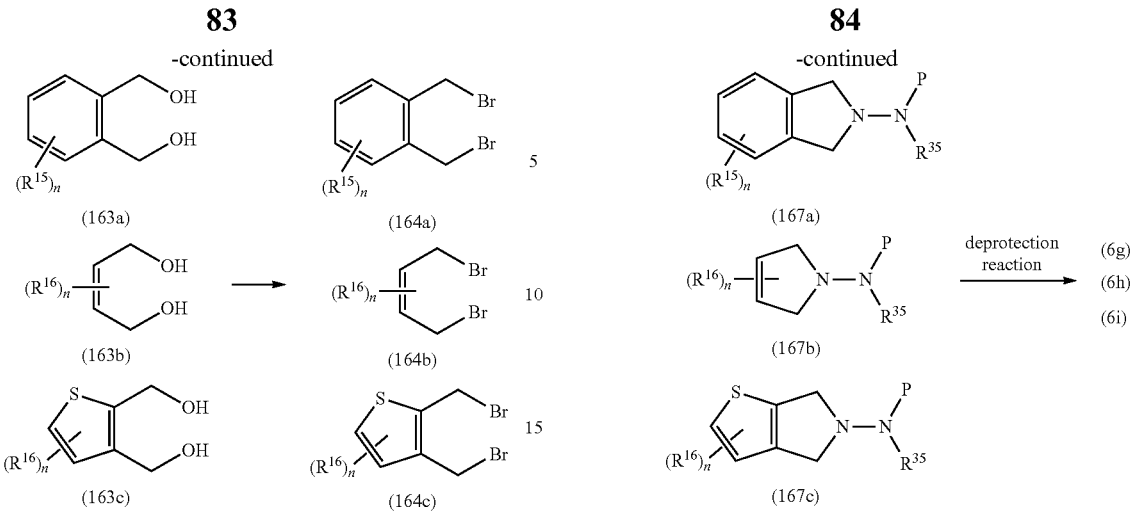

wherein $R^{15}$, $R^{16}$ and n are as defined above, and $R^{36}$ is hydrogen, a hydroxyl group or an alkoxy group.

Compound (162a), (162b) or (162c) is converted to an alcohol form (163a), (163b) or (163c) by reduction with lithium aluminum hydride and the like, which can be converted to compound (164a), (164b) or (164c) by a known method, for example, a method including bromination by warming in an aqueous hydrobromic acid solution, a method including bromination with phosphorus tribromide in an inert solvent, a method including bromination with carbon tetrabromide, and the like.

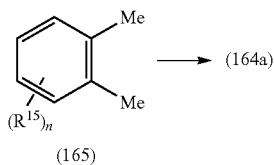

wherein $R^{15}$ and n are as defined above.

In addition, compound (164a) can also be synthesized by the method described in Journal of Organic Chemistry, 1988, 53, 1775-1779 and the like, that is, by warming an orthoxylene derivative (165) in an inert solvent (e.g., carbon tetrachloride etc.) in the presence of N-bromosuccinimide and a catalytic amount of a radical initiator (e.g., benzoyl peroxide, azobisbutyronitrile etc.) for bromination.

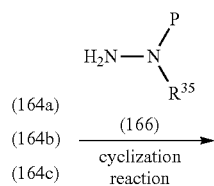

wherein $R^{15}$, $R^{16}$, $R^{35}$, n and P are as defined above.

The object compound (6g), (6h) or (6i) can be synthesized using compound (164a), (164b) or (164c) and according to the method described in U.S. Pat. No. 4,272,284, that is, by reacting the compounds with compound (166) with heating in an inert solvent of amide such as N,N-dimethylformamide, N-methylpyrrolidone and the like in the presence of a base such as triethylamine, N,N-diisopropylethylamine and the like at room temperature to 150° C. with warming, preferably 40° C.-100° C. with warming, to convert them to compound (167a), (167b) or (167c), and performing a deprotection reaction.

[Production Method 7 of Compound (6)]

In addition, an example of a production method of compound (6j) wherein A is (VII), $R^1$ is a $C_1$-$C_3$ alkyl group, W is =N—, g is 0, and D is =CH—$R^{17}$ (except when $R^{17}$ is an alkylamino group or an arylamino group), is shown below.

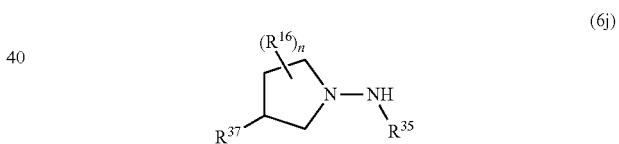

wherein $R^{16}$, $R^{35}$ and n are as defined above, and $R^{37}$ is hydrogen, $C_1$-$C_4$ alkyl, aryl, a $C_1$-$C_6$ alkoxy group or an aryloxy group.

Compound (6j) can be synthesized by, for example, the method shown below.

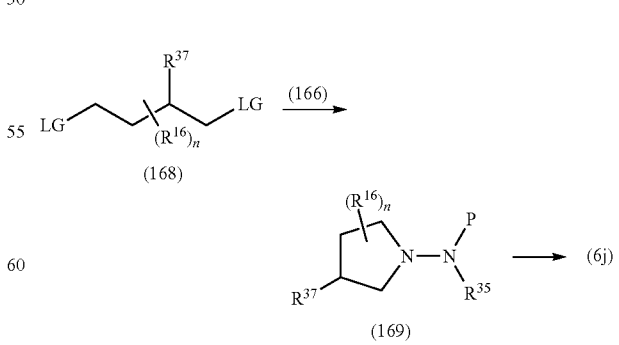

wherein $R^{16}$, $R^{37}$, n, P and LG are as defined above.

The object compound (6j) can be synthesized by warming a butane derivative (168) having a leaving group at the 1,4- position with compound (166) in the presence of an organic base such as triethylamine, N,N-diisopropylethylamine and the like at a temperature of not more than the boiling point of the organic base to give compound (169), and then performing a deprotection reaction.

[Production Method 1 of Compounds (8) and (11)]

Examples of the general production methods of starting material compounds (8) and (11) used for introducing —N($R^3$)-L-$R^2$, which is a partial structure of the formula (I), are shown below. When the nitrogen contained in $R^2$ is primary or secondary amine, compound (8), wherein nitrogen of $R^2$ is substituted by an amino-protecting group, is desirably used for producing compound (I), so that the NH($R^3$) group contained in the starting compound HN($R^3$)-L-$R^2$ will selectively react with compound (7).

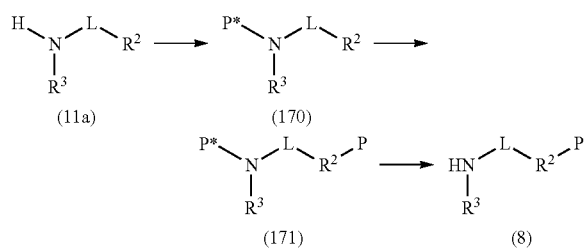

wherein $R^2$, $R^3$, L, P and P* are as defined above, an amino group contained in $R^2$ is a primary or secondary amino group, and P* is an amino-protecting group different from P.

As a production method of compound (8) wherein $R^2$ is as defined above, and the nitrogen contained is primary or secondary amine, for example, the amino group of ($R^3$)NH— of the above-mentioned compound (11a) is protected by a protecting group P*, and then the amino group contained in $R^2$ is protected by a protecting group P. Thereafter, the object compound (8) can be synthesized by removing the protecting group P*. Examples of the 2-nitrobenzenesulfonyl group as P* and a tert-butoxycarbonyl group as P are shown below.

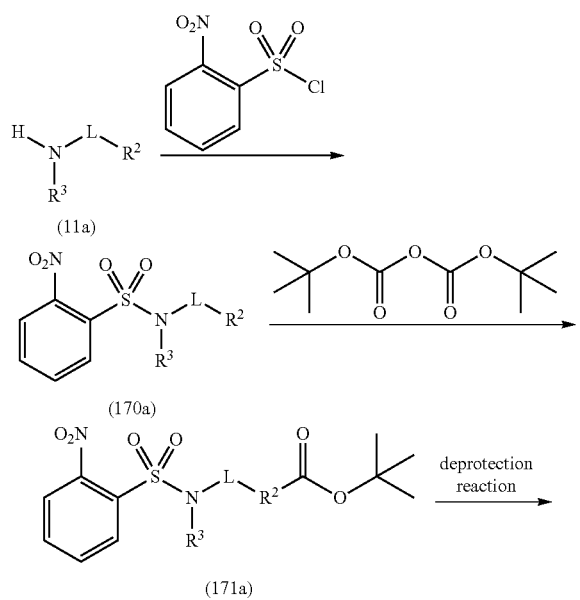

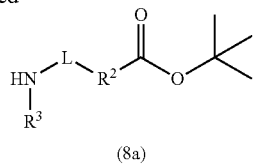

(8a)

wherein $R^2$, $R^3$ and L are as defined above, and the amino group contained in $R^2$ is primary or secondary amino group.

For example, using compound (11a) and 2-nitrobenzenesulfonyl chloride, the amino group of ($R^3$)NH— is selectively protected with a 2-nitrobenzenesulfonyl group in the presence of a base (triethylamine etc.) in an inert solvent (e.g., dichloromethane, tetrahydrofuran etc.) at −20° C. to room temperature, and then the amino group contained in $R^2$ is reacted with di-tert-butyl dicarbonate in an inert solvent (e.g., dichloromethane etc.) at −20° C. to room temperature to give compound (171a). Then, the object compound (8a) can be synthesized by reacting compound (171a) with benzenethiol in an inert solvent (e.g., acetonitrile, dichloromethane, N,N-dimethylformamide etc.) in the presence of a base (potassium carbonate, cesium carbonate, triethylamine etc.) at room temperature or under warming where necessary.

[Production Method 2 of Compounds (8) and (11)]

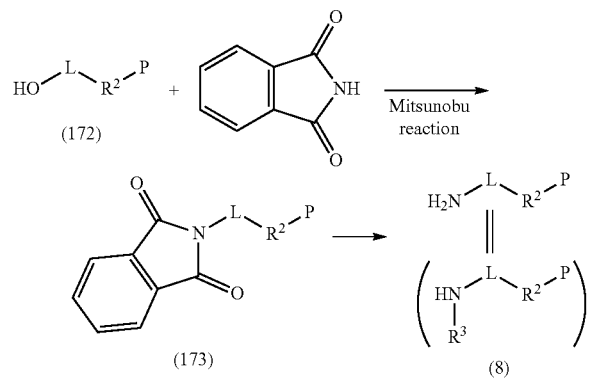

wherein $R^2$, L and P are as defined above.

Compound (8) can be synthesized by condensing a known compound (172) or a compound (172) easily synthesizable by a known method with phthalimide by a Mitsunobu reaction, followed by deprotection with hydrazine and the like.

[Production Method 3 of Compounds (8) and (11)]

Example of the production method of compound (11b), which is compound (11) wherein $R^2$ is N($R^{2a}$)($R^{2b}$) and both $R^{2a}$ and $R^{2b}$ are substituents other than hydrogen, is shown below.

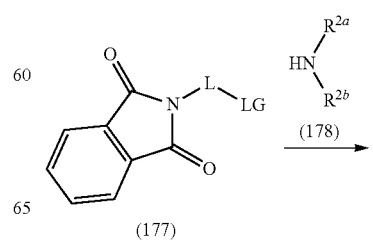

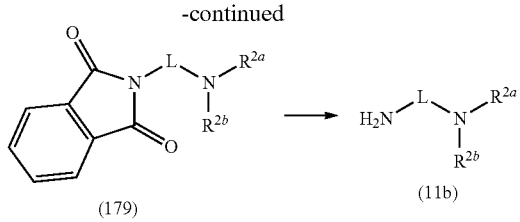

wherein $R^{2a}$, $R^{2b}$, L and LG are as defined above.

When $R^2$ is —$N(R^{2a})(R^{2b})$, and both $R^{2a}$ and $R^{2b}$ are substituents other than hydrogen, compound (11b) can be synthesized by condensing a known compound (177), or compound (177) easily synthesizable by a known method with compound (178) by an alkylation reaction to give compound (179), and then performing a deprotection reaction.

[Production Method 4 of Compounds (8) and (11)]

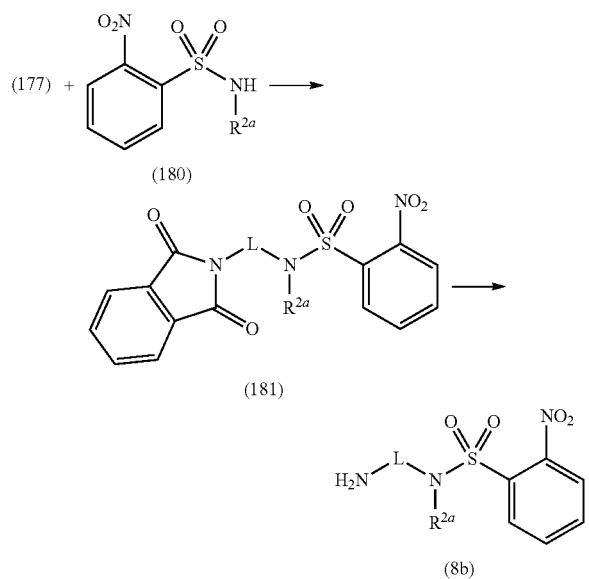

wherein $R^{2a}$ and L are as defined above.

In addition, when $R^2$ is —$N(R^{2a})(R^{2b})$ and at least one of $R^{2a}$ and $R^{2b}$ is hydrogen (for convenience, at least $R^{2b}$ is hydrogen), compound (8b) substituted by a 2-nitrobenzenesulfonyl group can be synthesized by condensing compound (177) and compound (180) by an alkylation reaction to give compound (181), and deprotecting the phthalimide side.

The compound of the formula (I) obtained as mentioned above and each intermediate are isolated and purified by conventional chemical operations such as extraction, crystallization, recrystallization, various chromatographies and the like.

As a salt of the above-mentioned compound of the formula (I), an acid addition salt or a base addition salt can be used. The kind of the salt is not particularly limited as long as it is physiologically acceptable.

The salt of the compound of the formula (I) and a solvate thereof can be produced from an amine derivative of the formula (I) by a known method.

When the compound of the formula (I) or a salt thereof contains an optically active form, it can be resolved into each optical isomer by a conventional optical resolution means. Alternatively, an optically active form of the compound of the formula (I) or a salt thereof may be synthesized by using an optically pure starting material or a compound having a known steric configuration.

The compound of the present invention has a homocysteine synthase inhibitory action, and can be used for the prophylaxis or treatment of diseases involving said enzyme in mammals (particularly human).

Particularly, the compound of the present invention is useful as a homocysteine synthase inhibitor, and is useful for the prophylaxis or treatment of hyperhomocysteinemia and the like.

While one or more kinds of the compound of the present invention may be administered to patients as is, it is preferably added with an active ingredient and a pharmacologically and pharmaceutically acceptable additive, and provided as a preparation in a form well known to those of ordinary skill in the art.

The compound of the present invention can be prepared, together with a suitable diluent and other additives generally used, into a suitable administration form (powder, injection, tablet, capsule, topical external preparation etc.), and administered to human or animal by a suitable administration method (e.g., intravenous administration, oral administration, transdermal administration or topical administration etc.) according to the administration form thereof.

As the pharmacologically and pharmaceutically acceptable additive, excipient, disintegrant, binder, lubricant, coating agent, dye, diluent, base, isotonicity agent and the like can be used.

Examples of the preparation suitable for oral administration include tablet, capsule, powder, fine granules, granules, liquid, syrup and the like, and examples of the preparation suitable for parenteral administration include injection, drip infusion, suppository and the like.

A preparation suitable for oral administration can contain, as additive, excipient, disintegrant, binder, lubricant, coating agent, base and the like. In addition, when the compound of the present invention is administered to a treatment subject patient, other agent suitable for the treatment of the target disease and the compound of the present invention may be used in combination.

The administration route of medicaments containing the compound of the present invention as an active ingredient, such as potent homocysteine synthase inhibitor, a therapeutic or prophylactic drug for hyperhomocysteinemia, and the like is not particularly limited, and they can be administered orally or parenterally. The dose is determined depending on the age, body weight, general health condition, sex, meal, administration time, administration method, clearance rate, combination of drugs, and the level of disease state for which the patients are undergoing treatment at that time, or in consideration of them or other factors. The compound of the present invention and an optical isomer thereof are low toxic and can be used safely. While the daily dose thereof varies depending on the condition and body weight of patients, the kind of compound, administration route and the like, it is desirably administered, for example, at about 0.1 to 1000 mg/patient/day, preferably 1 to 500 mg/patient/day, parenterally by subcutaneous, intravenous, intramuscular or intrarectal administration, or orally at about 0.1 to 1000 mg/patient/day, preferably 1 to 500 mg/patient/day.

EXAMPLES

The present invention is explained in more detail in the following by referring to Examples, which are not to be construed as limitative.

The "room temperature" in the following Reference Examples and Examples shows 0-30° C. In addition, the solvent ratio when a mixed solvent is used shows the volume ratio.

MS spectrum was measured according to any of the following methods.

<LC/MS manufactured by SHIMADZU Corporation>
apparatus: LC-2010
column: Chromolith SpeedROD RP-18e (4.6φ×50 mm) (manufactured by Merck)
mobile phase: SOLUTION A (0.05% trifluoroacetic acid/water), SOLUTION B (0.05% trifluoroacetic acid/acetonitrile), gradient elution from SOLUTION A:SOLUTION B=95:5 to SOLUTION A:SOLUTION B=0:100 over 4 min
flow rate: 4.0 ml/min
column temperature: room temperature
MS measurement mode: ESI (electrospray-ionization) method Positive <LC/MS manufactured by Waters>
apparatus: Acquity HPLC/ZQ
column: Acquity BEH C18 (2.0φ×50 mm) (manufactured by Waters)
mobile phase: SOLUTION A (0.05% trifluoroacetic acid/water), SOLUTION B (0.05% trifluoroacetic acid/acetonitrile), gradient elution from SOLUTION A:SOLUTION B=95:5 to SOLUTION A:SOLUTION B=2:98 over 1 min
flow rate: 0.6 ml/min
column temperature: 40° C.
MS measurement mode: ESI (electrospray-ionization) method Positive $^1$H-NMR (proton nuclear magnetic resonance spectrum) was measured at 300 MHz or 400 MHz. The chemical shift of $^1$H-NMR was measured using tetramethylsilane (TMS) as an internal standard and the relative delta (δ) value is shown in ppm. As for the coupling constant (J), obvious multiplicity is shown in hertz (Hz), using s (singlet), d (doublet), t (triplet), q (quartet), quintet (quintet), m (multiplet), broad showing broad absorption peak, and brs showing broad single absorption peak (broad singlet).

Other abbreviation used in the specification mean the following.
CDCl$_3$: deuterated chloroform
DMSO-d$_6$: deuterated dimethyl sulfoxide
TMW (Total Molecular Weight): total molecular weight
LC-MS: liquid chromatography-mass spectrometry
Found: mass spectrometry measurement value (shows [M+H]$^+$)
NT (Not Tested): not measured Reference Example 1 tert-butyl (2-aminoethyl)methylcarbamate hydrochloride

According to the method described in Synthetic Communications, 23 (17), 2443-2449 (1993), tert-butyl (2-aminoethyl)methylcarbamate from N-methylaminoethanol (10 g). Using 4N hydrochloric acid-dioxane solution to give the hydrochloride salt, the title compound (9 g) was obtained as a colorless solid.

$^1$H-NMR (300 MHz, DMSO-d$_6$); δ (ppm) 1.41 (s, 9H), 2.81 (s, 3H), 2.89 (q, J=6.1, 2H), 3.39 (t, J=6.5, 2H), 8.05 (brs, 3H).

Reference Example 2 tert-butyl (2-aminoethyl)ethylcarbamate

N-Ethylethylenediamine (21.02 g, 238 mmol) and triethylamine (51 ml, 366 mmol) were dissolved in dichloromethane (200 ml), 2-nitrobenzenesulfonyl chloride (54.45 g, 246 mmol) was gradually added with stirring under cooling at −20° C., further stirred at 0° C. for 8 hr, di-tert-butyl dicarbonate (53.48 g, 245 mmol) was added and the mixture was stood overnight at room temperature. The reaction mixture was diluted with ethyl acetate-hexane 1:1 mixed solvent and water, and the organic layer was extracted. The organic layer was washed with 10% aqueous citric acid solution, saturated aqueous sodium hydrogen carbonate and saturated brine and dried over sodium sulfate. The insoluble material was filtered off, and the solution was concentrated under reduced pressure to give tert-butyl ethyl[2-{[(2-nitrophenyl)sulfonyl]amino}ethyl]carbamate (98.05 g) as a crude orange oil. The obtained oil was dissolved in acetonitrile (800 ml), cesium carbonate (157 g, 482 mmol) and benzenethiol (37 ml, 360 mmol) were added and the mixture was stirred at room temperature for 90 min. The reaction mixture was diluted with water, concentrated under reduced pressure to evaporate most part of acetonitrile, and the aqueous layer was extracted with dichloromethane. The obtained organic layer was dried over potassium carbonate, the insoluble material was filtered off, and the solvent was concentrated under reduced pressure. The obtained oil was dissolved in toluene, and the mixture was extracted with 10% aqueous citric acid solution (500 ml). An aqueous sodium hydroxide solution was added to the aqueous layer to give a strong alkaline solution, and the suspending oil was extracted. The aqueous layer was extracted with dichloromethane, mixed with oil and dichloromethane solution, and the mixture was dried over potassium carbonate. The insoluble material was filtered off and the solution was concentrated under reduced pressure to give the title compound as a pale-yellow oil (35.54 g, yield 79%).

$^1$H-NMR (300 MHz, CDCl$_3$); δ (ppm) 1.11 (t, J=7.1, 3H), 1.25 (brs, 2H), 1.46 (s, 9H), 2.82 (t, J=6.7, 2H), 3.2-3.3 (m, 4H).

Reference Example 3 tert-butyl (2-aminoethyl)isopropylcarbamate

Step A tert-butyl isopropyl[2-{[(2-nitrophenyl)sulfonyl]amino}ethyl]carbamate

N-Isopropylethylenediamine (8.44 g, 82.60 mmol) and triethylamine (18 ml, 129 mmol) were dissolved in dichloromethane (80 ml), and 2-nitrobenzenesulfonyl chloride (18.31 g, 82.62 mmol) was gradually added with stirring under ice-cooling. The mixture was stirred at room temperature for 4 hr, ice-cooled again, di-tert-butyl-dicarbonate (19.35 g, 88.66 mmol) was added with stirring, and the mixture was stood overnight at room temperature. The reaction mixture was diluted with ethyl acetate-hexane=1:1 mixed solvent, washed with water, 10% aqueous citric acid solution, saturated aqueous sodium hydrogen carbonate and saturated brine and dried over anhydrous magnesium sulfate. The insoluble material was filtered off, and the solution was concentrated under reduced pressure to give the title compound (34.21 g) as a crude pale-yellow oil.

Step B tert-butyl (2-aminoethyl)isopropylcarbamate

The compound (34.21 g, 82.60 mmol) obtained in step A was dissolved in acetonitrile (300 ml), cesium carbonate (52.38 g, 161 mmol) and benzenethiol (12 ml, 117 mmol) were added and the mixture was stirred at room temperature for one day. The reaction mixture was diluted with water, and the aqueous layer was extracted with dichloromethane. The obtained organic layer was dried over potassium carbonate, the insoluble material was filtered off, and the solution was concentrated under reduced pressure. The obtained oil was dissolved in toluene, and the mixture was extracted with 1N aqueous hydrogensulfate potassium solution. An aqueous sodium hydroxide solution was added to the aqueous layer to give a strong alkaline solution, and the suspending oil was extracted. The aqueous layer was extracted with dichloromethane, mixed with oil and dichloromethane solution, and the mixture was dried over sodium sulfate. The insoluble material was filtered off and the solution was concentrated under reduced pressure to give the title compound as a pale-yellow oil (15.0 g, yield 79%).

$^1$H-NMR (300 MHz, CDCl$_3$); δ (ppm) 1.0-1.2 (broad, 2H), 1.13 (d, J=6.9, 6H), 1.46 (s, 9H), 2.80 (t, J=7.2, 2H), 3.11 (m, 2H), 4.0-4.4 (broad, 1H).

Reference Example 4

N-(3-aminopropyl)-N-isopropyl-2-nitrobenzenesulfonamide

Step A

N-isopropyl-2-nitrobenzenesulfonamide

Isopropylamine (11.07 g, 68.85 mmol) and triethylamine (13 ml, 93 mmol) were dissolved in dichloromethane (50 ml) and the mixture was stirred under ice-cooling. Thereto was added 2-nitrobenzenesulfonyl chloride (10.11 g, 45.62 mmol), and the mixture was stirred at room temperature for 6 hr. The reaction mixture was diluted with ethyl acetate-hexane=1:1 mixed solvent, and the organic layer was washed with diluted hydrochloric acid and water, and dried over anhydrous magnesium sulfate. The insoluble material was filtered off, the solution was concentrated under reduced pressure and the obtained solid was washed with hexane and air-dried to give the title compound (10.73 g, yield 96%) as a colorless solid.

$^1$H-NMR (300 MHz, CDCl$_3$); δ (ppm) 1.16 (d, J=6.2, 6H), 3.60-3.73 (m, 1H), 5.12 (d, J=7.1, 1H), 7.72-7.78 (m, 2H), 7.85-7.89 (m, 1H), 8.16-8.20 (m, 1H).

Step B

N-[3-(1,3-dioxo-1,3-dihydro-2H-isoindol-2-yl)propyl]-N-isopropyl-2-nitrobenzenesulfonamide The compound (6.29 g, 25.75 mmol) obtained in step A was dissolved in N-methylpyrrolidone (100 ml), and the mixture was stirred under ice-cooling. Thereto was added 60% sodium hydride (1.21 g, 30 mmol) and the mixture was stirred at room temperature for 20 min. After stirring, N-(3-bromopropyl)phthalimide (8.31 g, 31.0 mmol) was added and the mixture was stirred at 70° C. for 90 min. The reaction mixture was diluted with ethyl acetate, washed with water, saturated aqueous sodium hydrogen carbonate and saturated brine, and dried over anhydrous magnesium sulfate. The insoluble material was filtered off, and the solution was concentrated under reduced pressure. The obtained solid was washed with diethyl ether-hexane mixed solvent, and dried under reduced pressure to give the title compound (8.11 g, yield 73%) as a colorless solid.

$^1$H-NMR (300 MHz, CDCl$_3$); δ (ppm) 1.17 (d, J=6.6, 6H), 1.97-2.08 (m, 2H), 3.34 (t, J=7.8, 2H), 3.73 (t, J=7.1, 2H), 4.1-4.2 (m, 1H), 7.5-7.8 (m, 5H), 7.84-7.87 (m, 2H), 7.98-8.02 (m, 1H).

Step C

N-(3-aminopropyl)-N-isopropyl-2-nitrobenzenesulfonamide

The compound (8.11 g, 18.80 mmol) obtained in step B and hydrazine monohydrate (5 ml) were added to ethanol (200 ml) and the mixture was heated under reflux for 1 hr. The reaction mixture was cooled, and diluted with diethyl ether. The insoluble material was filtered off, and the solution was concentrated under reduced pressure. The obtained oil was dissolved in dichloromethane, and the solution was extracted with hydrochloric acid. The aqueous layer was alkalified with aqueous sodium hydroxide solution, extracted with dichloromethane, and the organic layer was dried over potassium carbonate. The insoluble material was filtered off, and the solution was concentrated under reduced pressure to give the title compound (5.62 g, yield 99%) as a yellow oil.

$^1$H-NMR (300 MHz, CDCl$_3$); δ (ppm) 1.18 (d, J=6.6, 6H), 1.38 (brs, 2H), 1.74-1.85 (m, 2H), 2.76 (t, J=6.9, 2H), 3.33 (t, J=7.7, 2H), 4.0-4.2 (m, 1H), 7.5-7.7 (m, 3H), 8.02-8.06 (m, 1H).

Reference Example 5

N-(3-aminopropyl)-N-methyl-2-nitrobenzenesulfonamide hydrochloride

Step A

N-methyl-2-nitrobenzenesulfonamide

Using methylamine hydrochloride (12.4 g) and according to the method of Reference Example 4, step A, the title compound (7.39 g, yield 32%) was obtained as a colorless solid.

$^1$H-NMR (300 MHz, CDCl$_3$); δ (ppm) 2.80 (d, J=5.3, 3H), 5.23 (brs, 1H), 7.7-7.9 (m, 3H), 8.1-8.2 (m, 1H).

Step B

N-[3-(1,3-dioxo-1,3-dihydro-2H-isoindol-2-yl)propyl]-N-methyl-2-nitrobenzenesulfonamide Using the compound (3.10 g, 14.34 mmol) obtained in step A and N-(3-bromopropyl)phthaltmide (3.80 g, 14.17 mmol), and according to the method of Reference Example 4, step B, the title compound (4.19 g, yield 73%) was obtained as a pale-yellow solid.

$^1$H-NMR (300 MHz, CDCl$_3$); δ (ppm) 1.93-2.04 (m, 2H), 2.95 (s, 3H), 3.35 (t, J=7.4, 2H), 3.73 (t, J=7.4, 2H), 7.62-7.75 (m, 5H), 7.83-7.87 (m, 2H), 7.96-8.00 (m, 1H).

Step C

N-(3-aminopropyl)-N-methyl-2-nitrobenzenesulfonamide hydrochloride

Using the compound (4.18 g, 10.36 mmol) obtained in step B and according to the method of Reference Example 4, step C, N-(3-aminopropyl)-N-methyl-2-nitrobenzenesulfonamide (3.20 g) was obtained as a crude oil. This was dissolved in dichloromethane (50 ml), 4N hydrochloric acid-dioxane solution (3 ml) was added, and diluted with diethyl ether to allow precipitation of a solid. The precipitated solid was filtered, and dried under reduced pressure to give the title compound (3.18 g, yield 99%) as a pale-yellow solid.

$^1$H-NMR (300 MHz, DMSO-d$_6$); δ (ppm) 1.8-1.9 (m, 2H), 2.7-2.8 (m, 2H), 2.86 (s, 3H), 3.29 (t, J=6.9, 2H), 7.8-8.1 (m, 7H (4H of Ar&NH$_3$)).

Reference Example 6

N-(2-aminoethyl)-N-methyl-2-nitrobenzenesulfonamide

Step A

N-[2-(1,3-dioxo-1,3-dihydro-2H-isoindol-2-yl)ethyl]-N-methyl-2-nitrobenzenesulfonamide Using the compound (4.26 g, 19.7 mmol) of Reference Example 5, step A, and N-(2-bromoethyl)phthalimide (5.05 g, 19.9 mmol), and according to the method of Reference Example 4, step B, the title compound (1.64 g, yield 21%) was obtained as pale-yellow crystals.

$^1$H-NMR (300 MHz, CDCl$_3$); δ (ppm) 3.06 (s, 3H), 3.56 (t, J=6.5, 2H), 3.90 (t, J=6.5, 2H), 7.40-7.55 (m, 1H), 7.58-7.62 (m, 2H), 7.68-7.72 (m, 2H), 7.80-7.84 (m, 2H), 7.93-7.97 (m, 1H).

Step B

N-(2-aminoethyl)-N-methyl-2-nitrobenzenesulfonamide

Using the compound (1.63 g, 4.19 mmol) obtained in step A and according to the method of Reference Example 4, step C, the title compound (0.95 g, yield 88%) as a yellow oil.

$^1$H-NMR (300 MHz, CDCl$_3$); δ (ppm) 2.90 (t, J=5.4, 2H), 2.92 (s, 3H), 3.30 (t, J=5.4, 2H), 7.61-7.64 (m, 1H), 7.66-7.74 (m, 2H), 8.00-8.04 (m, 1H).

Reference Example 7

N-(2-aminoethyl)-N-isopropyl-2-nitrobenzenesulfonamide

Step A tert-butyl[2-{[(2-nitrophenyl)sulfonyl]amino}ethyl]carbamate

Using tert-butyl (2-aminoethyl)carbamate (4.61 g) and according to the method of Reference Example 4, step A, the title compound (2.22 g, yield 22%) as a yellow oil.

$^1$H-NMR (300 MHz, CDCl$_3$); δ (ppm) 1.42 (s, 9H), 3.2-3.4 (m, 4H), 4.84 (brs, 1H), 5.71 (brs, 1H), 7.73-7.79 (m, 2H), 7.85-7.90 (m, 1H), 8.11-8.15 (m, 1H).

Step B

N-(2-aminoethyl)-N-isopropyl-2-nitrobenzenesulfonamide

The compound (2.22 g, 6.43 mmol) obtained in step A, isopropanol (0.65 ml, 8.46 mmol), and triphenylphosphine (1.85 g, 7.05 mmol) were dissolved in tetrahydrofuran (50 ml) and the mixture was stirred under ice-cooling. Thereto was slowly added 40% diisopropyl azodicarboxylate-toluene solution (5 ml), and the mixture was stirred at the same temperature for 1 hr. The reaction mixture was concentrated under reduced pressure and diluted with diethyl ether, and the precipitated colorless solid was filtered off. The mother liquor was concentrated under reduced pressure and the obtained oil was purified by silica gel column chromatography (ethyl acetate-hexane) to give tert-butyl[2-{isopropyl[(2-nitrophenyl)sulfonyl]amino}ethyl]carbamate (3.75 g) as a colorless crude oil. This was dissolved in dichloromethane (10 ml), 4N hydrochloric acid-dioxane solution 10 ml) was added at room temperature and the mixture was stirred for 1 hr. The reaction mixture was diluted with diethyl ether, and the mixture was extracted with water. The aqueous layer was alkalified with aqueous sodium hydroxide solution, extracted with dichloromethane, dried over sodium sulfate, the insoluble material was filtered off, and the solution was concentrated under reduced pressure to give the title compound (1.39 g, yield 75%) as a yellow oil.

$^1$H-NMR (300 MHz, CDCl$_3$); δ (ppm) 1.16 (d, J=6.9, 6H), 1.32 (brs, 2H), 2.91 (t, J=7.1, 2H), 3.30 (t, J=7.1, 2H), 4.0-4.2 (m, 1H), 7.6-7.8 (m, 3H), 8.0-8.1 (m, 1H).

Reference Example 8

[(2R)-1-(2-aminoethyl)pyrrolidin-2-yl]methanol

Step A

[(2R)-1-glycylpyrrolidin-2-yl]methanol

N-(tert-butoxycarbonyl)glycine (5.00 g, 28.5 mmol) and D-prolinol (3.50 g, 34.2 mmol) was dissolved in N,N-dimethylformamide (10 ml) and dichloromethane (100 ml), and the mixture was stirred at room temperature. At the same temperature, 1-hydroxybenzotriazole.monohydrate (7.70 g, 57.0 mmol) and N-(3-dimethylaminopropyl)-N'-ethylcarbodiimide hydrochloride (hereinafter to be indicated as WSC) (8.20 g, 42.8 mmol) were added, and the mixture was stirred at room temperature overnight. The reaction mixture was washed with diluted hydrochloric acid, diluted aqueous sodium hydroxide solution, water and saturated brine, and the organic layer was dried over anhydrous magnesium sulfate. The insoluble material was filtered off, and the solution was concentrated under reduced pressure, the obtained oil was purified by silica gel column chromatography (methanol-chloroform) to give a crude product. This was dissolved in ethyl acetate (30 ml) and methanol (20 ml), 4N hydrochloric acid-ethyl acetate solution (20 ml) was added, and the mixture was stirred at room temperature overnight. The solution was concentrated under reduced pressure, and to the obtained concentrate was added a saturated aqueous potassium carbonate solution, and the mixture was extracted with chloroform. The organic layer was dried over anhydrous magnesium sulfate, the insoluble material was filtered off, and the solution was concentrated under reduced pressure to give the title compound (1.00 g, yield 22%) as a pale-yellow oil.

Step B

[(2R)-1-(2-aminoethyl)pyrrolidin-2-yl]methanol

To tetrahydrofuran (30 ml) was added lithium aluminum hydride (720 mg, 19.0 mmol) and the mixture was stirred under ice-cooling. Then, a solution (20 ml) of the compound (1.00 g, 6.32 mmol) obtained in step A in tetrahydrofuran was gradually added, and the mixture was heated under reflux for 2 hr. The reaction mixture was cooled, water (0.72 ml), 1N aqueous sodium hydroxide solution (1.44 ml) and water (0.72 ml) were slowly added in this order with stirring, and the mixture was stirred at room temperature for 1 hr. The insoluble material was filtered off through celite, and the solution was concentrated under reduced pressure to give the title compound (718 mg, yield 79%) as a yellow oil.

$^1$H-NMR (300 MHz, DMSO-d$_6$); δ (ppm) 1.22-1.40 (m, 1H), 1.47-1.82 (m, 4H), 2.08-2.20 (m, 1H), 2.21-2.35 (m, 1H), 2.37-2.42 (m, 1H), 2.43-2.60 (m, 2H), 2.61-2.81 (m, 2H), 2.95-3.04 (m, 1H), 3.17-3.25 (m, 1H), 3.30-3.41 (m, 1H).

Reference Example 9 tert-butyl 4-aminopiperidine-1-carboxylate-hydrochloride

Step A tert-butyl 4-[(methylsulfonyl)oxy]piperidine-1-carboxylate

4-Hydroxypiperidine (4.88 g, 48.2 mmol) was dissolved in dichloromethane (50 ml) and triethylamine (6.7 ml) (48.1 mmol) was added, and the mixture was stirred under ice-cooling. Thereto was added di-tert-butyl dicarbonate (10.11 g, 46.3, mmol) dissolved in dichloromethane (30 ml) was added. The mixture was stirred at the same temperature for 2 hr, triethylamine (8.0 ml, 57.4 mmol) and methanesulfonyl-chloride (3.8 ml, 49.1 mmol) were added, and the mixture was stirred at room temperature for 3 hr. The reaction mixture was diluted with ethyl acetate-hexane=1:1 solution, washed with aqueous citric acid solution, water, saturated aqueous sodium hydrogen carbonate and saturated brine, and dried over anhydrous magnesium sulfate. The insoluble material was filtered off, and the obtained solution was concentrated under reduced pressure and the obtained solid was washed with hexane to give the title compound (8.60 g) (yield 66%) as a colorless solid.

$^1$H-NMR (300 MHz, CDCl$_3$); δ (ppm) 1.46 (s, 9H), 1.75-1.90 (m, 2H), 1.91-2.01 (m, 2H), 3.04 (s, 3H), 3.25-3.35 (m, 2H), 3.66-3.74 (m, 2H), 4.85-4.92 (m, 1H).

Step B tert-butyl 4-(1,3-dioxo-1,3-dihydro-2H-isoindol-2-yl)piperidine-1-carboxylate Using the compound (2.43 g, 8.70 mmol) obtained by the method of step A and potassium phthalimide (2.40 g, 12.96 mmol), and according to the method of Reference Example 4, step B, the title compound (846 mg, yield 29%) was obtained as a colorless solid.

$^1$H-NMR (300 MHz, CDCl$_3$); δ (ppm) 1.49 (s, 9H), 1.6-1.7 (m, 2H), 2.3-2.5 (m, 2H), 2.7-2.9 (m, 2H), 4.22-4.32 (m, 3H), 7.70-7.74 (m, 2H), 7.81-7.85 (m, 2H).

Step C tert-butyl 4-aminopiperidine-1-carboxylate hydrochloride

The compound (837 mg, 2.53 mmol) obtained in step B was added to ethanol (20 ml), hydrazine monohydrate (0.31 ml, 6.4 mmol) was added, and the mixture was heated under reflux for 1 hr. The reaction mixture was cooled, and diethyl ether was added to allow precipitation of a solid. The precipitated solid was filtered, and the obtained solution was concentrated under reduced pressure to give a colorless oil. The oil was dissolved in diethyl ether, 4N hydrochloric acid-dioxane solution (1 ml) was added at room temperature and the mixture was diluted with ethyl acetate to allow precipitation of a solid. This was filtered, washed with ethyl acetate, and dried under reduced pressure to give the title compound (598 mg, yield 100%) as a colorless solid.

$^1$H-NMR (300 MHz, DMSO-d$_6$); δ (ppm) 1.3-1.5 (m, 2H), 1.39 (s, 9H), 1.8-1.9 (m, 2H), 2.6-2.8 (m, 2H), 3.0-3.2 (m, 1H), 3.9-4.0 (m, 2H), 8.17 (brs, 3H).

Reference Example 10 tert-butyl 3-aminopiperidine-1-carboxylate hydrochloride

Step A tert-butyl 3-(1,3-dioxo-1,3-dihydro-2H-isoindol-2-yl)piperidine-1-carboxylate tert-Butyl 3-hydroxypiperidine-1-carboxylate (4.38 g) (21.76 mmol), phthalimide (4.82 g, 32.76 mmol), and triphenylphosphine (8.62 g, 32.86 mmol) were added to tetrahydrofuran (60 ml), 40% diethyl azodicarboxylate-toluene solution (15 ml) was slowly added at room temperature with stirring, and the mixture was stirred at the same temperature overnight. The reaction mixture was concentrated under reduced pressure, diluted with diethyl ether, and the precipitated colorless solid was filtered off. The mother liquor was concentrated under reduced pressure and the obtained oil was purified by silica gel column chromatography (ethyl acetate-hexane) to give the title compound (2.04 g, yield 28%) as a colorless solid.

$^1$H-NMR (300 MHz, CDCl$_3$); δ (ppm) 1.46 (s, 9H), 1.5-1.7 (m, 1H), 1.75-1.90 (m, 2H), 2.2-2.4 (m, 1H), 2.6-2.8 (m, 1H), 3.4-3.6 (m, 1H), 3.9-4.3 (m, 3H), 7.70-7.76 (m, 2H), 7.81-7.86 (m, 2H).

Step B tert-butyl 3-aminopiperidine-1-carboxylate hydrochloride

Using the compound (2.04 g, 6.17 mmol) obtained in step A and according to the method of Reference Example 9, step C, the title compound (1.45 g, yield 99%) was obtained as a colorless solid.

$^1$H-NMR (300 MHz, DMSO-d$_6$); δ (ppm) 1.3-1.6 (m, 2H), 1.43 (s, 9H), 1.6-1.8 (m, 1H), 1.9-2.0 (m, 1H), 2.7-3.1 (m, 3H), 3.6-3.8 (m, 1H), 3.9-4.0 (m, 1H), 8.23 (brs, 3H).

Reference Example 11 tert-butyl 3-aminopyrrolidine-1-carboxylate hydrochloride 3-(Trifluoroacetamido)pyrrolidine hydrochloride (4.60 g, 21.04 mmol) was added to dichloromethane (60 ml), triethylamine (3.5 ml, 25.1 mmol) and di-tert-butyl dicarbonate (4.61 g, 21.12 mmol) were added under ice-cooling, and the mixture was stirred at room temperature for 7 hr. The reaction mixture was dissolved in ethyl acetate-hexane=1:1 mixed solvent (100 ml), and the organic layer was washed with water, 10% aqueous citric acid solution and saturated brine, and dried over anhydrous magnesium sulfate. The insoluble material was filtered off, and the solution was concentrated under reduced pressure to give the title compound (6.66 g) as a crude colorless oil. This was dissolved in methanol (70 ml), potassium carbonate (14.46 g) dissolved in water (50 ml) was added under ice-cooling, and the mixture was stirred at room temperature for 5 hr. The reaction mixture was concentrated under reduced pressure, diluted with diethyl ether and washed with saturated brine and dried over sodium sulfate. The insoluble material was filtered off, and the solution was concentrated under reduced pressure to give an oil. This was dissolved in diethyl ether (50 ml), and 4N hydrochloric acid-dioxane solution (5.5 ml) was added. Hexane was added to the solution to allow crystallization, and the precipitated solid was filtered and dried under reduced pressure to give the title compound (4.22 g, yield 90%) as a colorless solid.

$^1$H-NMR (300 MHz, DMSO-$d_6$); δ (ppm) 1.41 (s, 9H), 1.8-2.0 (m, 1H), 2.0-2.2 (m, 1H), 3.2-3.6 (m, 4H), 3.7-4.0 (m, 1H), 8.40 (brs, 3H).

Reference Example 12 tert-butyl (2S)-2-(aminomethyl)pyrrolidine-1-carboxylate hydrochloride

Using tert-butyl (2S)-2-(hydroxymethyl)pyrrolidine-1-carboxylate (4.07 g, 20.22 mmol) and according to the methods of Reference Example 10, steps A and B, the title compound (4.34 g, yield 91%) was obtained as a colorless solid.

$^1$H-NMR (300 MHz, DMSO-$d_6$); δ (ppm) 1.41 (s, 9H), 1.6-2.0 (m, 4H), 2.6-2.8 (m, 1H), 2.8-3.0 (m, 1H), 3.1-3.3 (m, 2H), 3.8-4.0 (m, 1H), 8.16 (brs, 3H).

Reference Example 13 tert-butyl (2R)-2-(aminomethyl)pyrrolidine-1-carboxylate hydrochloride

Using tert-butyl (2R)-2-(hydroxymethyl)pyrrolidine-1-carboxylate (3.21 g, 15.95 mmol) and according to the methods of Reference Example 10, steps A and B, the title compound (3.31 g, yield 88%) was obtained as a colorless solid.

$^1$H-NMR (300 MHz, DMSO-$d_6$); δ (ppm) 1.42 (s, 9H), 1.6-2.0 (m, 4H), 2.6-2.8 (m, 1H), 2.8-3.0 (m, 1H), 3.1-3.3 (m, 2H), 3.8-4.0 (m, 1H), 8.09 (brs, 3H).

Reference Example 14

N-(2-aminoethyl)-2,2,2-trifluoro-N-(2,2,2-trifluoroethyl)acetamide hydrochloride

Step A tert-butyl {2-[(trifluoroacetyl)amino]ethyl}carbamate tert-Butyl (2-aminoethyl)carbamate (5.00 g, 31.2 mmol) and pyridine (3.0 ml, 37 mmol) were added to dichloromethane (100 ml), and the mixture was stirred under ice-cooling. Then, trifluoroacetic acid anhydride (4.9 ml, 34 mmol) was added dropwise. After the completion of the dropwise addition, the reaction mixture was stood at room temperature overnight. Water was added and the mixture was extracted with ethyl acetate, washed with diluted hydrochloric acid, diluted aqueous sodium hydroxide solution and saturated brine, and dried over anhydrous magnesium sulfate. The solution was concentrated under reduced pressure to give the title compound (6.57 g, yield 82%) as a colorless solid.

$^1$H-NMR (300 MHz, DMSO-$d_6$); δ (ppm) 1.37 (s, 9H), 3.00-3.10 (m, 2H), 3.15-3.24 (m, 2H), 6.91 (t, J=5.4, 1H), 9.35 (brs, 1H).

Step B tert-butyl {2-[(2,2,2-trifluoroethyl)amino]ethyl}carbamate

The compound (6.57 g, 25.6 mmol) obtained in step A was dissolved in tetrahydrofuran (100 ml), and the mixture was stirred under ice-cooling. Then, a suspension of lithium aluminum hydride (1.94 g, 51.2 mmol) in tetrahydrofuran (50 ml) was slowly added dropwise. Thereafter, the mixture was stood overnight at room temperature. The reaction mixture was ice-cooled again, water (2 ml), 1N aqueous sodium hydroxide solution (4 ml) and water (2 ml) were added in this order with stirring, and the mixture was stirred at room temperature for 5 hr. The insoluble material was filtered off through celite, and the obtained solution was concentrated under reduced pressure to give the title compound (4.56 g, yield 74%) as a yellow oil.

$^1$H-NMR (300 MHz, DMSO-$d_6$); δ (ppm) 1.37 (s, 9H), 2.51-2.68 (m, 2H), 2.98 (q, J=6.3, 2H), 3.15-3.25 (m, 2H), 6.74 (brs, 1H).

Step C tert-butyl {2-[(trifluoroacetyl)(2,2,2-trifluoroethyl)amino]ethyl}carbamate Using the compound (4.56 g, 18.8 mmol) obtained in step B and according to the method of Reference Example 14, step A, the title compound (3.05 g, yield 48%) was obtained as a pale-yellow oil.

$^1$H-NMR (300 MHz, DMSO-$d_6$); δ (ppm) 1.36 (s, 9H), 3.20-3.32 (m, 2H), 3.43-3.58 (m, 2H), 4.25-4.40 (m, 2H), 7.04 (brs, 1H).

Step D

N-(2-aminoethyl)-2,2,2-trifluoro-N-(2,2,2-trifluoroethyl)acetamide hydrochloride The compound (3.05 g, 9.02 mmol) obtained in step C was dissolved in ethyl acetate (20 ml), 4N hydrochloric acid-ethyl acetate solution (10 ml) was added, and the mixture was stirred at room temperature for 6 hr. The precipitated solid was collected by filtration, and the obtained solid was washed with ethyl acetate, and dried under reduced pressure to give the title compound (1.51 g, yield 61%) as a pale-bistered solid.

$^1$H-NMR (300 MHz, DMSO-$d_6$); δ (ppm) 3.02-3.19 (m, 2H), 3.68-3.88 (m, 2H), 4.31-4.63 (m, 2H), 8.34 (brs, 3H).

Reference Example 15

N-(2-aminoethyl)-N-ethyl-2,2,2-trifluoroacetamide hydrochloride

According to the method described in Synthetic Communications, 23 (17), 2443-2449 (1993), tert-butyl N-[2-(ethylamino)ethyl]carbamate (3.06 g, 16.25 mmol) was obtained from N-ethylethylenediamine (8.36 g) and di-tert-butyl dicarbonate (6.25 g). Using this compound, and according to the method of Reference Example 14, step A, tert-butyl {2-[ethyl(trifluoroacetyl)amino]ethyl}carbamate (4.92 g) was obtained as a crude pale-yellow oil. Using this compound and according to the method of Reference Example 14, step D, the title compound (1.91 g, yield 30%) was obtained as a colorless solid.

$^1$H-NMR (300 MHz, DMSO-d$_6$); δ (ppm) 1.09 (t, J=7.1, 0.8H), 1.17 (t, J=7.1, 2.2H), 2.9-3.1 (m, 2H), 3.40-3.51 (m, 2H), 3.59-3.69 (m, 2H), 8.12 (brs, 3H).

Reference Example 16

N-(tert-butyl)ethane-1,2-diamine

Step A

[benzyl(tert-butyl)amino]acetonitrile

Benzyl(tert-butyl)amine (10.0 g, 61.3 mmol) was dissolved in acetonitrile (100 ml), and bromoacetonitrile (4.5 ml, 64.6 mmol), potassium carbonate (16.9 g, 122.3 mmol) and sodium iodide (9.2 g, 61.4 mmol) were successively added with stirring at room temperature, and the mixture was stirred at the same temperature overnight. The reaction mixture was diluted with saturated aqueous potassium carbonate solution, extracted with ethyl acetate, washed with saturated brine, and dried over anhydrous magnesium sulfate. The insoluble material was filtered off, and the solution was concentrated under reduced pressure, and the obtained oil was purified by silica gel column chromatography (ethyl acetate-hexane) to give the title compound (10.8 g, yield 87%) as a pale-yellow oil.

$^1$H-NMR (300 MHz, CDCl$_3$); δ (ppm) 1.30 (s, 9H), 3.45 (s, 2H), 3.84 (s, 2H), 7.25-7.37 (m, 5H).

Step B

N-benzyl-N-(tert-butyl)ethane-1,2-diamine

The compound (5.00 g, 24.7 mmol) obtained in step A was dissolved in tetrahydrofuran (100 ml), and the mixture was stirred under ice-cooling. Lithium aluminum hydride (1.87 g, 49.4 mmol) was gradually added at the same temperature, and the mixture was stirred at room temperature for 2 hr. After ice-cooling again, water (1.9 ml), 1N aqueous sodium hydroxide solution (3.8 ml) and water (1.9 ml) were gradually added in this order, and the mixture was stirred at room temperature for 1 hr. The insoluble material was filtered off through celite, and the obtained solution was concentrated under reduced pressure to give the title compound (4.89 g, yield 96%) as a pale-yellow oil.

$^1$H-NMR (300 MHz, DMSO-d$_6$); δ (ppm) 1.06 (s, 9H), 2.28 (t, J=6.9, 2H), 2.47-2.53 (m, 2H), 3.33 (brs, 2H), 3.64 (s, 2H), 7.13-7.16 (m, 1H), 7.18-7.33 (m, 4H).

Step C

N-(tert-butyl)ethane-1,2-diamine

The compound (2.65 g, 12.8 mmol) obtained in step B was dissolved in ethanol (30 ml), and the mixture was stirred at room temperature. Then, 10% palladium carbon (containing water) (500 mg) was added, and the mixture was stirred under a hydrogen atmosphere at room temperature for 7 hr. The insoluble material was filtered off through celite, and the obtained solution was concentrated under reduced pressure to give the title compound (850 mg, yield 57%) as a pale-yellow oil.

$^1$H-NMR (300 MHz, CDCl$_3$); δ (ppm) 1.00 (s, 9H), 2.40-2.46 (m, 2H), 2.49-2.56 (m, 2H), 2.75-4.00 (broad, 3H).

Reference Example 17

N-methyl-1,3-dihydro-2H-isoindol-2-amine hydrochloride

Step A tert-butyl 1-methylhydrazinecarboxylate

According to the method described in Journal of Heterocyclic Chemistry, 2000, 37 (1), 47-55, the title compound (122.7 g) was obtained as a colorless oil from N-methylhydrazine (44.1 g).

$^1$H-NMR (300 MHz, CDCl$_3$); δ (ppm) 1.48 (s, 9H), 3.06 (s, 3H), 4.06 (brs, 2H).

Step B tert-butyl 1,3-dihydro-2H-isoindol-2-yl(methyl)carbamate

The step was performed according to the method described in U.S. Pat. No. 4,272,284. Xylylene dibromide (160 g, 606 mmol) and compound (88.52 g, 606 mmol) obtained in step A were dissolved in N-methylpyrrolidone (550 ml). While maintaining the reaction mixture at 50° C.-60° C., triethylamine (190 ml, 1.36 mol) was gradually added dropwise using infundibulum with stirring and, after the completion of the dropwise addition, the reaction mixture was stood overnight at room temperature. A 5% aqueous citric acid solution (700 ml) was added to the reaction mixture, and the precipitated solid was collected by filtration, washed with water and dried under reduced pressure to give the title compound (126 g, yield 84%) as a crude pale-pink solid.

$^1$H-NMR (300 MHz, CDCl$_3$); δ (ppm) 1.41 (s, 9H), 3.09 (s, 3H), 4.44 (s, 4H), 7.1-7.2 (m, 4H).

Step C

N-methyl-1,3-dihydro-2H-isoindol-2-amine hydrochloride

The compound (126 g) obtained in step B was dissolved in a mixed solvent of dichloromethane (150 ml) and ethanol (150 ml). A 4N hydrochloric acid-dioxane solution (500 ml) was added with stirring at room temperature and the mixture was stirred at the same temperature for 5 hr. The reaction mixture was diluted with dichloromethane and water and the aqueous layer was extracted. An ice-cooled aqueous sodium hydroxide solution was added to the ice-cooled aqueous layer to give a strongly-alkaline aqueous layer. The aqueous layer was extracted with dichloromethane. The organic layer was dried over potassium carbonate, and the insoluble material was filtered off. The solvent was evaporated under reduced pressure. The obtained oil was dissolved in diethyl ether (500 ml), and 4N hydrochloric acid-dioxane solution (140 ml) was added with stirring under ice-cooling to allow precipitation of a solid. This was filtered, washed with diethyl ether, and dried under reduced pressure to give the title compound (75.89 g, yield 81%) as a gray solid.

¹H-NMR (300 MHz, DMSO-d₆); δ (ppm) 2.77 (s, 3H), 4.43 (s, 4H), 7.2-7.4 (m, 4H), 11.0 (brs, 2H).

Reference Example 18

4-fluoro-N-methyl-1,3-dihydro-2H-isoindol-2-amine hydrochloride

Step A tert-butyl (4-fluoro-1,3-dihydro-2H-isoindol-2-yl) methylcarbamate

3-Fluoro-ortho-xylene (1.99 g, 16.03 mmol), N-bromosuccinimide (6.98 g, 39.22 mmol) and benzoyl peroxide (0.24 g) were added to carbon tetrachloride (60 ml), and the mixture was heated under reflux for 45 min. The reaction mixture was cooled, diluted with hexane, and the insoluble material was filtered off. The obtained solution was concentrated under reduced pressure. Using the obtained oil, the reaction was performed according to the method of Reference Example 17, step B. After completion of the reaction, 10% aqueous citric acid solution was added to the reaction mixture, and the mixture was extracted with ethyl acetate-hexane=1:1 mixed solvent, washed with water, saturated aqueous sodium hydrogen carbonate and saturated brine, and dried over anhydrous magnesium sulfate. The insoluble material was filtered off, and the solution was concentrated under reduced pressure. The obtained oil was purified by silica gel column chromatography (ethyl acetate-hexane) to give the title compound (826 mg, yield 19%) as a pale-yellow oil.
¹H-NMR (300 MHz, CDCl₃); δ (ppm) 1.41 (s, 9H), 3.09 (s, 3H), 4.47 (s, 2H), 4.48 (s, 2H), 6.87 (t, J=8.6, 1H), 6.94 (d, J=7.2, 1H), 7.1-7.2 (m, 1H).

Step B 4-fluoro-N-methyl-1,3-dihydro-2H-isoindol-2-amine hydrochloride

The compound (806 mg, 3.03 mmol) obtained in step A was dissolved in a dichloromethane (3 ml)-ethanol (0.3 ml) mixed solvent. 4N Hydrochloric acid-dioxane solution (3 ml) was added with stirring at room temperature, and the mixture was stirred at the same temperature for 100 min. Diethyl ether was added to the reaction mixture, and the precipitated solid was filtered, washed with diethyl ether and dried under reduced pressure to give the title compound (433 mg, yield 71%) as a gray solid.
¹H-NMR (300 MHz, DMSO-d₆); δ (ppm) 2.80 (s, 3H), 4.48 (s, 2H), 4.50 (s, 2H), 7.14 (t, J=8.9, 1H), 7.21 (d, J=7.2, 1H), 7.33-7.41 (m, 1H), 10.9 (brs, 2H).

Reference Example 19

5-fluoro-N-methyl-1,3-dihydro-2H-isoindol-2-amine hydrochloride

Step A tert-butyl (5-fluoro-1,3-dihydro-2H-isoindol-2-yl) methylcarbamate

Using 4-fluoro-ortho-xylene (20.05 g, 161.5 mmol) and according to the method of Reference Example 18, step A, the title compound (13.04 g, yield 30%) was obtained as a yellow bistered oil.
¹H-NMR (300 MHz, CDCl₃); δ (ppm) 1.41 (s, 9H), 3.08 (s, 3H), 4.39 (s, 2H), 4.43 (s, 2H), 6.85-6.95 (m, 2H), 7.07-7.13 (m, 1H).

Step B 5-fluoro-N-methyl-1,3-dihydro-2H-isoindol-2-amine hydrochloride

Using the compound (13.04 g, 48.97 mmol) of step A and according to the method of Reference Example 18, step B, the title compound (7.61 g, yield 77%) was obtained as a pale-yellow solid.
¹H-NMR (300 MHz, DMSO-d₆); δ (ppm) 2.77 (s, 3H), 4.39 (s, 2H), 4.42 (s, 2H), 7.09-7.17 (m, 1H), 7.20-7.24 (m, 1H), 7.34-7.40 (m, 1H), 10.9 (brs, 2H).

Reference Example 20

5-methoxy-N-methyl-1,3-dihydro-2H-isoindol-2-amine hydrochloride

Step A tert-butyl (5-methoxy-1,3-dihydro-2H-isoindol-2-yl) methylcarbamate

Using 4-methoxy-ortho-xylene (6.85 g, 50.3 mmol) and according to the method of Reference Example 18, step A, the title compound (2.11 g, yield 15%) was obtained as a brown oil.
¹H-NMR (300 MHz, CDCl₃); δ (ppm) 1.41 (s, 9H), 3.08 (s, 3H), 3.78 (s, 3H), 4.36 (brs, 2H), 4.41 (brs, 2H), 6.7-6.8 (m, 2H), 7.06 (d, J=8.1, 1H).

Step B 5-methoxy-N-methyl-1,3-dihydro-2H-isoindol-2-amine hydrochloride

Using the compound (2.10 g, 7.54 mmol) obtained in step A and according to the method of Reference Example 18, step B, the title compound (1.23 g, yield 76%) was obtained as a pale-yellow solid.
¹H-NMR (300 MHz, DMSO-d₆); δ (ppm) 2.76 (s, 3H), 3.74 (s, 3H), 4.36 (brs, 2H), 4.40 (brs, 2H), 6.86 (d, J=8.4, 1H), 6.93 (s, 1H), 7.24 (d, J=8.3, 1H), 10.9 (brs, 2H).

Reference Example 21

5-cyano-N-methyl-1,3-dihydro-2H-isoindol-2-amine hydrochloride

Step A tert-butyl (5-cyano-1,3-dihydro-2H-isoindol-2-yl) methylcarbamate

Using 4-bromo-ortho-xylene (5.88 g, 31.77 mmol) and according to the method of Reference Example 18, step A, 5-bromo-1,3-dihydro-2H-isoindol-2-yl(methyl)carbamate (2.52 g) was obtained as a crude brown oil. This oil, zinc cyanide (734 mg, 6.25 mmol), and tetrakis(triphenylphosphine)palladium(0) (1.74 g) were added to N,N-dimethylformamide (25 ml), and the reaction mixture was stirred with heating at 100° C. for 7 hr. The reaction mixture was cooled, diluted with ethyl acetate, and the insoluble material was filtered off. The filtrate was washed with aqueous ammonia and saturated brine, and dried over anhydrous magnesium sulfate. The insoluble material was filtered off, and the solution was concentrated under reduced pressure. The obtained oil was purified by silica gel column chromatography (ethyl acetate-hexane) to give the title compound (390 mg, yield 4%) as a colorless oil.

$^1$H-NMR (300 MHz, CDCl$_3$); δ (ppm) 1.41 (s, 9H), 3.09 (s, 3H), 4.49 (brs, 2H), 4.50 (brs, 2H), 7.27 (d, J=7.7, 1H), 7.46 (s, 1H), 7.50 (d, J=7.7, 1H).

Step B

5-cyano-N-methyl-1,3-dihydro-2H-isoindol-2-amine hydrochloride

Using the compound (370 mg, 1.35 mmol) of step A and according to the method of Reference Example 18, step B, the title compound (200 mg, yield 70%) was obtained as a gray solid.

$^1$H-NMR (300 MHz, DMSO-d$_6$); δ (ppm) 2.77 (s, 3H), 4.49 (brs, 2H), 4.52 (brs, 2H), 7.57 (d, J=7.8, 1H), 7.78 (d, J=7.8, 1H), 7.84 (s, 1H), 11.11 (brs, 2H).

Reference Example 22

N-ethyl-1,3-dihydro-2H-isoindol-2-amine hydrochloride

Step A tert-butyl 1-ethylhydrazinecarboxylate

According to the method described in Journal of Heterocyclic Chemistry, 2000, 37 (1), 47-55, the title compound (64.8 g) was obtained as a colorless oil from N-ethylhydrazine (25.0 g).

$^1$H-NMR (300 MHz, CDCl$_3$); δ (ppm) 1.12 (t, J=7.2, 3H), 1.47 (s, 9H), 3.06 (q, J=7.2, 2H), 3.96 (brs, 2H).

Step B tert-butyl 1,3-dihydro-2H-isoindol-2-yl(ethyl)carbamate

Using the compound (6.0 g, 38 mmol) obtained in step A and according to the method of Reference Example 17, step B, the title compound (6.5 g, yield 66%) was obtained as a crude pale-brown solid.

$^1$H-NMR (300 MHz, CDCl$_3$); δ (ppm) 1.21 (t, J=6.9, 3H), 1.38 (s, 9H), 3.47 (q, J=6.9, 2H), 4.48 (s, 4H), 7.12-7.26 (m, 4H).

Step C

N-ethyl-1,3-dihydro-2H-isoindol-2-amine hydrochloride

Using the compound (6.10 g, 23 mmol) obtained in step B and according to the method of Reference Example 18, step B, the title compound (4.15 g, yield 90%) was obtained as a gray solid.

$^1$H-NMR (300 MHz, DMSO-d$_6$); δ (ppm) 1.26 (brs, 3H), 3.19 (brs, 2H), 4.43 (s, 4H), 7.3-7.4 (m, 4H), 10.9 (brs, 2H).

Reference Example 23

N-methylindan-2-amine hydrochloride

Step A tert-butyl (2,3-dihydro-1H-inden-2-yl)carbamate

2-Aminoindane (3.10 g, 23.3 mmol) was dissolved in dichloromethane (50 ml), di-tert-butyl-dicarbonate (5.20 g, 23.8 mmol) and triethylamine (5 ml) were added under ice-cooling, and the mixture was stirred at room temperature for 2 hr. The reaction mixture was diluted with ethyl acetate-hexane=1:1 mixed solvent (100 ml), and the organic layer was washed with 10% aqueous citric acid solution, saturated aqueous sodium hydrogen carbonate and saturated brine and dried over anhydrous magnesium sulfate. The insoluble material was filtered off, and the solution was concentrated under reduced pressure to give the title compound (4.68 g, yield 86%) as a colorless oil.

$^1$H-NMR (300 MHz, CDCl$_3$); δ (ppm) 1.45 (s, 9H), 2.78 (dd, J=4.8, 15.9, 2H), 3.28 (dd, J=7.1, 15.9, 2H), 4.3-4.6 (broad, 1H), 4.6-4.9 (broad, 1H), 7.15-7.24 (m, 4H).

Step B

N-methylindan-2-amine hydrochloride

Lithium aluminum hydride (2.56 g, 67.46 mmol) and the compound (4.63 g, 19.84 mmol) obtained in step A were added to tetrahydrofuran (100 ml), and the mixture was heated under reflux for 3 hr. The reaction mixture was ice-cooled, and water (2.56 ml), 15% aqueous sodium hydroxide solution (2.56 ml), water (7.68 ml) and anhydrous magnesium sulfate were successively added with stirring. The insoluble material was filtered off through celite, and the solution was concentrated under reduced pressure to give an oil (3.15 g). This was dissolved in diethyl ether (50 ml), 4N hydrochloric acid-dioxane solution (6 ml) was added, and the precipitated solid was filtered, washed with diethyl ether and dried under reduced pressure to give the title compound (3.53 g, yield 97%) as a colorless solid.

$^1$H-NMR (300 MHz, DMSO-d$_6$); δ (ppm) 2.58 (t, J=5.3, 3H), 3.09 (dd, J=6.6, 16.2, 2H), 3.28 (dd, J=8.0, 16.4, 2H), 3.9-4.0 (m, 1H), 7.18-7.23 (m, 2H), 7.24-7.29 (m, 2H), 9.25 (brs, 2H).

Reference Example 24

N-ethylindan-2-amine hydrochloride

Step A

N-(2,3-dihydro-1H-inden-2-yl)acetamide

2-Aminoindane (1.07 g, 8.03 mmol) was dissolved in dichloromethane (20 ml), and acetic anhydride (0.76 ml, 8.04 mmol) and triethylamine (1.7 ml) were added under ice-cooling, and the mixture was stirred at room temperature for 50 min. The reaction mixture was diluted with ethyl acetate-hexane=1:1 mixed solvent (80 ml), and the organic layer was washed with diluted hydrochloric acid, saturated aqueous sodium hydrogen carbonate and saturated brine and dried over anhydrous magnesium sulfate. The insoluble material was filtered off, and the solution was concentrated under reduced pressure. The obtained solid was washed with diethyl ether-hexane-1:5 mixed solvent, and dried under reduced pressure to give the title compound (961 mg, yield 68%) as a pale-yellow solid.

$^1$H-NMR (300 MHz, CDCl$_3$); δ (ppm) 1.94 (s, 3H), 2.80 (dd, J=3.9, 16.2, 2H), 3.31 (dd, J=3.9, 16.2, 2H), 4.7-4.8 (m, 1H), 5.70 (brs, 1H), 7.15-7.30 (m, 4H).

Step B

N-ethylindan-2-amine hydrochloride

Using the compound (960 mg, 5.48 mmol) obtained in step A and according to the method of Reference Example 23, step B, the title compound (1.01 g, yield 94%) was obtained as a colorless solid.

$^1$H-NMR (300 MHz, DMSO-d$_6$); δ (ppm) 1.24 (t, J=7.2, 3H), 2.9-3.2 (m, 4H), 3.2-3.4 (m, 2H), 3.9-4.1 (m, 1H), 7.1-7.3 (m, 4H), 9.1-9.5 (broad, 2H).

Reference Example 25

5,N-dimethylindan-2-amine hydrochloride

Step A 6-methyl-1H-inden-1,2(3H)-dione 2-oxime

6-Methylindan-1-one (5.00 g, 34.2 mmol) and 4N hydrochloric acid-dioxane solution (2 ml) were added to ethanol (30 ml), isoamyl nitrite (5.1 ml, (37.6 mmol) was added under ice-cooling, and the mixture was stirred at room temperature for 3 hr. The precipitated solid was collected by filtration and washed with diisopropyl ether to give the title compound (5.36 g, yield 89%) as a pale-yellow solid.

$^1$H-NMR (300 MHz, DMSO-d$_6$); δ (ppm) 2.39 (s, 3H), 3.72 (s, 2H), 7.45-7.60 (m, 3H), 12.59 (s, 1H).

Step B 6-methyl-1H-inden-1,2(3H)-dione 2-{O-[tert-butyl (dimethyl)silyl]oxime}

To N,N-dimethylformamide (50 ml) were added at room temperature the compound (4.36 g, 24.9 mmol) obtained in step A, imidazole (5.10 g, 74.7 mmol) and tert-butyldimethylsilyl chloride (5.60 g, 37.4 mmol), and the mixture was stirred at 95° C. for 2 hr. After cooling to room temperature, water was added to the reaction solution with stirring and the precipitated solid was filtered, washed with water, and dried under reduced pressure to give the title compound (6.00 g, yield 83%) as a pale-bistered solid.

$^1$H-NMR (300 MHz, DMSO-d$_6$); δ (ppm) 0.25 (s, 6H), 0.96 (s, 9H), 2.40 (s, 3H), 3.80 (s, 2H), 7.48-7.62 (m, 3H).

Step C ethyl (1-hydroxy-6-methyl-2,3-dihydro-1H-inden-2-yl)carbamate

The compound (6.00 g, 20.7 mmol) obtained in step B was dissolved in tetrahydrofuran (100 ml), and the mixture was stirred with heating at 63° C. At the same temperature, 1 mol/L borane-tetrahydrofuran complex/tetrahydrofuran solution (41.4 ml, 41.4 mmol) was slowly added dropwise. The mixture was stirred at the same temperature for 2.5 hr, cooled to room temperature and methanol was slowly added dropwise with stirring. The reaction solution was concentrated under reduced pressure, methanol and toluene were added again, and the solution was concentrated under reduced pressure. This was repeated 4 times, and the obtained colorless solid and triethylamine (3.5 ml, 24.8 mmol) were dissolved in dichloromethane (50 ml) and the mixture was stirred under ice-cooling. Then, ethyl chloroformate (2.2 ml, 22.8 mmol) was added, and the mixture was stood at room temperature overnight. The reaction mixture was diluted with water and extracted with ethyl acetate. The organic layer was washed with diluted hydrochloric acid and saturated brine, and dried over anhydrous magnesium sulfate. The solution was concentrated under reduced pressure, and the obtained oil was purified by silica gel column chromatography (methanol-chloroform) to give the title compound (3.30 g, yield 67%) as a colorless oil.

$^1$H-NMR (300 MHz, DMSO-d$_6$); δ (ppm) 1.21 (t, J=7.2, 3H), 2.33 (s, 3H), 2.76-3.05 (m, 2H), 4.00-4.17 (m, 3H), 4.83 (t, J=5.8, 1H), 5.20 (d, J=5.8, 1H), 6.75 (d, J=7.3, 1H), 7.02-7.19 (m, 3H).

Step D ethyl (5-methyl-2,3-dihydro-1H-inden-2-yl)carbamate

With stirring at room temperature, the compound (3.30 g, 13.9 mmol) obtained in step C, triethylsilane (4.4 ml, (27.8 mmol) and boron trifluoride-diethyl ether complex (3.4 ml, 27.8 mmol) dissolved in 1,2-dichloroethane (20 ml) were added to 1,2-dichloroethane (90 ml), and the mixture was stirred at 83° C. for 1 hr. After cooling to room temperature, the reaction mixture was diluted with water, and extracted with dichloromethane. The organic layer was washed with diluted aqueous sodium hydroxide solution, diluted hydrochloric acid and saturated brine, and dried over anhydrous magnesium sulfate. The solution was concentrated under reduced pressure to give the title compound (2.76 g, yield 91%) as a pale-yellow solid.

$^1$H-NMR (300 MHz, DMSO-d$_6$); δ (ppm) 1.18 (t, J=6.9, 3H), 2.25 (s, 3H), 2.63-2.78 (m, 2H), 3.01-3.12 (m, 2H), 3.92-4.05 (m, 2H), 4.13-4.28 (m, 1H), 6.93 (d, J=7.8, 1H), 6.99 (s, 1H), 7.05 (d, J=7.5, 1H), 7.41 (d, J=6.6, 1H).

Step E

5,N-dimethylindan-2-amine hydrochloride

Using the compound (2.76 g, 12.6 mmol) obtained in step D and according to the method of Reference Example 23, step B, the title compound (1.52 g, yield 61%) was obtained as a pale-yellow solid.

$^1$H-NMR (300 MHz, DMSO-d$_6$); δ (ppm) 2.27 (s, 3H), 2.57 (t, J=5.4, 3H), 2.91-3.12 (m, 2H), 3.15-3.29 (m, 2H), 3.82-4.00 (m, 1H), 7.01 (d, J=7.5, 1H), 7.07 (s, 1H), 7.14 (d, J=7.5, 1H), 9.18 (brs, 2H).

Reference Example 26

4,N-dimethylindan-2-amine hydrochloride

Step A 4-methyl-1H-inden-1,2(3H)-dione 2-oxime

Using 4-methylindan-1-one (5.00 g, 34.2 mmol) and according to the method of Reference Example 25, step A, the title compound (4.03 g, yield 67%) was obtained as a pale-bistered solid.

¹H-NMR (300 MHz, DMSO-d₆); δ (ppm) 2.35 (s, 3H), 3.69 (s, 2H), 7.39 (t, J=7.5, 1H), 7.52-7.60 (m, 2H), 12.66 (s, 1H).

Step B 4-methyl-1H-inden-1,2(3H)-dione 2-{O-[tert-butyl (dimethyl)silyl]oxime}

Using the compound (4.03 g, 23.0 mmol) obtained in step A and according to the method of Reference Example 25, step B, the title compound (6.24 g, yield 94%) was obtained as a pale-bistered solid.
¹H-NMR (300 MHz, CDCl₃); δ (ppm) 0.27 (s, 6H), 1.04 (s, 9H), 2.38 (s, 3H), 3.70 (s, 2H), 7.34 (t, J=7.5, 1H), 7.46 (d, J=7.5, 1H), 7.73 (d, J=7.5, 1H).

Step C ethyl (1-hydroxy-4-methyl-2,3-dihydro-1H-inden-2-yl)carbamate

Using the compound (6.24 g, 21.6 mmol) obtained in step B and according to the method of Reference Example 25, step C, the title compound (2.73 g, yield 54%) was obtained as a pale-bistered solid.
¹H-NMR (300 MHz, DMSO-d₆); δ (ppm) 1.22 (t, J=7.2, 3H), 2.24 (s, 3H), 2.71-2.83 (m, 1H), 2.94-3.10 (m, 1H), 3.99-4.16 (m, 3H), 4.87 (t, J=6.0, 1H), 5.20 (d, J=6.0, 1H), 6.73 (d, J=7.2, 1H), 7.05-7.21 (m, 3H).

Step D ethyl (4-methyl-2,3-dihydro-1H-inden-2-yl)carbamate

Using the compound (2.73 g, 11.6 mmol) obtained in step C and according to the method of Reference Example 25, step D, the title compound (2.36 g, yield 93%) was obtained as a pale-bistered solid.
¹H-NMR (300 MHz, CDCl₃); δ (ppm) 1.23 (t, J=6.9, 3H), 2.24 (s, 3H), 2.65-2.85 (m, 2H), 3.18-3.33 (m, 2H), 4.05-4.19 (m, 2H), 4.50 (brs, 1H), 4.88 (brs, 1H), 6.93-7.12 (m, 3H).

Step E

4,N-dimethylindan-2-amine hydrochloride

Using the compound (2.36 g, 10.8 mmol) obtained in step D and according to the method of Reference Example 23, step B, the title compound (1.85 g, yield 87%) was obtained as a pale-bistered solid.
¹H-NMR (300 MHz, DMSO-d₆); δ (ppm) 2.22 (s, 3H), 2.57 (t, J=5.3, 3H), 2.95-3.32 (m, 4H), 3.85-3.96 (m, 1H), 6.95-7.14 (m, 3H), 9.47 (brs, 2H).

Reference Example 27

5-fluoro-N-methylindan-2-amine hydrochloride

Step A 5-fluoro-1H-inden-1,2(3H)-dione 2-oxime

Using 5-fluoroindan-1-one (5.00 g, 33.3 mmol) and according to the method of Reference Example 25, step A, the title compound (4.45 g, yield 75%) was obtained as a pale-bistered solid.

¹H-NMR (300 MHz, DMSO-d₆); δ (ppm) 3.78 (s, 2H), 7.21-7.37 (m, 1H), 7.40-7.51 (m, 1H), 7.75-7.90 (m, 1H), 12.67 (s, 1H).

Step B 5-fluoro-1H-inden-1,2(3H)-dione 2-{O-[tert-butyl (dimethyl)silyl]oxime}

Using the compound (4.45 g, 24.8 mmol) obtained in step A and according to the method of Reference Example 25, step B, the title compound (5.15 g, yield 71%) was obtained as a pale-yellow solid.
¹H-NMR (300 MHz, CDCl₃); δ (ppm) 0.27 (s, 6H), 0.97 (s, 9H), 3.82 (s, 2H), 7.02-7.18 (m, 2H), 7.85-7.98 (m, 1H).

Step C ethyl (1-hydroxy-5-fluoro-2,3-dihydro-1H-inden-2-yl)carbamate

Using the compound (5.15 g, 17.6 mmol) obtained in step B and according to the method of Reference Example 25, step C, the title compound (1.84 g, yield 44%) was obtained as a colorless solid.
¹H-NMR (300 MHz, DMSO-d₆); δ (ppm) 1.18 (t, J=7.2, 3H), 2.85-3.04 (m, 2H), 3.95-4.15 (m, 3H), 4.81 (d, J=5.4, 1H), 5.23 (brs, 1H), 6.77 (d, J=6.9, 1H), 6.96-7.07 (m, 2H), 7.35 (dd, J=5.1, 8.4, 1H).

Step D 5-fluoro-N-methylindan-2-amine hydrochloride

Using the compound (1.84 g, 7.69 mmol) obtained in step C and according to the method of Reference Example 25, step D, Reference Example 23, step B, the title compound (1.06 g, yield 68%) was obtained as a pale-bistered solid.
¹H-NMR (300 MHz, DMSO-d₆); δ (ppm) 2.57 (s, 3H), 3.09 (dt, J=6.6, 16.2, 2H), 3.20-3.33 (m, 2H), 3.90-4.01 (m, 1H), 6.95-7.05 (m, 1H), 7.09-7.14 (m, 1H), 7.28 (dd, J=6.6, 8.1, 1H), 9.35 (brs, 2H).

Reference Example 28

5-chloro-N-methylindan-2-amine hydrochloride

Step A 5-chloro-1H-inden-1,2(3H)-dione 2-oxime

Using 5-chloroindan-1-one (5.00 g, 30.0 mmol) and according to the method of Reference Example 25, step A, the title compound (4.67 g, yield 80%) was obtained as a pale-bistered solid.
¹H-NMR (300 MHz, DMSO-d₆); δ (ppm) 3.78 (s, 2H), 7.54 (d, J=7.8, 1H), 7.74-7.78 (m, 2H), 12.74 (s, 1H).

Step B ethyl (1-hydroxy-5-chloro-2,3-dihydro-1H-inden-2-yl)carbamate

Using the compound (4.45 g, 24.8 mmol) obtained in step A and according to the methods of Reference Example 25, steps B and C, the title compound (2.78 g, yield 39%) was obtained as a bistered oil.

¹H-NMR (300 MHz, DMSO-d₆); δ (ppm) 1.17 (t, J=7.2, 3H), 2.84-3.02 (m, 2H), 3.95-4.15 (m, 3H), 4.82 (t, J=5.1, 1H), 5.30 (d, J=5.4, 1H), 6.78 (d, J=7.5, 1H), 7.21-7.36 (m, 3H).

Step C ethyl (5-chloro-2,3-dihydro-1H-inden-2-yl)carbamate

Using the compound (2.78 g, 10.87 mmol) obtained in step B and according to the method of Reference Example 25, step D, the title compound (2.31 g, yield 89%) was obtained as a pale-yellow solid.

¹H-NMR (300 MHz, CDCl₃); δ (ppm) 1.20-1.28 (m, 3H), 2.70-2.85 (m, 2H), 3.15-3.32 (m, 2H), 4.02-4.21 (m, 2H), 4.43-4.52 (m, 1H), 4.85 (brs, 1H), 7.11-7.22 (m, 3H).

Step D

5-chloro-N-methylindan-2-amine hydrochloride

Using the compound (2.31 g, 9.64 mmol) obtained in step C and according to the method of Reference Example 23, step B, the title compound (1.79 g, yield 85%) was obtained as a pale-green solid.

¹H-NMR (300 MHz, DMSO-d₆); δ (ppm) 2.56 (t, J=5.3, 3H), 3.05-3.34 (m, 4H), 3.89-4.00 (m, 1H), 7.20-7.37 (m, 3H), 9.43 (brs, 2H).

Reference Example 29

5-methoxy-N-methylindan-2-amine hydrochloride

Step A

5-methoxy-1H-inden-1,2(3H)-dione 2-oxime

Using 5-methoxyindan-1-one (5.00 g, 30.8 mmol) and according to the method of Reference Example 25, step A, the title compound (5.35 g, yield 91%) was obtained as a bistered solid.

¹H-NMR (300 MHz, DMSO-d₆); δ (ppm) 3.73 (s, 2H), 3.89 (s, 3H), 7.02 (dd, J=2.1, 8.7, 1H), 7.15 (d, J=1.8, 1H), 7.69 (d, J=8.7, 1H), 12.45 (s, 1H).

Step B

5-methoxy-1H-inden-1,2(3H)-dione 2-{O-[tert-butyl(dimethyl)silyl]oxime}

Using the compound (3.40 g, 17.8 mmol) obtained in step A and according to the method of Reference Example 25, step B, the title compound (4.91 g, yield 90%) was obtained as a pale-bistered solid.

¹H-NMR (300 MHz, DMSO-d₆); δ (ppm) 0.01 (s, 6H), 0.72 (s, 9H), 3.56 (s, 2H), 3.66 (s, 3H), 6.80 (dd, J=2.1, 8.4, 1H), 6.93 (d, J=1.8, 1H), 7.49 (d, J=8.7, 1H).

Step C ethyl (1-hydroxy-5-methoxy-2,3-dihydro-1H-inden-2-yl)carbamate

Using the compound (4.91 g, 16.1 mmol) obtained in step B and according to the method of Reference Example 25, step C, the title compound (3.05 g, yield 81%) was obtained as a pale-yellow solid.

¹H-NMR (300 MHz, DMSO-d₆); δ (ppm) 1.17 (t, J=7.2, 3H), 2.79-3.00 (m, 2H), 3.72 (s, 3H), 3.95-4.10 (m, 3H), 4.75 (t, J=5.4, 1H), 5.07 (d, J=5.4, 1H), 6.72-6.80 (m, 3H), 7.23 (d, J=8.4, 1H).

Step D ethyl (5-methoxy-2,3-dihydro-1H-inden-2-yl)carbamate

Using the compound (3.05 g, 13.0 mmol) obtained in step C and according to the method of Reference Example 25, step D, the title compound (2.35 g, yield 77%) was obtained as a pale-bistered solid.

¹H-NMR (300 MHz, DMSO-d₆); δ (ppm) 1.16 (t, J=6.9, 3H), 2.71 (dt, J=6.9, 16.2, 2H), 3.06 (dt, J=7.5, 13.8, 2H), 3.70 (s, 3H), 3.99 (q, J=7.2, 2H), 4.23 (q, J=7.2, 1H), 6.69 (dd, J=2.4, 8.4, 1H), 6.77 (s, 1H), 7.07 (d, J=8.4, 1H), 7.39 (d, J=6.3, 1H).

Step E

5-methoxy-N-methylindan-2-amine hydrochloride

Using the compound (2.35 g, 9.99 mmol) obtained in step D and according to the method of Reference Example 23, step B, the title compound (1.98 g, yield 93%) was obtained as a pale-bistered solid.

¹H-NMR (300 MHz, DMSO-d₆); δ (ppm) 2.56 (t, J=5.4, 3H), 3.03-3.29 (m, 4H), 3.72 (s, 3H), 3.88-3.95 (m, 1H), 6.76 (dd, J=2.1, 8.1, 1H), 6.85 (d, J=1.8, 1H), 7.15 (d, J=8.4, 1H), 9.40 (brs, 2H).

Reference Example 30

5,6-dimethoxy-N-methylindan-2-amine hydrochloride

Step A

5,6-dimethoxy-1H-inden-1,2(3H)-dione 2-oxime

Using 5,6-dimethoxyindan-1-one (10.0 g, 52.0 mmol) and according to the method of Reference Example 25, step A, the title compound (11.64 g, yield 100%) was obtained as a pale-bistered solid.

¹H-NMR (300 MHz, DMSO-d₆); δ (ppm) 3.66 (s, 2H), 3.83 (s, 3H), 3.90 (s, 3H), 7.18 (s, 1H), 7.19 (s, 1H), 12.40 (s, 1H).

Step B

5,6-dimethoxy-1H-inden-1,2(3H)-dione 2-{O-[tert-butyl(dimethyl)silyl]oxime}

Using the compound (11.64 g, 52.0 mmol) obtained in step A and according to the method of Reference Example 25, step B, the title compound (16.70 g, yield 96%) was obtained as a pale-yellow solid.

¹H-NMR (300 MHz, CDCl₃); δ (ppm) 0.29 (s, 6H), 0.98 (s, 9H), 3.75 (s, 2H), 3.93 (s, 3H), 3.99 (s, 3H), 6.90 (s, 1H), 7.32 (s, 1H).

Step C ethyl (5,6-dimethoxy-2,3-dihydro-1H-inden-2-yl)carbamate

Using the compound (10.0 g, 29.8 mmol) obtained in step B and according to the methods of Reference Example 25, steps C and D, the title compound (3.31 g, yield 42%) was obtained as a bistered solid.

$^1$H-NMR (300 MHz, CDCl$_3$); δ (ppm) 1.23 (t, J=6.9, 3H), 2.73 (dd, J=4.8, 15.6, 2H), 3.24 (dd, J=7.2, 15.9, 2H), 3.85 (s, 6H), 4.11 (q, J=6.9, 2H), 4.50 (brs, 1H), 4.88 (brs, 1H), 6.73 (s, 2H).

Step D

5,6-dimethoxy-N-methylindan-2-amine hydrochloride

Using the compound (3.31 g, 12.48 mmol) obtained in step C and according to the method of Reference Example 23, step B, the title compound (3.03 g, yield 100%) was obtained as a pale-bistered solid.

$^1$H-NMR (300 MHz, DMSO-d$_6$); δ (ppm) 2.95-3.06 (m, 2H), 3.19 (dd, J=7.8, 15.9, 2H), 3.72 (s, 6H), 3.83-3.98 (m, 1H), 6.87 (s, 2H), 9.22 (brs, 2H).

The compounds of Reference Examples 1-30 are shown below.

TABLE 1

| Reference Example | Structural Formula |
|---|---|
| 1 | [H$_2$N-CH$_2$CH$_2$-N(CH$_3$)-C(=O)-O-C(CH$_3$)$_3$ · HCl] |
| 2 | [H$_2$N-CH$_2$CH$_2$-N(Et)-C(=O)-O-C(CH$_3$)$_3$] |
| 3 | [H$_2$N-CH$_2$CH$_2$-N(iPr)-C(=O)-O-C(CH$_3$)$_3$] |
| 4 | [H$_2$N-(CH$_2$)$_3$-N(iPr)-SO$_2$-C$_6$H$_4$-2-NO$_2$] |
| 5 | [H$_2$N-(CH$_2$)$_3$-N(CH$_3$)-SO$_2$-C$_6$H$_4$-2-NO$_2$ · HCl] |

TABLE 1-continued

| Reference Example | Structural Formula |
|---|---|
| 6 | [H$_2$N-CH$_2$CH$_2$-N(CH$_3$)-SO$_2$-C$_6$H$_4$-2-NO$_2$] |
| 7 | [H$_2$N-CH$_2$CH$_2$-N(iPr)-SO$_2$-C$_6$H$_4$-2-NO$_2$] |
| 8 | [H$_2$N-CH$_2$CH$_2$-N-pyrrolidinyl-2-CH$_2$OH] |
| 9 | [4-aminopiperidine-1-carboxylic acid tert-butyl ester · HCl] |
| 10 | [3-aminopiperidine-1-carboxylic acid tert-butyl ester · HCl] |
| 11 | [3-aminopyrrolidine-1-carboxylic acid tert-butyl ester · HCl] |
| 12 | [2-(aminomethyl)pyrrolidine-1-carboxylic acid tert-butyl ester · HCl] |
| 13 | [2-(aminomethyl)pyrrolidine-1-carboxylic acid tert-butyl ester · HCl] |
| 14 | [H$_2$N-CH$_2$CH$_2$-N(CH$_2$CF$_3$)-C(=O)CF$_3$ · HCl] |

TABLE 1-continued

| Reference Example | Structural Formula |
|---|---|
| 15 | H2N-CH2CH2-N(Et)-C(=O)-CF3 · HCl |
| 16 | H2N-CH2CH2-NH-C(CH3)3 |
| 17 | Me-NH-(isoindoline-2-yl) · HCl |
| 18 | Me-NH-(4-fluoroisoindolin-2-yl) · HCl |
| 19 | Me-NH-(5-fluoroisoindolin-2-yl) · HCl |
| 20 | Me-NH-(5-methoxyisoindolin-2-yl) · HCl |
| 21 | Me-NH-(5-cyanoisoindolin-2-yl) · HCl |
| 22 | Et-NH-(isoindolin-2-yl) · HCl |
| 23 | Me-NH-(indan-2-yl) · HCl |
| 24 | Et-NH-(indan-2-yl) · HCl |
| 25 | Me-NH-(5-methylindan-2-yl) · HCl |
| 26 | Me-NH-(4-methylindan-2-yl) · HCl |
| 27 | Me-NH-(5-fluoroindan-2-yl) · HCl |
| 28 | Me-NH-(5-chloroindan-2-yl) · HCl |
| 29 | Me-NH-(5-methoxyindan-2-yl) · HCl |
| 30 | Me-NH-(5,6-dimethoxyindan-2-yl) · HCl |

Reference Example 31

3,4-dichloro-N-methylaniline hydrochloride

Step A tert-butyl (3,4-dichlorophenyl)carbamate

Using 3,4-dichloroaniline (5.00 g, 30.9 mmol) and according to the method of Reference Example 23, step A, the title compound (4.62 g, yield 59%) was obtained as a colorless solid.
$^1$H-NMR (300 MHz, DMSO-$d_6$); δ (ppm) 1.47 (s, 9H), 7.38 (dd, J=2.3, 8.8, 1H), 7.50 (d, J=8.9, 1H), 7.78 (d, J=2.2, 1H), 9.71 (s, 1H).

Step B 3,4-dichloro-N-methylaniline hydrochloride

Using the compound (4.62 g, 17.6 mmol) obtained in step A and according to the method of Reference Example 23, step B, the title compound (3.38 g, yield 100%) was obtained as a colorless solid.
$^1$H-NMR (300 MHz, DMSO-$d_6$); δ (ppm) 2.67-2.71 (m, 3H), 6.51-7.18 (m, 2H), 7.25-7.40 (m, 1H), 9.2-10.9 (broad, 2H).

Reference Example 32

N-methylindane-5-amine hydrochloride

Step A tert-butyl (2,3-dihydro-1H-inden-5-yl)carbamate

Using 5-aminoindane (4.10 g, 30.9 mmol) and according to the method of Reference Example 23, step A, the title compound (6.98 g, yield 97%) was obtained as a bistered solid.
$^1$H-NMR (300 MHz, DMSO-$d_6$); δ (ppm) 1.63 (s, 9H), 2.08-2.21 (m, 2H), 2.90-2.99 (m, 4H), 7.23 (d, J=8.1, 1H), 7.32 (d, J=8.1, 1H), 7.53 (s, 1H), 9.34 (s, 1H).

Step B

N-methylindan-5-amine hydrochloride

Using the compound (6.98 g, 29.9 mmol) obtained in step A and according to the method of Reference Example 23, step B, the title compound (3.91 g, yield 71%) was obtained as a bistered solid.
$^1$H-NMR (300 MHz, DMSO-$d_6$); δ (ppm) 1.97-2.09 (m, 2H), 2.79-2.93 (m, 4H), 2.86 (s, 3H), 7.23-7.41 (m, 3H), 11.10 (brs, 2H).

Reference Example 33 trans-N-methyl-4-phenylcyclohexanamine hydrochloride

Step A tert-butyl(trans-4-phenylcyclohexyl)carbamate

Using hydrochloride (3.42 g, 16.15 mmol) of trans-4-phenylcyclohexylamine, which is the compound described in Journal of Organic Chemistry, 1952, 17, 1017-1022 and triethylamine (4.8 ml, 34 mmol), and according to the method of Reference Example 23, step A, the title compound (4.06 g, yield 91%) was obtained as a colorless solid.
$^1$H-NMR (300 MHz, CDCl$_3$); δ (ppm) 1.2-1.4 (m, 2H), 1.46 (s, 9H), 1.5-1.6 (m, 2H), 1.9-2.0 (m, 2H), 2.1-2.2 (m, 2H), 2.4-2.5 (m, 1H), 3.49 (brs, 1H), 4.42 (brs, 1H), 7.15-7.21 (m, 3H), 7.25-7.32 (m, 2H).

Step B trans-N-methyl-4-phenylcyclohexanamine hydrochloride

Using the compound (3.92 g, 14.23 mmol) obtained in step A and according to the method of Reference Example 23, step B, the title compound (3.11 g, yield 97%) was obtained as a colorless solid.
$^1$H-NMR (300 MHz, DMSO-$d_6$); δ (ppm) 1.4-1.6 (m, 4H), 1.8-2.0 (m, 2H), 2.0-2.2 (m, 2H), 2.4-2.6 (m, 1H), 2.54 (t, J=5.4, 3H), 2.9-3.1 (m, 1H), 7.16-7.32 (m, 5H), 8.89 (brs, 2H).

Reference Example 34

N-methyl-1,2,3,4-tetrahydronaphthalen-2-amine hydrochloride

Step A tert-butyl (1,2,3,4-tetrahydronaphthalen-2-yl)carbamate

Using hydrochloride (2.50 g, 13.61 mmol) of 1,2,3,4-tetrahydro-2-naphthylamine, which is the compound described in Journal of Medicinal Chemistry, 1980, 23, 745-749 and triethylamine (2.01 ml, 15.0 mmol), and according to the method of Reference Example 23, step A, the title compound (3.06 g, yield 91%) was obtained as a pale-bistered solid.
$^1$H-NMR (300 MHz, CDCl$_3$); δ (ppm) 1.28 (s, 9H), 1.65-1.80 (m, 1H), 1.95-2.15 (m, 1H), 2.62 (dd, J=8.3, 16.3, 1H), 2.84-2.90 (m, 2H), 3.12 (dd, J=5.0, 16.3, 1H), 3.98 (brs, 1H), 4.59 (brs, 1H), 7.04-7.15 (m, 4H).

Step B

N-methyl-1,2,3,4-tetrahydronaphthalen-2-amine hydrochloride

Using the compound (3.00 g, 12.13 mmol) obtained in step A and according to the method of Reference Example 23, step B, the title compound (1.66 g, yield 69%) was obtained as a colorless solid.
$^1$H-NMR (300 MHz, DMSO-$d_6$); δ (ppm) 1.71-1.85 (m, 1H), 2.20-2.30 (m, 1H), 2.60 (s, 3H), 2.73-2.95 (m, 3H), 3.13-3.24 (m, 1H), 3.31-3.41 (m, 1H), 7.09-7.19 (m, 4H), 9.36 (brs, 2H).

Reference Example 35

N-methylpyrrolidin-1-amine hydrochloride

Step A tert-butyl methyl(pyrrolidin-1-yl)carbamate

To N,N-diisopropylethylamine (25 ml, 144 mmol) were added the compound (5.00 g, 34.2 mmol) obtained in Reference Example 17, step A and 1,4-dibromobutane (7.40 g, 34.2 mmol), and the mixture was stirred with heating at 130° C. for 5 hr. The reaction mixture was cooled, diluted with ethyl acetate, and the precipitated solid was filtered off, and the obtained solution was concentrated under reduced pressure. The obtained oil was purified by silica gel column chromatography (ethyl acetate-hexane) to give the title compound (3.43 g, yield 50%) as a colorless oil.

$^1$H-NMR (300 MHz, CDCl$_3$); δ (ppm) 1.47 (s, 9H), 1.73-1.82 (m, 4H), 2.96 (s, 3H), 2.97-3.21 (m, 4H).

Step B

N-methylpyrrolidin-1-amine hydrochloride

The compound (3.43 g, 17.1 mmol) obtained in step A was dissolved in ethyl acetate (40 ml), and 4N hydrochloric acid-ethyl acetate solution (20 ml, 80.0 mmol) was added at room temperature. The mixture was stood at the same temperature overnight, and the solvent was concentrated under reduced pressure to give the title compound (3.42 g, yield >100%) as a bistered oil.

$^1$H-NMR (300 MHz, DMSO-d$_6$); δ (ppm) 1.83-1.92 (m, 4H), 2.64 (s, 3H), 3.19 (brs, 4H), 5.4-6.8 (br, 2H).

Reference Example 36

N-methyl-2,5-dihydro-1H-pyrrol-1-amine hydrochloride

Step A tert-butyl 2,5-dihydro-1H-pyrrol-1-yl(methyl)carbamate

Using tert-butyl 1-methylhydrazinecarboxylate (5.00 g, 34.2 mmol) and (2Z)-1,4-dichloro-2-butene (3.6 ml, 34.2 mmol), and according to the method of Reference Example 35, step A, the title compound (5.85 g, yield 86%) was obtained as a yellow oil.

$^1$H-NMR (300 MHz, DMSO-d$_6$); δ (ppm) 1.39 (s, 9H), 2.90 (s, 3H), 3.77 (s, 4H), 5.74 (s, 2H).

Step B

N-methyl-2,5-dihydro-1H-pyrrol-1-amine hydrochloride

Using the compound (5.85 g, 29.5 mmol) obtained in step A and according to the method of Reference Example 35, step B, the title compound (3.07 g, yield 77%) as a red bistered solid.

$^1$H-NMR (300 MHz, DMSO-d$_6$); δ (ppm) 2.64 (s, 3H), 3.95 (s, 4H), 5.87 (s, 2H), 7.83 (brs, 2H).

Reference Example 37

(3aR,7aS)-N-methyloctahydro-2H-isoindol-2-amine

Step A (3aR,7aS)-nitrosooctahydro-1H-isoindole cis-Octahydro-1H-isoindole (1.81 g, 14.5 mmol), which is the compound described in Tetrahedron, 55 (1999) 9439-9454, was dissolved in 1N hydrochloric acid (16 ml), and the mixture was stirred under ice-cooling, sodium nitrite (6.22 g, 90.1 mmol) dissolved in water (20 ml) was gradually added, and the mixture was stirred at the same temperature for 3 hr. The reaction mixture was extracted with diethyl ether, and the organic layer was washed with saturated aqueous sodium hydrogen carbonate and saturated brine, and dried over anhydrous magnesium sulfate. Me insoluble material was filtered off, and the solution was concentrated under reduced pressure to give the title compound (1.22 g, yield 55%) as a bistered oil.

$^1$H-NMR (300 MHz, CDCl$_3$); δ (ppm) 1.3-1.7 (m, 8H), 2.3-2.4 (m, 2H), 3.4-3.6 (m, 2H), 4.1-4.3 (m, 2H).

Step B (3aR,7aS)-N-methyleneoctahydro-2H-isoindol-2-amine

To lithium aluminum hydride (0.89 g, 23 mmol) was added diethyl ether (50 ml), the compound (1.20 g, 7.78 mmol) of step A was added under ice-cooling with stirring, and the mixture was stirred at room temperature for 4 hr. The reaction mixture was ice-cooled, and water (0.89 ml), 15% aqueous sodium hydroxide solution (0.89 ml), water (2.67 ml) and sodium sulfate were successively added with stirring. The insoluble material was filtered off through celite, and the solution was concentrated under reduced pressure to give (3a,7a)-cis-octahydro-2H-isoindol-2-amine (1.14 g) as a crude pale-yellow oil. To the obtained oil were added water (10 ml) and acetic acid (0.49 ml), 37% formalin (0.7 ml) was added under ice-cooling with stirring, and the mixture was stirred for 10 min. To the reaction mixture was added diluted aqueous sodium hydroxide solution. The reaction mixture was extracted with diethyl ether, and the organic layer was washed with saturated brine, and dried over anhydrous magnesium sulfate. The insoluble material was filtered off, and the solution was concentrated under reduced pressure. The obtained oil was purified by silica gel column chromatography (ethyl acetate-hexane) to give the title compound (956 mg, yield 81%) as a colorless oil.

$^1$H-NMR (300 MHz, CDCl$_3$); δ (ppm) 1.3-1.6 (m, 8H), 2.1-2.3 (m, 2H), 3.16 (dd, J=5.3, 9.8, 2H), 3.29 (dd, J=6.8, 9.6, 2H), 5.84 (d, J=11.6, 1H), 5.93 (d, J=11.6, 1H).

Step C (3aR,7aS)-N-methyloctahydro-2H-isoindol-2-amine

To lithium aluminum hydride (204 mg, 5.38 mmol) was added diethyl ether (50 ml) and the mixture was stirred under ice-cooling. Thereto was added the compound (505 mg, 3.39 mmol) obtained in step B and the mixture was heated under reflux for 1 hr. The reaction mixture was ice-cooled, and water (0.204 ml), 15% aqueous sodium hydroxide solution (0.204 ml), water (0.615 ml) and sodium sulfate were successively added with stirring. The insoluble material was filtered off through celite, and the solution was concentrated under reduced pressure to give the title compound (436 mg, yield 85%) as a colorless oil.

$^1$H-NMR (300 MHz, CDCl$_3$); δ (ppm) 1.2-1.7 (m, 8H), 2.0-2.3 (m, 2H), 2.60 (s, 3H), 2.70 (dd, J=5.9, 9.8, 2H), 3.00 (dd, J=7.4, 9.8, 2H).

Reference Example 38

(3aR,6aS)-cis-N-methylhexahydrocyclopenta[c]pyrrol-2(1H)-amine

Step A (3aR,6aS)-cis-N-methylenehexahydrocyclopenta[c]pyrrol-2(1H)-amine

To 3-amino-3-azabicyclo[3.3.0]octane hydrochloride (2.50 g, 15.4 mmol) were added water (4.5 ml) and sodium acetate (1.26 g, 15.4 mmol) and the mixture was stirred under ice-cooling. Thereto was added 37% formalin (1.37 ml) and the mixture was stirred for 5 min. To the reaction mixture was added diluted aqueous sodium hydroxide solution. The reaction mixture was extracted with dichloromethane, and the organic layer was washed with saturated brine, and dried over anhydrous magnesium sulfate. The insoluble material was filtered off, and the solution was concentrated under reduced pressure. The obtained oil was purified by silica gel column chromatography (ethyl acetate-hexane) to give the title compound (2.12 g, yield>100%) as a colorless oil.

$^1$H-NMR (300 MHz, CDCl$_3$); δ (ppm) 1.4-1.9 (m, 6H), 2.6-2.7 (m, 2H), 2.87 (dd, J=3.6, 9.6, 2H), 3.23 (t, J=8.6, 2H), 6.15 (s, 2H).

Step B (3aR,6aS)-cis-N-methylhexahydrocyclopenta[c]pyrrol-2 (1H)-amine

Using the compound (2.12 g) obtained in step A and according to the method of Reference Example 37, step C, the title compound (2.53 g, yield>100%) was obtained as a colorless oil.

$^1$H-NMR (300 MHz, CDCl$_3$); δ (ppm) 1.4-1.7 (m, 6H), 2.19-2.23 (m, 2H), 2.51-2.60 (m, 2H), 2.61 (s, 3H), 3.00 (t, J=9.0, 2H).

Reference Example 39

N-methylmorpholin-4-amine

Step A

N-methylenemorpholin-4-amine

Using N-aminomorpholine (2.50 g, 24.5 mmol) and according to the method of Reference Example 38, step A, the title compound (1.89 g, yield 68%) was obtained as a pale-yellow oil.

$^1$H-NMR (300 MHz, CDCl$_3$); δ (ppm) 3.01 (t, J=4.9, 4H), 3.83 (t, J=4.9, 4H), 6.35 (d, J=10.9, 1H), 6.52 (d, J=10.9, 1H).

Step B

N-methylmorpholin-4-amine

Using the compound (0.90 g, 7.9 mmol) obtained in step A and according to the method of Reference Example 37, step C, the title compound (0.89 g, yield 98%) as a red-bistered oil.

$^1$H-NMR (300 MHz, CDCl$_3$); δ (ppm) 2.59 (s, 3H), 2.61-2.73 (m, 4H), 3.74 (t, J=4.7, 4H).

Reference Example 40

N-methylthiomorpholin-4-amine

Step A 4-nitrosothiomorpholine

Using thiomorpholine (11.53 g, 111.7 mmol) and according to the method of Reference Example 37, step A, the title compound (7.26 g, yield 49%) was obtained as a yellow solid.

$^1$H-NMR (300 MHz, CDCl$_3$); δ (ppm) 2.57-2.61 (m, 2H), 2.4-2.89 (m, 2H), 4.05-4.10 (m, 2H), 4.49-4.53 (m, 2H).

Step B

N-methylenethiomorpholin-4-amine

Using the compound (3.00 g, 22.7 mmol) obtained in step A and according to the method of Reference Example 37, step B, the title compound (3.38 g, yield>100%) was obtained as a yellow oil.

$^1$H-NMR (300 MHz, CDCl$_3$); δ (ppm) 2.74 (t, J=5.2, 4H), 3.39 (t, J=5.2, 4H), 6.34 (d, J=10.8, 1H), 6.49 (d, J=10.9, 1H).

Step C

N-methylthiomorpholin-4-amine

Using the compound (3.38 g) obtained in step B and according to the method of Reference Example 37, step C, the title compound (3.50 g, yield>100%) was obtained as a pale-yellow oil.

$^1$H-NMR (300 MHz, CDCl$_3$); δ (ppm) 2.57 (s, 3H), 2.75 (d, J=3.6, 4H), 2.92 (t, J=2.8, 4H).

Reference Example 41

N-methylpiperidin-1-amine

Step A

N-methylenepiperidin-1-amine

Using N-nitrosopiperidine (2.50 g, 21.9 mmol) and according to the method of Reference Example 37, step B, the title compound (1.63 g, yield 66%) was obtained as a pale-yellow oil.

$^1$H-NMR (300 MHz, CDCl$_3$); δ (ppm) 1.46-1.55 (m, 2H), 1.66-1.74 (m, 4H), 2.99 (t, J=5.6, 4H), 6.27 (d, J=11.1, 1H), 6.46 (d, J=11.1, 1H).

Step B

N-methylpiperidin-1-amine

Using the compound (1.63 g, 14.5 mmol) obtained in step A and according to the method of Reference Example 37, step C, the title compound (1.65 g, yield>100%) was obtained as a yellow oil.

$^1$H-NMR (300 MHz, CDCl$_3$); δ (ppm) 1.39-1.42 (m, 2H), 1.60-1.68 (m, 4H), 1.83-1.90 (m, 4H), 2.59 (s, 3H).

Reference Example 42

N-methyl-3,4-dihydroisoquinolin-2 (1H)-amine

Step A 2-nitroso-1,2,3,4-tetrahydroisoquinoline

Using 1,2,3,4-tetrahydroisoquinoline (5.0 g, 37.5 mmol) and according to the method of Reference Example 37, step A, the title compound (3.33 g, yield 55%) was obtained as a pale-yellow solid.

$^1$H-NMR (300 MHz, CDCl$_3$); δ (ppm) 3.11 (t, J=5.9, 2H), 4.55 (t, J=5.9, 2H), 4.84 (s, 2H), 7.15-7.30 (m, 4H).

Step B

Using N-methylene-3,4-dihydroisoquinolin-2 (1H)-amine and the compound (3.00 g, 18.5 mmol) obtained in step A, and according to the method of Reference Example 37, step B, the title compound (2.86 g, yield 95%) was obtained as a pale-yellow oil.

$^1$H-NMR (300 MHz, CDCl$_3$); δ (ppm) 2.89 (t, J=5.8, 2H), 3.48 (t, J=5.8, 2H), 4.19 (s, 2H), 6.27 (d, J=10.8, 1H), 6.47 (d, J=10.8, 1H), 7.10-7.19 (m, 4H).

Step C

N-methyl-3,4-dihydroisoquinolin-2 (1H)-amine

Using the compound (2.86 g, 17.9 mmol) obtained in step B and according to the method of Reference Example 37, step C, the title compound (2.65 g, yield 92%) was obtained as a yellow oil.

$^1$H-NMR (300 MHz, CDCl$_3$); δ (ppm) 2.68 (s, 3H), 2.98 (s, 4H), 3.87 (s, 2H), 7.01-7.27 (m, 4H).

Reference Example 43

N-methylazepan-1-amine hydrochloride

Step A

N-methyleneazepan-1-amine

Using 1-aminohomopiperidine (2.00 g, 17.5 mmol) and according to the method of Reference Example 38, step A, the title compound (1.88 g, yield 85%) was obtained as a red-bistered oil.

$^1$H-NMR (300 MHz, CDCl$_3$); δ (ppm) 1.54-1.59 (m, 4H), 1.68-1.72 (m, 4H), 3.35 (t, J=5.5, 4H), 5.77 (d, J=11.1, 1H), 5.95 (d, J=11.1, 1H).

Step B

N-methylazepan-1-amine hydrochloride

A pale-yellow oil obtained using the compound (1.20 g, 9.5 mmol) obtained in step A and according to the method of Reference Example 37, step C was dissolved in diethyl ether (15 ml), 4N hydrochloric acid-dioxane solution (1.8 ml) was added with stirring under ice-cooling, and the solution was concentrated under reduced pressure to give the title compound (0.85 g, yield 53%) as a pale-yellow oil.

$^1$H-NMR (300 MHz, CDCl$_3$); δ (ppm) 1.66 (brs, 4H), 1.87 (brs, 4H), 2.83 (s, 3H), 3.38 (t, J=5.4, 4H), 9.36 (brs, 2H).

Reference Example 44

N-methyl-4-phenylpiperazin-1-amine

Step A

N-nitroso-4-phenylpiperazin-1-amine

Using 1-phenylpiperazine (5.00 g, 30.8 mmol) and according to the method of Reference Example 37, step A, the title compound (1.10 g, yield 19%) was obtained as a pale-yellow oil.

$^1$H-NMR (300 MHz, CDCl$_3$); δ (ppm) 3.19 (t, J=5.4, 2H), 3.42 (t, J=5.4, 2H), 3.98 (t, J=5.4, 2H), 4.42 (t, J=5.4, 2H), 6.92-6.98 (m, 3H), 7.2-7.4 (m, 2H).

Step B

N-methylene-4-phenylpiperazin-1-amine

Using the compound (1.10 g, 5.8 mmol) obtained in step A and according to the method of Reference Example 37, step B, the title compound (1.35 g, yield>100%) was obtained as a yellow oil.

$^1$H-NMR (300 MHz, CDCl$_3$); δ (ppm) 3.15-3.18 (m, 4H), 3.31-3.35 (m, 4H), 6.37 (d, J=10.9, 1H), 6.35 (d, J=10.9, 1H), 6.85-6.97 (m, 3H), 7.24-7.30 (m, 2H).

Step C

N-methyl-4-phenylpiperazin-1-amine

Using the compound (1.35 g) obtained in step B and according to the method of Reference Example 37, step C, the title compound (1.0 g, yield 90%) was obtained as a red-bistered oil.

$^1$H-NMR (300 MHz, CDCl$_3$); δ (ppm) 2.63 (s, 3H), 2.81 (t, J=4.8, 4H), 3.25 (t, J=4.8, 4H), 6.82-6.94 (m, 3H), 7.2-7.3 (m, 2H).

Reference Example 45

(2-fluorobenzyl)methylamine

To tetrahydrofuran (5 ml) was added under ice-cooling with stirring 40% aqueous methylamine solution (5 ml) and 2-fluorobenzylbromide (1.00 g, 5.29 mmol) dissolved in tetrahydrofuran (2 ml), and the mixture was stirred at the same temperature for 1 hr. The reaction mixture was diluted with ethyl acetate, and the organic layer was washed with water and saturated brine, and dried over anhydrous magnesium sulfate. The insoluble material was filtered off, and the solution was concentrated under reduced pressure. The obtained oil was purified by silica gel column chromatography to give the title compound (0.65 g, yield 87%) as a colorless oil.

$^1$H-NMR (300 MHz, CDCl$_3$); δ (ppm) 2.43 (s, 3H), 3.79 (s, 2H), 7.01-7.12 (m, 2H), 7.21-7.25 (m, 1H), 7.29-7.33 (m, 1H).

Reference Example 46 tert-butyl 4-(methylamino)piperidine-1-carboxylate

To tert-butyl 4-oxo-1-piperidinecarboxylate (3.99 g, 20 mmol) was added ethanol (30 ml), and methylamine hydrochloride (2.70 g, 40 mmol), triethylamine (5.6 ml, 40 mmol) and titanium(IV)isopropoxide (11.8 ml, 40 mmol) were added under ice-cooling with stirring, and the mixture was stirred at room temperature for 8 hr. Then, to the reaction mixture was added sodium borohydride (1.14 g, 30 mmol), and the mixture was stirred at room temperature for 15 hr. To the reaction mixture was added 28% aqueous ammonia, and the reaction solution was filtered off through celite. The filtrate was concentrated under reduced pressure, water was added to the residue, and the mixture was extracted with dichloromethane-ethanol=5:1 mixed solvent, and dried over anhydrous magnesium sulfate. The insoluble material was filtered off, and the solution was concentrated under reduced pressure. The obtained oil was purified by silica gel column chromatography (dichloromethane-methanol) to give the title compound (2.46 g, yield 57%) as a pale-yellow oil.

$^1$H-NMR (300 MHz, CDCl$_3$); δ (ppm) 1.16-1.29 (m, 2H), 1.46 (s, 9H), 1.83-1.87 (m, 2H), 2.44 (s, 3H), 2.46-2.53 (m, 1H), 2.80 (t, J=11.7, 2H), 4.02-4.05 (m, 2H).

Reference Example 47

N-methyl-4-[(2-nitrophenyl)sulfonyl]piperazin-1-amine

Step A 1-benzylideneamino-piperazine

According to the method described in West Germany patent application publication No. 2127171, the title compound (5.9 g) was obtained as a pale-yellow solid from piperazine (20.0 g).

$^1$H-NMR (300 MHz, CDCl$_3$); δ (ppm) 3.05-3.09 (m, 4H), 3.14-3.19 (m, 4H), 7.2-7.4 (m, 3H), 7.57-7.62 (m, 3H).

Step B 1-benzylideneamino-4-[(2-nitrophenyl)sulfonyl]piperazine

The compound (3.45 g, 18.24 mmol) obtained in step A was dissolved in dichloromethane (50 ml), triethylamine (3.8 ml, 27 mmol) and 2-nitrobenzenesulfonyl chloride (4.45 g, 20.1 mmol) were added, and the mixture was stirred at room temperature for 8 hr and directly stood overnight. The reaction mixture was diluted with diluted aqueous sodium hydroxide solution (200 ml), and extracted with diethyl ether (200 ml). The organic layer was washed with saturated brine, and dried over anhydrous magnesium sulfate. The insoluble material was filtered off, and the solution was concentrated under reduced pressure to give the title compound (6.61 g, yield 97%) as a yellow green amorphous solid.

$^1$H-NMR (300 MHz, CDCl$_3$); δ (ppm) 3.28 (t, J=5.5, 4H), 3.52 (t, J=5.3, 4H), 7.28-7.35 (m, 3H), 7.57-7.75 (m, 6H), 8.00-8.05 (m, 1H).

Step C

4-[(2-nitrophenyl)sulfonyl]piperazin-1-amine

To the compound (6.61 g, 17.67 mmol) obtained in step B was added 1N hydrochloric acid, and generated benzaldehyde was evaporated by azeotropic distillation in a flask mounted with Dean-Stark water removing apparatus (Dean-Stark trap) for 6 hr. The reaction mixture was cooled, washed with diethyl ether, and the aqueous layer was alkalified with potassium carbonate. The layer was extracted twice with ethyl acetate (150 ml), and the organic layer was combined. The mixture was washed with saturated brine, and dried over anhydrous magnesium sulfate. The insoluble material was filtered off, and the solvent was concentrated under reduced pressure to give the title compound (4.85 g, yield 96%) as a yellow oil.

$^1$H-NMR (300 MHz, CDCl$_3$); δ (ppm) 2.70 (t, J=4.8, 4H), 3.19 (brs, 2H), 3.38 (t, J=4.5, 4H), 7.61-7.75 (m, 3H), 7.96-8.00 (m, 1H).

Step D

N-methylene-4-[(2-nitrophenyl)sulfonyl]piperazin-1-amine

Using the compound (4.85 g, 16.94 mmol) obtained in step C and according to the method of Reference Example 38, step A, the title compound (4.93 g, yield 98%) was obtained as a pale-yellow oil.

$^1$H-NMR (300 MHz, CDCl$_3$); δ (ppm) 3.13 (t, J=5.1, 4H), 3.48 (t, J=4.8, 4H), 6.39 (d, J=10.8, 1H), 6.52 (d, J=10.5, 1H), 7.62-7.75 (m, 3H), 7.99-8.02 (m, 1H).

Step E

N-methyl-4-[(2-nitrophenyl)sulfonyl]piperazin-1-amine

To a methanol (50 ml)-tetrahydrofuran (30 ml) mixed solvent was added the compound (4.93 g, 16.53 mmol) obtained in step D, sodium cyanoborohydride (1.35 g, 21.49 mmol) was added under ice-cooling with stirring, and acetic acid (1 ml) and methanol (10 ml) solution were added dropwise by a small amount. After the completion of the dropwise addition, the mixture was further stirred at the same temperature for 30 min. The reaction mixture was poured into diluted aqueous sodium hydroxide solution, and the mixture was extracted with chloroform. The organic layer was washed with saturated brine, and dried over anhydrous magnesium sulfate. The insoluble material was filtered off, and the solution was concentrated under reduced pressure. The obtained oil was purified by silica gel column chromatography (chloroform-methanol) to give the title compound (2.77 g, yield 56%) as a pale-yellow oil.

$^1$H-NMR (300 MHz, CDCl$_3$); δ (ppm) 2.56 (s, 3H), 2.74 (t, J=4.9, 4H). 3.38 (t, J=4.9, 4H), 7.60-7.75 (m, 3H), 7.95-7.98 (m, 1H).

Reference Example 48

N-methyl-4-(methylsulfonyl)piperazin-1-amine

Step A 1-benzyl-4-(methylsulfonyl)piperazine

To dichloromethane (50 ml) was added 1-benzylpiperazine (10.0 g, 56.73 mmol), methanesulfonyl chloride (4.4 ml, 56.85 mmol) was added under ice-cooling with stirring, and the mixture was stirred at the same temperature for 1 hr. The reaction mixture was diluted with 10% aqueous sodium carbonate solution, and extracted with dichloromethane. The organic layer was washed with saturated brine, and dried over anhydrous magnesium sulfate. The insoluble material was filtered off, and the solution was concentrated under reduced pressure to give the title compound (9.58 g, yield 66%) as a pale-yellow solid.

$^1$H-NMR (300 MHz, CDCl$_3$); δ (ppm) 2.55 (t, J=5.0, 4H), 2.77 (s, 3H), 3.24 (t, J=5.0, 4H), 3.55 (s, 2H), 7.24-7.36 (m, 5H).

Step B 1-(methylsulfonyl)piperazine hydrochloride

To dichloromethane (70 ml) was added the compound (9.58 g, 37.66 mmol) obtained in step A and 1-chloroethyl chloroformate (4.53 ml, 41.43 mmol) was added under ice-cooling with stirring, and the mixture was stirred at room temperature for 1 hr. The reaction mixture was concentrated under reduced pressure, the residue was dissolved in methanol (70 ml), and the mixture was heated under reflux for 30 min. The reaction mixture was cooled to room temperature, and the precipitated solid was filtered and washed with a small amount of methanol. The filtrate was concentrated under reduced pressure, and the precipitated solid was filtered, and washed with a small amount of methanol. The obtained solid was combined, and the mixture was washed with diethyl ether to give the title compound (6.65 g, yield 88%) as a colorless solid.

$^1$H-NMR (300 MHz, DMSO-$d_6$); δ (ppm) 2.99 (s, 3H), 3.16 (t, J=5.4, 4H), 3.38 (t, J=5.7, 4H), 9.59 (brs, 1H), 9.90 (brs, 1H).

Step C 1-(methylsulfonyl)-4-nitrosopiperazine

Using the compound (6.65 g, 33.14 mmol) obtained in step B and according to the method of Reference Example 37, step A, the title compound (3.75 g, yield 59%) was obtained as a pale-yellow solid.

$^1$H-NMR (300 MHz, CDCl$_3$); δ (ppm) 2.85 (s, 3H), 3.25 (t, J=5.4, 2H), 3.51 (t, J=5.1, 2H), 3.96 (t, J=5.4, 2H), 4.39-4.56 (m, 2H).

Step D

N-methylene-4-(methylsulfonyl)piperazin-1-amine

Using the compound (3.75 g, 19.41 mmol) obtained in step C and according to the method of Reference Example 37, step B, the title compound (2.12 g, yield 57%) was obtained as a colorless solid.

$^1$H-NMR (300 MHz, CDCl$_3$); δ (ppm) 2.82 (s, 3H), 3.16 (t, J=4.9, 4H), 3.39 (t, J=4.9, 4H), 6.41 (d, J=10.5, 1H), 6.53 (d, J=10.6, 1H).

Step E

N-methyl-4-(methylsulfonyl)piperazin-1-amine

Using the compound (2.12 g, 11.08 mmol) obtained in step D and according to the method of Reference Example 37, step C, the title compound (1.73 g, yield 81%) was obtained as a yellow oil.

$^1$H-NMR (300 MHz, CDCl$_3$); δ (ppm) 2.39 (s, 3H), 2.78 (t, J=4.2, 4H), 2.80 (s, 3H), 3.33 (t, J=4.8, 4H).

Reference Example 49 methyl[2-(2-thienyl)ethyl]amine hydrochloride

Step A tert-butyl[2-(2-thienyl)ethyl]carbamate

Using [2-(2-thienyl)ethyl]amine (2.00 g, 15.72 mmol) and according to the method of Reference Example 23, step A, the title compound (3.86 g) was obtained as a yellow oil.

$^1$H-NMR (300 MHz, CDCl$_3$); δ (ppm) 1.44 (s, 9H), 3.12 (t, J=6.6, 2H), 3.39 (q, J=6.6, 2H), 4.65 (brs, 1H), 6.83 (dt, J=1.2, 3.6, 1H), 6.94 (dd, J=3.6, 5.1, 1H), 7.15 (dd, J=1.2, 5.1, 1H).

Step B methyl[2-(2-thienyl)ethyl]amine hydrochloride

Using the compound (3.86 g) obtained in step A and according to the method of Reference Example 23, step B, the title compound (2.44 g, total yield from step A 87%) was obtained as a colorless solid.

$^1$H-NMR (300 MHz, DMSO-$d_6$); δ (ppm) 2.55 (s, 3H), 3.09-3.24 (m, 4H), 6.97-7.01 (m, 2H), 7.42 (d, J=4.1, 1H), 9.23 (brs, 2H).

Reference Example 50

[2-(2-furyl)ethyl]methylamine

Step A

[2-(2-furyl)ethyl]amine

Tetrahydrofuran (50 ml) was added to lithium aluminum hydride (2.05 g, 53.91 mmol), and the mixture was stirred under ice-cooling. Thereto was added a solution of 2-(2-nitrovinyl)furan (2.50 g, 17.97 mmol) in tetrahydrofuran (30 ml) and the mixture was heated under reflux for 1 hr. The reaction mixture was ice-cooled, water-containing diethyl ether (80 ml), tetrahydrofuran (80 ml) and saturated aqueous sodium sulfate solution (14 ml) were successively added with stirring. The insoluble material was filtered off through celite, and the solution was concentrated under reduced pressure to give the title compound (1.87 g, yield 94%) as a red-bistered oil.

$^1$H-NMR (300 MHz, CDCl$_3$); δ (ppm) 2.77 (t, J=6.5, 2H), 2.98 (t, J=6.5, 2H), 6.06 (d, J=3.1, 1H), 6.29 (dd, J=2.5, 4.8, 1H), 7.33 (d, J=1.7, 1H).

Step B tert-butyl[2-(2-furyl)ethyl]carbamate

Using the compound (1.87 g, 16.83 mmol) obtained in step A and according to the method of Reference Example 23, step A, the title compound (3.94 g) was obtained as a red-bistered oil.

$^1$H-NMR (300 MHz, CDCl$_3$); δ (ppm) 1.44 (s, 9H), 2.82 (t, J=6.6, 2H), 3.41 (q, J=6.6, 2H), 4.67 (brs, 1H), 6.07 (d, J=3.3, 1H), 6.30 (dd, J=2.4, 5.1, 1H), 7.33 (d, J=1.2, 1H).

Step C

[2-(2-furyl)ethyl]methylamine

To lithium aluminum hydride (1.79 g, 47.16 mmol) was added tetrahydrofuran (40 ml) and the mixture was stirred under ice-cooling. Thereto was added a solution of the compound (3.94 g) obtained in step B in tetrahydrofuran (20 ml) and the mixture was heated under reflux for 3 hr. The reaction mixture was ice-cooled, water-containing diethyl ether (60 ml), tetrahydrofuran (60 ml) and saturated aqueous sodium sulfate solution (12 ml) were successively added with stirring. The insoluble material was filtered off through celite, and the solution was concentrated under reduced pressure to give the title compound (1.76 g, total yield from step B 84%) as a red-bistered oil.

$^1$H-NMR (300 MHz, CDCl$_3$); δ (ppm) 2.44 (s, 3H), 2.82-2.83 (m, 4H), 6.04 (d, J=2.4, 1H), 6.29 (dd, J=2.1, 3.0, 1H), 7.31 (t, J=1.5, 1H).

Reference Example 51

[2-(2-methoxyphenyl)ethyl]methylamine hydrochloride

Step A tert-butyl[2-(2-methoxyphenyl)ethyl]carbamate

Using [2-(2-methoxyphenyl)ethyl]amine (2.00 g, 13.23 mmol) and according to the method of Reference Example 23, step A, the title compound (4.44 g) was obtained as a pale-yellow oil.

$^1$H-NMR (300 MHz, CDCl$_3$); δ (ppm) 1.42 (s, 9H), 2.81 (t, J=6.8, 2H), 3.31-3.40 (m, 2H), 3.82 (s, 3H), 6.87 (t, J=8.4, 1H), 6.90 (t, J=7.6, 1H), 7.13 (d, J=7.4, 1H), 7.22 (dt, J=1.6, 8.0, 1H).

Step B

[2-(2-methoxyphenyl)ethyl]methylamine hydrochloride

Using the compound (4.44 g) obtained in step A and according to the method of Reference Example 23, step B, the title compound (2.47 g, total yield from step A 93%) was obtained as a colorless solid.

$^1$H-NMR (300 MHz, DMSO-d$_6$); δ (ppm) 2.52-2.56 (m, 3H), 2.89-3.08 (m, 4H), 3.80 (s, 3H), 6.91 (t, J=7.6, 1H), 7.00 (d, J=8.1, 1H), 7.18 (dd, J=1.4, 7.5, 1H), 7.26 (dt, J=1.5, 8.1, 1H), 9.15 (brs, 2H).

Reference Example 52

[2-(3-methoxyphenyl)ethyl]methylamine hydrochloride

Step A tert-butyl[2-(3-methoxyphenyl)ethyl]carbamate

Using [2-(3-methoxyphenyl)ethyl]amine (2.00 g, 13.23 mmol) and according to the method of Reference Example 23, step A, the title compound (4.53 g) was obtained as a pale-yellow oil.

$^1$H-NMR (300 MHz, CDCl$_3$); δ (ppm) 1.46 (s, 9H), 2.77 (t, J=7.0, 2H), 3.38 (q, J=6.5, 2H), 3.80 (s, 3H), 4.55 (brs, 1H), 6.73-6.80 (m, 3H), 7.22 (t, J=7.7, 1H).

Step B

[2-(3-methoxyphenyl)ethyl]methylamine hydrochloride

Using the compound (4.53 g) obtained in step A and according to the method of Reference Example 23, step B, the title compound (2.15 g, total yield from step A 81%) was obtained as a colorless solid.

$^1$H-NMR (300 MHz, DMSO-d$_6$); δ (ppm) 2.50-2.54 (m, 3H), 2.93 (t, J=6.8, 2H), 3.02-3.18 (m, 2H), 3.75 (s, 3H), 6.80-6.85 (m, 3H), 7.25 (t, J=8.0, 1H), 9.15 (brs, 2H).

Reference Example 53

[2-(4-methoxyphenyl)ethyl]methylamine hydrochloride

Step A tert-butyl[2-(4-methoxyphenyl)ethyl]carbamate

Using [2-(4-methoxyphenyl)ethyl]amine (2.00 g, 13.23 mmol) and according to the method of Reference Example 23, step A, the title compound (3.98 g) was obtained as a pale-yellow oil.

$^1$H-NMR (300 MHz, CDCl$_3$); δ (ppm) 1.43 (s, 9H), 2.73 (t, J=7.0, 2H), 3.34 (q, J=6.5, 2H), 3.79 (s, 3H), 4.54 (brs, 1H), 6.85 (d, J=8.6, 2H), 7.11 (d, J=8.6, 2H).

Step B

[2-(4-methoxyphenyl)ethyl]methylamine hydrochloride

Using the compound (3.98 g) obtained in step A and according to the method of Reference Example 23, step B, the title compound (2.15 g, total yield from step A 81%) was obtained as a colorless solid.

$^1$H-NMR (300 MHz, DMSO-d$_6$); δ (ppm) 2.50-2.55 (m, 3H), 2.88 (t, J=6.7, 2H), 2.95-3.15 (m, 2H), 3.73 (s, 3H), 6.89 (d, J=8.5, 2H), 7.18 (d, J=8.7, 2H), 9.12 (brs, 2H).

Reference Example 54

[2-(2-methylphenyl)ethyl]methylamine hydrochloride

Step A

1-methyl-2-(2-nitrovinyl)benzene

Ortho-tolualdehyde (10.00 g, 83.23 mmol) was dissolved in acetic acid (50 ml), ammonium acetate (6.93 g, 89.89 mmol) and nitromethane (7 ml, 129 mmol) were added, and the mixture was stirred at 110° C. for 8 hr and stood at room temperature overnight. The reaction mixture was diluted with water and extracted with ethyl acetate. The organic layer was washed with saturated brine, and dried over anhydrous magnesium sulfate. The insoluble material was filtered off, and the solution was concentrated under reduced pressure to give the title compound (12.71 g, yield 94%) as a bistered oil.

$^1$H-NMR (300 MHz, CDCl$_3$); δ (ppm) 2.49 (s, 3H), 7.23-7.29 (m, 2H), 7.36-7.42 (m, 1H), 7.48-7.53 (m, 2H), 8.30 (d, J=13.5, 1H).

Step B

[2-(2-methylphenyl)ethyl]amine hydrochloride

Using the compound (12.71 g, 77.89 mmol) obtained in step A and according to the method of Reference Example 50, step A, [2-(2-methylphenyl)ethyl]amine was obtained as a crude product. This was dissolved in ethyl acetate (200 ml), 4N hydrochloric acid-dioxane solution (20 ml) was added, and the precipitated solid was filtered, washed with diisopropyl ether, and dried under reduced pressure to give the title compound (4.30 g, yield 32%) as a colorless solid.

$^1$H-NMR (300 MHz, DMSO-d$_6$); δ (ppm) 2.30 (s, 3H), 2.92 (brs, 4H), 7.12-7.20 (m, 4H), 8.23 (brs, 3H).

Step C tert-butyl[2-(2-methylphenyl)ethyl]carbamate

Using the compound (2.50 g, 14.56 mmol) obtained in step B and triethylamine (3 ml) (21.8 mmol), and according to the method of Reference Example 23, step A, the title compound (3.73 g) was obtained as a pale-yellow oil.
$^1$H-NMR (300 MHz, CDCl$_3$); δ (ppm) 1.44 (s, 9H), 2.33 (s, 3H), 2.81 (t, J=7.1, 2H), 3.34 (q, J=6.7, 2H), 4.58 (brs, 1H), 7.05-7.15 (m, 4H).

Step D

[2-(2-methylphenyl)ethyl]methylamine hydrochloride

Using the compound (3.73 g) obtained in step C and according to the method of Reference Example 23, step B, the title compound (2.35 g, total yield from step C 87%) was obtained as a colorless solid.
$^1$H-NMR (300 MHz, DMSO-d$_6$); δ (ppm) 2.31 (s, 3H), 2.56 (s, 3H), 2.93-3.04 (m, 4H), 7.13-7.20 (m, 4H), 9.24 (brs, 2H).

Reference Example 55

[2-(3-methylphenyl)ethyl]methylamine hydrochloride

Step A 1-methyl-3-(2-nitrovinyl)benzene

Using meta-tolualdehyde (10.00 g, 83.23 mmol) and according to the method of Reference Example 54, step A, the title compound (12.75 g, yield 94%) was obtained as a bistered oil.
$^1$H-NMR (300 MHz, CDCl$_3$); δ (ppm) 2.40 (s, 3H), 7.30-7.36 (m, 4H), 7.58 (d, J=13.8, 1H), 7.98 (d, J=13.8, 1H).

Step B

[2-(3-methylphenyl)ethyl]amine hydrochloride

Using the compound (12.75 g, 78.14 mmol) obtained in step A and according to the method of Reference Example 50, step A, [2-(3-methylphenyl)ethyl]amine was obtained as a crude product. This was dissolved in ethyl acetate (100 ml), 4N hydrochloric acid-dioxane solution (21 ml) was added, and the precipitated solid was filtered, washed with diethyl ether, and dried under reduced pressure to give the title compound (3.27 g, yield 24%) as a pale-yellow solid.
$^1$H-NMR (300 MHz, DMSO-d$_6$); δ (ppm) 2.29 (s, 3H), 2.84-3.05 (m, 4H), 7.03-7.07 (m, 3H), 7.21 (t, J=7.9, 1H), 8.20 (brs, 3H).

Step C tert-butyl[2-(3-methylphenyl)ethyl]carbamate

Using the compound (2.50 g, 14.56 mmol) obtained in step B and triethylamine (3 ml) (21.9 mmol), and according to the method of Reference Example 23, step A, the title compound (3.78 g) was obtained as a yellow oil.
$^1$H-NMR (300 MHz, CDCl$_3$); δ (ppm) 1.44 (s, 9H), 2.33 (s, 3H), 2.76 (t, J=7.0, 2H), 3.37 (q, J=6.7, 2H), 4.54 (brs, 1H), 6.98-7.05 (m, 3H), 7.20 (t, J=7.4, 1H).

Step D

[2-(3-methylphenyl)ethyl]methylamine hydrochloride

Using the compound (3.78 g) obtained in step C and according to the method of Reference Example 23, step B, the title compound (2.24 g, total yield from step C 83%) was obtained as a colorless solid.
$^1$H-NMR (300 MHz, DMSO-d$_6$); δ (ppm) 2.29 (s, 3H), 2.54 (s, 3H), 2.89-2.95 (m, 2H), 3.05-3.11 (m, 2H), 7.03-7.08 (m, 3H), 7.22 (t, J=7.6, 1H), 9.15 (brs, 2H).

Reference Example 56

[2-(4-methylphenyl)ethyl]methylamine hydrochloride

Step A tert-butyl[2-(4-methylphenyl)ethyl]carbamate

Using [2-(4-methylphenyl)ethyl]amine (3.63 g, 26.85 mmol) and according to the method of Reference Example 23, step A, the title compound (7.13 g) was obtained as a yellow oil.
$^1$H-NMR (300 MHz, CDCl$_3$); δ (ppm) 1.43 (s, 9H), 2.33 (s, 3H), 2.75 (t, J=6.9, 2H), 3.35 (q, J=6.6, 2H), 4.53 (brs, 1H), 7.06-7.13 (m, 4H).

Step B

[2-(4-methylphenyl)ethyl]methylamine hydrochloride

Using the compound (7.13 g) obtained in step A and according to the method of Reference Example 23, step B, the title compound (3.85 g, total yield from step A 77%) was obtained as a colorless solid.
$^1$H-NMR (300 MHz, DMSO-d$_6$); δ (ppm) 2.28 (s, 3H), 2.53 (s, 3H), 2.87-2.94 (m, 2H), 3.03-3.09 (m, 2H), 7.14 (s, 4H), 9.13 (brs, 2H).

Reference Example 57 trans-N-methyl-2-phenylcyclopropanamine

Step A

N-(trans-2-phenylcyclopropyl)formamide trans-2-Phenylcyclopropylamine hydrochloride (2.74 g, 16.15 mmol) was dissolved in water (50 ml), and the solution was alkalified with potassium carbonate. The mixture was extracted with ethyl acetate. The organic layer was washed with saturated brine, and dried over anhydrous magnesium sulfate. The insoluble material was filtered off, and the solution was concentrated under reduced pressure. To the residue was added formic acid (18.5 ml), and the mixture was ice-cooled, and acetic anhydride (7 ml) was added dropwise with stirring. The reaction mixture was stood at room temperature overnight, ice-cooled again. Water (7 ml) was added, and the mixture was concentrated under reduced pressure. The residue was diluted with ethyl acetate, washed with 5% aqueous potassium carbonate solution and saturated brine, and dried over anhydrous magnesium sulfate. The insoluble material was filtered off, and the solution was concentrated under reduced pressure to give the title compound (2.36 g, yield 91%) as a pale-bistered solid.

$^1$H-NMR (300 MHz, CDCl$_3$); δ (ppm) 1.17-1.35 (m, 2H), 2.04-2.21 (m, 1H), 2.80-2.95 (m, 1H), 5.87 (brs, 0.6H), 6.52 (brs, 0.4H), 7.05-7.35 (m, 5H), 8.19 (s, 0.6H), 8.30 (d, J=11.7, 0.4H).

Step B trans-N-methyl-2-phenylcyclopropanamine

To a suspension of sodium borohydride (0.66 g, 17.57 mmol) in tetrahydrofuran (55 ml) was added dropwise at room temperature a solution of the compound (2.36 g, 14.64 mmol) obtained in step A in tetrahydrofuran (32 ml). Then, a solution of iodine (1.86 g, 7.33 mmol) in tetrahydrofuran (63 ml) was added dropwise, and the mixture was heated under reflux overnight. The reaction mixture was ice-cooled, methanol (125 ml) was added, and the mixture was concentrated under reduced pressure. To the residue was added 10% aqueous potassium carbonate solution, and the mixture was extracted with ethyl acetate. The organic layer was washed with saturated brine, and dried over anhydrous magnesium sulfate. The insoluble material was filtered off, and the solution was concentrated under reduced pressure. The obtained oil was purified by silica gel column chromatography (chloroform-methanol) to give the title compound (1.23 g, yield 57%) as a pale-yellow oil.

$^1$H-NMR (300 MHz, CDCl$_3$); δ (ppm) 0.94-1.00 (m, 1H), 1.05-1.10 (m, 1H), 1.87-1.95 (m, 1H), 2.29-2.35 (m, 1H), 2.51 (s, 3H), 7.04-7.35 (m, 5H).

Reference Example 58 methyl(3-phenylpropyl)amine

Step A tert-butyl(trans-2-phenylcyclopropyl)carbamate

Using trans-2-phenylcyclopropylamine hydrochloride (1.12 g, 6.60 mmol) and triethylamine (1.0 ml, 7.17 mmol), and according to the method of Reference Example 23, step A, the title compound (944 mg, yield 61%) was obtained as a pale-yellow solid.

$^1$H-NMR (300 MHz, CDCl$_3$); δ (ppm) 1.10-1.19 (m, 2H), 1.45 (s, 9H), 2.00-2.07 (m, 1H), 2.73 (brs, 1H), 4.85 (brs, 1H), 7.11-7.29 (m, 5H).

Step B methyl(3-phenylpropyl)amine

Using the compound (930 mg, 3.99 mmol) obtained in step A and according to the method of Reference Example 50, step C, the title compound (605 mg, yield>100%) was obtained as a pale-yellow oil.

$^1$H-NMR (300 MHz, CDCl$_3$); δ (ppm) 1.68-1.89 (m, 2H), 2.43 (s, 3H), 2.61 (t, J=7.5, 2H), 2.66 (t, J=7.5, 2H), 7.51-7.35 (m, 5H).

Reference Example 59

N-methyl-4,6-dihydro-5H-thieno[2,3-c]pyrrol-5-amine hydrochloride

Step A tert-butyl 4,6-dihydro-5H-thieno[2,3-c]pyrrol-5-yl (methyl)carbamate 2,3-bis(Bromomethyl)thiophene (3.59 g, 13.3 mmol) synthesized according to the method described in Journal of organic Chemistry, 1966, 31, 592-3595 and the compound (1.94 g, 13.3 mmol) of Reference Example 17, step A, were dissolved in N-methylpyrrolidone (100 ml), and triethylamine (5.0 ml, 35.9 mmol) was slowly added with stirring while keeping the reaction mixture at 80-85° C. The mixture was stirred by heating at the same temperature for 10 hr, and the mixture was stood overnight at room temperature. The reaction mixture was diluted with water and extracted with ethyl acetate-hexane=1:1 mixed solvent, and the organic layer was washed with saturated brine, and dried over anhydrous magnesium sulfate. The insoluble material was filtered off, and the solution was concentrated under reduced pressure. The obtained oil was purified by silica gel chromatography (ethyl acetate-hexane) to give the title compound (1.31 g, yield 39%) as an orange oil.

$^1$H-NMR (300 MHz, CDCl$_3$); δ (ppm) 1.40 (brs, 9H), 3.10 (s, 3H), 4.30 (brs, 2H), 4.42 (brs, 2H), 6.80 (d, J=4.8, 1H), 7.20 (d, J=4.8, 1H).

Step B

N-methyl-4,6-dihydro-5H-thieno[2,3-c]pyrrol-5-amine hydrochloride

Using the compound (1.31 g, 5.15 mmol) obtained in step A and according to the method of Reference Example 18, step B, the title compound (764 mg, yield 78%) was obtained as a pale-purple solid.

$^1$H-NMR (300 MHz, DMSO-d$_6$); δ (ppm) 2.75 (s, 3H), 4.32 (brs, 2H), 4.46 (brs, 2H), 6.97 (d, J=4.8, 1H), 7.55 (d, J=4.8, 1H), 11.05 (brs, 2H).

Reference Example 60

N,5-dimethyl-1,3-dihydro-2H-isoindol-2-amine hydrochloride

Step A (4-methyl-1,2-phenylene)dimethanol

To tetrahydrofuran (200 ml) was added lithium aluminum hydride (4.91 g, 129 mmol), and the mixture was stirred under ice-cooling. Then, a solution (100 ml) of 4-methylphthalic anhydride (10.4 g, 64.1 mmol) in tetrahydrofuran was added and the mixture was heated under reflux for 90 min. The reaction mixture was ice-cooled, and water (4.91 ml), 15% aqueous sodium hydroxide solution (4.91 ml), water (14.7 ml) and anhydrous magnesium sulfate were successively added with stirring. The insoluble material was filtered off through celite, and the solution was concentrated under reduced pressure to give the title compound (9.34 g, yield 96%) as a colorless oil.

$^1$H-NMR (300 MHz, CDCl$_3$); δ (ppm) 2.35 (s, 3H), 2.8-2.9 (m, 1H), 2.9-3.0 (m, 1H), 4.69 (s, 2H), 4.71 (2H, s), 7.12 (d, J=7.6, 1H), 7.17 (s, 1H), 7.23 (d, J=7.6, 1H).

Step B 1,2-bis(bromomethyl)-4-methylbenzene

To the compound (9.34 g, 61.4 mmol) obtained in step A was added 47% hydrobromic acid (60 ml), and the mixture was stirred with heating at 100° C. for 90 min. The reaction mixture was cooled, diluted with water, and extracted with ethyl acetate-hexane=1:1 mixed solvent. The organic layer was washed with saturated brine, and dried over anhydrous magnesium sulfate. The insoluble material was filtered off, and the solution was concentrated under reduced pressure to give the title compound (16.7 g, yield 98%) as an orange solid.
$^1$H-NMR (300 MHz, CDCl$_3$); δ (ppm) 2.33 (s, 3H), 4.63 (s, 2H), 4.64 (2H, s), 7.10 (d, J=7.7, 1H), 7.17 (s, 1H), 7.25 (d, J=7.7, 1H).

Step C tert-butyl methyl(5-methyl-1,3-dihydro-2H-isoindol-2-yl)carbamate

Using the compound (16.6 g, 59.7 mmol) obtained in step B and according to the method of Reference Example 17, step B, the title compound (13.8 g) was obtained as a crude red oil. This was directly used for the next step.

Step D

N,5-dimethyl-1,3-dihydro-2H-isoindol-2-amine hydrochloride

The compound (13.8 g) obtained in step C was dissolved in ethanol (65 ml), 4N hydrochloric acid-dioxane solution (65 ml) was added at room temperature, and the mixture was stirred at the same temperature for one day. To the reaction mixture was added activated carbon, the insoluble material was filtered off through celite, and the solution was concentrated under reduced pressure. The obtained solid was washed with an acetone-diethyl ether mixed solvent, dried under reduced pressure to give the title compound (5.68 g, yield from step C 48%) as a colorless solid.
$^1$H-NMR (300 MHz, DMSO-d$_6$); δ (ppm) 2.31 (s, 3H), 2.77 (brs, 3H), 4.36 (brs, 4H), 7.11 (d, J=7.5, 1H), 7.15 (s, 1H), 7.22 (d, J=7.5, 1H), 10.82 (brs, 2H).

The compounds of Reference Examples 31-60 are shown below.

TABLE 2

| Reference Example | Structural Formula |
|---|---|
| 31 | 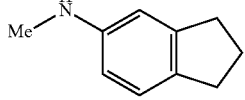 HCl |
| 32 | 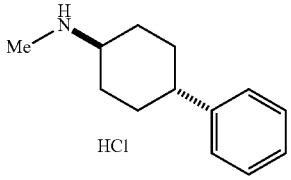 [SMILES: CN[C@H]1CC[C@H](c2ccccc2)CC1 ; Cl] HCl |
| 33 | 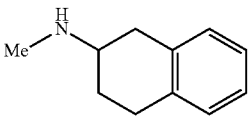 [SMILES: CNN1CCc2ccccc2C1] HCl |
| 34 | 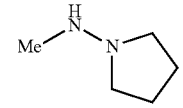 HCl |
| 35 | 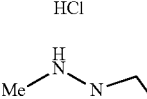 HCl |
| 36 | 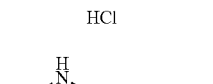 HCl |
| 37 |  |
| 38 | 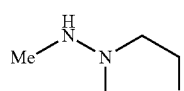 |
| 39 | 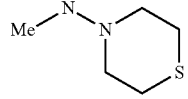 |
| 40 | 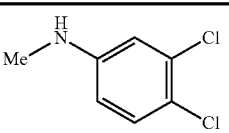 |
| 41 | 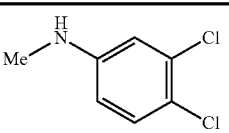 |

TABLE 2-continued

| Reference Example | Structural Formula |
|---|---|
| 42 | Me-NH-(1,2,3,4-tetrahydroisoquinolin-2-yl) |
| 43 | Me-NH-(azepan-1-yl) · HCl |
| 44 | Me-NH-(4-phenylpiperazin-1-yl) |
| 45 | Me-NH-CH2-(2-fluorophenyl) |
| 46 | Me-NH-(1-Boc-piperidin-4-yl) |
| 47 | Me-NH-(4-(2-nitrophenylsulfonyl)piperazin-1-yl) |
| 48 | Me-NH-(4-methylsulfonylpiperazin-1-yl) |
| 49 | Me-NH-CH2CH2-(thiophen-2-yl) · HCl |
| 50 | Me-NH-CH2CH2-(furan-2-yl) |
| 51 | Me-NH-CH2CH2-(2-methoxyphenyl) · HCl |
| 52 | Me-NH-CH2CH2-(3-methoxyphenyl) · HCl |
| 53 | Me-NH-CH2CH2-(4-methoxyphenyl) · HCl |
| 54 | Me-NH-CH2CH2-(2-methylphenyl) · HCl |
| 55 | Me-NH-CH2CH2-(3-methylphenyl) · HCl |
| 56 | Me-NH-CH2CH2-(4-methylphenyl) · HCl |
| 57 | Me-NH-(trans-2-phenylcyclopropyl), Racemic |
| 58 | Me-NH-CH2CH2CH2-phenyl |
| 59 | Me-NH-(4,6-dihydro-5H-thieno[2,3-c]pyrrol-5-yl) · HCl |

TABLE 2-continued

| Reference Example | Structural Formula |
|---|---|
| 60 | Me-NH-N(indoline)-Me · HCl |

Reference Example 61

N-(5-cyano-2-methylphenyl)iminodiacetic acid

Step A 4-methyl-3-nitrobenzoic acid tert-butyl ester 4-methyl-3-nitrobenzoic acid (40.0 g, 221 mmol), 4-dimethylaminopyridine (54.5 g, 446 mmol) and WSC (84.4 g, 440 mmol) were dissolved in dichloromethane (450 ml). tert-Butanol (34.4 g, 464 mmol) was added with stirring at room temperature, and the mixture was stirred at the same temperature overnight. The reaction mixture was concentrated under reduced pressure, and diluted with ethyl acetate-hexane=1:1 mixed solvent (500 ml). The organic layer was washed with water, 10% aqueous citric acid solution, saturated aqueous sodium hydrogen carbonate and saturated brine, and dried over anhydrous magnesium sulfate. The insoluble material was filtered off, and the solution was concentrated under reduced pressure to give the title compound (48.7 g, yield 93%) as a pale-yellow solid.

$^1$H-NMR (300 MHz, CDCl$_3$); δ (ppm) 1.61 (s, 9H), 2.65 (s, 3H), 7.40 (d, J=8.0, 1H), 8.09 (dd, J=1.4, 8.0, 1H), 8.52 (dd, J=1.4, 1H).

Step B 4-methyl-3-aminobenzoic acid tert-butyl ester

The compound (29.3 g, 123 mmol) of step A was dissolved in methanol (500 ml), ferric chloride (FeCl$_3$) (1.73 g, 10.7 mmol) and activated carbon (4.5 g) were added and the mixture was stirred at room temperature. Then, hydrazine monohydrate (20 ml, 412 mmol) was added, and the mixture was heated under reflux for 45 min. The reaction mixture was cooled, filtered through celite, and the solution was concentrated under reduced pressure. The obtained oil was diluted with an ethyl acetate-hexane=1:1 mixed solvent (300 ml), washed with saturated aqueous sodium hydrogen carbonate and saturated brine, and dried over anhydrous magnesium sulfate. The insoluble material was filtered off, and the solution was concentrated under reduced pressure to give the title compound (26.2 g) as a pale-yellow oil.

$^1$H-NMR (300 MHz, CDCl$_3$); δ (ppm) 1.57 (s, 9H), 2.20 (s, 3H), 3.67 (brs, 2H), 7.07 (d, J=7.6, 1H), 7.29 (d, J=1.5, 1H), 7.33 (dd, J=1.5, 7.6, 1H).

Step C

N-(5-tert-butoxycarbonyl-2-methylphenyl)iminodiacetic acid diethyl ester

The compound (26.2 g) obtained in step B, ethyl bromoacetate (80 ml, 719 mmol) and N,N-diisopropylethylamine (130 ml, 764 mmol) were mixed, and the mixture was stirred by heating at 140° C. for 200 min. The reaction mixture was cooled, diluted with an ethyl acetate-hexane=1:1 mixed solvent, and the organic layer was washed with 10% aqueous citric acid solution, saturated aqueous sodium hydrogen carbonate and saturated brine, and dried over anhydrous magnesium sulfate. The insoluble material was filtered off, and the solution was concentrated under reduced pressure. The obtained oil was purified by silica gel column chromatography (ethyl acetate-hexane) to give the title compound (46.3 g, yield from step B 99%) as a pale-yellow oil.

$^1$H-NMR (300 MHz, CDCl$_3$); δ (ppm) 1.25 (t, J=7.2, 6H), 1.58 (s, 9H), 2.38 (s, 3H), 4.03 (s, 4H), 4.15 (q, J=7.2, 4H), 7.19 (d, J=7.8, 1H), 7.60 (dd, J=1.7, 7.8, 1H), 7.78 (d, J=1.7, 1H).

Step D

N-(5-carboxy-2-methylphenyl)iminodiacetic acid diethyl ester

The compound (38.8 g, 102 mmol) obtained in step C was dissolved in dichloromethane (100 ml), trifluoroacetic acid (100 ml) was added under ice-cooling, and the mixture was stood for one day at room temperature. The reaction mixture was concentrated under reduced pressure, water was added to the obtained oil to allow precipitation of a solid. This was filtered, washed with water, and dried under reduced pressure to give the title compound (29.3 g, yield 89%) as a colorless solid.

$^1$H-NMR (300 MHz, DMSO-d$_6$); δ (ppm) 1.14 (t, J=7.2, 6H), 2.32 (s, 3H), 4.03 (s, 4H), 4.05 (q, J=7.2, 4H), 7.26 (d, J=8.1, 1H), 7.52 (dd, J=1.2, 8.1, 1H), 7.70 (d, J=1.2, 1H), 12.75 (brs, 1H).

Step E

N-[5-(aminocarbonyl)-2-methylphenyl]iminodiacetic acid diethyl ester

The compound (8.03 g, 24.8 mmol) obtained in step D was added to dichloromethane (160 ml), oxalyl chloride (3.0 ml, 35 mmol) and a catalytic amount of N,N-dimethylformamide were added under ice-cooling with stirring, and the mixture was stirred at room temperature for 2 hr. The reaction mixture was concentrated under reduced pressure, dissolved in tetrahydrofuran (100 ml), 28% aqueous ammonia (20 ml) was added under ice-cooling with stirring, and the mixture was stirred at the same temperature for 1 hr. The reaction mixture was diluted with ethyl acetate, washed with water and saturated brine, and the organic layer was dried over anhydrous magnesium sulfate. The insoluble material was filtered off, and the solution was concentrated under reduced pressure to give the title compound (8.77 g) as a colorless solid.

$^1$H-NMR (300 MHz, CDCl$_3$); δ (ppm) 1.24 (t, J=7.2, 6H), 2.39 (s, 3H), 4.04 (s, 4H), 4.14 (q, J=7.2, 4H), 5.4-6.2 (broad, 2H), 7.23 (d, J=7.8, 1H), 7.41 (dd, J=1.8, 7.8, 1H), 7.69 (d, J=1.8, 1H).

Step F

N-(5-cyano-2-methylphenyl)iminodiacetic acid diethyl ester

The compound (8.77 g) obtained in step E was dissolved in dichloromethane (150 ml), and the mixture was stirred under ice-cooling. Then, trichloroacetyl chloride (3.2 ml, 29 mmol)

and triethylamine (8.0 ml, 57 mmol) were successively added, and the mixture was stirred at the same temperature for 40 min. To the reaction mixture was added saturated aqueous sodium hydrogen carbonate, and the organic layer was extracted and the organic layer was washed with 10% aqueous citric acid solution and saturated brine, and dried over anhydrous magnesium sulfate. The insoluble material was filtered off, and the solution was concentrated under reduced pressure. The obtained solid was washed with hexane, and dried under reduced pressure to give the title compound (6.03 g, yield from step E 80%) as a pale-yellow solid.

$^1$H-NMR (300 MHz, CDCl$_3$); δ (ppm) 1.25 (t, J=7.2, 6H), 2.39 (s, 3H), 4.02 (s, 4H), 4.16 (q, J=7.2, 4H), 7.25-7.27 (m, 2H), 7.46 (s, 1H).

Step G

N-(5-cyano-2-methylphenyl)iminodiacetic acid

The compound (6.02 g, 19.8 mmol) obtained in step F was dissolved in a methanol-tetrahydrofuran=1:1 mixed solvent (100 ml). 1N sodium hydroxide (100 ml) was added with stirring at room temperature, and the mixture was stirred at the same temperature for 2 hr. The reaction mixture was concentrated under reduced pressure, 1N hydrochloric acid (110 ml) was added, and the aqueous layer was extracted 4 times with chloroform. The organic layer was mixed, and dried over anhydrous magnesium sulfate. The insoluble material was filtered off, and the solution was concentrated under reduced pressure, and the obtained solid was washed with diethyl ether-hexane mixed solvent, and dried under reduced pressure to give the title compound (4.26 g, yield 87%) as a colorless solid.

$^1$H-NMR (300 MHz, DMSO-d$_6$); δ (ppm) 2.32 (s, 3H), 3.95 (s, 4H), 7.33-7.37 (m, 2H), 7.42 (s, 1H), 12.54 (brs, 2H).

Reference Example 62

N-[2-methyl-5-(5-methyl-1,2,4-oxadiazol-3-yl)phenyl]iminodiacetic acid

Step A

N-[2-methyl-5-(5-methyl-1,2,4-oxadiazol-3-yl)phenyl]iminodiacetic acid diethyl ester To an ethanol (350 ml)-water (100 ml) mixed solvent were added the compound (12.97 g, 42.62 mmol) obtained in Reference Example 61, step F, sodium acetate (17.54 g, 214 mmol) and hydroxylammonium chloride (14.85 g, 214 mmol) and the mixture was heated under reflux for 2 hr. The reaction mixture was cooled, diluted with ethyl acetate (1000 ml), washed with saturated aqueous sodium hydrogen carbonate and saturated brine, and dried over anhydrous magnesium sulfate. The insoluble material was filtered off, and the solution was concentrated under reduced pressure to give a yellow oil. This was dissolved in toluene (50 ml), N,N-dimethylacetamide-dimethylacetal (26 ml) was added, and the mixture was stirred with heating at 100° C. for 45 min. The reaction mixture was cooled, diluted with an ethyl acetate-hexane=1:1 mixed solvent, and the organic layer was washed with water and saturated brine, and dried over anhydrous magnesium sulfate. The insoluble material was filtered off, and the solution was concentrated under reduced pressure, and the obtained oil was purified by silica gel column chromatography (ethyl acetate-hexane). The obtained solid was washed with a diethyl ether-hexane=1:1 mixed solvent, and dried under reduced pressure to give the title compound (10.38 g, yield 67%) as a colorless solid.

$^1$H-NMR (300 MHz, CDCl$_3$); δ (ppm) 1.24 (t, J=7.2, 6H), 2.40 (s, 3H), 2.63 (s, 3H), 4.07 (s, 4H), 4.15 (q, J=7.2, 4H), 7.26 (d, J=7.8, 1H), 7.68 (dd, J=1.5, 7.8, 1H), 7.90 (d, J=1.5, 1H).

Step B

N-[2-methyl-5-(5-methyl-1,2,4-oxadiazol-3-yl)phenyl]iminodiacetic acid

The compound (10.32 g, 28.56 mmol) obtained in step A was dissolved in a methanol (100 ml)-tetrahydrofuran (40 ml) mixed solvent. 1N sodium hydroxide (110 ml) was added with stirring at room temperature, and the mixture was stirred at the same temperature for 3 hr. The reaction mixture was concentrated under reduced pressure, 1N hydrochloric acid (150 ml) was added, and the precipitated solid was filtered, washed with water, and dried under reduced pressure to give the title compound (8.64 g, yield 99%) as a colorless solid.

$^1$H-NMR (300 MHz, DMSO-d$_6$); δ (ppm) 2.32 (s, 3H), 2.65 (s, 3H), 3.98 (s, 4H), 7.30 (d, J=8.1, 1H), 7.54 (dd, J=1.4, 8.1, 1H), 7.70 (d, J=1.4, 1H), 12.50 (brs, 2H).

Reference Example 63

N-(2-methylphenyl)iminodiacetic acid

Using o-toluidine (10.0 g, 93.3 mmol) and according to the methods of Reference Example 61, step C, Reference Example 62, step B, the title compound (19.12 g, yield 92%) was obtained as a colorless solid.

$^1$H-NMR (300 MHz, DMSO-d$_6$); δ (ppm) 2.24 (s, 3H), 3.91 (s, 4H), 6.87-6.93 (m, 1H), 7.04-7.13 (m, 3H), 12.43 (brs, 2H).

Reference Example 64

N-(3-chloro-2-methylphenyl)iminodiacetic acid

Using 3-chloro-2-methylaniline (1.88 g, 13.28 mmol) and according to the methods of Reference Example 61, step C, Reference Example 62, step B, the title compound (2.92 g, yield 85%) was obtained as a colorless solid.

$^1$H-NMR (300 MHz, DMSO-d$_6$); δ (ppm) 2.30 (s, 3H), 3.92 (s, 4H), 7.10 (brs, 3H), 12.45 (brs, 2H).

Reference Example 65

N-(5-chloro-2-methylphenyl)iminodiacetic acid

Using 5-chloro-2-methylaniline hydrochloride (5.03 g, 28.25 mmol) and according to the methods of Reference Example 61, step C, Reference Example 62, step B, the title compound (5.98 g, yield 82%) was obtained as a colorless solid.

$^1$H-NMR (300 MHz, DMSO-d$_6$); δ (ppm) 2.21 (s, 3H), 3.92 (s, 4H), 6.95 (dd, J=2.1, 8.1, 1H), 7.04 (d, J=2.1, 1H), 7.14 (d, J=8.1, 1H), 12.51 (brs, 2H).

Reference Example 66

N-(4-chloro-2-methylphenyl)iminodiacetic acid

Using 4-chloro-2-methylaniline (5.00 g, 35.3 mmol) and according to the methods of Reference Example 61, step C, Reference Example 62, step B, the title compound (3.88 g, yield 43%) was obtained as a pale-bistered solid.

$^1$H-NMR (300 MHz, CDCl$_3$); δ (ppm) 2.31 (s, 3H), 4.00 (s, 4H), 7.08-7.18 (m, 3H).

Reference Example 67

N-(5-acetyl-2-methylphenyl)iminodiacetic acid

Step A 2-methyl-5-(2-methyl-1,3-dioxolan-2-yl)aniline

To a flask mounted with Dean-Stark water removing apparatus (Dean-Stark trap) were added toluene (200 ml), 4-methyl-3-nitroacetophenone (9.77 g, 54.53 mmol), ethylene glycol (4.6 ml) and p-toluenesulfonic acid.monohydrate (0.79 g), and the mixture was heated under reflux for 100 min. The reaction mixture was cooled, washed with diluted aqueous sodium hydroxide solution and saturated brine, and dried over anhydrous magnesium sulfate. The insoluble material was filtered off, and the solution was concentrated under reduced pressure to give a crude brown oil (13.0 g). Using the crude oil and according to the method of Reference Example 61, step B, the title compound (9.89 g, yield 94%) was obtained as a pale-yellow solid.

$^1$H-NMR (300 MHz, CDCl$_3$); δ (ppm) 1.63 (s, 3H), 2.15 (s, 3H), 3.61 (brs, 2H), 3.76-3.82 (m, 2H), 3.98-4.04 (m, 2H), 6.80 (s, 1H), 6.82 (d, J=7.4, 1H), 7.02 (d, J=7.4, 1H).

Step B

N-(5-acetyl-2-methylphenyl)iminodiacetic acid diethyl ester

The compound (9.87 g, 51.08 mmol) obtained in step A, ethyl bromoacetate (23 ml, 207 mmol) and N,N-diisopropylethylamine (45 ml, 265 mmol) were mixed, and the mixture was stirred with heating at 140° C. for 200 min. The reaction mixture was cooled, diluted with an ethyl acetate-hexane=1:1 mixed solvent, and the organic layer was washed with 10% aqueous citric acid solution, saturated aqueous sodium hydrogen carbonate and saturated brine, and dried over anhydrous magnesium sulfate. The insoluble material was filtered off, and the solution was concentrated under reduced pressure. The obtained oil was dissolved in tetrahydrofuran (160 ml), 6N aqueous hydrochloric acid solution (25 ml) was added, and the mixture was stirred at room temperature for 30 min. To the reaction mixture were added water and an ethyl acetate-hexane=1:1 mixed solvent, and the organic layer was washed with saturated aqueous sodium hydrogen carbonate and saturated brine, and dried over anhydrous magnesium sulfate. The insoluble material was filtered off, and the solution was concentrated under reduced pressure. The obtained oil was purified by silica gel column chromatography (ethyl acetate-hexane) to give the title compound (16.30 g, yield 99%) as a yellow oil.

$^1$H-NMR (300 MHz, CDCl$_3$); δ (ppm) 1.24 (t, J=7.2, 6H), 2.40 (s, 3H), 2.55 (s, 3H), 4.04 (s, 4H), 4.14 (q, J=7.2, 4H), 7.24 (d, J=8.1, 1H), 7.57 (dd, J=1.8, 8.1, 1H), 7.80 (d, J=2.1, 1H).

Step C

N-(5-acetyl-2-methylphenyl)iminodiacetic acid

Using the compound (4.22 g, 13.13 mmol) obtained in step B and according to the method of Reference Example 61, step G, the title compound (2.63 g, yield 76%) was obtained as a colorless solid.

$^1$H-NMR (300 MHz, DMSO-d$_6$); δ (ppm) 2.32 (s, 3H), 2.50 (s, 3H), 3.96 (s, 4H), 7.28 (d, J=7.8, 1H), 7.54 (d, J=7.8, 1H), 7.63 (s, 1H), 12.46 (brs, 2H).

Reference Example 68

N-(4-cyano-2-methylphenyl)iminodiacetic acid

Step A 4-amino-3-methylbenzonitrile

To an ethanol (500 ml)-water (60 ml)-acetic acid (30 ml) mixed solvent were added 3-methyl-4-nitrobenzonitrile (8.40 g, 51.8 mmol) and reduced iron (18 g, 322 mmol), and the mixture was stirred with heating at 85° C. for 3 hr. The reaction mixture was cooled, filtered through celite, and the solution was concentrated under reduced pressure. The obtained residue was diluted with ethyl acetate, washed with diluted aqueous sodium hydroxide solution and saturated brine, and dried over anhydrous magnesium sulfate. The insoluble material was filtered off, and the solution was concentrated under reduced pressure to give the title compound (6.37 g, yield 93%) as a pale-yellow solid.

$^1$H-NMR (300 MHz, DMSO-d$_6$); δ (ppm) 2.04 (s, 3H), 5.89 (brs, 2H), 6.64 (d, J=8.1, 1H), 7.26-7.31 (m, 2H).

Step B

N-(4-cyano-2-methylphenyl)iminodiacetic acid

Using the compound (4.47 g, 33.8 mmol) obtained in step A and according to the methods of Reference Example 61, steps C and G, the title compound (2.60 g, yield 31%) was obtained as a pale-pink solid.

$^1$H-NMR (300 MHz, DMSO-d$_6$); δ (ppm) 2.26 (s, 3H), 4.01 (s, 4H), 7.01 (d, J=8.4, 1H), 7.49-7.55 (m, 2H), 12.64 (brs, 2H).

Reference Example 69

N-[2-methyl-4-(5-methyl-1,2,4-oxadiazol-3-yl)phenyl]iminodiacetic acid

Step A 3-methyl-4-nitrobenzoic acid tert-butyl ester

Using 3-methyl-4-nitrobenzoic acid (50.0 g, 276 mmol) and according to the method of Reference Example 61, step A, the title compound (55.6 g, yield 85%) was obtained as a pale-yellow solid.

$^1$H-NMR (300 MHz, CDCl$_3$); δ (ppm) 1.61 (s, 9H), 2.62 (s, 3H), 7.88-7.97 (m, 3H).

Step B 4-amino-3-methylbenzoic acid tert-butyl ester

The compound (55.6 g, 234 mmol) obtained in step A was dissolved in an ethanol (200 ml)-tetrahydrofuran (100 ml) mixed solvent. Then, 10% palladium carbon (containing water) (10 g) suspended in ethanol (20 ml) was added. Under a hydrogen atmosphere and at room temperature, the reaction mixture was stirred for 5 hr, and filtered off through celite. The obtained solution was concentrated under reduced pressure to give the title compound (51.5 g) as a bistered oil.

¹H-NMR (300 MHz, CDCl₃); δ (ppm) 1.57 (s, 9H), 2.17 (s, 3H), 3.95 (brs, 2H), 6.62 (d, J=8.1, 1H), 7.66-7.70 (m, 2H).

Step C

N-(4-tert-butoxycarbonyl-2-methylphenyl)iminodiacetic acid diethyl ester

The compound (51.5 g) obtained in step B, ethyl bromoacetate (160 ml, 1.44 mol) and N,N-diisopropylethylamine (250 ml, 1.47 mol) were mixed, and the mixture was stirred with heating at 140° C. for 10 hr. The reaction mixture was cooled, diluted with ethyl acetate, and the organic layer was washed with 20% aqueous citric acid solution and saturated brine, and dried over anhydrous magnesium sulfate. The insoluble material was filtered off, and the solution was concentrated under reduced pressure. The obtained oil was purified by silica gel column chromatography (ethyl acetate-hexane) to give a mixture of the title compound and N-(4-tert-butoxycarbonyl-2-methyl)phenylglycine ethyl ester. To this mixture were added ethyl bromoacetate (80 ml, 719 mmol) and N,N-diisopropylethylamine (125 ml, 735 mmol), and the mixture was stirred again with heating at 140° C. for 11 hr, which was followed by the purification similar to the above to give the title compound (95.3 g) as a yellow oil.

¹H-NMR (300 MHz, CDCl₃); δ (ppm) 1.24 (t, J=7.3, 6H), 1.57 (s, 9H), 2.34 (s, 3H), 4.06 (s, 4H), 4.15 (q, J=7.3, 4H), 7.10 (d, J=8.3, 1H), 7.74 (dd, J=2.1, 8.3, 1H), 7.78 (d, J=2.1, 1H).

Step D

N-(4-carboxy-2-methylphenyl)iminodiacetic acid diethyl ester

Using the compound (15.0 g, 39.5 mmol) obtained by the method of step C and according to the method of Reference Example 61, step D, the title compound (14.1 g) was obtained as a pale-yellow oil.

¹H-NMR (300 MHz, CDCl₃); δ (ppm) 1.25 (t, J=7.2, 6H), 2.36 (s, 3H), 4.10 (s, 4H), 4.17 (q, J=6.9, 4H), 7.10 (d, J=8.4, 1H), 7.86 (dd, J=1.9, 8.4, 1H), 7.90 (d, J=1.9, 1H), 9.77 (brs, 1H)

Step E

N-[4-(aminocarbonyl)-2-methylphenyl]iminodiacetic acid diethyl ester

Using the compound (14.1 g) obtained in step D and according to the method of Reference Example 61, step E, the title compound (11.2 g, yield from step D 88%) was obtained as a colorless solid.

¹H-NMR (300 MHz, CDCl₃); δ (ppm) 1.24 (t, J=6.9, 6H), 2.36 (s, 3H), 4.06 (s, 4H), 4.14 (q, J=6.9, 4H), 5.90-5.99 (broad, 2H), 7.14 (d, J=8.4, 1H), 7.55 (dd, J=2.1, 8.4, 1H), 7.65 (d, J=2.1, 1H).

Step F

N-(4-cyano-2-methylphenyl)iminodiacetic acid diethyl ester

Using the compound (11.2 g, 34.8 mmol) obtained in step E and according to the method of Reference Example 61, step F, the title compound (9.64 g, yield 91%) was obtained as a colorless solid.

¹H-NMR (300 MHz, CDCl₃); δ (ppm) 1.25 (t, J=7.5, 6H), 2.33 (s, 3H), 4.06 (s, 4H), 4.17 (q, J=7.5, 4H), 7.12 (d, J=8.2, 1H), 7.38-7.43 (m, 2H).

Step G

N-[2-methyl-4-(5-methyl-1,2,4-oxadiazol-3-yl)phenyl]iminodiacetic acid diethyl ester Using the compound (9.64 g, 31.67 mmol) obtained in step F and according to the method of Reference Example 62, step A, the title compound (8.03 g, yield 71%) was obtained as a colorless solid.

¹H-NMR (300 MHz, CDCl₃); δ (ppm) 1.24 (t, J=7.2, 6H), 2.38 (s, 3H), 2.64 (s, 3H), 4.08 (s, 4H), 4.15 (q, J=7.5, 4H), 7.21 (d, J=8.4, 1H), 7.81 (dd, J=2.1, 8.4, 1H), 7.86 (d, J=2.1, 1H).

Step H

N-[2-methyl-4-(5-methyl-1,2,4-oxadiazol-3-yl)phenyl]iminodiacetic acid

Using the compound (8.03 g, 22.22 mmol) obtained in step G and according to the method of Reference Example 62, step B, the title compound (7.74 g, yield>100%) was obtained as a colorless solid.

¹H-NMR (300 MHz, DMSO-d₆); δ (ppm) 2.31 (s, 3H), 2.63 (s, 3H), 3.99 (s, 4H), 7.10 (d, J=8.4, 1H), 7.69 (dd, J=1.8, 8.4, 1H), 7.74 (d, J=1.8, 1H), 12.58 (brs, 2H).

Reference Example 70

N-[4-{[2-(tert-butoxycarbonyl)-2-methylhydrazino]carbonyl}-2-methylphenyl]iminodiacetic acid

Step A

N-[4-{[2-(tert-butoxycarbonyl)-2-methylhydrazino]carbonyl}-2-methylphenyl]iminodiacetic acid diethyl ester The compound (2.50 g, 7.7 mmol) of Reference Example 69, step D, was dissolved in dichloromethane (85 ml), oxalyl chloride (1.00 ml, 11.6 mmol) and a catalytic amount of N,N-dimethylformamide were added with stirring under ice-cooling, and the mixture was stirred at room temperature for 2 hr. The reaction mixture was concentrated, the obtained oil was dissolved in dichloromethane (85 ml), tert-butyl 1-methylhydrazine carboxylate (1.70 g, 11.6 mmol) and triethylamine (4.3 ml, 31 mmol) were added with stirring under ice-cooling, and the mixture was stirred at room temperature for 2 hr. The reaction mixture was concentrated, and the obtained oil was dissolved in ethyl acetate, washed with water and saturated brine, and dried over anhydrous magnesium sulfate. The insoluble material was filtered off, and the solution was concentrated under reduced pressure. The obtained oil was purified by silica gel column chromatography (methanol-chloroform) to give the title compound (3.15 g, yield 81%) as a pale-yellow oil.

¹H-NMR (300 MHz, CDCl₃); δ (ppm) 1.24 (t, J=7.1, 6H), 1.46 (brs, 9H), 2.27 (brs, 3H), 3.17 (brs, 3H), 4.03 (brs, 4H), 4.13 (q, J=6.8, 4H), 6.95-7.09 (m, 1H), 7.53-7.56 (m, 1H), 7.63 (s, 1H), 8.7-9.22 (m, 1H).

Step B

N-[4-{[2-(tert-butoxycarbonyl)-2-methylhydrazino]carbonyl}-2-methylphenyl]iminodiacetic acid Using the compound (3.15 g, 6.97 mmol) obtained in step A and according to the method of Reference Example 61, step G, the title compound (2.29 g, yield 83%) was obtained as a colorless oil.

$^1$H-NMR (300 MHz, DMSO-$d_6$); δ (ppm) 1.33 (s, 9H), 2.28 (s, 3H), 3.09 (s, 3H), 3.98 (s, 4H), 7.00 (d, J=8.4, 1H), 7.52-7.60 (m, 2H), 10.4 (s, 1H), 12.5 (brs, 2H).

Reference Example 71

N-[4-{[2-(tert-butoxycarbonyl)-2-ethylhydrazino]carbonyl}-2-methylphenyl]iminodiacetic acid Step A N-[4-{[2-(tert-butoxycarbonyl)-2-ethylhydrazino]carbonyl}-2-methylphenyl]iminodiacetic acid diethyl ester Using the compound (2.50 g, 7.7 mmol) of Reference Example 69, step D and tert-butyl 1-ethylhydrazinecarboxylate (1.86 g, 11.6 mmol), and according to the method of Reference Example 70, step A, the title compound (2.60 g, yield 72%) was obtained as a pale-yellow oil.

$^1$H-NMR (300 MHz, CDCl$_3$); δ (ppm) 1.14 (t, J=4.2, 3H), 1.24 (t, J=7.5, 6H), 1.46 (brs, 9H), 2.30 (brs, 3H), 3.60 (q, J=7.2, 2H), 4.04 (brs, 4H), 4.14 (q, J=7.2, 4H), 7.09 (brs, 1H), 7.53 (d, J=8.1, 1H), 7.62 (s, 1H).

Step B

N-[4-{[2-(tert-butoxycarbonyl)-2-ethylhydrazino]carbonyl}-2-methylphenyl]iminodiacetic acid Using the compound (2.60 g, 5.58 mmol) obtained in step A and according to the method of Reference Example 61, step G, the title compound (1.9 g, yield 83%) was obtained as a colorless oil.

$^1$H-NMR (300 MHz, DMSO-$d_6$); δ (ppm) 1.00-1.07 (m, 3H), 1.33 (s, 9H), 2.28 (s, 3H), 3.43 (q, J=7.2, 2H), 3.98 (s, 4H), 7.02 (d, J=8.4, 1H), 7.55-7.68 (m, 2H), 10.3 (s, 1H), 12.2 (brs, 2H).

Reference Example 72

N-[5-(tert-butoxycarbonyl)-2-methylphenyl]iminodiacetic acid

Using the compound (7.44 g, 19.6 mmol) of Reference Example 61, step C, and according to the method of Reference Example 62, step B, the title compound (5.46 g, yield 86%) was obtained as a colorless solid.

$^1$H-NMR (300 MHz, CDCl$_3$); δ (ppm) 1.52 (s, 9H), 2.30 (s, 3H), 3.94 (s, 4H), 7.23 (d, J=8.1, 1H), 7.44 (dd, J=0.9, 8.1, 1H), 7.62 (d, J=0.9, 1H), 12.48 (brs, 2H).

Reference Example 73

N-[5-(aminocarbonyl)-2-methylphenyl]iminodiacetic acid

Using the compound (3.16 g, 9.80 mmol) of Reference Example 61, step E, and according to the method of Reference Example 62, step B, the title compound (2.56 g, yield 98%) was obtained as a colorless solid.

$^1$H-NMR (300 MHz, DMSO-$d_6$); δ (ppm) 2.28 (s, 3H), 3.94 (s, 4H), 7.17 (d, J=7.8, 1H), 7.18 (brs, 1H), 7.41 (d, J=7.8, 1H), 7.60 (s, 1H), 7.85 (brs, 1H), 12.41 (brs, 2H).

Reference Example 74

N-[5-{[2-(tert-butoxycarbonyl)-2-methylhydrazino]carbonyl}-2-methylphenyl]iminodiacetic acid Step A N-[5-{[2-(tert-butoxycarbonyl)-2-methylhydrazino]carbonyl}-2-methylphenyl]iminodiacetic acid diethyl ester Using the compound (15.92 g, 49.24 mmol) of Reference Example 61, step D, and tert-butyl 1-methylhydrazinecarboxylate (9.93 g, 67.93 mmol), and according to the method of Reference Example 70, step A, the title compound (24.27 g) was obtained as a crude orange oil. This was directly used for the next step.

Step B

N-[5-{[2-(tert-butoxycarbonyl)-2-methylhydrazino]carbonyl}-2-methylphenyl]iminodiacetic acid Using the compound (24.27 g) obtained in step A and according to the method of Reference Example 62, step B, the title compound (16.51 g, yield from step A 85%) was obtained as a colorless solid.

$^1$H-NMR (300 MHz, DMSO-$d_6$); δ (ppm) 1.33 (s, 5.4H), 1.45 (s, 3.6H), 2.30 (s, 3H), 3.02 (s, 1.2H), 3.08 (s, 1.8H), 3.96 (s, 4H), 7.22 (d, J=7.8, 1H), 7.32-7.43 (m, 1H), 7.5-7.6 (m, 1H), 10.50 (s, 0.6H), 10.54 (s, 0.4H), 12.45 (brs, 2H).

Reference Example 75

N-[5-{[2-(tert-butoxycarbonyl)-2-ethylhydrazino]carbonyl}-2-methylphenyl]iminodiacetic acid Step A N-[5-{[2-(tert-butoxycarbonyl)-2-ethylhydrazino]carbonyl}-2-methylphenyl]iminodiacetic acid diethyl ester Using the compound (1.50 g, 4.63 mmol) of Reference Example 61, step D, and tert-butyl 1-ethylhydrazinecarboxylate (1.12 g, 7 mmol), and according to the method of Reference Example 70, step A, the title compound (2.10 g, yield 98%) was obtained as a colorless oil.

¹H-NMR (300 MHz, CDCl₃); δ (ppm) 1.09-1.28 (m, 9H), 1.47 (s, 9H), 2.37 (s, 3H), 3.62 (q, J=7.1, 2H), 4.02 (s, 4H), 4.14 (q, J=7.1, 4H), 7.18 (brs, 1H), 7.38 (d, J=7.6, 1H), 7.65 (s, 1H).

Step B

N-[5-{[2-(tert-butoxycarbonyl)-2-ethylhydrazino]carbonyl}-2-methylphenyl]iminodiacetic acid Using the compound (2.10 g, 4.5 mmol) obtained in step A and according to the method of Reference Example 61, step G, the title compound (1.71 g, yield 93%) was obtained as a colorless oil.

¹H-NMR (300 MHz, DMSO-d₆); δ (ppm) 1.08 (t, J=6.9, 3H), 1.33-1.43 (m, 9H), 2.29 (s, 3H), 3.36-3.45 (m, 2H), 3.95 (s, 4H), 7.21 (d, J=7.8, 1H), 7.34-7.41 (m, 1H), 7.53-7.66 (m, 1H), 10.38-10.43 (m, 1H), 12.45 (brs, 2H).

Reference Example 76

N-[5-(tert-butoxycarbonylamino)-2-methylphenyl]iminodiacetic acid

Step A

N-[5-(tert-butoxycarbonylamino)-2-methylphenyl]iminodiacetic acid diethyl ester

To toluene (20 ml) were added the compound (3.06 g, 9.46 mmol) of Reference Example 61, step D, diphenylphosphoryl azide (2.24 ml, 10.4 mmol) and triethylamine (1.45 ml, 10.4 mmol), and the mixture was heated under reflux for 90 min. Then, to the reaction mixture was added tert-butanol (9.0 ml), and the mixture was further heated under reflux for 7 hr. The reaction mixture was cooled to room temperature and concentrated under reduced pressure. The residue was diluted with dichloromethane, and the organic layer was washed with water and dried over anhydrous magnesium sulfate. The insoluble material was filtered off, and the solution was concentrated under reduced pressure. The obtained crude product was purified by silica gel column chromatography (ethyl acetate-hexane) to give the title compound (3.39 g, yield 85%) as a pale-yellow oil.

¹H-NMR (300 MHz, CDCl₃); δ (ppm) 1.24 (t, J=6.9, 6H), 1.50 (s, 9H), 2.27 (s, 3H), 4.01 (s, 4H), 4.14 (q, J=6.9, 4H), 6.35 (brs, 1H), 7.04 (m, 2H), 7.15 (s, 1H).

Step B

N-[5-(tert-butoxycarbonylamino)-2-methylphenyl]iminodiacetic acid

Using the compound (3.38 g, 8.00 mmol) obtained by the method of step A and according to the method of Reference Example 62, step B, the title compound (2.39 g, yield 81%) was obtained as a pale-yellow amorphous solid.

¹H-NMR (300 MHz, DMSO-d₆); δ (ppm) 1.45 (s, 9H), 2.15 (s, 3H), 3.88 (s, 4H), 6.94-6.98 (m, 2H), 7.22 (s, 1H), 9.12 (s, 1H), 12.4 (brs, 2H).

Reference Example 77

N-[5-(ethoxycarbonyl)-2-methylphenyl]iminodiacetic acid

Step A

N-[5-(ethoxycarbonyl)-2-methylphenyl]iminodiacetic acid diethyl ester

Using the compound (1.00 g, 3.1 mmol) of Reference Example 61, step D, and ethanol (0.4 ml, 6.2 mmol), and according to the method of Reference Example 61, step A, the title compound (1.20 g, yield>100%) was obtained as a pale-yellow oil.

¹H-NMR (300 MHz, CDCl₃); δ (ppm) 1.25 (t, J=7.5, 6H), 1.37 (t, J=7.5, 3H), 2.39 (s, 3H), 4.05 (s, 4H), 4.15 (q, J=7.2, 4H), 4.35 (q, J=7.2, 2H), 7.22 (d, J=7.8, 1H), 7.66 (dd, J=7.8, 1.2, 1H), 7.85 (d, J=1.2, 1H).

Step B

N-[5-(ethoxycarbonyl)-2-methylphenyl]iminodiacetic acid

The compound (0.62 g, 1.76 mmol) obtained in step A was dissolved in a ethanol (10 ml)-tetrahydrofuran (5 ml) mixed solvent, 1N sodium hydroxide (3.53 ml, 3.53 mmol) was added at room temperature with stirring, and the mixture was stirred at the same temperature for 90 min. To the reaction mixture was added 1N hydrochloric acid (5 ml), and the mixture was extracted with ethyl acetate. The organic layer was washed with diluted hydrochloric acid and saturated brine, and dried over anhydrous magnesium sulfate. The insoluble material was filtered off, and the solution was concentrated under reduced pressure to give the title compound (0.52 g) as a crude colorless oil.

Reference Example 78

N-[2-methyl-5-(5-methyl-1,3-oxazol-2-yl)phenyl]iminodiacetic acid

Step A

N-[2-methyl-5-{[(2-oxopropyl)amino]carbonyl}phenyl]iminodiacetic acid diethyl ester The compound (2.00 g, 6.18 mmol) of Reference Example 61, step D, was dissolved in dichloromethane (60 ml), oxalyl chloride (0.80 ml, 9.28 mmol) and a catalytic amount of N,N-dimethylformamide were added under ice-cooling with stirring, and the mixture was stirred at room temperature for 2 hr. The reaction mixture was concentrated, the obtained oil was dissolved again in dichloromethane (60 ml), 1-aminopropan-2-one hydrochloride (1.10 g, 9.89 mmol) and triethylamine (2.8 ml, 20 mmol) were added under ice-cooling with stirring, and the mixture was stirred at room temperature for 2 hr. The reaction mixture was concentrated, and the obtained oil was diluted with ethyl acetate, washed with water and saturated brine, and dried over anhydrous magnesium sulfate. The insoluble material was filtered off, and the solution was concentrated under reduced pressure. The obtained crude product was purified by silica gel column chromatography (methanol-dichloromethane) to give the title compound (2.60 g, yield>100%) as a pale-yellow oil.

¹H-NMR (300 MHz, CDCl₃); δ (ppm) 1.24 (t, J=6.9, 6H), 2.26 (s, 3H), 2.38 (s, 3H), 4.04 (s, 4H), 4.15 (q, J=6.9, 4H), 4.33 (d, J=4.5, 2H), 6.87 (brs, 1H), 7.22 (d, J=7.9, 1H), 7.41 (dd, J=1.5, 7.9, 1H), 7.67 (d, J=1.5, 1H).

Step B

N-[2-methyl-5-(5-methyl-1,3-oxazol-2-yl)phenyl]iminodiacetic acid diethyl ester

To the compound (555 mg, 1.47 mmol) obtained in step A was added phosphorus oxychloride (8.00 g), and the mixture was stirred at 120° C. for 3 hr. The reaction mixture was cooled to room temperature and slowly added to ice water. The solution was extracted with ethyl acetate, and washed with water, saturated aqueous sodium hydrogen carbonate and saturated brine, and dried over anhydrous magnesium sulfate. The insoluble material was filtered off, and the solution was concentrated under reduced pressure. The obtained oil was purified by silica gel chromatography (ethyl acetate-hexane) to give the title compound (0.30 g, yield 57%) as a yellow oil.
¹H-NMR (300 MHz, CDCl₃); δ (ppm) 1.23 (t, J=7.2, 6H), 2.37 (s, 3H), 2.38 (s, 3H), 4.07 (s, 4H), 4.14 (q, J=7.2, 4H), 6.79 (s, 1H), 7.22 (d, J=7.8, 1H), 7.62 (dd, J=1.5, 7.8, 1H), 7.82 (s, 1H).

Step C

N-[2-methyl-5-(5-methyl-1,3-oxazol-2-yl)phenyl]iminodiacetic acid

Using the compound (0.30 g, 0.83 mmol) obtained in step B and according to the method of Reference Example 62, step B, the title compound (0.21 g, yield 84%) was obtained as a yellow solid.
¹H-NMR (300 MHz, DMSO-d₆); δ (ppm) 2.29 (s, 3H), 2.37 (s, 3H), 3.98 (s, 4H), 6.94 (s, 1H), 7.254 (d, J=7.8, 1H), 7.47 (dd, J=1.2, 7.8, 1H), 7.63 (d, J=1.2, 1H), 12.5 (brs, 2H).

Reference Example 79

N-[2-methyl-5-(4-methyl-1,3-thiazol-2-yl)phenyl]iminodiacetic acid

Step A

N-[5-(aminocarbonothioyl)-2-methylphenyl]iminodiacetic acid diethyl ester

The compound (0.84 g, 2.6 mmol) of Reference Example 61, step E, and Lawesson reagent (1.20 g, 3.4 mmol) were dissolved in 1,4-dioxane (36 ml), and the mixture was stirred at 80° C. for 1 hr. The reaction mixture was concentrated under reduced pressure, and the obtained oil was purified by silica gel chromatography (NH silica gel use, methanol-chloroform) to give the title compound (0.80 g, yield 91%) as a yellow oil.
¹H-NMR (300 MHz, CDCl₃); δ (ppm) 1.26 (t, J=7.2, 6H), 2.36 (s, 3H), 4.04 (s, 4H), 4.14 (q, J=7.2, 4H), 7.16 (d, J=8.1, 1H), 7.4-7.6 (broad, 1H), 7.47 (d, J=8.1, 1H), 7.78 (s, 1H), 7.95 (brs, 1H).

Step B

N-[2-methyl-5-(4-methyl-1,3-thiazol-2-yl)phenyl]iminodiacetic acid

The compound (0.70 g, 2.1 mmol) obtained in step A was dissolved in a ethanol (14 ml)-N,N-dimethylformamide (4 ml) mixed solvent. Then, chloroacetone (0.18 ml, 2.3 mmol) was added, and the mixture was stirred at 80° C. for 3 hr. The reaction mixture was concentrated under reduced pressure, and the obtained oil was diluted with dichloromethane, washed with water, saturated aqueous sodium hydrogen carbonate and saturated brine, and dried over anhydrous magnesium sulfate. The insoluble material was filtered off, and the solution was concentrated under reduced pressure to give a crude oil of the title compound containing N,N-dimethylformamide. Using this oil and according to the method of Reference Example 62, step B, the title compound (0.56 g, yield 83%) was obtained as a pale-yellow oil.
¹H-NMR (300 MHz, DMSO-d₆); δ (ppm) 2.36 (s, 3H), 2.48 (s, 3H), 4.08 (s, 4H), 6.84 (s, 1H), 7.18 (d, J=7.8, 1H), 7.45 (d, J=7.8, 1H), 7.77 (s, 1H), 12.0 (brs, 2H).

Reference Example 80

N-[2-methyl-5-(5-methyl-1,3-thiazol-2-yl)phenyl]iminodiacetic acid

Step A

N-[2-methyl-5-(5-methyl-1,3-thiazol-2-yl)phenyl]iminodiacetic acid diethyl ester The compound (1.30 g, 3.43 mmol) of Reference Example 78, step A, and a Lawesson reagent (1.84 g, 4.56 mmol) were dissolved in 1,4-dioxane (30 ml), and the mixture was stirred at 80° C. for 3 hr. The reaction mixture was concentrated under reduced pressure, and the obtained oil was purified by silica gel chromatography (ethyl acetate-hexane) to give the title compound (1.28 g, yield 100%) as a yellow oil.
¹H-NMR (300 MHz, CDCl₃); δ (ppm) 1.23 (t, J=7.3, 6H), 2.37 (s, 3H), 2.49 (s, 3H), 4.07 (s, 4H), 4.15 (q, J=7.0, 4H), 7.20 (d, J=7.9, 1H), 7.45-7.52 (m, 2H), 7.73 (d, J=1.7, 1H).

Step B

N-[2-methyl-5-(5-methyl-1,3-thiazol-2-yl)phenyl]iminodiacetic acid

Using the compound (0.80 g, 2.12 mmol) obtained in step A and according to the method of Reference Example 62, step B, the title compound (0.68 g, yield 100%) was obtained as a pale-yellow solid.
¹H-NMR (300 MHz, DMSO-d₆); δ (ppm) 2.28 (s, 3H), 2.49 (s, 3H), 3.97 (s, 4H), 7.11 (d, J=7.5, 1H), 7.22 (d, J=8.1, 1H), 7.54 (s, 1H), 7.59 (s, 1H), 12.5 (brs, 2H).

Reference Example 81

N-[2-methyl-5-(4-ethyl-1,3-thiazol-2-yl)phenyl]iminodiacetic acid

Using the compound (1.44 g, 4.26 mmol) of Reference Example 79, step A, and 1-bromo-2-butanone (0.5 ml, 4.90 mmol), and according to the method of Reference Example 79, step B, the title compound (0.91 g, yield 64%) was obtained as a yellow solid.
¹H-NMR (300 MHz, DMSO-d₆); δ (ppm) 1.26 (t, J=7.5, 3H), 2.29 (s, 3H). 2.77 (q, J=7.5, 2H), 3.98 (s, 4H), 7.22-7.27 (m, 2H), 7.44 (d, J=8.1, 1H), 7.62 (s, 1H), 12.5 (brs, 2H).

Reference Example 82

N-[2-methyl-5-(4-tert-butyl-1,3-thiazol-2-yl)phenyl]iminodiacetic acid

Using the compound (1.44 g, 4.26 mmol) of Reference Example 79, step A, and 1-chloropinacolone (0.61 ml, 4.7 mmol), and according to the method of Reference Example 79, step B, the title compound (0.95 g, yield 62%) was obtained as a colorless solid.

$^1$H-NMR (300 MHz, DMSO-$d_6$); δ (ppm) 1.33 (s, 9H), 2.29 (s, 3H), 3.98 (s, 4H), 7.22-7.25 (m, 2H), 7.45 (dd, J=1.2, 7.5, 1H), 7.59 (d, J=1.2, 1H), 12.5 (brs, 2H).

Reference Example 83

N-[2-methyl-5-(5-methyl-1,3,4-oxadiazol-2-yl)phenyl]iminodiacetic acid

Step A

N'-acetyl-4-methyl-3-nitrobenzohydrazide

4-Methyl-3-nitrobenzoic acid (3.00 g, 16.5 mmol) was added to dichloromethane (50 ml), triethylamine (3.0 ml, 21.3 mmol) and isobutyl chloroformate (2.80 ml, 21.5 mmol) were added under ice-cooling with stirring, and the mixture was stirred at room temperature for 3 hr. The reaction mixture was ice-cooled again, acetohydrazide (2.45 g, 33.1 mmol) was added with stirring, and the mixture was stirred at room temperature for about 3 hr. The reaction mixture was diluted with ethyl acetate, washed with 10% aqueous citric acid solution, and dried over anhydrous magnesium sulfate. The insoluble material was filtered off, and the solution was concentrated under reduced pressure. The obtained solid was washed with diethyl ether and hexane to give the title compound (1.72 g, yield 44%) as a colorless solid.

$^1$H-NMR (300 MHz, CDCl$_3$); δ (ppm) 1.94 (s, 3H), 2.59 (s, 3H), 7.66 (d, J=8.1, 1H), 8.10 (dd, J=1.8, 8.1, 1H), 8.47 (d, J=1.8, 1H), 10.01 (s, 1H), 10.6 (s, 1H).

Step B

2-methyl-5-(4-methyl-3-nitrophenyl)-1,3,4-oxadiazole

The compound (0.70 g, 2.95 mmol) obtained in step A and polyphosphoric acid (8.0 g) were mixed, and the mixture was stirred with heating at 120° C. After cooling to room temperature, the reaction mixture was poured into ice water, and diluted with ethyl acetate. The mixture was washed with water and saturated aqueous sodium hydrogen carbonate, and dried over anhydrous magnesium sulfate. The insoluble material was filtered off, and the solution was concentrated under reduced pressure to give the title compound (0.91 g) as a colorless solid.

$^1$H-NMR (300 MHz, CDCl$_3$); δ (ppm) 2.66 (s, 3H), 2.67 (s, 3H), 7.52 (d, J=8.1, 1H), 8.19 (dd, J=1.8, 8.1, 1H), 8.59 (d, J=1.8, 1H).

Step C

2-methyl-5-(5-methyl-1,3,4-oxadiazol-2-yl)aniline

Using the compound (0.91 g) obtained in step B and according to the method of Reference Example 61, step B, the title compound (0.71 g) was obtained as a colorless oil. This was directly used for the next step.

Step D

N-[2-methyl-5-(5-methyl-1,3,4-oxadiazol-2-yl)phenyl]iminodiacetic acid diethyl ester

Using the compound (0.71 g) obtained in step C and according to the method of Reference Example 61, step C, the title compound (0.68 g, yield from step B 64%) was obtained as a pale-yellow oil.

$^1$H-NMR (300 MHz, CDCl$_3$); δ (ppm) 1.24 (t, J=7.4, 6H), 2.41 (s, 3H), 2.60 (s, 3H), 4.00-4.21 (m, 8H), 7.29 (d, J=8.0, 1H), 7.65 (dd, J=1.3, 8.0, 1H), 7.85 (d, J=1.3, 1H).

Step E

N-[2-methyl-5-(5-methyl-1,3,4-oxadiazol-2-yl)phenyl]iminodiacetic acid

Using the compound (0.68 g, 1.9 mmol) obtained in step D and according to the method of Reference Example 61, step G, the title compound (0.51 g, yield 89%) was obtained as a colorless oil.

$^1$H-NMR (300 MHz, DMSO-$d_6$); δ (ppm) 2.32 (s, 3H), 2.77 (s, 3H), 4.00 (s, 4H), 7.29 (d, J=7.8, 1H), 7.43 (d, J=7.8, 1H), 7.64 (s, 1H), 12.5 (brs, 2H).

Reference Example 84

N-[2-methyl-5-(5-methyl-1,3,4-thiadiazol-2-yl)phenyl]iminodiacetic acid

Step A

N-{[5-(2-acetylhydrazino)carbonyl]-2-methylphenyl}iminodiacetic acid diethyl ester

The compound (3.00 g, 9.27 mmol) of Reference Example 61, step D, was dissolved in dichloromethane (100 ml), and the mixture was stirred under ice-cooling. Then, oxalyl chloride (1.25 ml, 14.6 mmol) and a catalytic amount of N,N-dimethylformamide were added, and the mixture was stirred at room temperature for 2 hr. The reaction mixture was concentrated under reduced pressure, and the obtained oil was dissolved in dichloromethane (100 ml) again. While stirring the solution under ice-cooling, acetohydrazide (1.20 g, 16.2 mmol) and triethylamine (5.8 ml, 42 mmol) were successively added, and the mixture was stirred at room temperature overnight. The reaction mixture was concentrated under reduced pressure, and the obtained oil was dissolved in ethyl acetate. The organic layer was washed with saturated brine, and dried over anhydrous magnesium sulfate. The insoluble material was filtered off, and the solution was concentrated under reduced pressure. The obtained oil was purified by silica gel column chromatography (methanol-dichloromethane) to give the title compound (2.61 g, yield 74%) as a pale-yellow oil.

Step B

N-[2-methyl-5-(5-methyl-1,3,4-thiadiazol-2-yl)phenyl]iminodiacetic acid diethyl ester

Using the compound (2.61 g, 6.88 mmol) obtained in step A and according to the method of Reference Example 80, step A, the title compound (2.36 g, yield 91%) was obtained as a yellow oil.

Step C

N-[2-methyl-5-(5-methyl-1,3,4-thiadiazol-2-yl)phenyl]iminodiacetic acid

Using the compound (2.36 g, 6.25 mmol) obtained in step B and according to the method of Reference Example 62, step B, the title compound (1.40 g, yield 70%) was obtained as a colorless solid.

$^1$H-NMR (300 MHz, DMSO-d$_6$); δ (ppm) 2.31 (s, 3H), 2.76 (s, 3H), 3.99 (s, 4H), 7.29 (d, J=7.8, 1H), 7.36-7.44 (m, 1H), 7.63 (s, 1H), 12.5 (brs, 2H).

Reference Example 85

N-[2-methyl-5-(5-oxo-4,5-dihydro-1,3,4-oxadiazol-2-yl)phenyl]iminodiacetic acid

Step A

N-[5-{[2-(methoxycarbonyl)hydrazino]carbonyl}-2-methylphenyl]iminodiacetic acid diethyl ester Using the compound (3.00 g, 9.28 mmol) of Reference Example 61, step D, and methyl carbazate (1.25 g, 13.9 mmol), and according to the method of Reference Example 84, step A, the title compound (3.67 g, yield 100%) was obtained as a pale-yellow oil.

$^1$H-NMR (300 MHz, CDCl$_3$); δ (ppm) 1.21 (t, J=6.5, 6H), 2.35 (s, 3H), 3.62 (s, 3H), 4.00 (s, 4H), 4.12 (q, J=6.5, 4H), 7.14 (d, J=7.6, 1H), 7.45 (d, J=7.6, 1H), 7.74 (s, 1H).

Step B

N-[2-methyl-5-(5-oxo-4,5-dihydro-1,3,4-oxadiazol-2-yl)phenyl]iminodiacetic acid diethyl ester To the compound (3.67 g, 9.28 mmol) obtained in step A was added phosphorus oxychloride (30 g), and the mixture was stirred at 110° C. for 2.5 hr. After cooling to room temperature, the reaction mixture was poured into ice water, and the solution was extracted with ethyl acetate. The organic layer was washed with water, saturated aqueous sodium hydrogen carbonate and saturated brine, and dried over anhydrous magnesium sulfate. The insoluble material was filtered off, and the solution was concentrated under reduced pressure to give the title compound (2.00 g, yield 59%) as a colorless solid.

$^1$H-NMR (300 MHz, CDCl$_3$); δ (ppm) 1.25 (t, J=6.9, 6H), 2.39 (s, 3H), 4.06 (s, 4H), 4.16 (q, J=6.9, 4H), 7.25 (d, J=8.1, 1H), 7.46 (dd, J=1.5, 8.1, 1H), 7.68 (d, J=1.5, 1H), 9.94 (brs, 1H).

Step C

N-[2-methyl-5-(5-oxo-4,5-dihydro-1,3,4-oxadiazol-2-yl)phenyl]iminodiacetic acid

Using the compound (1.20 g, 3.30 mmol) obtained by the method of step B and according to the method of Reference Example 62, step B, the title compound (0.94 g, yield 92%) was obtained as a colorless solid.

$^1$H-NMR (300 MHz, DMSO-d$_6$); δ (ppm) 2.31 (s, 3H), 3.97 (s, 4H), 7.27-7.35 (m, 2H), 7.45 (s, 1H), 12.40-12.65 (broad, 1H), 12.5 (brs, 2H).

Reference Example 86

N-(4-bromo-2-methylphenyl)iminodiacetic acid

Using 4-bromo-2-methylaniline (10.0 g, 53.7 mmol) and according to the methods of Reference Example 61, step C, and Reference Example 62, step B, the title compound (10.89 g, yield 67%) was obtained as a pale-bistered solid.

$^1$H-NMR (300 MHz, DMSO-d$_6$); δ (ppm) 2.4 (s, 3H), 3.90 (s, 4H), 7.01 (d, J=8.4, 1H), 7.24 (dd, J=2.4, 8.4, 1H), 7.31 (d, J=2.4, 1H), 12.45 (brs, 2H).

Reference Example 87

N-(2,6-dimethylphenyl)iminodiacetic acid

Using 2,6-dimethylaniline (5.00 g, 41.3 mmol) and according to the methods of Reference Example 61, step C, and Reference Example 62, step B, the title compound (8.16 g, yield 83%) was obtained as a colorless solid.

$^1$H-NMR (300 MHz, DMSO-d$_6$); δ (ppm) 2.35 (s, 6H), 3.81 (s, 4H), 6.88-6.99 (m, 3H), 12.42 (brs, 2H).

Reference Example 88

N-(4-bromo-2,6-dimethylphenyl)iminodiacetic acid

Using 4-bromo-2,6-dimethylaniline (10.00 g, 50.0 mmol) and according to the methods of Reference Example 61, step C, Reference Example 62, step B, the title compound (8.90 g, yield 56%) was obtained as a colorless solid.

$^1$H-NMR (300 MHz, DMSO-d$_6$); δ (ppm) 2.35 (s, 6H), 3.80 (s, 4H), 7.17 (s, 2H), 12.45 (brs, 2H).

Reference Example 89

N-(5-bromo-2-methylphenyl)iminodiacetic acid

Step A

N-(5-bromo-2-methylphenyl)iminodiacetic acid diethyl ester

Using 5-bromo-2-methylaniline (10.27 g, 55.22 mmol) and according to the method of Reference Example 69, step C, the title compound (18.90 g, yield 96%) was obtained as a pale-yellow oil.

$^1$H-NMR (300 MHz, CDCl$_3$); δ (ppm) 1.25 (t, J=7.2, 6H), 2.28 (s, 3H), 4.00 (s, 4H), 4.15 (q, J=7.2, 4H), 7.01 (d, J=8.1, 1H), 7.11 (dd, J=1.8, 8.1, 1H), 7.32 (d, J=1.8, 1H), Step B N-(5-bromo-2-methylphenyl)iminodiacetic acid Using the compound (7.03 g, 19.62 mmol) obtained in step A and according to the method of Reference Example 62, step B, the title compound (4.40 g, yield 74%) was obtained as a colorless solid.

¹H-NMR (300 MHz, DMSO-d₆); δ (ppm) 2.20 (s, 3H), 3.92 (s, 4H), 7.08 (brs, 2H), 7.17 (s, 1H), 12.51 (brs, 2H).

Reference Example 90

N-(2-methyl-5-pyrimidin-2-ylphenyl)iminodiacetic acid

Step A 2-(4-methyl-3-nitrophenyl)pyrimidine

To a toluene (40 ml)-ethanol (40 ml) mixed solvent were added 4-methyl-3-nitrophenylboronic acid (2.66 g, 14.7 mmol), 2-bromopyrimidine (3.15 g, 19.81 mmol), tetrakis (triphenylphosphine)palladium(0) (1.01 g, 0.874 mmol) and sodium carbonate (3.93 g, 37.08 mmol), and the mixture was heated under reflux for 24 hr. The reaction mixture was cooled, diluted with ethyl acetate, washed with diluted aqueous sodium hydroxide solution and saturated brine, and dried over anhydrous magnesium sulfate. The insoluble material was filtered off, and the solution was concentrated under reduced pressure to give a solid. This was purified by silica gel column chromatography (ethyl acetate-dichloromethane) to give the title compound (1.74 g, yield 55%) as a colorless solid.

¹H-NMR (300 MHz, CDCl₃); δ (ppm) 2.67 (s, 3H), 7.24-7.28 (t, J=4.8, 1H), 7.47 (d, J=8.1, 1H), 8.58 (dd, J=1.8, 8.1, 1H), 8.83 (d, J=4.8, 2H), 9.07 (d, J=1.8, 1H).

Step B 2-methyl-5-pyrimidin-2-ylaniline

Using the compound (1.72 g, 7.99 mmol) obtained in step A and according to the method of Reference Example 61, step B, the title compound (1.43 g, yield 97%) was obtained as a colorless solid.

¹H-NMR (300 MHz, CDCl₃); δ (ppm) 2.24 (s, 3H), 3.72 (brs, 2H), 7.14 (d, J=4.8, 1H), 7.18 (d, J=8.1, 1H), 7.77-7.81 (m, 2H), 8.77 (d, J=4.8, 2H).

Step C

N-(2-methyl-5-pyrimidin-2-ylphenyl)iminodiacetic acid

Using the compound (1.01 g, 5.45 mmol) obtained in step B and according to the methods of Reference Example 61, step C, and Reference Example 62, step B, the title compound (1.22 g, yield 74%) was obtained as a pale-yellow solid.

¹H-NMR (300 MHz, DMSO-d₆); δ (ppm) 2.33 (s, 3H), 4.00 (s, 4H), 7.28 (d, J=8.1, 1H), 7.41 (t, J=5.1, 1H), 7.97 (dd, J=1.5, 8.1, 1H), 8.17 (d, J=1.5, 1H), 8.88 (d, J=5.1, 2H), 12.47 (brs, 2H).

The compounds of Reference Examples 61-90 are shown below.

TABLE 3

| Reference Example | Structural Formula |
|---|---|
| 61 | 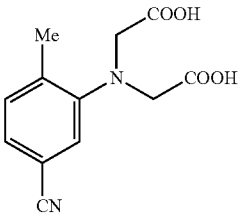 |
| 62 | 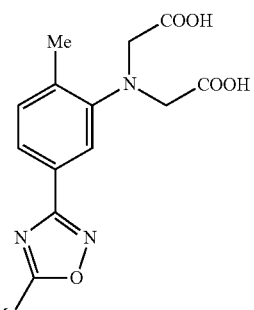 |
| 63 | 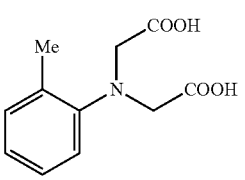 [SMILES: Cc1ccccc1N(CC(=O)O)CC(=O)O] |
| 64 | 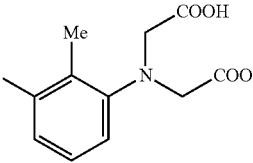 |
| 65 | 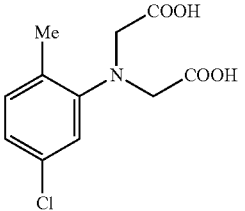 |
| 66 | 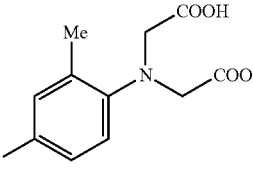 |

TABLE 3-continued

| Reference Example | Structural Formula |
|---|---|
| 67 | 2-methyl-5-acetyl phenyl N,N-bis(carboxymethyl)amine |
| 68 | 2-methyl-4-cyano phenyl N,N-bis(carboxymethyl)amine |
| 69 | 2-methyl-4-(5-methyl-1,2,4-oxadiazol-3-yl)phenyl N,N-bis(carboxymethyl)amine |
| 70 | 3-methyl-4-[N,N-bis(carboxymethyl)amino]-N'-methyl-N'-(tert-butoxycarbonyl)benzohydrazide |
| 71 | 3-methyl-4-[N,N-bis(carboxymethyl)amino]-N'-ethyl-N'-(tert-butoxycarbonyl)benzohydrazide |
| 72 | 4-methyl-3-[N,N-bis(carboxymethyl)amino]benzoic acid tert-butyl ester |
| 73 | 4-methyl-3-[N,N-bis(carboxymethyl)amino]benzamide |
| 74 | 4-methyl-3-[N,N-bis(carboxymethyl)amino]-N'-methyl-N'-(tert-butoxycarbonyl)benzohydrazide |
| 75 | 4-methyl-3-[N,N-bis(carboxymethyl)amino]-N'-ethyl-N'-(tert-butoxycarbonyl)benzohydrazide |
| 76 | 4-methyl-3-[N,N-bis(carboxymethyl)amino]-5-(tert-butoxycarbonylamino)benzene |
| 77 | 4-methyl-3-[N,N-bis(carboxymethyl)amino]benzoic acid ethyl ester |
| 78 | 4-methyl-3-[N,N-bis(carboxymethyl)amino]-5-(5-methyloxazol-2-yl)benzene |

TABLE 3-continued

| Reference Example | Structural Formula |
|---|---|
| 79 | 4-methyl-2-(3-(bis(carboxymethyl)amino)-4-methylphenyl)thiazole |
| 80 | 5-methyl-2-(3-(bis(carboxymethyl)amino)-4-methylphenyl)thiazole |
| 81 | 4-ethyl-2-(3-(bis(carboxymethyl)amino)-4-methylphenyl)thiazole |
| 82 | 4-tert-butyl-2-(3-(bis(carboxymethyl)amino)-4-methylphenyl)thiazole |
| 83 | 5-methyl-2-(3-(bis(carboxymethyl)amino)-4-methylphenyl)-1,3,4-oxadiazole |
| 84 | 5-methyl-2-(3-(bis(carboxymethyl)amino)-4-methylphenyl)-1,3,4-thiadiazole |
| 85 | 5-(3-(bis(carboxymethyl)amino)-4-methylphenyl)-1,3,4-oxadiazol-2(3H)-one |
| 86 | N,N-bis(carboxymethyl)-4-bromo-2-methylaniline |
| 87 | N,N-bis(carboxymethyl)-2,6-dimethylaniline |
| 88 | N,N-bis(carboxymethyl)-4-bromo-2,6-dimethylaniline |

TABLE 3-continued

| Reference Example | Structural Formula |
|---|---|
| 89 | Me-C6H3(Br)-N(CH2COOH)2 |
| 90 | Me-C6H3(2-pyrimidinyl)-N(CH2COOH)2 |

Reference Example 91

N-(2-methyl-5-pyrimidin-4-ylphenyl)iminodiacetic acid

Step A

N-[2-methyl-(5-tri-n-butylstanyl)phenyl]iminodiacetic acid diethyl ester

To toluene (70 ml) were added the compound (3.92 g, 10.94 mmol) of Reference Example 89, step A, bis(tri-n-butyltin) (9.0 ml, 17.8 mmol), and tetrakis(triphenylphosphine)palladium(0) (574 mg, 0.497 mmol), and the mixture was heated under reflux for 2 hr. The reaction mixture was cooled, water was added, and the mixture was vigorously stirred. The precipitated solid was filtered off through celite, and the organic layer was extracted and dried over anhydrous magnesium sulfate. The insoluble material was filtered off, and the solution was concentrated under reduced pressure. The obtained oil was purified by silica gel column chromatography (ethyl acetate-hexane) to give the title compound (3.56 g, yield 57%) as a colorless oil.

$^1$H-NMR (300 MHz, CDCl$_3$); δ (ppm) 0.88 (t, J=7.2, 9H), 0.98-1.05 (m, 6H), 1.23 (t, J=7.1, 6H), 1.28-1.34 (m, 6H), 1.5-1.6 (m, 6H), 2.32 (s, 3H), 4.04 (s, 4H), 4.14 (q, J=7.1, 4H), 7.06 (d, J=7.4, 1H), 7.12 (d, J=7.4, 1H), 7.24 (s, 1H).

Step B

N-[5-(6-chloropyrimidin-4-yl)-2-methylphenyl]iminodiacetic acid diethyl ester

To toluene (40 ml) were added the compound (1.40 g, 2.46 mmol) obtained in step A, 4,6-dichloropyrimidine (606 mg, 4.07 mmol) and bis(triphenylphosphine)palladium(II)dichloride (138 mg, 0.261 mmol), and the mixture was heated under reflux for 3 hr. The reaction mixture was cooled, diluted with an ethyl acetate-hexane=1:1 mixed solvent, washed with water and saturated brine, and dried over anhydrous magnesium sulfate. The insoluble material was filtered off, and the solution was concentrated under reduced pressure. The obtained oil was purified by silica gel column chromatography (ethyl acetate-hexane) to give the title compound (747 mg, yield 77%) as a pale-yellow solid.

$^1$H-NMR (300 MHz, CDCl$_3$); δ (ppm) 1.24 (t, J=7.2, 6H), 2.42 (s, 3H), 4.10 (s, 4H), 4.15 (q, J=7.2, 4H), 7.30 (d, J=8.1, 1H), 7.68 (dd, J=1.5, 8.1, 1H), 7.68 (s, 1H), 7.98 (d, J=1.5, 1H), 8.99 (s, 1H).

Step C

N-(2-methyl-5-pyrimidin-4-ylphenyl)iminodiacetic acid diethyl ester

The compound (696 mg, 1.78 mmol) obtained in step B was dissolved in a ethanol (25 ml)-tetrahydrofuran (2 ml) mixed solvent. Then, sodium acetate (164 mg, 2.00 mmol) and 10% palladium carbon (containing water) (0.68 g) were added, and the mixture was stirred at room temperature for 5 hr under a hydrogen atmosphere. The insoluble material was filtered off through celite, and the solution was concentrated under reduced pressure. The obtained oil was purified by silica gel column chromatography (ethyl acetate-hexane) to give the title compound (466 mg, yield 73%) as a colorless oil.

$^1$H-NMR (300 MHz, CDCl$_3$); δ (ppm) 1.24 (t, J=7.2, 6H), 2.42 (s, 3H), 4.10 (s, 4H), 4.15 (q, J=7.2, 4H), 7.30 (d, J=8.1, 1H), 7.67 (dd, J=1.2, 5.4, 1H), 7.71 (dd, J=1.5, 8.1, 1H), 8.01 (d, J=1.5, 1H), 8.72 (d, J=5.4, 1H), 9.23 (d, J=1.2, 1H).

Step D

N-(2-methyl-5-pyrimidin-4-ylphenyl)iminodiacetic acid

Using the compound (450 mg, 1.26 mmol) obtained in step C and according to the method of Reference Example 62, step B, the title compound (378 mg, yield 100%) was obtained as a yellow solid.

$^1$H-NMR (300 MHz, DMSO-d$_6$); δ (ppm) 2.29 (s, 3H), 4.01 (s, 4H), 7.31 (d, J=7.8, 1H), 7.74 (d, J=7.8, 1H), 7.96 (s, 1H), 8.00 (d, J=5.3, 1H), 8.82 (d, J=5.3, 1H), 9.21 (s, 1H), 12.48 (brs, 2H).

Reference Example 92

N-(2-methyl-5-pyrimidin-5-ylphenyl)iminodiacetic acid

Step A

N-(2-methyl-5-pyrimidin-5-ylphenyl)iminodiacetic acid diethyl ester

Using the compound (685 mg, 1.21 mmol) of Reference Example 91, step A, and 5-bromopyrimidine (316 mg, 1.99 mmol), and according to the method of Reference Example 91, step B, the title compound (334 mg, yield 77%) was obtained as a colorless solid.

$^1$H-NMR (300 MHz, CDCl$_3$); δ (ppm) 1.23 (t, J=7.2, 6H), 2.41 (s, 3H), 4.09 (s, 4H), 4.15 (q, J=7.2, 4H), 7.20 (dd, J=1.7, 7.8, 1H), 7.31 (d, J=7.8, 1H), 7.43 (d, J=1.7, 1H), 8.91 (s, 2H), 9.18 (s, 1H

Step B

N-(2-methyl-5-pyrimidin-5-ylphenyl)iminodiacetic acid

Using the compound (329 mg, 0.921 mmol) obtained in step A and according to the method of Reference Example 62, step B, the title compound (270 mg, yield 97%) was obtained as a colorless solid.
$^1$H-NMR (300 MHz, DMSO-$d_6$); δ (ppm) 2.31 (s, 3H), 4.00 (s, 4H), 7.29 (d, J=8.0, 1H), 7.34 (d, J=8.0, 1H), 7.42 (s, 1H), 9.06 (s, 2H), 9.16 (s, 1H).

Reference Example 93

N-(2-methyl-5-pyridin-3-ylphenyl)iminodiacetic acid

Step A

N-(2-methyl-5-pyridin-3-ylphenyl)iminodiacetic acid diethyl ester

Using the compound (2.90 g, 5.10 mmol) of Reference Example 91, step A, and 3-bromopyridine (0.75 ml, 7.79 mmol), and according to the method of Reference Example 91, step B, the title compound (1.08 g, yield 59%) was obtained as a colorless oil.
$^1$H-NMR (300 MHz, CDCl$_3$); δ (ppm) 1.23 (t, J=7.2, 6H), 2.39 (s, 3H), 4.09 (s, 4H), 4.15 (q, J=7.2, 4H), 7.19-7.23 (m, 1H), 7.26-7.36 (m, 2H), 7.43 (d, J=1.8, 1H), 7.81-7.84 (m, 1H), 8.55-8.58 (m, 1H), 8.81 (d, J=2.1, 1H).

Step B

N-(2-methyl-5-pyridin-3-ylphenyl)iminodiacetic acid

Using the compound (1.06 g, 2.97 mmol) obtained in step B and according to the method of Reference Example 62, step B, the title compound (740 mg, yield 83%) was obtained as a pale-yellow solid.
$^1$H-NMR (300 MHz, DMSO-$d_6$); δ (ppm) 2.30 (s, 3H), 4.00 (s, 4H), 7.26 (s, 2H), 7.35 (s, 1H), 7.45-7.50 (m, 1H), 7.96-8.00 (m, 1H), 8.53-8.56 (m, 1H), 8.80 (d, J=2.1, 1H), 12.49 (brs, 2H).

Reference Example 94

N-(5-cyano-2-ethylphenyl)iminodiacetic acid

Step A

3-nitro-4-vinylbenzonitrile

To N,N-dimethylformamide (50 ml) were added 4-chloro-3-nitrobenzonitrile (2.81 g, 15.39 mmol), tri-n-butylvinyltin (5.23 g, 16.49 mmol) and bis(triphenylphosphine)palladium (II) dichloride (701 mg, 0.999 mmol), and the mixture was stirred with heating at 100° C. for 160 min. The reaction mixture was cooled, diluted with an ethyl acetate-hexane=1:1 mixed solvent, washed with water and saturated brine, and dried over anhydrous magnesium sulfate. The insoluble material was filtered off, and the solution was concentrated under reduced pressure. The obtained oil was purified by silica gel column chromatography (ethyl acetate-hexane) to give the title compound (2.21 g, yield 82%) as a yellow solid.
$^1$H-NMR (300 MHz, CDCl$_3$); δ (ppm) 5.69 (d, J=11.3, 1H), 5.90 (d, J=17.3, 1H), 7.20 (dd, J=11.3, 17.3, 1H), 7.78 (d, J=8.1, 1H), 7.85 (dd, J=1.5, 8.1, 1H), 8.24 (d, J=1.5, 1H).

Step B

3-amino-4-ethylbenzonitrile

The compound (1.90 g, 10.9 mmol) obtained in step A was dissolved in ethanol (100 ml). Then, 10% palladium carbon (containing water) (1.93 g) was added, and the mixture was stirred at room temperature for 3 hr under a hydrogen atmosphere. The insoluble material was filtered off through celite, and the solution was concentrated under reduced pressure to give the title compound (1.56 g, yield 98%) as a pale-yellow solid.
$^1$H-NMR (300 MHz, CDCl$_3$); δ (ppm) 1.26 (t, J=7.5, 3H), 2.53 (q, J=7.5, 2H), 3.82 (brs, 2H), 6.90 (d, J=1.5, 1H), 7.02 (dd, J=1.5, 7.7, 1H), 7.13 (d, J=7.7, 1H).

Step C

N-(5-cyano-2-ethylphenyl)iminodiacetic acid

Using the compound (1.70 g, 11.63 mmol) obtained in step B and according to the methods of Reference Example 61, steps C and G, the title compound (2.26 g, yield 74%) as a pale-yellow oil.
$^1$H-NMR (300 MHz, DMSO-$d_6$); δ (ppm) 1.19 (t, J=7.5, 3H), 2.72 (q, J=7.5, 2H), 3.93 (s, 4H), 7.38 (d, J=7.8, 1H), 7.44 (dd, J=1.2, 7.8, 1H), 7.52 (d, J=1.2, 1H), 12.52 (brs, 2H).

Reference Example 95

N-(2-benzylphenyl)iminodiacetic acid

Using 2-benzylaniline (8.00 g, 43.7 mmol) and according to the methods of Reference Example 61, steps C and G, the title compound (15.0 g, yield>100%) was obtained as a colorless oil.
$^1$H-NMR (300 MHz, DMSO-$d_6$); δ (ppm) 3.88 (s, 4H), 4.07 (s, 2H), 6.91-6.95 (m, 2H), 7.09-7.29 (m, 7H), 12.4 (brs, 2H).

Reference Example 96

N-(2-chlorophenyl)iminodiacetic acid

Using 2-chloroaniline (10.0 g, 78.4 mmol) and according to the methods of Reference Example 69, step C, and Reference Example 62, step B, the title compound (4.13 g, yield 22%) was obtained as a colorless solid.
$^1$H-NMR (300 MHz, DMSO-$d_6$); δ (ppm) 4.07 (s, 4H), 6.98 (dd, J=1.5, 7.8, 1H), 7.12 (dd, J=1.5, 8.4, 1H), 7.21 (dd, J=1.5, 7.2, 1H), 7.35 (dd, J=1.5, 7.8, 1H), 12.54 (brs, 2H).

Reference Example 97

N-(3-chlorophenyl)iminodiacetic acid

Using 3-chloroaniline (1.00 g, 7.84 mmol) and according to the methods of Reference Example 61, step C, and Reference Example 62, step B, the title compound (1.70 g, yield 89%) was obtained as a colorless solid.
$^1$H-NMR (300 MHz, DMSO-$d_6$); δ (ppm) 4.02 (s, 4H), 6.41-6.43 (m, 2H), 6.67 (d, J=8.4, 1H), 7.16 (t, J=8.1, 1H).

Reference Example 98

N-(2,5-dichlorophenyl)iminodiacetic acid

Step A

N-(2,5-dichlorophenyl)iminodiacetic acid diethyl ester

Using 2,5-dichloroaniline (1.00 g, 6.17 mmol) and according to the method of Reference Example 69, step C, the title compound (648 mg, yield 31%) was obtained as a pale-yellow solid.
$^1$H-NMR (300 MHz, CDCl3); δ (ppm) 1.26 (t, J=7.1, 6H), 4.15-4.22 (m, 8H), 6.94 (dd, J=2.3, 8.4, 1H), 7.14 (d, J=2.3, 1H), 7.24-7.26 (m, 1H).

Step B

N-(2,5-dichlorophenyl)iminodiacetic acid

Using the compound (647 mg, 1.94 mmol) obtained in step A and according to the method of Reference Example 62, step B, the title compound (474 mg, yield 88%) was obtained as a colorless solid.
$^1$H-NMR (300 MHz, DMSO-$d_6$); δ (ppm) 4.08 (s, 4H), 7.03 (dd, J=2.4, 8.4, 1H), 7.10 (d, J=2.7, 1H), 7.38 (d, J=8.7, 1H), 12.59 (brs, 2H

Reference Example 99

N-(2,4-dichlorophenyl)iminodiacetic acid

Using 2,4-dichloroaniline (5.00 g, 30.9 mmol) and according to the methods of Reference Example 61, step C, and Reference Example 62, step B, the title compound (480 mg, yield 6%) was obtained as a colorless solid.
$^1$H-NMR (300 MHz, CDCl$_3$); δ (ppm) 4.10 (s, 4H), 7.18-7.26 (m, 2H), 7.41 (d, J=2.1, 1H).

Reference Example 100

N-(2-chloro-5-cyanophenyl)iminodiacetic acid

Step A 3-amino-4-chlorobenzonitrile

Using 4-chloro-3-nitrobenzonitrile (11.40 g, 62.45 mmol) and according to the method of Reference Example 61, step B, the title compound (8.00 g, yield 84%) was obtained as a colorless solid.
$^1$H-NMR (300 MHz, CDCl$_3$); δ (ppm) 4.28 (brs, 2H), 6.95 (dd, J=1.5, 8.1, 1H), 7.00 (d, J=1.5, 1H), 7.33 (d, J=8.1, 1H).

Step B

N-(2-chloro-5-cyanophenyl)iminodiacetic acid

Using the compound (8.00 g, 52.43 mmol) obtained in step A and according to the methods of Reference Example 69, step C, and Reference Example 62, step B, the title compound (1.92 g, yield 14%) was obtained as a pale-pink solid.
$^1$H-NMR (300 MHz, DMSO-$d_6$); δ (ppm) 4.11 (s, 4H), 7.41 (dd, J=2.1, 8.4, 1H), 7.55 (d, J=2.1, 1H), 7.57 (d, J=8.4, 1H), 12.66 (brs, 2H).

Reference Example 101

N-(5-tert-butoxycarbonyl-2-chlorophenyl)iminodiacetic acid

Step A 4-chloro-3-nitrobenzoic acid tert-butyl ester

Using 4-chloro-3-nitrobenzoic acid (18.0 g, 89.3 mmol) and according to the method of Reference Example 61, step A, the title compound (13.62 g, yield 59%) was obtained as a pale-yellow solid.
$^1$H-NMR (300 MHz, CDCl$_3$); δ (ppm) 1.61 (s, 9H), 7.62 (d, J=8.7, 1H), 8.11 (dd, J=2.1, 8.4, 1H), 8.43 (d, J=1.8, 1H).

Step B

N-(5-tert-butoxycarbonyl-2-chlorophenyl)iminodiacetic acid diethyl ester

Using the compound (6.00 g, 23.3 mmol) obtained in step A and according to the methods of Reference Example 61, steps B and C, the title compound (2.21 g, yield 24%) was obtained as a yellow oil.
$^1$H-NMR (300 MHz, CDCl$_3$); δ (ppm) 1.26 (t, J=7.2, 6H), 1.57 (s, 9H), 4.08-4.22 (m, 8H), 7.36 (d, J=8.3, 1H), 7.56 (dd, J=2.0, 8.3, 1H), 7.86 (d, J=2.0, 1H).

Step C

N-(5-tert-butoxycarbonyl-2-chlorophenyl)iminodiacetic acid

Using the compound (2.21 g, 5.53 mmol) obtained in step B and according to the method of Reference Example 62, step B, the title compound (1.19 g, yield 63%) was obtained as a colorless solid.
$^1$H-NMR (300 MHz, DMSO-$d_6$); δ (ppm) 1.53 (s, 9H), 4.09 (s, 4H), 7.40-7.51 (m, 2H), 7.62 (s, 1H), 12.66 (brs, 2H).

Reference Example 102

N-(5-chloro-2-fluorophenyl)iminodiacetic acid

Using 5-chloro-2-fluoroaniline (5.0 g, 34.4 mmol) and according to the methods of Reference Example 61, step C, and Reference Example 62, step B, the title compound (1.94 g, yield 22%) was obtained as a colorless solid.
$^1$H-NMR (300 MHz, DMSO-$d_6$); δ (ppm) 4.06 (s, 4H), 6.70-6.83 (m, 2H), 7.10 (dd, J=8.7, 14.1, 1H), 12.65 (brs, 2H).

Reference Example 103

N-(5-cyano-2-fluorophenyl)iminodiacetic acid

Step A 3-amino-4-fluorobenzonitrile

Using 4-fluoro-3-nitrobenzonitrile (13.64 g, 82.11 mmol) and according to the method of Reference Example 68, step A, the title compound (10.16 g, yield 91%) was obtained as a pale-yellow solid.
$^1$H-NMR (300 MHz, CDCl$_3$); δ (ppm) 3.94 (brs, 2H), 7.00-7.09 (m, 3H).

Step B

N-(5-cyano-2-fluorophenyl)iminodiacetic acid

Using the compound (10.16 g, 74.63 mmol) obtained in step A and according to the methods of Reference Example 69, step C, and Reference Example 62, step B, the title compound (5.42 g, yield 29%) was obtained as a colorless solid.
$^1$H-NMR (300 MHz, DMSO-$d_6$); δ (ppm) 4.11 (s, 4H), 7.19-7.33 (m, 3H), 12.69 (brs, 2H).

Reference Example 104

N-biphenyl-3-yliminodiacetic acid

Step A

N-biphenyl-3-yliminodiacetic acid diethyl ester

Using biphenyl-3-ylamine (5.00 g, 29.5 mmol) and according to the method of Reference Example 61, step C, the title compound (10.0 g, yield 99%) was obtained as a pale-yellow oil.
$^1$H-NMR (300 MHz, CDCl$_3$); δ (ppm) 1.26 (t, J=7.2, 6H), 4.12-4.25 (m, 8H), 6.61 (d, J=8.1, 1H), 6.82 (s, 1H), 7.00 (d, J=7.8, 1H), 7.25-7.42 (m, 4H), 7.53 (d, J=7.8, 2H).

Step B

N-(biphenyl-3-yl)iminodiacetic acid

Using the compound (10.0 g, 29.3 mmol) obtained by the method of step A and according to the method of Reference Example 62, step B, the title compound (8.39 g, yield>100%) was obtained as a colorless solid.
$^1$H-NMR (300 MHz, DMSO-$d_6$); δ (ppm) 4.17 (s, 4H), 6.51 (d, J=8.1, 1H), 6.71 (s, 1H), 6.94 (d, J=7.5, 1H), 7.25 (t, J=8.1, 1H), 7.34 (t, J=7.2, 1H), 7.44 (t, J=7.8, 2H), 7.58 (d, J=7.5, 2H), 12.7 (brs, 2H).

Reference Example 105

N-biphenyl-2-yliminodiacetic acid

Step A

N-biphenyl-2-yliminodiacetic acid diethyl ester

Using biphenyl-2-ylamine (5.00 g, 29.5 mmol) and according to the method of Reference Example 61, step C, the title compound (9.51 g, yield 94%) was obtained as a colorless oil.
$^1$H-NMR (300 MHz, CDCl$_3$); δ (ppm) 1.18 (t, J=7.2, 6H), 3.85 (s, 4H), 4.08 (q, J=7.2, 4H), 7.05-7.14 (m, 2H), 7.21-7.32 (m, 3H), 7.39 (t, J=7.8, 2H), 7.66 (d, J=7.0, 2H).

Step B

N-biphenyl-2-yliminodiacetic acid

Using the compound (0.91 g, 29.3 mmol) obtained by the method of step A and according to the method of Reference Example 62, step B, the title compound (0.72 g, yield 95%) was obtained as a colorless solid.
$^1$H-NMR (300 MHz, DMSO-$d_6$); δ (ppm) 3.74 (s, 4H), 7.01 (t, J=7.5, 1H), 7.12 (q, J=7.8, 2H), 7.22 (t, J=7.5, 1H), 7.32 (d, J=7.2, 1H), 7.41 (t, J=7.2, 2H), 7.71 (d, J=7.8, 2H), 12.4 (s, 2H).

Reference Example 106

N-(4-cyanobiphenyl-2-yl)iminodiacetic acid

Step A 2-nitrobiphenyl-4-carbonitrile

To N-methylpyrrolidone (25 ml) were added 4-chloro-3-nitrobenzonitrile (1.79 g, 9.80 mmol), phenylboronic acid (1.53 g, 12.5 mmol), cesium fluoride (3.90 g, 25.7 mmol) and bis(triphenylphosphine)palladium(II) dichloride (447 mg, 0.637 mmol), and the mixture was stirred with heating at 100° C. for 9 hr. The reaction mixture was cooled, diluted with ethyl acetate and water, and the insoluble material was filtered off through celite. The organic layer was extracted and dried over anhydrous magnesium sulfate. The insoluble material was filtered off, and the solution was concentrated under reduced pressure. The obtained oil was purified by silica gel column chromatography (ethyl acetate-hexane) to give the title compound (1.74 g, yield 79%) as a yellow solid.
$^1$H-NMR (300 MHz, CDCl$_3$); δ (ppm) 7.30-7.34 (m, 2H), 7.45-7.49 (m, 3H), 7.61 (d, J=8.2, 1H), 7.90 (dd, J=1.5, 8.2, 1H), 8.14 (d, J=1.5, 1H).

Step B 2-aminobiphenyl-4-carbonitrile

Using the compound (1.72 g, 7.67 mmol) obtained in step A and according to the method of Reference Example 61, step B, the title compound (1.59 g) was obtained as a colorless oil.
$^1$H-NMR (300 MHz, CDCl$_3$); δ (ppm) 3.95 (brs, 2H), 6.99 (d, J=1.5, 1H), 7.08 (dd, J=1.5, 7.5, 1H), 7.18 (d, J=7.5, 1H), 7.40-7.51 (m, 5H).

Step C

N-(4-cyanobiphenyl-2-yl)iminodiacetic acid

Using the compound (1.59 g) obtained in step B and according to the methods of Reference Example 69, step C, and Reference Example 62, step B, the title compound (483 mg, yield from step B 20%) was obtained as a colorless solid.
$^1$H-NMR (300 MHz, DMSO-$d_6$); δ (ppm) 3.78 (s, 4H), 7.33 (d, J=8.1, 1H), 7.36-7.49 (m, 5H), 7.72 (d, J=8.1, 2H), 12.49 (brs, 2H).

Reference Example 107

N-1-naphthyliminodiacetic acid

Using 1-naphthylamine (10.0 g, 69.84 mmol) and according to the methods of Reference Example 61, step C, and Reference Example 62, step B, the title compound (16.64 g, yield 92%) was obtained as a pale-green solid.
$^1$H-NMR (300 MHz, CDCl$_3$); δ (ppm) 4.24 (s, 4H), 7.37-7.40 (m, 2H), 7.42-7.55 (m, 2H), 7.60-70 (m, 1H), 7.85 (dd, J=1.5, 8.6, 1H), 8.14 (dd, J=1.2, 9.1, 1H) 8.85 (brs, 2H).

Reference Example 108

N-(4-chloro-1-naphthyl)iminodiacetic acid

Using 1-amino-4-chloronaphthalene (3.0 g, 16.89 mmol) and according to the methods of Reference Example 61, step C, and Reference Example 62, step B, the title compound (4.56 g, yield 92%) was obtained as a pale-yellow solid.
¹H-NMR (300 MHz, DMSO-d$_6$); δ (ppm) 4.11 (s, 4H), 7.25 (d, J=8.2, 1H), 7.60 (d, J=8.2, 1H), 7.62-7.71 (m, 2H), 8.15 (dd, J=1.7, 7.6, 1H), 8.24 (dd, J=1.7, 7.8, 1H), 12.58 (brs, 2H).

Reference Example 109

N-(3-methoxy-2-naphthyl)iminodiacetic acid

Step A (3-methoxy-2-naphthyl)amine

3-Amino-2-naphthol (7.96 g, 50.0 mmol) was dissolved in N-methylpyrrolidone (190 ml), and the mixture was stirred under ice-cooling. Then, 60% sodium hydride (2.08 g, 52 mmol) was added, and the mixture was stirred at the same temperature for 40 min. Then, ethyl iodide (3.3 ml, 53 mmol) was added, and the mixture was stirred at the same temperature for 2 hr. To the reaction mixture was added diluted aqueous sodium hydroxide solution, and the mixture was extracted with an ethyl acetate-hexane=1:1 mixed solvent. The organic layer was washed with diluted aqueous sodium hydroxide solution, water and saturated brine, and dried over anhydrous magnesium sulfate. The insoluble material was filtered off, and the solution was concentrated under reduced pressure. The obtained oil was purified by silica gel column chromatography (ethyl acetate-hexane), and the obtained solid was washed with hexane and dried under reduced pressure to give the title compound (4.53 g, yield 52%) as a colorless solid.
¹H-NMR (300 MHz, CDCl$_3$); δ (ppm) 3.98 (s, 3H), 4.07 (brs, 2H), 7.00 (s, 1H), 7.05 (s, 1H), 7.18-7.29 (m, 2H), 7.55 (dd, J=1.5, 7.5, 1H), 7.63 (dd, J=1.5, 7.5, 1H).

Step B

N-(3-methoxy-2-naphthyl)iminodiacetic acid

Using the compound (4.51 g, 26.0 mmol) obtained in step A and according to the methods of Reference Example 61, step C, and Reference Example 62, step B, the title compound (6.06 g, yield 80%) was obtained as a colorless solid.
¹H-NMR (300 MHz, DMSO-d$_6$); δ (ppm) 3.86 (s, 3H), 4.12 (s, 4H), 7.03 (s, 1H), 7.25 (s, 1H), 7.22-7.29 (m, 2H), 7.59-7.64 (m, 1H), 7.65-7.71 (m, 1H), 12.45 (brs, 2H).

Reference Example 110

N-(5,6,7,8-tetrahydronaphthalen-1-yl)iminodiacetic acid

Using 5,6,7,8-tetrahydronaphthalen-1-ylamine (5.34 g, 36.27 mmol) and according to the methods of Reference Example 61, step C, and Reference Example 62, step B, the title compound (8.28 g, yield 87%) was obtained as a pale-showy pink solid.
¹H-NMR (300 MHz, DMSO-d$_6$); δ (ppm) 1.55-1.75 (m, 4H), 2.64-2.73 (m, 4H), 3.86 (s, 4H), 6.75 (dd, J=1.2, 7.1, 1H), 6.92-7.01 (m, 2H), 12.40 (brs, 2H).

Reference Example 111

N-(2,3-dihydro-1H-inden-4-yl)iminodiacetic acid

Using 4-aminoindane (5.0 g, 37.54 mmol) and according to the methods of Reference Example 61, step C, and Reference Example 62, step B, the title compound (8.53 g, yield 91%) was obtained as a pale-bistered solid.
¹H-NMR (300 MHz, DMSO-d$_6$); δ (ppm) 1.85-2.00 (m, 2H), 2.75-2.82 (m, 4H), 3.99 (s, 4H), 6.49 (d, J=7.8, 1H), 6.75 (d, J=7.2, 1H), 6.96 (t, J=7.5, 1H), 12.51 (brs, 2H).

Reference Example 112

N-(5-cyano-2,3-dihydro-1-benzofuran-7-yl)iminodiacetic acid

Step A tert-butyl (5-bromo-2,3-dihydro-1-benzofuran-7-yl)carbamate

To toluene (30 ml) were added 5-bromo-2,3-dihydro-1-benzofuran-7-carboxylic acid (5.00 g, 20.6 mmol), N,N-diisopropylethylamine (4.3 ml, 24.7 mmol), diphenylphosphorylazide (6.36 g, 22.7 mmol) and tert-butanol (25 ml), and the mixture was heated under reflux for 10 hr.

The reaction mixture was concentrated under reduced pressure, diluted with ethyl acetate, washed with diluted hydrochloric acid, diluted aqueous sodium hydroxide solution and saturated brine, and dried over anhydrous magnesium sulfate. The solution was concentrated under reduced pressure. The obtained oil was purified by silica gel column chromatography (ethyl acetate-hexane) to give the title compound (6.27 g, yield 97%) as a pale-yellow oil.
¹H-NMR (300 MHz, DMSO-d$_6$); δ (ppm) 1.44 (s, 9H), 3.20 (t, J=8.7, 2H), 4.55 (t, J=8.7, 2H), 7.12 (d, J=1.5, 1H), 7.50 (s, 1H), 8.60 (s, 1H).

Step B (5-bromo-2,3-dihydro-1-benzofuran-7-yl)amine hydrochloride

The compound (6.27 g, 20.0 mmol) obtained in step A was dissolved in ethyl acetate, 4N hydrochloric acid-ethyl acetate solution (25 ml, 100 mmol) was added at room temperature with stirring, and the mixture was stirred at the same temperature overnight. The precipitated solid was filtered, washed with ethyl acetate, and dried under reduced pressure to give the title compound (4.65 g, yield 93%) as a colorless solid.
¹H-NMR (300 MHz, DMSO-d$_6$); δ (ppm) 3.23 (t, J=8.7, 2H), 4.62 (t, J=8.7, 2H), 7.13-7.22 (m, 2H), 8.00 (brs, 3H).

Step C

N-(5-bromo-2,3-dihydro-1-benzofuran-7-yl)iminodiacetic acid diethyl ester

Using the compound (4.65 g, 18.6 mmol) obtained in step B and according to the method of Reference Example 69, step C, the title compound (6.04 g, yield 84%) was obtained as a yellow oil.
¹H-NMR (300 MHz, CDCl$_3$); δ (ppm) 1.27 (t, J=7.1, 6H), 3.13 (t, J=8.8, 2H), 4.15 (s, 4H), 4.20 (q, J=7.1, 4H), 4.52 (t, J=8.8, 2H), 6.62 (d, J=1.6, 1H), 6.85 (s, 1H).

Step D

N-(5-cyano-2,3-dihydro-1-benzofuran-7-yl)iminodiacetic acid diethyl ester

To N,N-dimethylformamide (50 ml) were added the compound (6.04 g, 15.6 mmol) obtained in step C, zinc cyanide (1.84 g, 15.6 mmol) and tetrakis(triphenylphosphine)palladium(0) (3.61 g, 3.12 mmol), and the mixture was stirred with heating at 100° C. for 5 hr. The reaction mixture was cooled to room temperature, diluted aqueous ammonia was added, and the mixture was extracted with ethyl acetate. The organic layer was washed with water and saturated brine, and dried over anhydrous magnesium sulfate. The insoluble material was filtered off, and the solution was concentrated under reduced pressure. The obtained oil was purified by silica gel column chromatography (ethyl acetate-hexane) to give the title compound (1.91 g, yield 37%) as a pale-bistered solid.

$^1$H-NMR (300 MHz, DMSO-d$_6$); δ (ppm) 1.18 (t, J=7.1, 6H), 3.16 (t, J=8.9, 2H), 4.10 (q, J=6.9, 4H), 4.19 (s, 4H), 4.55 (t, J=8.9, 2H), 6.84 (s, 1H), 7.16 (s, 1H).

Step E

N-(5-cyano-2,3-dihydro-1-benzofuran-7-yl)iminodiacetic acid

Using the compound (1.91 g, 5.75 mmol) obtained in step D and according to the method of Reference Example 62, step B, the title compound (1.58 g, yield 99%) was obtained as a colorless solid.

$^1$H-NMR (300 MHz, DMSO-d$_6$); δ (ppm) 3.16 (t, J=8.4, 2H), 4.12 (s, 4H), 4.57 (t, J=8.4, 2H), 6.77 (s, 1H), 7.14 (s, 1H), 12.54 (brs, 2H).

Reference Example 113

N-(1,7-dimethyl-2-oxo-1,2,3,4-tetrahydroquinolin-6-yl)iminodiacetic acid

Step A 7-methyl-6-nitro-3,4-dihydroquinolin-2 (1H)-one

7-Methyl-3,4-dihydroquinolin-2 (1H)-one (10.0 g, 62.0 mmol) obtained by the method described in Chemical & Pharmaceutical Bulletin, 367 (1968) was suspended in nitromethane (200 ml), and the suspension was stirred under ice-cooling. Then, an ice-cooled nitric acid (8.3 ml)-water (18.2 ml)-sulfuric acid (116 ml) mixed solution was slowly added dropwise, and thereafter added dropwise at room temperature. The mixture was stirred for 2 hr. To the reaction mixture was added ice water, the solution was extracted with ethyl acetate, and the organic layer was washed with saturated brine, and dried over anhydrous magnesium sulfate. The solution was concentrated under reduced pressure, and the precipitated solid was washed with ethyl acetate and dried under reduced pressure to give the title compound (3.14 g, yield 25%) as a pale-bistered solid.

$^1$H-NMR (300 MHz, DMSO-d$_6$); δ (ppm) 2.48-2.55 (m, 5H), 2.96 (t, J=7.8, 2H), 6.82 (s, 1H), 7.96 (s, 1H), 10.55 (brs, 1H).

Step B 6-amino-1,7-dimethyl-3,4-dihydroquinolin-2 (1H)-one

The compound (3.14 g, 15.2 mmol) obtained in step A was dissolved in N,N-dimethylformamide (30 ml), 60% sodium hydride (730 mg, 18.2 mmol) was added under ice-cooling with stirring, and thereafter the mixture was stirred at room temperature for 30 min. The reaction mixture was ice-cooled again, methyl iodide (1.9 ml, 30.4 mmol) was added with stirring, and the mixture was stirred at room temperature for 1 hr. To the reaction mixture was added water, and the precipitated solid was collected by filtration, washed with water, and dried under reduced pressure to give a bistered solid. Using this solid and according to the method of Reference Example 116, step B, the title compound (1.76 g, yield 61%) was obtained as a pale-bistered solid.

$^1$H-NMR (300 MHz, CDCl$_3$); δ (ppm) 2.17 (s, 3H), 2.55-2.61 (m, 2H), 2.75-2.80 (m, 2H), 3.31 (s, 3H), 3.51 (brs, 2H), 6.50 (s, 1H), 6.69 (s, 1H).

Step C

N-(1,7-dimethyl-2-oxo-1,2,3,4-tetrahydroquinolin-6-yl)iminodiacetic acid diethyl ester Using the compound (1.50 g, 7.88 mmol) obtained in step B and according to the method of Reference Example 61, step C, the title compound (1.85 g, yield 65%) was obtained as a pale-yellow solid.

$^1$H-NMR (300 MHz, DMSO-d$_6$); δ (ppm) 1.15 (t, J=7.2, 6H), 2.27 (s, 3H), 2.44-2.54 (m, 2H), 2.75 (t, J=7.4, 2H), 3.20 (s, 3H), 3.94 (s, 4H), 4.05 (q, J=7.2, 4H), 6.87 (s, 1H), 7.02 (s, 1H).

Step D

N-(1,7-dimethyl-2-oxo-1,2,3,4-tetrahydroquinolin-6-yl)iminodiacetic acid

Using the compound (1.85 g, 5.10 mmol) obtained in step C and according to the method of Reference Example 62, step B, the title compound (1.05 g, yield 67%) was obtained as a colorless solid.

$^1$H-NMR (300 MHz, DMSO-d$_6$); δ (ppm) 2.26 (s, 3H), 2.43-2.55 (m, 2H), 2.75 (t, J=7.4, 2H), 3.20 (s, 3H), 3.87 (s, 4H), 6.87 (s, 1H), 6.99 (s, 1H), 12.35 (brs, 2H).

Reference Example 114

N-(1-ethyl-7-methyl-2-oxo-1,2,3,4-tetrahydroquinolin-6-yl)iminodiacetic acid

Step A 7-methyl-2-oxo-1,2,3,4-tetrahydroquinoline-6-carboxylic acid

7-Methyl-3,4-dihydroquinolin-2 (1H)-one (80.0 g, 500 mmol) obtained by the method described in Chemical & Pharmaceutical Bulletin, 367 (1968), and chloroacetylchloride (85.0 g, 750 mmol) were dissolved in 1,2-dichloroethane (800 ml), aluminum chloride (165 g, 1.25 mol) was gradually added at room temperature with stirring, and thereafter the mixture was stirred at 40° C. for 1 hr. The reaction mixture was slowly poured into ice water, the precipitated solid was collected by filtration, and the obtained solid was washed with water and dried under reduced pressure to give a colorless solid. This solid was added to pyridine (750 ml) at room temperature, and then the mixture was stirred at 90° C. for 30 min. The reaction mixture was cooled to room temperature, and the precipitated solid was collected by filtration, and dried under reduced pressure. The obtained solid was added to 10% aqueous sodium hydroxide solution (1000 ml), and the mixture was stirred at 90° C. for 2.5 hr. The reaction mixture was cooled to room temperature, activated carbon was added, and the insoluble material was filtered off through celite. Concentrated hydrochloric acid was added to adjust the obtained solution to pH 1, and the precipitated solid was collected by filtration, washed with water, and dried under reduced pressure to give the title compound (78.0 g, yield 76%) as a colorless solid.

$^1$H-NMR (300 MHz, DMSO-d$_6$); δ (ppm) 2.43-2.53 (m, 5H), 2.87 (t, J=7.5, 2H), 6.71 (s, 1H), 7.70 (s, 1H), 10.28 (s, 1H), 12.48 (brs, 1H).

Step B

7-methyl-2-oxo-1,2,3,4-tetrahydroquinoline-6-carboxylic acid ethyl ester

To the compound (40.0 g, 195 mmol) obtained in step A were added ethanol (600 ml) and concentrated sulfuric acid (60 ml), and the mixture was heated under reflux for 24 hr. After cooling to room temperature, the solution was concentrated under reduced pressure. The obtained oil was diluted with water, and extracted with chloroform. The organic layer was washed with diluted aqueous sodium hydroxide solution, and dried over anhydrous magnesium sulfate. The insoluble material was filtered off, and the solution was concentrated under reduced pressure. The obtained solid was recrystallized from ethanol to give the title compound (32.0 g, yield 70%) as a colorless solid.

$^1$H-NMR (300 MHz, DMSO-d$_6$); δ (ppm) 1.30 (t, J=6.9, 3H), 2.43-2.52 (m, 2H), 2.45 (s, 3H), 2.89 (t, J=7.4, 2H), 4.24 (q, J=6.9, 2H), 6.73 (s, 1H), 7.69 (s, 1H), 10.34 (brs, 1H).

Step C

1-ethyl-7-methyl-2-oxo-1,2,3,4-tetrahydroquinoline-6-carboxylic acid ethyl ester Using the compound (10.0 g, 42.9 mmol) obtained in step B and ethyl iodide (6.86 ml, 85.8 mmol), and according to the method of Reference Example 113, step B, the title compound (9.54 g, yield 85%) was obtained as a colorless solid.

$^1$H-NMR (300 MHz, CDCl$_3$); δ (ppm) 1.27 (t, J=7.2, 3H), 1.39 (t, J=7.2, 3H), 2.61-2.67 (m, 2H), 2.62 (s, 3H), 2.86-2.92 (m, 2H), 4.00 (q, J=7.2, 2H), 4.35 (q, J=7.2, 2H), 6.84 (s, 1H), 7.76 (s, 1H).

Step D

1-ethyl-7-methyl-2-oxo-1,2,3,4-tetrahydroquinoline-6-carboxylic acid

The compound (9.54 g, 36.5 mmol) obtained in step C was dissolved in methanol (100 ml), 1N sodium hydroxide (100 ml) was added at room temperature with stirring, and the mixture was stirred at the same temperature overnight. The reaction mixture was concentrated under reduced pressure, 1N hydrochloric acid (160 ml) was added, and the solution was extracted with ethyl acetate. The organic layer was washed with saturated brine, and dried over anhydrous magnesium sulfate. The insoluble material was filtered off, and the solution was concentrated under reduced pressure. The obtained solid was washed with a diisopropyl ether-isopropanol mixed solvent, and dried under reduced pressure to give the title compound (8.17 g, yield 96%) as a colorless solid.

$^1$H-NMR (300 MHz, DMSO-d$_6$); δ (ppm) 1.13 (t, J=6.9, 3H), 2.50-2.56 (m, 2H), 2.55 (s, 3H), 2.85 (t, J=7.2, 2H), 3.92 (q, J=6.9, 2H), 7.03 (s, 1H), 7.71 (s, 1H), 12.58 (brs, 1H).

Step E tert-butyl (1-ethyl-7-methyl-2-oxo-1,2,3,4-tetrahydroquinolin-6-yl)carbamate Using the compound (4.65 g, 18.6 mmol) obtained in step D and according to the method of Reference Example 112, step A, the title compound (6.07 g, yield 57%) was obtained as a colorless solid.

$^1$H-NMR (300 MHz, DMSO-d$_6$); δ (ppm) 1.11 (t, J=6.9, 3H), 1.45 (s, 9H), 2.18 (s, 3H), 2.44-2.51 (m, 2H), 2.73-2.79 (m, 2H), 3.87 (q, J=6.9, 2H), 6.93 (s, 1H), 7.11 (s, 1H), 8.46 (brs, 1H).

Step F

6-amino-1-ethyl-7-methyl-3,4-dihydroquinolin-2(1H)-one hydrochloride

Using the compound (6.07 g, 19.9 mmol) obtained in step E and according to the method of Reference Example 112, step B, the title compound (4.41 g, yield 92%) was obtained as a colorless solid.

$^1$H-NMR (300 MHz, DMSO-d$_6$); δ (ppm) 1.12 (t, J=6.9, 3H), 2.35 (s, 3H), 2.48-2.54 (m, 2H), 2.76-2.84 (m, 2H), 3.90 (q, J=6.9, 2H), 7.09 (s, 1H), 07.23 (s, 1H), 9.61-10.39 (broad, 3H).

Step G

N-(1-ethyl-7-methyl-2-oxo-1,2,3,4-tetrahydroquinolin-6-yl)iminodiacetic acid Using the compound (4.41 g, 18.3 mmol) obtained in step F and according to the methods of Reference Example 61, step C, and Reference Example 62, step B, the title compound (3.81 g, yield 65%) was obtained as a colorless solid.

$^1$H-NMR (300 MHz, DMSO-d$_6$); δ (ppm) 1.11 (t, J=6.9, 3H), 2.26 (s, 3H), 2.43-2.52 (m, 2H), 2.70-2.76 (m, 2H), 3.80-3.89 (m, 2H), 3.88 (s, 4H), 6.90 (s, 1H), 6.98 (s, 1H), 12.39 (brs, 2H).

Reference Example 115

N-(3-methoxy-8-oxo-5,6,7,8-tetrahydronaphthalen-2-yl)iminodiacetic acid

Step A

6-methoxy-7-nitro-3,4-dihydronaphthalen-1(2H)-one

6-Methoxy-1-tetralone (12.0 g, 68.1 mmol) was dissolved in acetic anhydride (60 ml), a fuming nitric acid (4.8 ml)-acetic acid (4.2 ml) mixed solvent was slowly added dropwise under ice-cooling with stirring, and thereafter the mixture was stirred at the same temperature for 2 hr. The reaction mixture was diluted with ether, and the precipitated solid was collected by filtration and dried under reduced pressure. The obtained solid was recrystallized from benzene (100 ml), and the precipitated solid was filtered, dried under reduced pressure to give the title compound (3.62 g, yield 24%) as a colorless solid.

$^1$H-NMR (300 MHz, CDCl$_3$); δ (ppm) 2.17 (m, 2H), 2.66 (t, J=6.2, 2H), 3.01 (t, J=6.0, 2H), 4.01 (s, 3H), 6.90 (s, 1H), 8.50 (s, 1H).

Step B

7-amino-6-methoxy-3,4-dihydronaphthalen-1(2H)-one

Using the compound (0.50 g, 2.26 mmol) obtained in step A and according to the method of Reference Example 68, step A, the title compound (0.50 g) was obtained as a red-bistered oil.

$^1$H-NMR (300 MHz, CDCl$_3$); δ (ppm) 2.08 (m, 2H), 2.56 (t, J=6.3, 2H), 2.85 (t, J=6.3, 2H), 3.80 (brs, 2H), 3.90 (s, 3H), 6.58 (s, 1H), 7.35 (s, 1H).

Step C

N-(3-methoxy-8-oxo-5,6,7,8-tetrahydronaphthalen-2-yl)iminodiacetic acid diethyl ester Using the compound (0.50 g) obtained in step B and according to the method of Reference Example 61, step C, the title compound (0.94 g) was obtained as a pale-yellow solid.

$^1$H-NMR (300 MHz, CDCl$_3$); δ (ppm) 1.27 (t, J=7.2, 6H), 2.04-2.11 (m, 2H), 2.55 (t, J=6.3, 2H), 2.86 (t, J=6.0, 2H), 3.87 (s, 3H), 4.12 (s, 4H), 4.19 (q, J=7.2, 4H), 6.63 (s, 1H), 7.51 (s, 1H).

Step D

N-(3-methoxy-8-oxo-5,6,7,8-tetrahydronaphthalen-2-yl)iminodiacetic acid

Using the compound (0.94 g) obtained by the method of step C and according to the method of Reference Example 62, step B, the title compound (0.70 g, yield from step B>100%) was obtained as a colorless solid.

$^1$H-NMR (300 MHz, DMSO-d$_6$); δ (ppm) 1.96-2.01 (m, 2H), 2.45-2.52 (m, 2H), 2.82-2.87 (m, 2H), 3.82 (s, 3H), 3.99 (s, 4H), 6.84 (s, 1H), 7.22 (s, 1H), 12.42 (brs, 2H).

Reference Example 116

N-(3,6-dimethyl-1,2-benzisoxazol-5-yl)iminodiacetic acid

Step A

N-(4-methoxy-2-methylphenyl)acetamide

4-Methoxy-2-methylaniline (26.06 g, 190 mmol) and triethylamine (43 ml, 309 mmol) were dissolved in dichloromethane, acetic anhydride (25 ml, 265 mmol) was added under ice-cooling, and the mixture was stirred at the same temperature for 80 min. To the reaction mixture was added 10% aqueous citric acid solution, and the mixture was extracted with ethyl acetate. The organic layer was washed with diluted hydrochloric acid, saturated aqueous sodium hydrogen carbonate and saturated brine, and dried over anhydrous magnesium sulfate. The insoluble material was filtered off, and the solution was concentrated under reduced pressure. The obtained solid was filtered, washed with hexane, and dried under reduced pressure to give the title compound (30.78 g, yield 90%) as a pale-pink solid.

$^1$H-NMR (300 MHz, DMSO-d$_6$); δ (ppm) 2.00 (s, 3H), 2.14 (s, 3H), 3.71 (s, 3H), 6.71 (dd, J=3.0, 8.7, 1H), 6.77 (d, J=3.0, 1H), 7.18 (d, J=8.7, 1H), 9.16 (s, 1H).

Step B

N-(5-acetyl-4-hydroxy-2-methylphenyl)acetamide

The compound (31.43 g, 175.4 mmol) obtained by the method of step A was dissolved in dichloromethane (500 ml). Acetyl chloride (40 ml, 561 mmol) and aluminum chloride (93.3 g, 700 mmol) were successively added thereto under ice-cooling with stirring, and the mixture was heated under reflux for 2 hr. The reaction mixture was cooled, poured into ice water, directly stirred for 2 hr, and extracted with dichloromethane. The organic layer was washed with saturated brine, and dried over anhydrous magnesium sulfate. The insoluble material was filtered off, and the solution was concentrated under reduced pressure. The obtained solid was filtered, and washed with hexane to give the title compound (35.46 g, yield 98%) as a colorless solid.

$^1$H-NMR (300 MHz, DMSO-d$_6$); δ (ppm) 2.03 (s, 3H), 2.19 (s, 3H), 2.57 (s, 3H), 6.83 (s, 1H), 7.77 (s, 1H), 9.32 (s, 1H), 11.81 (s, 1H).

Step C

N-[4-hydroxy-5-(N-hydroxyethanimidoyl)-2-methylphenyl]acetamide

To an ethanol (560 ml)-water (180 ml) mixed solvent were added the compound (35.46 g, 171.1 mmol) obtained in step B, hydroxylammonium chloride (19.41 g, 279.3 mmol) and sodium acetate (22.83 g, 278.3 mmol), and the mixture was heated under reflux for 70 min. The reaction mixture was cooled, water (500 ml) was added, and the solution was concentrated under reduced pressure (about 300 ml) to allow precipitation of a solid. Water (500 ml) was added hereto again, and the precipitated solid was filtered, washed with water, and dried under reduced pressure to give the title compound (32.7 g, yield 86%) as a colorless solid.

$^1$H-NMR (300 MHz, DMSO-d$_6$); δ (ppm) 2.01 (s, 3H), 2.12 (s, 3H), 2.19 (s, 3H), 6.72 (s, 1H), 7.35 (s, 1H), 9.22 (s, 1H), 11.37 (s, 1H), 11.46 (s, 1H).

Step D

3,6-dimethyl-1,2-benzisoxazol-5-amine

To N,N-dimethylformamide-dimethylacetal (90 ml) was added the compound (32.7 g, 147 mmol) obtained in step C, and the mixture was stirred with heating at 100° C. for 7 min. The reaction mixture was cooled, water (700 ml) was added, and the mixture was extracted with ethyl acetate. The organic layer was washed with saturated brine, and dried over anhydrous magnesium sulfate. The insoluble material was filtered off, and the solution was concentrated under reduced pressure to to give a brown solid (20.45 g). This was added to 3N aqueous hydrochloric acid solution (600 ml), and the mixture was heated under reflux for 80 min. The reaction mixture was ice-cooled, and an aqueous solution of sodium hydroxide (80 g) was added at the same temperature. The precipitated solid was collected by filtration, washed with water, and dried under reduced pressure to give the title compound (12.6 g, yield 53%) as a yellow bistered solid.

$^1$H-NMR (300 MHz, CDCl$_3$); δ (ppm) 2.32 (s, 3H), 2.50 (s, 3H), 3.64 (brs, 2H), 6.81 (s, 1H), 7.26 (s, 1H).

Step E

N-(3,6-dimethyl-1,2-benzisoxazol-5-yl)iminodiacetic acid diethyl ester

Using the compound (11.5 g, 71.0 mmol) obtained in step D and according to the method of Reference Example 61, step C, the title compound (19.8 g, yield 83%) was obtained as a pale-yellow solid.

$^1$H-NMR (300 MHz, CDCl$_3$); δ (ppm) 1.22 (t, J=7.2, 6H), 2.51 (s, 3H), 2.53 (s, 3H), 4.05 (s, 4H), 4.13 (q, J=7.2, 4H), 7.35 (s, 1H), 7.55 (s, 1H).

Step F

N-(3,6-dimethyl-1,2-benzisoxazol-5-yl)iminodiacetic acid

Using the compound (16.59 g, 49.62 mmol) obtained in step E and according to the method of Reference Example 62, step B, the title compound (13.58 g, yield 98%) was obtained as a colorless solid.

$^1$H-NMR (300 MHz, DMSO-d$_6$); δ (ppm) 2.44 (s, 3H), 2.48 (s, 3H), 3.95 (s, 4H), 7.49 (s, 1H), 7.58 (s, 1H), 12.40 (brs, 2H).

Reference Example 117

N-(3,5-dimethyl-1,2-benzisoxazol-6-yl)iminodiacetic acid

Step A

N-(5-methoxy-2-methylphenyl)acetamide

Using 5-methoxy-2-methylaniline (10.22 g, 74.5 mmol) and according to the method of Reference Example 116, step A, the title compound (10.88 g, yield 81%) was obtained as a yellow solid.

$^1$H-NMR (300 MHz, DMSO-d$_6$); δ (ppm) 1.99 (s, 3H), 2.11 (s, 3H), 3.69 (s, 3H), 6.65 (dd, J=2.4, 8.3, 1H), 7.07 (d, J=2.4, 1H), 7.08 (d, J=8.3, 1H), 9.18 (brs, 1H).

Step B

N-(4-acetyl-5-hydroxy-2-methylphenyl)acetamide

Using the compound (3.58 g, 19.98 mmol) obtained in step A and according to the method of Reference Example 116, step B, the title compound (3.00 g, yield 72%) was obtained as a pale-yellow solid.

$^1$H-NMR (300 MHz, DMSO-d$_6$); δ (ppm) 2.13 (s, 3H), 2.22 (s, 3H), 2.58 (s, 3H), 7.47 (s, 1H), 7.70 (s, 1H), 9.21 (s, 1H), 11.96 (s, 1H).

Step C

N-[5-hydroxy-4-(N-hydroxyethanimidoyl)-2-methylphenyl]acetamide

Using the compound (2.99, 14.43 mmol) obtained in step B and according to the method of Reference Example 116, step C, the title compound (2.94 g, yield 92%) was obtained as a colorless solid.

$^1$H-NMR (300 MHz, DMSO-d$_6$); δ (ppm) 2.07 (s, 3H), 2.16 (s, 3H), 2.22 (s, 3H), 7.17 (s, 1H), 7.27 (s, 1H), 9.13 (s, 1H), 11.35 (s, 1H), 11.38 (s, 1H).

Step D 3,5-dimethyl-1,2-benzisoxazol-6-amine

Using the compound (2.94 g, 13.23 mmol) obtained in step C and according to the method of Reference Example 116, step D, the title compound (1.14 g, yield 53%) was obtained as a dark green solid.

$^1$H-NMR (300 MHz, CDCl$_3$); δ (ppm) 2.25 (s, 3H), 2.47 (s, 3H), 3.99 (brs, 2H), 6.74 (s, 1H), 7.24 (s, 1H).

Step E

N-(3,5-dimethyl-1,2-benzisoxazol-6-yl)iminodiacetic acid diethyl ester

Using the compound (1.13 g, 6.97 mmol) obtained in step D and according to the method of Reference Example 69, step C, the title compound (1.02 g, yield 44%) was obtained as a pale-yellow oil.

$^1$H-NMR (300 MHz, CDCl$_3$); δ (ppm) 1.24 (t, J=7.2, 6H), 2.43 (s, 3H), 2.51 (s, 3H), 4.10 (s, 4H), 4.15 (q, J=7.2, 4H), 7.31 (s, 1H), 7.38 (s, 1H).

Step F

N-(3,5-dimethyl-1,2-benzisoxazol-6-yl)iminodiacetic acid

Using the compound (1.02 g, 3.05 mmol) obtained in step E and according to the method of Reference Example 62, step B, the title compound (698 mg, yield 82%) was obtained as a colorless solid.

$^1$H-NMR (300 MHz, DMSO-d$_6$); δ (ppm) 2.35 (s, 3H), 2.46 (s, 3H), 4.02 (s, 4H), 7.22 (s, 1H), 7.55 (s, 1H), 12.57 (brs, 2H).

Reference Example 118

N-(6-methyl-1,3-benzodioxol-5-yl)iminodiacetic acid

Step A 5-methyl-6-nitro-1,3-benzodioxole

5-Methyl-1,3-benzodioxole (8.00 g, 58.8 mmol) was dissolved in chloroform (160 ml), and the mixture was stirred under ice-cooling. To this solution was gradually added 60% nitric acid (20 ml), and the mixture was stirred at room temperature for 30 min. The reaction mixture was diluted with dichloromethane, washed with water and saturated aqueous sodium hydrogen carbonate, and dried over potassium carbonate. The insoluble material was filtered off, and the solution was concentrated under reduced pressure to give the title compound (9.58 g, yield 90%) as a pale-yellow solid.

$^1$H-NMR (300 MHz, CDCl$_3$); δ (ppm) 2.55 (s, 3H), 6.08 (s, 2H), 6.70 (s, 1H), 7.50 (s, 1H).

Step B 6-methyl-1,3-benzodioxol-5-amine

Using the compound (9.58 g, 52.9 mmol) obtained in step A and according to the method of Reference Example 61, step B, the title compound (8.00 g, yield 100%) was obtained as a colorless solid.

$^1$H-NMR (300 MHz, CDCl$_3$); δ (ppm) 2.08 (s, 3H), 3.31 (brs, 2H), 5.81 (s, 2H), 6.28 (s, 1H), 6.56 (s, 1H).

Step C

N-(6-methyl-1,3-benzodioxol-5-yl)iminodiacetic acid diethyl ester

Using the compound (8.00 g, 52.9 mmol) obtained in step B and according to the method of Reference Example 61, step C, the title compound (15.8 g, yield 92%) was obtained as a colorless solid.
$^1$H-NMR (300 MHz, CDCl$_3$); δ (ppm) 1.23 (t, J=7.2, 6H), 2.27 (s, 3H), 3.93 (s, 4H), 4.13 (q, J=7.2, 4H), 5.87 (s, 2H), 6.63 (s, 1H), 6.87 (s, 1H).

Step D

N-(6-methyl-1,3-benzodioxol-5-yl)iminodiacetic acid

Using the compound (5.00 g, 15.5 mmol) obtained in step C and according to the method of Reference Example 62, step B, the title compound (3.11 g, yield 75%) was obtained as a colorless solid.
$^1$H-NMR (300 MHz, DMSO-d$_6$); δ (ppm) 2.18 (s, 3H), 3.82 (s, 4H), 5.90 (s, 2H), 6.71 (s, 1H), 6.81 (s, 1H), 12.4 (brs, 2H).

Reference Example 119

N-(3,6-dimethyl-2-oxo-2,3-dihydro-1,3-benzoxazol-5-yl)iminodiacetic acid

Step A 3,6-dimethyl-1,3-benzoxazol-2 (3H)-one

3-Methyl-2-oxo-2,3-dihydro-1,3-benzoxazole-6-carbaldehyde (4.41 g, 24.9 mmol) obtained by the method described in JP-A-10-139780 was dissolved in ethyl acetate (100 ml), 10% palladium carbon (containing water) (2.0 g) and acetic acid (20 ml) were added, and the mixture was stirred at room temperature for 12 hr under a hydrogen atmosphere. The insoluble material was filtered off through celite, and the solution was concentrated under reduced pressure to give the title compound (3.33 g, yield 82%) as a colorless solid.
$^1$H-NMR (300 MHz, DMSO-d$_6$); δ (ppm) 2.34 (s, 3H), 3.31 (s, 3H), 7.04 (d, J=8.1, 1H), 7.13 (d, J=8.1, 1H), 7.17 (s, 1H).

Step B 3,6-dimethyl-5-nitro-1,3-benzoxazol-2 (3H)-one

The compound (3.33 g, 20.4 mmol) obtained in step A was dissolved in trifluoroacetic acid (60 ml), sodium nitrite (1.41 g, 20.4 mmol) was gradually added under ice-cooling with stirring, and the mixture was stirred at room temperature for 3 hr. The reaction solution was poured into ice water, and the precipitated solid was collected by filtration, washed with water, and dried under reduced pressure to give the title compound (2.75 g, yield 65%) as a pale-bistered solid.
$^1$H-NMR (300 MHz, DMSO-d$_6$); δ (ppm) 2.54 (s, 3H), 3.38 (s, 3H), 7.51 (s, 1H), 8.00 (s, 1H).

Step C 5-amino-3,6-dimethyl-1,3-benzoxazol-2 (3H)-one

Using the compound (2.75 g, 13.2 mmol) obtained in step B to and according to the method of Reference Example 69, step B, the title compound (1.95 g, yield 83%) was obtained as a pale-pink solid.
$^1$H-NMR (300 MHz, DMSO-d$_6$); δ (ppm) 2.06 (s, 3H), 3.23 (s, 3H), 4.83 (brs, 2H), 6.43 (s, 1H), 6.92 (s, 1H).

Step D

N-(3,6-dimethyl-2-oxo-2,3-dihydro-1,3-benzoxazol-5-yl)iminodiacetic acid

Using the compound (1.95 g, 10.94 mmol) obtained in step C and according to the methods of Reference Example 61, step C, and Reference Example 62, step B, the title compound (2.45 g, yield 76%) was obtained as a bistered solid.
$^1$H-NMR (300 MHz, DMSO-d$_6$); δ (ppm) 2.29 (s, 3H), 3.28 (s, 3H), 3.91 (s, 4H), 7.09 (s, 1H), 7.13 (s, 1H), 12.39 (brs, 2H).

Reference Example 120

N-(3,5-dimethyl-2-oxo-2,3-dihydro-1,3-benzoxazol-6-yl)iminodiacetic acid

Step A 5-methyl-1,3-benzoxazol-2 (3H)-one

2-Amino-4-methylphenol (5.00 g, 40.6 mmol) and triethylamine (17 ml, 122 mmol) were dissolved in chloroform (100 ml), ethyl chloroformate (5.8 ml, 61 mmol) was added at room temperature with stirring, and thereafter the mixture was stood at the same temperature overnight. Water was added to the reaction mixture, the mixture was extracted with chloroform, and the organic layer was dried over anhydrous magnesium sulfate. The insoluble material was filtered off, and the solution was concentrated under reduced pressure. N,N-Dimethylformamide (35 ml) and potassium carbonate (11.2 g, 81.2 mmol) were added to the obtained residue, and the mixture was stirred at 70° C. for 9 hr. The reaction mixture was cooled to room temperature, and 3N hydrochloric acid was added with stirring. The precipitated solid was filtered, washed with water, and dried under reduced pressure to give the title compound (4.94 g, yield 82%) as a pale-bistered solid.
$^1$H-NMR (300 MHz, DMSO-d$_6$); δ (ppm) 2.31 (s, 3H), 6.85-6.90 (m, 2H), 7.14 (d, J=7.8, 1H), 11.53 (brs, 1H).

Step B 5-methyl-6-nitro-1,3-benzoxazol-2 (3H)-one

Using the compound (3.94 g, 26.4 mmol) obtained in the same manner as in step A and according to the method of Reference Example 119, step B, the title compound (2.60 g, yield 51%) was obtained as a pale-bistered solid.
$^1$H-NMR (300 MHz, DMSO-d$_6$); δ (ppm) 2.56 (s, 3H), 7.17 (s, 1H), 8.03 (s, 1H), 12.28 (brs, 1H).

Step C 3,5-dimethyl-6-nitro-1,3-benzoxazol-2 (3H)-one

Using the compound (3.26 g, 16.8 mmol) obtained by the method of step B and methyl iodide (2.09 ml, 33.6 mmol), and according to the method of Reference Example 113, step B, the title compound (3.21 g, yield 92%) was obtained as a pale-yellow solid.

$^{1}$H-NMR (300 MHz, DMSO-d$_{6}$); δ (ppm) 2.60 (s, 3H), 3.37 (s, 3H), 7.40 (s, 1H), 8.09 (s, 1H).

Step D

6-amino-3,5-dimethyl-1,3-benzoxazol-2 (3H)-one

Using the compound (3.21 g, 15.4 mmol) obtained by the method of step C and according to the method of Reference Example 69, step B, the title compound (764 mg, yield 28%) was obtained as a colorless solid.

$^{1}$H-NMR (300 MHz, DMSO-d$_{6}$); δ (ppm) 2.08 (s, 3H), 3.23 (s, 3H), 4.78 (brs, 2H), 6.60 (s, 1H), 6.83 (s, 1H).

Step E

N-(3,5-dimethyl-2-oxo-2,3-dihydro-1,3-benzoxazol-6-yl)iminodiacetic acid

Using the compound (764 mg, 4.29 mmol) obtained in step D and according to the methods of Reference Example 61, step C, and Reference Example 62, step B, the title compound (678 mg, yield 54%) was obtained as a bistered solid.

$^{1}$H-NMR (300 MHz, DMSO-d$_{6}$); δ (ppm) 2.32 (s, 3H), 3.28 (s, 3H), 3.88 (s, 4H), 7.04 (s, 1H), 7.19 (s, 1H), 12.42 (brs, 2H).

The compounds of Reference Examples 91-120 are shown below.

TABLE 4

| Reference Example | Structural Formula |
|---|---|
| 91 | (structure) |
| 92 | (structure) |
| 93 | (structure) |
| 94 | (structure) |
| 95 | (structure) |
| 96 | (structure) |
| 97 | (structure) |
| 98 | (structure) |
| 99 | (structure) |

TABLE 4-continued
| Reference Example | Structural Formula |
|---|---|
| 100 | 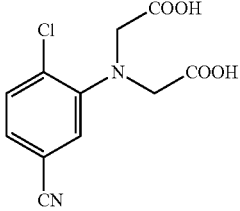 |
| 101 | 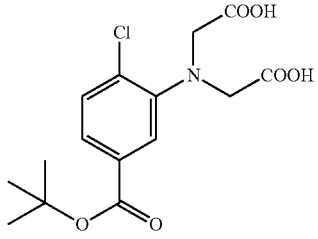 [SMILES: Cc1ccc(C(=O)OC(C)(C)C)cc1N(CC(=O)O)CC(=O)O] |
| 102 | 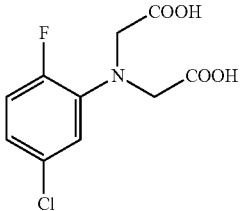 [SMILES: O=C(O)CN(CC(=O)O)c1cc(Cl)ccc1F] |
| 103 | 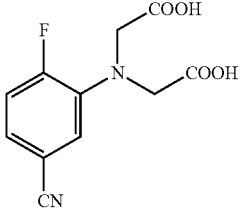 |
| 104 | 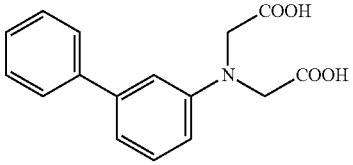 [SMILES: O=C(O)CN(CC(=O)O)c1cccc(-c2ccccc2)c1] |
| 105 | 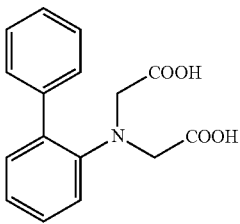 [SMILES: O=C(O)CN(CC(=O)O)c1ccccc1-c1ccccc1] |
| 106 | 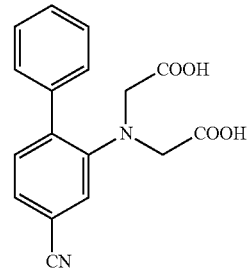 [SMILES: N#Cc1ccc(-c2ccccc2)c(N(CC(=O)O)CC(=O)O)c1] |
| 107 | 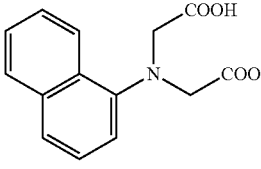 |
| 108 | 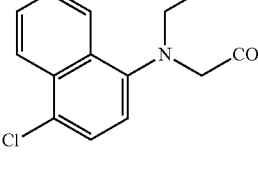 |
| 109 | 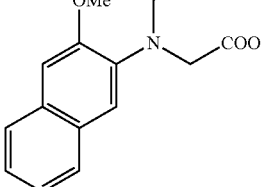 |
| 110 | 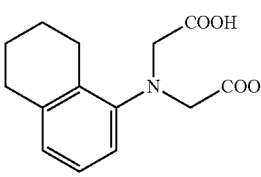 |
| 111 | 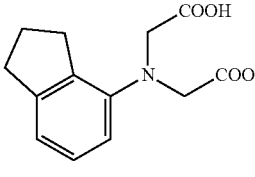 |
| 112 | 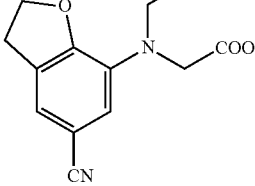 |

TABLE 4-continued

| Reference Example | Structural Formula |
|---|---|
| 113 | 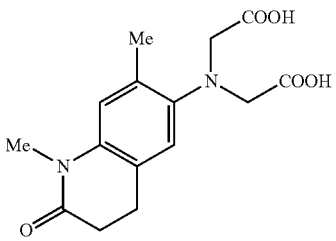 [SMILES: Cc1cc2c(cc1N(CC(=O)O)CC(=O)O)CCC(=O)N2C] |
| 114 | 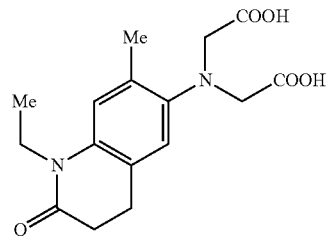 [SMILES: CCN1C(=O)CCc2cc(N(CC(=O)O)CC(=O)O)c(C)cc21] |
| 115 | 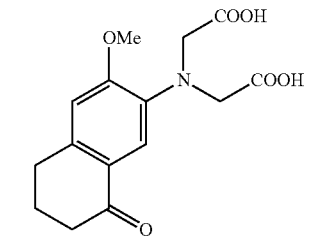 [SMILES: COc1cc2c(cc1N(CC(=O)O)CC(=O)O)C(=O)CCC2] |
| 116 | 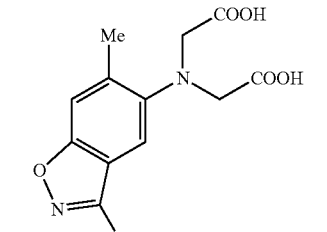 |
| 117 | 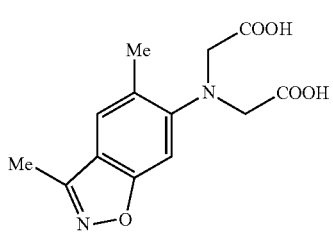 [SMILES: Cc1cc2c(C)noc2cc1N(CC(=O)O)CC(=O)O] |
| 118 | 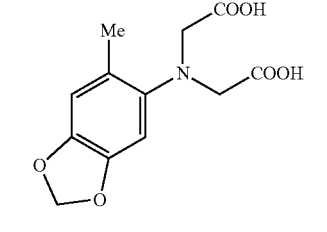 [SMILES: Cc1cc2c(cc1N(CC(=O)O)CC(=O)O)OCO2] |
| 119 |  |
| 120 |  |

Reference Example 121

N-(4-iodo-2-methylphenyl)iminodiacetic acid

Step A

N-(4-iodo-2-methylphenyl)iminodiacetic acid diethyl ester

Using 4-iodo-2-methylaniline (4.66 g, 20.0 mmol) and according to the method of Reference Example 61, step C, the title compound (8.05 g, yield 99%) was obtained as a brown oil.

$^1$H-NMR (400 MHz, DMSO-d$_6$); δ (ppm) 1.14 (t, J=7.0, 6H), 2.21 (s, 3H), 3.98 (s, 4H), 4.04 (q, J=7.1, 4H), 6.90 (d, J=8.5, 1H), 7.40 (dd, J=8.4, 2.0, 1H), 7.49 (d, J=1.8, 1H).

Step B

N-(4-iodo-2-methylphenyl)iminodiacetic acid

Using the compound (8.05 g, 1.99 mmol) obtained in step A and according to the method of Reference Example 61, step G, the title compound (6.93 g, yield 100%) was obtained as a colorless solid.

$^1$H-NMR (400 MHz, DMSO-d$_6$); δ (ppm) 2.20 (s, 3H), 3.90 (s, 4H), 6.86 (d, J=8.5, 1H), 7.40 (dd, J=8.5, 2.0, 1H), 7.47 (d, J=1.9, 1H), 12.45 (brs, 2H).

Reference Example 122

N-[2-methyl-4-(3-methylisoxazol-5-yl)phenyl]iminodiacetic acid

Step A

N-[2-methyl-4-(3-methylisoxazol-5-yl)phenyl]iminodiacetic acid diethyl ester

To toluene (4 ml) were added the compound (810 mg, 2.00 mmol) of Reference Example 121, step A, 5-(tri-n-butylstanyl)-3-methylisoxazole (1.12 g, 3.01 mmol), which is the compound described in Tetrahedron, 47 (1991) 5111-5118, bis(triphenylphosphine)palladium(II)dichloride (140 mg, 0.199 mmol) and lithium chloride (170 mg, 4.01 mmol), and the mixture was heated under reflux for 2 hr. The reaction mixture was cooled, diluted with ethyl acetate, washed with water and saturated brine, and dried over anhydrous magnesium sulfate. The insoluble material was filtered off, and the solution was concentrated under reduced pressure. The obtained oil was purified by silica gel column chromatography (ethyl acetate-hexane) to give the title compound (428 mg, yield 59%) as a brown oil.

$^1$H-NMR (400 MHz, DMSO-d$_6$); δ (ppm) 1.15 (t, J=7.2, 6H), 2.26 (s, 3H), 2.30 (s, 3H), 4.06 (s, 4H), 4.07 (q, J=7.2, 4H), 6.71 (s, 1H), 7.13 (d, J=8.5, 1H), 7.54 (dd, J=8.4, 2.0, 1H), 7.60 (d, J=1.6, 1H).

Step B

N-[2-methyl-4-(3-methylisoxazol-5-yl)phenyl]iminodiacetic acid

Using the compound (428 mg, 1.19 mmol) obtained in step A and according to the method of Reference Example 61, step G, the title compound (388 mg, yield>100%) was obtained as a brown solid.

$^1$H-NMR (400 MHz, DMSO-d$_6$); δ (ppm) 2.25 (s, 3H), 2.30 (s, 3H), 3.98 (s, 4H), 6.69 (s, 1H), 7.08 (d, J=8.4, 1H), 7.52-7.54 (m, 1H), 7.58 (d, J=1.7, 1H), 12.55 (brs, 2H).

Reference Example 123

N-[2-methyl-5-(3-methylisoxazol-5-yl)phenyl]iminodiacetic acid

Step A

N-[2-methyl-5-(3-methylisoxazol-5-yl)phenyl]iminodiacetic acid diethyl ester

Using the compound (716 mg, 2.00 mmol) of Reference Example 89, step A, and 5-(tri-n-butylstanyl)-3-methylisoxazole (819 mg, 2.20 mmol), and according to the method of Reference Example 122, step A, the title compound (388 mg, yield 54%) was obtained as a pale-yellow oil.

$^1$H-NMR (400 MHz, DMSO-d$_6$); δ (ppm) 1.13 (t, J=7.1, 6H), 2.27 (s, 3H), 2.30 (s, 3H), 4.05 (q, J=7.2, 4H), 4.06 (s, 4H), 6.78 (s, 1H), 7.28 (d, J=7.9, 1H), 7.39-7.41 (m, 1H), 7.53 (s, 1H).

Step B

N-[2-methyl-5-(3-methylisoxazol-5-yl)phenyl]iminodiacetic acid

Using the compound (388 mg, 1.08 mmol) obtained in step A and according to the method of Reference Example 61, step G, the title compound (333 mg, yield>100%) was obtained as a pale-yellow solid.

$^1$H-NMR (400 MHz, DMSO-d$_6$); δ (ppm) 2.27 (s, 3H), 2.30 (s, 3H), 3.98 (s, 4H), 6.76 (s, 1H), 7.27 (d, J=7.9, 1H), 7.36 (dd, J=7.8, 1.2, 1H), 7.48 (d, J=1.2, 1H), 12.50 (brs, 2H).

Reference Example 124

N-(4-acetyl-2-methylphenyl)iminodiacetic acid

Step A 1-(4-amino-3-methylphenyl)ethanone

Using 1-(3-methyl-4-nitrophenyl)ethanone (5.46 g, 30.5 mmol) and according to the method of Reference Example 68, step A, the title compound (4.33 g, yield 95%) was obtained as a yellow solid.

$^1$H-NMR (400 MHz, CDCl$_3$); δ (ppm) 2.19 (s, 3H), 2.51 (s, 3H), 4.07 (brs, 2H), 6.64 (d, J=8.2, 1H), 7.68 (d, J=2.0, 1H), 7.71 (dd, J=2.0, 8.2, 1H).

Step B

N-(4-acetyl-2-methylphenyl)iminodiacetic acid diethyl ester

Using the compound (4.33 g, 29.0 mmol) obtained in step A and according to the method of Reference Example 61, step C, the title compound (5.87 g, yield 63%) was obtained as a yellow oil.

$^1$H-NMR (400 MHz, CDCl$_3$); δ (ppm) 1.25 (t, J=7.1, 6H), 2.36 (s, 3H), 2.54 (s, 3H), 4.09 (s, 4H), 4.17 (q, J=7.1, 4H), 7.10 (d, J=8.4, 1H), 7.72 (dd, J=1.8, 8.4, 1H), 7.78 (d, J=1.8, 1H).

Step C

N-(4-acetyl-2-methylphenyl)iminodiacetic acid

Using the compound (5.86 g, 18.2 mmol) obtained in step B and according to the method of Reference Example 61, step G, the title compound (3.43 g, yield 71%) was obtained as a pale-yellow solid.

$^1$H-NMR (400 MHz, DMSO-d$_6$); δ (ppm) 2.29 (s, 3H), 2.48 (s, 3H), 4.01 (s, 4H), 6.97 (d, J=8.4, 1H), 7.67 (d, J=1.9, 1H), 7.70 (dd, J=1.9, 8.4, 1H), 12.61 (brs, 2H).

Reference Example 125

N-(6-methyl-1-oxo-2,3-dihydro-1H-inden-5-yl)iminodiacetic acid

Step A

N-(5-iodo-2-methylphenyl)iminodiacetic acid diethyl ester

Using 5-iodo-2-methylaniline (4.66 g, 20 mmol) and according to the method of Reference Example 61, step C, the title compound (8.31 g, yield>100%) was obtained as a pale-yellow oil.

$^1$H-NMR (400 MHz, DMSO-d$_6$); δ (ppm) 1.15 (t, J=7.1, 6H), 2.20 (s, 3H), 3.98 (s, 4H), 4.06 (q, J=7.1, 4H), 6.93 (d, J=8.0, 1H), 7.28 (dd, J=7.9, 1.5, 1H), 7.39 (d, J=1.4, 1H).

Step B

N-[5-(3-tert-butoxy-3-oxopropyl)-2-methylphenyl]iminodiacetic acid diethyl ester To N,N-dimethylformamide (43 ml) were added the compound (2.03 g, 5.00 mmol) obtained in step A, tert-butyl acrylate (3.20 g, 25.00 mmol), [1,1'-bis(diphenylphosphino)ferrocene]palladium(II)dichloride—dichloromethane complex (1:1) (204 mg, 0.250 mmol), tetra-n-butylammoniumiodide (2.78 g, 7.50 mmol), water (6.9 ml) and triethylamine (6.9 ml), and the mixture was heated at 80° C. for 2 hr. The reaction mixture was cooled, diluted with ethyl acetate, washed with water and saturated brine, and dried over anhydrous magnesium sulfate. The insoluble material was filtered off, the solution was concentrated under reduced pressure, and the obtained oil was purified by silica gel column chromatography (ethyl acetate-hexane). To the obtained colorless oil (1.86 g) in ethanol (23 ml) was added 10% palladium carbon (containing water) (186 mg), and the mixture was stirred at room temperature for 3 hr. The insoluble material was filtered off, and the solution was concentrated under reduced pressure. The obtained oil was purified by silica gel column chromatography (ethyl acetate-hexane) to give the title compound (1.79 g, yield 88%) as a colorless oil.

$^1$H-NMR (400 MHz, DMSO-d$_6$); δ (ppm) 1.14 (t, J=7.2, 6H), 1.37 (s, 9H), 2.20 (s, 3H), 2.43 (t, J=7.6, 2H), 2.70 (t, J=7.5, 2H), 3.96 (s, 4H), 4.05 (q, J=7.1, 4H), 6.78 (dd, J=7.7, 1.1, 1H), 6.94 (d, J=1.1, 1H), 7.02 (d, 1H).

Step C

N-[5-(2-carboxyethyl)-2-methylphenyl]iminodiacetic acid diethyl ester

To dichloromethane (8.8 ml) were added the compound (1.79 g, 4.40 mmol) obtained in step B and 4N hydrochloric acid-dioxane solution (8.8 ml), and the mixture was stirred at room temperature for 2 hr. The reaction mixture was diluted with dichloromethane, washed with water, and dried over sodium sulfate. The insoluble material was filtered off, and the solution was concentrated under reduced pressure. The obtained oil was purified by silica gel column chromatography (ethyl acetate-hexane) to give the title compound (1.21 g, yield 79%) as a colorless oil.

$^1$H-NMR (400 MHz, DMSO-d$_6$); δ (ppm) 1.14 (t, J=7.1, 6H), 2.20 (s, 3H), 2.45 (t, J=7.7, 2H), 2.71 (t, J=7.7, 2H), 3.97 (s, 4H), 4.05 (q, J=7.1, 4H), 6.78 (dd, J=7.8, 1.1, 1H), 6.94 (d, J=1.1, 1H), 7.02 (d, J=7.7, 1H), 12.11 (brs, 1H).

Step D

N-(6-methyl-1-oxo-2,3-dihydro-1H-inden-5-yl)iminodiacetic acid diethyl ester

To dichloromethane (68 ml) were added the compound (4.79 g, 13.6 mmol) obtained in step C, N,N-dimethylformamide (5 drops) and oxalyl chloride (2.59 g, 20.4 mmol), and the mixture was stirred at 40° C. for 3 hr. The reaction mixture was concentrated under reduced pressure, and the obtained oil was diluted with dichloroethane (68 ml) and cooled in an ice water bath. To this solution was added aluminum chloride (2.54 g, 19.0 mmol) by small portions, and the mixture was stirred at 90° C. for 4 hr. The reaction mixture was diluted with dichloromethane, washed with water and saturated brine, and dried over sodium sulfate. The insoluble material was filtered off, and the solution was concentrated under reduced pressure. The obtained oil was purified by silica gel column chromatography (ethyl acetate-hexane) to give the title compound (2.59 g, yield 57%) as a colorless oil.

$^1$H-NMR (400 MHz, DMSO-d$_6$); δ (ppm) 1.17 (t, J=7.1, 6H), 2.27 (s, 3H), 2.54 (t, J=5.8, 2H), 2.96 (t, J=5.6, 2H), 4.08-4.12 (m, 8H), 7.07 (s, 1H), 7.39 (s, 1H).

Step E

N-(6-methyl-1-oxo-2,3-dihydro-1H-inden-5-yl)iminodiacetic acid

Using the compound (1.59 g, 7.77 mmol) obtained in step D and according to the method of Reference Example 61, step G, the title compound (1.91 g, yield 89%) was obtained as a yellow solid.

$^1$H-NMR (400 MHz, DMSO-d$_6$); δ (ppm) 2.27 (s, 3H), 2.52-2.55 (m, 2H), 2.96 (t, J=5.2, 2H), 4.03 (s, 4H), 7.00 (s, 1H), 7.38 (s, 1H), 12.59 (brs, 2H).

Reference Example 126

N-(6-methyl-3-oxo-2,3-dihydro-1H-inden-5-yl)iminodiacetic acid

Step A 5-methyl-6-nitroindan-1-one

This step was performed according to the method described in Journal of Medicinal Chemistry, 2006, 49, 7502-7512. 5-Methylindan-1-one (3.27 g, 22.4 mmol) was dissolved in concentrated sulfuric acid (27 ml), a solution of potassium nitrate (2.28 g, 22.6 mmol) in concentrated sulfuric acid (5 ml) was added dropwise over 10 min under ice-cooling with stirring, and the mixture was stirred at the same temperature for 2 hr. The reaction mixture was added to ice water, and extracted with an ethyl acetate-hexane=1:1 mixed solvent. The organic layer was washed with saturated aqueous sodium hydrogen carbonate and saturated brine, and dried over anhydrous magnesium sulfate. The insoluble material was filtered off, and the solution was concentrated under reduced pressure. The obtained oil was purified by silica gel column chromatography (ethyl acetate-hexane) to give the title compound (2.37 g, yield 55%) as a colorless solid.

$^1$H-NMR (400 MHz, CDCl$_3$); δ (ppm) 2.68 (s, 3H), 2.77-2.81 (m, 2H), 3.18-3.22 (m, 2H), 7.47 (s, 1H), 8.31 (s, 1H).

Step B 6-amino-5-methylindan-1-one

Using the compound (2.36 g, 12.3 mmol) obtained in step A and according to the method of Reference Example 68, step A, the title compound (1.51 g, yield 76%) was obtained as a pale-yellow solid.

$^1$H-NMR (400 MHz, CDCl$_3$); δ (ppm) 2.25 (s, 3H), 2.62-2.66 (m, 2H), 2.98-3.02 (m, 2H), 3.71 (brs, 2H), 7.00 (s, 1H), 7.17 (s, 1H).

Step C

N-(6-methyl-3-oxo-2,3-dihydro-1H-inden-5-yl)iminodiacetic acid

Using the compound (1.50 g, 9.31 mmol) obtained in step B and according to the methods of Reference Example 61, steps C and G, the title compound (2.28 g, yield 88%) was obtained as a pale-yellow solid.

$^1$H-NMR (400 MHz, DMSO-d$_6$); δ (ppm) 2.36 (s, 3H), 2.56-2.60 (m, 2H), 2.95-2.99 (m, 2H), 3.94 (s, 4H), 7.31 (s, 1H), 7.35 (s, 1H), 12.47 (brs, 2H).

Reference Example 127

N-(3-methyl-8-oxo-5,6,7,8-tetrahydronaphthalen-2-yl)iminodiacetic acid

Step A 6-methyl-7-nitro-3,4-dihydronaphthalen-1 (2H)-one

Using 6-methyl-3,4-dihydronaphthalen-1 (2H)-one (4.74 g, 29.6 mmol) and according to the method of Reference Example 126, step A, the title compound (3.02 g, yield 50%) was obtained as a pale-yellow solid.
$^1$H-NMR (400 MHz, CDCl$_3$); δ (ppm) 2.14-2.21 (m, 2H), 2.63 (s, 3H), 2.67-2.71 (m, 2H), 3.00 (t, J=6.1, 2H), 7.25 (s, 1H), 8.61 (s, 1H).

Step B 7-amino-6-methyl-3,4-dihydronaphthalen-1 (2H)-one

Using the compound (3.00 g, 14.6 mmol) obtained in step A and according to the method of Reference Example 68, step A, the title compound (2.32 g, yield 91%) was obtained as a pale-yellow solid.
$^1$H-NMR (400 MHz, CDCl$_3$); δ (ppm) 2.04-2.12 (m, 2H), 2.20 (s, 3H), 2.57-2.61 (m, 2H), 2.83 (t, J=6.1, 2H), 3.62 (brs, 2H), 6.95 (s, 1H), 7.31 (s, 1H).

Step C

N-(3-methyl-8-oxo-5,6,7,8-tetrahydronaphthalen-2-yl)iminodiacetic acid

Using the compound (2.31 g, 13.2 mmol) obtained in step B and according to the methods of Reference Example 61, steps C and G, the title compound (3.15 g, yield 82%) was obtained as a pale-yellow solid.
$^1$H-NMR (400 MHz, DMSO-d$_6$); δ (ppm) 1.95-2.02 (m, 2H), 2.29 (s, 3H), 2.40-2.55 (m, 2H), 2.82 (t, J=5.8, 2H), 3.92 (s, 4H), 7.12 (s, 1H), 7.59 (s, 1H), 12.44 (brs, 2H).

Reference Example 128

N-(5-cyano-4-fluoro-2-methylphenyl)iminodiacetic acid

Step A

N-(5-bromo-4-fluoro-2-methylphenyl)iminodiacetic acid diethyl ester

Using 1-bromo-2-fluoro-4-methyl-5-nitrobenzene (5.00 g, 21.4 mmol) and according to the methods of Reference Example 61, steps B and C, the title compound (6.82 g, yield 85%) as a pale-yellow oil.
$^1$H-NMR (400 MHz, DMSO-d$_6$); δ (ppm) 1.14 (t, J=7.0, 6H), 2.24 (s, 3H), 3.97 (s, 4H), 4.05 (q, J=7.2, 4H), 7.19 (d, J=9.8, 1H), 7.41 (d, J=6.5, 1H).

Step B

N-(5-cyano-4-fluoro-2-methylphenyl)iminodiacetic acid diethyl ester

Using the compound (5.74 g, 15.3 mmol) obtained in step A and according to the method of Reference Example 112, step D, the title compound (4.03 g, yield 82%) was obtained as a pale-yellow solid.
$^1$H-NMR (400 MHz, DMSO-d$_6$); δ (ppm) 1.15 (t, J=7.1, 6H), 2.36 (s, 3H), 4.00-4.08 (m, 8H), 7.36 (d, J=10.2, 1H), 7.66 (d, J=6.2, 1H).

Step C

N-(5-cyano-4-fluoro-2-methylphenyl)iminodiacetic acid

Using the compound (4.03 g, 12.5 mmol) obtained in step B and according to the method of Reference Example 61, step G, the title compound (3.31 g, yield 99%) was obtained as a colorless solid.
$^1$H-NMR (400 MHz, DMSO-d$_6$); δ (ppm) 2.35 (s, 3H), 3.92 (s, 4H), 7.35 (d, J=10.2, 1H), 7.57 (d, J=6.1, 1H), 12.54 (brs, 2H).

Reference Example 129

N-[2-methyl-4-(3-methyl-1,2,4-oxadiazol-5-yl)phenyl]iminodiacetic acid

The compound (5.40 g, 16.8 mmol) of Reference Example 69, step E was dissolved in toluene (10 ml), then N,N-dimethylacetamide dimethylacetal (10 ml) was added, and the mixture was stirred at 100° C. for 1 hr. The reaction mixture was concentrated under reduced pressure, and the obtained oil was dissolved in 1,4-dioxane (50 ml). Hydroxylammonium chloride (2.30 g, 33.1 mmol), sodium acetate (2.72 g, 33.2 mmol) and acetic acid (5 ml) were added, and the mixture was stirred with heating at 90° C. for 110 min. The reaction mixture was cooled to room temperature, and diluted with an ethyl acetate-hexane=1:1 mixed solvent. The organic layer was washed with water, 10% aqueous citric acid solution, saturated aqueous sodium hydrogen carbonate and saturated brine, and dried over anhydrous magnesium sulfate. The insoluble material was filtered off, and the solution was concentrated under reduced pressure. The obtained oil was purified by silica gel column chromatography (ethyl acetate-hexane) to give a colorless oil (6.52 g). Using this oil and according to the method of Reference Example 62, step B, the title compound (3.98 g, yield 78%) was obtained as a colorless solid.
$^1$H-NMR (300 MHz, DMSO-d$_6$); δ (ppm) 2.32 (s, 3H), 2.38 (s, 3H), 4.04 (s, 4H), 7.08 (d, J=8.5, 1H), 7.79 (dd, J=2.0, 8.5, 1H), 7.83 (d, J=2.0, 1H), 12.65 (brs, 2H).

Reference Example 130

N-[2-methyl-4-(4-methyl-1,3-thiazol-2-yl)phenyl]iminodiacetic acid

Step A

N-[4-(aminocarbonothioyl)-2-methylphenyl]iminodiacetic acid diethyl ester

Using the compound (3.68 g, 11.4 mmol) of Reference Example 69, step E and according to the method of Reference Example 79, step A, the title compound (2.13 g, yield 55%) was obtained as a yellow oil.
$^1$H-NMR (400 MHz, CDCl$_3$); δ (ppm) 1.25 (t, J=7.2, 6H), 2.36 (s, 3H), 4.07 (s, 4H), 4.16 (q, J=7.2, 4H), 7.08 (d, J=8.4, 1H), 7.09 (brs, 1H), 7.46 (brs, 1H), 7.62 (dd, J=2.3, 8.4, 1H), 7.77 (d, J=2.3, 1H).

Step B

N-[2-methyl-4-(4-methyl-1,3-thiazol-2-yl)phenyl]iminodiacetic acid

Using the compound (2.21 g, 6.53 mmol) obtained in step A and according to the method of Reference Example 79, step B, the title compound (1.58 g, yield 76%) was obtained as a pale-yellow solid.

$^1$H-NMR (400 MHz, DMSO-d$_6$); δ (ppm) 2.30 (s, 3H), 2.39 (d, J=0.8, 3H), 3.98 (s, 4H), 7.06 (d, J=8.4, 1H), 7.21 (d, J=0.8, 1H), 7.61 (dd, J=2.2, 8.4, 1H), 7.66 (d, J=2.2, 1H), 12.54 (brs, 2H).

Reference Example 131

N-[2-methyl-4-(5-methyl-1,3-thiazol-2-yl)phenyl]iminodiacetic acid

Step A

N-[4-{[(2-hydroxypropyl)amino]carbonyl}-2-methylphenyl]iminodiacetic acid diethyl ester Using the compound (2.97 g, 9.19 mmol) of Reference Example 69, step D, and 1-amino-2-propanol (1.4 ml), and according to the method of Reference Example 70, step A, the title compound (3.47 g, yield 99%) was obtained as a yellow oil.

$^1$H-NMR (400 MHz, CDCl$_3$); δ (ppm) 1.15-1.30 (m, 3H), 1.24 (t, J=7.2, 6H), 2.35 (s, 3H), 2.74 (d, J=4.4, 1H), 3.25-3.32 (m, 1H), 3.59-3.66 (m, 1H), 3.95-4.05 (m, 1H), 4.06 (s, 4H), 4.15 (q, J=7.2, 4H), 6.55 (t, J=5.4, 1H), 7.14 (d, J=8.4, 1H), 7.52 (dd, J=2.1, 8.4, 1H), 7.62 (d, J=2.1, 1H).

Step B

N-[2-methyl-4-{[(2-oxopropyl)amino]carbonyl}phenyl]iminodiacetic acid diethyl ester The compound (3.11 g, 8.17 mmol) obtained in step B was dissolved in dichloromethane (40 ml), Dess-Martin Periodinane (5.07 g, 12.0 mmol) was added at room temperature, and the mixture was stirred at the same temperature for 3 hr. To the reaction mixture was added saturated aqueous sodium hydrogen carbonate (80 ml) containing sodium sulfite (20 g), the mixture was stirred at room temperature and diluted with dichloromethane, and the organic layer was extracted. The organic layer was washed with saturated brine, and dried over anhydrous magnesium sulfate. The insoluble material was filtered off, and the solution was concentrated under reduced pressure. The obtained oil was purified by silica gel column chromatography (ethyl acetate-hexane) to give the title compound (2.39 g, yield 77%) as a yellow oil.

$^1$H-NMR (400 MHz, CDCl$_3$); δ (ppm) 1.24 (t, J=7.2, 6H), 2.26 (s, 3H), 2.36 (s, 3H), 4.06 (s, 4H), 4.15 (q, J=7.2, 4H), 4.34 (d, J=4.4, 2H), 6.83 (broad t, 1H), 7.15 (d, J=8.4, 1H), 7.57 (dd, J=2.2, 8.4, 1H), 7.64 (d, J=2.2, 1H).

Step C

N-[2-methyl-4-(5-methyl-1,3-thiazol-2-yl)phenyl]iminodiacetic acid diethyl ester Using the compound (1.24 g, 3.28 mmol) obtained in step B and according to the method of Reference Example 80, step A, the title compound (859 mg, yield 70%) was obtained as a pale-yellow oil.

$^1$H-NMR (400 MHz, CDCl$_3$); δ (ppm) 1.24 (t, J=7.2, 6H), 2.38 (s, 3H), 2.49 (s, 3H), 4.06 (s, 4H), 4.15 (q, J=7.2, 4H), 7.18 (d, J=8.4, 1H), 7.44 (s, 1H), 7.61 (dd, J=2.2, 8.4, 1H), 7.72 (d, J=2.2, 1H).

Step D

N-[2-methyl-4-(5-methyl-1,3-thiazol-2-yl)phenyl]iminodiacetic acid

Using the compound (833 mg, 2.21 mmol) obtained in step C and according to the method of Reference Example 62, step B, the title compound (589 mg, yield 83%) was obtained as a pale-yellow solid.

$^1$H-NMR (400 MHz, DMSO-d$_6$); δ (ppm) 2.30 (s, 3H), 2.46 (d, J=1.1, 3H), 3.97 (s, 4H), 7.07 (d, J=8.4, 1H), 7.51 (d, J=1.1, 1H), 7.57 (dd, J=2.2, 8.4, 1H), 7.62 (d, J=2.2, 1H), 12.53 (brs, 2H).

Reference Example 132

N-[2-methyl-4-(5-methyl-1,3,4-thiadiazol-2-yl)phenyl]iminodiacetic acid

Step A

N-{4-[(2-acetylhydrazino)carbonyl]-2-methylphenyl}iminodiacetic acid diethyl ester Using the compound (3.08 g, 9.53 mmol) of Reference Example 69, step D, and acetohydrazide (1.18 g, 15.9 mmol), and according to the method of Reference Example 84, step A, the title compound (3.13 g, yield 87%) was obtained as a pale-yellow oil.

$^1$H-NMR (400 MHz, CDCl$_3$); δ (Ppm) 1.24 (t, J=7.2, 6H), 2.07 (s, 3H), 2.31 (s, 3H), 4.06 (s, 4H), 4.15 (q, J=7.2, 4H), 7.09 (d, J=8.4, 1H), 7.60 (dd, J=2.0, 8.4, 1H), 7.65 (d, J=2.0, 1H), 9.35 (d, J=5.2, 1H), 9.48 (d, J=5.2, 1H).

Step B

N-[2-methyl-4-(5-methyl-1,3,4-thiadiazol-2-yl)phenyl]iminodiacetic acid diethyl ester Using the compound (3.12 g, 8.22 mmol) obtained in step A and according to the method of Reference Example 80, step A, the title compound (2.42 g, yield 78%) was obtained as a yellow oil.

$^1$H-NMR (400 MHz, CDCl$_3$); δ (ppm) 1.25 (t, J=7.2, 6H), 2.39 (s, 3H), 2.79 (s, 3H), 4.08 (s, 4H), 4.16 (q, J=7.2, 4H), 7.19 (d, J=8.3, 1H), 7.65 (dd, J=2.2, 8.3, 1H), 7.77 (d, J=2.2, 1H).

Step C

N-[2-methyl-4-(5-methyl-1,3,4-thiadiazol-2-yl)phenyl]iminodiacetic acid

Using the compound (2.40 g, 6.36 mmol) obtained in step B and according to the method of Reference Example 62, step B, the title compound (1.92 g, yield 94%) was obtained as a pale-yellow solid.

$^1$H-NMR (400 MHz, DMSO-d$_6$); δ (ppm) 2.31 (s, 3H), 2.74 (s, 3H), 4.00 (s, 4H), 7.09 (d, J=8.4, 1H), 7.63 (dd, J=2.0, 8.4, 1H), 7.68 (d, J=2.0, 1H), 12.57 (brs, 2H).

The compounds of Reference Examples 121-132 are shown below.

TABLE 5

| Reference Example | Structural Formula |
|---|---|
| 121 | *(4-iodo-2-methylphenyl)-N,N-bis(carboxymethyl)amine* |
| 122 | *2-methyl-4-(3-methylisoxazol-5-yl)phenyl-N,N-bis(carboxymethyl)amine* |
| 123 | *2-methyl-5-(3-methylisoxazol-5-yl)phenyl-N,N-bis(carboxymethyl)amine* |
| 124 | *4-acetyl-2-methylphenyl-N,N-bis(carboxymethyl)amine* |
| 125 | *(6-methyl-3-oxo-2,3-dihydro-1H-inden-5-yl)-N,N-bis(carboxymethyl)amine* |
| 126 | *(5-methyl-3-oxo-2,3-dihydro-1H-inden-6-yl)-N,N-bis(carboxymethyl)amine* |

TABLE 5-continued

| Reference Example | Structural Formula |
|---|---|
| 127 | *(3-methyl-8-oxo-5,6,7,8-tetrahydronaphthalen-2-yl)-N,N-bis(carboxymethyl)amine* |
| 128 | *4-cyano-5-fluoro-2-methylphenyl-N,N-bis(carboxymethyl)amine* |
| 129 | *2-methyl-4-(3-methyl-1,2,4-oxadiazol-5-yl)phenyl-N,N-bis(carboxymethyl)amine* |
| 130 | *2-methyl-4-(4-methylthiazol-2-yl)phenyl-N,N-bis(carboxymethyl)amine* |
| 131 | *2-methyl-4-(5-methylthiazol-2-yl)phenyl-N,N-bis(carboxymethyl)amine* |
| 132 | *2-methyl-4-(5-methyl-1,3,4-thiadiazol-2-yl)phenyl-N,N-bis(carboxymethyl)amine* |

Reference Example 133

N-[6-methyl-1-(tetrahydro-2H-pyran-2-yl)-1H-indazol-5-yl]iminodiacetic acid

Step A 6-methyl-5-nitro-1-(tetrahydro-2H-pyran-2-yl)-1H-indazole

6-Methyl-5-nitro-1H-indazole (15.1 g, 85.2 mmol), 2,3-dichloro-5,6-dicyano-p-benzoquinone (DDQ) (1.94 g, 8.55 mmol) and 3,4-dihydro-2H-pyran (9.0 ml, 98.4 mmol) were dissolved in acetonitrile (300 ml), and the mixture was heated under reflux for 4.5 hr. The reaction mixture was concentrated under reduced pressure, and the residue was diluted with an ethyl acetate-hexane=1:1 mixed solvent, washed with saturated brine, and dried over anhydrous magnesium sulfate. The insoluble material was filtered off, and the solution was concentrated under reduced pressure. The obtained oil was purified by silica gel column chromatography (ethyl acetate-hexane) to give the title compound (16.0 g, yield 72%) as an orange solid.
$^1$H-NMR (400 MHz, CDCl$_3$); δ (ppm) 1.6-1.9 (m, 3H), 2.0-2.2 (m, 2H). 2.4-2.6 (m, 1H), 2.75 (s, 3H), 3.74-3.81 (m, 1H), 4.00-4.04 (m, 1H), 5.73 (dd, J=2.5, 9.1, 1H), 7.49 (s, 1H), 8.13 (s, 1H), 8.50 (s, 1H).

Step B 6-methyl-1-(tetrahydro-2H-pyran-2-yl)-1H-indazol-5-amine

Using the compound (16.0 g, 61.2 mmol) of step A and according to the method of Reference Example 61, step B, the title compound (11.7 g, yield 83%) was obtained as a colorless solid.
$^1$H-NMR (400 MHz, CDCl$_3$); δ (ppm) 1.5-1.8 (m, 3H), 2.0-2.2 (m, 2H), 2.34 (s, 3H), 2.5-2.6 (m, 1H), 3.55 (brs, 2H), 3.70-3.77 (m, 1H), 4.01-4.04 (m, 1H), 5.63 (dd, J=2.5, 9.4, 1H), 6.93 (s, 1H), 7.31 (s, 1H), 7.80 (s, 1H).

Step C

N-[6-methyl-1-(tetrahydro-2H-pyran-2-yl)-1H-indazol-5-yl]iminodiacetic acid

Using the compound (11.7 g, 50.6 mmol) of step B and according to the methods of Reference Example 61, steps C and G, the title compound (12.9 g, yield 73%) was obtained as a pale-yellow solid.
$^1$H-NMR (400 MHz, DMSO-d$_6$); δ (ppm) 1.5-1.7 (m, 2H), 1.7-1.8 (m, 1H), 1.89-2.05 (m, 2H), 2.3-2.5 (m, 1H), 2.42 (s, 3H), 3.68-3.75 (m, 1H), 3.85-3.90 (m, 1H), 3.93 (s, 4H), 5.73 (dd, J=2.2, 9.6, 1H), 7.49 (s, 1H), 7.52 (s, 1H), 7.94 (s, 1H), 12.35 (brs, 2H).

Reference Example 134

N-[5-methyl-1-(tetrahydro-2H-pyran-2-yl)-1H-indazol-6-yl]iminodiacetic acid

Step A 5-methyl-6-nitro-1H-indazole

Using 2,4-dimethylaniline (49.6 g, 409 mmol), and according to the method described in WO2003/068754, the title compound (66.2 g, yield 91%) was obtained as a red bistered solid.
$^1$H-NMR (400 MHz, DMSO-d$_6$); δ (ppm) 2.54 (s, 3H), 7.85 (s, 1H), 8.20 (s, 1H), 8.22 (s, 1H), 13.57 (brs, 1H).

Step B 5-methyl-6-nitro-1-(tetrahydro-2H-pyran-2-yl)-1H-indazole

Using the compound (8.47 g, 47.8 mmol) of step A and according to the method of Reference Example 133, step A, the title compound (11.5 g, yield 92%) was obtained as a red bistered solid.
$^1$H-NMR (400 MHz, CDCl$_3$); δ (ppm) 1.7-1.9 (m, 3H), 2.0-2.2 (m, 2H), 2.45-2.60 (m, 1H), 2.65 (s, 3H), 3.74-3.81 (m, 1H), 4.00-4.06 (m, 1H), 5.75 (dd, J=2.7, 9.2, 1H), 7.65 (s, 1H), 8.04 (s, 1H), 8.27 (s, 1H).

Step C 5-methyl-1-(tetrahydro-2H-pyran-2-yl)-1H-indazol-6-amine

Using the compound (11.5 g, 44.0 mmol) of step B and according to the method of Reference Example 61, step B, the title compound (9.62 g, yield 95%) was obtained as a yellow amorphous solid.
$^1$H-NMR (400 MHz, CDCl$_3$); δ (ppm) 1.5-1.8 (m, 3H), 2.0-2.2 (m, 2H), 2.25 (s, 3H), 2.5-2.6 (m, 1H), 3.68-3.75 (m, 1H), 3.83 (brs, 2H), 3.99-4.04 (m, 1H), 5.56 (dd, J=2.7, 9.4, 1H), 6.77 (s, 1H), 7.36 (s, 1H), 7.80 (s, 1H).

Step D

N-[5-methyl-1-(tetrahydro-2H-pyran-2-yl)-1H-indazol-6-yl]iminodiacetic acid

Using the compound (9.62 g, 41.6 mmol) of step C and according to the methods of Reference Example 61, step C, and Reference Example 62, step B, the title compound (7.34 g, yield 51%) was obtained as a colorless solid.
$^1$H-NMR (400 MHz, DMSO-d$_6$); δ (ppm) 1.5-1.6 (m, 2H), 1.65-1.80 (m, 1H), 1.80-1.95 (m, 1H), 1.95-2.05 (m, 1H), 2.3-2.4 (m, 1H), 2.34 (s, 3H), 3.66-3.74 (m, 1H), 3.8-3.9 (m, 1H), 3.99 (s, 4H), 5.70 (dd, J=2.4, 9.6, 1H), 7.35 (s, 1H), 7.49 (s, 1H), 7.88 (s, 1H), 12.47 (brs, 2H).

Reference Example 135

N-(3-iodo-1,5-dimethyl-1H-indazol-6-yl)iminodiacetic acid

Step A 3-iodo-5-methyl-6-nitro-1H-indazole

The compound (34.9 g, 197 mmol) of Reference Example 134, step A was dissolved in N,N-dimethylformamide (400 ml), iodine (103 g, 406 mmol) and potassium hydroxide pellet (52 g, 927 mmol) were successively added under ice-cooling with stirring, and the mixture was stirred at room temperature for 1 hr. The reaction mixture was poured into 10% aqueous sodium bisulfite solution (2000 ml), and the precipitated solid was collected by filtration, washed with water, and dried under reduced pressure to give the title compound (45.1 g, yield 76%) as a brown solid.

¹H-NMR (400 MHz, DMSO-d₆); δ (ppm) 2.56 (s, 3H), 7.54 (s, 1H), 8.25 (s, 3H), 13.98 (s, 1H).

Step B 3-iodo-1,5-dimethyl-6-nitro-1H-indazole

The compound (16.1 g, 53.1 mmol) of step A was dissolved in N,N-dimethylformamide (200 ml), 60% sodium hydride (2.41 g, 60.3 mmol) was added under ice-cooling with stirring, and the mixture was stirred at 0° C. for 45 min. Then, methyl iodide (5.0 ml, 80.3 mmol) was added, and the mixture was stirred at the same temperature for 100 min. To the reaction mixture was added diluted hydrochloric acid, and the mixture was extracted with ethyl acetate. The organic layer was washed with saturated brine, and dried over anhydrous magnesium sulfate. The insoluble material was filtered off, and the solution was concentrated. The obtained solid was purified by silica gel column chromatography (hexane:dichloromethane:ethyl acetate-10:1:1) to give the title compound (6.09 g, yield 36%) as a yellow solid.

¹H-NMR (400 MHz, DMSO-d₆); δ (ppm) 2.56 (s, 3H), 4.14 (s, 3H), 7.52 (s, 1H), 8.49 (s, 1H).

Step C 3-iodo-1,5-dimethyl-1H-indazol-6-amine

Using the compound (6.09 g, 19.2 mmol) of step B and according to the method of Reference Example 61, step B, the title compound (4.68 g, yield 85%) was obtained as a pale-yellow solid.

¹H-NMR (400 MHz, CDCl₃); δ (ppm) 2.28 (s, 3H), 3.91 (brs, 2H), 3.95 (s, 3H), 6.51 (s, 1H), 7.10 (s, 1H).

Step D

N-(3-iodo-1,5-dimethyl-1H-indazol-6-yl)iminodiacetic acid diethyl ester

Using the compound (4.68 g, 16.3 mmol) of step C and according to the method of Reference Example 61, step C, the title compound (3.99 g, yield 53%) was obtained as a colorless solid.

¹H-NMR (400 MHz, CDCl₃); δ (ppm) 1.23 (t, J=7.0, 6H), 2.45 (s, 3H), 4.02 (s, 3H), 4.12 (s, 4H), 4.14 (q, J=7.0, 4H), 7.18 (s, 1H), 7.23 (s, 1H).

Step E

N-(3-iodo-1,5-dimethyl-1H-indazol-6-yl)iminodiacetic acid

Using the compound (3.74 g, 8.14 mmol) of step D and according to the method of Reference Example 62, step B, the title compound (3.15 g, yield 96%) was obtained as a pale-yellow solid.

¹H-NMR (400 MHz, DMSO-d₆); δ (ppm) 2.37 (s, 3H), 3.96 (s, 3H), 4.00 (s, 4H), 7.14 (s, 1H), 7.25 (s, 1H), 12.48 (brs, 2H).

Reference Example 136

N-(3-iodo-1,6-dimethyl-1H-indazol-5-yl)iminodiacetic acid

Step A 3-iodo-6-methyl-5-nitro-1H-indazole

Using 6-methyl-5-nitro-1H-indazole (5.15 g, 29.1 mmol) and according to the method of Reference Example 135, step A, the title compound (8.65 g, yield 98%) was obtained as a yellow solid.

¹H-NMR (400 MHz, DMSO-d₆); δ (ppm) 2.64 (s, 3H), 7.63 (s, 1H), 8.15 (s, 1H), 13.94 (brs, 1H).

Step B 3-iodo-1,6-dimethyl-5-nitro-1H-indazole

Using the compound (6.07 g, 20.0 mmol) of step A and according to the method of Reference Example 135, step B, the title compound (3.36 g, yield 51%) was obtained as a yellow bistered solid.

¹H-NMR (400 MHz, DMSO-d₆); δ (ppm) 2.65 (s, 3H), 4.09 (s, 3H), 7.80 (s, 1H), 8.13 (s, 1H).

Step C 3-iodo-1,6-dimethyl-1H-indazol-5-amine

Using the compound (3.36 g, 10.6 mmol) of step B and according to the method of Reference Example 61, step B, the title compound (2.61 g, yield 86%) was obtained as a pale-yellow solid.

¹H-NMR (400 MHz, CDCl₃); δ (ppm) 2.34 (s, 3H), 3.63 (brs, 2H), 4.01 (s, 3H), 6.66 (s, 1H), 7.09 (s, 1H).

Step D

N-(3-iodo-1,6-dimethyl-1H-indazol-5-yl)iminodiacetic acid diethyl ester

Using the compound (2.59 g, 9.02 mmol) of step C and according to the method of Reference Example 61, step C, the title compound (2.59 g, yield 63%) was obtained as an orange oil.

¹H-NMR (400 MHz, CDCl₃); δ (ppm) 1.25 (t, J=7.1, 6H), 2.53 (s, 3H), 4.02 (s, 3H), 4.06 (s, 4H), 4.14 (q, J=7.1, 4H), 7.17 (s, 1H), 7.31 (s, 1H).

Step E

N-(3-iodo-1,6-dimethyl-1H-indazol-5-yl)iminodiacetic acid

Using the compound (2.58 g, 5.62 mmol) of step D and according to the method of Reference Example 62, step B, the title compound (1.97 g, yield 87%) was obtained as a colorless solid.

$^1$H-NMR (400 MHz, DMSO-d$_6$); δ (ppm) 2.43 (s, 3H), 3.95 (s, 4H), 3.98 (s, 3H), 7.13 (s, 1H), 7.45 (s, 1H), 12.42 (brs, 2H).

Reference Example 137

N-(2,3,5-trimethyl-2H-indazol-6-yl)iminodiacetic acid

Step A 3-iodo-5-methyl-6-nitro-1-(tetrahydro-2H-pyran-2-yl)-1H-indazole

Using the compound (18.0 g, 59.4 mmol) of Reference Example 135, step A and according to the method of Reference Example 133, step A, the title compound (17.0 g, yield 74%) was obtained as a pale-yellow solid.

$^1$H-NMR (400 MHz, CDCl$_3$); δ (ppm) 1.6-1.8 (m, 3H), 2.0-2.2 (m, 2H), 2.4-2.6 (m, 1H), 2.66 (s, 3H), 3.72-3.79 (m, 1H), 3.99-4.04 (m, 1H), 5.72 (dd, J=2.8, 9.2, 1H), 7.40 (s, 1H), 8.24 (s, 1H).

Step B 3,5-dimethyl-6-nitro-1-(tetrahydro-2H-pyran-2-yl)-1H-indazole

The compound (5.60 g, 14.5 mmol) of step A, trimethylboroxine (2.20 ml, 15.8 mmol), bis(tricyclohexylphosphine)palladium(II)dichloride (926 mg, 1.25 mmol) and 1.27 mol/l aqueous potassium phosphate solution (35.0 ml, 44.5 mmol) were added to 1,4-dioxane (150 ml), and the mixture was heated under reflux for 18 hr. The reaction mixture was cooled to room temperature, and the solution was concentrated under reduced pressure. The residue was diluted with ethyl acetate, and the organic layer was washed with saturated brine, and dried over anhydrous magnesium sulfate. The insoluble material was filtered off, and the solution was to concentrated under reduced pressure. The obtained oil was purified by silica gel column chromatography (ethyl acetate-hexane) to give the title compound (2.73 g, yield 68%) as a yellow solid.

$^1$H-NMR (400 MHz, CDCl$_3$); δ (ppm) 1.6-1.9 (m, 3H), 2.0-2.2 (m, 2H), 2.46-2.56 (m, 1H), 2.58 (s, 3H), 2.65 (s, 3H), 3.72-3.79 (m, 1H), 4.04-4.09 (m, 1H), 5.64 (dd, J=2.6, 9.9, 1H), 7.54 (s, 1H), 8.18 (s, 1H).

Step C 3,5-dimethyl-1-(tetrahydro-2H-pyran-2-yl)-1H-indazol-6-amine

Using the compound (2.71 g, 9.84 mmol) of step B and according to the method of Reference Example 61, step B, the title compound (1.85 g, yield 77%) was obtained as a pale-yellow solid.

$^1$H-NMR (400 MHz, CDCl$_3$); δ (ppm) 1.5-1.8 (m, 3H), 1.97-2.02 (m, 1H), 2.09-2.13 (m, 1H), 2.25 (s, 3H), 2.47 (s, 3H), 2.48-2.59 (m, 1H), 3.66-3.73 (m, 1H), 3.80 (brs, 2H), 4.03-4.08 (m, 1H), 5.47 (dd, J=2.6, 10.0, 1H), 6.70 (s, 1H), 7.27 (s, 1H).

Step D

N-[3,5-dimethyl-1-(tetrahydro-2H-pyran-2-yl)-1H-indazol-6-yl]iminodiacetic acid ethyl ester Using the compound (1.82 g, 7.42 mmol) of step C and according to the method of Reference Example 61, step C, the title compound (2.53 g, yield 82%) was obtained as a yellow oil.

$^1$H-NMR (400 MHz, CDCl$_3$); δ (ppm) 1.23 (t, J=7.1, 6H), 1.55-1.65 (m, 1H), 1.7-1.8 (m, 2H), 1.95-2.00 (m, 1H), 2.05-2.15 (m, 1H), 2.43 (s, 3H), 2.50 (s, 3H), 2.5-2.6 (m, 1H), 3.68-3.76 (m, 1H), 4.0-4.1 (m, 1H), 4.11 (s, 4H), 4.14 (q, J=7.1, 4H), 5.52 (dd, J=2.5, 10.1, 1H), 7.29 (s, 1H), 7.39 (s, 1H).

Step E

N-(3,5-dimethyl-1H-indazol-6-yl)iminodiacetic acid ethyl ester

The compound (2.53 g, 6.06 mmol) of step D was dissolved in ethanol (75 ml), concentrated sulfuric acid (0.5 ml) was added at room temperature, and thereafter the mixture was heated under reflux for 70 min. The reaction mixture was concentrated under reduced pressure, and the residue was diluted with ethyl acetate. The organic layer was washed with sodium bicarbonate water and saturated brine, and dried over anhydrous magnesium sulfate. The insoluble material was filtered off, the solution was concentrated under reduced pressure, and the obtained oil was purified by silica gel column chromatography (ethyl acetate-hexane) to give the title compound (1.72 g, yield 85%) as a yellow oil.

$^1$H-NMR (400 MHz, CDCl$_3$); δ (ppm) 1.22 (t, J=7.2, 6H), 2.44 (s, 3H), 2.51 (s, 3H), 4.09 (s, 4H), 4.13 (q, J=7.2, 4H), 7.27 (s, 1H), 7.44 (s, 1H), 9.46 (brs, 1H).

Step F

N-(2,3,5-trimethyl-2H-indazol-6-yl)iminodiacetic acid diethyl ester

The compound (500 mg, 1.50 mmol) of step E was dissolved in dichloromethane (10 ml), trimethyloxonium tetrafluoroborate (290 mg, 1.96 mmol) was added at room temperature, and the mixture was stirred at the same temperature for 140 min. Water was added to the reaction mixture, and the organic layer was extracted with dichloromethane, and dried over anhydrous magnesium sulfate. The insoluble material was filtered off, and the solution was concentrated under reduced pressure. The obtained oil was purified by silica gel column chromatography (ethyl acetate-hexane) to give the title compound (248 mg, yield 48%) as a pale-yellow oil.

$^1$H-NMR (400 MHz, CDCl$_3$); δ (ppm) 1.23 (t, J=7.2, 6H), 2.41 (s, 3H), 2.53 (s, 3H), 4.03 (s, 3H), 4.07 (s, 4H), 4.13 (q, J=7.2, 4H), 7.30 (s, 1H), 7.34 (s, 1H).

Step G

N-(2,3,5-trimethyl-2H-indazol-6-yl)iminodiacetic acid

Using the compound (243 mg, 0.699 mmol) of step F and according to the method of Reference Example 62, step B, the title compound (152 mg, yield 75%) was obtained as a colorless solid.

¹H-NMR (400 MHz, DMSO-d₆); δ (ppm) 2.31 (s, 3H), 2.51 (s, 3H), 3.93 (s, 4H), 3.95 (s, 3H), 7.08 (s, 1H), 7.35 (s, 1H), 12.41 (brs, 2H).

Reference Example 138

N-(2-ethyl-3,5-dimethyl-2H-indazol-6-yl)iminodiacetic acid

Step A

N-(2-ethyl-3,5-dimethyl-2H-indazol-6-yl)iminodiacetic acid diethyl ester

Using the compound (503 mg, 1.51 mmol) of Reference Example 137, step E, and 1 mol/l triethyloxonium tetrafluoroborate dichloromethane solution (1.8 ml), and according to the method of Reference Example 137, step F, the title compound (205 mg, yield 38%) was obtained as a yellow oil.
¹H-NMR (400 MHz, CDCl₃); δ (ppm) 1.24 (t, J=7.2, 6H), 1.50 (t, J=7.3, 3H), 2.41 (s, 3H), 2.54 (s, 3H), 4.07 (s, 4H), 4.14 (q, J=7.2, 4H), 4.33 (q, J=7.3, 2H), 7.32 (s, 1H), 7.36 (s, 1H).

Step B

N-(2-ethyl-3,5-dimethyl-2H-indazol-6-yl)iminodiacetic acid

Using the compound (267 mg, 0.739 mmol) of step A and according to the method of Reference Example 62, step B, the title compound (185 mg, yield 82%) was obtained as a pale-yellow solid.
¹H-NMR (400 MHz, DMSO-d₆); δ (ppm) 1.37 (t, J=7.2, 3H), 2.30 (s, 3H), 2.52 (s, 3H), 3.93 (s, 4H), 4.28 (q, J=7.2, 2H), 7.10 (s, 1H), 7.36 (s, 1H), 12.40 (brs, 2H).

Reference Example 139

N-(1-ethyl-3,5-dimethyl-1H-indazol-6-yl)iminodiacetic acid

Step A

N-(1-ethyl-3,5-dimethyl-1H-indazol-6-yl)iminodiacetic acid diethyl ester

Using the compound (193 mg, 0.579 mmol) of Reference Example 137, step E, and ethyl iodide (0.10 ml, 1.25 mmol), and according to the method of Reference Example 135, step B, the title compound (119 mg, yield 57%) was obtained as a pale-yellow oil.
¹H-NMR (400 MHz, CDCl₃); δ (ppm) 1.22 (t, J=7.1, GH), 1.44 (t, J=7.2, 3H), 2.43 (s, 3H), 2.50 (s, 3H), 4.11 (s, 4H), 4.13 (q, J=7.1, 4H), 4.28 (q, J=7.2, 2H), 7.17 (s, 1H), 7.41 (s, 1H).

Step B

N-(1-ethyl-3,5-dimethyl-1H-indazol-6-yl)iminodiacetic acid

Using the compound (117 mg, 0.324 mmol) of step A and according to the method of Reference Example 62, step B, the title compound (86 mg, yield 87%) was obtained as a colorless solid.
¹H-NMR (400 MHz, DMSO-d₆); 1.30 (t, J=7.2, 3H), 2.33 (s, 3H), 2.38 (s, 3H), 3.98 (s, 4H), 4.22 (q, J=7.2, 2H), 7.16 (s, 1H), 7.40 (s, 1H), 12.44 (brs, 2H).

Reference Example 140

N-[2-(2,2-difluoroethyl)-3,5-dimethyl-2H-indazol-6-yl]iminodiacetic acid

Step A

N-[2-(2,2-difluoroethyl)-3,5-dimethyl-2H-indazol-6-yl]iminodiacetic acid diethyl ester The compound (664 mg, 1.99 mmol) of Reference Example 137, step E, 2,2-difluoroethyl trifluoromethanesulfonate (654 mg, 3.05 mmol) and N,N-dicyclohexylmethylamine (0.70 ml, 3.30 mmol) were dissolved in tetrahydrofuran (15 ml), and the mixture was heated under reflux for 6 hr. The reaction mixture was concentrated under reduced pressure, and the residue was purified by silica gel column chromatography (ethyl acetate-hexane) to give the title compound (541 mg, yield 68%) as a colorless oil.
¹H-NMR (400 MHz, CDCl₃); δ (ppm) 1.24 (t, J=7.1, 6H), 2.41 (s, 3H), 2.57 (s, 3H), 4.08 (s, 4H), 4.14 (q, J=7.1, 4H), 4.62 (dt, J=4.4, 13, 2H), 6.22 (tt, J=4.4, 57, 1H), 7.31 (s, 1H), 7.33 (s, 1H).

Step B

N-[2-(2,2-difluoroethyl)-3,5-dimethyl-2H-indazol-6-yl]iminodiacetic acid

Using the compound (525 mg, 1.32 mmol) of step A and according to the method of Reference Example 62, step B, the title compound (387 mg, yield 86%) was obtained as a colorless solid.
¹H-NMR (400 MHz, DMSO-d₆); 2.31 (s, 3H), 2.55 (s, 3H), 3.94 (s, 4H), 4.79 (dt, J=3.9, 15, 2H), 6.46 (tt, J=3.9, 55, 1H), 7.09 (s, 1H), 7.40 (s, 1H), 12.42 (brs, 2H).

Reference Example 141

N-(3-ethyl-2,5-dimethyl-2H-indazol-6-yl)iminodiacetic acid

Step A 5-methyl-6-nitro-1-(tetrahydro-2H-pyran-2-yl)-3-vinyl-1H-indazole

To toluene (160 ml) were added the compound (8.78 g, 22.7 mmol) of Reference Example 137, step A, tri-n-butylvinyltin (8.7 ml, 29.6 mmol), bis(triphenylphosphine)palladium(II)dichloride (1.47 g, 2.09 mmol) and lithium chloride (3.92 g, 92.5 mmol), and the mixture was heated under reflux for 210 min. The reaction mixture was cooled, diluted with ethyl acetate, washed with saturated brine, and dried over anhydrous magnesium sulfate. The insoluble material was filtered off, and the solution was concentrated under reduced pressure. The obtained oil was purified by silica gel column chromatography (ethyl acetate-hexane) to give an orange solid (7.09 g). This was washed with hexane and dried under reduced pressure to give the title compound (5.42 g, yield 83%) as, a yellow solid.
¹H-NMR (400 MHz, CDCl₃); δ (ppm) 1.6-1.9 (m, 3H), 2.0-2.2 (m, 2H), 2.46-2.57 (m, 1H), 2.67 (s, 3H), 3.73-3.80

(m, 1H), 4.02-4.07 (m, 1H), 5.59 (dd, J=1.0, 11, 1H), 5.72 (dd, J=2.8, 9.3, 1H), 6.11 (dd, J=1.0, 18, 1H), 7.01 (dd, J=11, 18, 1H), 7.81 (s, 1H), 8.24 (s, 1H).

Step B

3-ethyl-5-methyl-1-(tetrahydro-2H-pyran-2-yl)-1H-indazol-6-amine

The compound (3.04 g, 10.6 mmol) of step A was dissolved in an ethanol (100 ml)-tetrahydrofuran (10 ml) mixed solvent, and the mixture was stirred at room temperature. Then, 10% palladium carbon (containing water) (3.20 g) was added, and the mixture was stirred at room temperature for 5 hr under a hydrogen atmosphere. The insoluble material was filtered off through celite, and the obtained solution was concentrated under reduced pressure to give the title compound (2.69 g, yield 98%) as a pale-yellow oil.

$^1$H-NMR (400 MHz, CDCl$_3$); δ (ppm) 1.36 (t, J=7.6, 3H), 1.5-1.8 (m, 3H), 1.96-2.01 (m, 1H), 2.09-2.13 (m, 1H), 2.25 (s, 3H), 2.50-2.55 (m, 1H), 2.90 (q, J=7.6, 2H), 3.5-4.0 (broad, 2H), 3.66-3.73 (m, 1H), 4.03-4.09 (m, 1H), 5.48 (dd, J=2.6, 10, 1H), 6.71 (s, 1H), 7.31 (s, 1H).

Step C

N-(3-ethyl-5-methyl-1H-indazol-6-yl)iminodiacetic acid diethyl ester

Using the compound (2.67 g, 10.3 mmol) of step B and according to the methods of Reference Example 61, step C, and Reference Example 137, step E, the title compound (2.60 g, yield 75%) was obtained as an orange oil.

$^1$H-NMR (400 MHz, CDCl$_3$); δ (ppm) 1.22 (t, J=7.1, 6H), 1.38 (t, J=7.6, 3H), 2.44 (s, 3H), 2.94 (q, J=7.6, 2H), 4.09 (s, 4H), 4.13 (q, J=7.1, 4H), 7.28 (s, 1H), 7.48 (s, 1H), 9.56 (brs, 1H).

Step D

N-(3-ethyl-2,5-dimethyl-2H-indazol-6-yl)iminodiacetic acid diethyl ester

Using the compound (722 mg, 2.08 mmol) of step C, and trimethyloxonium tetrafluoroborate (527 mg, 3.56 mmol), and according to the method of Reference Example 137, step F, the title compound (248 mg, yield 33%) was obtained as a yellow oil.

$^1$H-NMR (400 MHz, CDCl$_3$); δ (ppm) 1.23 (t, J=7.1, 6H), 1.31 (t, J=7.6, 3H), 2.41 (s, 3H), 2.97 (q, J=7.6, 2H), 4.05 (s, 3H), 4.07 (s, 4H), 4.13 (q, J=7.1, 4H), 7.34-7.36 (m, 2H).

Step E

N-(3-ethyl-2,5-dimethyl-2H-indazol-6-yl)iminodiacetic acid

Using the compound (241 mg, 0.667 mmol) of step D and according to the method of Reference Example 62, step B, the title compound (128 mg, yield 63%) was obtained as a colorless solid.

$^1$H-NMR (400 MHz, DMSO-d$_6$); 1.22 (t, J=7.6, 3H), 2.30 (s, 3H), 2.97 (q, J=7.6, 2H), 3.93 (s, 4H), 3.98 (s, 3H), 7.09 (s, 1H), 7.39 (s, 1H), 12.41 (brs, 2H).

Reference Example 142

N-(2,3-diethyl-5-methyl-2H-indazol-6-yl)iminodiacetic acid

Step A

N-(2,3-diethyl-5-methyl-2H-indazol-6-yl)iminodiacetic acid ethyl ester

Using the compound (692 mg, 1.99 mmol) of Reference Example 141, step C, and 1 mol/l triethyloxonium tetrafluoroborate dichloromethane solution (2.3 ml), and according to the method of Reference Example 137, step F, the title compound (298 mg, yield 40%) was obtained as a yellow oil.

$^1$H-NMR (400 MHz, CDCl$_3$); δ (ppm) 1.24 (t, J=7.1, 6H), 1.33 (t, J=7.6, 3H), 1.53 (t, J=7.3, 3H), 2.41 (s, 3H), 2.97 (q, J=7.6, 2H), 4.07 (s, 4H), 4.14 (q, J=7.1, 4H), 4.33 (q, J=7.3, 2H), 7.36 (s, 1H), 7.37 (s, 1H).

Step B

N-(2,3-diethyl-5-methyl-2H-indazol-6-yl)iminodiacetic acid

Using the compound (375 mg, 0.999 mmol) of step A and according to the method of Reference Example 62, step B, the title compound (266 mg, yield 63%) was obtained as a pale-yellow solid.

$^1$H-NMR (400 MHz, DMSO-d$_6$); 1.23 (t, J=7.6, 3H), 1.40 (t, J=7.2, 3H), 2.31 (s, 3H), 2.98 (q, J=7.6, 2H), 3.93 (s, 4H), 4.28 (q, J=7.2, 2H), 7.11 (s, 1H), 7.39 (s, 1H), 12.40 (brs, 2H).

Reference Example 143

N-[2-(2,2-difluoroethyl)-3-ethyl-5-methyl-2H-indazol-6-yl]iminodiacetic acid

Step A

N-[2-(2,2-difluoroethyl)-3-ethyl-5-methyl-2H-indazol-6-yl]iminodiacetic acid diethyl ester Using the compound (721 mg, 2.07 mmol) of Reference Example 141, step C and according to the method of Reference Example 140, step A, the title compound (538 mg, yield 63%) was obtained as an orange oil.

$^1$H-NMR (400 MHz, CDCl$_3$); δ (ppm) 1.24 (t, J=7.2, 6H), 1.33 (t, J=7.6, 3H), 2.41 (s, 3H), 3.01 (q, J=7.6, 2H), 4.08 (s, 4H), 4.13 (q, J=7.2, 4H), 4.61 (dt, J=4.4, 13, 2H), 6.27 (tt, J=4.4, 56, 1H), 7.32 (s, 1H), 7.38 (s, 1H).

Step B

N-[2-(2,2-difluoroethyl)-3-ethyl-5-methyl-2H-indazol-6-yl]iminodiacetic acid Using the compound (533 mg, 1.30 mmol) of step A and according to the method of Reference Example 62, step B, the title compound (410 mg, yield 89%) was obtained as a pale-yellow solid.

$^1$H-NMR (400 MHz, DMSO-$d_6$); 1.23 (t, J=7.6, 3H), 2.31 (s, 3H), 3.02 (q, J=7.6, 2H), 3.94 (s, 4H), 4.79 (dt, J=4.0, 15, 2H), 6.48 (tt, J=4.0, 55, 1H), 7.10 (s, 1H), 7.44 (s, 1H), 12.42 (brs, 2H).

Reference Example 144

N-[1-(2,2-difluoroethyl)-3-ethyl-5-methyl-1H-indazol-6-yl]iminodiacetic acid

Step A

N-[1-(2,2-difluoroethyl)-3-ethyl-5-methyl-1H-indazol-6-yl]iminodiacetic acid diethyl ester Using the compound (312 mg, 0.898 mmol) of Reference Example 141, step C, and 2,2-difluoroethyl trifluoromethanesulfonate (264 mg, 1.23 mmol), and according to the method of Reference Example 135, step B, the title compound (254 mg, yield 69%) was obtained as a pale-yellow oil.
$^1$H-NMR (400 MHz, CDCl$_3$); δ (ppm) 1.23 (t, J=7.2, 6H), 1.36 (t, J=7.6, 3H), 2.44 (s, 3H), 2.91 (q, J=7.6, 2H), 4.11 (s, 4H), 4.14 (q, J=7.2, 4H), 4.56 (dt, J=4.4, 14, 2H), 6.08 (tt, J=4.4, 56, 1H), 7.19 (s, 1H), 7.46 (s, 1H).

Step B

N-[1-(2,2-difluoroethyl)-3-ethyl-5-methyl-1H-indazol-6-yl]iminodiacetic acid

Using the compound (253 mg, 0.615 mmol) of step A and according to the method of Reference Example 62, step B, the title compound (182 mg, yield 89%) was obtained as a colorless solid.
$^1$H-NMR (400 MHz, DMSO-$d_6$); 1.27 (t, J=7.6, 3H), 2.34 (s, 3H), 2.84 (q, J=7.6, 2H), 3.98 (s, 4H), 4.70 (dt, J=3.7, 15, 2H), 6.32 (tt, J=3.7, 55, 1H), 7.29 (s, 1H), 7.48 (s, 1H), 12.43 (brs, 2H).

Reference Example 145

N-[1-(2,2-difluoroethyl)-7-methyl-2-oxo-1,2,3,4-tetrahydroquinolin-6-yl]iminodiacetic acid Step A 1-(2,2-difluoroethyl)-7-methyl-2-oxo-1,2,3,4-tetrahydroquinoline-6-carboxylic acid ethyl ester The compound (4.57 g, 19.6 mmol) of Reference Example 114, step B was dissolved in N,N-dimethylformamide (70 ml), 60% sodium hydride (970 mg, 24.3 mmol) was added under ice-cooling with stirring, and thereafter the mixture was stirred at room temperature for 30 min. The reaction mixture was ice-cooled again, 2,2-difluoroethyl trifluoromethanesulfonate (5.98 g, 27.9 mmol) was added with stirring, and the mixture was stirred at 0° C. for 100 min. To the reaction mixture was added 10% citric acid water, and the mixture was extracted with an ethyl acetate:hexane=1:1 mixed solvent. The organic layer was washed with saturated aqueous sodium hydrogen carbonate and saturated brine, and dried over anhydrous magnesium sulfate. The insoluble material was filtered off, and the solution was concentrated under reduced pressure. The obtained oil was purified by silica gel column chromatography (ethyl acetate-hexane) to give the title compound (4.73 g, yield 81%) as a colorless solid.

$^1$H-NMR (400 MHz, CDCl$_3$); δ (ppm) 1.39 (t, J=7.2, 3H), 2.62 (s, 3H), 2.68-2.72 (m, 2H), 2.92-2.96 (m, 2H), 4.27 (dt, J=4.6, 13, 2H), 4.35 (q, J=7.2, 2H), 6.10 (tt, J=4.6, 56, 1H), 6.96 (s, 1H), 7.78 (s, 1H).

Step B 1-(2,2-difluoroethyl)-7-methyl-2-oxo-1,2,3,4-tetrahydroquinoline-6-carboxylic acid Using the compound (4.73 g, 15.9 mmol) of step A and according to the method of Reference Example 114, step D, the title compound (4.31 g, yield 100%) was obtained as a colorless solid.
$^1$H-NMR (400 MHz, DMSO-$d_6$); δ (ppm) 2.53 (s, 3H), 2.59-2.64 (m, 2H), 2.86-2.91 (m, 2H), 4.41 (dt, J=4.1, 15, 2H), 6.22 (tt, J=4.1, 56, 1H), 7.19 (s, 1H), 7.73 (s, 1H), 12.64 (brs, 1H).

Step C tert-butyl[1-(2,2-difluoroethyl)-7-methyl-2-oxo-1,2,3,4-tetrahydroquinolin-6-yl]carbamate Using the compound (4.30 g, 16.0 mmol) of step B and according to the method of Reference Example 112, step A, the title compound (2.38 g, yield 44%) was obtained as a pale-yellow oil.
$^1$H-NMR (400 MHz, CDCl$_3$); δ (ppm) 1.53 (s, 9H), 2.26 (s, 3H), 2.62-2.68 (m, 2H), 2.86-2.92 (m, 2H), 4.21 (dt, J=4.5, 14, 2H), 6.09 (tt, J=4.5, 56, 1H), 6.20 (brs, 1H), 6.90 (s, 1H), 7.66 (s, 1H).

Step D 6-amino-1-(2,2-difluoroethyl)-7-methyl-3,4-dihydroquinolin-2(1H)-one

The compound (2.29 g, 6.73 mmol) of step C was dissolved in dichloromethane (15 ml), 4N hydrochloric acid-dioxane solution (15 ml, 60 mmol) was added at room temperature, and the mixture was stirred at the same temperature for 2 hr. To the reaction mixture was added saturated aqueous sodium hydrogen carbonate, the mixture was extracted with ethyl acetate, and the organic layer was dried over saturated brine. The insoluble material was filtered off, and the solution was concentrated under reduced pressure to give the title compound (1.43 g, yield 88%) as a colorless solid.
$^1$H-NMR (400 MHz, CDCl$_3$); δ (ppm) 2.18 (s, 3H), 2.60-2.65 (m, 2H), 2.78-2.83 (m, 2H), 3.51 (brs, 2H), 4.19 (dt, J=4.7, 13, 2H), 6.09 (tt, J=4.7, 57, 1H), 6.50 (s, 1H), 6.82 (s, 1H).

Step E

N-[1-(2,2-difluoroethyl)-7-methyl-2-oxo-1,2,3,4-tetrahydroquinolin-6-yl]iminodiacetic acid Using the compound (1.42 g, 5.91 mmol) of step D and according to the methods of Reference Example 61, step C, and Reference Example 62, step B, the title compound (1.64 g, yield 79%) was obtained as a colorless solid.
$^1$H-NMR (400 MHz, DMSO-$d_6$); δ (ppm) 2.25 (s, 3H), 2.53-2.56 (m, 2H), 2.75-2.80 (m, 2H), 3.88 (s, 4H), 4.30 (dt, J=4.1, 14, 2H), 6.19 (tt, J=4.1, 53, 1H), 6.99 (s, 1H), 7.03 (s, 1H), 12.39 (brs, 2H).

Reference Example 146

N-[2-(2,2-difluoroethyl)-6-methyl-3-oxo-2,3-dihydro-1H-isoindol-5-yl]iminodiacetic acid

Step A

4-bromo-2-methylbenzoic acid ethyl ester

4-Bromo-2-methylbenzoic acid (9.97 g, 46.4 mmol) and concentrated sulfuric acid (1.0 ml) were dissolved in ethanol (170 ml), and the mixture was heated under reflux for 33 hr. The reaction mixture was concentrated under reduced pressure, and the residue was diluted with an ethyl acetate-hexane=1:1 mixed solvent, washed with water, saturated aqueous sodium hydrogen carbonate and saturated brine, and dried over anhydrous magnesium sulfate. The insoluble material was filtered off, and the solution was concentrated under reduced pressure to give the title compound (10.5 g, yield 93%) as a colorless oil.

$^1$H-NMR (400 MHz, CDCl$_3$); δ (ppm) 1.39 (t, J=7.1, 3H), 2.58 (s, 3H), 4.35 (q, J=7.1, 2H), 7.38 (dd, J=1.8, 8.4, 1H), 7.41 (d, J=1.8, 1H), 7.78 (d, J=8.4, 1H).

Step B

5-bromo-2-(2,2-difluoroethyl)isoindolin-1-one

To carbon tetrachloride (160 ml) were added the compound (10.5 g, 43.2 mmol) of step A, N-bromosuccinimide (8.08 g, 45.4 mmol) and benzoyl peroxide (724 mg), and the mixture was heated under reflux for 50 min. The reaction mixture was cooled and diluted with hexane, the insoluble material was filtered off, and the obtained solution was concentrated under reduced pressure. The obtained oil (18.0 g) was dissolved in N,N-dimethylformamide (180 ml), 2,2-difluoroethylamine (5.99 g, 73.9 mmol) and triethylamine (12.0 ml, 86.1 mmol) were added, and the mixture was stirred at room temperature for 14 hr. The reaction mixture was diluted with an ethyl acetate-hexane=1:1 mixed solvent, washed with water, 10% aqueous citric acid solution, saturated aqueous sodium hydrogen carbonate and saturated brine, and dried over anhydrous magnesium sulfate. The insoluble material was filtered off, and the solution was concentrated under reduced pressure. The obtained oil was purified by silica gel column chromatography (ethyl acetate-hexane) to give the title compound (5.80 g, yield 49%) as a colorless oil.

$^1$H-NMR (400 MHz, CDCl$_3$); δ (ppm) 3.96 (dt, J=4.2, 15, 2H), 4.53 (s, 2H), 5.99 (tt, J=4.2, 56, 1H), 7.63 (d, J=8.7, 1H), 7.64 (s, 1H), 7.74 (d, J=8.7, 1H).

Step C

2-(2,2-difluoroethyl)-5-methylisoindolin-1-one

The compound (5.77 g, 20.9 mmol) of step B, trimethylboroxine (3.00 ml, 21.6 mmol), bis(tricyclohexylphosphine)palladium(II) dichloride (1.53 g, 2.07 mmol) and 1.27 mol/l aqueous potassium phosphate solution (50 ml, 63.5 mmol) were added to 1,4-dioxane (200 ml), and the mixture was heated under reflux for 110 min. The reaction mixture was cooled to room temperature, and concentrated under reduced pressure. The residue was diluted with ethyl acetate, and the organic layer was washed with saturated brine, and dried over anhydrous magnesium sulfate. The insoluble material was filtered off, and the solution was concentrated under reduced pressure. The obtained oil was purified by silica gel column chromatography (NH silica gel use, ethyl acetate-hexane) to give the title compound (4.39 g, yield 99%) as a pale-yellow solid.

$^1$H-NMR (400 MHz, CDCl$_3$); δ (ppm) 2.47 (s, 3H), 3.95 (dt, J=4.2, 15, 2H), 4.49 (s, 2H), 5.98 (tt, J=4.2, 56, 1H), 7.26 (s, 1H), 7.29 (d, J=7.8, 1H), 7.75 (d, J=7.8, 1H).

Step D

6-amino-2-(2,2-difluoroethyl)-5-methylisoindolin-1-one

The compound (4.31 g, 20.4 mmol) of step C was dissolved in concentrated sulfuric acid (40 ml), 70% nitric acid (d=1.42) (1.50 ml, 23.7 mmol) was added dropwise over 5 min under ice-cooling with stirring, and the mixture was stirred at the same temperature for 1 hr. The reaction mixture was poured into ice water, and extracted with ethyl acetate. The organic layer was washed with saturated aqueous sodium hydrogen carbonate and saturated brine, and dried over anhydrous magnesium sulfate. The insoluble material was filtered off, and the solution was concentrated under reduced pressure. The obtained oil was purified by silica gel column chromatography (ethyl acetate-hexane) to give a colorless solid (4.79 g). This was dissolved in methanol (150 ml), then ferric chloride (FeCl$_3$) (733 mg, 4.52 mmol) and activated carbon (1.6 g) were added, and the mixture was stirred at room temperature. Hydrazine (monohydrate 5.0 ml) was added, and the mixture was heated under reflux for 30 min. The reaction mixture was cooled and filtered through celite, and concentrated under reduced pressure. The obtained oil was purified by silica gel column chromatography (ethyl acetate-hexane) to give the title compound (3.36 g, yield 73%) as a colorless solid.

$^1$H-NMR (400 MHz, CDCl$_3$); δ (ppm) 2.25 (s, 3H), 3.78 (brs, 2H), 3.93 (dt, J=4.2, 15, 2H), 4.40 (s, 2H), 5.97 (tt, J=4.2, 56, 1H), 7.12 (s, 1H), 7.13 (s, 1H).

Step E

N-[2-(2,2-difluoroethyl)-6-methyl-3-oxo-2,3-dihydro-1H-isoindol-5-yl]iminodiacetic acid Using the compound (3.36 g, 14.8 mmol) of step D and according to the methods of Reference Example 61, step C, and Reference Example 62, step B, the title compound (4.57 g, yield 90%) was obtained as a colorless solid.

$^1$H-NMR (400 MHz, DMSO-d$_6$); δ (ppm) 2.36 (s, 3H), 3.93 (dt, J=3.6, 16, 2H), 3.96 (s, 4H), 4.46 (s, 2H), 6.26 (tt, J=3.6, 55, 1H), 7.38 (s, 1H), 7.41 (s, 1H), 12.47 (brs, 2H).

Reference Example 147

N-(2-ethyl-6-methyl-3-oxo-2,3-dihydro-1H-isoindol-5-yl)iminodiacetic acid

Step A

5-bromo-2-ethylisoindolin-1-one

Using the compound (7.83 g, 32.2 mmol) of Reference Example 146, step A, and 70% aqueous ethylamine solution (4.0 ml), and according to the method of Reference Example 146, step B, the title compound (2.37 g, yield 31%) was obtained as a colorless solid.

$^1$H-NMR (400 MHz, CDCl$_3$); δ (ppm) 1.27 (t, J=7.2, 3H), 3.67 (q, J=7.2, 2H), 4.37 (s, 2H), 7.59 (dd, J=1.6, 8.3, 1H), 7.61 (d, J=1.6, 1H), 7.70 (d, J=8.3, 1H).

Step B 2-ethyl-5-methylisoindolin-1-one

Using the compound (2.32 g, 10.5 mmol) of step A and according to the method of Reference Example 146, step C, the title compound (1.71 g, yield 93%) was obtained as a pale-yellow solid.
$^1$H-NMR (400 MHz, CDCl$_3$); δ (ppm) 1.26 (t, J=7.2, 3H), 2.45 (s, 3H), 3.66 (q, J=7.2, 2H), 4.33 (s, 2H), 7.26 (d, J=7.7, 1H), 7.27 (s, 1H), 7.72 (d, J=7.7, 1H).

Step C 6-amino-2-ethyl-5-methylisoindolin-1-one

Using the compound (1.68 g, 9.59 mmol) of step B and according to the method of Reference Example 146, step D, the title compound (572 mg, yield 31%) was obtained as a colorless solid.
$^1$H-NMR (400 MHz, CDCl$_3$); δ (ppm) 1.24 (t, J=7.2, 3H), 2.25 (s, 3H), 3.64 (q, J=7.2, 2H), 3.74 (brs, 2H), 4.25 (s, 2H), 7.11 (s, 2H).

Step D

N-(2-ethyl-6-methyl-3-oxo-2,3-dihydro-1H-isoindol-5-yl)iminodiacetic acid

Using the compound (557 mg, 2.93 mmol) of step C and according to the methods of Reference Example 61, step C, and Reference Example 62, step B, the title compound (682 mg, yield 76%) was obtained as a colorless solid.
$^1$H-NMR (400 MHz, DMSO-d$_6$); δ (ppm) 1.14 (t, J=7.2, 3H), 2.35 (s, 3H), 3.50 (q, J=7.2, 2H), 3.95 (s, 4H), 4.34 (s, 2H), 7.34 (s, 1H), 7.36 (s, 1H), 12.45 (brs, 2H).

Reference Example 148

N-(2-methyl-8,9,10,11-tetrahydro-7H-azepino[1,2-b]indazol-3-yl)iminodiacetic acid Step A 3-iodo-5-methyl-1-(tetrahydro-2H-pyran-2-yl)-1H-indazol-6-amine Using the compound (32.3 g, 83.4 mmol) of Reference Example 137, step A and according to the method of Reference Example 61, step B, the title compound (24.5 g, yield 82%) was obtained as a colorless solid.
$^1$H-NMR (400 MHz, CDCl$_3$); δ (ppm) 1.6-1.8 (m, 3H), 1.98-2.06 (m, 1H), 2.07-2.18 (m, 1H), 2.27 (s, 3H), 2.47-2.57 (m, 1H), 3.65-3.74 (m, 1H), 3.90 (brs, 2H), 3.98-4.06 (m, 1H), 5.52 (dd, J=3.1, 9.2, 1H), 6.72 (s, 1H), 7.10 (s, 1H).

Step B

N-[3-iodo-5-methyl-1-(tetrahydro-2H-pyran-2-yl)-1H-indazol-6-yl]glycine diethyl ester Using the compound (24.5 g, 68.6 mmol) of step A and according to the method of Reference Example 61, step C, the title compound (37.9 g) was obtained as a yellow oil.
$^1$H-NMR (400 MHz, CDCl$_3$); δ (ppm) 1.23 (t, J=7.2, 6H), 1.6-1.8 (m, 3H), 1.97-2.05 (m, 1H), 2.08-2.17 (m, 1H), 2.44 (s, 3H), 2.48-2.60 (m, 1H), 3.68-3.76 (m, 1H), 3.98-4.05 (m, 1H), 4.11 (s, 4H), 4.14 (q, J=7.2, 4H), 5.59 (dd, J=3.1, 9.7, 1H), 7.22 (s, 1H), 7.33 (s, 1H).

Step C

N-[3-(5-chloropentyl)-5-methyl-1-(tetrahydro-2H-pyran-2-yl)-1H-indazol-6-yl]glycine diethyl ester Using the compound (5.52 g, 10.4 mmol) of step B, and trans-5-chloro-1-penten-1-ylboronic acid pinacol ester (2.94 g, 12.8 mmol), and according to the methods of Reference Example 137, step B, and Reference Example 141, step B, the title compound (2.35 g, yield 44%) was obtained as a pale-yellow oil.
$^1$H-NMR (400 MHz, CDCl$_3$); δ (ppm) 1.24 (t, J=7.2, 6H), 1.5-1.7 (m. 3H), 1.7-1.9 (m, 6H), 1.93-2.01 (m, 1H), 2.06-2.17 (m, 1H), 2.43 (s, 3H), 2.47-2.57 (m, 1H), 2.90 (t, J=7.7, 2H), 3.53 (t, J=6.6, 2H), 3.68-3.77 (m, 1H), 4.03-4.08 (m, 1H), 4.11 (s, 4H), 4.14 (q, J=7.2, 4H), 5.54 (dd, J=2.6, 9.7, 1H), 7.30 (s, 1H), 7.41 (s, 1H).

Step D

N-[3-(5-chloropentyl)-5-methyl-1H-indazol-6-yl]glycine diethyl ester

Using the compound (2.33 g, 4.59 mmol) of step C and according to the method of Reference Example 137, step E, the title compound (1.80 g, yield 93%) was obtained as a colorless oil.
$^1$H-NMR (400 MHz, CDCl$_3$); δ (ppm) 1.22 (t, J=7.2, 6H), 1.5-1.6 (m, 2H), 1.78-1.89 (m, 4H), 2.44 (s, 3H), 2.93 (t, J=7.7, 2H), 3.54 (t, J=6.6, 2H), 4.10 (s, 4H), 4.13 (q, J=7.2, 4H), 7.28 (s, 1H), 7.45 (s, 1H), 9.57 (brs, 1H).

Step E

N-(2-methyl-8,9,10,11-tetrahydro-7H-azepino[1,2-b]indazol-3-yl)iminodiacetic acid diethyl ester The compound (1.78 g, 4.20 mmol) of step D was dissolved in N,N-dimethylformamide (120 ml), 60% sodium hydride (206 mg, 5.15 mmol) was added under ice-cooling with stirring, and the mixture was stirred at room temperature for 3 hr. The reaction mixture was diluted with an ethyl acetate-hexane=1:1 mixed solvent of, and the organic layer was washed with water and saturated brine, and dried over anhydrous magnesium sulfate. The insoluble material was filtered off, and the solution was concentrated under reduced pressure. The obtained oil was purified by silica gel column chromatography (ethyl acetate-hexane) to give the title compound (1.31 g, yield 80%) as an orange oil.
$^1$H-NMR (400 MHz, CDCl$_3$); δ (ppm) 1.23 (t, J=7.2, 6H), 1.69-1.78 (m, 2H), 1.81-1.89 (m, 2H), 1.89-1.98 (m, 2H), 2.41 (s, 3H), 3.01-3.05 (m, 2H), 4.07 (s, 4H), 4.13 (q, J=7.2, 4H), 4.46-4.52 (m, 2H), 7.30 (s, 1H), 7.36 (s, 1H).

Step F

N-(2-methyl-8,9,10,11-tetrahydro-7H-azepino[1,2-b]indazol-3-yl)iminodiacetic acid Using the compound (1.30 g, 3.36 mmol) of step E and according to the method of Reference Example 62, step B, the title compound (847 mg, yield 76%) was obtained as a pale-yellow solid.

$^1$H-NMR (400 MHz, DMSO-d$_6$); δ (ppm) 1.55-1.66 (m, 2H), 1.66-1.76 (m, 2H), 1.82-1.94 (m, 2H), 2.30 (s, 3H), 3.01-3.06 (m, 2H), 3.93 (s, 4H), 4.41-4.44 (m, 2H), 7.10 (s, 1H), 7.36 (s, 1H), 12.40 (brs, 2H).

Reference Example 149

N-(2-methyl-7,8,9,10-tetrahydropyrido[1,2-b]indazol-3-yl)iminodiacetic acid

Step A

N-<3-[4-{[tert-butyl(dimethyl)silyl]oxy}butyl]-5-methyl-1-(tetrahydro-2H-pyran-2-yl)-1H-indazol-6-yl>glycine diethyl ester Using the compound (7.19 g, 13.6 mmol) of Reference Example 148, step B, and trans-4-(tert-butyldimethylsiloxy)-1-buten-1-ylboronic acid pinacol ester (4.93 g, 15.8 mmol), and according to the methods of Reference Example 137, step B, and Reference Example 141, step B, the title compound (4.37 g, yield 54%) was obtained as a colorless oil.

$^1$H-NMR (400 MHz, CDCl$_3$); δ (ppm) 0.04 (s, 6H), 0.88 (s, 9H), 1.24 (t, J=7.2, 6H), 1.55-1.67 (m, 3H), 1.70-1.86 (m, 4H), 1.92-2.00 (m, 1H), 2.06-2.17 (m, 1H), 2.42 (s, 3H), 2.46-2.58 (m, 1H), 2.90 (t, J=7.7, 2H), 3.64 (t, J=6.4, 2H), 3.68-3.76 (m, 1H), 4.01-4.08 (m, 1H), 4.11 (s, 4H), 4.14 (q, J=7.2, 4H), 5.53 (dd, J=2.6, 9.9, 1H), 7.30 (s, 1H), 7.42 (s, 1H).

Step B

N-[3-(4-hydroxybutyl)-5-methyl-1-(tetrahydro-2H-pyran-2-yl)-1H-indazol-6-yl]glycine diethyl ester The compound (4.36 g, 7.39 mmol of step A was dissolved in tetrahydrofuran (60 ml), 1 mol/l tetrabutylammonium fluoride-tetrahydrofuran solution (9.0 ml) was added at room temperature with stirring, and the mixture was stirred at the same temperature for 22 hr. The reaction mixture was diluted with an ethyl acetate-hexane=1:1 mixed solvent, and the organic layer was washed with saturated brine, and dried over anhydrous magnesium sulfate. The insoluble material was filtered off, and the solution was concentrated under reduced pressure. The obtained oil was purified by silica gel column chromatography (ethyl acetate-hexane) to give the title compound (2.95 g, yield 84%) as a colorless oil.

$^1$H-NMR (400 MHz, CDCl$_3$); δ (ppm) 1.24 (t, J=7.2, 6H), 1.55-1.93 (m, 8H), 1.93-2.03 (m, 1H), 2.06-2.17 (m, 1H), 2.43 (s, 3H), 2.45-2.57 (m, 1H), 2.94 (t, J=7.4, 2H), 3.65 (t, J=6.2, 2H), 3.68-3.77 (m, 1H), 4.03-4.08 (m, 1H), 4.11 (s, 4H), 4.14 (q, J=7.2, 4H), 5.53 (dd, J=2.6, 10.2, 1H), 7.30 (s, 1H), 7.42 (s, 1H).

Step C

N-[3-(4-chlorobutyl)-5-methyl-1-(tetrahydro-2H-pyran-2-yl)-1H-indazol-6-yl]glycine diethyl ester The compound (2.91 g, 6.12 mmol) of step B was dissolved in a dichloromethane (20 ml)-carbon tetrachloride (10 ml) mixed solvent, triphenylphosphine (2.55 g, 9.72 mmol) was added at room temperature, and the mixture was stirred with heating at 50° C. for 2 hr. The reaction mixture was concentrated, and the obtained oil was purified by silica gel column chromatography (ethyl acetate-hexane) to give the title compound (2.04 g, yield 67%) as a colorless oil.

$^1$H-NMR (400 MHz, CDCl$_3$); δ (ppm) 1.24 (t, J=7.2, 6H), 1.6-2.0 (m, 8H), 2.06-2.18 (m, 1H), 2.43 (s, 3H), 2.46-2.60 (m, 1H), 2.92 (t, J=7.7, 2H), 3.57 (t, J=6.4, 2H), 3.67-3.77 (m, 1H), 4.01-4.08 (m, 1H), 4.11 (s, 4H), 4.14 (q, J=7.2, 4H), 5.54 (dd, J=2.6, 9.8, 1H), 7.30 (s, 1H), 7.41 (s, 1H).

Step D

N-(2-methyl-7,8,9,10-tetrahydropyrido[1,2-b]indazol-3-yl)iminodiacetic acid diethyl ester Using the compound (2.02 g, 4.09 mmol) of step C and according to the methods of Reference Example 148, steps D and E, the title compound (1.26 g, yield 82%) was obtained as an orange oil.

$^1$H-NMR (400 MHz, CDCl$_3$); δ (ppm) 1.23 (t, J=7.2, 6H), 1.94-2.02 (m, 2H), 2.09-2.18 (m, 2H), 2.41 (s, 3H), 3.04 (t, J=6.4, 2H), 4.08 (s, 4H), 4.13 (q, J=7.2, 4H), 4.39 (t, J=5.6, 2H), 7.33 (s, 1H), 7.36 (s, 1H).

Step E

N-(2-methyl-7,8,9,10-tetrahydropyrido[1,2-b]indazol-3-yl)iminodiacetic acid

Using the compound (1.25 g, 3.35 mmol) of step D and according to the method of Reference Example 62, step B, the title compound (924 mg, yield 87%) was obtained as a colorless solid.

$^1$H-NMR (400 MHz, DMSO-d$_6$); δ (ppm) 1.64-1.95 (m, 2H), 1.97-2.08 (m, 2H), 2.30 (s, 3H), 2.96 (t, J=6.2, 2H), 3.93 (s, 4H), 4.27 (t, J=5.8, 2H), 7.10 (s, 1H), 7.34 (s, 1H), 12.40 (brs, 2H).

Reference Example 150

N-(8-methyl-2,3-dihydro-1H-pyrrolo[1,2-b]indazol-7-yl)iminodiacetic acid

Step A

N-[3-(3-hydroxypropyl)-5-methyl-1-(tetrahydro-2H-pyran-2-yl)-1H-indazol-6-yl]glycine diethyl ester Using the compound (9.50 g, 17.9 mmol) of Reference Example 148, step B, and trans-2-chloromethylvinylboronic acid (4.93 g, 15.8 mmol), and according to the methods of Reference Example 137, step B, and Reference Example 141, step B, the title compound (584 mg, yield 7%) was obtained as a yellow oil.

$^1$H-NMR (400 MHz, CDCl$_3$); δ (ppm) 1.24 (t, J=7.2, 6H), 1.55-1.85 (m, 3H), 1.95-2.20 (m, 4H), 2.42 (s, 3H), 2.45-2.55 (m, 1H), 3.03 (t, J=7.0, 2H), 3.65-3.80 (m, 3H), 4.00-4.08 (m, 1H), 4.11 (s, 4H), 4.14 (q, J=7.2, 4H), 5.54 (dd, J=2.5, 9.7, 1H), 7.30 (s, 1H), 7.43 (s, 1H).

Step B

N-(8-methyl-2,3-dihydro-1H-pyrrolo[1,2-b]indazol-7-yl)iminodiacetic acid diethyl ester Using the compound (584 mg, 1.27 mmol) of step A and according to the methods of Reference Example 149, steps C and D, the title compound (302 mg, yield 66%) was obtained as a red-bistered oil.

¹H-NMR (400 MHz, CDCl₃); δ (ppm) 1.23 (t, J=7.2, 6H), 2.41 (s, 3H), 2.68-2.77 (m, 2H), 3.13 (t, J=7.2, 2H), 4.08 (s, 4H), 4.13 (q, J=7.2, 4H), 4.38 (t, J=7.2, 2H), 7.35 (s, 1H), 7.40 (s, 1H).

Step C

N-(8-methyl-2,3-dihydro-1H-pyrrolo[1,2-b]indazole-7-yl)iminodiacetic acid

Using the compound (291 mg, 0.810 mmol) of step B and according to the method of Reference Example 62, step B, the title compound (190 mg, yield 77%) was obtained as a colorless solid.

¹H-NMR (400 MHz, DMSO-d₆); δ (ppm) 2.30 (s, 3H), 2.60-2.69 (m, 2H), 3.07 (t, J=7.2, 2H), 3.93 (s, 4H), 4.29 (t, J=7.4, 2H), 7.15 (s, 1H), 7.35 (s, 1H), 12.41 (brs, 2H).

Reference Example 151

N-{5-[4-(aminocarbonyl)-1,3-thiazol-2-yl]-2-methylphenyl}iminodiacetic acid

Step A

2-{3-[bis(2-ethoxy-2-oxoethyl)amino]-4-methylphenyl}-1,3-thiazole-4-carboxylic acid To N,N-dimethylformamide (80 ml) were added the compound (7.93 g, 23.4 mmol) of Reference Example 79, step A, and 3-bromopyruvic acid (4.10 g, 24.6 mmol), and the mixture was stirred at 80° C. for 30 min. The reaction mixture was cooled, water was added, and the mixture was extracted with ethyl acetate. The organic layer was washed with saturated brine, and dried over anhydrous magnesium sulfate. The insoluble material was filtered off, and the solution was concentrated under reduced pressure. The obtained oil was purified by silica gel column chromatography (ethyl acetate-hexane) to give the title compound (9.19 g, yield 97%) as a brown oil.

¹H-NMR (400 MHz, DMSO-d₆); δ (ppm) 1.15 (t, J=7.2, 6H), 2.32 (s, 3H), 4.06 (q, J=7.2, 4H), 4.08 (s, 4H), 7.30 (d, J=8.2, 1H), 7.54 (dd, J=2.0, 8.2, 1H), 7.70 (d, J=2.0, 8.2, 1H), 8.45 (s, 1H), 13.11 (brs, 1H).

Step B

N-{5-[4-(aminocarbonyl)-1,3-thiazol-2-yl]-2-methylphenyl}iminodiacetic acid diethyl ester The compound (4.59 g, 11.3 mmol) of step A was dissolved in N,N-dimethylformamide (60 ml), 3H-[1,2,3]triazolo[4,5-b]pyridin-3-ol (1.97 g, 14.5 mmol) and WSC (2.80 g, 14.6 mmol) were added at room temperature, and the mixture was stirred at the same temperature for 70 min. Then, to the reaction mixture was added 28% aqueous ammonia (10 ml), and the mixture was further stirred at room temperature for 2 hr. The reaction mixture was diluted with ethyl acetate and water, and the organic layer was extracted. The organic layer was washed with saturated brine, dried over anhydrous magnesium sulfate, the insoluble material was filtered off, and the solution was concentrated under reduced pressure. The obtained solid was washed with a diethyl ether-hexane=1:1 mixed solvent, and dried under reduced pressure to give the title compound (4.23 g, yield 92%) as a colorless solid.

¹H-NMR (400 MHz, DMSO-d₆); δ (ppm) 1.15 (t, J=7.2, 6H), 2.32 (s, 3H), 4.06 (q, J=7.2, 4H), 4.08 (s, 4H), 7.29 (d, J=8.2, 1H), 7.61 (d, J=7.7, 1H), 7.68 (brs, 1H), 7.74 (s, 1H), 7.85 (brs, 1H), 8.23 (s, 1H).

Step C

N-{5-[4-(aminocarbonyl)-1,3-thiazol-2-yl]-2-methylphenyl}iminodiacetic acid

Using the compound (1.82 g, 4.49 mmol) of step B and according to the method of Reference Example 62, step B, the title compound (1.50 g, yield 96%) was obtained as a pale-yellow solid.

¹H-NMR (400 MHz, DMSO-d₆); δ (ppm) 2.31 (s, 3H), 3.17 (s, 3H), 4.00 (s, 4H), 7.28 (d, J=7.7, 1H), 7.58 (d, J=7.7, 1H), 7.69 (brs, 1H), 7.70 (s, 1H), 7.84 (brs, 1H), 8.23 (s, 1H), 12.53 (brs, 2H).

Reference Example 152

N-[2-methyl-5-{4-[(methylamino)carbonyl]-1,3-thiazol-2-yl}phenyl]iminodiacetic acid Using the compound (2.29 g, 5.63 mmol) of Reference Example 151, step A, and 40% aqueous methylamine solution (5.0 ml), and according to the methods of Reference Example 151, step B, and Reference Example 62, step B, the title compound (1.45 g, yield 71%) was obtained as a colorless solid.

¹H-NMR (400 MHz, DMSO-d₆); δ (ppm) 2.32 (s, 3H), 2.83 (d, J=5.1, 3H), 4.00 (s, 4H), 7.29 (d, J=7.7, 1H), 7.60 (d, J=7.7, 1H), 7.68 (s, 1H), 8.21 (s, 1H), 8.42 (broad q, 1H), 12.53 (brs, 2H).

Reference Example 153

N-[5-{4-[(dimethylamino)carbonyl]-1,3-thiazol-2-yl}-2-methylphenyl]iminodiacetic acid Using the compound (2.29 g, 5.63 mmol) of Reference Example 151, step A, and 50% aqueous dimethylamine solution (5.0 ml), and according to the methods of Reference Example 151, step B, and Reference Example 62, step B, the title compound (1.65 g, yield 78%) was obtained as a pale-yellow solid.

¹H-NMR (400 MHz, DMSO-d₆); δ (ppm) 2.30 (s, 3H), 3.02 (s, 3H), 3.17 (s, 3H), 3.99 (s, 4H), 7.27 (d, J=8.2, 1H), 7.49 (d, J=7.7, 1H), 7.66 (s, 1H), 8.05 (s, 1H), 12.54 (brs, 2H).

The compounds of Reference Examples 133-153 are shown below.

TABLE 6

| Reference Example | Structural Formula |
|---|---|
| 133 | 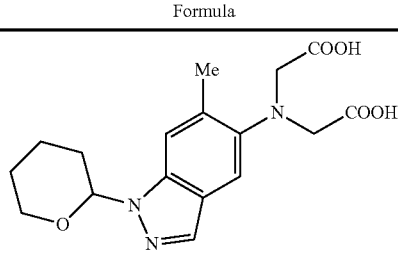 |

TABLE 6-continued

| Reference Example | Structural Formula |
|---|---|
| 134 | 5-Me, 6-N(CH2COOH)2, 1-(tetrahydropyran-2-yl)-1H-indazole |
| 135 | 3-I, 5-Me, 6-N(CH2COOH)2, 1-Me-1H-indazole |
| 136 | 1-Me, 3-I, 6-Me, 5-N(CH2COOH)2-1H-indazole |
| 137 | 3-Me, 5-Me, 6-N(CH2COOH)2, 2-Me-2H-indazole |
| 138 | 3-Me, 6-Me, 5-N(CH2COOH)2, 2-Et-2H-indazole |
| 139 | 3-Me, 5-Me, 6-N(CH2COOH)2, 1-Et-1H-indazole |
| 140 | 3-Me, 5-Me, 6-N(CH2COOH)2, 2-(2,2-difluoroethyl)-2H-indazole |
| 141 | 3-Et, 5-Me, 6-N(CH2COOH)2, 2-Me-2H-indazole |
| 142 | 3-Et, 5-Me, 6-N(CH2COOH)2, 1-Et-1H-indazole |
| 143 | 3-Et, 5-Me, 6-N(CH2COOH)2, 2-(2,2-difluoroethyl)-2H-indazole |

TABLE 6-continued
| Reference Example | Structural Formula |
|---|---|
| 144 | 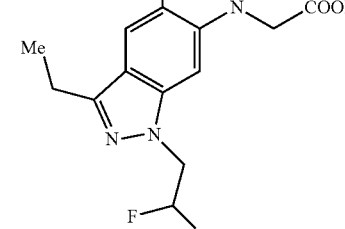 |
| 145 | 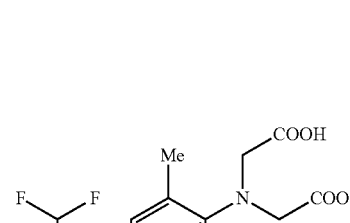 |
| 146 | 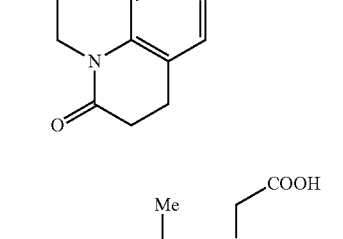 |
| 147 | 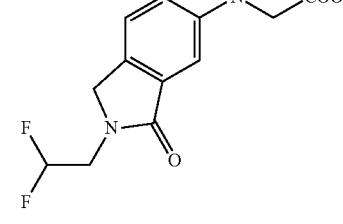 |
| 148 | 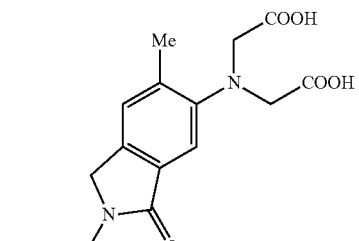 |
| 149 | 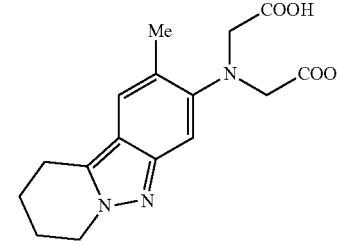 |
| 150 | 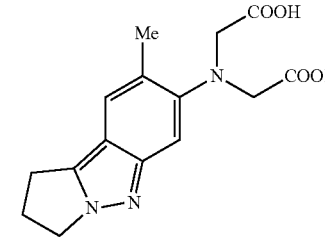 |
| 151 | 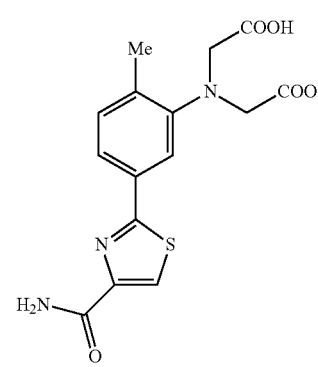 |
| 152 | 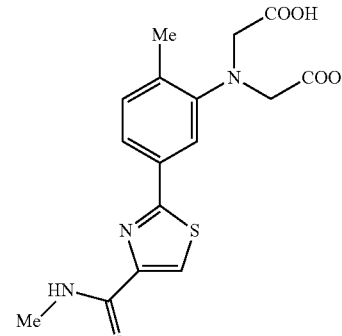 |
| 153 | 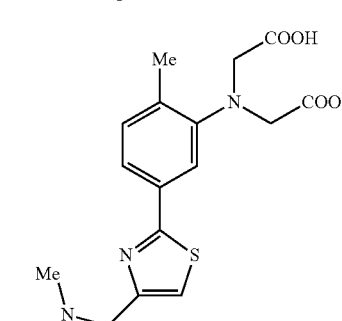 |

Example 1

N²-(5-cyano-2-methylphenyl)-N²-{2-[1,3-dihydro-2H-isoindol-2-yl(methyl)amino]-2-oxoethyl}-N¹-[2-(isopropylamino)ethyl]glycinamide dihydrochloride

Step A

N-(5-cyano-2-methylphenyl)-N-{2-[1,3-dihydro-2H-isoindol-2-yl(methyl)amino]-2-oxoethyl}glycine The compound (3.00 g, 12.1 mmol) of Reference Example 61 was dissolved in a dichloromethane (60 ml)-N,N-dimethylformamide (3 ml) mixed solvent, WSC (4.71 g, 24.6 mmol) was added at room temperature, and the mixture was stirred at the same temperature overnight. The reaction mixture was diluted with an ethyl acetate-hexane=1:1 mixed solvent, washed with water and saturated brine, and dried over anhydrous magnesium sulfate. The insoluble material was filtered off, and the reaction mixture was concentrated under reduced pressure. The obtained oil was dissolved in dichloromethane (100 ml), the compound of Reference Example 17 (3.00 g, 16.2 mmol) and 1,8-diazabicyclo[5.4.0]undeca-7-ene (4.8 ml, 32 mmol) were added under ice-cooling with stirring, and the mixture was stirred at room temperature for 7 hr. The reaction mixture was acidified with diluted hydrochloric acid, and the organic layer was extracted with dichloromethane, and dried over anhydrous magnesium sulfate. The insoluble material was filtered off, and the solution was concentrated under reduced pressure. The obtained oil was purified by silica gel column chromatography (chloroform) to give the title compound (3.38 g, yield 74%) as a pale-yellow amorphous solid.

$^1$H-NMR (300 MHz, CDCl$_3$); δ (ppm) 2.37 (s, 3H), 3.08 (s, 3H), 3.95 (s, 2H), 4.19 (d, J=11.7, 2H), 4.31 (d, J=11.7, 2H), 4.32 (s, 2H), 7.21-7.34 (m, 6H), 7.47 (d, J=1.1, 1H), 13.3 (brs, 1H).

Step B

N²-(5-cyano-2-methylphenyl)-N²-{2-[1,3-dihydro-2H-isoindol-2-yl(methyl)amino]-2-oxoethyl}-N¹-{2-[(tert-butoxycarbonyl)(isopropyl)amino]ethyl}glycinamide The compound (2.32 g, 6.13 mmol) obtained in step A, the compound of Reference Example 3 (1.67 g, 8.26 mmol) and 1-hydroxybenzotriazole (1.19 g, 8.81 mmol) were dissolved in an N,N-dimethylformamide (3 ml)-dichloromethane (40 ml) mixed solvent, WSC (1.80 g, 9.39 mmol) was added under ice-cooling, and the mixture was stirred at room temperature overnight. The reaction mixture was diluted with an ethyl acetate-hexane=1:1 (250 ml) mixed solvent, washed with water, 10% aqueous citric acid solution, diluted aqueous sodium hydroxide solution and saturated brine, and dried over anhydrous magnesium sulfate. The insoluble material was filtered off, and the solution was concentrated under reduced pressure. The obtained solid was washed with a diethyl ether-hexane=1:1 mixed solvent, and dried under reduced pressure to give the title compound (2.81 g, yield 81%) as a colorless solid.

$^1$H-NMR (300 MHz, CDCl$_3$); δ (ppm) 1.11 (d, J=6.6, 6H), 1.43 (brs, 9H), 2.40 (s, 3H), 2.96 (s, 3H), 3.0-3.2 (m, 2H), 3.34-3.42 (m, 2H), 3.84 (s, 2H), 3.9-4.3 (broad, 1H), 4.15 (d, J=11.7, 2H), 4.24 (s, 2H), 4.27 (d, J=11.7, 2H), 7.19-7.33 (m, 6H), 7.50 (s, 1H), 7.8-8.5 (broad, 1H).

Step C

N²-(5-cyano-2-methylphenyl)-N²-{2-[1,3-dihydro-2H-isoindol-2-yl(methyl)amino]-2-oxoethyl}-N¹-[2-(isopropylamino)ethyl]glycinamide dihydrochloride The compound (2.81 g, 4.99 mmol) obtained in step B was dissolved in dichloromethane (15 ml), 4N hydrochloric acid-dioxane solution (15 ml, 60 mmol) was added at room temperature, and the mixture was stirred at the same temperature for 2 hr. Diethyl ether was added to the reaction mixture, and the precipitated solid was collected by filtration, washed with diethyl ether, and dried under reduced pressure to give the title compound (2.60 g, yield 97%) as a colorless solid.

$^1$H-NMR (300 MHz, DMSO-d$_6$); δ (ppm) 1.18 (d, J=6.3, 6H), 2.33 (s, 3H), 2.8-3.0 (m, 2H), 2.89 (s, 3H), 3.1-3.4 (m, 3H), 3.90 (s, 2H), 4.13 (d, J=11.7, 2H), 4.26 (d, J=11.7, 2H), 4.30 (s, 2H), 7.25-7.35 (m, 6H), 7.45 (s, 1H), 8.27 (t, J=5.7, 1H), 8.60 (brs, 2H).

Example 2

N²-(5-cyano-2-methylphenyl)-N²-{2-[1,3-dihydro-2H-isoindol-2-yl(methyl)amino]-2-oxoethyl}-N¹-[2-(ethylamino)ethyl]glycinamide dihydrochloride

Step A

N²-(5-cyano-2-methylphenyl)-N²-{2-[1,3-dihydro-2H-isoindol-2-yl(methyl)amino]-2-oxoethyl}-N¹-{2-[(tert-butoxycarbonyl)(ethyl)amino]ethyl}glycinamide Using the compound (1.73 g, 4.57 mmol) of Example 1, step A, and the compound of Reference Example 2 (1.12 g, 5.95 mmol), and according to the method of Example 1, step B, the title compound (2.11 g, yield 84%) was obtained as a pale-yellow amorphous solid.

$^1$H-NMR (300 MHz, CDCl$_3$); δ (ppm) 1.05 (t, J=6.9, 3H), 1.41 (brs, 9H), 2.39 (s, 3H), 2.97 (s, 3H), 3.16 (q, J=6.9, 2H), 3.2-3.3 (m, 2H), 3.38-3.45 (m, 2H), 3.82 (s, 2H), 4.16 (d, J=11.7, 2H), 4.24 (s, 2H), 4.27 (d, J=11.7, 2H), 7.19-7.30 (m, 6H), 7.49 (s, 1H), 7.9-8.5 (broad, 1H).

Step B

N²-(5-cyano-2-methylphenyl)-N²-{2-[1,3-dihydro-2H-isoindol-2-yl(methyl)amino]-2-oxoethyl}-N¹-[2-(ethylamino)ethyl]glycinamide dihydrochloride Using the compound (469 mg, 0.855 mmol) obtained in step A and according to the method of Example 1, step C, the title compound (443 mg, yield 99%) was obtained as a colorless solid.

$^1$H-NMR (300 MHz, DMSO-d$_6$); δ (ppm) 1.17 (t, J=7.2, 3H), 2.34 (s, 3H), 2.8-3.0 (m, 4H), 2.88 (s, 3H), 3.34-3.41 (m, 2H), 3.90 (s, 2H), 4.14 (d, J=11.7, 2H), 4.26 (d, J=11.7, 2H), 4.32 (s, 2H), 7.23-7.34 (m, 6H), 7.45 (s, 1H), 8.32 (broad, 1H), 9.01 (brs, 2H).

Example 3

N²-(5-cyano-2-methylphenyl)-N²-{2-[(5-methoxy-1, 3-dihydro-2H-isoindol-2-yl)(methyl)amino]-2-oxoethyl}-N¹-[2-(isopropylamino)ethyl]glycinamide dihydrochloride

Step A

N-(5-cyano-2-methylphenyl)-N-{2-[(5-methoxy-1,3-dihydro-2H-isoindol-2-yl)(methyl)amino]-2-oxoethyl}glycine Using the compound (401 mg, 1.62 mmol) of Reference Example 61, and the compound (529 mg, 2.46 mmol) of Reference Example 20, and according to the method of Example 1, step A, the title compound (430 mg, yield 65%) was obtained as a pale-yellow amorphous solid.

$^1$H-NMR (300 MHz, CDCl$_3$); δ (ppm) 2.37 (s, 3H), 3.07 (s, 3H), 3.80 (s, 3H), 3.94 (s, 2H), 4.0-4.3 (m, 4H), 4.31 (s, 2H), 6.7-6.9 (m, 2H), 7.12 (d, J=8.4, 1H), 7.2-7.4 (m, 2H), 7.46 (s, 1H), 13.4 (brs, 1H).

Step B

N²-(5-cyano-2-methylphenyl)-N²-{2-[(5-methoxy-1, 3-dihydro-2H-isoindol-2-yl)(methyl)amino]-2-oxoethyl}-N¹-{2-[(tert-butoxycarbonyl)(isopropyl)amino]ethyl}glycinamide Using the compound (411 mg, 1.01 mmol) obtained in step A, and the compound (318 mg, 1.57 mmol) of Reference Example 3, and according to the method of Example 1, step B, the title compound (280 mg, yield 47%) was obtained as a colorless amorphous solid.

$^1$H-NMR (300 MHz, CDCl$_3$); δ (ppm) 1.11 (d, J=6.8, 6H), 1.43 (brs, 9H), 2.40 (s, 3H), 2.95 (s, 3H), 3.0-3.2 (m, 2H), 3.34-3.42 (m, 2H), 3.80 (s, 3H), 3.83 (s, 2H), 4.0-4.3 (m, 5H), 4.24 (s, 2H), 6.77 (d, J=2.1, 1H), 6.82 (dd, J=2.1, 8.3, 1H), 7.12 (d, J=8.3, 1H), 7.2-7.3 (m, 2H), 7.49 (s, 1H), 7.8-8.6 (broad, 1H).

Step C

N²-(5-cyano-2-methylphenyl)-N²-{2-[(5-methoxy-1, 3-dihydro-2H-isoindol-2-yl)(methyl)amino]-2-oxoethyl}-N¹-[2-(isopropylamino)ethyl]glycinamide dihydrochloride Using the compound (280 mg, 0.472 mmol) obtained in step B and according to the method of Example 1, step C, the title compound (214 mg, yield 80%) was obtained as a colorless solid.

$^1$H-NMR (300 MHz, DMSO-d$_6$); δ (ppm) 1.19 (d, J=6.5, 6H), 2.33 (s, 3H), 2.8-3.0 (m, 2H), 2.87 (s, 3H), 3.1-3.4 (m, 3H), 3.73 (s, 3H), 3.89 (s, 2H), 4.0-4.3 (m, 4H), 4.30 (s, 2H), 6.81 (dd, J=2.1, 8.3, 1H), 6.86 (d, J=2.1, 1H), 7.16 (d, J=8.3, 1H), 7.30 (broad, 2H), 7.45 (s, 1H), 8.27 (m, 1H), 8.68 (brs, 2H).

Example 4

N²-(5-cyano-2-methylphenyl)-N²-{2-[(5-fluoro-1,3-dihydro-2H-isoindol-2-yl)(methyl)amino]-2-oxoethyl}-N¹-[2-(isopropylamino)ethyl]glycinamide dihydrochloride

Step A

N-(5-cyano-2-methylphenyl)-N-{2-[(5-fluoro-1,3-dihydro-2H-isoindol-2-yl)(methyl)amino]-2-oxoethyl}glycine To an N,N-dimethylformamide (0.5 ml)-dichloromethane (20 ml) mixed solvent were added the compound (970 mg, 3.91 mmol) of Reference Example 61 and WSC (786 mg, 4.10 mmol), and the mixture was stirred at room temperature for 150 min. The reaction mixture was ice-cooled, the compound (1.05 g, 5.18 mmol) of Reference Example 19 and 1,8-diazabicyclo[5.4.0]undeca-7-ene (1.8 ml, 12 mmol) were added, and the mixture was stirred at room temperature for 7 hr. The reaction mixture was acidified with diluted hydrochloric acid, and the organic layer was extracted with dichloromethane, and dried over anhydrous magnesium sulfate. The insoluble material was filtered off, and the solution was concentrated under reduced pressure. The obtained oil was purified by silica gel column chromatography (methanol-dichloromethane) to give the title compound (946 mg, yield 61%) as a colorless amorphous solid.

$^1$H-NMR (300 MHz, DMSO-d$_6$); δ (ppm) 2.31 (s, 3H), 2.87 (s, 3H), 3.99 (s, 2H), 4.10-4.24 (m, 4H), 4.30 (s, 2H), 7.0-7.2 (m, 2H), 7.27-7.33 (m, 3H), 7.42 (s, 1H), 12.51 (brs, 1H).

Step B

N²-(5-cyano-2-methylphenyl)-N²-{2-[(5-fluoro-1,3-dihydro-2H-isoindol-2-yl)(methyl)amino]-2-oxoethyl}-N¹-{2-[(tert-butoxycarbonyl)(isopropyl)amino]ethyl}glycinamide Using the compound (944 mg, 2.38 mmol) obtained in step A, and the compound (665 mg, 3.29 mmol) of Reference Example 3, and according to the method of Example 1, step B, the title compound (1.28 g, yield 93%) was obtained as a colorless solid.

$^1$H-NMR (300 MHz, CDCl$_3$); δ (ppm) 1.11 (d, J=6.9, 6H), 1.43 (brs, 9H), 2.40 (s, 3H), 2.96 (s, 3H), 3.0-3.2 (m, 2H), 3.34-3.42 (m, 2H), 3.83 (s, 2H), 3.9-4.3 (m, 5H), 4.23 (s, 2H), 6.9-7.0 (m, 2H), 7.15-7.27 (m, 3H), 7.49 (s, 1H), 7.8-8.4 (broad, 1H).

Step C

N²-(5-cyano-2-methylphenyl)-N²-{2-[(5-fluoro-1,3-dihydro-2H-isoindol-2-yl)(methyl)amino]-2-oxoethyl}-N¹-[2-(isopropylamino)ethyl]glycinamide dihydrochloride Using the compound (422 mg, 0.727 mmol) obtained in step B and according to the method of Example 1, step C, the title compound (384 mg, yield 95%) was obtained as a colorless solid.

$^1$H-NMR (300 MHz, DMSO-d$_6$); δ (ppm) 1.19 (d, J=6.3, 6H), 2.34 (s, 3H), 2.8-3.0 (m, 2H), 2.88 (s, 3H), 3.1-3.5 (m, 3H), 3.89 (s, 2H), 4.0-4.3 (m, 4H), 4.30 (s, 2H), 7.0-7.2 (m, 2H), 7.27-7.33 (m, 3H), 7.45 (s, 1H), 8.27 (broad t, 1H), 8.73 (brs, 2H).

Example 5

$N^2$-(5-cyano-2-methylphenyl)-$N^2$-{2-[1,3-dihydro-2H-isoindol-2-yl(ethyl)amino]-2-oxoethyl}-$N^1$-[2-(ethylamino)ethyl]glycinamide dihydrochloride

Step A $N^2$-(5-cyano-2-methylphenyl)-$N^2$-{2-[1,3-dihydro-2H-isoindol-2-yl(ethyl)amino]-2-oxoethyl}glycine Using the compound (0.80 g, 3.22 mmol) of Reference Example 61, and the compound (0.96 g, 4.83 mmol) of Reference Example 22, and according to the method of Example 1, step A, the title compound (0.81 g, yield 64%) was obtained as a gray amorphous solid.
$^1$H-NMR (300 MHz, CDCl$_3$); δ (ppm) 1.36 (t, J=6.9, 3H), 2.36 (s, 3H), 3.59 (q, J=7.2, 2H), 3.97 (s, 2H), 4.19-4.35 (m, 6H), 7.20-7.30 (m, 6H), 7.45 (s, 1H).

Step B $N^2$-(5-cyano-2-methylphenyl)-$N^2$-{2-[1,3-dihydro-2H-isoindol-2-yl(ethyl)amino]-2-oxoethyl}-$N^1$-{2-[(tert-butoxycarbonyl)(ethyl)amino]ethyl}glycinamide Using the compound (0.40 g, 1.02 mmol) obtained in step A, and the compound (0.30 g, 1.59 mmol) of Reference Example 2, and according to the method of Example 1, step B, the title compound (0.42 g, yield 73%) was obtained as a colorless amorphous solid.
$^1$H-NMR (300 MHz, CDCl$_3$); δ (ppm) 1.05 (t, J=6.8, 3H), 1.29 (t, J=7.1, 3H), 1.42 (s, 9H), 2.39 (s, 3H), 3.14-3.29 (m, 4H), 3.40-3.53 (m, 4H), 3.83 (s, 2H), 4.15-4.32 (m, 6H), 7.24-7.30 (m, 6H), 7.48 (s, 1H), 8.12 8.20 (2brs, 1H).

Step C $N^2$-(5-cyano-2-methylphenyl)-$N^2$-{2-[1,3-dihydro-2H-isoindol-2-yl(ethyl)amino]-2-oxoethyl}-$N^1$-[2-(ethylamino)ethyl]glycinamide dihydrochloride Using the compound (0.42 g, 0.75 mmol) obtained in step B and according to the method of Example 1, step C, the title compound (0.30 g, yield 82%) was obtained as a colorless solid.
$^1$H-NMR (300 MHz, DMSO-d$_6$); δ (ppm) 1.06-1.21 (m, 6H), 2.33 (s, 3H), 2.8-3.1 (m, 4H), 3.3-3.5 (m, 4H), 3.91 (s, 2H), 4.08-4.28 (m, 6H), 7.20-7.48 (m, 7H), 8.29 (m, 1H), 8.79 (brs, 2H).

Example 6

$N^2$-(5-cyano-2-methylphenyl)-$N^2$-{2-[methyl (5-methyl-2,3-dihydro-1H-inden-2-yl)amino]-2-oxoethyl}-$N^1$-[2-(isopropylamino)ethyl]glycinamide hydrochloride

Step A

N-(5-cyano-2-methylphenyl)-N-{2-[methyl(5-methyl-2,3-dihydro-1H-inden-2-yl)amino]-2-oxoethyl}glycine Using the compound (1.27 g, 5.11 mmol) of Reference Example 61, and the compound (1.50 g, 7.67 mmol) of Reference Example 25, and according to the method of Example 4, step A, the title compound (1.20 g, yield. 60%) was obtained as a pale-bistered amorphous solid.
$^1$H-NMR (300 MHz, DMSO-d$_6$); δ (ppm) 2.26 (s, 3H), 2.32 (s, 3H), 2.64 (s, 1.2H), 2.74 (s, 1.8H), 2.74-3.08 (m, 4H), 3.94-3.96 (m, 2H), 4.09 (s, 1.2H), 4.23 (s, 0.8H), 4.82-4.86 (m, 0.4H), 5.25-5.28 (m, 0.6H), 6.95 (d, J=7.8, 1H), 7.02 (s, 1H), 7.09 (d, J=7.8, 1H), 7.29-7.36 (m, 2H), 7.47 (d, J=9.0, 1H), 12.62 (brs, 1H).

Step B $N^2$-(5-cyano-2-methylphenyl)-$N^2$-{2-[methyl(5-methyl-2,3-dihydro-1H-inden-2-yl)amino]-2-oxoethyl}-$N^1$-{2-[(tert-butoxycarbonyl)(isopropyl)amino]ethyl}glycinamide Using the compound (600 mg, 1.53 mmol) obtained in step A, and the compound (464 mg, 2.30 mmol) of Reference Example 3, and according to the method of Example 1, step B, the title compound (819 mg, yield 93%) was obtained as a colorless amorphous solid.
$^1$H-NMR (300 MHz, DMSO-d$_6$); δ (ppm) 1.03 (d, J=6.3, 6H), 1.39 (s, 9H), 2.26 (s, 3H), 2.34 (s, 3H), 2.50 (s, 1.2H), 2.66 (s, 1.8H), 2.66-3.22 (m, 8H), 3.79-3.81 (m, 2H), 3.89-4.20 (m, 1H), 4.08 (s, 1.2H), 4.23 (s, 0.8H), 4.76-4.84 (m, 0.4H), 5.25-5.33 (m, 0.6H), 6.95 (d, J=7.8, 1H), 7.02 (s, 1H), 7.08 (d, J=7.5, 1H), 7.28-7.35 (m, 2H), 7.48 (d, J=8.7, 1H), 8.12-8.18 (m, 1H).

Step C $N^2$-(5-cyano-2-methylphenyl)-$N^2$-{2-[methyl (5-methyl-2,3-dihydro-1H-inden-2-yl)amino]-2-oxoethyl}-$N^1$-[2-(isopropylamino)ethyl]glycinamide hydrochloride Using the compound (300 mg, 0.52 mmol) obtained in step B and according to the method of Example 1, step C, the title compound (212 mg, yield 80%) was obtained as a colorless amorphous solid.
$^1$H-NMR (300 MHz, DMSO-d$_6$); δ (ppm) 1.21 (d, J=6.3, 6H), 2.26 (s, 3H), 2.75 (s, 3H), 2.66 (s, 1.2H), 2.75 (s, 1.8H), 2.75-3.18 (m, 6H), 3.24-3.28 (m, 1H), 3.34-3.42 (m, 2H), 3.85-3.88 (m, 2H), 4.09 (s, 1.2H), 4.25 (s, 0.8H), 4.77-4.85 (m, 0.4H), 5.25-5.32 (m, 0.6H), 6.96 (d, J=7.5, 1H), 7.02 (s, 1H), 7.09 (d, J=7.5, 1H), 7.28-7.35 (m, 2H), 7.49 (d, J=9.0, 1H), 8.35-8.39 (m, 1H), 8.79 (brs, 2H).

Example 7

$N^2$-(5-cyano-2-methylphenyl)-$N^2$-{2-[methyl-(5-methyl-2,3-dihydro-1H-inden-2-yl)amino]-2-oxoethyl}-$N^1$-[2-(ethylamino)ethyl]glycinamide hydrochloride

Step A $N^2$-(5-cyano-2-methylphenyl)-$N^2$-{2-[methyl(5-methyl-2,3-dihydro-1H-inden-2-yl)amino]-2-oxoethyl}-$N^1$-{2-[(tert-butoxycarbonyl)(ethyl)amino]ethyl}glycinamide Using the compound (600 mg, 1.53 mmol) obtained in Example 6, step A, and the compound (432 mg, 2.30 mmol) of Reference Example 2, and according to the method of Example 1, step B, the title compound (819 mg, yield 95%) was obtained as a pale-yellow amorphous solid.

$^1$H-NMR (300 MHz, DMSO-d$_6$); δ (ppm) 0.96 (t, J=6.6, 3H), 1.37 (s, 9H), 2.25 (s, 3H), 2.34 (s, 3H), 2.65 (s, 1.2H), 2.74 (s, 1.8H), 2.74-3.20 (m, 10H), 3.77-3.81 (m, 2H), 4.07 (s, 1.2H), 4.23 (s, 0.8H), 4.76-4.84 (m, 0.4H), 5.23-5.32 (m, 0.6H), 6.95 (d, J=7.8, 1H), 7.02 (s, 1H), 7.09 (d, J=7.8, 1H), 7.28-7.34 (m, 2H), 7.47 (d, J=8.7, 1H), 8.10-8.13 (m, 1H).

Step B

N$^2$-(5-cyano-2-methylphenyl)-N$^2$-{2-[methyl(5-methyl-2,3-dihydro-1H-inden-2-yl)amino]-2-oxoethyl}-N$^1$-[2-(ethylamino)ethyl]glycinamide hydrochloride Using the compound (300 mg, 0.53 mmol) obtained in step A and according to the method of Example 1, step C, the title compound (242 mg, yield 92%) was obtained as a pale-yellow amorphous solid.

$^1$H-NMR (300 MHz, DMSO-d$_6$); δ (ppm) 1.18 (t, J=7.2, 3H), 2.26 (s, 3H), 2.35 (s, 3H), 2.58-3.17 (m, 8H), 2.66 (s, 1.2H), 2.75 (s, 1.8H), 3.34-3.41 (m, 2H), 3.84-3.88 (m, 2H), 4.10 (s, 1.2H), 4.25 (s, 0.8H), 4.78-4.85 (m, 0.4H), 5.25-5.32 (m, 0.6H), 6.96 (d, J=7.5, 1H), 7.03 (s, 1H), 7.09 (d, J=7.8, 1H), 7.29-7.35 (m, 2H), 7.49 (d, –J=9.0, 1H), 8.34-8.37 (m, 1H), 8.77-9.01 (broad, 2H).

Example 8

N$^2$-(5-cyano-2-methylphenyl)-N$^2$-{2-[methyl(5-methoxy-2,3-dihydro-1H-inden-2-yl)amino]-2-oxoethyl}-N$^1$-[2-(isopropylamino)ethyl]glycinamide hydrochloride Step A N-(5-cyano-2-methylphenyl)-N-{2-[methyl(5-methoxy-2,3-dihydro-1H-inden-2-yl)amino]-2-oxoethyl}glycine Using the compound (1.53 g, 6.17 mmol) of Reference Example 61, and the compound (1.98 g, 9.26 mmol) of Reference Example 29, and according to the method of Example 4, step A, the title compound (1.60 g, yield 64%) was obtained as a pale-bistered amorphous solid.

$^1$H-NMR (300 MHz, DMSO-d$_6$); δ (ppm) 2.33 (s, 3H), 2.51-3.10 (m, 7H), 3.71 (s, 3H), 3.94-3.96 (m, 2H), 4.09 (s, 1.2H), 4.23 (s, 0.8H), 4.83-4.86 (m, 0.4H), 5.24-5.31 (m, 0.6H), 6.71 (d, J=7.8, 1H), 6.80 (s, 1H), 7.10 (d, J=8.1, 1H), 7.29-7.33 (m, 2H), 7.45-7.50 (m, 1H), 12.60 (brs, 1H).

Step B

N$^2$-(5-cyano-2-methylphenyl)-N$^2$-{2-[methyl(5-methoxy-2,3-dihydro-1H-inden-2-yl)amino]-2-oxoethyl}-N$^1$-{2-[(tert-butoxycarbonyl)(isopropyl)amino]ethyl}glycinamide Using the compound (800 mg, 1.96 mmol) obtained in step A, and the compound (595 mg, 2.94 mmol) of Reference Example 3, and according to the method of Example 1, step B, the title compound (1.11 g, yield 96%) was obtained as a pale-yellow amorphous solid.

$^1$H-NMR (300 MHz, DMSO-d$_6$); δ (ppm) 1.03 (d, J=6.6, 6H), 1.37-1.41 (m, 9H), 2.34 (s, 3H), 2.60-3.22 (m, 12H), 3.71 (s, 3H), 3.79-3.81 (m, 2H), 4.08 (s, 1.2H), 4.23 (s, 0.8H), 4.77-4.85 (m, 0.4H), 5.26-5.34 (m, 0.6H), 6.71 (d, J=8.1, 1H), 6.80 (s, 1H), 7.10 (d, J=8.1, 1H), 7.28-7.34 (m, 2H), 7.47 (d, J=9.0, 1H), 8.14 (brs, 1H).

Step C

N$^2$-(5-cyano-2-methylphenyl)-N$^2$-{2-[methyl(5-methoxy-2,3-dihydro-1H-inden-2-yl)amino]-2-oxoethyl}-N$^1$-[2-(isopropylamino)ethyl]glycinamide hydrochloride Using the compound (500 mg, 0.84 mmol) obtained in step B and according to the method of Example 1, step C, the title compound (386 mg, yield 87%) was obtained as a colorless amorphous solid.

$^1$H-NMR (300 MHz, DMSO-d$_6$); δ (ppm) 1.21 (d, J=6.6, 6H), 2.35 (s, 3H), 2.66 (s, 1.2H), 2.76 (s, 1.8H), 2.76-3.17 (m, 6H), 3.20-3.43 (m, 3H), 3.71 (s, 3H), 3.84-3.88 (m, 2H), 4.10 (s, 1.2H), 4.26 (s, 0.8H), 4.79-4.85 (m, 0.4H), 5.26-5.30 (m, 0.6H), 6.71 (d, J=8.2, 1H), 6.80 (s, 1H), 7.10 (d, J=8.2, 1H), 7.29-7.35 (m, 2H), 7.47-7.51 (m, 1H), 8.37-8.40 (m, 1H), 8.89 (brs, 2H).

Example 9

N$^2$-(5-cyano-2-methylphenyl)-N$^2$-{2-[methyl(5-methoxy-2,3-dihydro-1H-inden-2-yl)amino]-2-oxoethyl}-N$^1$-[2-(ethylamino)ethyl]glycinamide hydrochloride Step A N$^2$-(5-cyano-2-methylphenyl)-N$^2$-{2-[methyl(5-methoxy-2,3-dihydro-1H-inden-2-yl)amino]-2-oxoethyl}-N$^1$-{2-[(tert-butoxycarbonyl)(ethyl)amino]ethyl}glycinamide Using the compound (800 mg, 1.96 mmol) obtained in Example 8, step A, and the compound (554 mg, 2.94 mmol) of Reference Example 2, and according to the method of Example 1, step B, the title compound (1.10 g, yield 97%) was obtained as a pale-yellow amorphous solid.

$^1$H-NMR (300 MHz, DMSO-d$_6$); δ (ppm) 0.94-0.99 (m, 3H), 1.36-1.39 (m, 9H), 2.33 (s, 3H), 2.65-3.24 (m, 13H), 3.71 (s, 3H), 3.79 3.80 (2s, 2H), 4.07 (s, 1.2H), 4.23 (s, 0.8H), 4.77-4.83 (m, 0.4H), 5.27-5.33 (m, 0.6H), 6.71 (d, J=8.4, 1H), 6.80 (s, 1H), 7.10 (d, J=8.1, 1H), 7.28-7.35 (m, 2H), 7.47 (d, J=9.0, 1H), 8.11 (brs, 1H).

Step B

N$^2$-(5-cyano-2-methylphenyl)-N$^2$-{2-[methyl(5-methoxy-2,3-dihydro-1H-inden-2-yl)amino]-2-oxoethyl}-N$^1$-[2-(ethylamino)ethyl]glycinamide hydrochloride Using the compound (500 mg, 0.87 mmol) obtained in step A and according to the method of Example 1, step C, the title compound (409 mg, yield 91%) was obtained as a colorless amorphous solid.

$^1$H-NMR (300 MHz, DMSO-d$_6$); δ (ppm) 1.18 (t, J=7.2, 3H), 2.35 (s, 3H), 2.57-3.19 (m, 11H), 3.34-3.41 (m, 2H), 3.71 (s, 3H), 3.85-3.88 (m, 2H), 4.10 (s, 1.2H), 4.26 (s, 0.6H), 4.79-4.86 (m, 0.4H), 5.26-5.30 (m, 0.6H), 6.72 (d, J=8.4, 1H), 6.80 (s, 1H), 7.10 (d, J=8.1, 1H), 7.28-735 (m, 2H), 7.47-7.51 (m, 1H), 8.35-8.37 (m, 1H), 8.89 (brs, 2H).

Example 10

N²-(5-cyano-2-methylphenyl)-N²-{2-[(5-fluoro-2,3-dihydro-1H-inden-2-yl)(methyl)amino]-2-oxoethyl}-N¹-[2-(isopropylamino)ethyl]glycinamide hydrochloride

Step A

N²-(5-cyano-2-methylphenyl)-N²-{2-[(5-fluoro-2,3-dihydro-1H-inden-2-yl)(methyl)amino]-2-oxoethyl}-N¹-{2-[(tert-butoxycarbonyl)(isopropyl)amino]ethyl}glycinamide Using the compound (870 mg, 3.50 mmol) of Reference Example 61, the compound (1.06 g, 5.26 mmol) of Reference Example 27, and the compound (756 mg, 3.74 mmol) of Reference Example 3, and according to the methods of Example 4, step A, and Example 1, step B, the title compound (1.40 g, yield 69%) was obtained as a pale-yellow amorphous solid.

$^1$H-NMR (300 MHz, CDCl$_3$); δ (ppm) 1.03 (d, J=6.6, 6H), 1.38 (s, 9H), 2.34 (s, 3H), 2.64-3.18 (m, 11H), 3.78-3.81 (m, 2H), 3.89-4.20 (m, 1H), 4.09 (s, 1.2H), 4.24 (s, 0.8H), 4.82-4.89 (m, 0.4H), 5.27-5.34 (m, 0.6H), 6.96 (t, J=8.7, 1H), 7.05 (d, J=9.3, 1H), 7.19-7.25 (m, 1H), 7.28-7.34 (m, 2H), 7.48 (d, J=9.9, 1H), 8.09-8.14 (m, 1H).

Step B

N²-(5-cyano-2-methylphenyl)-N²-{2-[(5-fluoro-2,3-dihydro-1H-inden-2-yl)(methyl)amino]-2-oxoethyl}-N¹-[2-(isopropylamino)ethyl]glycinamide hydrochloride Using the compound (700 mg, 1.21 mmol) obtained in step A and according to the method of Example 1, step C, the title compound (609 mg, yield 97%) was obtained as a colorless amorphous solid.

$^1$H-NMR (300 MHz, DMSO-d$_6$); δ (ppm) 1.21 (d, J=6.3, 6H), 2.36 (s, 3H), 2.65-3.19 (m, 9H), 3.20-3.43 (m, 3H), 3.85-3.87 (m, 2H), 4.26 (s, 1.2H), 4.38 (s, 0.8H), 4.84-4.87 (m, 0.4H), 5.27-5.34 (m, 0.6H), 6.96 (t, J=8.7, 1H), 7.05 (d, J=9.1, 1H), 7.20-7.25 (m, 1H), 7.29-7.32 (m, 2H), 7.49 (d, J=10.2, 1H), 8.38 (t, J=5.6, 1H), 8.86 (brs, 2H).

Example 11

N²-{2-[(5-chloro-2,3-dihydro-1H-inden-2-yl)(methyl)amino]-2-oxoethyl}-N²-(5-cyano-2-methylphenyl)-N¹-[2-(isopropylamino)ethyl]glycinamide hydrochloride

Step A

N²-{2-[(5-chloro-2,3-dihydro-1H-inden-2-yl)(methyl)amino]-2-oxoethyl}-N²-(5-cyano-2-methylphenyl)-N¹-{2-[(tert-butoxycarbonyl)(isopropyl)amino]ethyl}glycinamide Using the compound (1.36 g, 5.48 mmol) of Reference Example 61, the compound (1.79 g, 8.21 mmol) of Reference Example 28, and the compound (1.07 g, 5.28 mmol) of Reference Example 3, and according to the methods of Example 4, step A, and Example 1, step B, the title compound (2.00 g, yield 61%) was obtained as a bistered amorphous solid.

$^1$H-NMR (300 MHz, CDCl$_3$); δ (ppm) 1.03 (d, J=6.5, 6H), 1.39 (s, 9H), 2.34 (s, 3H), 2.65-2.77 (m, 3H), 2.80-3.19 (m, 8H), 3.79-3.81 (m, 2H), 3.89-4.20 (m, 1H), 4.09 (s, 1.2H), 4.23 (s, 0.8H), 4.83-4.90 (m, 0.4H), 5.26-5.34 (m, 0.6H), 7.16-7.34 (m, 5H), 7.46-7.50 (m, 1H), 8.11-8.13 (m, 1H).

Step B

N²-{2-[(5-chloro-2,3-dihydro-1H-inden-2-yl)(methyl)amino]-2-oxoethyl}-N²-(5-cyano-2-methylphenyl)-N¹-[2-(isopropylamino)ethyl]glycinamide hydrochloride Using the compound (1.00 g, 1.68 mmol) obtained in step A and according to the method of Example 1, step C, the title compound (853 mg, yield 95%) was obtained as a pale-yellow amorphous solid.

$^1$H-NMR (300 MHz, DMSO-d$_6$); δ (ppm) 1.21 (d, J=6.6, 6H), 2.35 (s, 3H), 2.66-2.76 (m, 3H), 2.84-3.19 (m, 6H), 3.21-3.45 (m, 3H), 3.84-3.87 (m, 2H), 4.10 (s, 1.2H), 4.25 (s, 0.8H), 4.82-4.87 (m, 0.4H), 5.26-5.35 (m, 0.6H), 7.16-7.36 (m, 5H), 7.47-7.51 (m, 1H), 8.32-8.36 (m, 1H), 8.73 (brs, 2H).

Example 12

N²-(5-cyano-2-methylphenyl)-N²-{2-[methyl(4-methyl-2,3-dihydro-1H-inden-2-yl)amino]-2-oxoethyl}-N¹-[2-(isopropylamino)ethyl]glycinamide hydrochloride

Step A

N²-(5-cyano-2-methylphenyl)-N²-{2-[methyl(4-methyl-2,3-dihydro-1H-inden-2-yl)amino]-2-oxoethyl}-N¹-{2-[(tert-butoxycarbonyl)(isopropyl)amino]ethyl}glycinamide Using the compound (1.55 g, 6.24 mmol) of Reference Example 61, the compound (1.85 g, 9.36 mmol) of Reference Example 26, and the compound (1.32 g, 6.51 mmol) of Reference Example 3, and according to the methods of Example 4, step A, and Example 1, step B, the title compound (2.52 g, yield 70%) was obtained as a bistered oil.

$^1$H-NMR (300 MHz, CDCl$_3$); δ (ppm) 1.03 (d, J=6.6, 6H), 1.39 (s, 9H), 2.19 (s, 3H), 2.35 (s, 3H), 2.58-3.21 (m, 11H), 3.79-3.82 (m, 2H), 3.90-4.19 (m, 1H), 4.09 (s, 1.2H), 4.25 (s, 0.8H), 4.80-4.86 (m, 0.4H), 5.28-5.35 (m, 0.6H), 6.94-7.08 (m, 3H), 7.28-7.35 (m, 2H), 7.46-7.51 (m, 1H), 8.13-8.15 (m, 1H).

Step B

N²-(5-cyano-2-methylphenyl)-N²-{2-[methyl(4-methyl-2,3-dihydro-1H-inden-2-yl)amino]-2-oxoethyl}-N³-[2-(isopropylamino)ethyl]glycinamide hydrochloride Using the compound (1.25 g, 2.17 mmol) obtained in step A and according to the method of Example 1, step C, the title compound (1.04 g, yield 94%) was obtained as a pale-yellow amorphous solid.

$^1$H-NMR (300 MHz, DMSO-d$_6$); δ (ppm) 1.22 (d, J=6.4, 6H), 2.19 (s, 3H), 2.36 (s, 3H), 2.60-3.48 (m, 12H), 3.86-3.89 (m, 2H), 4.12 (s, 1.2H), 4.28 (s, 0.8H), 4.81-4.88 (m, 0.4H), 5.27-5.34 (m, 0.6H), 6.94-7.08 (m, 3H), 7.28-7.32 (m, 2H), 7.47-7.52 (m, 1H), 8.42-8.45 (m, 1H), 9.06 (brs, 2H).

Example 13

$N^2$-(5-cyano-2-methylphenyl)-$N^2$-{2-[methyl(1,2,3,4-tetrahydronaphthalen-2-yl)amino]-2-oxoethyl}-$N^1$-[2-(isopropylamino)ethyl]glycinamide hydrochloride

Step A

N-(5-cyano-2-methylphenyl)-N-{2-[methyl(1,2,3,4-tetrahydronaphthalen-2-yl)amino]-2-oxoethyl}glycine Using the compound (1.00 g, 4.03 mmol) of Reference Example 61, and the compound (1.20 g, 6.05 mmol) of Reference Example 34, and according to the method of Example 4, step A, the title compound (1.02 g, yield 64%) was obtained as a colorless amorphous solid.

$^1$H-NMR (300 MHz, DMSO-$d_6$); δ (ppm) 1.65-1.98 (m, 2H), 2.29 2.34 (2s, 3H), 2.58-3.05 (m, 7H), 3.90 3.96 (2s, 2H), 4.10-4.80 (m, 3H), 7.08 (s, 4H), 7.30-7.33 (m, 2H), 7.48 (d, J=11.4, 1H), 12.62 (brs, 1H).

Step B $N^2$-(5-cyano-2-methylphenyl)-$N^2$-{2-[methyl(1,2,3,4-tetrahydronaphthalen-2-yl)amino]-2-oxoethyl}-$N^1$-{2-[(tert-butoxycarbonyl)(isopropyl)amino]ethyl}glycinamide Using the compound (1.02 g, 2.60 mmol) obtained in step A, and the compound (789 mg, 3.90 mmol) of Reference Example 3, and according to the method of Example 1, step B, the title compound (1.40 g, yield 93%) was obtained as a pale-yellow amorphous solid.

$^1$H-NMR (300 MHz, CDCl$_3$); δ (ppm) 2.21 (d, J=6.9, 6H), 1.43 (s, 9H), 1.75-2.05 (m, 2H), 2.39 2.42 (2s, 3H), 2.64-3.48 (m, 12H), 3.86 (brs, 2H), 3.97-4.02 (m, 2H), 4.00-4.18 (m, 0.4H), 4.84-4.91 (m, 0.6H), 7.03-7.18 (m, 4H), 7.26 (s, 3H), 7.48 (s, 1H).

Step C $N^2$-(5-cyano-2-methylphenyl)-$N^2$-{2-[methyl(1,2,3,4-tetrahydronaphthalen-2-yl)amino]-2-oxoethyl}-$N^1$-[2-(isopropylamino)ethyl]glycinamide hydrochloride Using the compound (700 mg, 1.22 mmol) obtained in step B and according to the method of Example 1, step C, the title compound (480 mg, yield 77%) was obtained as a colorless amorphous solid.

$^1$H-NMR (300 MHz, DMSO-$d_6$); δ (ppm) 1.20 (d, J=6.3, 6H), 1.62-2.00 (m, 2H), 2.33 2.37 (2s, 3H), 2.64-3.08 (m, 9H), 3.17-3.42 (m, 3H), 3.56-4.71 (m, 5H), 7.09 (s, 4H), 7.28-7.33 (m, 2H), 7.49 (d, J=9.0, 1H), 8.38-8.41 (m, 1H), 8.82 (brs, 2H).

Example 14

$N^2$-(5-cyano-2-methylphenyl)-$N^2$-[2-{methyl[4-(methylsulfonyl)piperazin-1-yl]amino}-2-oxoethyl]-$N^1$-[2-(isopropylamino)ethyl]glycinamide dihydrochloride

Step A $N^2$-(5-cyano-2-methylphenyl)-$N^2$-[2-{methyl[4-(methylsulfonyl)piperazin-1-yl]amino}-2-oxoethyl]-$N^1$-{2-[(tert-butoxycarbonyl)(isopropyl)amino]ethyl}glycinamide Using the compound (267 mg, 1.08 mmol) of Reference Example 61, the compound (222 mg, 1.15 mmol) of Reference Example 48, and the compound (328 mg, 1.62 mmol) of Reference Example 3, and according to the methods of Example 4, step A, and Example 1, step B, the title compound (476 mg, yield 73%) was obtained as a colorless amorphous solid.

$^1$H-NMR (300 MHz, CDCl$_3$); δ (ppm) 1.12 (d, J=6.9, 6H), 1.44 (brs, 9H), 2.38 (s, 3H), 2.7-2.8 (m, 2H), 2.84 (s, 3H), 2.90-3.05 (m, 7H), 3.1-3.2 (m, 2H), 3.3-3.4 (m, 2H), 3.7-3.9 (m, 2H), 3.79 (s, 2H), 3.9-4.3 (broad, 1H), 4.16 (s, 2H), 7.2-7.3 (m, 2H), 7.44 (s, 1H), 7.7-8.4 (broad, 1H).

Step B $N^2$-(5-cyano-2-methylphenyl)-$N^2$-[2-{methyl[4-(methylsulfonyl)piperazin-1-yl]amino}-2-oxoethyl]-$N^1$-[2-(isopropylamino)ethyl]glycinamide dihydrochloride Using the compound (475 mg, 0.782 mmol) obtained in step A and according to the method of Example 1, step C, the title compound (375 mg, yield 83%) was obtained as a colorless solid.

$^1$H-NMR (300 MHz, DMSO-$d_6$); δ (ppm) 1.21 (d, J=6.6, 6H), 2.32 (s, 3H), 2.7-3.0 (m, 8H), 2.84 (s, 3H), 2.92 (s, 3H), 3.1-3.4 (m, 3H), 3.5-3.6 (m, 2H), 3.90 (s, 2H), 4.25 (s, 2H), 7.30 (broad, 2H), 7.42 (s, 1H), 8.35 (t, J=5.7, 1H), 8.81 (brs, 2H).

Example 15

$N^2$-{2-[1,3-dihydro-2H-isoindol-2-yl(methyl)amino]-2-oxoethyl}-$N^2$-[2-methyl-5-(5-methyl-1,2,4-oxadiazol-3-yl)phenyl]-$N^1$-[2-(isopropylamino)ethyl]glycinamide dihydrochloride

Step A

N-{2-[1,3-dihydro-2H-isoindol-2-yl(methyl)amino]-2-oxoethyl}-N-[2-methyl-5-(5-methyl-1,2,4-oxadiazol-3-yl)phenyl]glycine Using the compound (2.66 g, 8.71 mmol) of Reference Example 62, and the compound (2.47 g, 13.4 mmol) of Reference Example 17, and according to the method of Example 1, step A, the title compound (3.46 g, yield 91%) was obtained as a gray amorphous solid.

$^1$H-NMR (300 MHz, CDCl$_3$); δ (ppm) 2.38 (s, 3H), 2.63 (s, 3H), 3.06 (s, 3H), 3.94 (s, 2H), 4.17 (d, J=11.7, 2H), 4.28 (d, J=11.7, 2H), 4.31 (s, 2H), 7.19-7.31 (m, 5H), 7.75 (dd, J=1.2, 7.8, 1H), 7.92 (d, J=1.2, 1H), 13.53 (brs, 1H).

Step B

N²-{2-[1,3-dihydro-2H-isoindol-2-yl(methyl)amino]-2-oxoethyl}-N²-[2-methyl-5-(5-methyl-1,2,4-oxadiazol-3-yl)phenyl]-N¹-{2-[(tert-butoxycarbonyl)(isopropyl)amino]ethyl}glycinamide Using the compound (3.45 g, 7.92 mmol) obtained in step A, and the compound (2.33 g, 11.5 mmol) of Reference Example 3, and according to the method of Example 1, step B, the title compound (4.07 g, yield 83%) was obtained as a colorless amorphous solid.

¹H-NMR (300 MHz, CDCl₃); δ (ppm) 1.11 (d, J=6.9, 6H), 1.46 (brs, 9H), 2.41 (s, 3H), 2.62 (s, 3H), 2.94 (s, 3H), 3.0-3.2 (m, 2H), 3.37-3.45 (m, 2H), 3.82 (s, 2H), 3.9-4.3 (broad, 1H), 4.15 (d, J=11.7, 2H), 4.23 (d, J=11.7, 2H), 4.27 (s, 2H), 7.18-7.29 (m, 5H), 7.69 (d, J=7.2, 1H), 7.94 (d, J=1.5, 1H), 8.1-8.7 (broad, 1H).

Step C

N²-{2-[1,3-dihydro-2H-isoindol-2-yl(methyl)amino]-2-oxoethyl}-N²-[2-methyl-5-(5-methyl-1,2,4-oxadiazol-3-yl)phenyl]-N¹-[2-(isopropylamino)ethyl]glycinamide dihydrochloride Using the compound (4.05 g, 6.53 mmol) obtained in step B and according to the method of Example 1, step C, the title compound (3.57 g, yield 92%) was obtained as a colorless solid.

¹H-NMR (300 MHz, DMSO-d₆); δ (ppm) 1.18 (d, J=6.5, 6H), 2.34 (s, 3H), 2.65 (s, 3H), 2.8-3.0 (m, 2H), 2.88 (s, 3H), 3.1-3.3 (m, 1H), 3.35-3.42 (m, 2H), 3.92 (s, 2H), 4.13 (d, J=11.7, 2H), 4.27 (d, J=11.7, 2H), 4.35 (s, 2H), 7.2-7.3 (m, 5H), 7.51 (d, J=7.6, 1H), 7.75 (s, 1H), 8.36 (t, J=5.7, 1H), 8.72 (brs, 2H).

Example 16

N²-{2-[1,3-dihydro-2H-isoindol-2-yl(methyl)amino]-2-oxoethyl}-N²-[2-methyl-5-(5-methyl-1,2,4-oxadiazol-3-yl)phenyl]-N¹-[2-(ethylamino)ethyl]glycinamide dihydrochloride Step A N²-{2-[1,3-dihydro-2H-isoindol-2-yl(methyl)amino]-2-oxoethyl}-N²-[2-methyl-5-(5-methyl-1,2,4-oxadiazol-3-yl)phenyl]-N¹-{2-[(tert-butoxycarbonyl)(ethyl)amino]ethyl}glycinamide Using the compound (1.63 g, 2.97 mmol) of Example 2, step A and according to the method of Reference Example 62, step A, the title compound (1.26 g, yield 70%) was obtained as a colorless amorphous solid.

¹H-NMR (300 MHz, CDCl₃); δ (ppm) 1.04 (t, J=7.2, 3H), 1.44 (brs, 9H), 2.40 (s, 3H), 2.62 (s, 3H), 2.95 (s, 3H), 3.0-3.2 (m, 2H), 3.2-3.3 (m, 2H), 3.4-3.5 (m, 2H), 3.81 (s, 2H), 4.16 (d, J=11.7, 2H), 4.24 (d, J=11.7, 2H), 4.28 (s, 2H), 7.18-7.29 (m, 5H), 7.68 (dd, J=1.2, 8.4, 1H), 7.94 (d, J=1.2, 1H), 8.38 8.63 (2brs, 1H).

Step B

N²-{2-[1,3-dihydro-2H-isoindol-2-yl(methyl)amino]-2-oxoethyl}-N²-[2-methyl-5-(5-methyl-1,2,4-oxadiazol-3-yl)phenyl]-N¹-[2-(ethylamino)ethyl]glycinamide dihydrochloride Using the compound (1.25 g, 2.06 mmol) obtained in step A and according to the method of Example 1, step C, the title compound (1.12 g, yield 94%) was obtained as a colorless solid.

¹H-NMR (300 MHz, DMSO-d₆); δ (ppm) 1.15 (t, J=7.2, 3H), 2.33 (s, 3H), 2.65 (s, 3H), 2.8-3.0 (m, 4H), 2.88 (s, 3H), 3.3-3.4 (m, 2H), 3.92 (s, 2H), 4.13 (d, J=11.7, 2H), 4.26 (d, J=11.7, 2H), 4.35 (s, 2H), 7.2-7.3 (m, 5H), 7.51 (dd, J=1.2, 7.6, 1H), 7.75 (d, J=1.2, 1H), 8.34 (t, J=5.7, 1H), 8.70 (brs, 2H).

Example 17

N²-{2-[1,3-dihydro-2H-isoindol-2-yl(methyl)amino]-2-oxoethyl}-N²-[2-methyl-5-(5-methyl-1,2,4-oxadiazol-3-yl)phenyl]-N¹-[2-(4-hydroxypiperidin-1-yl)ethyl]glycinamide dihydrochloride Step A N²-{2-[1,3-dihydro-2H-isoindol-2-yl(methyl)amino]-2-oxoethyl}-N²-[2-methyl-5-(5-methyl-1,2,4-oxadiazol-3-yl)phenyl]-N¹-(2-bromoethyl)glycinamide Using the compound (1.24 g, 2.85 mmol) of Example 15, step A, 2-bromoethylamine hydrobromide (786 mg, 3.84 mmol), and N,N-diisopropylethylamine (0.70 ml, 4.1 mmol), and according to the method of Example 1, step B, the title compound (1.08 g, yield 70%) was obtained as a colorless solid.

¹H-NMR (300 MHz, CDCl₃); δ (ppm) 2.44 (s, 3H), 2.62 (s, 3H), 2.96 (s, 3H), 3.47 (t, J=6.3, 2H), 3.7-3.8 (m, 2H), 3.80 (s, 2H), 4.17 (d, J=11.7, 2H), 4.24 (d, J=11.7, 2H), 4.33 (s, 2H), 7.18-7.31 (m, 5H), 7.71 (dd, J=1.2, 7.8, 1H), 7.95 (d, J=1.2, 1H), 8.87 (t, J=5.7, 1H).

Step B

N²-{2-[1,3-dihydro-2H-isoindol-2-yl(methyl)amino]-2-oxoethyl}-N²-[2-methyl-5-(5-methyl-1,2,4-oxadiazol-3-yl)phenyl]-N¹-[2-(4-hydroxypiperidin-1-yl)ethyl]glycinamide The compound (1.08 g, 1.99 mmol) obtained in step A and 4-hydroxypiperidine (1.44 g, 14.2 mmol) were dissolved in N,N-dimethylformamide (15 ml), and the mixture was stirred with heating at 60° C. for 100 min. The reaction mixture was cooled, diluted with water, and extracted with ethyl acetate. The organic layer was washed with saturated brine, and dried over anhydrous magnesium sulfate. The insoluble material was filtered off, and the solution was concentrated under reduced pressure. The obtained oil was purified by silica gel column chromatography (ammonia-containing methanol-dichloromethane) to give the title compound (967 mg, yield 87%) as a colorless amorphous solid.

¹H-NMR (300 MHz, CDCl₃); δ (ppm) 1.37 (d, J=4.8, 1H), 1.4-1.6 (m, 2H), 1.8-1.9 (m, 2H), 2.0-2.2 (m, 2H), 2.4-2.5 (m, 2H), 2.44 (s, 3H), 2.62 (s, 3H), 2.7-2.8 (m, 2H), 2.94 (s, 3H), 3.35-3.42 (m, 2H), 3.5-3.7 (m, 1H), 3.85 (s, 2H), 4.15 (d, J=11.7, 2H), 4.24 (d, J=11.7, 2H), 4.26 (s, 2H), 7.18-7.29 (m, 5H), 7.68 (dd, J=1.2, 7.7, 1H), 7.95 (d, J=1.2, 1H), 8.24 (broad t, 1H).

Step C $N^2$-{2-[1,3-dihydro-2H-isoindol-2-yl(methyl)amino]-2-oxoethyl}-$N^2$-[2-methyl-5-(5-methyl-1,2,4-oxadiazol-3-yl)phenyl]-$N^1$-[2-(4-hydroxypiperidin-1-yl)ethyl]glycinamide dihydrochloride The compound (927 mg, 1.65 mmol) obtained in step B was dissolved in ethyl acetate (10 ml), and 4N hydrochloric acid-dioxane solution (1.0 ml, 4.0 mmol) was added at room temperature with stirring. The reaction mixture was diluted with ethyl acetate, and the precipitated solid was filtered, and dried under reduced pressure to give the title compound (901 mg, yield 86%) as a colorless solid.

$^1$H-NMR (300 MHz, DMSO-$d_6$); δ (ppm) 1.5-2.0 (m, 4H), 2.34 (s, 3H), 2.65 (s, 3H), 2.7-2.9 (m, 1H), 2.88 (s, 3H), 3.0-3.6 (m, 8H), 3.93 (s, 2H), 4.13 (d, J=11.7, 2H), 4.26 (d, J=11.7, 2H), 4.34 (s, 2H), 7.2-7.3 (m, 5H), 7.51 (d, J=7.5, 1H), 7.74 (s, 1H), 8.37 (t, J=5.7, 1H), 9.95 (brs, 1H).

Example 18

$N^2$-{2-[1,3-dihydro-2H-isoindol-2-yl(methyl)amino]-2-oxoethyl}-$N^2$-[2-methyl-5-(5-methyl-1,2,4-oxadiazol-3-yl)phenyl]-$N^1$-[2-(3-hydroxypyrrolidin-1-yl)ethyl]glycinamide dihydrochloride

Step A $N^2$-{2-[1,3-dihydro-2H-isoindol-2-yl(methyl)amino]-2-oxoethyl}-$N^2$-[2-methyl-5-(5-methyl-1,2,4-oxadiazol-3-yl)phenyl]-$N^1$-[2-(3-hydroxypyrrolidin-1-yl)ethyl]glycinamide Using the compound (453 mg, 0.837 mmol) of Example 17, step A, and 3-pyrrolidinol (0.5 ml), and according to the method of Example 17, step B, the title compound (426 mg, yield 93%) was obtained as a colorless amorphous solid.

$^1$H-NMR (300 MHz, CDCl$_3$); δ (ppm) 1.7-1.9 (m, 1H), 2.0-2.3 (m, 3H), 2.42 (s, 3H), 2.5-2.7 (m, 2H), 2.62 (s, 3H), 2.95 (s, 3H), 2.95-3.15 (m, 2H), 3.3-3.5 (m, 2H), 3.6-3.8 (m, 2H), 4.0-4.4 (m, 7H), 7.1-7.3 (m, 5H), 7.69 (dd, J=1.5, 7.8, 1H), 7.94 (d, J=1.5, 1H), 8.90 (broad t, 1H).

Step B $N^2$-{2-[1,3-dihydro-2H-isoindol-2-yl(methyl)amino]-2-oxoethyl}-$N^2$-[2-methyl-5-(5-methyl-1,2,4-oxadiazol-3-yl)phenyl]-$N^1$-[2-(3-hydroxypyrrolidin-1-yl)ethyl]glycinamide dihydrochloride Using the compound (419 mg, 0.765 mmol) obtained in step A and according to the method of Example 17, step C, the title compound (403 mg, yield 85%) was obtained as a colorless solid.

$^1$H-NMR (300 MHz, DMSO-$d_6$); δ (ppm) 1.6-2.0 (m, 2H), 2.0-2.2 (m, 1H), 2.34 (s, 3H), 2.65 (s, 3H), 2.88 2.89 (2s, 3H), 2.9-3.6 (m, 8H), 3.93 3.94 (2s, 2H), 4.13 (d, J=11.7, 2H), 4.26 (d, J=11.7, 2H), 4.33 4.35 (2s, 2H), 7.19-7.30 (m, 5H), 7.51 (d, J=7.8, 1H), 7.75 (d, J=1.2, 1H), 8.33 (broad t, 1H), 10.13 10.58 (2brs, 1H).

Example 19

$N^2$-{2-[(4-fluoro-1,3-dihydro-2H-isoindol-2-yl)(methyl)amino]-2-oxoethyl}-$N^2$-[2-methyl-5-(5-methyl-1,2,4-oxadiazol-3-yl)phenyl]-$N^1$-[2-(ethylamino)ethyl]glycinamide dihydrochloride

Step A

N-{2-[(4-fluoro-1,3-dihydro-2H-isoindol-2-yl)(methyl)amino]-2-oxoethyl}-N-[2-methyl-5-(5-methyl-1,2,4-oxadiazol-3-yl)phenyl]glycine Using the compound (471 mg, 1.54 mmol) of Reference Example 62, and the compound (431 mg, 2.13 mmol) of Reference Example 18, and according to the method of Example 1, step A, the title compound (442 mg, yield 63%) was obtained as a brown oil.

$^1$H-NMR (300 MHz, CDCl$_3$); δ (ppm) 2.38 (s, 3H), 2.63 (s, 3H), 3.06 (s, 3H), 3.94 (s, 2H), 4.2-4.4 (m, 6H), 6.92-7.02 (m, 2H), 7.22-7.32 (m, 2H), 7.75 (dd, J=1.5, 7.8, 1H), 7.92 (d, J=1.5, 1H), 13.2 (brs, 1H).

Step B $N^2$-{2-[(4-fluoro-1,3-dihydro-2H-isoindol-2-yl)(methyl)amino]-2-oxoethyl}-$N^2$-[2-methyl-5-(5-methyl-1,2,4-oxadiazol-3-yl)phenyl]-$N^1$-{2-[(tert-butoxycarbonyl)(ethyl)amino]ethyl}glycinamide Using the compound (436 mg, 0.961 mmol) obtained in step A, and the compound (278 mg, 1.48 mmol) of Reference Example 2, and according to the method of Example 1, step B, the title compound (503 mg, yield 84%) was obtained as a colorless amorphous solid.

$^1$H-NMR (300 MHz, CDCl$_3$); δ (ppm) 1.05 (t, J=7.2, 3H), 1.44 (brs, 9H), 2.40 (s, 3H), 2.62 (s, 3H), 2.95 (s, 3H), 3.1-3.4 (m, 4H), 3.4-3.5 (m, 2H), 3.80 (s, 2H), 4.1-4.4 (m, 6H), 6.9-7.0 (m, 2H), 7.2-7.3 (m, 2H), 7.69 (d, J=7.2, 1H), 7.93 (d, J=1.5, 1H), 8.2-8.7 (broad, 1H).

Step C $N^2$-{2-[(4-fluoro-1,3-dihydro-2H-isoindol-2-yl)(methyl)amino]-2-oxoethyl}-$N^2$-[2-methyl-5-(5-methyl-1,2,4-oxadiazol-3-yl)phenyl]-$N^1$-[2-(ethylamino)ethyl]glycinamide dihydrochloride Using the compound (502 mg, 0.805 mmol) obtained in step B and according to the method of Example 1, step C, the title compound (424 mg, yield 88%) was obtained as a colorless solid.

$^1$H-NMR (300 MHz, DMSO-$d_6$); δ (ppm) 1.14 (t, J=7.2, 3H), 2.34 (s, 3H), 2.65 (s, 3H), 2.8-3.0 (m, 4H), 2.89 (s, 3H), 3.34-3.41 (m, 2H), 3.91 (s, 2H), 4.1-4.4 (m, 6H), 7.06-7.15 (m, 2H), 7.26-7.34 (m, 2H), 7.52 (dd, J=1.2, 7.8, 1H), 7.76 (d, J=1.2, 1H), 8.32 (t, J=5.7, 1H), 8.60 (brs, 2H).

Example 20

N²-{2-[(5-fluoro-1,3-dihydro-2H-isoindol-2-yl)(methyl)amino]-2-oxoethyl}-N²-[2-methyl-5-(5-methyl-1,2,4-oxadiazol-3-yl)phenyl]-N¹-[2-(ethylamino)ethyl]glycinamide hydrochloride

Step A

N²-{2-[(5-fluoro-1,3-dihydro-2H-isoindol-2-yl)(methyl)amino]-2-oxoethyl}-N²-[2-methyl-5-(5-methyl-1,2,4-oxadiazol-3-yl)phenyl]-N¹-{2-[(tert-butoxycarbonyl)(ethyl)amino]ethyl}glycinamide The compound (2.00 g, 6.55 mmol) of Reference Example 62 was dissolved in N,N-dimethylformamide (20 ml), WSC (1.27 g, 6.62 mmol) was added at room temperature, and the mixture was stirred at the same temperature for 1 hr. Then, the reaction mixture was stirred under ice-cooling, the compound (1.35 g, 6.66 mmol) of Reference Example 19 and N,N-diisopropylethylamine (1.15 ml, 6.76 mmol) were added, and the mixture was stirred for 2 hr under ice-cooling. Then, to the reaction mixture were added the compound (1.30 g, 6.90 mmol) of Reference Example 2, WSC (1.33 g, 6.94 mmol) and 1-hydroxybenzotriazole (940 mg, 6.96 mmol), and the mixture was stirred at room temperature for 4 hr. The reaction mixture was diluted with an ethyl acetate-hexane=1:1 mixed solvent, and the organic layer was washed with water, 10% aqueous citric acid solution, diluted aqueous sodium hydroxide solution and saturated brine, and dried over anhydrous magnesium sulfate. The insoluble material was filtered off, and the solution was concentrated under reduced pressure. The obtained oil was purified by silica gel column chromatography (ethyl acetate-methanol) to give a pale-yellow amorphous solid (3.88 g). This was dissolved in diethyl ether (50 ml), and stood in a refrigerator overnight to allow precipitation of a solid, which was collected by filtration, washed with diethyl ether, and dried under reduced pressure to give the title compound (3.11 g, yield 76%) as a colorless solid.

¹H-NMR (300 MHz, CDCl₃); δ (ppm) 1.05 (t, J=7.2, 3H), 1.44 (brs, 9H), 2.40 (s, 3H), 2.63 (s, 3H), 2.94 (s, 3H), 3.02-3.22 (m, 2H), 3.22-3.38 (m, 2H), 3.40-3.49 (m, 2H), 3.79 (s, 2H), 4.05-4.35 (m, 6H), 6.88-6.99 (m, 2H), 7.12-7.20 (m, 1H), 7.28 (d, J=8.1, 1H), 7.69 (dd, J=1.2, 8.1, 1H), 7.93 (d, J=1.2, 1H), 8.38, 8.64 (2broad, 1H).

Step B

N²-{2-[(5-fluoro-1,3-dihydro-2H-isoindol-2-yl)(methyl)amino]-2-oxoethyl}-N²-[2-methyl-5-(5-methyl-1,2,4-oxadiazol-3-yl)phenyl]-N¹-[2-(ethylamino)ethyl]glycinamide hydrochloride The compound (3.10 g, 4.97 mmol) obtained in step A was dissolved in dichloromethane (16 ml), trifluoroacetic acid (10 ml) was added at room temperature, and the mixture was stirred at the same temperature for 90 min. To the reaction mixture were added dichloromethane and aqueous ammonia to alkalify the aqueous layer and to extract the organic layer. The aqueous layer was extracted with dichloromethane again, the organic layer was mixed, and the mixture was washed with saturated brine, and dried over sodium sulfate. The insoluble material was filtered off, and the solution was concentrated under reduced pressure to give a colorless amorphous solid (2.67 g). This was dissolved in ethyl acetate (30 ml), 4N hydrochloric acid-ethyl acetate solution (1.25 ml, 5 mmol) was added at room temperature, and the mixture was stirred at the same temperature to allow precipitation of a solid. This was collected by filtration, washed with ethyl acetate, and dried under reduced pressure to give a colorless solid (2.06 g). This was dissolved in ethanol (40 ml) with heating, and the mixture was gradually cooled by stirring to allow precipitation of a solid. This was collected by filtration, washed with ethanol (10 ml), and dried under reduced pressure to give the title compound (1.83 g, yield 66%) as a colorless solid.

¹H-NMR (300 MHz, DMSO-d₆); δ (ppm) 1.14 (t, J=7.2, 3H), 2.33 (s, 3H), 2.65 (s, 3H), 2.8-3.0 (m, 4H), 2.88 (s, 3H), 3.3-3.4 (m, 2H), 3.92 (s, 2H), 4.0-4.3 (m, 4H), 4.33 (s, 2H), 7.0-7.2 (m, 2H), 7.27-7.33 (m, 2H), 7.52 (dd, J=1.2, 8.1, 1H), 7.75 (d, J=1.2, 1H), 8.32 (t, J=5.7, 1H), 8.57 (brs, 2H).

Example 21

N²-{2-[(5-fluoro-1,3-dihydro-2H-isoindol-2-yl)(methyl)amino]-2-oxoethyl}-N²-[2-methyl-5-(5-methyl-1,2,4-oxadiazol-3-yl)phenyl]-N¹-[2-(isopropylamino)ethyl]glycinamide dihydrochloride

Step A

N²-{2-[(5-fluoro-1,3-dihydro-2H-isoindol-2-yl)(methyl)amino]-2-oxoethyl}-N²-[2-methyl-5-(5-methyl-1,2,4-oxadiazol-3-yl)phenyl]-N¹-{2-[(tert-butoxycarbonyl)(isopropyl)amino]ethyl}glycinamide Using the compound (845 mg, 1.46 mmol) obtained in Example 4, step B and according to the method of Reference Example 62, step A, the title compound (631 mg, yield 68%) was obtained as a colorless solid.

¹H-NMR (300 MHz, CDCl₃); δ (ppm) 1.12 (d, J=6.6, 6H), 1.45 (brs, 9H), 2.41 (s, 3H), 2.62 (s, 3H), 2.93 (s, 3H), 3.1-3.3 (m, 2H), 3.35-3.50 (m, 2H), 3.80 (s, 2H), 4.0-4.3 (m, 7H), 6.8-7.0 (m, 2H), 7.1-7.2 (m, 1H), 7.25-7.33 (m, 1H), 7.69 (dd, J=1.2, 8.1, 1H), 7.94 (d, J=1.2, 1H), 8.2-8.8 (broad, 1H).

Step B

N²-{2-[(5-fluoro-1,3-dihydro-2H-isoindol-2-yl)(methyl)amino]-2-oxoethyl}-N²-[2-methyl-5-(5-methyl-1,2,4-oxadiazol-3-yl)phenyl]-N¹-[2-(isopropylamino)ethyl]glycinamide dihydrochloride Using the compound (627 mg, 0.983 mmol) obtained in step A and according to the method of Example 1, step C, the title compound (560 mg, yield 93%) was obtained as a colorless solid.

¹H-NMR (300 MHz, DMSO-d₆); δ (ppm) 1.18 (d, J=6.6, 6H), 2.34 (s, 3H), 2.65 (s, 3H), 2.8-3.0 (m, 2H), 2.88 (s, 3H), 3.1-3.3 (m, 1H), 3.35-3.42 (m, 2H), 3.92 (s, 2H), 4.0-4.3 (m, 4H), 4.34 (s, 2H), 7.0-7.2 (m, 2H), 7.26-7.32 (m, 2H), 7.52 (dd, J=1.2, 8.1, 1H), 7.75 (d, J=1.2, 1H), 8.34 (broad t, 1H), 8.64 (brs, 2H).

Example 22

N²-{2-[(5-cyano-1,3-dihydro-2H-isoindol-2-yl)(methyl)amino]-2-oxoethyl}-N²-[2-methyl-5-(5-methyl-1,2,4-oxadiazol-3-yl)phenyl]-N¹-[2-(isopropylamino)ethyl]glycinamide dihydrochloride

Step A

N-{2-[(5-cyano-1,3-dihydro-2H-isoindol-2-yl)(methyl)amino]-2-oxoethyl}-N-[2-methyl-5-(5-methyl-1,2,4-oxadiazol-3-yl)phenyl]glycine Using the compound (225 mg, 0.737 mmol) of Reference Example 62 and the compound (195 mg, 0.930 mmol) of Reference Example 21, and according to the method of Example 4, step A, the title compound (302 mg, yield 89%) was obtained as a bistered amorphous solid.

$^1$H-NMR (300 MHz, CDCl$_3$); δ (ppm) 2.38 (s, 3H), 2.63 (s, 3H), 3.06 (s, 3H), 3.93 (s, 2H), 4.19-4.35 (m, 6H), 7.30 (d, J=8.1, 1H), 7.34 (d, J=7.8, 1H), 7.51 (s, 1H), 7.58 (d, J=8.1, 1H), 7.76 (dd, J=1.2, 7.8, 1H), 7.91 (d, J=1.2, 1H), 13.1 (brs, 1H).

Step B

N$^2$-{2-[(5-cyano-1,3-dihydro-2H-isoindol-2-yl)(methyl)amino]-2-oxoethyl}-N$^2$-[2-methyl-5-(5-methyl-1,2,4-oxadiazol-3-yl)phenyl]-N$^1$-{2-[(tert-butoxycarbonyl)(isopropyl)amino]ethyl}glycinamide Using the compound (298 mg, 0.647 mmol) obtained in step A, and the compound (209 mg, 1.03 mmol) of Reference Example 3, and according to the method of Example 1, step B, the title compound (370 mg, yield 89%) was obtained as a colorless amorphous solid.

$^1$H-NMR (300 MHz, CDCl$_3$); δ (ppm) 1.12 (d, J=6.8, 6H), 1.45 (s, 9H), 2.40 (s, 3H), 2.63 (s, 3H), 2.94 (s, 3H), 3.1-3.3 (m, 2H), 3.38-3.45 (m, 2H), 3.79 (s, 2H), 4.1-4.3 (m, 7H), 7.29-7.34 (m, 2H), 7.55 (s, 1H), 7.57 (dd, J=1.1, 7.6, 1H), 7.71 (dd, J=1.1, 7.7, 1H), 7.92 (d, J=1.4, 1H), 8.1-8.7 (broad, 1H).

Step C

N$^2$-{2-[(5-cyano-1,3-dihydro-2H-isoindol-2-yl)(methyl)amino]-2-oxoethyl}-N$^2$-[2-methyl-5-(5-methyl-1,2,4-oxadiazol-3-yl)phenyl]-N$^1$-[2-(isopropylamino)ethyl]glycinamide dihydrochloride Using the compound (361 mg, 0.560 mmol) obtained in step B and according to the method of Example 1, step C, the title compound (315 mg, yield 91%) was obtained as a colorless solid.

$^1$H-NMR (300 MHz, DMSO-d$_6$); δ (ppm) 1.18 (d, J=6.6, 6H), 2.33 (s, 3H), 2.65 (s, 3H), 2.8-3.0 (m, 5H), 3.2-3.3 (m, 1H), 3.35-3.45 (m, 2H), 3.91-4.35 (m, 8H), 7.28 (d, J=7.8, 1H), 7.47-7.53 (m, 2H), 7.72-7.77 (m, 3H), 8.30-8.35 (m, 1H), 8.5-8.9 (broad, 2H).

Example 23

N$^2$-{2-[(5-methoxy-1,3-dihydro-2H-isoindol-2-yl)(methyl)amino]-2-oxoethyl}-N$^2$-[2-methyl-5-(5-methyl-1,2,4-oxadiazol-3-yl)phenyl]-N$^1$-[2-(isopropylamino)ethyl]glycinamide dihydrochloride

Step A

N-{2-[(5-methoxy-1,3-dihydro-2H-isoindol-2-yl)(methyl)amino]-2-oxoethyl}-N-[2-methyl-5-(5-methyl-1,2,4-oxadiazol-3-yl)phenyl]glycine Using the compound (1.15 g, 3.77 mmol) of Reference Example 62 and the compound (1.23 g, 5.73 mmol) of Reference Example 20, and according to the method of Example 4, step A, the title compound (1.36 g, yield 77%) was obtained as a pale-yellow amorphous solid.

$^1$H-NMR (300 MHz, CDCl$_3$); δ (ppm) 2.38 (s, 3H), 2.63 (s, 3H), 3.05 (s, 3H), 3.79 (s, 3H), 3.94 (s, 2H), 4.0-4.3 (m, 4H), 4.31 (s, 2H), 6.75 (d, J=2.1, 1H), 6.81 (dd, J=2.1, 8.4, 1H), 7.11 (d, J=8.4, 1H), 7.29 (d, J=7.8, 1H), 7.75 (dd, J=1.2, 7.8, 1H), 7.92 (d, J=1.2, 1H), 13.5 (brs, 1H).

Step B

N$^2$-{2-[(5-methoxy-1,3-dihydro-2H-isoindol-2-yl)(methyl)amino]-2-oxoethyl}-N$^2$-[2-methyl-5-(5-methyl-1,2,4-oxadiazol-3-yl)phenyl]-N$^1$-{2-[(tert-butoxycarbonyl)(isopropyl)amino]ethyl}glycinamide Using the compound (667 mg, 1.43 mmol) obtained in step A, and the compound (393 mg, 1.94 mmol) of Reference Example 3, and according to the method of Example 1, step B, the title compound (794 mg, yield 85%) was obtained as a colorless amorphous solid.

$^1$H-NMR (300 MHz, CDCl$_3$); δ (ppm) 1.11 (d, J=6.8, 6H), 1.45 (brs, 9H), 2.40 (s, 3H), 2.62 (s, 3H), 2.93 (s, 3H), 3.0-3.2 (m, 2H), 3.37-3.45 (m, 2H), 3.79 (s, 3H), 3.81 (s, 2H), 4.0-4.3 (m, 7H), 6.73 (d, J=2.3, 1H), 6.80 (dd, J=2.3, 8.3, 1H), 7.09 (d, J=8.3, 1H), 7.27 (d, J=8.1, 1H), 7.69 (dd, J=1.2, 8.1, 1H), 7.94 (d, J=1.2, 1H), 8.2-8.7 (broad, 1H).

Step C

N$^2$-{2-[(5-methoxy-1,3-dihydro-2H-isoindol-2-yl)(methyl)amino]-2-oxoethyl}-N$^2$-[2-methyl-5-(5-methyl-1,2,4-oxadiazol-3-yl)phenyl]-N$^1$-[2-(isopropylamino)ethyl]glycinamide dihydrochloride Using the compound (788 mg, 1.21 mmol) obtained in step B and according to the method of Example 1, step C, the title compound (716 mg, yield 95%) was obtained as a colorless solid.

$^1$H-NMR (300 MHz, DMSO-d$_6$); δ (ppm) 1.18 (d, J=6.6, 6H), 2.34 (s, 3H), 2.65 (s, 3H), 2.8-3.0 (m, 2H), 2.87 (s, 3H), 3.1-3.3 (m, 1H), 3.34-3.42 (m, 2H), 3.73 (s, 3H), 3.92 (s, 2H), 4.0-4.3 (m, 4H), 4.34 (s, 2H), 6.81 (dd, J=2.3, 8.3, 1H), 6.86 (d, J=2.3, 1H), 7.16 (d, J=8.3, 1H), 7.28 (d, J=8.0, 1H), 7.51 (dd, J=1.2, 8.0, 1H), 7.75 (d, J=1.2, 1H), 8.35 (t, J=5.7, 1H), 8.72 (brs, 2H).

Example 24

N$^2$-{2-[(5-methoxy-1,3-dihydro-2H-isoindol-2-yl)(methyl)amino]-2-oxoethyl}-N$^2$-[2-methyl-5-(5-methyl-1,2,4-oxadiazol-3-yl)phenyl]-N$^1$-[2-(ethylamino)ethyl]glycinamide dihydrochloride

Step A

N$^2$-{2-[(5-methoxy-1,3-dihydro-2H-isoindol-2-yl)(methyl)amino]-2-oxoethyl}-N$^2$-[2-methyl-5-(5-methyl-1,2,4-oxadiazol-3-yl)phenyl]-N$^1$-{2-[(tert-butoxycarbonyl)(ethyl)amino]ethyl}glycinamide Using the compound (688 mg, 1.48 mmol) obtained in Example 23, step A, and the compound (423 mg, 2.25 mmol) of Reference Example 2, and according to the method of Example 1, step B, the title compound (816 mg, yield 87%) was obtained as a colorless amorphous solid.

$^1$H-NMR (300 MHz, CDCl$_3$); δ (ppm) 1.04 (t, J=7.2, 3H), 1.44 (brs, 9H), 2.39 (s, 3H), 2.62 (s, 3H), 2.93 (s, 3H), 3.0-3.2 (m, 2H), 3.2-3.3 (m, 2H), 3.4-3.5 (m, 2H), 3.79 (s, 3H), 3.80 (s, 2H), 4.0-4.3 (m, 6H), 6.73 (d, J=2.1, 1H), 6.79 (dd, J=2.1, 8.3, 1H), 7.09 (d, J=8.3, 1H), 7.27 (d, J=8.0, 1H), 7.68 (dd, J=1.2, 8.0, 1H), 7.94 (d, J=1.2, 1H), 8.3-8.7 (broad, 1H).

Step B

N²-{2-[(5-methoxy-1,3-dihydro-2H-isoindol-2-yl)(methyl)amino]-2-oxoethyl}-N²-[2-methyl-5-(5-methyl-1,2,4-oxadiazol-3-yl)phenyl]-N¹-[2-(ethylamino)ethyl]glycinamide dihydrochloride Using the compound (810 mg, 1.27 mmol) obtained in step A and according to the method of Example 1, step C, the title compound (744 mg, yield 96%) was obtained as a colorless solid.

¹H-NMR (300 MHz, DMSO-$d_6$); δ (ppm) 1.15 (t, J=7.2, 3H), 2.33 (s, 3H), 2.65 (s, 3H), 2.8-3.0 (m, 4H), 2.87 (s, 3H), 3.3-3.4 (m, 2H), 3.73 (s, 3H), 3.92 (s, 2H), 4.0-4.3 (m, 4H), 4.34 (s, 2H), 6.81 (dd, J=2.1, 8.1, 1H), 6.86 (d, J=2.1, 1H), 7.16 (d, J=8.1, 1H), 7.28 (d, J=7.8, 1H), 7.51 (d, J=7.8, 1H), 7.75 (s, 1H), 8.33 (t, J=5.7, 1H), 8.71 (brs, 2H).

The compounds of Examples 1-24 are shown below.

TABLE 7

| Example | Structural Formula | TMW | LC-MS (found) |
|---|---|---|---|
| 1 | 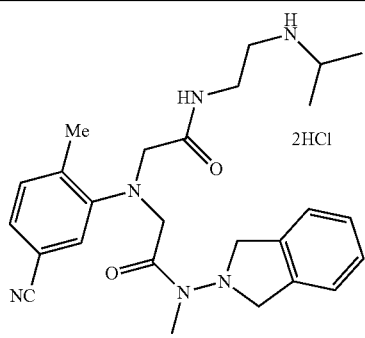 | 535.51 | 463 |
| 2 | 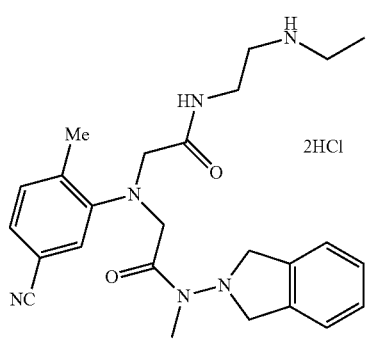 [SMILES: CCNCCNC(=O)CN(CC(=O)N(C)N1Cc2ccccc2C1)c1cc(C#N)ccc1C ; "2HCl"] | 521.48 | 449 |
| 3 | 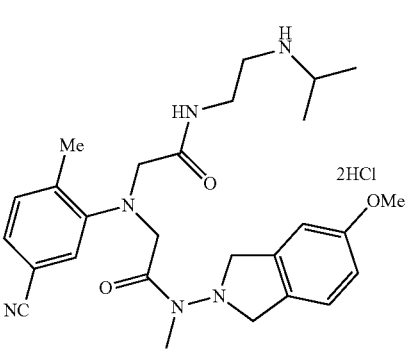 [SMILES: COc1ccc2c(c1)CN(N(C)C(=O)CN(CC(=O)NCCNC(C)C)c1cc(C#N)ccc1C)C2 ; "2HCl"] | 565.53 | 493 |

TABLE 7-continued
| Example | Structural Formula | TMW | LC-MS (found) |
|---|---|---|---|
| 4 | 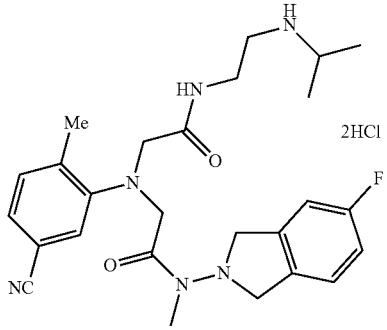 [SMILES: Cc1ccc(C#N)cc1N(CC(=O)NCCNC(C)C)CC(=O)N(C)N1Cc2ccc(F)cc2C1 ; "2HCl"] 2HCl | 553.50 | 481 |
| 5 | 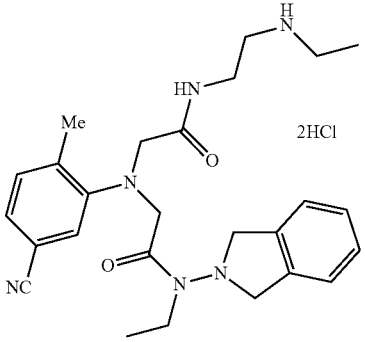 [SMILES: CCNCCNC(=O)CN(CC(=O)N(CC)N1Cc2ccccc2C1)c1cc(C#N)ccc1C ; "2HCl"] 2HCl | 535.51 | 463 |
| 6 | 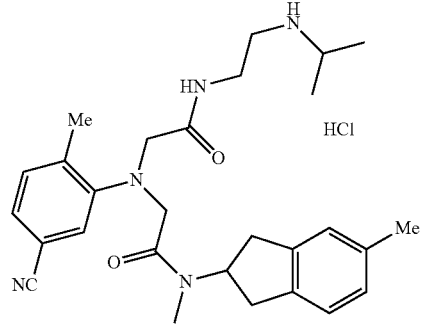 [SMILES: Cc1ccc2c(c1)CC(N(C)C(=O)CN(CC(=O)NCCNC(C)C)c1cc(C#N)ccc1C)C2 ; Cl] HCl | 512.09 | 476 |
| 7 | 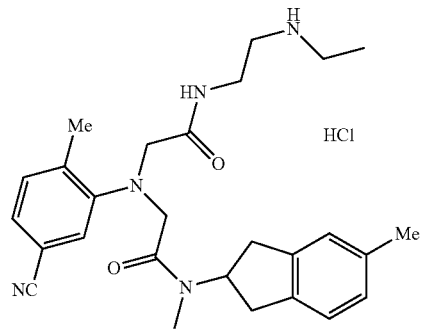 [SMILES: CCNCCNC(=O)CN(CC(=O)N(C)C1Cc2ccc(C)cc2C1)c1cc(C#N)ccc1C ; Cl] HCl | 498.06 | 462 |

TABLE 7-continued

| Example | Structural Formula | TMW | LC-MS (found) |
|---|---|---|---|
| 8 | | 528.09 | 492 |
| 9 | | 514.06 | 478 |
| 10 | | 516.05 | 480 |
| 11 | | 532.50 | 496 |

TABLE 7-continued
| Example | Structural Formula | TMW | LC-MS (found) |
|---|---|---|---|
| 12 | 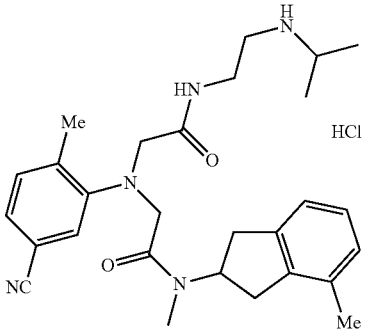 [SMILES: Cc1ccc(C#N)cc1N(CC(=O)NCCNC(C)C)CC(=O)N(C)C1Cc2cccc(C)c2C1 ; Cl] HCl | 512.09 | 476 |
| 13 | 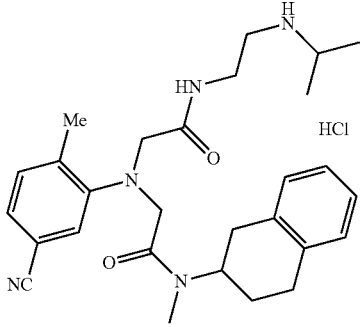 [SMILES: Cc1ccc(C#N)cc1N(CC(=O)NCCNC(C)C)CC(=O)N(C)C1CCc2ccccc2C1 ; Cl] HCl | 512.09 | 476 |
| 14 | 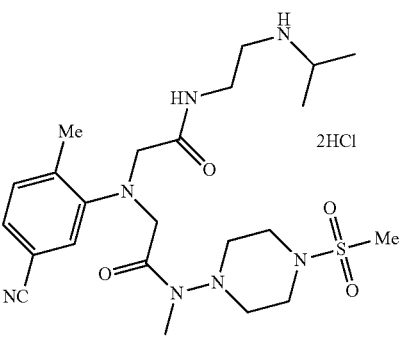 [SMILES: Cc1ccc(C#N)cc1N(CC(=O)NCCNC(C)C)CC(=O)N(C)N1CCN(S(C)(=O)=O)CC1 ; "2HCl"] 2HCl | 580.57 | 508 |
| 15 | 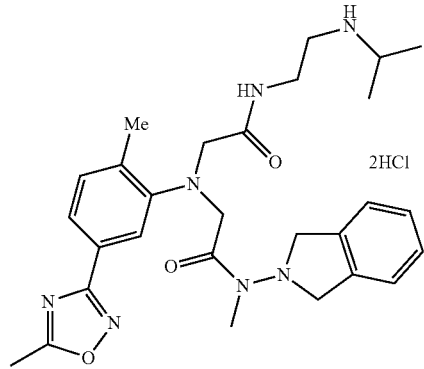 [SMILES: Cc1nc(-c2ccc(C)c(N(CC(=O)NCCNC(C)C)CC(=O)N(C)N3Cc4ccccc4C3)c2)no1 ; "2HCl"] 2HCl | 592.56 | 520 |

TABLE 7-continued

| Example | Structural Formula | TMW | LC-MS (found) |
|---|---|---|---|
| 16 | | 578.53 | 506 |
| 17 | | 634.60 | 562 |
| 18 | | 620.57 | 548 |
| 19 | | 596.52 | 524 |

TABLE 7-continued
| Example | Structural Formula | TMW | LC-MS (found) |
|---|---|---|---|
| 20 | 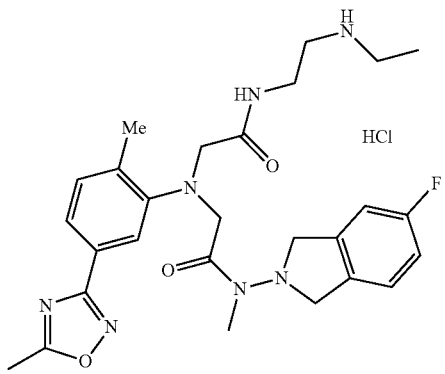 [SMILES: CCNCCNC(=O)CN(CC(=O)N(C)N1Cc2ccc(F)cc2C1)c1cc(-c2noc(C)n2)ccc1C ; Cl] HCl | 560.06 | 524 |
| 21 | 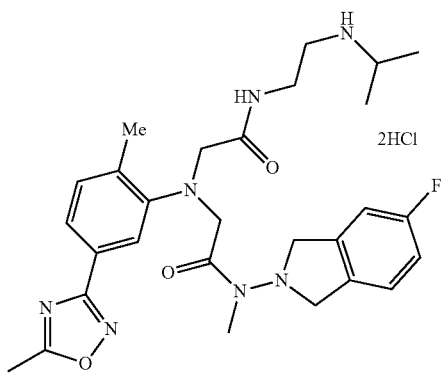 [SMILES: Cc1nc(-c2ccc(C)c(N(CC(=O)NCCNC(C)C)CC(=O)N(C)N3Cc4ccc(F)cc4C3)c2)no1 ; "2HCl"] 2HCl | 610.55 | 538 |
| 22 | 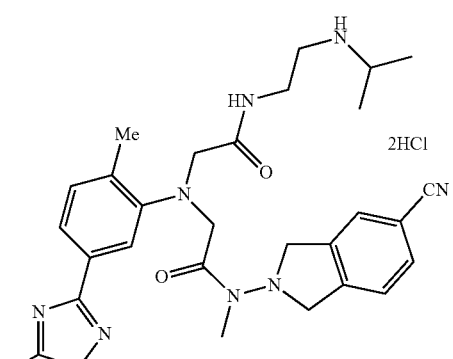 2HCl | 617.57 | 545 |
| 23 | 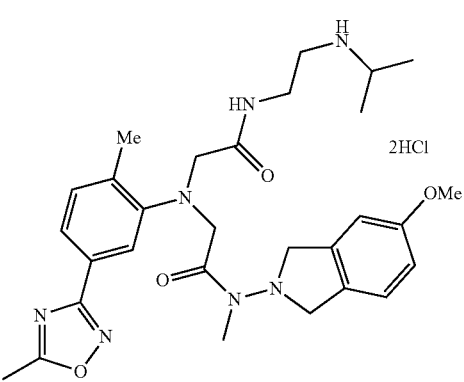 [SMILES: COc1ccc2c(c1)CN(N(C)C(=O)CN(CC(=O)NCCNC(C)C)c1cc(-c3noc(C)n3)ccc1C)C2 ; "2HCl"] 2HCl | 622.59 | 550 |

TABLE 7-continued

| Example | Structural Formula | TMW | LC-MS (found) |
|---|---|---|---|
| 24 | (structure shown: compound with Me-phenyl, oxadiazole, isoindoline-OMe, amide linkages, ethylamino group; 2HCl salt) | 608.56 | 536 |

Example 25

N²-{2-[2,3-dihydro-1H-inden-2-yl(methyl)amino]-2-oxoethyl}-N²-[2-methyl-5-(5-methyl-1,2,4-oxadiazol-3-yl)phenyl]-N¹-[2-(isopropylamino)ethyl]glycinamide hydrochloride

Step A

N-{2-[2,3-dihydro-1H-inden-2-yl(methyl)amino]-2-oxoethyl}-N-[2-methyl-5-(5-methyl-1,2,4-oxadiazol-3-yl)phenyl]glycine Using the compound (601 mg, 1.97 mmol) of Reference Example 62 and the compound of Reference Example 23 (576 mg, 3.14 mmol), and according to the method of Example 1, step A, the title compound (729 mg, yield 85%) was obtained as a colorless amorphous solid.

$^1$H-NMR (300 MHz, CDCl$_3$); δ (ppm) 2.39 (s, 3H), 2.64 2.65 (2s, 3H), 2.76 2.90 (2s, 3H), 2.91-3.34 (m, 4H), 3.95 3.96 (2s, 2H), 4.02 4.17 (2s, 2H), 4.5-4.6 (m, 0.4H), 5.6-5.7 (m, 0.6H), 7.16-7.25 (m, 4H), 7.31 (d, J=8.0, 1H), 7.77 (d, J=8.0, 1H), 7.92 7.93 (2s, 1H), 13.9 (brs, 1H).

Step B

N²-{2-[2,3-dihydro-1H-inden-2-yl(methyl)amino]-2-oxoethyl}-N²-[2-methyl-5-(5-methyl-1,2,4-oxadiazol-3-yl)phenyl]-N¹-{2-[(tert-butoxycarbonyl)(isopropyl)amino]ethyl}glycinamide Using the compound (360 mg, 0.829 mmol) obtained in step A, and the compound (253 mg, 1.25 mmol) of Reference Example 3, and according to the method of Example 1, step B, the title compound (459 mg, yield 89%) was obtained as a colorless amorphous solid.

$^1$H-NMR (300 MHz, CDCl$_3$); δ (ppm) 1.11 (d, J=6.6, 6H), 1.45 (brs, 9H), 2.43 (s, 3H), 2.63 2.64 (2s, 3H), 2.74 2.78 (2s, 3H), 2.8-3.2 (m, 6H), 3.35-3.45 (m, 2H), 3.84 (s, 2H), 3.94 4.09 (2s, 2H), 4.1-4.4 (broad, 1H), 4.6-4.7 (m, 0.4H), 5.5-5.7 (m, 0.6H), 7.18 (broad, 4H), 7.29 (d, J=8.1, 1H), 7.71 (d, J=8.1, 1H), 7.92 7.94 (2s, 1H), 8.1-8.8 (broad, 1H).

Step C

N²-{2-[2,3-dihydro-1H-inden-2-yl(methyl)amino]-2-oxoethyl}-N²-[2-methyl-5-(5-methyl-1,2,4-oxadiazol-3-yl)phenyl]-N¹-[2-(isopropylamino)ethyl]glycinamide hydrochloride Using the compound (455 mg, 0.735 mmol) obtained in step B and according to the method of Example 1, step C, the title compound (362 mg, yield 89%) was obtained as a colorless solid.

$^1$H-NMR (300 MHz, DMSO-d$_6$); δ (ppm) 1.19 (d, J=6.3, 6H), 2.36 (s, 3H), 2.66 (s, 3H), 2.68 2.77 (2s, 3H), 2.8-3.2 (m, 6H), 3.2-3.3 (m, 1H), 3.35-3.42 (m, 2H), 3.88 3.91 (2s, 2H), 4.10 4.27 (2s, 2H), 4.8-4.9 (m, 0.4H), 5.2-5.4 (m, 0.6H), 7.16 7.20 (2broad, 4H), 7.30 (d, J=8.0, 1H), 7.53 (d, J=8.0, 1H), 7.75 7.79 (2s, 1H), 8.42 (broad t, 1H), 8.69 (brs, 2H).

Example 26

N²-{2-[2,3-dihydro-1H-inden-2-yl(methyl)amino]-2-oxoethyl}-N²-[2-methyl-5-(5-methyl-1,2,4-oxadiazol-3-yl)phenyl]-N¹-[2-(ethylamino)ethyl]glycinamide hydrochloride

Step A

N²-{2-[2,3-dihydro-1H-inden-2-yl(methyl)amino]-2-oxoethyl}-N²-[2-methyl-5-(5-methyl-1,2,4-oxadiazol-3-yl)phenyl]-N¹-(2-[(tert-butoxycarbonyl)(ethyl)amino]ethyl)glycinamide Using the compound (359 mg, 0.826 mmol) of Example 25, step A, and the compound (246 mg, 1.31 mmol) of Reference Example 2, and according to the method of Example 1, step B, the title compound (417 mg, yield 83%) was obtained as a colorless amorphous solid.

$^1$H-NMR (300 MHz, CDCl$_3$); δ (ppm) 1.04 (t, J=7.1, 3H), 1.44 (brs, 9H), 2.42 (s, 3H), 2.63 2.64 (2s, 3H), 2.74 2.79 (2s, 3H), 2.8-3.3 (m, 8H), 3.4-3.5 (m, 2H), 3.84 (s, 2H), 3.94 4.09 (2s, 2H), 4.6-4.7 (m, 0.4H), 5.5-5.7 (m, 0.6H), 7.18 (broad, 4H), 7.29 (d, J=7.8, 1H), 7.71 (d, J=7.8, 1H), 7.91 7.93 (2s, 1H), 8.34 8.62 (2broad, 1H).

Step B

N²-{2-[2,3-dihydro-1H-inden-2-yl(methyl)amino]-2-oxoethyl}-N²-[2-methyl-5-(5-methyl-1,2,4-oxadiazol-3-yl)phenyl]-N¹-[2-(ethylamino)ethyl]glycinamide hydrochloride Using the compound (414 mg, 0.685 mmol) obtained in step A and according to the method of Example 1, step C, the title compound (328 mg, yield 88%) was obtained as a colorless solid.

¹H-NMR (300 MHz, DMSO-d₆); δ (ppm) 1.16 (t, J=7.2, 3H), 2.36 (s, 3H), 2.66 (s, 3H), 2.67 2.77 (2s, 3H), 2.8-3.2 (m, 8H), 3.34-3.41 (m, 2H), 3.88 3.91 (2s, 2H), 4.10 4.27 (2s, 2H), 4.8-4.9 (m, 0.4H), 5.2-5.4 (m, 0.6H), 7.16 7.20 (2broad, 4H), 7.30 (d, J=8.0, 1H), 7.53 (d, J=8.0, 1H), 7.75 7.79 (2s, 1H), 8.40 (broad t, 1H), 8.73 (brs, 2H).

Example 27

N²-{2-[methyl(5-methyl-2,3-dihydro-1H-inden-2-yl)amino]-2-oxoethyl}-N²-[2-methyl-5-(5-methyl-1,2,4-oxadiazol-3-yl)phenyl]-N¹-[2-(isopropylamino)ethyl]glycinamide hydrochloride Using the compound (519 mg, 0.901 mmol) of Example 6, step B and according to the methods of Reference Example 62, step A, and Example 1, step C, the title compound (322 mg, yield 63%) was obtained as a pale-yellow amorphous solid.

¹H-NMR (300 MHz, DMSO-d₆); δ (ppm) 1.20 (d, J=6.1, 6H), 1.91 (s, 3H), 2.04-3.15 (m, 15H), 3.17-3.42 (m, 3H), 3.87-3.91 (m, 2H), 4.27 (s, 1.2H), 4.48 (s, 0.8H), 4.81-4.84 (m, 0.4H), 5.26-5.34 (m, 0.6H), 6.95 (d, J=7.4, 1H), 7.02 (s, 1H), 7.08 (d, J=7.5, 1H), 7.29 (d, J=7.9, 1H), 7.53 (d, J=7.7, 1H), 7.74-7.79 (m, 1H), 8.42-8.47 (m, 1H), 8.90 (brs, 2H).

Example 28

N²-{2-[methyl(5-methyl-2,3-dihydro-1H-inden-2-yl)amino]-2-oxoethyl}-N²-[2-methyl-5-(5-methyl-1,2,4-oxadiazol-3-yl)phenyl]-N¹-[2-(ethylamino)ethyl]glycinamide hydrochloride Using the compound (519 mg, 0.924 mmol) of Example 7, step A and according to the methods of Reference Example 62, step A, and Example 1, step C, the title compound (309 mg, yield 60%) was obtained as a pale-yellow amorphous solid.

¹H-NMR (300 MHz, DMSO-d₆); δ (ppm) 1.13-1.20 (m, 3H), 1.91 (s, 3H), 2.26 (s, 3H), 2.36 (s, 3H), 2.52-3.10 (m, 11H), 3.33-3.41 (m, 2H), 3.87-3.92 (m, 2H), 4.26 (s, 1.2H), 4.48 (s, 0.8H), 4.81-4.85 (m, 0.4H), 5.27-5.33 (m, 0.6H), 6.95 (d, J=7.2, 1H), 7.02 (s, 1H), 7.08 (d, J=7.5, 1H), 7.30 (d, J=7.8, 1H), 7.53 (d, J=7.8, 1H), 7.75-7.79 (m, 1H), 8.39-8.42 (m, 1H), 8.82 (brs, 2H).

Example 29

N²-{2-[(5-methoxy-2,3-dihydro-1H-inden-2-yl)(methyl)amino]-2-oxoethyl}-N²-[2-methyl-5-(5-methyl-1,2,4-oxadiazol-3-yl)phenyl]-N¹-[2-(isopropylamino)ethyl]glycinamide hydrochloride Using the compound (610 mg, 1.03 mmol) of Example 8, step B and according to the methods of Reference Example 62, step A, and Example 1, step C, the title compound (357 mg, yield 59%) was obtained as a pale-yellow amorphous solid.

¹H-NMR (300 MHz, DMSO-d₆); δ (ppm) 1.07-1.21 (m, 6H), 2.36 (s, 3H), 2.64-3.17 (m, 12H), 3.20-3.45 (m, 3H), 3.71 (s, 3H), 3.87-3.91 (m, 2H), 4.11 (s, 1.2H), 4.27 (s, 0.8H), 4.85-4.89 (m, 0.4H), 5.28-5.36 (m, 0.6H), 6.71 (d, J=8.2, 1H), 6.80 (s, 1H), 7.10 (d, J=8.2, 1H), 7.29 (d, J=8.0, 1H), 7.51-7.55 (m, 1H), 7.74-7.79 (m, 1H), 8.44-8.47 (m, 1H), 8.95 (brs, 2H).

Example 30

N²-{2-[(5-methoxy-2,3-dihydro-1H-inden-2-yl)(methyl)amino]-2-oxoethyl}-N²-[2-methyl-5-(5-methyl-1,2,4-oxadiazol-3-yl)phenyl]-N¹-[2-(ethylamino)ethyl]glycinamide hydrochloride Using the compound (600 mg, 1.04 mmol) obtained in Example 9, step A and according to the methods of Reference Example 62, step A, and Example 1, step C, the title compound (406 mg, yield 68%) was obtained as a pale-yellow amorphous solid.

¹H-NMR (300 MHz, DMSO-d₆); δ (ppm) 1.13-1.20 (m, 3H), 2.35 (s, 3H), 2.64-3.15 (m, 14H), 3.34-3.40 (m, 2H), 3.71 (s, 3H), 3.87-3.91 (m, 2H), 4.26 (s, 1.2H), 4.48 (s, 0.8H), 4.81-4.85 (m, 0.4H), 5.27-5.34 (m, 0.6H), 6.72 (d, J=8.3, 1H), 6.80 (s, 1H), 7.10 (d, J=7.9, 1H), 7.30 (d, J=7.9, 1H), 7.51-7.55 (m, 1H), 7.74-7.79 (m, 1H), 8.40-8.42 (m, 1H), 8.76 (brs, 2H).

Example 31

N²-{2-[(5-fluoro-2,3-dihydro-1H-inden-2-yl)(methyl)amino]-2-oxoethyl}-N²-[2-methyl-5-(5-methyl-1,2,4-oxadiazol-3-yl)phenyl]-N¹-[2-(isopropylamino)ethyl]glycinamide hydrochloride Using the compound (700 mg, 1.21 mmol) of Example 10, step A and according to the methods of Reference Example 62, step A, and Example 1, step C, the title compound (531 mg, yield 77%) was obtained as a pale-yellow amorphous solid.

¹H-NMR (300 MHz, DMSO-d₆); δ (ppm) 1.19 (d, J=6.6, 6H), 2.36 (s, 3H), 2.66 (s, 3H), 2.67-2.78 (m, 3H), 2.85-3.27 (m, 6H), 3.28-3.34 (m, 1H), 3.35-3.47 (m, 2H), 3.87-3.91 (m, 2H), 4.11 (s, 1.2H), 4.27 (s, 0.8H), 4.86-4.93 (m, 0.4H), 5.28-5.35 (m, 0.6H), 6.96 (t, J=8.7, 1H), 7.04 (d, J=6.3, 1H), 7.20-7.24 (m, 1H), 7.30 (d, J=7.8, 1H), 7.52-7.56 (m, 1H), 7.73-7.79 (m, 1H), 8.41-8.44 (m, 1H), 8.80 (brs, 2H).

Example 32

N²-{2-[(5-chloro-2,3-dihydro-1H-inden-2-yl)(methyl)amino]-2-oxoethyl}-N²-[2-methyl-5-(5-methyl-1,2,4-oxadiazol-3-yl)phenyl]-N¹-[2-(isopropylamino)ethyl]glycinamide hydrochloride Using the compound (1.00 g, 1.68 mmol) of Example 11, step A and according to the methods of Reference Example 62, step A, and Example 1, step C, the title compound (703 mg, yield 71%) was obtained as a pale-yellow amorphous solid.

¹H-NMR (300 MHz, DMSO-d₆); δ (ppm) 1.20 (d, J=6.4, 6H), 2.36 (s, 3H), 2.64-3.19 (m, 12H), 6.20-6.31 (m, 1H), 6.32-6.47 (m, 2H), 3.86-3.92 (m, 2H), 4.11 (s, 1.2H), 4.27 (s, 0.8H), 4.86-4.94 (m, 0.4H), 5.26-5.33 (m, 0.6H), 7.16-7.31 (m, 4H), 7.51-7.55 (m, 1H), 7.73-7.79 (m, 1H), 8.40-8.43 (m, 1H), 8.86 (brs, 2H).

Example 33

$N^2$-{2-[methyl(4-methyl-2,3-dihydro-1H-inden-2-yl)amino]-2-oxoethyl}-$N^2$-[2-methyl-5-(5-methyl-1,2,4-oxadiazol-3-yl)phenyl]-$N^1$-[2-(isopropylamino)ethyl]glycinamide hydrochloride Using the compound (1.25 g, 2.17 mmol) of Example 12, step A and according to the methods of Reference Example 62, step A, and Example 1, step C, the title compound (608 mg, yield 49%) was obtained as a pale-yellow amorphous solid.

$^1$H-NMR (300 MHz, DMSO-d$_6$); δ (ppm) 1.20 (d, J=6.6, 6H), 2.18 (s, 3H), 2.37 (s, 3H), 2.66 (s, 3H), 2.67-3.18 (m, 9H), 3.18-3.23 (m, 1H), 3.24-3.48 (m, 2H), 3.87-3.92 (m, 2H), 4.11 (s, 1.2H), 4.29 (s, 0.8H), 4.83-4.88 (m, 0.4H), 5.28-5.35 (m, 0.6H), 6.94-7.08 (m, 3H), 7.30 (d, J=8.1, 1H), 7.53 (dd, J=1.5, 7.8, 1H), 7.74-7.80 (m, 1H), 8.31-8.45 (m, 1H), 8.91 (brs, 2H).

Example 34

$N^2$-{2-[(5,6-dimethoxy-2,3-dihydro-1H-inden-2-yl)(methyl)amino]-2-oxoethyl}-$N^2$-[2-methyl-5-(5-methyl-1,2,4-oxadiazol-3-yl)phenyl]-$N^1$-[2-(isopropylamino)ethyl]glycinamide hydrochloride

Step A

N-(5-cyano-2-methylphenyl)-N-(2-[(5,6-dimethoxy-2,3-dihydro-1H-inden-2-yl)(methyl)amino]-2-oxoethyl)glycine Using the compound (1.00 g, 4.03 mmol) of Reference Example 61 and the compound (1.47 g, 6.05 mmol) of Reference Example 30, and according to the method of Example 4, step A, the title compound (966 mg, yield 55%) was obtained as a pale-yellow amorphous solid.

$^1$H-NMR (300 MHz, DMSO-d$_6$); δ (ppm) 2.33 (s, 3H), 2.64 2.75 (2s, 3H), 2.73-3.04 (m, 4H), 3.70 (s, 6H), 3.95 3.96 (2s, 2H), 4.09 4.24 (2s, 2H), 4.82-4.88 (m, 0.4H), 5.26-5.34 (m, 0.6H), 6.82 (s, 2H), 7.29-7.36 (m, 2H), 7.45-7.49 (m, 1H), 12.61 (brs, 1H).

Step B $N^2$-(5-cyano-2-methylphenyl)-$N^2$-{2-[(5,6-dimethoxy-2,3-dihydro-1H-inden-2-yl)(methyl)amino]-2-oxoethyl}-$N^1$-{2-[(tert-butoxycarbonyl)(isopropyl)amino]ethyl}glycinamide Using the compound (966 mg, 2.21 mmol) obtained in step A, and the compound (671 mg, 3.32 mmol) of Reference Example 3, and according to the method of Example 1, step B, the title compound (1.23 g, yield 90%) was obtained as a pale-yellow amorphous solid.

$^1$H-NMR (300 MHz, CDCl$_3$); δ (ppm) 1.12 (d, J=6.6, 6H), 1.44 (s, 9H), 2.42 (s, 3H), 2.73-3.45 (m, 11H), 3.75-4.21 (m, 5H), 3.86 (s, 6H), 4.59-4.66 (m, 0.4H), 5.52-5.61 (m, 0.6H), 6.74 (s, 2H), 7.23-7.34 (m, 2H), 7.49 (s, 1H), 7.78-8.59 (broad, 1H).

Step C $N^2$-{2-[(5,6-dimethoxy-2,3-dihydro-1H-inden-2-yl)(methyl)amino]-2-oxoethyl}-$N^2$-[2-methyl-5-(5-methyl-1,2,4-oxadiazol-3-yl)phenyl]-$N^1$-[2-(isopropylamino)ethyl]glycinamide hydrochloride Using the compound (730 mg, 1.17 mmol) obtained in step B and according to the methods of Reference Example 62, step A, and Example 1, step C, the title compound (369 mg, yield 52%) was obtained as a colorless amorphous solid.

$^1$H-NMR (300 MHz, DMSO-d$_6$); δ (ppm) 1.20 (d, J=6.5, 6H), 2.36 (s, 3H), 2.58-3.16 (m, 9H), 2.66 (s, 3H), 3.21-3.25 (m, 1H), 3.36-3.43 (m, 2H), 3.70 (s, 6H), 3.88 3.91 (2s, 2H), 4.11 4.27 (2s, 2H), 4.82-4.88 (m, 0.4H), 5.28-5.35 (m, 0.6H), 6.81 (s, 2H), 7.29 (d, J=7.9, 1H), 7.53 (d, J=7.8, 1H), 7.75-7.79 (m, 1H), 8.43-8.47 (m, 1H), 8.98 (brs, 2H).

Example 35

$N^2$-[2-methyl-5-(5-methyl-1,2,4-oxadiazol-3-yl)phenyl]-$N^2$-{2-[methyl(1,2,3,4-tetrahydronaphthalen-2-yl)amino]-2-oxoethyl}-$N^1$-[2-(isopropylamino)ethyl]glycinamide hydrochloride Using the compound (700 mg, 1.22 mmol) of Example 13, step B and according to the methods of Reference Example 62, step A, and Example 1, step C, the title compound (387 mg, yield 52%) was obtained as a colorless amorphous solid.

$^1$H-NMR (300 MHz, DMSO-d$_6$); δ (ppm) 1.19 (d, J=6.6, 6H), 1.64-1.98 (m, 2H), 2.32 2.37 (2s, 3H), 2.65 (s, 3H), 2.66-3.12 (m, 9H), 3.20-3.43 (m, 3H), 3.50-4.68 (m, 5H), 7.03-7.09 (m, 4H), 7.29 (t, J=6.9, 1H), 7.53 (d, J=7.5, 1H), 7.76 (d, J=11.4, 1H), 8.46 (t, J=5.4, 1H), 8.84 (brs, 2H).

Example 36

$N^2$-[2-methyl-5-(5-methyl-1,2,4-oxadiazol-3-yl)phenyl]-$N^2$-[2-{methyl[(3aR,7aS)-octahydro-2H-isoindol-2-yl]amino}-2-oxoethyl]-$N^1$-[2-(isopropylamino)ethyl]glycinamide dihydrochloride

Step A

N-[2-methyl-5-(5-methyl-1,2,4-oxadiazol-3-yl)phenyl]-N-[2-{methyl[(3aR,7aS)-octahydro-2H-isoindol-2-yl]amino}-2-oxoethyl]glycine Using the compound (689 mg, 2.26 mmol) of Reference Example 62 and the compound (436 mg, 2.83 mmol) of Reference Example 37, and according to the method of Example 4, step A, the title compound (844 mg, yield 85%) was obtained as a colorless amorphous solid.

$^1$H-NMR (300 MHz, CDCl$_3$); δ (ppm) 1.2-1.7 (m, 8H), 2.0-2.2 (m, 2H), 2.36 (s, 3H), 2.65 2.66 (2s, 3H), 2.7-2.8 (m, 2H), 2.8-3.0 (m, 2H), 2.99 3.03 (2s, 3H), 3.93 3.96 (2s, 2H), 4.19 4.21 (2s, 2H), 7.30 (d, J=7.8, 1H), 7.74 (dd, J=1.8, 7.8, 1H), 7.94 (d, J=1.8, 1H), 13.7 (brs, 1H).

Step B $N^2$-[2-methyl-5-(5-methyl-1,2,4-oxadiazol-3-yl)phenyl]-$N^2$-[2-{methyl[(3aR,7aS)-octahydro-2H-isoindol-2-yl]amino}-2-oxoethyl]-$N^1$-{2-[(tert-butoxycarbonyl)(isopropyl)amino]ethyl}glycinamide Using the compound (410 mg, 0.929 mmol) obtained in step A, and the compound (284 mg, 1.40 mmol) of Reference Example 3, and according to the method of Example 1, step B, the title compound (553 mg, yield 95%) was obtained as a colorless amorphous solid.

$^1$H-NMR (300 MHz, CDCl$_3$); δ (ppm) 1.10 (d, J=6.9, 6H), 1.2-1.8 (m, 8H), 1.46 (brs, 9H), 2.0-2.2 (m, 2H), 2.39 (s, 3H), 2.63 (s, 3H), 2.7-2.8 (m, 2H), 2.8-3.0 (m, 2H), 2.87 2.91 (2s, 3H), 3.0-3.2 (m, 2H), 3.3-3.5 (m, 2H), 3.79 3.82 (2s, 2H), 3.9-4.3 (broad, 1H), 4.16 4.17 (2s, 2H), 7.27 (d, J=7.8, 1H), 7.67 (d, J=7.8, 1H), 7.93 (s, 1H), 8.2-8.8 (broad, 1H).

Step C

N$^2$-[2-methyl-5-(5-methyl-1,2,4-oxadiazol-3-yl)phenyl]-N$^2$-[2-{methyl[(3aR,7aS)-octahydro-2H-isoindol-2-yl]amino}-2-oxoethyl]-N$^1$-[2-(isopropylamino)ethyl]glycinamide dihydrochloride Using the compound (540 mg, 0.863 mmol) obtained in step B and according to the method of Example 1, step C, the title compound (438 mg, yield 85%) was obtained as a colorless solid.

$^1$H-NMR (300 MHz, DMSO-d$_6$); δ (ppm) 1.18 (d, J=6.5, 6H), 1.2-1.6 (m, 8H), 2.0-2.2 (m, 2H), 2.33 (s, 3H), 2.6-2.7 (m, 2H), 2.64 (s, 3H), 2.79 2.82 (2s, 3H), 2.8-3.0 (m, 4H), 3.2-3.5 (m, 3H), 3.91 3.93 (2s, 2H), 4.24 4.27 (2s, 2H), 7.29 (d, J=7.8, 1H), 7.50 (d, J=7.8, 1H), 7.71 (s, 1H), 8.3-8.5 (m, 1H), 8.55 (brs, 2H).

Example 37

N$^2$-[2-methyl-5-(5-methyl-1,2,4-oxadiazol-3-yl)phenyl]-N$^2$-[2-{methyl[(3aR,7aS)-octahydro-2H-isoindol-2-yl]amino}-2-oxoethyl]-N$^1$-[2-(ethylamino)ethyl]glycinamide dihydrochloride Step A N$^2$-[2-methyl-5-(5-methyl-1,2,4-oxadiazol-3-yl)phenyl]-N$^2$-[2-{methyl[(3aR,7aS)-octahydro-2H-isoindol-2-yl]amino}-2-oxoethyl]-N$^1$-{2-[(tert-butoxycarbonyl)(ethyl)amino]ethyl}glycinamide Using the compound (429 mg, 0.972 mmol) obtained in Example 36, step A, and the compound (302 mg, 1.60 mmol) of Reference Example 2, and according to the method of Example 1, step B, the title compound (557 mg, yield 94%) was obtained as a colorless amorphous solid.

$^1$H-NMR (300 MHz, CDCl$_3$); δ (ppm) 1.02 (t, J=7.2, 3H), 1.2-1.7 (m, 8H), 1.45 (brs, 9H), 2.0-2.2 (m, 2H), 2.38 (s, 3H), 2.63 (s, 3H), 2.7-2.8 (m, 2H), 2.8-3.0 (m, 2H), 2.88 2.91 (2s, 3H), 3.0-3.3 (m, 4H), 3.4-3.5 (m, 2H), 3.79 3.81 (2s, 2H), 4.15 4.17 (2s, 2H), 7.27 (d, J=7.5, 1H), 7.67 (d, J=7.5, 1H), 7.92 (s, 1H), 8.3-8.8 (broad, 1H).

Step B

N$^2$-[2-methyl-5-(5-methyl-1,2,4-oxadiazol-3-yl)phenyl]-N$^2$-[2-{methyl[(3aR,7aS)-octahydro-2H-isoindol-2-yl]amino}-2-oxoethyl]-N$^1$-[2-(ethylamino)ethyl]glycinamide dihydrochloride Using the compound (553 mg, 0.904 mmol) obtained in step A and according to the method of Example 1, step C, the title compound (429 mg, yield 81%) was obtained as a colorless solid.

$^1$H-NMR (300 MHz, DMSO-d$_6$); δ (ppm) 1.15 (t, J=7.2, 3H), 1.2-1.6 (m, 8H), 2.0-2.2 (m, 2H), 2.33 (s, 3H), 2.6-2.8 (m, 2H), 2.64 (s, 3H), 2.78 2.82 (2s, 3H), 2.8-3.0 (m, 6H), 3.34-3.41 (m, 2H), 3.91 3.93 (2s, 2H), 4.24 4.26 (2s, 2H), 7.28 (d, J=7.9, 1H), 7.50 (d, J=7.9, 1H), 7.71 (s, 1H), 8.3-8.5 (m, 1H), 8.62 (brs, 2H).

Example 38

N$^2$-{2-[3,4-dihydroisoquinolin-2 (1H)-yl(methyl)amino]-2-oxoethyl}-N$^2$-[2-methyl-5-(5-methyl-1,2,4-oxadiazol-3-yl)phenyl]-N$^1$-[2-(isopropylamino)ethyl]glycinamide dihydrochloride Step A N-{2-[3,4-dihydroisoquinolin-2 (1H)-yl(methyl)amino]-2-oxoethyl}-N-[2-methyl-5-(5-methyl-1,2,4-oxadiazol-3-yl)phenyl]glycine Using the compound (593 mg, 2.26 mmol) of Reference Example 62 and the compound (414 mg, 2.55 mmol) of Reference Example 42, and according to the method of Example 4, step A, the title compound (915 mg, yield>100%) was obtained as a colorless amorphous solid.

$^1$H-NMR (300 MHz, CDCl$_3$); δ (ppm) 2.35 (s, 3H), 2.62 (s, 3H), 2.8-3.3 (m, 4H), 3.11 (s, 3H), 3.76 (d, J=14.1, 1H), 3.93 3.94 (2s, 2H), 4.17 (d, J=14.1, 1H), 4.23 4.26 (2s, 2H), 6.9-7.1 (m, 1H), 7.11-7.19 (m, 3H), 7.27 (d, J=7.8, 1H), 7.72 (dd, J=1.5, 7.8, 1H), 7.88 (d, J=1.5, 1H), 13.51 (brs, 1H).

Step B

N$^2$-{2-[3,4-dihydroisoquinolin-2 (1H)-yl(methyl)amino]-2-oxoethyl}-N$^2$-[2-methyl-5-(5-methyl-1,2,4-oxadiazol-3-yl)phenyl]-N$^1$-{2-[(tert-butoxycarbonyl)(isopropyl)amino]ethyl}glycinamide Using the compound (510 mg, 1.13 mmol) obtained in step A, and the compound (332 mg, 1.64 mmol) of Reference Example 3, and according to the method of Example 1, step B, the title compound (594 mg, yield 83%) was obtained as a colorless amorphous solid.

$^1$H-NMR (300 MHz, CDCl$_3$); δ (ppm) 1.11 (d, J=6.8, 6H), 1.45 (brs, 9H), 2.38 (s, 3H), 2.62 (s, 3H), 2.7-2.9 (m, 1H), 2.9-3.3 (m, 5H), 2.98 (s, 3H), 3.3-3.5 (m, 2H), 3.69 (d, J=14.1, 1H), 3.80 (s, 2H), 3.9-4.3 (broad, 1H), 4.10 (d, J=14.1, 1H), 4.17 (d, J=17.5, 1H), 4.26 (d, J=17.5, 1H), 6.97-7.01 (m, 1H), 7.1-7.2 (m, 3H), 7.25 (d, J=7.8, 1H), 7.66 (dd, J=1.2, 7.8, 1H), 7.87 (d, J=1.2, 1H), 8.2-8.7 (broad, 1H).

Step C

N$^2$-{2-[3,4-dihydroisoquinolin-2 (1H)-yl(methyl)amino]-2-oxoethyl}-N$^2$-[2-methyl-5-(5-methyl-1,2,4-oxadiazol-3-yl)phenyl]-N$^1$-[2-(isopropylamino)ethyl]glycinamide dihydrochloride Using the compound (590 mg, 0.931 mmol) obtained in step B and according to the method of Example 1, step C, the title compound (482 mg, yield 85%) was obtained as a colorless solid.

$^1$H-NMR (300 MHz, DMSO-d$_6$); δ (ppm) 1.17 (d, J=6.4, 6H), 2.30 (s, 3H), 2.65 (s, 3H), 2.8-3.3 (m, 7H), 2.98 (s, 3H), 3.34-3.42 (m, 2H), 3.77 (d, J=14.4, 1H), 3.92 (s, 2H), 4.11 (d, J=14.4, 1H), 4.23 (d, J=17.7, 1H), 4.38 (d, J=17.7, 1H), 6.9-7.1 (m, 1H), 7.14-7.18 (m, 3H), 7.26 (d, J=7.8, 1H), 7.49 (dd, J=1.2, 7.8, 1H), 7.69 (d, J=1.2, 1H), 8.38 (t, J=5.7, 1H), 8.68 (brs, 2H).

Example 39

N²-[2-methyl-5-(5-methyl-1,2,4-oxadiazol-3-yl)phenyl]-N²-[2-{methyl[4-(methylsulfonyl)piperazin-1-yl]amino}-2-oxoethyl]-N¹-[2-(isopropylamino)ethyl]glycinamide dihydrochloride

Step A

N²-[2-methyl-5-(5-methyl-1,2,4-oxadiazol-3-yl)phenyl]-N²-[2-{methyl[4-(methylsulfonyl)piperazin-1-yl]amino}-2-oxoethyl]-N¹-{2-[(tert-butoxycarbonyl)(isopropyl)amino]ethyl}glycinamide Using the compound (531 mg, 1.74 mmol) of Reference Example 62, the compound (442 mg, 2.29 mmol) of Reference Example 48 and the compound (552 mg, 2.73 mmol) of Reference Example 3, and according to the methods of Example 4, step A, and Example 1, step B, the title compound (1.07 g, yield 92%) was obtained as a colorless amorphous solid.

$^1$H-NMR (300 MHz, CDCl$_3$); δ (ppm) 1.13 (d, J=6.9, 6H), 1.46 (brs, 9H), 2.39 (s, 3H), 2.64 (s, 3H), 2.7-2.8 (m, 2H), 2.84 (s, 3H), 2.91 (s, 3H), 2.95-3.05 (m, 4H), 3.05-3.20 (m, 2H), 3.3-3.5 (m, 2H), 3.6-3.8 (m, 4H), 3.9-4.3 (broad, 1H), 4.22 (s, 2H), 7.28 (d, J=8.1, 1H), 7.69 (dd, J=1.2, 8.1, 1H), 7.87 (d, J=1.2, 1H), 8.2-8.8 (broad, 1H).

Step B

N²-[2-methyl-5-(5-methyl-1,2,4-oxadiazol-3-yl)phenyl]-N²-[2-{methyl[4-(methylsulfonyl)piperazin-1-yl]amino}-2-oxoethyl]-N¹-[2-(isopropylamino)ethyl]glycinamide dihydrochloride Using the compound (1.04 g, 1.56 mmol) obtained in step A and according to the method of Example 1, step C, the title compound (951 mg, yield 96%) was obtained as a colorless solid.

$^1$H-NMR (300 MHz, DMSO-d$_6$); δ (ppm) 1.19 (d, J=6.4, 6H), 2.33 (s, 3H), 2.64 (s, 3H), 2.7-3.0 (m, 8H), 2.83 (s, 3H), 2.91 (s, 3H), 3.1-3.3 (m, 1H), 3.3-3.4 (m, 2H), 3.4-3.5 (m, 2H), 3.93 (s, 2H), 4.30 (s, 2H), 7.29 (d, J=7.8, 1H), 7.50 (dd, J=1.1, 7.8, 1H), 7.68 (d, J=1.1, 1H), 8.42 (broad t, 1H), 8.81 (brs, 2H).

Example 40

N²-{2-[(1-acetylpiperidin-4-yl)(methyl)amino]-2-oxoethyl}-N²-[2-methyl-5-(5-methyl-1,2,4-oxadiazol-3-yl)phenyl]-N¹-[2-(isopropylamino)ethyl]glycinamide hydrochloride

Step A

N-[2-{[1-(tert-butoxycarbonyl)piperidin-4-yl](methyl)amino}-2-oxoethyl]-N-[2-methyl-5-(5-methyl-1,2,4-oxadiazol-3-yl)phenyl]glycine Using the compound (929 mg, 3.04 mmol) of Reference Example 62 and the compound (782 mg, 3.65 mmol) of Reference Example 46, and according to the method of Example 1, step A, the title compound (1.65 g, yield 100%) was obtained as a pale-yellow amorphous solid.

$^1$H-NMR (300 MHz, CDCl$_3$); δ (ppm) 1.46 (s, 9H), 1.56-1.67 (m, 4H), 2.37 (s, 3H), 2.65 (s, 3H), 2.80-2.96 (m, 5H), 3.95 (s, 2H), 4.02 (s, 2H), 4.23-4.24 (m, 2H), 4.69 (m, 1H), 7.30 (dd, J=3.0, 8.1, 1H), 7.76 (dd, J=1.5, 8.1, 1H), 7.92 (dd, J=1.5, 7.8, 1H).

Step B

N²-[2-{[1-(tert-butoxycarbonyl)piperidin-4-yl](methyl)amino}-2-oxoethyl]-N²-[2-methyl-5-(5-methyl-1,2,4-oxadiazol-3-yl)phenyl]-N¹-[2-{(isopropyl)[(2-nitrophenyl)sulfonyl]amino}ethyl]glycinamide Using the compound (744 mg, 1.48 mmol) obtained in step A, and the compound (469 mg, 1.63 mmol) of Reference Example 7, and according to the method of Example 1, step B, the title compound (1.04 g, yield 91%) was obtained as a yellow amorphous solid.

$^1$H-NMR (300 MHz, CDCl$_3$); δ (ppm) 1.15 (d, J=6.9, 6H), 1.45 (s, 9H), 1.53-1.60 (m, 4H), 2.43 (s, 3H), 2.63 (s, 3H), 2.77-2.79 (m, 5H), 3.35-3.37 (m, 2H), 3.49-3.51 (m, 2H), 3.87 (s, 2H), 3.99 (s, 2H), 4.05-4.16 (m, 3H), 4.60-4.62 (m, 1H), 7.29 (m, 1H), 7.58-7.69 (m, 4H), 7.89 (m, 1H), 7.99-8.02 (m, 1H), 8.50-8.52 (m, 1H).

Step C

N²-[2-methyl-5-(5-methyl-1,2,4-oxadiazol-3-yl)phenyl]-N²-[2-{methyl(piperidin-4-yl)amino}-2-oxoethyl]-N¹-[2-{(isopropyl)[(2-nitrophenyl)sulfonyl]amino}ethyl]glycinamide hydrochloride Using the compound (1.04 g, 1.35 mmol) obtained in step B and according to the method of Example 1, step C, the title compound (950 mg, yield 100%) was obtained as a yellow solid.

$^1$H-NMR (300 MHz, DMSO-d$_6$); δ (ppm) 1.00-1.04 (m, 6H), 1.60-1.91 (m, 4H), 2.50 (s, 3H), 2.62 (s, 3H), 2.79 (s, 3H), 2.97 (m, 2H), 3.15-3.37 (m, 6H), 3.78-4.13 (m, 5H), 4.48-4.52 (m, 1H), 7.26-7.30 (m, 1H), 7.49-7.52 (m, 1H), 7.72-7.76 (m, 1H), 7.81-7.92 (m, 2H), 7.95-8.04 (m, 2H), 8.24-8.30 (m, 1H), 8.43 (brs, 1H), 8.65 (brs, 1H).

Step D

N²-{2-[(1-acetylpiperidin-4-yl)(methyl)amino]-2-oxoethyl}-N²-[2-methyl-5-(5-methyl-1,2,4-oxadiazol-3-yl)phenyl]-N¹-[2-{(isopropyl)[(2-nitrophenyl)sulfonyl]amino}ethyl]glycinamide The compound (300 mg, 0.424 mmol) obtained in step C was dissolved in dichloromethane (3 ml), triethylamine (0.14 ml, 1.0 mmol) and acetyl chloride (0.042 ml, 0.59 mmol) were added under ice-cooling with stirring, and the mixture was stirred at room temperature for 5 hr. Water was added to the reaction mixture, and the mixture was extracted with dichloromethane. The organic layer was washed with diluted hydrochloric acid, and dried over anhydrous magnesium sulfate. The insoluble material was filtered off, and the solution was concentrated under reduced pressure. The obtained oil was purified by silica gel column chromatography (methanol-dichloromethane) to give the title compound (266 mg, yield 88%) as a pale-yellow amorphous solid.

$^1$H-NMR (300 MHz, CDCl$_3$); δ (ppm) 1.16 (d, J=6.6, 6H), 1.54-1.67 (m, 4H), 2.10 (s, 3H), 2.43 (s, 3H), 2.5-2.6 (m, 1H), 2.64 (s, 3H), 2.77 (s, 3H), 3.1-3.2 (m, 1H), 3.37-3.40 (m, 2H), 3.48-3.52 (m, 2H), 3.87-3.89 (m, 3H), 4.00-4.14 (m, 3H), 4.67-4.75 (m, 2H), 7.26-7.30 (m, 1H), 7.58-7.61 (m, 1H), 7.67-7.70 (m, 3H), 7.89-7.92 (m, 1H), 8.00-8.03 (m, 1H), 8.52 (brs, 1H).

Step E $N^2$-{2-[(1-acetylpiperidin-4-yl)(methyl)amino]-2-oxoethyl}-$N^2$-[2-methyl-5-(5-methyl-1,2,4-oxadiazol-3-yl)phenyl]-$N^1$-[2-(isopropylamino)ethyl]glycinamide The compound (260 mg, 0.365 mmol) obtained in step D was dissolved in acetonitrile (3 ml). Then, benzenethiol (0.057 ml, 0.547 mmol) and cesium carbonate (594 mg, 1.82 mmol) were added, and the mixture was stirred at room temperature for 10 hr. The reaction mixture was diluted with dichloromethane, and the organic layer was washed with diluted aqueous sodium hydroxide solution, and dried over anhydrous magnesium sulfate. The insoluble material was filtered off, and the solution was concentrated under reduced pressure. The obtained oil was purified by silica gel column chromatography (NH silica gel use, methanol-dichloromethane) to give the title compound (161 mg, yield 84%) as a pale-yellow amorphous solid. This was directly used for the next step.

Step F $N^2$-{2-[(1-acetylpiperidin-4-yl)(methyl)amino]-2-oxoethyl}-$N^2$-[2-methyl-5-(5-methyl-1,2,4-oxadiazol-3-yl)phenyl]-$N^1$-[2-(isopropylamino)ethyl]glycinamide hydrochloride The compound (161 mg, 0.303 mmol) obtained in step E was dissolved in ethyl acetate (2 ml), 4N hydrochloric acid-ethyl acetate solution (0.16 ml) was added at room temperature with stirring, and the mixture was stirred at the same temperature for 2.5 hr. To the reaction mixture was added diethyl ether (2 ml), the precipitated solid was collected by filtration, washed with diethyl ether, and dried under reduced pressure to give the title compound (164 mg, yield 96%) as a colorless solid.
$^1$H-NMR (300 MHz, DMSO-$d_6$); δ (ppm) 1.18 (d, J=6.1, 6H), 1.45-1.62 (m, 4H), 1.99 (s, 3H), 2.34 (s, 3H), 2.65 (s, 3H), 2.77 (s, 3H), 2.90 (broad, 2H), 3.03-3.07 (m, 1H), 3.28-3.37 (m, 4H), 3.84-3.88 (m, 3H), 4.12 (d, J=11.7, 2H), 4.44-4.48 (m, 2H), 7.28-7.32 (m, 1H), 7.51 (m, 1H), 7.75 (d, J=13.1, 1H), 8.40 (broad, 3H).

Example 41

$N^2$-[2-methyl-5-(5-methyl-1,2,4-oxadiazol-3-yl)phenyl]-$N^2$-[2-{methyl[1-(methylsulfonyl)piperidin-4-yl]amino}-2-oxoethyl]-$N^1$-[2-(isopropylamino)ethyl]glycinamide hydrochloride Step A $N^2$-[2-methyl-5-(5-methyl-1,2,4-oxadiazol-3-yl)phenyl]-$N^2$-[2-{methyl[1-(methylsulfonyl)piperidin-4-yl]amino}-2-oxoethyl]-$N^1$-[2-{(isopropyl)[(2-nitrophenyl)sulfonyl]amino}ethyl]glycinamide The compound (300 mg, 0.42 mmol) of Example 40, step C was dissolved in dichloromethane (3 ml), triethylamine (0.14 ml, 1.0 mmol) and methanesulfonylchloride (0.043 ml, 0.56 mmol) were added under ice-cooling with stirring, and the mixture was stirred at room temperature for 7 hr. The reaction mixture was diluted with dichloromethane, and the organic layer was washed with water and diluted hydrochloric acid, and dried over anhydrous magnesium sulfate. The insoluble material was filtered off, and the solution was concentrated under reduced pressure. The obtained oil was purified by silica gel column chromatography (methanol-dichloromethane) to give the title compound (224 mg, yield 71%) as a yellow oil.
$^1$H-NMR (300 MHz, CDCl$_3$); δ (ppm) 1.15 (d, J=6.6, 6H), 1.73 (m, 4H), 2.43 (s, 3H), 2.64 (s, 3H), 2.79-2.81 (m, 8H), 3.38-3.50 (m, 4H), 3.87 (m, 4H), 4.02-4.11 (m, 3H), 7.26-7.30 (m, 1H), 7.62-7.70 (m, 4H), 7.89-7.99 (m, 2H), 8.59 (brs, 1H).

Step B $N^2$-[2-methyl-5-(5-methyl-1,2,4-oxadiazol-3-yl)phenyl]-$N^2$-[2-{methyl[1-(methylsulfonyl)piperidin-4-yl]amino}-2-oxoethyl]-$N^1$-[2-(isopropylamino)ethyl]glycinamide hydrochloride Using the compound (220 mg, 0.294 mmol) obtained in step A and according to the methods of Example 40, steps E and F, the title compound (133 mg, yield 76%) was obtained as a colorless solid.
$^1$H-NMR (300 MHz, DMSO-$d_6$); δ (ppm) 1.18 (d, J=6.3, 6H), 1.51-1.76 (m, 4H), 2.34 (s, 3H), 2.65-2.87 (m, 13H), 3.26-3.38 (m, 3H), 3.58-3.63 (m, 2H), 3.85-3.89 (m, 2H), 4.08-4.17 (m, 2H), 4.33 (m, 1H), 7.28-7.32 (m, 1H), 7.51-7.54 (m, 1H), 7.75 (d, J=15.6, 1H), 8.38-8.43 (m, 1H), 8.56 (brs, 2H).

Example 42

$N^2$-[2-{[1-(methoxycarbonyl)piperidin-4-yl](methyl)amino}-2-oxoethyl]-$N^2$-[2-methyl-5-(5-methyl-1,2,4-oxadiazol-3-yl)phenyl]-$N^1$-[2-(isopropylamino)ethyl]glycinamide hydrochloride Step A $N^2$-[2-methyl-5-(5-methyl-1,2,4-oxadiazol-3-yl)phenyl]-$N^2$-[2-{methyl[1-(methoxycarbonyl)piperidin-4-yl]amino}-2-oxoethyl]-$N^1$-[2-{(isopropyl)[(2-nitrophenyl)sulfonyl]amino}ethyl]glycinamide The compound (300 mg, 0.424 mmol) of Example 40, step C was dissolved in dichloromethane (3 ml), triethylamine (0.14 ml, 1.0 mmol) and methyl chloroformate (0.043 ml, 0.56 mmol) were added under ice-cooling with stirring, and the mixture was stirred at room temperature for 7 hr. The reaction mixture was diluted with dichloromethane, and the organic layer was washed with water and diluted hydrochloric acid, and dried over anhydrous magnesium sulfate. The insoluble material was filtered off, and the solution was concentrated under reduced pressure. The obtained oil was purified by silica gel column chromatography (methanol-dichloromethane) to give the title compound (276 mg, yield 89%) as a yellow amorphous solid.
$^1$H-NMR (300 MHz, CDCl$_3$); δ (ppm) 1.15 (d, J=6.3, 6H), 1.56 (m, 4H), 2.43 (s, 3H), 2.63 (s, 3H), 2.77-2.84 (m, 5H), 3.36-3.51 (m, 4H), 3.69 (s, 3H), 3.87 (s, 2H), 3.99-4.21 (m, 5H), 4.62 (m, 1H), 7.26-7.29 (m, 1H), 7.58-7.61 (m, 1H), 7.64-7.70 (m, 3H), 7.89-7.92 (m, 1H), 7.99-8.02 (m, 1H), 8.50 (brs, 1H).

Step B

N²-[2-methyl-5-(5-methyl-1,2,4-oxadiazol-3-yl)phenyl]-N²-[2-{[1-(methoxycarbonyl)piperidin-4-yl](methyl)amino}-2-oxoethyl]-N¹-[2-(isopropylamino)ethyl]glycinamide hydrochloride Using the compound (270 mg, 0.37 mmol) obtained in step A and according to the methods of Example 40, steps E and F, the title compound (165 mg, yield 77%) was obtained as a pale-yellow solid.

$^1$H-NMR (300 MHz, DMSO-$d_6$); δ (ppm) 1.18 (d, J=6.6, 6H), 1.45-1.59 (m, 4H), 2.34 (s, 3H), 2.65-2.66 (m, 4H), 2.77-2.90 (m, 6H), 3.23-3.38 (m, 3H), 3.58 (s, 3H), 3.83-3.88 (m, 2H), 4.02-4.16 (m, 4H), 4.38-4.40 (m, 1H), 7.28-7.32 (m, 1H), 7.51-7.53 (m, 1H), 7.75 (d, J=12.9, 1H), 8.39-8.47 (m, 3H).

Example 43

N²-{2-[1,3-dihydro-2H-isoindol-2-yl(methyl)amino]-2-oxoethyl}-N²-(2-methylphenyl)-N¹-[2-(isopropylamino)ethyl]glycinamide dihydrochloride Step A N-{2-[1,3-dihydro-2H-isoindol-2-yl(methyl)amino]-2-oxoethyl}-N-(2-methylphenyl)glycine Using the compound (500 mg, 2.24 mmol) of Reference Example 63 and the compound (620 mg, 3.36 mmol) of Reference Example 17, and according to the method of Example 1, step A, the title compound (650 mg, yield 82%) was obtained as a bistered amorphous solid.

$^1$H-NMR (300 MHz, DMSO-$d_6$); δ (ppm) 2.22 (s, 3H), 2.88 (s, 3H), 3.95-4.11 (m, 4H), 4.22-4.26 (m, 4H), 6.87-6.90 (m, 1H), 7.04-7.11 (m, 3H), 7.23-7.31 (m, 4H), 12.46 (brs, 1H).

Step B

N²-{2-[1,3-dihydro-2H-isoindol-2-yl(methyl)amino]-2-oxoethyl}-N²-(2-methylphenyl)-N¹-{2-[(tert-butoxycarbonyl)(isopropyl)amino]ethyl}glycinamide Using the compound (650 mg, 1.84 mmol) obtained in step A, and the compound (558 mg, 2.76 mmol) of Reference Example 3, and according to the method of Example 1, step B, the title compound (870 mg, yield 88%) was obtained as a bistered oil.

$^1$H-NMR (300 MHz, CDCl$_3$); δ (ppm) 1.09 (d, J=6.9, 6H), 1.45 (s, 9H), 2.34 (s, 3H), 2.94 (s, 3H), 3.10 (brs, 2H), 3.33-3.41 (m, 2H), 3.83 (s, 2H), 4.05-4.24 (m, 7H), 6.97-7.02 (m, 1H), 7.10-7.28 (m, 7H), 8.01-8.45 (broad, 1H).

Step C

N²-{2-[1,3-dihydro-2H-isoindol-2-yl(methyl)amino]-2-oxoethyl}-N²-(2-methylphenyl)-W-[2-(isopropylamino)ethyl]glycinamide dihydrochloride Using the compound (870 mg, 1.62 mmol) obtained in step B and according to the method of Example 1, step C, the title compound (641 mg, yield 78%) was obtained as a pale-bistered amorphous solid.

$^1$H-NMR (300 MHz, DMSO-$d_6$); δ (ppm) 1.20 (d, J=6.5, 6H), 2.29 (s, 3H), 2.79-2.98 (m, 5H), 3.17-3.29 (m, 1H), 3.36-3.44 (m, 2H), 3.91 (s, 2H), 4.10 (d, J=11.4, 2H), 4.25 (d, J=11.7, 2H), 4.34 (s, 2H), 6.92 (t, J=7.2, 1H), 7.06-7.30 (m, 7H), 8.44 (t, J=5.5, 1H), 9.00 (brs, 2H).

Example 44

N²-(3-chloro-2-methylphenyl)-N²-{2-[1,3-dihydro-2H-isoindol-2-yl(methyl)amino]-2-oxoethyl}-N¹-[2-(isopropylamino)ethyl]glycinamide dihydrochloride Step A N-(3-chloro-2-methylphenyl)-N-{2-[1,3-dihydro-2H-isoindol-2-yl(methyl)amino]-2-oxoethyl}glycine Using the compound (382 mg, 1.48 mmol) of Reference Example 64 and the compound (426 mg, 2.31 mmol) of Reference Example 17, and according to the method of Example 1, step A, the title compound (386 mg, yield 67%) was obtained as a pale-yellow amorphous solid.

$^1$H-NMR (300 MHz, CDCl$_3$); δ (ppm) 2.28 (s, 3H), 3.05 (s, 3H), 3.89 (s, 2H), 4.16 (d, J=11.7, 2H), 4.25 (s, 2H), 4.27 (d, J=11.7, 2H), 7.0-7.1 (m, 1H), 7.17-7.29 (m, 6H), 13.3 (brs, 1H).

Step B

N²-(3-chloro-2-methylphenyl)-N²-{2-[1,3-dihydro-2H-isoindol-2-yl(methyl)amino]-2-oxoethyl}-N¹-{2-[(tert-butoxycarbonyl)isopropylamino]ethyl}glycinamide Using the compound (382 mg, 0.985 mmol) obtained in step A, and the compound (284 mg, 1.41 mmol) of Reference Example 3, and according to the method of Example 1, step B, the title compound (485 mg, yield 86%) was obtained as a colorless amorphous solid.

$^1$H-NMR (300 MHz, CDCl$_3$); δ (ppm) 1.09 (d, J=6.9, 6H), 1.44 (brs, 9H), 2.38 (s, 3H), 2.95 (s, 3H), 3.0-3.2 (m, 2H), 3.32-3.39 (m, 2H), 3.85 (s, 2H), 4.0-4.3 (broad, 1H), 4.09 (d, J=11.7, 2H), 4.14 (s, 2H), 4.23 (d, J=11.7, 2H), 7.02-7.13 (m, 2H), 7.19-7.28 (m, 5H), 7.8-8.1 (broad, 1H).

Step C

N²-(3-chloro-2-methylphenyl)-N²-{2-[1,3-dihydro-2H-isoindol-2-yl(methyl)amino]-2-oxoethyl}-N¹-[2-(isopropylamino)ethyl]glycinamide dihydrochloride Using the compound (482 mg, 0.842 mmol) obtained in step B and according to the method of Example 1, step C, the title compound (406 mg, yield 88%) was obtained as a colorless solid.

$^1$H-NMR (300 MHz, DMSO-$d_6$); δ (ppm) 1.19 (d, J=6.5, 6H), 2.30 (s, 3H), 2.8-3.0 (m, 2H), 2.87 (s, 3H), 3.1-3.3 (m, 1H), 3.3-3.5 (m, 2H), 3.87 (s, 2H), 4.10 (d, J=11.7, 2H), 4.24

(d, J=11.7, 2H), 4.26 (s, 2H), 7.05-7.15 (m, 3H), 7.26 (broad, 4H), 8.2-8.3 (m, 1H), 8.9 (broad, 2H).

Example 45

$N^2$-(5-chloro-2-methylphenyl)-$N^2$-{2-[1,3-dihydro-2H-isoindol-2-yl(methyl)amino]-2-oxoethyl}-$N^1$-(2-pyrrolidin-1-ylethyl)glycinamide

Step A

N-(5-chloro-2-methylphenyl)-N-{2-[1,3-dihydro-2H-isoindol-2-yl(methyl)amino]-2-oxoethyl}glycine Using the compound (1.12 g, 4.35 mmol) of Reference Example 65 and the compound (843 mg, 4.56 mmol) of Reference Example 17, and according to the method of Example 1, step A, the title compound (1.59 g, yield 95%) was obtained as a bistered amorphous solid.

$^1$H-NMR (300 MHz, CDCl$_3$); δ (ppm) 2.26 (s, 3H), 3.06 (s, 3H), 3.89 (s, 2H), 4.16-4.31 (m, 6H), 7.02 (dd, J=2.1, 8.1, 1H), 7.10 (d, J=8.1, 1H), 7.21-7.29 (m 5H).

Step B

$N^2$-(5-chloro-2-methylphenyl)-$N^2$-{2-[1,3-dihydro-2H-isoindol-2-yl(methyl)amino]-2-oxoethyl}-$N^1$-(2-pyrrolidin-1-ylethyl)glycinamide Using the compound (300 mg, 0.77 mmol) obtained in step A, and 1-(2-aminoethyl)pyrrolidine (0.11 ml, 0.85 mmol), and according to the method of Example 1, step B, the title compound (275 mg, yield 74%) was obtained as a pale-yellow amorphous solid.

$^1$H-NMR (300 MHz, CDCl$_3$); δ (ppm) 1.72 (m, 4H), 2.30 (s, 3H), 2.46-2.57 (m, 6H), 2.95 (s, 3H), 3.35-3.41 (m, 2H), 3.83 (s, 2H), 4.11-4.27 (m, 6H), 6.95 (dd, J=2.1, 8.1, 1H), 7.07 (d, J=8.1, 1H), 7.21-7.29 (m, 5H), 8.08 (brs, 1H).

Example 46

$N^2$-(5-chloro-2-methylphenyl)-$N^2$-{2-[1,3-dihydro-2H-isoindol-2-yl(methyl)amino]-2-oxoethyl}-$N^1$-[2-(methylamino)ethyl]glycinamide

Step A

$N^2$-(5-chloro-2-methylphenyl)-$N^2$-{2-[1,3-dihydro-2H-isoindol-2-yl(methyl)amino]-2-oxoethyl}-$N^1$-{2-[(tert-butoxycarbonyl)(methyl)amino]ethyl}glycinamide Using the compound (330 mg, 0.85 mmol) of Example 45, step A, the compound (197 mg, 0.94 mmol) of Reference Example 1 and triethylamine (0.13 ml, 0.94 mmol), and according to the method of Example 1, step B, the title compound (295 mg, yield 64%) was obtained as a pale-yellow amorphous solid.

$^1$H-NMR (300 MHz, CDCl$_3$); δ (ppm) 1.44 (s, 9H), 2.28 (s, 3H), 2.80 (s, 3H), 2.96 (s, 3H), 3.33 (m, 2H), 3.39-3.43 (m, 2H), 3.76 (s, 2H), 4.13-4.28 (m, 6H), 6.96 (d, J=8.1, 1H), 7.08 (d, J=8.4, 1H), 7.21-7.26 (m, 5H).

Step B

$N^2$-(5-chloro-2-methylphenyl)-$N^2$-{2-[1,3-dihydro-2H-isoindol-2-yl(methyl)amino]-2-oxoethyl}-$N^1$-[2-(methylamino)ethyl]glycinamide The compound (294 mg, 0.54 mmol) obtained in step A was dissolved in dichloromethane (5.5 ml), 4N hydrochloric acid-ethyl acetate solution (1.35 ml) was added, and the mixture was stirred at room temperature for 8 hr. The aqueous layer was alkalified by addition of saturated aqueous sodium hydrogen carbonate, and the organic layer was extracted with dichloromethane, and dried over sodium sulfate. The insoluble material was filtered off, and the solution was concentrated under reduced pressure. The obtained oil was purified by silica gel column chromatography (NH silica gel use, methanol-dichloromethane) to give the title compound (179 mg, yield 75%) as a pale-yellow amorphous solid.

$^1$H-NMR (300 MHz, CDCl$_3$); δ (ppm) 2.30 (s, 3H), 2.37 (s, 3H), 2.68 (t, J=6.0, 2H), 2.98 (s, 3H), 3.40 (q, J=6.0, 2H), 3.79 (s, 2H), 4.13-4.28 (m, 6H), 6.97 (dd, J=1.8, 8.1, 1H), 7.09 (d, J=8.4, 1H), 7.21-7.29 (m, 5H), 8.35 (brs, 1H).

Example 47

$N^2$-(5-chloro-2-methylphenyl)-$N^2$-{2-[1,3-dihydro-2H-isoindol-2-yl(methyl)amino]-2-oxoethyl}-$N^1$-[2-(isopropylamino)ethyl]glycinamide

Step A

$N^2$-(5-chloro-2-methylphenyl)-$N^2$-{2-[1,3-dihydro-2H-isoindol-2-yl(methyl)amino]-2-oxoethyl}-$N^1$-{2-[(tert-butoxycarbonyl)(isopropyl)amino]ethyl}glycinamide Using the compound (330 mg, 0.85 mmol) of Example 45, step A, and the compound (189 mg, 0.94 mmol) of Reference Example 3, and according to the method of Example 1, step B, the title compound (374 mg, yield 77%) was obtained as a pale-yellow amorphous solid.

$^1$H-NMR (300 MHz, CDCl$_3$); δ (ppm) 1.11 (d, J=6.6, 6H), 1.45 (s, 9H), 2.29 (s, 3H), 2.96 (s, 3H), 3.12 (m, 2H), 3.35-3.42 (m, 2H), 3.79 (s, 2H), 4.12-4.27 (m, 7H), 6.96 (d, J=9.3, 1H), 7.08 (d, 1.5 J=8.1, 1H), 7.20-7.29 (m, 5H).

Step B

$N^2$-(5-chloro-2-methylphenyl)-$N^2$-{2-[1,3-dihydro-2H-isoindol-2-yl(methyl)amino]-2-oxoethyl}-$N^1$-[2-(isopropylamino)ethyl]glycinamide Using the compound (370 mg, 0.65 mmol) obtained in step A and according to the method of Example 46, step B, the title compound (241 mg, yield 79%) was obtained as a pale-yellow amorphous solid.

$^1$H-NMR (300 MHz, CDCl$_3$); δ (ppm) 1.00 (d, J=6.0, 6H), 2.30 (s, 3H), 2.69-2.80 (m, 3H), 2.97 (s, 3H), 3.39 (q, J=6.0, 2H), 3.79 (s, 2H), 4.13-4.28 (m, 6H), 6.97 (dd, J=2.1, 8.1, 1H), 7.08 (d, J=8.1, 1H), 7.21-7.29 (m, 5H), 8.39 (brs, 1H).

Example 48

N²-(5-chloro-2-methylphenyl)-N²-{2-[1,3-dihydro-2H-isoindol-2-yl(methyl)amino]-2-oxoethyl}-N¹-(2-aminoethyl)glycinamide dihydrochloride Using the compound (400 mg, 1.03 mmol) of Example 45, step A, and tert-butyl (2-aminoethyl)carbamate (215 mg, 1.34 mmol), and according to the methods of Example 1, steps B and C, the title compound (372 mg, yield 72%) was obtained as a colorless solid.

¹H-NMR (300 MHz, DMSO-d₆); δ (ppm) 2.22 (s, 3H), 2.77-2.84 (m, 2H), 2.89 (s, 3H), 3.28-3.35 (m, 2H), 3.86 (s, 2H), 4.11 (d, J=11.4, 2H), 4.26 (d, J=11.4, 2H), 4.28 (s, 2H), 6.92 (dd, J=2.1, 8.4, 1H), 7.09 (d, J=2.1, 1H), 7.11 (d, J=8.4, 1H), 7.2-7.3 (m, 4H), 7.89 (brs, 3H), 8.23 (t, J=5.7, 1H).

The compounds of Examples 25-48 are shown below.

TABLE 8

| Example | Structural Formula | TMW | LC-MS (found) |
|---|---|---|---|
| 25 | 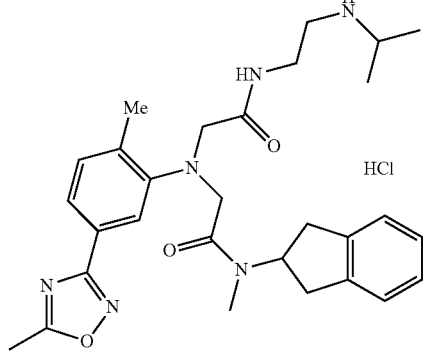 | 555.11 | 519 |
| 26 | 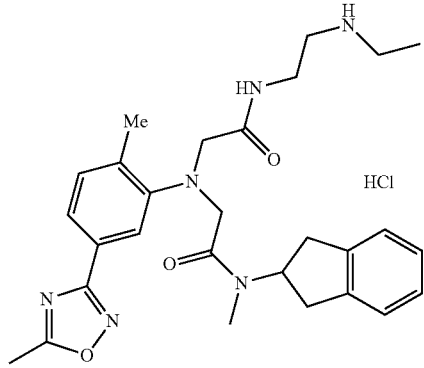 [SMILES: CCNCCNC(=O)CN(CC(=O)N(C)C1Cc2ccccc2C1)c1cc(-c2noc(C)n2)ccc1C ; Cl] | 541.08 | 505 |
| 27 | 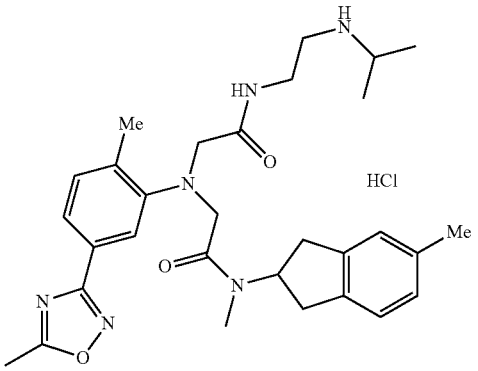 [SMILES: Cc1ccc2c(c1)CC(N(C)C(=O)CN(CC(=O)NCCNC(C)C)c1cc(-c3noc(C)n3)ccc1C)C2 ; Cl] | 569.14 | 533 |

TABLE 8-continued

| Example | Structural Formula | TMW | LC-MS (found) |
|---------|-------------------|-----|---------------|
| 28 | | 555.11 | 519 |
| 29 | | 585.14 | 549 |
| 30 | | 571.11 | 535 |
| 31 | | 573.10 | 537 |

TABLE 8-continued

| Example | Structural Formula | TMW | LC-MS (found) |
|---|---|---|---|
| 32 | | 589.56 | 553 |
| 33 | | 569.14 | 533 |
| 34 | | 615.16 | 579 |
| 35 | | 569.14 | 533 |

TABLE 8-continued
| Example | Structural Formula | TMW | LC-MS (found) |
|---|---|---|---|
| 36 | 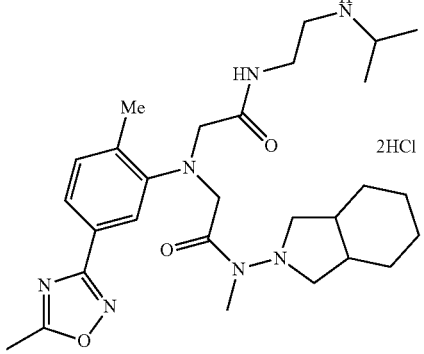 2HCl | 598.61 | 526 |
| 37 | 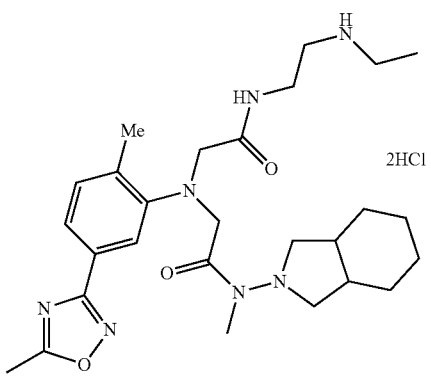 [SMILES: CCNCCNC(=O)CN(CC(=O)N(C)N1CC2CCCCC2C1)c1cc(-c2noc(C)n2)ccc1C ; "2HCl"] 2HCl | 584.58 | 512 |
| 38 | 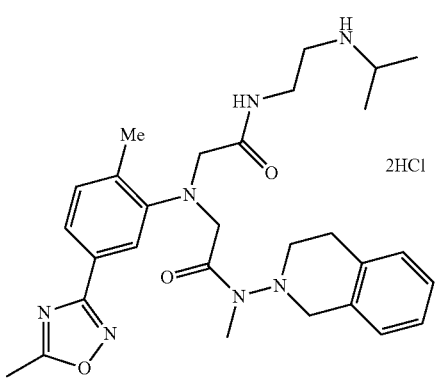 [SMILES: Cc1nc(-c2ccc(C)c(N(CC(=O)NCCNC(C)C)CC(=O)N(C)N3CCc4ccccc4C3)c2)no1 ; "2HCl"] 2HCl | 606.59 | 534 |
| 39 | 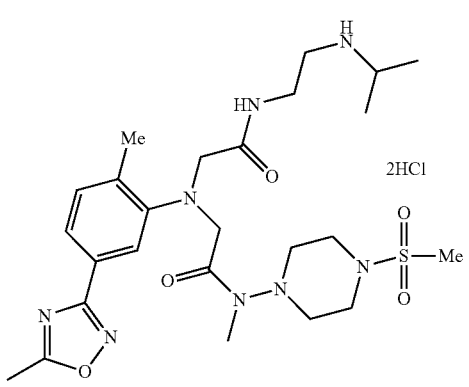 [SMILES: Cc1nc(-c2ccc(C)c(N(CC(=O)NCCNC(C)C)CC(=O)N(C)N3CCN(S(C)(=O)=O)CC3)c2)no1 ; "2HCl"] 2HCl | 637.62 | 565 |

TABLE 8-continued

| Example | Structural Formula | TMW | LC-MS (found) |
|---|---|---|---|
| 40 | | 564.12 | 528 |
| 41 | | 600.17 | 564 |
| 42 | | 580.12 | 544 |
| 43 | | 510.50 | 438 |

TABLE 8-continued

| Example | Structural Formula | TMW | LC-MS (found) |
|---------|-------------------|--------|---------------|
| 44 | | 544.94 | 472 |
| 45 | | 484.03 | 484 |
| 46 | | 443.97 | 444 |
| 47 | | 472.02 | 472 |

| Example | Structural Formula | TMW | LC-MS (found) |
| --- | --- | --- | --- |
| 48 | (structure shown) 2HCl | 502.86 | 430 |

Example 49

N²-(5-chloro-2-methylphenyl)-N²-{2-[1,3-dihydro-2H-isoindol-2-yl(methyl)amino]-2-oxoethyl}-N¹-[2-(ethylamino)ethyl]glycinamide dihydrochloride Using the compound (400 mg, 1.03 mmol) of Example 45, step A, and the compound (252 mg, 1.34 mmol) of Reference Example 2, and according to the methods of Example 1, steps B and C, the title compound (487 mg, yield 89%) was obtained as a colorless solid.

$^1$H-NMR (300 MHz, DMSO-$d_6$); δ (ppm) 1.15 (t, J=7.2, 3H), 2.23 (s, 3H), 2.8-3.0 (m, 4H), 2.89 (s, 3H), 3.3-3.5 (m, 2H), 3.87 (s, 2H), 4.11 (d, J=11.7, 2H), 4.26 (d, J=11.7, 2H), 4.28 (s, 2H), 6.92 (dd, J=2.1, 8.1, 1H), 7.09 (d, J=2.1, 1H), 7.11 (d, J=8.1, 1H), 7.2-7.3 (m, 4H), 8.27 (t, J=5.7, 1H), 8.64 (brs, 2H).

Example 50

N²-(5-chloro-2-methylphenyl)-N²-{2-[1,3-dihydro-2H-isoindol-2-yl(methyl)amino]-2-oxoethyl}-N¹-[3-(methylamino)propyl]glycinamide dihydrochloride

Step A

N²-(5-chloro-2-methylphenyl)-N²-{2-[1,3-dihydro-2H-isoindol-2-yl(methyl)amino]-2-oxoethyl}-N¹-[3-{methyl[(2-nitrophenyl)sulfonyl]amino}propyl]glycinamide Using the compound (400 mg, 1.03 mmol) of Example 45, step A, the compound (408 mg, 1.32 mmol) of Reference Example 5 and triethylamine (0.19 ml, 1.36 mmol), and according to the method of Example 1, step B, the title compound (629 mg) as a yellow oil. This was used for the next step as is.

Step B

N²-(5-chloro-2-methylphenyl)-N²-{2-[1,3-dihydro-2H-isoindol-2-yl(methyl)amino]-2-oxoethyl}-N¹-[3-(methylamino)propyl]glycinamide dihydrochloride The compound (629 mg) obtained in step A was dissolved in acetonitrile (20 ml). Then, benzenethiol (0.19 ml, 1.85 mmol) and cesium carbonate (1.00 g, 3.07 mmol) were added, and the mixture was stirred at room temperature for 3 hr. The reaction mixture was diluted with dichloromethane, washed with saturated brine, and dried over sodium sulfate. The insoluble material was filtered off, and the solution was concentrated under reduced pressure. The obtained oil was purified by silica gel column chromatography (NH silica gel, methanol-dichloromethane) to give a colorless amorphous solid (290 mg). This was dissolved in diethyl ether (6 ml), 4N hydrochloric acid-dioxane solution (0.5 ml, 2.0 mmol) was added, and the mixture was stirred at room temperature. The precipitated solid was collected by filtration, washed with diethyl ether, and dried under reduced pressure to give the title compound (307 mg, yield 56%) as a colorless solid.

$^1$H-NMR (300 MHz, DMSO-$d_6$); δ (ppm) 1.6-1.8 (m, 2H), 2.23 (s, 3H), 2.45 (t, J=5.4, 3H), 2.6-2.8 (m, 2H), 2.90 (s, 3H), 3.0-3.2 (m, 2H), 3.83 (s, 2H), 4.12 (d, J=11.4, 2H), 4.26 (s, 2H), 4.27 (d, J=11.4, 2H), 6.93 (dd, J=2.1, 8.4, 1H), 7.09 (d, J=2.1, 1H), 7.12 (d, J=8.4, 1H), 7.2-7.3 (m, 4H), 8.20 (t, J=5.7, 1H), 8.61 (brs, 2H).

Example 51

N²-(5-chloro-2-methylphenyl)-N²-{2-[1,3-dihydro-2H-isoindol-2-yl(methyl)amino]-2-oxoethyl}-N¹-[2-(tert-butylamino)ethyl]glycinamide dihydrochloride Using the compound (616 mg, 1.59 mmol) of Example 45, step A, and the compound (257 mg, 1.32 mmol) of Reference Example 16, and according to the methods of Example 1, step B, and Example 17, step C, the title compound (386 mg, yield 43%) was obtained as a colorless solid.

$^1$H-NMR (300 MHz, DMSO-$d_6$); δ (ppm) 1.24 (s, 9H), 2.24 (s, 3H), 2.7-2.9 (m, 2H), 2.89 (s, 3H), 3.3-3.5 (m, 2H), 3.88 (s, 2H), 4.12 (d, J=11.7, 2H), 4.26 (d, J=11.7, 2H), 4.29 (s, 2H), 6.92 (dd, J=1.8, 8.1, 1H), 7.08 (d, J=1.8, 1H), 7.11 (d, 1H), 7.2-7.3 (m, 4H), 8.32 (broad t, 1H), 8.82 (brs, 2H).

Example 52

N²-(5-chloro-2-methylphenyl)-N²-[2-{methyl[4-(methylsulfonyl)piperazin-1-yl]amino}-2-oxoethyl]-N¹-[2-(isopropylamino)ethyl]glycinamide dihydrochloride

Step A

N²-(5-chloro-2-methylphenyl)-N²-[2-{methyl[4-(methylsulfonyl)piperazin-1-yl]amino}-2-oxoethyl]-N¹-{2-[(tert-butoxycarbonyl)(isopropyl)amino]ethyl}glycinamide Using the compound (357 mg, 1.39 mmol) of Reference Example 65, the compound (288 mg, 1.49 mmol) of Reference Example 48 and the compound (387 mg, 1.91 mmol) of Reference Example 3, and according to the methods of Example 4, step A, and Example 1, step B, the title compound (741 mg, yield 86%) was obtained as a colorless amorphous solid.

$^1$H-NMR (300 MHz, CDCl$_3$); δ (ppm) 1.12 (d, J=6.9, 6H), 1.46 (brs, 9H), 2.27 (s, 3H), 2.6-2.8 (m, 2H), 2.84 (s, 3H), 2.89-3.03 (m, 4H), 2.93 (s, 3H), 3.0-3.2 (m, 2H), 3.35-3.43 (m, 2H), 3.7-3.9 (m, 4H), 3.9-4.4 (m, 3H), 6.97 (dd, J=2.1, 8.4, 1H), 7.09 (d, J=8.4, 1H), 7.17 (d, J=2.1, 1H), 7.8-8.4 (broad, 1H).

Step B

N²-(5-chloro-2-methylphenyl)-N²-[2-{methyl[4-(methylsulfonyl)piperazin-1-yl]amino}-2-oxoethyl]-N¹-[2-(isopropylamino)ethyl]glycinamide dihydrochloride Using the compound (735 mg, 1.19 mmol) obtained in step A and according to the method of Example 1, step C, the title compound (675 mg, yield 96%) was obtained as a colorless solid.

$^1$H-NMR (300 MHz, DMSO-d$_6$); δ (ppm) 1.20 (d, J=6.3, 6H), 2.22 (s, 3H), 2.7-3.0 (m, 8H), 2.84 (s, 3H), 2.92 (s, 3H), 3.1-3.3 (m, 1H), 3.34-3.42 (m, 2H), 3.5-3.6 (m, 2H), 3.87 (s, 2H), 4.22 (s, 2H), 6.91 (dd, J=2.1, 8.4, 1H), 7.06 (d, J=2.1, 1H), 7.12 (d, J=8.4, 1H), 8.36 (t, J=5.7, 1H), 8.78 (brs, 2H).

Example 53

N²-(4-chloro-2-methylphenyl)-N²-{2-[1,3-dihydro-2H-isoindol-2-yl(methyl)amino]-2-oxoethyl}-N¹-[2-(isopropylamino)ethyl]glycinamide dihydrochloride

Step A

N-(4-chloro-2-methylphenyl)-N-{2-[1,3-dihydro-2H-isoindol-2-yl(methyl)amino]-2-oxoethyl}glycine Using the compound (446 mg, 1.73 mmol) of Reference Example 66 and the compound (479 mg, 2.60 mmol) of Reference Example 17, and according to the method of Example 1, step A, the title compound (452 mg, yield 67%) was obtained as a colorless amorphous solid.

$^1$H-NMR (300 MHz, DMSO-d$_6$); δ (ppm) 2.22 (s, 3H), 2.87 (s, 3H), 3.94 (s, 2H), 4.10 (d, J=11.4, 2H), 4.24 (d, J=11.4, 2H), 4.25 (s, 2H), 7.01-7.15 (m, 3H), 7.22-7.31 (m, 4H), 12.45 (brs, 1H).

Step B

N²-(4-chloro-2-methylphenyl)-N²-{2-[1,3-dihydro-2H-isoindol-2-yl(methyl)amino]-2-oxoethyl}-N¹-[2-(isopropylamino)ethyl]glycinamide dihydrochloride Using the compound (452 mg, 1.17 mmol) obtained in step A, and the compound (355 mg, 1.76 mmol) of Reference Example 3, and according to the methods of Example 1, steps B and C, the title compound (519 mg, yield 81%) was obtained as a pale-bistered amorphous solid.

$^1$H-NMR (300 MHz, DMSO-d$_6$); δ (ppm) 1.20 (d, J=6.3, 6H), 2.26 (s, 3H), 2.87 (brs, 5H), 3.17-3.27 (m, 1H), 3.39 (q, J=6.0, 2H), 3.85 (s, 2H), 4.10 (d, J=11.4, 2H), 4.22-4.28 (m, 4H), 7.07-7.18 (m, 3H), 7.23-7.32 (m, 4H), 8.33 (t, J=5.7, 1H), 8.92 (brs, 2H).

Example 54

N²-(4-chloro-2-methylphenyl)-N²-{2-[2,3-dihydro-1H-inden-5-yl(methyl)amino]-2-oxoethyl}-N¹-[2-(isopropylamino)ethyl]glycinamide hydrochloride

Step A

N-(4-chloro-2-methylphenyl)-N-{2-[2,3-dihydro-1H-inden-5-yl(methyl)amino]-2-oxoethyl}glycine Using the compound (500 mg, 1.94 mmol) of Reference Example 66 and the compound (535 mg, 2.91 mmol) of Reference Example 32, and according to the method of Example 4, step A, the title compound (532 mg, yield 71%) was obtained as a pale-bistered solid.

$^1$H-NMR (300 MHz, DMSO-d$_6$); δ (ppm) 2.04 (t, J=7.5, 2H), 2.10 (s, 3H), 2.81-2.87 (m, 4H), 3.10 (s, 3H), 3.34 (s, 2H), 3.92 (s, 2H), 6.95-7.14 (m, 5H), 7.26 (d, J=7.8, 1H), 12.44 (brs, 1H).

Step B

N²-(4-chloro-2-methylphenyl)-N²-{2-[2,3-dihydro-1H-inden-5-yl(methyl)amino]-2-oxoethyl}-N¹-[2-(isopropylamino)ethyl]glycinamide hydrochloride Using the compound (532 mg, 1.37 mmol) obtained in step A, and the compound (416 mg, 2.06 mmol) of Reference Example 3, and according to the methods of Example 1, steps B and C, the title compound (493 mg, yield 71%) was obtained as a colorless amorphous solid.

$^1$H-NMR (300 MHz, DMSO-d$_6$); δ (ppm) 1.21 (d, J=6.3, 6H), 2.07 (t, J=7.3, 2H), 2.13 (s, 3H), 2.78-2.94 (m, 6H), 3.10 (s, 3H), 3.21-3.27 (m, 1H), 3.35-3.40 (m, 2H), 3.68 (s, 2H), 3.82 (s, 2H), 6.97-7.04 (m, 3H), 7.09-7.16 (m, 2H), 7.27 (d, J=7.8, 1H), 8.30-8.34 (m, 1H), 8.78-8.93 (broad, 2H).

Example 55

N²-(4-chloro-2-methylphenyl)-N²-{2-[(3,4-dichlorophenyl)(methyl)amino]-2-oxoethyl}-N¹-[2-(isopropylamino)ethyl]glycinamide hydrochloride

Step A

N-(4-chloro-2-methylphenyl)-N-{2-[(3,4-dichlorophenyl)(methyl)amino]-2-oxoethyl}glycine Using the compound (500 mg, 1.94 mmol) of Reference Example 66 and the compound (559 mg, 2.91 mmol) of Reference Example 31, and according to the method of Example 1, step A, the title compound (545 mg, yield 68%) was obtained as a pale-bistered oil.

$^1$H-NMR (300 MHz, DMSO-$d_6$); δ (ppm) 1.96 (s, 3H), 2.98 (s, 3H), 3.16 (s, 2H), 3.70 (s, 2H), 6.82-7.00 (m, 3H), 7.18 (d, J=8.1, 1H), 7.49 (d, J=8.4, 2H), 12.29 (brs, 1H).

Step B

$N^2$-(4-chloro-2-methylphenyl)-$N^2$-{2-[(3,4-dichlorophenyl)(methyl)amino]-2-oxoethyl}-$N^1$-[2-(isopropylamino)ethyl]glycinamide hydrochloride Using the compound (545 mg, 1.31 mmol) obtained in step A, and the compound (397 mg, 1.97 mmol) of Reference Example 3, and according to the methods of Example 1, steps B and C, the title compound (576 mg, yield 82%) was obtained as a colorless amorphous solid.

$^1$H-NMR (300 MHz, DMSO-$d_6$); δ (ppm) 1.19 (d, J=6.5, 6H), 2.15 (s, 3H), 2.83-2.89 (m, 2H), 3.01-3.41 (m, 6H), 3.67-3.92 (m, 4H), 7.01-7.15 (m, 3H), 7.34 (d, J=7.8, 1H), 7.64-7.70 (m, 2H), 8.22-8.26 (m, 1H), 8.78 (brs, 2H).

Example 56

$N^2$-(5-acetyl-2-methylphenyl)-$N^2$-{2-[1,3-dihydro-2H-isoindol-2-yl(methyl)amino]-2-oxoethyl}-$N^1$-[2-(isopropylamino)ethyl]glycinamide dihydrochloride

Step A

N-(5-acetyl-2-methylphenyl)-N-{2-[1,3-dihydro-2H-isoindol-2-yl(methyl)amino]-2-oxoethyl}glycine Using the compound (567 mg, 2.14 mmol) of Reference Example 67 and the compound (518 mg, 2.81 mmol) of Reference Example 17, and according to the method of Example 1, step A, the title compound (692 mg, yield 82%) was obtained as a pale-yellow amorphous solid.

$^1$H-NMR (300 MHz, CDCl$_3$); δ (ppm) 2.38 (s, 3H), 2.55 (s, 3H), 3.06 (s, 3H), 3.93 (s, 2H), 4.18 (d, J=11.7, 2H), 4.29 (d, J=11.7, 2H), 4.31 (s, 2H), 7.19-7.29 (m, 5H), 7.62 (dd, J=1.5, 7.8, 1H), 7.81 (d, J=1.5, 1H), 13.5 (brs, 1H).

Step B

$N^2$-(5-acetyl-2-methylphenyl)-$N^2$-{2-[1,3-dihydro-2H-isoindol-2-yl(methyl)amino]-2-oxoethyl}-$N^1$-{2-[(tert-butoxycarbonyl)(isopropyl)amino]ethyl}glycinamide Using the compound (680 mg, 1.72 mmol) obtained in step A, and the compound (496 mg, 2.45 mmol) of Reference Example 3, and according to the method of Example 1, step B, the title compound (934 mg, yield 94%) was obtained as a colorless amorphous solid.

$^1$H-NMR (300 MHz, CDCl$_3$); δ (ppm) 1.11 (d, J=6.9, 6H), 1.45 (brs, 9H), 2.41 (s, 3H), 2.55 (s, 3H), 2.94 (s, 3H), 3.0-3.2 (m, 2H), 3.36-3.44 (m, 2H), 3.82 (s, 2H), 3.9-4.3 (broad, 1H), 4.15 (d, J=11.7, 2H), 4.24 (d, J=11.7, 2H), 4.26 (s, 2H), 7.2-7.3 (m, 5H), 7.58 (dd, J=1.4, 7.8, 1H), 7.84 (d, J=1.4, 1H), 8.0-8.7 (broad, 1H).

Step C

$N^2$-(5-acetyl-2-methylphenyl)-$N^2$-{2-[1,3-dihydro-2H-isoindol-2-yl(methyl)amino]-2-oxoethyl}-$N^1$-[2-(isopropylamino)ethyl]glycinamide dihydrochloride Using the compound (933 mg, 1.61 mmol) obtained in step B and according to the method of Example 1, step C, the title compound (866 mg, yield 97%) was obtained as a colorless solid.

$^1$H-NMR (300 MHz, DMSO-$d_6$); δ (ppm) 1.19 (d, J=6.5, 6H), 2.34 (s, 3H), 2.51 (s, 3H), 2.8-3.0 (m, 2H), 2.88 (s, 3H), 3.1-3.3 (m, 1H), 3.34-3.42 (m, 2H), 3.90 (s, 2H), 4.12 (d, J=11.7, 2H), 4.26 (d, J=11.7, 2H), 4.33 (s, 2H), 7.2-7.3 (m, 5H), 7.51 (d, J=7.9, 1H), 7.66 (d, J=1.5, 1H), 8.37 (t, J=5.7, 1H), 8.80 (brs, 2H).

Example 57

$N^2$-(5-acetyl-2-methylphenyl)-$N^2$-{2-[1,3-dihydro-2H-isoindol-2-yl(methyl)amino]-2-oxoethyl}-$N^1$-[2-(ethylamino)ethyl]glycinamide hydrochloride

Step A

$N^2$-(5-acetyl-2-methylphenyl)-$N^2$-{2-[1,3-dihydro-2H-isoindol-2-yl(methyl)amino]-2-oxoethyl}-$N^1$-{2-[(tert-butoxycarbonyl)(ethyl)amino]ethyl}glycinamide Using the compound (4.33 g, 10.95 mmol) of Example 56, step A, and the compound (2.78 g, 14.77 mmol) of Reference Example 2, and according to the method of Example 1, step B, the title compound (5.51 g, yield 89%) was obtained as a colorless solid.

$^1$H-NMR (300 MHz, CDCl$_3$); δ (ppm) 1.05 (t, J=7.1, 3H), 1.43 (brs, 9H), 2.40 (s, 3H), 2.55 (s, 3H), 2.95 (s, 3H), 3.0-3.2 (m, 2H), 3.2-3.3 (m, 2H), 3.39-3.46 (m, 2H), 3.80 (s, 2H), 4.17 (d, J=11.7, 2H), 4.25 (d, J=11.7, 2H), 4.27 (s, 2H), 7.2-7.3 (m, 5H), 7.57 (dd, J=1.3, 7.6, 1H), 7.83 (d, J=1.3, 1H), 8.2-8.7 (broad, 1H).

Step B

$N^2$-(5-acetyl-2-methylphenyl)-$N^2$-{2-[1,3-dihydro-2H-isoindol-2-yl(methyl)amino]-2-oxoethyl}-$N^1$-[2-(ethylamino)ethyl]glycinamide hydrochloride The compound (5.45 g, 9.63 mmol) obtained in step A was dissolved in dichloromethane (25 ml), 4N hydrochloric acid-dioxane solution (25 ml) was added, and the mixture was stirred at room temperature for 100 min. To the reaction mixture were added dichloromethane and aqueous ammonia to extract the organic layer. Furthermore, the aqueous layer was extracted twice with dichloromethane, the organic layer was mixed and the mixture was dried over sodium sulfate. The insoluble material was filtered off, and the solution was concentrated under reduced pressure. The obtained oil was dissolved in dichloromethane (10 ml), and 4N hydrochloric acid-ethyl acetate (2.4 ml, 9.6 mmol) was added. Then, diethyl ether (150 ml) was added to allow precipitation of a solid. This was collected by filtration, washed with diethyl ether, and dried under reduced pressure to give the title compound (4.23 g, yield 87%) as a colorless solid.

$^1$H-NMR (300 MHz, DMSO-$d_6$); δ (ppm) 1.14 (t, J=7.2, 3H), 2.33 (s, 3H), 2.51 (s, 3H), 2.8-3.0 (m, 4H), 2.89 (s, 3H), 3.3-3.4 (m, 2H), 3.90 (s, 2H), 4.11 (d, J=11.7, 2H), 4.26 (d, J=11.7, 2H), 4.31 (s, 2H), 7.2-7.3 (m, 5H), 7.52 (dd, J=1.2, 7.8, 1H), 7.66 (d, J=1.2, 1H), 8.32 (t, J=5.7, 1H), 8.44 (brs, 2H).

Example 58

$N^2$-(5-acetyl-2-methylphenyl)-$N^2$-{2-[(5-fluoro-1,3-dihydro-2H-isoindol-2-yl)(methyl)amino]-2-oxoethyl}-$N^1$-[2-(isopropylamino)ethyl]glycinamide dihydrochloride

Step A

N-(5-acetyl-2-methylphenyl)-N-{2-[(5-fluoro-1,3-dihydro-2H-isoindol-2-yl)(methyl)amino]-2-oxoethyl}glycine Using the compound (810 mg, 3.05 mmol) of Reference Example 67 and the compound (806 mg, 3.98 mmol) of Reference Example 19, and according to the method of Example 4, step A, the title compound (1.21 g, yield 96%) was obtained as a pale-yellow amorphous solid.

$^1$H-NMR (300 MHz, CDCl$_3$); δ (ppm) 2.38 (s, 3H), 2.55 (s, 3H), 3.06 (s, 3H), 3.94 (s, 2H), 4.08-4.26 (m, 4H), 4.30 (s, 2H), 6.9-7.0 (m, 2H), 7.14-7.20 (m, 1H), 7.25-7.29 (m, 1H), 7.62 (dd, J=1.5, 7.8, 1H), 7.81 (d, J=1.5, 1H), 13.4 (brs, 1H).

Step B $N^2$-(5-acetyl-2-methylphenyl)-$N^2$-{2-[(5-fluoro-1,3-dihydro-2H-isoindol-2-yl)(methyl)amino]-2-oxoethyl}-$N^1$-{2-[(tert-butoxycarbonyl)(isopropyl)amino]ethyl}glycinamide Using the compound (545 mg, 1.32 mmol) obtained in step A, and the compound (396 mg, 1.96 mmol) of Reference Example 3, and according to the method of Example 1, step B, the title compound (762 mg, yield 97%) was obtained as a pale-yellow amorphous solid.

$^1$H-NMR (300 MHz, CDCl$_3$); δ (ppm) 1.12 (d, J=6.8, 6H), 1.44 (brs, 9H), 2.41 (s, 3H), 2.55 (s, 3H), 2.94 (s, 3H), 3.0-3.2 (m, 2H), 3.36-3.44 (m, 2H), 3.81 (s, 2H), 3.9-4.3 (m, 5H), 4.25 (s, 2H), 6.9-7.0 (m, 2H), 7.1-7.3 (m, 2H), 7.57 (dd, J=1.5, 7.8, 1H), 7.83 (d, J=1.5, 1H), 8.0-8.7 (broad, 1H).

Step C $N^2$-(5-acetyl-2-methylphenyl)-$N^2$-{2-[(5-fluoro-1,3-dihydro-2H-isoindol-2-yl)(methyl)amino]-2-oxoethyl}-$N^1$-[2-(isopropylamino)ethyl]glycinamide dihydrochloride Using the compound (755 mg, 1.26 mmol) obtained in step B and according to the method of Example 1, step C, the title compound (688 mg, yield 96%) was obtained as a colorless solid.

$^1$H-NMR (300 MHz, DMSO-d$_6$); δ (ppm) 1.19 (d, J=6.6, 6H), 2.34 (s, 3H), 2.51 (s, 3H), 2.8-3.0 (m, 2H), 2.88 (s, 3H), 3.1-3.4 (m, 3H), 3.90 (s, 2H), 4.0-4.3 (m, 4H), 4.32 (s, 2H), 7.0-7.2 (m, 2H), 7.24-7.33 (m, 2H), 7.51 (dd, J=1.5, 7.8, 1H), 7.66 (d, J=1.5, 1H), 8.35 (broad t, 1H), 8.74 (brs, 2H).

Example 59

$N^2$-(5-acetyl-2-methylphenyl)-$N^2$-{2-[(5-fluoro-1,3-dihydro-2H-isoindol-2-yl)(methyl)amino]-2-oxoethyl}-$N^1$-[2-(ethylamino)ethyl]glycinamide dihydrochloride

Step A $N^2$-(5-acetyl-2-methylphenyl)-$N^2$-{2-[(5-fluoro-1,3-dihydro-2H-isoindol-2-yl)(methyl)amino]-2-oxoethyl}-$N^1$-{2-[(tert-butoxycarbonyl)(ethyl)amino]ethyl}glycinamide Using the compound (638 mg, 1.54 mmol) of Example 58, step A, and the compound (440 mg, 2.34 mmol) of Reference Example 2, and according to the method of Example 1, step B, the title compound (924 mg, yield>100%) was obtained as a colorless amorphous solid.

$^1$H-NMR (300 MHz, CDCl$_3$); δ (ppm) 1.05 (t, J=7.1, 3H), 1.43 (brs, 9H), 2.40 (s, 3H), 2.55 (s, 3H), 2.94 (s, 3H), 3.0-3.2 (m, 2H), 3.25-3.35 (m, 2H), 3.39-3.47 (m, 2H), 3.79 (s, 2H), 4.08-4.22 (m, 4H), 4.26 (s, 2H), 6.9-7.0 (m, 2H), 7.1-7.3 (m, 2H), 7.57 (dd, J=1.5, 8.1, 1H), 7.83 (d, J=1.5, 1H), 8.1-8.7 (broad, 1H).

Step B $N^2$-(5-acetyl-2-methylphenyl)-$N^2$-{2-[(5-fluoro-1,3-dihydro-2H-isoindol-2-yl)(methyl)amino]-2-oxoethyl}-$N^1$-[2-(ethylamino)ethyl]glycinamide dihydrochloride Using the compound (924 mg) obtained in step A and according to the method of Example 1, step C, the title compound (688 mg, yield 81%) was obtained as a colorless solid.

$^1$H-NMR (300 MHz, DMSO-d$_6$); δ (ppm) 1.16 (t, J=7.2, 3H), 2.33 (s, 3H), 2.51 (s, 3H), 2.8-3.0 (m, 4H), 2.88 (s, 3H), 3.35-3.42 (m, 2H), 3.90 (s, 2H), 4.0-4.3 (m, 4H), 4.32 (s, 2H), 7.0-7.2 (m, 2H), 7.24-7.33 (m, 2H), 7.51 (dd, J=1.2, 8.1, 1H), 7.66 (d, J=1.2, 1H), 8.34 (t, J=5.7, 1H), 8.81 (brs, 2H).

Example 60

$N^2$-{2-[1,3-dihydro-2H-isoindol-2-yl(methyl)amino]-2-oxoethyl}-$N^2$-[5-(1-hydroxyethyl)-2-methylphenyl]-$N^1$-[2-(ethylamino)ethyl]glycinamide dihydrochloride

Step A $N^2$-{2-[1,3-dihydro-2H-isoindol-2-yl(methyl)amino]-2-oxoethyl}-$N^2$-[5-(1-hydroxyethyl)-2-methylphenyl]-$N^1$-{2-[(tert-butoxycarbonyl)(ethyl)amino]ethyl}glycinamide The compound (421 mg, 0.744 mmol) of Example 57, step A JO was dissolved in an ethanol (4 ml)-dichloromethane (1 ml) mixed solvent. Thereto was added sodium borohydride (151 mg, 3.99 mmol), and the mixture was stirred at room temperature for 2 hr. To the reaction mixture was added 10% aqueous citric acid solution, and the reaction mixture was extracted with ethyl acetate. The organic layer was washed with saturated aqueous sodium hydrogen carbonate and saturated brine, and dried over anhydrous magnesium sulfate. The insoluble material was filtered off, and the solution was concentrated under reduced pressure. The obtained oil was purified by silica gel column chromatography (methanol-dichloromethane) to give the title compound (431 mg, yield>100%) as a colorless amorphous solid.

$^1$H-NMR (300 MHz, CDCl$_3$); δ (ppm) 1.01 (t, J=7.1, 3H), 1.41 (brs, 9H), 1.45 (d, J=6.6, 3H), 2.30 (s, 3H), 2.96 (s, 3H), 3.0-3.2 (m, 2H), 3.2-3.3 (m, 2H), 3.3-3.4 (m, 2H), 3.81 (s, 2H), 4.09 (d, J=11.7, 2H), 4.18 (s, 2H), 4.23 (d, J=11.7, 2H), 4.7-4.9 (m, 1H), 6.98-7.02 (m, 1H), 7.14 (d, J=7.8, 1H), 7.18-7.28 (m, 5H), 8.2-8.6 (broad, 1H).

Step B

N$^2$-{2-[1,3-dihydro-2H-isoindol-2-yl(methyl)amino]-2-oxoethyl}-N$^2$-[5-(1-hydroxyethyl)-2-methylphenyl]-W-[2-(ethylamino)ethyl]glycinamide dihydrochloride Using the compound (420 mg, 0.74 mmol) obtained in step A and according to the method of Example 1, step C, the title compound (281 mg, yield 70%) was obtained as a colorless solid.

$^1$H-NMR (300 MHz, DMSO-d$_6$); δ (ppm) 1.16 (t, J=7.2, 3H), 1.26 (d, J=6.6, 3H), 2.23 (s, 3H), 2.8-3.0 (m, 4H), 2.89 (s, 3H), 3.3-3.4 (m, 2H), 3.84 (s, 2H), 4.08 (d, J=11.7, 2H), 4.24 (d, J=11.7, 2H), 4.26 (s, 2H), 4.5-4.6 (m, 1H), 6.88 (dd, J=1.2, 7.8, 1H), 7.04 (d, J=7.8, 1H), 7.13 (d, J=1.2, 1H), 7.25 (broad, 4H), 8.42 (t, J=5.7, 1H), 8.66 (brs, 2H).

Example 61

N$^2$-(4-cyano-2-methylphenyl)-N$^2$-{2-[1,3-dihydro-2H-isoindol-2-yl(methyl)amino]-2-oxoethyl}-N$^1$-[2-(isopropylamino)ethyl]glycinamide dihydrochloride

Step A

N-(4-cyano-2-methylphenyl)-N-{2-[1,3-dihydro-2H-isoindol-2-yl(methyl)amino]-2-oxoethyl}glycine Using the compound (1.00 g, 4.03 mmol) of Reference Example 68 and the compound (1.12 g, 6.05 mmol) of Reference Example 17, and according to the method of Example 1, step A, the title compound (1.34 g, yield 88%) was obtained as a bistered amorphous solid.

$^1$H-NMR (300 MHz, DMSO-d$_6$); δ (ppm) 2.24 (s, 3H), 2.90 (s, 3H), 4.05 (s, 2H), 4.16 (d, 11.7, 2H), 4.27 (d, J=11.7, 2H), 4.38 (s, 2H), 6.95 (d, J=8.4, 1H), 7.22-7.30 (m, 4H), 7.45-7.50 (m, 2H), 12.65 (brs, 1H).

Step B

N$^2$-(4-cyano-2-methylphenyl)-N$^2$-{2-[1,3-dihydro-2H-isoindol-2-yl(methyl)amino]-2-oxoethyl}-N$^1$-{2-[(tert-butoxycarbonyl)(isopropyl)amino]ethyl}glycinamide Using the compound (670 mg, 1.77 mmol) obtained in step A, and the compound (537 mg, 2.66 mmol) of Reference Example 3, and according to the method of Example 1, step B, the title compound (957 mg, yield 96%) was obtained as a bistered amorphous solid.

$^1$H-NMR (300 MHz, DMSO-d$_6$); δ (ppm) 1.03 (d, J=5.4, 6H), 1.38 (s, 9H), 2.27 (s, 3H), 2.89-3.21 (m, 7H), 3.90 (s, 2H), 3.99-4.07 (m, 1H), 4.16 (d, J=11.7, 2H), 4.29 (d, J=11.7, 2H), 4.39 (s, 2H), 6.95 (d, J=8.1, 1H), 7.22-7.30 (m, 4H), 7.45-7.51 (m, 2H), 8.13-8.17 (m, 1H).

Step C

N$^2$-(4-cyano-2-methylphenyl)-N$^2$-{2-[1,3-dihydro-2H-isoindol-2-yl(methyl)amino]-2-oxoethyl}-N$^1$-[2-(isopropylamino)ethyl]glycinamide dihydrochloride Using the compound (200 mg, 0.36 mmol) obtained in step B and according to the method of Example 1, step C, the title compound (171 mg, yield 89%) was obtained as a pale-bistered solid.

$^1$H-NMR (300 MHz, DMSO-d$_6$); δ (ppm) 1.20 (d, J=6.5, 6H), 2.27 (s, 3H), 2.78-2.95 (m, 2H), 2.91 (s, 3H), 3.21-3.29 (m, 1H), 3.36-3.43 (m, 2H), 3.97 (s, 2H), 4.17 (d, J=11.7, 2H), 4.29 (d, J=11.7, 2H), 4.42 (s, 2H), 6.95 (d, J=8.3, 1H), 7.23-7.31 (m, 4H), 7.44-7.51 (m, 2H), 8.38 (t, J=5.6, 1H), 8.92 (brs, 2H).

Example 62

N$^2$-(4-cyano-2-methylphenyl)-N$^2$-{2-[1,3-dihydro-2H-isoindol-2-yl(methyl)amino]-2-oxoethyl}-N$^1$-[2-(ethylamino)ethyl]glycinamide dihydrochloride

Step A

N$^2$-(4-cyano-2-methylphenyl)-N$^2$-{2-[1,3-dihydro-2H-isoindol-2-yl(methyl)amino]-2-oxoethyl}-N$^1$-{2-[(tert-butoxycarbonyl)(ethyl)amino]ethyl}glycinamide Using the compound (670 mg, 1.77 mmol) of Example 61, step A, and the compound (500 mg, 2.66 mmol) of Reference Example 2 (500 mg, 2.66 mmol), and according to the method of Example 1, step B, the title compound (902 mg, yield 93%) was obtained as a brown amorphous solid.

$^1$H-NMR (300 MHz, DMSO-d$_6$); δ (ppm) 0.91-1.02 (m, 3H), 1.37 (s, 9H), 2.26 (s, 3H), 2.91 (s, 3H), 3.02-3.24 (m, 6H), 3.89 (s, 2H), 4.16 (d, J=11.7, 2H), 4.28 (d, J=11.7, 2H), 4.39 (s, 2H), 6.94 (d, J=8.4, 1H), 7.22-7.31 (m, 4H), 7.44-7.50 (m, 2H), 8.11-8.20 (m, 1H).

Step B

N$^2$-(4-cyano-2-methylphenyl)-N$^2$-{2-[1,3-dihydro-2H-isoindol-2-yl(methyl)amino]-2-oxoethyl}-N$^1$-[2-(ethylamino)ethyl]glycine amide 2 hydrochloride Using the compound (200 mg, 0.36 mmol) obtained in step A and according to the method of Example 1, step C, the title compound (181 mg, yield 96%) was obtained as a pale-brown solid.

$^1$H-NMR (300 MHz, DMSO-d$_6$); δ (ppm) 1.16 (t, J=7.2, 3H), 2.27 (s, 3H), 2.78-2.93 (m, 4H), 3.35-3.41 (m, 2H), 3.97 (s, 2H), 4.17 (d, J=11.7, 2H), 4.29 (d, J=11.7, 2H), 4.42 (s, 2H), 6.95 (d, J=8.1, 1H), 7.23-7.31 (m, 4H), 7.44-7.50 (m, 2H), 8.34 (t, J=5.7, 1H), 8.83 (brs, 2H).

Example 63

N$^2$-(4-cyano-2-methylphenyl)-N$^2$-{2-[2,3-dihydro-1H-inden-2-yl(methyl)amino]-2-oxoethyl}-N$^1$-[2-(isopropylamino)ethyl]glycine amide hydrochloride

Step A

N-(5-cyano-2-methylphenyl)-N-{2-[2,3-dihydro-1H-inden-2-yl(methyl)amino]-2-oxoethyl}glycine Using the compound of Reference Example 68 (1.00 g, 4.03 mmol) and the compound of Reference Example 23

(1.11 g, 6.05 mmol), and according to the method of Example 1, step A, the title compound (810 mg, yield 53%) was obtained as a colorless amorphous solid.

$^1$H-NMR (300 MHz, DMSO-$d_6$); δ (ppm) 2.26 (s, 3H), 2.67-2.77 (m, 3H), 2.88-3.12 (m, 4H), 4.03 (s, 2H), 4.16 (s, 1.2H), 4.32 (s, 0.8H), 4.81-4.84 (m, 0.4H), 5.27-5.31 (m, 0.6H), 7.00 (t, J=8.6, 1H), 7.13-7.23 (m, 4H), 7.47-7.53 (m, 2H), 12.70 (brs, 1H).

Step B $N^2$-(4-cyano-2-methylphenyl)-$N^2$-{2-[2,3-dihydro-1H-inden-2-yl(methyl)amino]-2-oxoethyl}-$N^1$-{2-[(tert-butoxycarbonyl)(isopropyl)amino]ethyl}glycine amide Using the compound (810 mg, 2.15 mmol) obtained in step A, and the compound of Reference Example 3 (652 mg, 3.23 mmol), and according to the method of Example 1, step B, the title compound (1.13 g, yield 94%) was obtained as a colorless amorphous solid.

$^1$H-NMR (300 MHz, CDCl$_3$); δ (ppm) 1.09 (d, J=6.6, 6H), 1.42 (s, 9H), 2.35 (s, 3H), 2.75-2.96 (m, 5H), 2.98-3.38 (m, 6H), 3.89-4.20 (m, 1H), 3.95 (s, 2H), 4.02 (s, 1.2H), 4.16 (s, 0.8H), 4.58-4.65 (m, 0.4H), 5.52-5.62 (m, 0.6H), 7.12-7.27 (m, 5H), 7.38-7.42 (m, 2H), 7.80-8.15 (broad, 1H).

Step C $N^2$-(4-cyano-2-methylphenyl)-$N^2$-{2-[2,3-dihydro-1H-inden-2-yl(methyl)amino]-2-oxoethyl}-$N^1$-[2-(isopropylamino)ethyl]glycine amide hydrochloride Using the compound (500 mg, 0.89 mmol) obtained in step B and according to the method of Example 1, step C, the title compound (374.7 mg, yield 85%) was obtained as a colorless amorphous solid.

$^1$H-NMR (300 MHz, DMSO-$d_6$); δ (ppm) 1.21 (d, J=6.3, 6H), 2.28 (s, 3H), 2.69-2.78 (m, 3H), 2.80-3.45 (m, 9H), 3.95 (s, 2H), 4.20 (s, 1.2H), 4.37 (s, 0.8H), 4.76-4.83 (m, 0.4H), 5.29-5.36 (m, 0.6H), 6.98 (t, J=7.8, 1H), 7.14-7.25 (m, 4H), 7.49 (d, J=8.7, 1H), 7.52 (s, 1H), 8.45 (t, J=5.4, 1H), 8.88 (brs, 2H).

Example 64

$N^2$-{2-[1,3-dihydro-2H-isoindol-2-yl(methyl)amino]-2-oxoethyl}-$N^2$-[2-methyl-4-(5-methyl-1,2,4-oxadiazol-3-yl)phenyl]-$N^1$-[2-(isopropylamino)ethyl]glycine amide dihydrochloride To ethanol (7.5 ml) were added the compound (757 mg, 1.35 mmol) obtained in Example 61, step B, hydroxylamine hydrochloride (131 mg, 1.89 mmol) and sodium acetate (155 mg, 1.35 mmol), and the mixture was heated under reflux for 7 hr. The reaction mixture was cooled to room temperature, and concentrated under reduced pressure. Water was added to the residue, and the mixture was extracted with ethyl acetate. The organic layer was washed with saturated brine, and dried over anhydrous magnesium sulfate. The insoluble material was filtered off, and the solution was concentrated under reduced pressure to give an oil. To this was added N,N-dimethylacetamide dimethylacetal (2.0 ml), and the mixture was stirred at 100° C. for 6.5 hr. The reaction mixture was cooled to room temperature, water was added, and the mixture was extracted with diethyl ether. The organic layer was washed with saturated brine, and dried over anhydrous magnesium sulfate. The solution was concentrated under reduced pressure, and the obtained oil was purified by silica gel column chromatography (methanol-chloroform) to give a colorless oil. Using this oil and according to the method of Example 1, step C, the title compound (338 mg, yield 41%) was obtained as a pale-yellow solid.

$^1$H-NMR (300 MHz, DMSO-$d_6$); δ (ppm) 1.19 (d, J=6.6, 6H), 2.33 (s, 3H), 2.63 (s, 3H), 2.79-2.99 (m, 2H), 2.91 (s, 3H), 3.16-3.32 (m, 1H), 3.34-3.45 (m, 2H), 3.96 (s, 2H), 4.15 (d, J=11.7, 2H), 4.28 (d, J=11.7, 2H), 4.39 (s, 2H), 7.09 (d, J=8.4, 1H), 7.22-7.31 (m, 4H), 7.64-7.71 (m, 2H), 8.36-8.39 (m, 1H), 8.91 (brs, 2H).

Example 65

$N^2$-{2-[1,3-dihydro-2H-isoindol-2-yl(methyl)amino]-2-oxoethyl}-$N^2$-[2-methyl-4-(5-methyl-1,2,4-oxadiazol-3-yl)phenyl]-$N^1$-[2-(ethylamino)ethyl]glycinamide dihydrochloride Using the compound (702 mg, 1.28 mmol) of Example 62, step A and according to the method of Example 64, the title compound (236 mg, yield 32%) was obtained as a pale-bistered solid.

$^1$H-NMR (300 MHz, DMSO-$d_6$); δ (ppm) 1.16 (t, J=7.2, 3H), 2.32 (s, 3H), 2.63 (s, 3H), 2.80-2.99 (m, 4H), 2.91 (s, 3H), 3.36-3.47 (m, 2H), 3.96 (s, 2H), 4.15 (d, J=11.9, 2H), 4.28 (d, J=11.6, 2H), 4.39 (s, 2H), 7.09 (d, J=8.3, 1H), 7.24-7.32 (m, 4H), 7.67 (d, J=8.4, 1H), 7.71 (s, 1H), 8.34-8.38 (m, 1H), 8.77-9.00 (broad, 2H).

Example 66

$N^2$-{2-[2,3-dihydro-1H-inden-2-yl(methyl)amino]-2-oxoethyl}-$N^2$-[2-methyl-4-(5-methyl-1,2,4-oxadiazol-3-yl)phenyl]-$N^1$-[2-(isopropylamino)ethyl]glycinamide hydrochloride Using the compound (630 mg, 1.12 mmol) of Example 63, step B and according to the method of Example 64, the title compound (350 mg, yield 56%) was obtained as a pale-yellow amorphous solid.

$^1$H-NMR (300 MHz, DMSO-$d_6$); δ (ppm) 1.15-1.22 (m, 6H), 2.28-2.35 (m, 3H), 2.63-2.79 (m, 6H), 2.80-3.49 (m, 9H), 3.90-3.94 (m, 2H), 4.16 (s, 1.2H), 4.32 (s, 0.8H), 4.83-4.87 (m, 0.4H), 5.31-5.37 (m, 0.6H), 7.09-7.24 (m, 5H), 7.66-7.70 (m, 1H), 7.73 (s, 1H), 8.43-8.45 (m, 1H), 8.79 (brs, 2H).

Example 67

$N^2$-{2-[1,3-dihydro-2H-isoindol-2-yl(methyl)amino]-2-oxoethyl}-$N^2$-[2-methyl-4-(4-methyl-5-oxo-4,5-dihydro-1,3,4-oxadiazol-2-yl)phenyl]-$N^1$-[2-(isopropylamino)ethyl]glycinamide dihydrochloride Step A N-[4-{[2-(tert-butoxycarbonyl)-2-methylhydrazino]carbonyl}-2-methylphenyl]-N-{2-[1,3-dihydro-2H-isoindol-2-yl(methyl)amino]-2-oxoethyl}glycine Using the compound (2.50 g, 6.32 mmol) of Reference Example 70 and the compound (1.75 g, 9.47 mmol) of Reference Example 17, and according to the method of Example 1, step A, the title compound (3.42 g, yield>100%) was obtained as a gray amorphous solid.

¹H-NMR (300 MHz, CDCl₃); δ (ppm) 1.47 (brs, 9H), 2.13-2.26 (m, 3H), 3.03 (s, 3H), 3.18 (s, 3H), 3.95 (brs, 2H), 4.16-4.31 (m, 6H), 6.88-7.31 (m, 5H), 7.48-7.61 (m, 2H), 8.31-9.45 (broad, 1H).

Step B

N-{2-[1,3-dihydro-2H-isoindol-2-yl(methyl)amino]-2-oxoethyl}-N-{2-methyl-4-[(2-methylhydrazino)carbonyl]phenyl}glycine dihydrochloride The compound (3.42 g) obtained in step A was dissolved in dichloromethane (18 ml). To this solution was added 4N hydrochloric acid-dioxane (9.8 ml, 39 mmol), and the mixture was stirred at room temperature for 3 hr. Diethyl ether was added to the reaction mixture, and the precipitated solid was collected by filtration, and dried under reduced pressure to give the title compound (3.06 g, yield 97%) as a colorless solid. This was directly used for the next step.

Step C

N²-{2-[1,3-dihydro-2H-isoindol-2-yl(methyl)amino]-2-oxoethyl}-N²-{2-methyl-4-[(2-methylhydrazino)carbonyl]phenyl}-N¹-{2-[(tert-butoxycarbonyl)(isopropyl)amino]ethyl}glycinamide Using the compound (1.00 g, 2.01 mmol) obtained in step B, the compound (0.45 g, 2.22 mmol) of Reference Example 3 and triethylamine (0.60 ml, 4.21 mmol), and according to the method of Example 1, step B, the title compound (1.15 g, yield 94%) was obtained as a colorless amorphous solid.

¹H-NMR (300 MHz, CDCl₃); δ (ppm) 1.08 1.14 (2d, J=6.8, 6H), 1.42 1.48 (2s, 9H), 2.36 (s, 3H), 2.70 2.88 (2s, 3H), 2.96 (s, 3H), 2.99-3.21 (m, 2H), 3.34 (q, J=6.8, 2H), 3.90 (s, 2H), 4.12-4.29 (m, 6H), 7.18-7.29 (m, 4H), 7.46-7.50 (m, 2H), 7.61 (s, 1H), 7.78 (brs, 1H), 8.01 (broad, 1H).

Step D

N²-{2-[1,3-dihydro-2H-isoindol-2-yl(methyl)amino]-2-oxoethyl}-N²-[2-methyl-4-(4-methyl-5-oxo-4,5-dihydro-1,3,4-oxadiazol-2-yl)-phenyl]-N¹-{2-[(tert-butoxycarbonyl)(isopropyl)amino]ethyl}glycinamide The compound (1.15 g, 1.88 mmol) obtained in step C was dissolved in tetrahydrofuran (33 ml), triphosgene (0.21 g, 0.63 mmol) and pyridine (0.76 ml, 9.42 mmol) were added under ice-cooling with stirring, and the mixture was stirred at room temperature for 30 min. The reaction mixture was concentrated, and the obtained oil was diluted with ethyl acetate, washed with 10% aqueous citric acid solution and saturated brine, and dried over anhydrous magnesium sulfate. The insoluble material was filtered off, and the solution was concentrated under reduced pressure. The obtained oil was purified by silica gel column chromatography (methanol-dichloromethane) to give the title compound (1.06 g, yield 90%) as a pale-yellow amorphous solid.

¹H-NMR (300 MHz, CDCl₃); δ (ppm) 1.08 1.14 (2d, J=6.8, 6H), 1.42 1.48 (s, 9H), 2.37 (s, 3H), 2.98 (s, 3H), 3.04-3.11 (brs, 2H), 3.32-3.41 (m, 2H), 3.47 (s, 3H), 3.93 (s, 2H), 4.06-4.39 (m, 7H), 7.21-7.28 (m, 5H), 7.55-7.62 (m, 2H), 8.04-8.22 (broad, 1H).

Step E

N²-{2-[1,3-dihydro-2H-isoindol-2-yl(methyl)amino]-2-oxoethyl}-N²-[2-methyl-4-(4-methyl-5-oxo-4,5-dihydro-1,3,4-oxadiazol-2-yl)phenyl]-N¹-[2-(isopropylamino)ethyl]glycinamide dihydrochloride Using the compound (1.06 g, 1.67 mmol) obtained in step D and according to the method of Example 1, step C, the title compound (795 mg, yield 78%) was obtained as a colorless solid.

¹H-NMR (300 MHz, DMSO-d₆); δ (ppm) 1.19 (d, J=6.3, 6H), 2.31 (s, 3H), 2.90 (s, 5H), 3.23-3.32 (m, 1H), 3.37-3.42 (m, 5H), 3.95 (s, 2H), 4.16 (d, J=11.9, 2H), 4.28 (d, J=11.9, 2H), 4.39 (s, 2H), 7.05 (d, J=8.4, 1H), 7.27 (s, 4H), 7.46-7.51 (m, 2H), 8.34-8.39 (m, 1H), 8.88 (brs, 2H).

Example 68

N²-{2-[1,3-dihydro-2H-isoindol-2-yl(methyl)amino]-2-oxoethyl}-N²-[2-methyl-4-(4-methyl-5-oxo-1,3,4-oxadiazol-2-yl)phenyl]-N¹-[2-(ethylamino)ethyl]glycinamide dihydrochloride Step A N²-{2-[1,3-dihydro-2H-isoindol-2-yl(methyl)amino]-2-oxoethyl}-N²-{2-methyl-4-[(2-methylhydrazino) carbonyl]phenyl}-N¹-{2-[(tert-butoxycarbonyl)(ethyl)amino]ethyl}glycinamide Using the compound (1.00 g, 2.01 mmol) obtained in Example 67, step B, the compound (0.42 g, 2.23 mmol) of Reference Example 2 and triethylamine (0.60 ml, 4.21 mmol), and according to the method of Example 1, step B, the title compound (1.21 g, yield>100%) was obtained as a colorless amorphous solid.

¹H-NMR (300 MHz, CDCl₃); δ (ppm) 1.00 (t, J=7.0, 3H), 1.41 (s, 9H), 2.35 (s, 3H), 2.69 2.88 (2s, 3H), 2.95 (s, 3H), 3.08 (q, J=7.0, 2H), 3.20 (brs, 2H), 3.33-3.40 (m, 2H), 3.88 (s, 2H), 4.10-4.29 (m, 6H), 7.17-7.29 (m, 5H), 7.49 (dd, J=1.5, 8.4, 1H), 7.61-7.71 (m, 1H), 7.94-8.2 (broad, 2H).

Step B

N²-{2-[1,3-dihydro-2H-isoindol-2-yl(methyl)amino]-2-oxoethyl}-N²-[2-methyl-4-(4-methyl-5-oxo-4,5-dihydro-1,3,4-oxadiazol-2-yl)phenyl]-N¹-{2-[(tert-butoxycarbonyl)(ethyl)amino]ethyl}glycinamide Using the compound (1.21 g) obtained in step A and according to the method of Example 67, step D, the title compound (880 mg, yield 73%) was obtained as a pale-yellow amorphous solid.

¹H-NMR (300 MHz, CDCl₃); δ (ppm) 1.00 (t, J=6.9, 3H), 1.40 (s, 9H), 2.36 (s, 3H), 2.98 (s, 3H), 3.06-3.14 (m, 2H), 3.21 (brs, 2H), 3.38 (q, J=6.0, 2H), 3.47 (s, 3H), 3.91 (s, 2H), 4.08-4.30 (m, 6H), 7.21-7.29 (m, 5H), 7.55-7.61 (m, 2H), 8.01 8.22 (2brs, 1H).

Step C

N²-{2-[1,3-dihydro-2H-isoindol-2-yl(methyl)amino]-2-oxoethyl}-N²-[2-methyl-4-(4-methyl-5-oxo-1,3,4-oxadiazol-2-yl)phenyl]-N¹-[2-(ethylamino)ethyl]glycinamide dihydrochloride Using the compound (880 mg, 1.42 mmol) obtained in step B and according to the method of Example 1, step C, the title compound (732 mg, yield 87%) was obtained as a colorless solid.

$^1$H-NMR (300 MHz, DMSO-d$_6$); δ (ppm) 1.16 (t, J=6.9, 3H), 2.30 (s, 3H), 2.90 (m, 5H), 3.37 (m, 5H), 3.96 (s, 2H), 4.02-4.3 (m, 4H), 4.39 (s, 2H), 7.05 (d, J=8.4, 1H), 7.26-7.33 (m, 4H), 7.45-7.50 (m, 2H), 8.35 (brs, 1H), 8.93 (brs, 2H).

Example 69

N$^2$-{2-[1,3-dihydro-2H-isoindol-2-yl(methyl)amino]-2-oxoethyl}-N$^2$-[4-(4-ethyl-5-oxo-4,5-dihydro-1,3,4-oxadiazol-2-yl)-2-methylphenyl]-N$^1$-[2-(isopropylamino)ethyl]glycinamide dihydrochloride Step A N-[4-{[2-(tert-butoxycarbonyl)-2-ethylhydrazino]carbonyl}-2-methylphenyl]-N-{2-[1,3-dihydro-2H-isoindol-2-yl(methyl)amino]-2-oxoethyl}glycine Using the compound (3.31 g, 8.08 mmol) of Reference Example 71 and the compound (2.30 g, 12.45 mmol) of Reference Example 17, and according to the method of Example 1, step A, the title compound (3.19 g, yield 73%) was obtained as a gray amorphous solid.
$^1$H-NMR (300 MHz, CDCl$_3$); δ (ppm) 1.14 (t, J=7.2, 3H), 1.46 (brs, 9H), 2.19 (brs, 3H), 3.03 (s, 3H), 3.59 (q, J=7.2, 2H), 3.95 (s, 2H), 4.19-4.32 (m, 6H), 6.94-7.14 (broad, 1H), 7.23-7.29 (m, 4H), 7.48-7.62 (m, 2H), 8.35 9.32 (2broad, 1H).

Step B

N-{2-[1,3-dihydro-2H-isoindol-2-yl(methyl)amino]-2-oxoethyl}-N-{4-[(2-ethylhydrazino)carbonyl]-2-methylphenyl}glycine dihydrochloride Using the compound (3.19 g, 5.91 mmol) obtained by the method of step A and according to the method of Example 67, step B, the title compound (2.81 g, yield 93%) was obtained as a colorless solid.

Step C

N$^2$-{2-[1,3-dihydro-2H-isoindol-2-yl(methyl)amino]-2-oxoethyl}-N$^2$-{4-[(2-ethylhydrazino)carbonyl]-2-methylphenyl}-N$^1$-{2-[(tert-butoxycarbonyl)(isopropyl)amino]ethyl}glycinamide Using the compound (1.00 g, 1.95 mmol) obtained in step B, the compound (0.43 g, 2.13 mmol) of Reference Example 3 and triethylamine (0.57 ml, 4.1 mmol), and according to the method of Example 1, step B, the title compound (1.36 g, yield>100%) was obtained as a colorless amorphous solid.
$^1$H-NMR (300 MHz, CDCl$_3$); δ (ppm) 1.06-1.18 (m, 9H), 1.42 1.47 (2s, 9H), 2.35 (s, 3H), 2.87-3.03 (m, 5H), 3.09 (brs, 2H), 3.31-3.38 (m, 2H), 3.90 (s, 2H), 4.12-4.29 (m, 7H), 7.18-7.30 (m, 4H), 7.49-7.63 (m, 2H), 7.8-8.3 (broad, 2H).

Step D

N$^2$-{2-[1,3-dihydro-2H-isoindol-2-yl(methyl)amino]-2-oxoethyl}-N$^2$-[4-(4-ethyl-5-oxo-4,5-dihydro-1,3,4-oxadiazol-2-yl)-2-methylphenyl]-N$^1$-{2-[(tert-butoxycarbonyl)(isopropyl)amino]ethyl}glycinamide Using the compound (1.36 g) obtained in step C and according to the method of Example 67, step D, the title compound (0.70 g, yield 55%) was obtained as a pale-yellow amorphous solid.
$^1$H-NMR (300 MHz, CDCl$_3$); δ (ppm) 1.08 (d, J=6.9, 6H), 1.32-1.43 (m, 12H), 2.37 (s, 3H), 2.98 (s, 3H), 3.10 (brs, 2H), 3.35 (q, J=6.9, 2H), 3.82 (q, J=7.2, 2H), 3.92 (s, 2H), 4.04-4.30 (m, 7H), 7.22-7.31 (m, 5H), 7.56-7.63 (m, 2H), 7.8-8.4 (broad, 1H).

Step E

N$^2$-[4-(4-ethyl-5-oxo-4,5-dihydro-1,3,4-oxadiazol-2-yl)-2-methylphenyl]-N$^2$-{2-[1,3-dihydro-2H-isoindol-2-yl(methyl)amino]-2-oxoethyl}-N$^1$-[2-(isopropylamino)ethyl]glycinamide dihydrochloride Using the compound (0.70 g, 1.08 mmol) obtained in step D and according to the method of Example 1, step C, the title compound (515 mg, yield 77%) was obtained as a colorless solid.
$^1$H-NMR (300 MHz, DMSO-d$_6$); δ (ppm) 1.20 (d, 6H), 1.28 (t, J=7.0, 3H), 2.31 (s, 3H), 2.90 (m, 5H), 3.23-3.25 (m, 1H), 3.37-3.42 (m, 2H), 3.74 (q, J=7.0, 2H), 3.96 (s, 2H), 4.13-4.40 (m, 6H), 7.05 (d, J=8.3, 1H), 7.27 (m, 4H), 7.46-7.52 (m, 2H), 8.38 (brs, 1H), 8.95 (brs, 2H).

Example 70

N$^2$-{2-[1,3-dihydro-2H-isoindol-2-yl(methyl)amino]-2-oxoethyl}-N$^2$-[4-(4-ethyl-5-oxo-4,5-dihydro-1,3,4-oxadiazol-2-yl)-2-methylphenyl]-N$^1$-[2-(ethylamino)ethyl]glycinamide dihydrochloride Step A N$^2$-{2-[1,3-dihydro-2H-isoindol-2-yl(methyl)amino]-2-oxoethyl}-N$^2$-{4-[(2-ethylhydrazino)carbonyl]-2-methylphenyl}-N$^1$-{2-[(tert-butoxycarbonyl)(ethyl)amino]ethyl}glycinamide Using the compound (1.00 g, 1.95 mmol) of Example 69, step B, the compound (0.40 g, 2.13 mmol) of Reference Example 2 and triethylamine (0.57 ml, 4.09 mmol), and according to the method of Example 1, step B, the title compound (1.43 g, yield>100%) was obtained as a colorless amorphous solid.
$^1$H-NMR (300 MHz, CDCl$_3$); δ (ppm) 0.96 (t, J=6.6, 3H), 1.09 (t, J=7.2, 3H), 1.38 1.43 (2s, 9H), 2.31 (s, 3H), 2.84-2.94 (m, 5H), 3.05 (q, J=6.9, 2H), 3.17 (brs, 2H), 3.32-3.43 (m, 2H), 3.85 (s, 2H), 4.09-4.26 (m, 6H), 7.13-7.27 (m, 5H), 7.46-7.59 (m, 2H), 7.97 (broad, 2H).

Step B

N$^2$-{2-[1,3-dihydro-2H-isoindol-2-yl(methyl)amino]-2-oxoethyl}-N$^2$-[4-(4-ethyl-5-oxo-4,5-dihydro-1,3,4-oxadiazol-2-yl)-2-methylphenyl]-N$^1$-{2-[(tert-butoxycarbonyl)(ethyl)amino]ethyl}glycinamide Using the compound (1.43 g) obtained in step A and according to the method of Example 67, step D, the title compound (0.98 g, yield 79%) was obtained as a pale-yellow amorphous solid.
$^1$H-NMR (300 MHz, CDCl$_3$); δ (ppm) 1.00 (t, J=6.9, 3H), 1.36-1.41 (m, 12H), 2.36 (s, 3H), 2.98 (s, 3H), 3.08 (q, J=6.6, 2H), 3.21 (brs, 2H), 3.34-3.40 (m, 2H), 3.82 (q, J=7.2, 2H), 3.91 (s, 2H), 4.08-4.31 (m, 6H), 7.21-7.29 (m, 5H), 7.57 (dd, J=1.8, 8.4, 2H), 8.03 8.25 (2brs, 1H).

Step C

N²-{2-[1,3-dihydro-2H-isoindol-2-yl(methyl)amino]-2-oxoethyl}-N²-[4-(4-ethyl-5-oxo-4,5-dihydro-1,3,4-oxadiazol-2-yl)-2-methylphenyl]-N¹-[2-(ethylamino)ethyl]glycinamide dihydrochloride Using the compound (0.98 g, 1.54 mmol) obtained in step B and according to the method of Example 1, step C, the title compound (0.69 g, yield 73%) was obtained as a colorless solid.
¹H-NMR (300 MHz, DMSO-d₆); δ (ppm) 1.16 (t, J=6.9, 3H), 1.27 (t, J=7.2, 3H), 2.31 (s, 3H), 2.8-3.0 (m, 7H), 3.38 (q, J=6.9, 2H), 3.74 (q, J=7.2, 2H), 3.95 (s, 2H), 4.13-4.40 (m, 6H), 7.04 (d, J=8.4, 1H), 7.20-7.32 (m, 4H), 7.46-7.51 (m, 2H), 8.34-8.39 (m, 1H), 8.95 (brs, 2H).

Example 71

N²-(5-cyano-2-methylphenyl)-N²-{2-[1,3-dihydro-2H-isoindol-2-yl(methyl)amino]-2-oxoethyl}-N¹-{2-[(2R)-2-(hydroxymethyl)pyrrolidin-1-yl]ethyl}glycinamide dihydrochloride Using the compound (911 mg, 2.41 mmol) of Example 1, step A, compound (718 mg, 4.98 mmol) of Reference Example 8, and according to the methods of Example 1, step B, Example 17, step C, the title compound (244 mg, yield 18%) was obtained as a pale-bistered solid.
¹H-NMR (300 MHz, DMSO-d₆); δ (ppm) 1.61-2.16 (m, 6H), 2.34 (s, 3H), 2.88 (s, 3H), 2.89-3.10 (m, 2H), 3.25-3.58 (m, 4H), 3.59-3.77 (m, 2H), 3.90 (s, 2H), 4.00-4.15 (m, 1H), 4.14 (d, J=11.9, 2H), 4.26 (d, J=11.9, 2H), 4.30 (s, 2H), 7.24-7.32 (m, 6H), 7.45 (s, 1H), 8.26-8.30 (m, 1H), 9.83 (brs, 1H).

Example 72

N²-(5-cyano-2-methylphenyl)-N²-{2-[1,3-dihydro-2H-isoindol-2-yl(methyl)amino]-2-oxoethyl}-N¹-{2-[(2,2,2-trifluoroethyl)amino]ethyl}glycinamide dihydrochloride Using the compound (500 mg, 1.32 mmol) of Example 1, step A, and the compound (544 mg, 1.98 mmol) of Reference Example 14, and according to the method of Example 1, step B, a brown oil was obtained. This was dissolved in a methanol (5 ml)-water (1 ml) mixed solvent, then potassium carbonate (300 mg, 2.17 mmol) was added, and the mixture was stirred at room temperature overnight. The reaction mixture was diluted with water, and extracted with ethyl acetate. The organic layer was washed with saturated brine, and dried over anhydrous magnesium sulfate. The insoluble material was filtered off, and the solution was concentrated under reduced pressure. The obtained oil was purified by silica gel column chromatography (methanol-chloroform) to give the title compound (salt free) as an oil. Using this oil and according to the method of Example 17, step C, the title compound (269 mg, yield 35%) was obtained as a pale-bistered amorphous solid.
¹H-NMR (300 MHz, DMSO-d₆); δ (ppm) 2.33 (s, 3H), 2.89 (s, 3H), 3.04-3.09 (m, 2H), 3.42-3.47 (m, 2H), 3.90 (s, 2H), 4.03-4.16 (m, 4H), 4.26 (d, J=12.6, 2H), 4.30 (s, 2H), 7.25-7.31 (m, 6H), 7.44 (s, 1H), 8.30-8.34 (m, 1H), 9.25-10.48 (broad, 2H).

The compounds of Examples 49-72 are shown below.

TABLE 9

| Example | Structural Formula | TMW | LC-MS (found) |
|---|---|---|---|
| 49 | 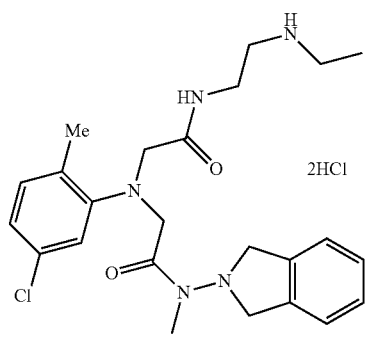 [SMILES: CCNCCNC(=O)CN(CC(=O)N(C)N1Cc2ccccc2C1)c1cc(Cl)ccc1C ; "2HCl"] | 530.92 | 458 |
| 50 | 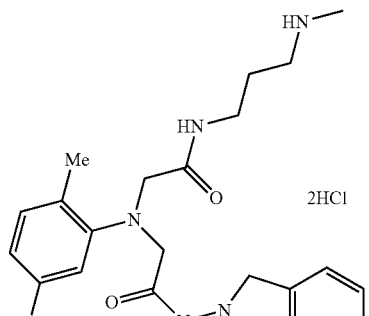 | 530.92 | 458 |

TABLE 9-continued
| Example | Structural Formula | TMW | LC-MS (found) |
|---|---|---|---|
| 51 | 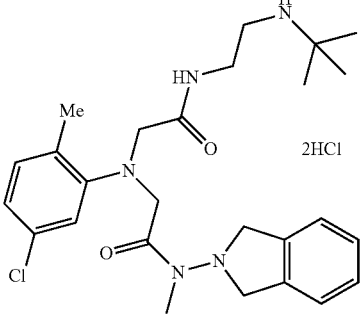 | 558.97 | 486 |
| 52 | 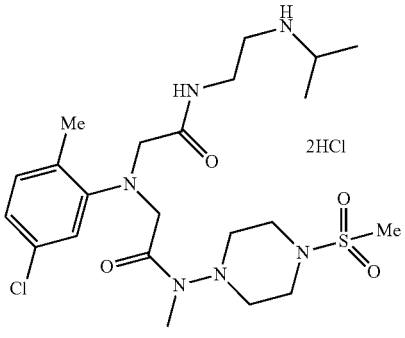 [SMILES: Cc1ccc(Cl)cc1N(CC(=O)NCCNC(C)C)CC(=O)N(C)N1CCN(S(C)(=O)=O)CC1 ; "2HCl"] | 590.01 | 517 |
| 53 | 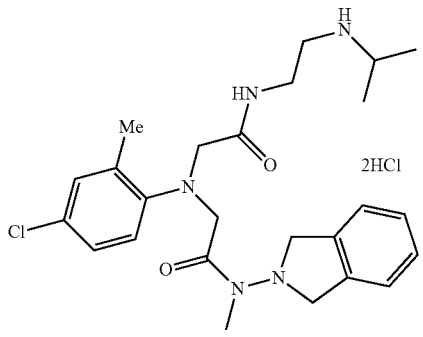 [SMILES: Cc1cc(Cl)ccc1N(CC(=O)NCCNC(C)C)CC(=O)N(C)N1Cc2ccccc2C1 ; "2HCl"] | 544.94 | 472 |
| 54 | 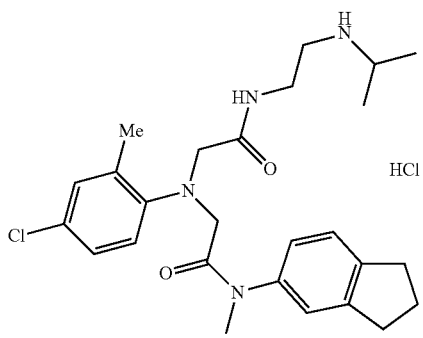 [SMILES: Cc1cc(Cl)ccc1N(CC(=O)NCCNC(C)C)CC(=O)N(C)c1ccc2c(c1)CCC2 ; Cl] | 507.50 | 471 |

TABLE 9-continued

| Example | Structural Formula | TMW | LC-MS (found) |
|---|---|---|---|
| 55 | | 536.32 | 499 |
| 56 | | 552.54 | 480 |
| 57 | | 502.05 | 466 |
| 58 | | 570.53 | 498 |

TABLE 9-continued

| Example | Structural Formula | TMW | LC-MS (found) |
|---|---|---|---|
| 59 | | 556.50 | 484 |
| 60 | | 540.53 | 486 |
| 61 | | 535.51 | 463 |
| 62 | | 521.48 | 449 |

TABLE 9-continued
| Example | Structural Formula | TMW | LC-MS (found) |
|---|---|---|---|
| 63 | 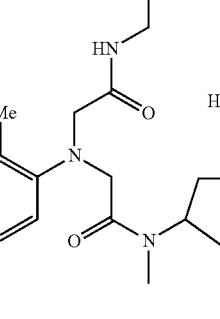 | 498.06 | 462 |
| 64 | 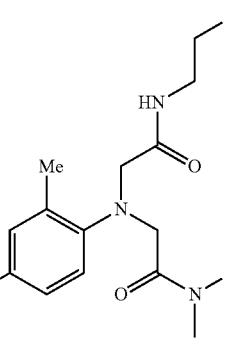 | 592.56 | 520 |
| 65 | 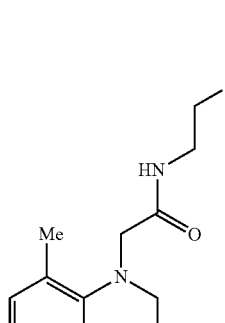 | 578.53 | 506 |
| 66 | 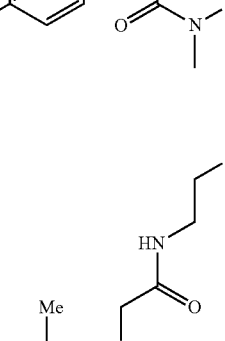 | 555.11 | 519 |

TABLE 9-continued

| Example | Structural Formula | TMW | LC-MS (found) |
|---|---|---|---|
| 67 | | 608.56 | 536 |
| 68 | | 594.53 | 522 |
| 69 | | 622.59 | 550 |
| 70 | | 608.56 | 536 |

TABLE 9-continued

| Example | Structural Formula | TMW | LC-MS (found) |
|---------|-------------------|--------|---------------|
| 71 | 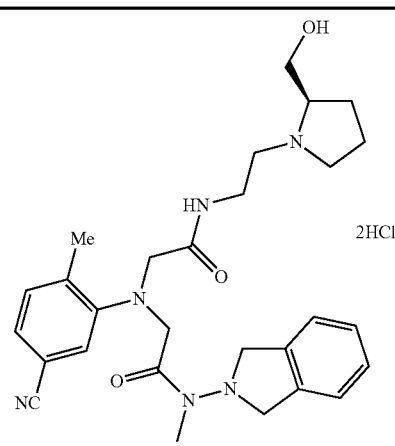 | 577.55 | 505 |
| 72 | 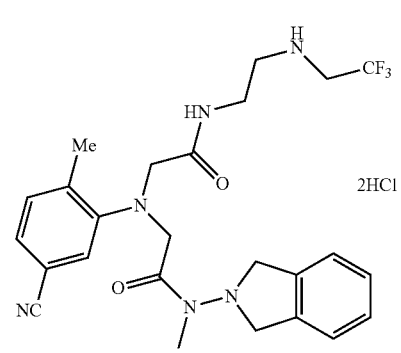 [SMILES: Cc1ccc(C#N)cc1N(CC(=O)NCCNCC(F)(F)F)CC(=O)N(C)N1Cc2ccccc2C1 ; "2HCl"] | 575.45 | 503 |

Example 73

$N^2$-(5-cyano-2-methylphenyl)-$N^2$-{2-[2,3-dihydro-1H-inden-2-yl(methyl)amino]-2-oxoethyl}-$N^1$-{2-[(2,2,2-trifluoroethyl)amino]ethyl}glycinamide hydrochloride

Step A

N-(5-cyano-2-methylphenyl)-N-{2-[2,3-dihydro-1H-inden-2-yl(methyl)amino]-2-oxoethyl}glycine Using the compound (1.00 g, 4.03 mmol) of Reference Example 61 and the compound (1.11 g, 6.05 mmol) of Reference Example 23, and according to the method of Example 4, step A, the title compound (820 mg, yield 54%) was obtained as a colorless amorphous solid.

$^1$H-NMR (300 MHz, DMSO-$d_6$); δ (ppm) 2.33 (s, 3H), 2.66 (s, 1.2H), 2.76 (s, 1.8H), 2.79-3.17 (m, 4H), 3.95 (s, 2H), 4.09 (s, 1.2H), 4.24 (s, 0.8H), 4.83-4.99 (m, 0.4H), 5.24-5.31 (m, 0.6H), 7.13-7.24 (m, 4H), 7.29-7.36 (m, 2H), 7.48 (d, J=12.0, 1H), 12.60 (brs, 1H).

Step B $N^2$-(5-cyano-2-methylphenyl)-$N^2$-{2-[2,3-dihydro-1H-inden-2-yl(methyl)amino]-2-oxoethyl}-$N^1$-{2-[(2,2,2-trifluoroethyl)amino]ethyl}glycinamide hydrochloride Using the compound (500 mg, 1.32 mmol) obtained in step A and the compound (544 mg, 1.98 mmol) of Reference Example 14, and according to the method of Example 72, the title compound (293 mg, yield 41%) was obtained as a colorless amorphous solid.

$^1$H-NMR (300 MHz, DMSO-$d_6$); δ (ppm) 2.35 (s, 3H), 2.68 (s, 1.2H), 2.76 (s, 1.8H), 2.79-3.17 (m, 6H), 3.41-3.48 (m, 2H), 3.86-3.88 (m, 2H), 4.04-4.27 (m, 4H), 4.78-4.88 (m, 0.4H), 5.27-5.35 (m, 0.6H), 7.12-7.24 (m, 4H), 7.31-7.35 (m, 2H), 7.48 (d, J=10.2, 1H), 8.41-8.45 (m, 1H), 9.55-10.80 (broad, 2H).

Example 74

$N^2$-{2-[1,3-dihydro-2H-isoindol-2-yl(methyl)amino]-2-oxoethyl}-$N^2$-[2-methyl-5-(5-oxo-4,5-dihydro-1,2,4-oxadiazol-3-yl)phenyl]-$N^1$-[2-(isopropylamino)ethyl]glycinamide dihydrochloride

Step A

N-(5-cyano-2-methylphenyl)-N-{2-[1,3-dihydro-2H-isoindol-2-yl(methyl)amino]-2-oxoethyl}glycine tert-butyl ester The compound (2.06 g, 5.44 mmol) of Example 1, step A, 4-dimethylaminopyridine (1.40 g, 11.5 mmol) and WSC (1.46 g, 7.62 mmol) were dissolved in dichloromethane (22 ml), tert-butanol (1.0 ml, 10 mmol) was added at room temperature, and the mixture was stirred at the same temperature overnight. The reaction mixture was diluted with an ethyl acetate-hexane=1:1 mixed solvent, and the organic layer was washed with 10% aqueous citric acid solution, water, diluted aqueous sodium hydroxide solution and saturated brine, and dried over anhydrous magnesium sulfate. The insoluble material was filtered off, and the solution was concentrated under reduced pressure. The obtained oil was purified by silica gel column chromatography (ethyl acetate-hexane) to give the title compound (1.76 g, yield 74%) as a colorless solid.

$^1$H-NMR (300 MHz, CDCl$_3$); δ (ppm) 1.41 (s, 9H), 2.37 (s, 3H), 2.95 (s, 3H), 4.00 (s 2H), 4.15 (d, J=11.4, 2H), 4.26 (d, J=11.4, 2H), 4.36 (s, 2H), 7.19-7.29 (m, 6H), 7.44 (s, 1H).

Step B

N-{2-[1,3-dihydro-2H-isoindol-2-yl(methyl)amino]-2-oxoethyl}-N-[2-methyl-5-(5-oxo-4,5-dihydro-1,2,4-oxadiazol-3-yl)phenyl]glycine tert-butyl ester To an ethanol (20 ml)-water (5 ml) solution were added the compound (584 mg, 1.34 mmol) obtained in step A, hydroxylamine hydrochloride (775 mg, 11.2 mmol) and sodium acetate (956 mg, 11.7 mmol), and the mixture was heated under reflux for 3 hr. The reaction mixture was cooled, and diluted with ethyl acetate and water to extract the organic layer. The organic layer washed with saturated aqueous sodium hydrogen carbonate and saturated brine, and dried over anhydrous magnesium sulfate. The insoluble material was filtered off, and the solution was concentrated under reduced pressure to give a colorless oil. This oil was dissolved in pyridine (10 ml), ethyl chloroformate (0.17 ml, 1.8 mmol) was added under ice-cooling, and the mixture was stirred at room temperature for 30 min and stirred with heating at 130° C. for 90 min. The reaction mixture was cooled, diluted with 10% aqueous citric acid solution, and the organic layer was extracted with ethyl acetate. The organic layer was washed with saturated brine, and dried over anhydrous magnesium sulfate. The insoluble material was filtered off, and the solution was concentrated under reduced pressure. The obtained oil was purified by silica gel column chromatography (ethyl acetate-hexane) to give the title compound (474 mg, yield 71%) as a pale-yellow amorphous solid $^1$H-NMR (300 MHz, CDCl$_3$); δ (ppm) 1.35 (s, 9H), 2.39 (s, 3H), 2.98 (s, 3H), 4.06 (s, 2H), 4.23 (d, J=13.5, 2H), 4.29 (d, J=13.5, 2H), 4.46 (s, 2H), 7.19-7.30 (m, 6H), 7.56 (d, J=1.2, 1H), 10.53 (brs, 1H).

Step C

N-{2-[1,3-dihydro-2H-isoindol-2-yl(methyl)amino]-2-oxoethyl}-N-[2-methyl-5-(5-oxo-4,5-dihydro-1,2,4-oxadiazol-3-yl)phenyl]glycine The compound (449 mg, 0.910 mmol) obtained in step B was dissolved in dichloromethane (4 ml), trifluoroacetic acid (4 ml) was added under ice-cooling and the mixture was stirred at room temperature for 3 hr. The reaction mixture was concentrated under reduced pressure, and the obtained oil was purified by silica gel column chromatography (methanol-chloroform) to give the title compound (407 mg, yield>100%) as a colorless amorphous solid.

$^1$H-NMR (300 MHz, CDCl$_3$); δ (ppm) 2.35 (s, 3H), 3.06 (s, 3H), 4.05 (s, 2H), 4.20 (d, J=11.7, 2H), 4.30 (d, J=11.7, 2H), 4.35 (s, 2H), 7.19-7.31 (m, 5H), 7.50 (dd, J=1.5, 7.8, 1H), 7.59 (d, J=1.5, 1H), 11.07 (brs, 1H).

Step D

N$^2$-{2-[1,3-dihydro-2H-isoindol-2-yl(methyl)amino]-2-oxoethyl}-N$^2$-[2-methyl-5-(5-oxo-4,5-dihydro-1,2,4-oxadiazol-3-yl)phenyl]-N$^1$-{2-[(tert-butoxycarbonyl)(isopropyl)amino]ethyl}glycinamide Using the compound (397 mg, 0.908 mmol) obtained in step C, and the compound (232 mg, 1.15 mmol) of Reference Example 3, and according to the method of Example 1, step B, the title compound (275 mg, yield 49%) was obtained as a colorless solid.

$^1$H-NMR (300 MHz, CDCl$_3$); δ (ppm) 1.15 (broad, 6H), 1.37 (brs, 9H), 2.41 (s, 3H), 2.95 (s, 3H), 3.1-3.5 (m, 4H), 3.9-4.2 (broad, 1H), 3.95 (s, 2H), 4.14 (d, J=11.7, 2H), 4.24 (d, J=11.7, 2H), 4.26 (s, 2H), 7.19-7.29 (m, 5H), 7.56 (d, J=7.5, 1H), 7.80 (brs, 1H), 8.63 (brs, 1H), 11.50 (brs, 1H).

Step E

N$^2$-{2-[1,3-dihydro-2H-isoindol-2-yl(methyl)amino]-2-oxoethyl}-N$^2$-[2-methyl-5-(5-oxo-4,5-dihydro-1,2,4-oxadiazol-3-yl)phenyl]-N$^1$-[2-(isopropylamino)ethyl]glycinamide dihydrochloride Using the compound (269 mg, 0.433 mmol) obtained in step D and according to the method of Example 1, step C, the title compound (242 mg, yield 94%) was obtained as a colorless solid.

$^1$H-NMR (300 MHz, DMSO-d$_6$); δ (ppm) 1.19 (d, J=6.6, 6H), 2.34 (s, 3H), 2.8-3.0 (m, 2H), 2.88 (s, 3H), 3.1-3.3 (m, 1H), 3.34-3.42 (m, 2H), 3.92 (s, 2H), 4.12 (d, J=11.7, 2H), 4.26 (d, J=11.7, 2H), 4.33 (s, 2H), 7.22-7.36 (m, 6H), 7.59 (s, 1H), 8.33 (broad t, 1H), 8.79 (brs, 2H), 12.97 (s, 1H).

Example 75

N$^2$-{2-[1,3-dihydro-2H-isoindol-2-yl(methyl)amino]-2-oxoethyl}-N$^2$-[2-methyl-5-(4-methyl-5-oxo-4,5-dihydro-1,2,4-oxadiazol-3-yl)phenyl]-N$^1$-[2-(isopropylamino)ethyl]glycinamide dihydrochloride Step A N-{2-[1,3-dihydro-2H-isoindol-2-yl(methyl)amino]-2-oxoethyl}-N-[2-methyl-5-(4-methyl-5-oxo-4,5-dihydro-1,2,4-oxadiazol-3-yl)phenyl]glycine tert-butyl ester The compound (680 mg, 1.38 mmol) of Example 74, step B was dissolved in N,N-dimethylformamide (10 ml) and the mixture was stirred under ice-cooling. Then, 60% sodium hydride (74 mg, 1.85 mmol) was added, and the mixture was stirred at room temperature for 10 min. After ice-cooling again, methyl iodide (0.5 ml) was added with stirring, and the mixture was stirred under ice-cooling for 40 min. The reaction mixture was diluted with 10% citric acid, and extracted with ethyl acetate. The organic layer was washed with saturated aqueous sodium hydrogen carbonate and saturated brine, and dried over anhydrous magnesium sulfate. The insoluble material was filtered off, and the solution was concentrated under reduced pressure. The obtained oil was purified by silica gel column chromatography (ethyl acetate-hexane) to give the title compound (678 mg, yield 97%) as a pale-yellow amorphous solid $^1$H-NMR (300 MHz, CDCl$_3$); δ (ppm) 1.40 (s, 9H), 2.40 (s, 3H), 2.94 (s, 3H), 3.31 (s, 3H), 4.05 (s, 2H), 4.15 (d, J=11.7, 2H), 4.26 (d, J=11.7, 2H), 4.38 (s, 2H), 7.15-7.31 (m, 6H), 7.43 (d, J=1.5, 1H).

Step B

N-{2-[1,3-dihydro-2H-isoindol-2-yl(methyl)amino]-2-oxoethyl}-N-[2-methyl-5-(4-methyl-5-oxo-4,5-dihydro-1,2,4-oxadiazol-3-yl)phenyl]glycine Using the compound (666 mg, 1.31 mmol) obtained in step A and according to the method of Example 74, step C, the title compound (582 mg, yield 98%) was obtained as a pale-yellow amorphous solid $^1$H-NMR (300 MHz, CDCl$_3$); δ (ppm) 2.38 (s, 3H), 3.08 (s, 3H), 3.30 (s, 3H), 3.98 (s, 2H), 4.20 (d, J=11.5, 2H), 4.31 (d, J=11.5, 2H), 4.36 (s, 2H), 7.2-7.3 (m, 5H), 7.36 (d, J=7.8, 1H), 7.44 (d, J=1.5, 1H).

Step C

N$^2$-{2-[1,3-dihydro-2H-isoindol-2-yl(methyl)amino]-2-oxoethyl}-N$^2$-[2-methyl-5-(4-methyl-5-oxo-4,5-dihydro-1,2,4-oxadiazol-3-yl)phenyl]-N$^1$-{2-[(tert-butoxycarbonyl)(isopropyl)amino]ethyl}glycinamide Using the compound (576 mg, 1.28 mmol) obtained in step B, and the compound (387 mg, 1.91 mmol) of Reference Example 3, and according to the method of Example 1, step B, the title compound (691 mg, yield 85%) was obtained as a pale-yellow amorphous solid $^1$H-NMR (300 MHz, CDCl$_3$); δ (ppm) 1.10 (d, J=6.9, 6H), 1.42 (brs, 9H), 2.42 (s, 3H), 2.96 (s, 3H), 3.0-3.2 (m, 2H), 3.3-3.4 (m, 2H), 3.32 (s, 3H), 3.89 (s, 2H), 3.9-4.3 (broad, 1H), 4.15 (d, J=11.4, 2H), 4.26 (s, 2H), 4.27 (d, J=11.4, 2H), 7.2-7.3 (m, 5H), 7.33 (d, J=7.8, 1H), 7.47 (d, J=1.2, 1H), 7.9-8.5 (broad, 1H).

Step D

N$^2$-{2-[1,3-dihydro-2H-isoindol-2-yl(methyl)amino]-2-oxoethyl}-N$^2$-[2-methyl-5-(4-methyl-5-oxo-4,5-dihydro-1,2,4-oxadiazol-3-yl)phenyl]-N$^1$-[2-(isopropylamino)ethyl]glycinamide dihydrochloride Using the compound (685 mg, 1.08 mmol) obtained in step C and according to the method of Example 1, step C, the title compound (578 mg, yield 88%) was obtained as a colorless solid.

$^1$H-NMR (300 MHz, DMSO-d$_6$); δ (ppm) 1.18 (d, J=6.3, 6H), 2.35 (s, 3H), 2.8-3.0 (m, 2H), 2.89 (s, 3H), 3.19 (s, 3H), 3.2-3.5 (m, 3H), 3.92 (s, 2H), 4.12 (d, J=11.7, 2H), 4.26 (d, J=11.7, 2H), 4.33 (s, 2H), 7.22 (dd, J=1.2, 7.8, 1H), 7.26 (broad, 4H), 7.34 (d, J=7.8, 1H), 7.39 (d, J=1.2, 1H), 8.30 (t, J=5.7, 1H), 8.56 (brs, 2H).

Example 76

N$^2$-(5-carboxy-2-methylphenyl)-N$^2$-{2-[1,3-dihydro-2H-isoindol-2-yl(methyl)amino]-2-oxoethyl}-N$^1$-[2-(isopropylamino)ethyl]glycinamide dihydrochloride Step A N$^2$-(5-tert-butoxycarbonyl-2-methylphenyl)-N$^2$-{2-[1,3-dihydro-2H-isoindol-2-yl(methyl)amino]-2-oxoethyl}glycine Using the compound (2.42 g, 7.48 mmol) of Reference Example 72 and the compound (2.07 g, 11.2 mmol) of Reference Example 17, and according to the method of Example 1, step A, the title compound (3.89 g, yield>100%) was obtained as a gray amorphous solid.

$^1$H-NMR (300 MHz, DMSO-d$_6$); δ (ppm) 1.55 (s, 9H), 2.35 (s, 3H), 3.04 (s, 3H), 3.94 (s, 2H), 4.15-4.31 (m, 6H), 7.17-7.28 (m, 5H), 7.64 (dd, J=1.62, 7.82, 1H), 7.84 (d, J=1.23, 1H).

Step B

N$^2$-(5-tert-butoxycarbonyl-2-methylphenyl)-N$^2$-{2-[1,3-dihydro-2H-isoindol-2-yl(methyl)amino]-2-oxoethyl}-N$^1$-[2-{(isopropyl)[(2-nitrophenyl)sulfonyl]amino}ethyl]glycinamide Using the compound (3.89 g) obtained in step A, and the compound (3.82 g, 13.3 mmol) of Reference Example 7, and according to the method of Example 1, step B, the title compound (4.01 g, yield 74%) was obtained as a colorless amorphous solid.

$^1$H-NMR (300 MHz, CDCl$_3$); δ (ppm) 1.18 (d, J=6.8, 6H), 1.56 (s, 9H), 2.40 (s, 3H), 2.95 (s, 3H), 3.36-3.39 (m, 2H), 3.48-3.52 (m, 2H), 3.79 (s, 2H), 4.08-4.23 (m, 5H), 4.30 (s, 2H), 7.18-7.28 (m, 5H), 7.58-7.69 (m, 4H), 7.85 (d, J=1.3, 1H), 8.00 (d, J=9.1, 1H), 8.75 (m, 1H).

Step C

N$^2$-(5-tert-butoxycarbonyl-2-methylphenyl)-N$^2$-{2-[1,3-dihydro-2H-isoindol-2-yl(methyl)amino]-2-oxoethyl}-N$^1$-[2-(isopropylamino)ethyl]glycinamide Using the compound (0.80 g, 1.11 mmol) obtained in step B and according to the method of Example 40, step E, the title compound (0.55 g, yield 92%) was obtained as a colorless solid.

$^1$H-NMR (300 MHz, CDCl$_3$); δ (ppm) 1.01 (d, J=6.8, 6H), 1.56 (s, 9H), 2.40 (s, 3H), 2.72-2.79 (m, 3H), 2.95 (s, 3H), 3.39-3.42 (m, 2H), 3.79 (s, 2H), 4.12-4.24 (m, 6H), 7.19-7.31 (m, 5H), 7.60-7.63 (m, 1H), 7.85 (s, 1H), 8.52 (s, 1H).

Step D

N$^2$-(5-carboxy-2-methylphenyl)-N$^2$-{2-[1,3-dihydro-2H-isoindol-2-yl(methyl)amino]-2-oxoethyl}-N$^1$-[2-(isopropylamino)ethyl]glycinamide The compound (0.30 g, 0.56 mmol) obtained in step C was dissolved in dichloromethane (10 ml), trifluoroacetic acid (1.36 ml) was added, and the mixture was stirred at room temperature overnight. The reaction mixture was concentrated under reduced pressure, water was added, and the mixture was extracted with dichloromethane. The organic layer was dried over anhydrous magnesium sulfate, and the insoluble material was filtered off, and the solution was concentrated under reduced pressure. The obtained oil was purified by silica gel column chromatography (methanol-dichloromethane) to give the title compound (0.32 g) as a colorless amorphous solid. This was directly used for the next step.

Step E $N^2$-(5-carboxy-2-methylphenyl)-$N^2$-{2-[1,3-dihydro-2H-isoindol-2-yl(methyl)amino]-2-oxoethyl}-$N^1$-[2-(isopropylamino)ethyl]glycinamide dihydrochloride Using the compound (0.32 g) obtained in step D and according to the method of Example 17, step C, the title compound (0.25 g, yield from step D 81%) was obtained as a colorless solid.

$^1$H-NMR (300 MHz, DMSO-$d_6$); δ (ppm) 1.19 (d, J=6.5, 6H), 2.32 (s, 3H), 2.87 (m, 5H), 3.21-3.26 (m, 1H), 3.38 (q, J=7.1, 2H), 3.89 (s, 2H), 4.10-4.34 (m, 6H), 7.20-7.26 (m, 5H), 7.46 (d, J=7.6, 1H), 7.70 (s, 1H), 8.35-8.40 (m, 1H), 8.91 (brs, 2H).

Example 77

$N^2$-{2-[1,3-dihydro-2H-isoindol-2-yl(methyl)amino]-2-oxoethyl}-$N^2$-{2-methyl-5-[(methylamino)carbonyl]phenyl}-$N^1$-[2-(isopropylamino)ethyl]glycinamide dihydrochloride Step A $N^2$-(5-carboxy-2-methylphenyl)-$N^2$-{2-[1,3-dihydro-2H-isoindol-2-yl(methyl)amino]-2-oxoethyl}-$N^1$-[2-{(isopropyl)[(2-nitrophenyl)sulfonyl]amino}ethyl]glycinamide Using the compound (3.18 g, 4.4 mmol) of Example 76, step B and according to the method of Reference Example 61, step D, the title compound (3.17 g, yield>100%) was obtained as a colorless solid.

$^1$H-NMR (300 MHz, CDCl$_3$); δ (ppm) 1.11-1.20 (m, 6H), 2.38 2.41 (2s, 3H), 2.93 2.97 (2s, 3H), 3.35-3.40 (m, 2H), 3.49-3.54 (m, 2H), 3.90 (s, 2H), 4.09-4.36 (m, 7H), 7.19-7.27 (m, 5H), 7.58-7.71 (m, 4H), 7.95-7.99 (m, 2H), 8.96 (m, 1H).

Step B $N^2$-{2-[1,3-dihydro-2H-isoindol-2-yl(methyl)amino]-2-oxoethyl}-$N^2$-{2-methyl-5-[(methylamino)carbonyl]phenyl}-$N^1$-[2-{(isopropyl)[(2-nitrophenyl)sulfonyl]amino}ethyl]glycinamide The compound (0.70 g, 1.05 mmol) obtained in step A was dissolved in dichloromethane (10 ml). Under ice-cooling with stirring, triethylamine (0.20 ml, 1.43 mmol) and isobutyl chloroformate (0.20 ml, 1.52 mmol) were added, and the mixture was stirred at room temperature for 3 hr. Then, under ice-cooling with stirring, 40% methylamine-methanol solution (0.45 g) was added, and the mixture was stirred at room temperature for 2 hr. The reaction mixture was diluted with dichloromethane, washed with saturated brine, and dried over anhydrous magnesium sulfate. The insoluble material was filtered off, and the solution was concentrated under reduced pressure. The obtained oil was purified by silica gel column chromatography (NH silica gel use, methanol-dichloromethane) to give the title compound (0.70 g, yield 98%) as a colorless solid.

$^1$H-NMR (300 MHz, CDCl$_3$); δ (ppm) 1.15 (d, J=6.7, 6H), 2.37 (s, 3H), 2.94 (s, 6H), 3.29-3.35 (m, 2H), 3.43-3.51 (m, 2H), 3.84 (s, 2H), 4.02-4.28 (m, 7H), 6.42 (brs, 1H), 7.18-7.28 (m, 5H), 7.44 (d, J=7.8, 1H), 7.57-7.69 (m, 4H), 7.95-7.99 (m, 1H), 8.57-8.60 (m, 1H).

Step C $N^2$-{2-[1,3-dihydro-2H-isoindol-2-yl(methyl)amino]-2-oxoethyl}-$N^2$-{2-methyl-5-[(methylamino)carbonyl]phenyl}-$N^1$-[2-(isopropylamino)ethyl]glycinamide dihydrochloride Using the compound (0.70 g, 1.03 mmol) obtained in step B and according to the method of Example 50, step B, the title compound (0.45 g, yield 77%) was obtained as a colorless solid.

$^1$H-NMR (300 MHz, DMSO-$d_6$); δ (ppm) 1.15 (d, J=6.6, 6H), 2.30 (s, 3H), 2.74 (s, 3H), 2.8-3.0 (m, 5H), 3.20-3.28 (m, 1H), 3.34-3.42 (m, 2H), 3.92 (s, 2H), 4.11 (d, J=11.7, 2H), 4.25 (d, J=11.7, 2H), 4.32 (s, 2H), 7.15-7.39 (m, 6H), 7.65 (s, 1H), 8.36-8.41 (m, 2H), 8.89 (brs, 2H).

Example 78

$N^2$-[5-(aminocarbonyl)-2-methylphenyl]-$N^2$-{2-[1,3-dihydro-2H-isoindol-2-yl(methyl)amino]-2-oxoethyl}-$N^1$-[2-(isopropylamino)ethyl]glycinamide dihydrochloride Step A $N^2$-[5-(aminocarbonyl)-2-methylphenyl]-$N^2$-{2-[1,3-dihydro-2H-isoindol-2-yl(methyl)amino]-2-oxoethyl}-$N^1$-[2-{(isopropyl)[(2-nitrophenyl)sulfonyl]amino}ethyl]glycinamide Using the compound (0.70 g, 1.05 mmol) of Example 77, step A, and a 7N ammonia-methanol solution (0.8 ml), and according to the method of Example 77, step B, the title compound (0.70 g, yield 100%) was obtained as a colorless solid.

$^1$H-NMR (300 MHz, CDCl$_3$); δ (ppm) 1.14 (d, J=6.3, 6H), 2.38 (s, 3H), 2.95 (s, 3H), 3.29-3.34 (m, 2H), 3.44-3.48 (m, 2H), 3.87 (s, 2H), 4.01-4.29 (m, 7H), 6.00 6.60 (2brs, 2H), 7.20-7.28 (m, 6H), 7.45-7.49 (m, 1H), 7.57-7.59 (m, 1H), 7.64-7.68 (m, 1H), 7.77 (s, 1H), 7.95-7.97 (m, 1H), 8.62-8.64 (m, 1H).

Step B $N^2$-[5-(aminocarbonyl)-2-methylphenyl]-$N^2$-{2-[1,3-dihydro-2H-isoindol-2-yl(methyl)amino]-2-oxoethyl}-$N^1$-[2-(isopropylamino)ethyl]glycinamide Using the compound (0.70 g, 1.05 mmol) obtained in step A and according to the method of Example 46, step B, the title compound (0.45 g, yield 89%) was obtained as a colorless solid.

$^1$H-NMR (300 MHz, CDCl$_3$); δ (ppm) 0.98 (d, J=6.3, 6H), 2.37 (s, 3H), 2.65-2.78 (m, 3H), 2.95 (s, 3H), 3.33-3.40 (m, 2H), 3.87 (s, 2H), 4.12-4.25 (m, 6H), 6.21 (broad, 1H), 6.81

(broad, 1H), 7.18-7.29 (m, 5H), 7.48 (dd, J=0.9, 7.5, 1H), 7.78 (d, J=1.5, 1H), 8.40-8.45 (m, 1H).

Step C

N$^2$-[5-(aminocarbonyl)-2-methylphenyl]-N$^2$-{2-[1,3-dihydro-2H-isoindol-2-yl(methyl)amino]-2-oxoethyl}-N$^1$-[2-(isopropylamino)ethyl]glycinamide dihydrochloride Using the compound (0.40 g, 0.83 mmol) obtained in step B and according to the method of Example 17, step C, the title compound (0.46 g, yield>100%) was obtained as a colorless solid.

$^1$H-NMR (300 MHz, DMSO-d$_6$); δ (ppm) 1.19 (d, J=6.3, 6H), 2.31 (s, 3H), 2.8-3.0 (m, 5H), 3.21-3.26 (m, 1H), 3.34-3.42 (m, 2H), 3.90 (s, 2H), 4.10-4.33 (m, 6H), 7.14-7.26 (m, 5H), 7.41 (d, J=7.5, 1H), 7.67 (s, 1H), 8.37-8.40 (m, 1H), 8.90 (brs, 2H).

Example 79

N$^2$-[5-(aminocarbonyl)-2-methylphenyl]-N$^2$-{2-[(5-fluoro-1,3-dihydro-2H-isoindol-2-yl)(methyl)amino]-2-oxoethyl}-N$^1$-[2-(isopropylamino)ethyl]glycinamide Step A N-[5-(aminocarbonyl)-2-methylphenyl]-N-{2-[(5-fluoro-1,3-dihydro-2H-isoindol-2-yl)(methyl)amino]-2-oxoethyl}glycine Using the compound (1.18 g, 4.43 mmol) of Reference Example 73 and the compound (1.12 g, 5.53 mmol) of Reference Example 19, and according to the method of Example 4, step A, the title compound (1.22 g, yield 66%) was obtained as a colorless solid.

$^1$H-NMR (300 MHz, DMSO-d$_6$); δ (ppm) 2.27 (s, 3H), 2.87 (s, 3H), 3.99 (s, 2H), 4.0-4.3 (m, 4H), 4.27 (s, 2H), 7.0-7.2 (m, 4H), 7.27-7.32 (m, 1H), 7.39 (d, J=7.8, 1H), 7.61 (s, 1H), 7.83 (brs, 1H), 12.44 (brs, 1H).

Step B

N$^2$-[5-(aminocarbonyl)-2-methylphenyl]-N$^2$-{2-[(5-fluoro-1,3-dihydro-2H-isoindol-2-yl)(methyl)amino]-2-oxoethyl}-N$^1$-{2-[(tert-butoxycarbonyl)(isopropyl)amino]ethyl}glycinamide Using the compound (1.21 g, 2.92 mmol) obtained in step A and the compound (808 mg, 3.99 mmol) of Reference Example 3, and according to the method of Example 1, step B, the title compound (1.70 g, yield 97%) was obtained as a colorless solid.

$^1$H-NMR (300 MHz, CDCl$_3$); δ (ppm) 1.12 (d, J=6.6, 6H), 1.42 (brs, 9H).

2.38 (s, 3H), 2.94 (s, 3H), 3.0-3.3 (m, 2H), 3.35-3.44 (m, 2H), 3.83 (s, 2H), 4.0-4.3 (m, 5H), 4.23 (s, 2H), 5.4-5.7 (broad, 0.6H), 6.0-6.7 (broad, 0.4H), 6.9-7.0 (m, 2H), 7.1-7.3 (m, 3H), 7.4-7.5 (m, 1H), 7.75 (brs, 1H), 8.2-8.7 (broad, 1H).

Step C

N$^2$-[5-(aminocarbonyl)-2-methylphenyl]-N$^2$-{2-[(5-fluoro-1,3-dihydro-2H-isoindol-2-yl)(methyl)amino]-2-oxoethyl}-N$^1$-[2-(isopropylamino)ethyl]glycinamide Using the compound (466 mg, 778 mmol) obtained in step B and according to the method of Example 46, step B, the title compound (377 mg, yield 97%) was obtained as a colorless solid.

$^1$H-NMR (300 MHz, CDCl$_3$); δ (ppm) 0.99 (d, J=6.3, 6H), 2.39 (s, 3H), 2.6-2.8 (m, 3H), 2.95 (s, 3H), 3.35-3.42 (m, 2H), 3.83 (s, 2H), 4.0-4.3 (m, 4H), 4.24 (s, 2H), 5.3-6.5 (broad, 2H), 6.9-7.0 (m, 2H), 7.14-7.26 (m, 2H), 7.45 (dd, J=1.5, 7.8, 1H), 7.71 (d, J=1.5, 1H), 8.42 (broad t, 1H).

Example 80

N$^2$-{2-[(5-fluoro-1,3-dihydro-2H-isoindol-2-yl)(methyl)amino]-2-oxoethyl}-N$^2$-[2-methyl-5-(5-methyl-1H-1,2,4-triazol-3-yl)phenyl]-N$^1$-[2-(isopropylamino)ethyl]glycinamide trihydrochloride Step A N$^2$-{2-[(5-fluoro-1,3-dihydro-2H-isoindol-2-yl)(methyl)amino]-2-oxoethyl}-N$^2$-[2-methyl-5-(5-methyl-1H-1,2,4-triazol-3-yl)phenyl]-N$^1$-{2-[(tert-butoxycarbonyl)(isopropyl)amino]ethyl}glycinamide The compound (612 mg, 1.02 mmol) of Example 79, step B was dissolved in N,N-dimethylacetamide dimethylacetal (3 ml), and the mixture was stirred at 110° C. for 40 min. The reaction mixture was concentrated under reduced pressure, and the obtained residue was dissolved in acetic acid (2 ml). Then, hydrazine monohydrate (0.04 ml) was added, and the mixture was stirred with heating at 110° C. for 10 min. The reaction mixture was cooled to room temperature, diluted with an ethyl acetate-hexane-1:1 mixed solvent, washed with diluted aqueous sodium hydroxide solution and saturated brine, and dried over anhydrous magnesium sulfate. The insoluble material was filtered off, and the solution was concentrated under reduced pressure to give a solid. This was washed with diethyl ether, and dried under reduced pressure to give the title compound (536 mg, yield 79%) as a pale-pink solid.

$^1$H-NMR (300 MHz, CDCl$_3$); δ (ppm) 1.0-1.2 (broad d, 6H), 1.44 (brs, 9H), 2.36 (s, 3H), 2.47 (s, 3H), 2.99 (s, 3H), 3.0-3.3 (m, 2H), 3.38-3.45 (m, 2H), 3.85 (s, 2H), 3.9-4.3 (m, 7H), 6.8-7.0 (m, 2H), 7.10-7.15 (m, 1H), 7.25 (d, J=7.8, 1H), 7.72 (dd, J=1.2, 7.8, 1H), 7.92 (brs, 1H), 8.4-8.9 (broad, 1H).

Step B

N$^2$-{2-[(5-fluoro-1,3-dihydro-2H-isoindol-2-yl)(methyl)amino]-2-oxoethyl}-N$^2$-[2-methyl-5-(5-methyl-1H-1,2,4-triazol-3-yl)phenyl]-N$^1$-[2-(isopropylamino)ethyl]glycinamide trihydrochloride Using the compound (527 mg, 0.828 mmol) obtained in step A and according to the method of Example 1, step C, the title compound (528 mg, yield 99%) was obtained as a pale-yellow solid.

$^1$H-NMR (300 MHz, DMSO-d$_6$); δ (ppm) 1.19 (d, J=6.6, 6H), 2.33 (s, 3H), 2.53 (s, 3H), 2.8-3.0 (m, 2H), 2.87 (s, 3H), 3.1-3.3 (m, 1H), 3.36-3.43 (m, 2H), 3.93 (s, 2H), 4.0-4.3 (m, 4H), 4.35 (s, 2H), 7.0-7.2 (m, 2H), 7.26-7.33 (m, 2H), 7.57 (dd, J=1.2, 8.1, 1H), 7.84 (d, J=1.2, 1H), 8.36 (t, J=5.7, 1H), 8.83 (brs, 2H).

Example 81

$N^2$-{2-[1,3-dihydro-2H-isoindol-2-yl(methyl)amino]-2-oxoethyl}-$N^2$-[2-methyl-5-(1H-1,2,4-triazol-3-yl)phenyl]-$N^1$-[2-(isopropylamino)ethyl]glycinamide trihydrochloride

Step A

N-[5-(aminocarbonyl)-2-methylphenyl]-N-{2-[1,3-dihydro-2H-isoindol-2-yl(methyl)amino]-2-oxoethyl}glycine Using the compound (1.00 g, 3.76 mmol) of Reference Example 73 and the compound (763 mg, 4.13 mmol) of Reference Example 17, and according to the method of Example 1, step A, the title compound (1.11 g, yield 83%) was obtained as a pale-bistered amorphous solid.
$^1$H-NMR (300 MHz, CDCl$_3$); δ (ppm) 2.36 (s, 3H), 3.06 (s, 3H), 3.93 (s, 2H), 4.17-4.31 (m, 6H), 7.20-7.29 (m, 5H), 7.46 (dd, J=1.5, 7.8, 1H), 7.70 (d, J=1.5, 1H).

Step B

N-[5-(aminocarbonyl)-2-methylphenyl]-N-{2-[1,3-dihydro-2H-isoindol-2-yl(methyl)amino]-2-oxoethyl}glycine tert-butyl ester Using the compound (1.11 g, 2.80 mmol) obtained in step A and according to the method of Example 74, step A, the title compound (917 mg, yield 72%) as a pale-yellow amorphous solid
$^1$H-NMR (300 MHz, CDCl$_3$); δ (ppm) 1.39 (s, 9H), 2.37 (s, 3H), 2.93 (s, 3H), 4.04 (s, 2H), 4.13 (d, J=11.4, 2H), 4.23 (d, J=11.4, 2H), 4.37 (s, 2H), 7.19-7.29 (m, 5H), 7.39 (dd, J=1.8, 7.8, 1H), 7.65 (d, J=1.8, 1H).

Step C

N-{2-[1,3-dihydro-2H-isoindol-2-yl(methyl)amino]-2-oxoethyl}-N-[2-methyl-5-(1H-1,2,4-triazol-3-yl)phenyl]glycine Using the compound (350 mg, 0.77 mmol) obtained in step B, and N,N-dimethylformamide dimethylacetal (2.5 ml), and according to the methods of Example 80, step A, Example 74, step C, the title compound (162 mg, yield 50%) was obtained as a pale-bistered amorphous solid.
$^1$H-NMR (300 MHz, CDCl$_3$); δ (ppm) 2.35 (s, 3H), 3.04 (s, 3H), 3.98 (s, 2H), 4.17 (d, J=12.0, 2H), 4.27 (d, J=12.0, 2H), 4.33 (s, 2H), 7.18-7.29 (m, 5H), 7.72 (dd, J=1.2, 7.5, 1H), 7.90 (d, J=1.2, 1H), 8.24 (s, 1H).

Step D $N^2$-{2-[1,3-dihydro-2H-isoindol-2-yl(methyl)amino]-2-oxoethyl}-$N^2$-[2-methyl-5-(1H-1,2,4-triazol-3-yl)phenyl]-$N^1$-{2-[(tert-butoxycarbonyl)(isopropyl)amino]ethyl}glycinamide Using the compound (160 mg, 0.38 mmol) obtained in step C, and the compound (92 mg, 0.46 mmol) of Reference Example 3, and according to the method of Example 1, step B, the title compound (96 mg, yield 42%) was obtained as a pale-yellow amorphous solid
$^1$H-NMR (300 MHz, CDCl$_3$); δ (ppm) 1.11-1.25 (m, 6H), 1.43 (8, 9H), 2.36 (s, 3H), 2.95 (s, 3H), 3.09-3.44 (m, 4H), 3.86 (s, 2H), 4.09-4.24 (m, 7H), 7.18-7.30 (m, 5H), 7.78 (d, J=7.2, 1H), 8.04 (m, 1H), 8.79 (brs, 1H).

Step E $N^2$-{2-[1,3-dihydro-2H-isoindol-2-yl(methyl)amino]-2-oxoethyl}-$N^2$-[2-methyl-5-(1H-1,2,4-triazol-3-yl)phenyl]-$N^1$-[2-(isopropylamino)ethyl]glycinamide trihydrochloride Using the compound (95 mg, 0.16 mmol) obtained in step D and according to the method of Example 1, step C, the title compound (86 mg, yield 89%) was obtained as a pale-yellow solid.
$^1$H-NMR (300 MHz, CD$_3$OD); δ (ppm) 1.31 (d, J=6.6, 6H), 2.46 (s, 3H), 2.99 (s, 3H), 3.13 (m, 2H), 3.50-3.52 (m, 2H), 4.06-4.13 (m, 4H), 4.29 (d, J=11.7, 2H), 4.44 (s, 2H), 7.21 (m, 4H), 7.44 (d, J=7.8, 1H), 7.63 (d, J=7.8, 1H), 7.92 (s, 1H), 9.23 (s, 1H).

Example 82

$N^2$-{2-[1,3-dihydro-2H-isoindol-2-yl(methyl)amino]-2-oxoethyl}-$N^2$-[2-methyl-5-(5-methyl-1H-1,2,4-triazol-3-yl)phenyl]-$N^1$-[2-(isopropylamino)ethyl]glycinamide trihydrochloride

Step A $N^2$-[5-(aminocarbonyl)-2-methylphenyl]-$N^2$-{2-[1,3-dihydro-2H-isoindol-2-yl(methyl)amino]-2-oxoethyl}-$N^1$-{2-[(tert-butoxycarbonyl)(isopropyl)amino]ethyl}glycinamide Using the compound (0.35 g, 0.883 mmol) of Example 81, step A, and the compound (267 mg, 1.32 mmol) of Reference Example 3, and according to the method of Example 1, step B, the title compound (0.36 g, yield 71%) was obtained as a colorless amorphous solid.
$^1$H-NMR (300 MHz, CDCl$_3$); δ (ppm) 1.11 (d, J=6.6, 6H), 1.42 (brs, 9H), 2.38 (s, 3H), 2.94 (s, 3H), 3.17 (brs, 2H), 3.38 (q, J=6.6, 2H), 3.83 (s, 2H), 3.9-4.3 (m, 7H), 5.55-6.60 (broad, 2H), 7.19-7.28 (m, 5H), 7.48-7.51 (m, 1H), 7.74 (s, 1H), 8.39-8.44 (broad, 1H).

Step B $N^2$-{2-[1,3-dihydro-2H-isoindol-2-yl(methyl)amino]-2-oxoethyl}-$N^2$-[2-methyl-5-(5-methyl-1H-1,2,4-triazol-3-yl)phenyl]-$N^1$-{2-[(tert-butoxycarbonyl)(isopropyl)amino]ethyl}glycinamide Using the compound (0.36 g, 0.62 mmol) obtained in step A and according to the method of Example 80, step A, the title compound (0.46 g, yield>100%) was obtained as a colorless amorphous solid.
$^1$H-NMR (300 MHz, CDCl$_3$); δ (ppm) 1.09 (d, J=6.5, 6H), 1.44 (s, 9H), 2.36 (s, 3H), 2.44 (s, 3H), 3.00 (s, 3H), 3.16 (brs, 2H), 3.38-3.50 (m, 2H), 3.86 (s, 2H), 4.00-4.30 (m, 7H), 7.15-7.29 (m, 5H), 7.71 (d, J=8.0, 1H), 7.95 (s, 1H), 8.53-8.69 (broad, 1H).

Step C

N²-{2-[1,3-dihydro-2H-isoindol-2-yl(methyl)
amino]-2-oxoethyl}-N²-[2-methyl-5-(5-methyl-1H-
1,2,4-triazol-3-yl)phenyl]-N¹-[2-(isopropylamino)
ethyl]glycinamide trihydrochloride Using the compound (0.46 g) obtained in step B and according to the method of Example 1, step C, the title compound (0.28 g, yield 72%) was obtained as a colorless solid.
¹H-NMR (300 MHz, DMSO-d₆); δ (ppm) 1.21 (d, J=5.7, 6H), 2.36 (s, 3H), 2.65 (s, 3H), 2.87 (m, 5H), 3.24-3.57 (m, 3H), 3.97 (s, 2H), 4.14-4.28 (m, 4H), 4.39 (s, 2H), 7.26-7.35 (m, 5H), 7.66-7.69 (m, 1H), 7.91 (s, 1H), 8.40 (brs, 1H), 9.09 (brs, 2H).

Example 83

N²-{2-[1,3-dihydro-2H-isoindol-2-yl(methyl)amino]-2-oxoethyl}-N²-[2-methyl-5-(1,2,4-oxadiazol-5-yl)phenyl]-N¹-[2-(isopropylamino)ethyl]glycinamide Step A N-{2-[1,3-dihydro-2H-isoindol-2-yl(methyl)amino]-
2-oxoethyl}-N-[2-methyl-5-(1,2,4-oxadiazol-5-yl)
phenyl]glycine tert-butyl ester The compound (400 mg, 0.88 mmol) of Example 81, step B, was dissolved in N,N-dimethylformamide dimethylacetal (2.5 ml), and the mixture was stirred at 110° C. for 1 hr. The reaction mixture was concentrated and the obtained residue was dissolved in 1,4-dioxane (1.5 ml). Then, acetic acid (1.5 ml), hydroxylamine hydrochloride (95 mg, 1.33 mmol) and 2N aqueous sodium hydroxide solution (0.7 ml, 1.4 mmol) were added, and the mixture was stirred at 90° C. for 30 min. The reaction mixture was concentrated under reduced pressure, diluted with water, and extracted with dichloromethane. The organic layer was dried over anhydrous magnesium sulfate, the insoluble material was filtered off, and the solution was concentrated under reduced pressure. The obtained oil was purified by silica gel column chromatography (ethyl acetate-dichloromethane) to give the title compound (219 mg, yield 52%) as a pale-yellow amorphous solid
¹H-NMR (300 MHz, CDCl₃); δ (ppm) 1.42 (s, 9H), 2.42 (s, 3H), 2.95 (s. 3H), 4.07 (s, 2H), 4.16 (d, J=11.4, 2H), 4.26 (d, J=11.4, 2H), 4.42 (s, 2H), 7.20-7.30 (m, 5H), 7.71 (dd, J=1.5, 8.1, 1H), 7.93 (d, J=1.5, 1H), 8.43 (s, 1H).

Step B

N²-{2-[1,3-dihydro-2H-isoindol-2-yl(methyl)
amino]-2-oxoethyl}-N²-[2-methyl-5-(1,2,4-oxadia-
zol-5-yl)phenyl]-N¹-{2-[(tert-butoxycarbonyl)(iso-
propyl)amino]ethyl}glycinamide Using the compound (210 mg, 0.44 mmol) obtained in step A and the compound (92 mg, 0.45 mmol) of Reference Example 3, and according to the methods of Example 74, step C, and Example 1, step B, the title compound (196 mg, yield 75%) was obtained as a pale-yellow amorphous solid
¹H-NMR (300 MHz, CDCl₃); δ (ppm) 1.11 (d, J=6.6, 6H), 1.44 (s, 9H), 2.44 (s, 3H), 3.96 (s, 3H), 3.18 (brm, 2H), 3.37-3.44 (m, 2H), 3.86 (s, 2H), 4.13-4.30 (m, 7H), 7.20-7.28 (m, 4H), 7.33 (d, J=7.8, 1H), 7.77 (d, J=7.8, 1H), 8.02 (d, J=1.5, 1H), 8.43 (s, 1H).

Step C

N²-{2-[1,3-dihydro-2H-isoindol-2-yl(methyl)
amino]-2-oxoethyl}-N²-[2-methyl-5-(1,2,4-oxadia-
zol-5-yl)phenyl]-N¹-[2-(isopropylamino)ethyl]glyci-
namide Using the compound (190 mg, 0.31 mmol) obtained in step B and according to the method of Example 46, step B, the title compound (59 mg, yield 37%) was obtained as a colorless solid.
¹H-NMR (300 MHz, CDCl₃); δ (ppm) 1.01 (d, J=6.3, 6H), 2.42 (s, 3H), 2.71-2.79 (m, 3H), 2.96 (s, 3H), 3.36-3.42 (m, 2H), 4.08-4.26 (m, 8H), 7.04 (brs, 1H), 7.18-7.29 (m, 4H), 7.61 (d, J=7.5, 1H), 8.00 (s, 1H), 8.38-8.40 (m, 1H), 8.47 (s, 1H).

Example 84

N²-{2-[1,3-dihydro-2H-isoindol-2-yl(methyl)
amino]-2-oxoethyl}-N²-[2-methyl-5-(3-methyl-1,2,
4-oxadiazol-5-yl)phenyl]-N¹-[2-(isopropylamino)
ethyl]glycinamide Step A N-{2-[1,3-dihydro-2H-isoindol-2-yl(methyl)amino]-
2-oxoethyl}-N-[2-methyl-5-(3-methyl-1,2,4-oxadia-
zol-5-yl)phenyl]glycine tert-butyl ester Using the compound (500 mg, 1.11 mmol) of Example 81, step B, and N,N-dimethylacetamide dimethylacetal (2.5 ml), and according to the method of Example 83, step A, the title compound (406 mg, yield 75%) was obtained as a pale-bistered amorphous solid.
¹H-NMR (300 MHz, CDCl₃); δ (ppm) 1.42 (s, 9H), 2.40 (s, 3H), 2.45 (s, 3H), 2.94 (s, 3H), 4.07 (s, 2H), 4.15 (d, J=11.7, 2H), 4.25 (d, J=11.7, 2H), 4.41 (s, 2H), 7.19-7.28 (m, 5H), 7.66 (dd, J=1.5, 7.8, 1H), 7.89 (d, J=1.5, 1H).

Step B

N-{2-[1,3-dihydro-2H-isoindol-2-yl(methyl)amino]-
2-oxoethyl}-N-[2-methyl-5-(3-methyl-1,2,4-oxadia-
zol-5-yl)phenyl]glycine Using the compound (500 mg, 1.11 mmol) obtained in step A and according to the method of Example 74, step C, the title compound (310 mg, yield 88%) was obtained as a pale-bistered amorphous solid.
¹H-NMR (300 MHz, CDCl₃); δ (ppm) 2.40 (s, 3H), 2.45 (s, 3H), 3.07 (s, 3H), 3.96 (s, 2H), 4.19 (d, J=11.4, 2H), 4.30 (d, J=11.4, 2H), 4.33 (s, 2H), 7.20-7.29 (m, 4H), 7.34 (d, J=8.1, 1H), 7.78 (dd, J=1.5, 8.1, 1H), 7.96 (d, J=1.2, 1H).

Step C

N²-{2-[1,3-dihydro-2H-isoindol-2-yl(methyl)
amino]-2-oxoethyl}-N²-[2-methyl-5-(3-methyl-1,2,
4-oxadiazol-5-yl)phenyl]-N¹-{2-[(tert-butoxycarbo-
nyl)(isopropyl)amino]ethyl}glycinamide Using the compound (310 mg, 0.71 mmol) obtained in step B, and the compound (158 mg, 0.78 mmol) of Reference Example 3, and according to the method of Example 1, step B, the title compound (373 mg, yield 84%) was obtained as a pale-yellow amorphous solid ¹H-NMR (300 MHz, CDCl₃); δ (ppm) 1.11 (d, J=6.6, 6H), 1.45 (s, 9H), 2.43 (s, 3H), 2.45 (s, 3H), 2.95 (s, 3H), 3.18 (broad, 2H), 3.37-3.44 (m, 2H), 3.84 (s, 2H), 4.11-4.29 (m, 7H), 7.20-7.28 (m, 4H), 7.31 (d, J=8.1, 1H), 7.73 (d, J=8.1, 1H), 7.98 (d, J=1.2, 1H).

Step D

N²-{2-[1,3-dihydro-2H-isoindol-2-yl(methyl)amino]-2-oxoethyl}-N²-[2-methyl-5-(3-methyl-1,2,4-oxadiazol-5-yl)phenyl]-N¹-[2-(isopropylamino)ethyl]glycinamide Using the compound (370 mg, 0.60 mmol) obtained in step C and according to the method of Example 46, step B, the title compound (247 mg, yield 80%) was obtained as a colorless solid.

¹H-NMR (300 MHz, CDCl₃); δ (ppm) 1.02 (d, J=6.3, 6H), 2.44 (s, 6H), 2.72-2.80 (m, 3H), 2.96 (s, 3H), 3.39-3.45 (m, 2H), 3.83 (s, 2H), 4.17 (d, J=11.4, 2H), 4.25 (d, J=11.4, 2H), 4.30 (s, 2H), 7.20-7.28 (m, 4H), 7.32 (d, J=8.1, 1H), 7.73 (d, J=8.1, 1H), 7.99 (s, 1H), 8.49 (brs, 1H).

Example 85

N²-{2-[1,3-dihydro-2H-isoindol-2-yl(methyl)amino]-2-oxoethyl}-N²-[2-methyl-5-(3-methyl-1,2,4-oxadiazol-5-yl)phenyl]-N¹-[2-(ethylamino)ethyl]glycinamide dihydrochloride Step A N²-[5-(aminocarbonyl)-2-methylphenyl]-N²-{2-[1,3-dihydro-2H-isoindol-2-yl(methyl)amino]-2-oxoethyl}-N¹-{2-[(tert-butoxycarbonyl)ethylamino]ethyl}glycinamide Using the compound (483 mg, 1.22 mmol) of Example 81, step A, and the compound (258 mg, 1.37 mmol) of Reference Example 2, and according to the method of Example 1, step B, the title compound (559 mg, yield 81%) was obtained as a pale-bistered amorphous solid.

¹H-NMR (300 MHz, CDCl₃); δ (ppm) 1.05 (t, J=7.2, 3H), 1.36 (s, 9H), 2.36 (s, 3H), 2.95 (s, 3H), 3.17 (q, J=7.2, 2H), 3.32-3.42 (m, 4H), 3.80 (s, 2H), 4.12-4.26 (m, 6H), 7.20-7.28 (m, 5H), 7.53 (m, 1H), 7.78 (m, 1H), 8.55 (brs, 1H).

Step B

N²-{2-[1,3-dihydro-2H-isoindol-2-yl(methyl)amino]-2-oxoethyl}-N²-[2-methyl-5-(3-methyl-1,2,4-oxadiazol-5-yl)phenyl]-N¹-{2-[(tert-butoxycarbonyl)ethylamino]ethyl}glycinamide Using the compound (550 mg, 0.97 mmol) obtained in step A and according to the method of Example 84, step A, the title compound (477 mg, yield 81%) was obtained as a yellow amorphous solid.

¹H-NMR (300 MHz, CDCl₃); δ (ppm) 1.05 (t, J=7.2, 3H), 1.43 (s, 9H), 2.42 (s, 3H), 2.45 (s, 3H), 2.95 (s, 3H), 3.17 (broad, 2H), 3.29-3.31 (m, 2H), 3.40-3.47 (m, 2H), 3.82 (s, 2H), 4.13-4.29 (m, 6H), 7.19-7.28 (m, 4H), 7.31 (d, J=8.1, 1H), 7.72 (d, J=6.5, 1H), 7.97 (s, 1H) 8.28-8.56 (brs, 1H).

Step C

N²-{2-[1,3-dihydro-2H-isoindol-2-yl(methyl)amino]-2-oxoethyl}-N²-[2-methyl-5-(3-methyl-1,2,4-oxadiazol-5-yl)phenyl]-N¹-[2-(ethylamino)ethyl]glycinamide dihydrochloride Using the compound (470 mg, 0.78 mmol) obtained in step B and according to the method of Example 1, step C, the title compound (316 mg, yield 91%) was obtained as a pale-yellow solid.

¹H-NMR (300 MHz, DMSO-d₆); δ (ppm) 1.14 (t, J=7.2, 3H), 2.36 (s, 3H), 2.41 (s, 3H), 2.89-2.91 (m, 7H), 3.25-3.39 (m, 2H), 3.95 (s, 2H), 4.13 (d, J=11.4, 2H), 4.27 (d, J=11.4, 2H), 4.35 (s, 2H), 7.26 (m, 4H), 7.35 (d, J=8.1, 1H), 7.61 (d, J=7.8, 1H), 7.82 (d, J=1.2, 1H), 8.29 (t, J=5.4, 1H) 8.47 (brs, 2H).

Example 86

N²-{2-[(5-fluoro-1,3-dihydro-2H-isoindol-2-yl)(methyl)amino]-2-oxoethyl}-N²-[2-methyl-5-(3-methyl-1,2,4-oxadiazol-5-yl)phenyl]-N¹-[2-(isopropylamino)ethyl]glycinamide dihydrochloride Step A N²-{2-[(5-fluoro-1,3-dihydro-2H-isoindol-2-yl)(methyl)amino]-2-oxoethyl}-N²-[2-methyl-5-(3-methyl-1,2,4-oxadiazol-5-yl)phenyl]-N¹-{2-[(tert-butoxycarbonyl)isopropylamino]ethyl}glycinamide Using the compound (618 mg, 1.03 mmol) of Example 79, step B and according to the method of Example 84, step A, the title compound (492 mg, yield 75%) was obtained as a colorless solid.

¹H-NMR (300 MHz, CDCl₃); δ (ppm) 1.12 (d, J=6.9, 6H), 1.45 (brs, 9H), 2.43 (s, 3H), 2.45 (s, 3H), 2.95 (s, 3H), 3.0-3.3 (m, 2H), 3.37-3.45 (m, 2H), 3.83 (s, 2H), 3.9-4.3 (m, 5H), 4.28 (s, 2H), 6.9-7.0 (m, 2H), 7.13-7.18 (m, 1H), 7.31 (d, J=7.8, 1H), 7.73 (dd, J=1.5, 7.8, 1H), 7.97 (d, J=1.5, 1H), 8.0-8.6 (broad, 1H).

Step B

N²-{2-[(5-fluoro-1,3-dihydro-2H-isoindol-2-yl)(methyl)amino]-2-oxoethyl}-N²-[2-methyl-5-(3-methyl-1,2,4-oxadiazol-5-yl)phenyl]-N¹-[2-(isopropylamino)ethyl]glycinamide dihydrochloride Using the compound (491 mg, 0.77 mmol) obtained in step A and according to the method of Example 1, step C, the title compound (426 mg, yield 91%) was obtained as a colorless solid.

¹H-NMR (300 MHz, DMSO-d₆); δ (ppm) 1.18 (d, J=6.6, 6H), 2.37 (s, 3H), 2.41 (s, 3H), 2.8-3.0 (m, 2H), 2.88 (s, 3H), 3.1-3.3 (m, 1H), 3.35-3.42 (m, 2H), 3.94 (s, 2H), 4.0-4.3 (m, 4H), 4.35 (s, 2H), 7.04-7.16 (m, 2H), 7.27-7.33 (m, 1H), 7.35 (d, J=7.8, 1H), 7.60 (d, J=7.8, 1H), 7.81 (s, 1H), 8.33 (broad t, 1H), 8.73 (brs, 2H).

Example 87

N²-{2-[(5-fluoro-1,3-dihydro-2H-isoindol-2-yl)(methyl)amino]-2-oxoethyl}-N²-[2-methyl-5-(3-methyl-1,2,4-oxadiazol-5-yl)phenyl]-N¹-[2-(ethylamino)ethyl]glycinamide dihydrochloride

Step A

N²-[5-(aminocarbonyl)-2-methylphenyl]-N²-{2-[(5-fluoro-1,3-dihydro-2H-isoindol-2-yl)(methyl)amino]-2-oxoethyl}-N¹-{2-[(tert-butoxycarbonyl)(ethyl)amino]ethyl}glycinamide Using the compound (683 mg, 1.65 mmol) of Example 79, step A, and the compound (500 mg, 2.66 mmol) of Reference Example 2, and according to the method of Example 1, step B, the title compound (558 mg, yield 58%) was obtained as a colorless solid.

¹H-NMR (300 MHz, CDCl₃); δ (ppm) 1.06 (t, J=7.1, 3H), 1.38 (brs, 9H), 2.37 (s, 3H), 2.94 (s, 3H), 3.18 (q, J=7.1, 2H), 3.2-3.4 (m, 2H), 3.39-3.46 (m, 2H), 3.80 (s, 2H), 4.0-4.2 (m, 4H), 4.22 (s, 2H), 5.2-6.8 (broad, 2H), 6.9-7.0 (m, 2H), 7.1-7.3 (m, 2H), 7.50 (brs, 1H), 7.76 (brs, 1H), 8.4-8.7 (broad, 1H).

Step B

N²-{2-[(5-fluoro-1,3-dihydro-2H-isoindol-2-yl)(methyl)amino]-2-oxoethyl}-N²-[2-methyl-5-(3-methyl-1,2,4-oxadiazol-5-yl)phenyl]-N¹-{2-[(tert-butoxycarbonyl)ethylamino]ethyl}glycinamide Using the compound (550 mg, 0.941 mmol) obtained in step A and according to the method of Example 84, step A, the title compound (521 mg, yield 89%) was obtained as a pale-orange oil.

¹H-NMR (300 MHz, CDCl₃); δ (ppm) 1.05 (t, J=7.1, 3H), 1.43 (brs, 9H), 2.42 (s, 3H), 2.45 (s, 3H), 2.95 (s, 3H), 3.15-3.25 (m, 2H), 3.25-3.35 (m, 2H), 3.4-3.5 (m, 2H), 3.82 (s, 2H), 4.05-4.25 (m, 4H), 4.29 (s, 2H), 6.9-7.0 (m, 2H), 7.13-7.18 (m, 1H), 7.31 (d, J=7.8, 1H), 7.73 (dd, J=1.2, 7.8, 1H), 7.96 (d, J=1.2, 1H), 8.1-8.7 (broad, 1H).

Step C

N²-{2-[(5-fluoro-1,3-dihydro-2H-isoindol-2-yl)(methyl)amino]-2-oxoethyl}-N²-[2-methyl-5-(3-methyl-1,2,4-oxadiazol-5-yl)phenyl]-N¹-[2-(ethylamino)ethyl]glycinamide dihydrochloride Using the compound (520 mg, 0.834 mmol) obtained in step B and according to the method of Example 1, step C, the title compound (370 mg, yield 74%) was obtained as a colorless solid.

¹H-NMR (300 MHz, DMSO-d₆); δ (ppm) 1.14 (t, J=7.2, 3H), 2.36 (s, 3H), 2.41 (s, 3H), 2.8-3.0 (m, 4H), 2.88 (s, 3H), 3.33-3.40 (m, 2H), 3.94 (s, 2H), 4.0-4.3 (m, 4H), 4.35 (s, 2H), 7.04-7.16 (m, 2H), 7.27-7.33 (m, 1H), 7.35 (d, J=8.1, 1H), 7.60 (d, J=8.1, 1H), 7.82 (s, 1H), 8.30 (broad, 1H), 8.4-8.8 (broad, 2H).

Example 88

N²-{2-[1,3-dihydro-2H-isoindol-2-yl(methyl)amino]-2-oxoethyl}-N²-[2-methyl-5-(4-methyl-5-oxo-4,5-dihydro-1,3,4-oxadiazol-2-yl)phenyl]-N¹-[2-(isopropylamino)ethyl]glycinamide dihydrochloride

Step A

N-[5-{[2-(tert-butoxycarbonyl)-2-methylhydrazino]carbonyl}-2-methylphenyl]-N-{2-[1,3-dihydro-2H-isoindol-2-yl(methyl)amino]-2-oxoethyl}glycine Using the compound (2.44 g, 6.17 mmol) of Reference Example 74 and the compound (1.71 g, 9.26 mmol) of Reference Example 17, and according to the method of Example 1, step A, the title compound (2.78 g, yield 68%) was obtained as a gray amorphous solid.

¹H-NMR (300 MHz, CDCl₃); δ (ppm) 1.46 (brs, 9H), 2.26-2.32 (brs, 3H), 3.04 (s, 3H), 3.20 (s, 3H), 3.90 (s, 2H), 4.18-4.31 (m, 6H), 7.21-7.30 (m, 5H), 7.39-7.42 (m, 1H), 7.70 (brs, 1H).

Step B

N-{2-[1,3-dihydro-2H-isoindol-2-yl(methyl)amino]-2-oxoethyl}-N-{2-methyl-5-[(2-methylhydrazino)carbonyl]phenyl}glycine dihydrochloride Using the compound (2.32 g, 4.41 mmol) obtained in step A and according to the method of Example 1, step C, the title compound (1.81 g, yield 81%) was obtained as a colorless solid.

¹H-NMR (300 MHz, DMSO-d₆); δ (ppm) 2.31 (s, 3H), 2.49 (s, 3H), 2.87 (s, 3H), 4.03 (s, 2H), 4.11-4.31 (m, 5H), 7.25-7.28 (m, 5H), 7.45-7.48 (m, 1H), 7.65 (s, 1H), 11.89 (s, 1H).

Step C

N²-{2-[1,3-dihydro-2H-isoindol-2-yl(methyl)amino]-2-oxoethyl}-N²-{2-methyl-5-[(2-methylhydrazino)carbonyl]phenyl}-N¹-{2-[(tert-butoxycarbonyl)(isopropyl)amino]ethyl}glycinamide Using the compound (351 mg, 0.70 mmol) obtained in step B, the compound (157 mg, 0.78 mmol) of Reference Example 3, and triethylamine (0.21 ml, 1.5 mmol), and according to the method of Example 1, step B, the title compound (440 mg, yield>100%) was obtained as a colorless amorphous solid.

¹H-NMR (300 MHz, CDCl₃); δ (ppm) 1.11 (d, J=6.6, 6H), 1.41 1.47 (2s, 9H), 2.37 (s, 3H), 2.71 (s, 3H), 2.95 (s, 3H), 3.11-3.18 (m, 2H), 3.33-3.42 (m, 2H), 3.83 (s, 2H), 4.08-4.29 (m, 7H), 7.19-7.28 (m, 5H), 7.42-7.46 (m, 1H), 7.67 (m, 1H), 8.01-8.35 (broad, 2H).

Step D

N²-{2-[1,3-dihydro-2H-isoindol-2-yl(methyl)amino]-2-oxoethyl}-N²-[2-methyl-5-(4-methyl-5-oxo-4,5-dihydro-1,3,4-oxadiazol-2-yl)phenyl]-N¹-{2-[(tert-butoxycarbonyl)(isopropyl)amino]ethyl}glycinamide Using the compound (440 mg) obtained in step C and according to the method of Example 67, step D, the title compound (440 mg, yield 99%) was obtained as a pale-yellow amorphous solid ¹H-NMR (300 MHz, CDCl₃); δ (ppm) 1.11 (d, J=6.9, 6H), 1.44 1.48 (2s, 9H), 2.39 (s, 3H), 2.95 (s, 3H), 3.17 (brs, 2H), 3.34-3.44 (m, 2H), 3.47 (s, 3H), 3.82 (brs, 2H), 4.08-4.28 (m, 7H), 7.20-7.29 (m, 5H), 7.42-7.45 (m, 1H), 7.69 (s, 1H).

Step E

N²-{2-[1,3-dihydro-2H-isoindol-2-yl(methyl)amino]-2-oxoethyl}N²-[2-methyl-5-(4-methyl-5-oxo-4,5-dihydro-1,3,4-oxadiazol-2-yl)phenyl]-N¹-[2-(isopropylamino)ethyl]glycinamide dihydrochloride Using the compound (440 mg, 0.69 mmol) obtained in step D and according to the method of Example 1, step C, the title compound (340 mg, yield 81%) was obtained as a colorless solid.
¹H-NMR (300 MHz, DMSO-d₆); δ (ppm) 1.19 (d, J=6.6, 6H), 2.33 (s, 3H), 2.87-2.95 (m, 5H), 3.22-3.31 (m, 1H), 3.34-3.46 (m, 5H), 3.92 (s, 2H), 4.10-4.35 (m, 6H), 7.23-7.33 (m, 6H), 7.52 (s, 1H), 8.34-8.39 (m, 1H), 8.90 (brs, 2H).

Example 89

N²-{2-[1,3-dihydro-2H-isoindol-2-yl(methyl)amino]-2-oxoethyl}-N²-[2-methyl-5-(4-methyl-5-oxo-4,5-dihydro-1,3,4-oxadiazol-2-yl)phenyl]-N¹-[2-(ethylamino)ethyl]glycinamide dihydrochloride Step A N²-{2-[1,3-dihydro-2H-isoindol-2-yl(methyl)amino]-2-oxoethyl}-N²-{2-methyl-5-[(2-methylhydrazino)carbonyl]phenyl}-N¹-{2-[(tert-butoxycarbonyl)(ethyl)amino]ethyl}glycinamide Using the compound (1.00 g, 2.01 mmol) of Example 88, step B, the compound (0.42 g, 2.23 mmol) of Reference Example 2 and triethylamine (0.60 ml, 4.21 mmol), and according to the method of Example 1, step B, the title compound (0.70 g, yield 59%) was obtained as a colorless amorphous solid.
¹H-NMR (300 MHz, CDCl₃); δ (ppm) 1.05 (t, J=7.2, 3H), 1.38 (brs, 9H), 2.35 (s, 3H), 2.70 (s, 3H), 2.95 (s, 3H), 3.17 (q, J=7.0, 2H), 3.30 (brs, 2H), 3.35-3.45 (m, 2H), 3.80 (s, 2H), 4.08-4.26 (m, 6H), 7.20-7.30 (m, 5H), 7.46-7.49 (m, 1H), 7.70 (s, 1H), 8.49 (broad, 2H).

Step B

N²-{2-[1,3-dihydro-2H-isoindol-2-yl(methyl)amino]-2-oxoethyl}-N²-[2-methyl-5-(4-methyl-5-oxo-4,5-dihydro-1,3,4-oxadiazol-2-yl)phenyl]-N¹-{2-[(tert-butoxycarbonyl)(ethyl)amino]ethyl}glycinamide Using the compound (0.70 g, 1.18 mmol) obtained in step A and according to the method of Example 67, step D, the title compound (0.70 g, yield 96%) was obtained as a pale-yellow amorphous solid
¹H-NMR (300 MHz, CDCl₃); δ (ppm) 1.04 (t, J=7.2, 3H), 1.43 (s, 9H), 2.38 (s, 3H), 2.96 (s, 3H), 3.15-3.36 (m, 4H), 3.39-3.47 (m, 5H), 3.81 (s, 2H), 4.08-4.50 (m, 6H), 7.14-7.30 (m, 5H), 7.43 (d, J=8.4, 1H), 7.69 (d, J=1.2, 1H), 8.25 8.54 (2brs, 1H).

Step C

N²-{2-[1,3-dihydro-2H-isoindol-2-yl(methyl)amino]-2-oxoethyl}-N²-[2-methyl-5-(4-methyl-5-oxo-4,5-dihydro-1,3,4-oxadiazol-2-yl)phenyl]-N¹-[2-(ethylamino)ethyl]glycinamide dihydrochloride Using the compound (0.70 g, 1.13 mmol) obtained in step B and according to the method of Example 1, step C, the title compound (0.51 g, yield 89%) was obtained as a colorless solid.
¹H-NMR (300 MHz, DMSO-d₆); δ (ppm) 1.16 (t, J=7.1, 3H), 2.50 (s, 3H), 2.87 (m, 7H), 3.35-3.39 (m, 5H), 3.92 (s, 2H), 4.10-4.34 (m, 6H), 7.26-7.32 (m, 6H), 7.52 (s, 1H), 8.32-8.37 (m, 1H), 8.91 (brs, 2H).

Example 90

N²-{2-[1,3-dihydro-2H-isoindol-2-yl(methyl)amino]-2-oxoethyl}-N²-{2-methyl-5-[(2-methylhydrazino)carbonyl]phenyl}-N¹-[2-(ethylamino)ethyl]glycinamide dihydrochloride Using the compound (0.54 g, 0.91 mmol) of Example 89, step A and according to the method of Example 1, step C, the title compound (0.45 g, yield 86%) was obtained as a colorless solid.
¹H-NMR (300 MHz, DMSO-d₆); δ (ppm) 1.18 (t, J=7.2, 3H), 2.34 (s, 3H), 2.88 (m, 8H), 3.35-3.42 (m, 4H), 3.95 (s, 2H), 4.15 (d, J=12.0, 2H), 4.26 (d, J=12.0, 2H), 4.35 (s, 2H), 7.26 (m, 5H), 7.48-7.51 (m, 1H), 7.71 (s, 1H), 8.35 (m, 1H), 9.03 (brs, 2H), 12.04 (s, 1H).

Example 91

N²-{2-[1,3-dihydro-2H-isoindol-2-yl(methyl)amino]-2-oxoethyl}-N²-[5-(4-ethyl-5-oxo-4,5-dihydro-1,3,4-oxadiazol-2-yl)-2-methylphenyl]-N¹-[2-(isopropylamino)ethyl]glycinamide dihydrochloride Step A N-[5-{[2-(tert-butoxycarbonyl)-2-ethylhydrazino]carbonyl}-2-methylphenyl]-N-{2-[1,3-dihydro-2H-isoindol-2-yl(methyl)amino]-2-oxoethyl}glycine Using the compound (2.25 g, 5.50 mmol) of Reference Example 75 and the compound (1.53 g, 8.29 mmol) of Reference Example 17, and according to the method of Example 1, step A, the title compound (2.41 g, yield 81%) was obtained as a gray amorphous solid.
¹H-NMR (300 MHz, CDCl₃); δ (ppm) 1.14 (t, J=7.2, 3H), 1.45 (brs, 9H), 2.22 (brs, 3H), 3.03 (s, 3H), 3.58 (q, J=7.1, 2H), 3.88 (s, 2H), 4.19-4.30 (m, 6H), 7.14-7.34 (m, 6H), 7.73 (s, 1H), 9.25 (brs, 1H).

Step B

N-{2-[1,3-dihydro-2H-isoindol-2-yl(methyl)amino]-2-oxoethyl}-N-{5-[(2-ethylhydrazino)carbonyl]-2-methylphenyl}glycine dihydrochloride Using the compound (1.00 g, 1.85 mmol) obtained by the method of step A and according to the method of Example 1, step C, the title compound (0.89 g, yield>100%) was obtained as a colorless solid.

$^1$H-NMR (300 MHz, DMSO-d$_6$); δ (ppm) 1.25 (t, J=7.2, 3H), 2.31 (s, 3H), 2.87 (s, 3H), 3.27 (q, J=7.2, 2H), 4.03 (s, 2H), 4.11-4.32 (m, 6H), 7.25-7.28 (m, 5H), 7.48 (d, J=7.5, 1H), 7.66 (s, 1H), 11.85 (s, 1H).

Step C

N$^2$-{2-[1,3-dihydro-2H-isoindol-2-yl(methyl)amino]-2-oxoethyl}-N$^2$-{5-[(2-ethylhydrazino)carbonyl]-2-methylphenyl}-N$^1$-{2-[(tert-butoxycarbonyl)(isopropyl)amino]ethyl}glycinamide Using the compound (0.50 g, 1.14 mmol) obtained in step B, the compound (0.36 g, 1.78 mmol) of Reference Example 3 and triethylamine (0.40 ml, 2.39 mmol), and according to the method of Example 1, step B, the title compound (0.60 g, yield 85%) was obtained as a colorless amorphous solid.

$^1$H-NMR (300 MHz, CDCl$_3$); δ (ppm) 1.12 (d, J=6.8, 6H), 1.15-1.29 (m. 3H), 1.46 (s, 9H), 2.21 (s, 3H), 2.92 2.94 (2s, 3H), 3.23-3.40 (m, 6H), 3.64 (m, 1H), 3.78-3.80 (m, 2H), 4.08-4.22 (m, 6H), 7.13-7.29 (m, 6H), 7.68-7.75 (m, 1H).

Step D

N$^2$-{2-[1,3-dihydro-2H-isoindol-2-yl(methyl)amino]-2-oxoethyl}-N$^2$-[5-(4-ethyl-5-oxo-4,5-dihydro-1,3,4-oxadiazol-2-yl)-2-methylphenyl]-N$^1$-{2-[(tert-butoxycarbonyl)(isopropyl)amino]ethyl}glycinamide Using the compound (0.60 g, 0.96 mmol) obtained in step C and according to the method of Example 67, step D, the title compound (0.18 g, yield 24%) was obtained as a pale-yellow amorphous solid $^1$H-NMR (300 MHz, CDCl$_3$); δ (ppm) 1.12 (d, J=6.8, 6H), 1.36-1.48 (m, 12H), 2.40 (s, 3H), 2.95 (s, 3H), 3.19 (brs, 2H), 3.36-3.42 (m, 2H), 3.78-3.87 (m, 4H), 4.08-4.27 (m, 6H), 7.20-7.29 (m, 5H), 7.42-7.46 (m, 1H), 7.70 (d, J=1.6, 1H).

Step E

N$^2$-{2-[1,3-dihydro-2H-isoindol-2-yl(methyl)amino]-2-oxoethyl}-N$^2$-[5-(4-ethyl-5-oxo-4,5-dihydro-1,3,4-oxadiazol-2-yl)-2-methylphenyl]-N$^1$-[2-(isopropylamino)ethyl]glycinamide dihydrochloride Using the compound (0.18 g, 0.28 mmol) obtained in step D and according to the method of Example 1, step C, the title compound (0.21 g, yield>100%) was obtained as a colorless amorphous solid.

$^1$H-NMR (300 MHz, DMSO-d$_6$); (ppm) 1.18-1.33 (m, 9H), 2.33 (s, 3H), 2.88 (m, 5H), 3.24-3.40 (m, 3H), 3.73-3.82 (m, 2H), 3.92 (s, 2H), 4.13 (d, J=11.7, 2H), 4.26 (d, J=11.7, 2H), 4.35 (s, 2H), 7.26-7.33 (m, 6H), 7.51 (s, 1H), 8.35-8.37 (m, 1H), 8.8 (brs, 2H).

Example 92

N$^2$-{2-[1,3-dihydro-2H-isoindol-2-yl(methyl)amino]-2-oxoethyl}-N$^2$-[5-(4-ethyl-5-oxo-4,5-dihydro-1,3,4-oxadiazol-2-yl)-2-methylphenyl]-N$^1$-[2-(ethylamino)ethyl]glycinamide dihydrochloride Step A N$^2$-{2-[1,3-dihydro-2H-isoindol-2-yl(methyl)amino]-2-oxoethyl}-N$^2$-{5-[(2-ethylhydrazino)carbonyl]-2-methylphenyl}-N$^1$-{2-[(tert-butoxycarbonyl)(ethyl)amino]ethyl}glycinamide Using the compound (0.85 g, 1.66 mmol) obtained in Example 91, step B, the compound (0.34 g, 1.81 mmol) of Reference Example 2, and triethylamine (0.50 ml, 3.49 mmol), and according to the method of Example 1, step B, the title compound (0.84 g, yield 83%) was obtained as a colorless amorphous solid.

$^1$H-NMR (300 MHz, CDCl$_3$); δ (ppm) 1.04 (t, J=6.9, 3H), 1.13 (t, J=6.9, 3H), 1.36 (s, 3H), 2.35 (s, 3H), 2.95 (m, 5H), 3.15-3.44 (m, 6H), 3.97 (s, 2H), 4.11-4.26 (m, 6H), 7.20-7.29 (m, 5H), 7.45 (brs, 1H), 7.68 (brs, 1H), 8.49-8.61 (broad, 2H).

Step B

N$^2$-{2-[1,3-dihydro-2H-isoindol-2-yl(methyl)amino]-2-oxoethyl}-N$^2$-[5-(4-ethyl-5-oxo-4,5-dihydro-1,3,4-oxadiazol-2-yl)-2-methylphenyl]-N$^1$-{2-[(tert-butoxycarbonyl)(ethyl)amino]ethyl}glycinamide Using the compound (0.84 g, 1.38 mmol) obtained in step A and according to the method of Example 67, step D, the title compound (0.69 g, yield 79%) was obtained as a pale-yellow amorphous solid $^1$H-NMR (300 MHz, CDCl$_3$); δ (ppm) 1.05 (t, J=7.1, 3H), 1.37-1.44 (m, 12H), 2.39 (s, 3H), 2.96 (s, 3H), 3.16-3.19 (m, 2H), 3.28-3.31 (m, 2H), 3.43 (q, J=6.3, 2H), 3.79-3.87 (m, 4H), 4.08-4.28 (m, 6H), 7.20-7.30 (m, 5H), 7.42-7.46 (d, J=8.3, 1H), 7.69 (d, J=1.1, 1H), 8.25 8.52 (2broad, 1H).

Step C

N$^2$-{2-[1,3-dihydro-2H-isoindol-2-yl(methyl)amino]-2-oxoethyl}-N$^2$-[5-(4-ethyl-5-oxo-4,5-dihydro-1,3,4-oxadiazol-2-yl)-2-methylphenyl]-N$^1$-[2-(ethylamino)ethyl]glycinamide dihydrochloride Using the compound (0.69 g, 1.09 mmol) obtained in step B and according to the method of Example 1, step C, the title compound (0.48 g, yield 73%) was obtained as a colorless solid.

$^1$H-NMR (300 MHz, DMSO-d$_6$); δ (ppm) 1.16 (t, J=7.1, 3H), 1.29 (t, J=7.2, 3H), 2.33 (s, 3H), 2.88 (m, 7H), 3.37-3.42 (m, 2H), 3.77 (q, J=7.2, 2H), 3.92 (s, 2H), 4.05-4.29 (m, 4H), 4.35 (s, 2H), 7.26-7.34 (m, 6H), 7.51 (s, 1H), 8.33-8.37 (m, 1H), 8.93 (brs, 2H).

Example 93

N$^2$-[5-(acetylamino)-2-methylphenyl]-N$^2$-{2-[1,3-dihydro-2H-isoindol-2-yl(methyl)amino]-2-oxoethyl}-N$^1$-[2-(isopropylamino)ethyl]glycinamide dihydrochloride Step A N-[5-(tert-butoxycarbonylamino)-2-methylphenyl]-N-{2-[1,3-dihydro-2H-isoindol-2-yl(methyl)amino]-2-oxoethyl}glycine Using the compound (1.00 g, 2.73 mmol) of Reference Example 76 and the compound of Reference Example 17

(555 mg, 3.00 mmol), and according to the method of Example 1, step A, the title compound (1.13 g, yield 88%) was obtained as a pale-bistered amorphous solid.

$^1$H-NMR (300 MHz, CDCl$_3$); δ (ppm) 1.49 (s, 9H), 2.24 (s, 3H), 3.05 (s, 3H), 3.90 (s, 2H), 4.11-4.29 (m, 6H), 6.40 (brs, 1H), 7.01-7.09 (m, 2H), 7.20-7.23 (m, 3H), 7.23-7.28 (m, 2H).

Step B

N$^2$-[5-(tert-butoxycarbonylamino)-2-methylphenyl]-N$^2$-(2-[1,3-dihydro-2H-isoindol-2-yl(methyl)amino]-2-oxoethyl)-N$^1$-[2-{(isopropyl)[(2-nitrophenyl)sulfonyl]amino}ethyl]glycinamide Using the compound (1.13 g, 2.41 mmol) obtained in step A and the compound (762 mg, 2.65 mmol) of Reference Example 7, and according to the method of Example 1, step B, the title compound (774 mg, yield 44%) was obtained as a pale-yellow solid.

$^1$H-NMR (300 MHz, CDCl$_3$); δ (ppm) 1.16 (d, J=6.6, 6H), 1.49 (s, 9H), 2.27 (s, 3H), 2.96 (s, 3H), 3.29-3.33 (m, 2H), 3.44-3.50 (m, 2H), 3.80 (s, 2H), 4.08-4.26 (m, 7H), 6.44 (brs, 1H), 7.05-7.14 (m, 2H), 7.19-7.23 (m, 5H), 7.56-7.59 (m, 1H), 7.65-7.68 (m, 2H), 7.98-8.01 (m, 1H), 8.56-8.59 (m, 1H).

Step C

N$^2$-[5-amino-2-methylphenyl]-N-{2-[1,3-dihydro-2H-isoindol-2-yl(methyl)amino]-2-oxoethyl}-N$^1$-[2-{(isopropyl)[(2-nitrophenyl)sulfonyl]amino}ethyl]glycinamide To a dichloromethane (10 ml)-ethyl acetate (5 ml) mixed solvent was added the compound (774 mg, 1.05 mmol) obtained in step B, 4N hydrochloric acid-ethyl acetate solution (2.6 ml, 10 mmol) was added at room temperature, and the mixture was stirred at the same temperature for 6.5 hr. The reaction mixture was concentrated under reduced pressure, diluted with dichloromethane, and the organic layer was washed with saturated aqueous sodium hydrogen carbonate, and dried over anhydrous magnesium sulfate. The insoluble material was filtered off, and the solution was concentrated under reduced pressure to give the title compound (662 mg, yield 99%) as a yellow amorphous solid.

$^1$H-NMR (300 MHz, CDCl$_3$); δ (ppm) 1.16 (d, J=6.9, 6H), 2.21 (s, 3H), 2.96 (s, 3H), 3.27-3.32 (m, 2H), 3.42-3.49 (m, 2H), 3.53 (brs, 2H), 3.80 (s, 2H), 4.10-4.25 (m, 7H), 6.35 (dd, J=2.4, 8.1, 1H), 6.65 (d, J=2.4, 1H), 6.78 (d, J=8.1, 1H), 7.20-7.26 (m, 4H), 7.58-7.59 (m, 1H), 7.65-7.68 (m, 2H), 7.99-8.02 (m, 1H), 8.51-8.53 (m, 1H).

Step D

N$^2$-[5-acetylamino-2-methylphenyl]-N$^2$-{2-[1,3-dihydro-2H-isoindol-2-yl(methyl)amino]-2-oxoethyl}-N$^1$-[2-{(isopropyl)[(2-nitrophenyl)sulfonyl]amino}ethyl]glycinamide Using the compound (220 mg, 0.35 mmol) obtained in step C and according to the method of Example 40, step D, the title compound (220 mg, yield 94%) was obtained as a yellow amorphous solid.

$^1$H-NMR (300 MHz, CDCl$_3$); δ (ppm) 1.13 (d, J=6.6, 6H), 2.13 (s, 3H), 2.28 (s, 3H), 2.96 (s, 3H), 3.32 (t, J=6.9, 2H), 3.45-3.52 (m, 2H), 3.82 (s, 2H), 4.07-4.25 (m, 7H), 7.11 (d, J=8.4, 1H), 7.18-7.25 (m, 4H), 7.35 (s, 1H), 7.45 (m, 1H), 7.60 (m, 1H), 7.66-7.69 (m, 2H), 7.96 (m, 1H), 8.70 (brt, J=6.0, 1H).

Step E

N$^2$-[5-acetylamino-2-methylphenyl]-N$^2$-{2-[1,3-dihydro-2H-isoindol-2-yl(methyl)amino]-2-oxoethyl}-N$^1$-[2-(isopropylamino)ethyl]glycinamide dihydrochloride Using the compound (220 mg, 0.32 mmol) obtained in step D and according to the methods of Example 40, steps E and F, the title compound (154 mg, yield 84%) was obtained as a yellow solid.

$^1$H-NMR (300 MHz, CD$_3$OD); δ (ppm) 1.31 (d, J=6.6, 6H), 2.08 (s, 3H), 2.30 (s, 3H), 2.98 (s, 3H), 3.12 (t, J=6.0, 2H), 3.35-3.38 (m, TH), 3.50-3.54 (m, 2H), 3.93 (s, 2H), 4.08 (d, J=11.4, 2H), 4.18 (d, J=13.2, 2H), 4.29 (s, 2H), 7.09-7.15 (m, 2H), 7.22-7.24 (m, 4H), 7.59 (s, 1H).

Example 94

N$^2$-{2-[1,3-dihydro-2H-isoindol-2-yl(methyl)amino]-2-oxoethyl}-N$^2$-{2-methyl-5-[(methylsulfonyl)amino]phenyl}-N$^1$-[2-(isopropylamino)ethyl]glycinamide dihydrochloride Step A N$^2$-[2-methyl-5-(methylsulfonylamino)phenyl]-N$^2$-{2-[1,3-dihydro-2H-isoindol-2-yl(methyl)amino]-2-oxoethyl}-N$^1$-[2-{(isopropyl)[(2-nitrophenyl)sulfonyl]amino}ethyl]glycinamide Using the compound (220 mg, 0.35 mmol) obtained in Example 93, step C and according to the method of Example 41, step A, the title compound (224 mg, yield 91%) was obtained as a yellow amorphous solid.

$^1$H-NMR (300 MHz, CDCl$_3$); δ (ppm) 1.14 (d, J=6.9, 6H), 2.30 (s, 3H), 2.97 (s, 3H), 2.98 (s, 3H), 3.32 (t, J=6.9, 2H), 3.40-3.48 (m, 2H), 3.86 (s, 2H), 4.06-4.28 (m, 7H), 6.49 (s, 1H), 6.89-6.92 (m, 1H), 7.07-7.13 (m, 2H), 7.20-7.24 (m, 4H), 7.59-7.61 (m, 1H), 7.66-7.69 (m, 2H), 7.98-8.02 (m, 1H), 8.46-8.48 (m, 1H).

Step B

N$^2$-{2-[1,3-dihydro-2H-isoindol-2-yl(methyl)amino]-2-oxoethyl}-N$^2$-{2-methyl-5-[(methylsulfonyl)amino]phenyl}-N$^1$-[2-(isopropylamino)ethyl]glycinamide dihydrochloride Using the compound (220 mg, 0.31 mmol) obtained in step A and according to the methods of Example 40, steps E and F, the title compound (115 mg, yield 62%) was obtained as a pale-yellow solid.

$^1$H-NMR (300 MHz, DMSO-d$_6$); δ (ppm) 1.18 (d, J=6.0, 6H), 2.19 (s, 3H), 2.90-2.91 (m, 8H), 3.25-3.36 (m, 3H), 3.85 (s, 2H), 4.11 (d, J=11.7, 2H), 4.26-4.29 (m, 4H), 6.70 (d, J=9.9, 1H), 7.03 (d, J=8.1, 1H), 7.26 (m, 4H), 8.30 (brs, 3H), 9.51 (s, 1H).

Example 95

N$^2$-{2-[1,3-dihydro-2H-isoindol-2-yl(methyl)amino]-2-oxoethyl}-N$^2$-{5-[(methoxycarbonyl)amino]-2-methylphenyl}-N$^1$-[2-(isopropylamino)ethyl]glycinamide dihydrochloride Step A N$^2$-{2-[1,3-dihydro-2H-isoindol-2-yl(methyl)amino]-2-oxoethyl}-N$^2$-{5-[(methoxycarbonyl)amino]-2-methylphenyl}-N$^1$-[2-{(isopropyl)[(2-nitrophenyl)sulfonyl]amino}ethyl]glycinamide Using the compound (220 mg, 0.35 mmol) of Example 93, step C and according to the method of Example 42, step A, the title compound (191 mg, yield 80%) was obtained as a yellow amorphous solid.

$^1$H-NMR (300 MHz, CDCl$_3$); δ (ppm) 1.15 (d, J=6.9, 6H), 2.28 (s, 3H), 2.96 (s, 3H), 3.29-3.33 (m, 2H), 3.43-3.50 (m, 2H), 3.74 (s, 3H), 3.81 (s, 2H), 4.05-4.25 (m, 7H), 6.58 (s, 1H), 7.07-7.10 (m, 1H), 7.19-7.23 (m, 5H), 7.56-7.59 (m, 1H), 7.65-7.68 (m, 2H), 7.98-8.01 (m, 1H), 8.55 (m, 1H).

Step B

N$^2$-{2-[1,3-dihydro-2H-isoindol-2-yl(methyl)amino]-2-oxoethyl}-N$^2$-{5-[(methoxycarbonyl)amino]-2-methylphenyl}-N$^1$-[2-(isopropylamino)ethyl]glycinamide dihydrochloride Using the compound (190 mg, 0.27 mmol) obtained in step A and according to the methods of Example 40, steps E and F, the title compound (133 mg, yield 83%) was obtained as a pale-yellow solid.

$^1$H-NMR (300 MHz, DMSO-d$_6$); δ (ppm) 1.19 (d, J=6.6, 6H), 2.18 (s, 3H), 2.89 (brm, 5H), 3.26-3.28 (m, 1H), 3.36-3.42 (m, 2H), 3.63 (s, 3H), 3.81 (s, 2H), 4.09-4.27 (m, 6H), 6.99 (m, 2H), 7.24-7.29 (m, 5H), 8.37 (broad t, J=5.7, 1H), 8.61 (brs, 2H), 9.44 (s, 1H).

Example 96

N$^2$-{2-[1,3-dihydro-2H-isoindol-2-yl(methyl)amino]-2-oxoethyl}-N$^2$-[5-(ethoxycarbonyl)-2-methylphenyl]-N$^1$-[2-(isopropylamino)ethyl]glycinamide dihydrochloride Step A N-{2-[1,3-dihydro-2H-isoindol-2-yl(methyl)amino]-2-oxoethyl}-N-[5-(ethoxycarbonyl)-2-methylphenyl]glycine Using the compound (0.52 g, 1.76 mmol) of Reference Example 77 and the compound (0.50 g, 2.71 mmol) of Reference Example 17, and according to the method of Example 1, step A, the title compound (0.58 g, yield 77%) was obtained as a gray amorphous solid.

Step B

N$^2$-{2-[1,3-dihydro-2H-isoindol-2-yl(methyl)amino]-2-oxoethyl}-N$^2$-[5-(ethoxycarbonyl)-2-methylphenyl]-N$^1$-{2-[(tert-butoxycarbonyl)(isopropyl)amino]ethyl}glycinamide Using the compound (0.29 g, 0.68 mmol) obtained in step A and the compound (214 mg, 1.06 mmol) of Reference Example 3, and according to the method of Example 1, step B, the title compound (0.20 g, yield 49%) was obtained as a colorless amorphous solid.

$^1$H-NMR (300 MHz, CDCl$_3$); δ (ppm) 1.12 (d, J=6.8, 6H), 1.36 (t, J=7.1, 3H), 1.45 (s, 9H), 2.40 (s, 3H), 2.95 (s, 3H), 3.17 (brs, 2H), 3.40 (q, J=7.8, 2H), 3.81 (s, 2H), 4.08-4.25 (m, 7H), 4.34 (q, J=7.3, 2H), 7.19-7.29 (m, 5H), 7.67 (d, 1H), 7.90 (s, 1H), 8.33-8.55 (broad, 1H).

Step C

N$^2$-{2-[1,3-dihydro-2H-isoindol-2-yl(methyl)amino]-2-oxoethyl}-N$^2$-[5-(ethoxycarbonyl)-2-methylphenyl]-N$^1$-[2-(isopropylamino)ethyl]glycinamide dihydrochloride Using the compound (0.20 g, 0.33 mmol) obtained in step B and according to the method of Example 1, step C, the title compound (0.15 g, yield 81%) was obtained as a colorless solid.

$^1$H-NMR (300 MHz, DMSO-d$_6$); δ (ppm) 1.19 (d, J=6.3, 6H), 1.30 (t, J=6.9, 3H), 2.33 (s, 3H), 2.88 (s, 3H), 3.22-3.27 (m, 1H), 3.38-3.40 (m, 2H), 3.56-3.62 (m, 2H), 3.90 (s, 2H), 4.10-4.34 (m, 8H), 7.22-7.26 (m, 5H), 7.46-7.50 (d, J=7.8, 1H), 7.67 (s, 1H), 8.35 (s, 1H), 8.82 (brs, 2H).

The compounds of Examples 73-96 are shown below.

TABLE 10

| Example | Structural Formula | TMW | LC-MS (found) |
|---|---|---|---|
| 73 | 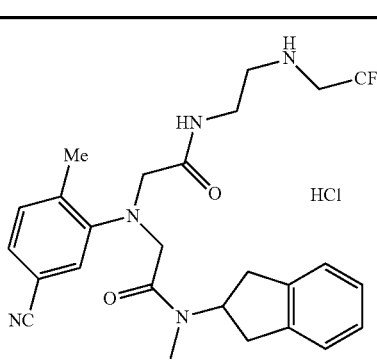 | 538.00 | 502 |

TABLE 10-continued

| Example | Structural Formula | TMW | LC-MS (found) |
|---|---|---|---|
| 74 | (structure) 2HCl | 594.53 | 522 |
| 75 | (structure) 2HCl | 608.56 | 536 |
| 76 | (structure) 2HCl | 554.51 | 482 |
| 77 | (structure) 2HCl | 567.55 | 495 |

TABLE 10-continued
| Example | Structural Formula | TMW | LC-MS (found) |
|---|---|---|---|
| 78 | 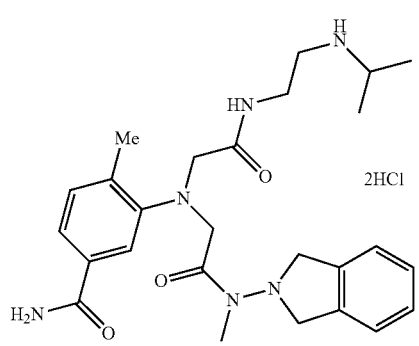 [SMILES: Cc1ccc(C(N)=O)cc1N(CC(=O)NCCNC(C)C)CC(=O)N(C)N1Cc2ccccc2C1 ; "2HCl"] 2HCl | 552.52 | 481 |
| 79 | 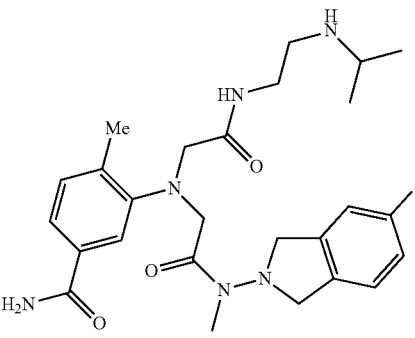 | 498.59 | 499 |
| 80 | 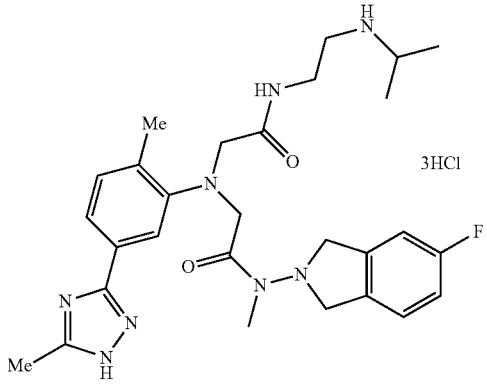 [SMILES: Cc1nc(-c2ccc(C)c(N(CC(=O)NCCNC(C)C)CC(=O)N(C)N3Cc4ccc(F)cc4C3)c2)n[nH]1 ; "3HCl"] 3HCl | 646.03 | 537 |
| 81 | 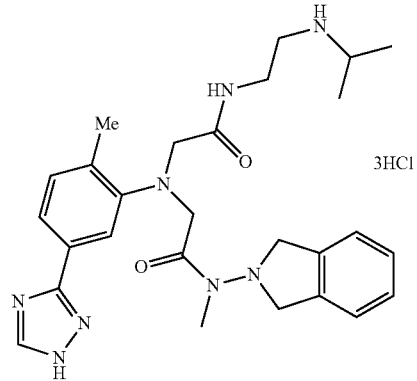 [SMILES: Cc1ccc(-c2nc[nH]n2)cc1N(CC(=O)NCCNC(C)C)CC(=O)N(C)N1Cc2ccccc2C1 ; "3HCl"] 3HCl | 614.01 | 505 |

TABLE 10-continued

| Example | Structural Formula | TMW | LC-MS (found) |
|---------|--------------------|-----|---------------|
| 82 | | 628.04 | 519 |
| 83 | | 505.61 | NT |
| 84 | | 519.64 | 520 |
| 85 | | 578.53 | 506 |

TABLE 10-continued

| Example | Structural Formula | TMW | LC-MS (found) |
|---------|-------------------|-----|---------------|
| 86 | | 610.55 | 538 |
| 87 | | 596.52 | 524 |
| 88 | | 608.56 | 536 |
| 89 | | 594.53 | 522 |

TABLE 10-continued

| Example | Structural Formula | TMW | LC-MS (found) |
|---|---|---|---|
| 90 | | 568.54 | 496 |
| 91 | | 622.59 | 550 |
| 92 | | 608.56 | 536 |
| 93 | | 567.55 | 495 |

TABLE 10-continued

| Example | Structural Formula | TMW | LC-MS (found) |
|---|---|---|---|
| 94 | | 603.61 | 531 |
| 95 | | 583.55 | 511 |
| 96 | | 582.56 | 510 |

Example 97

N²-{2-[1,3-dihydro-2H-isoindol-2-yl(methyl)amino]-2-oxoethyl}-N²-[5-(ethoxycarbonyl)-2-methylphenyl]-N¹-[2-(ethylamino)ethyl]glycinamide dihydrochloride

Step A

N²-{2-[1,3-dihydro-2H-isoindol-2-yl(methyl)amino]-2-oxoethyl}-N²-[5-(ethoxycarbonyl)-2-methylphenyl]-N¹-{2-[(tert-butoxycarbonyl)(ethyl)amino]ethyl}glycinamide Using the compound (0.29 g, 0.68 mmol) of Example 96, step A, and the compound (0.20 g, 1.06 mmol) of Reference Example 2, and according to the method of Example 1, step B, the title compound (0.22 g, yield 54%) was obtained as a colorless amorphous solid.

$^1$H-NMR (300 MHz, CDCl$_3$); δ (ppm) 1.05 (t, J=7.2, 3H), 1.36 (t, J=7.5, 3H), 1.43 (s, 9H), 2.39 (s, 3H), 2.95 (s, 3H), 3.16-3.19 (m, 2H), 3.28-3.31 (m, 2H), 3.44 (q, J=6.6, 2H), 3.79 (s, 2H), 4.07-4.26 (m, 6H), 4.34 (q, J=6.9, 2H), 7.19-7.30 (m, 5H), 7.66 (d, J=8.1, 1H), 7.89 (d, J=0.9, 1H), 8.34-8.60 (broad, 1H).

Step B

N²-{2-[1,3-dihydro-2H-isoindol-2-yl(methyl)amino]-2-oxoethyl}-N²-[5-(ethoxycarbonyl)-2-methylphenyl]-N¹-[2-(ethylamino)ethyl]glycinamide dihydrochloride Using the compound (0.22 g, 0.37 mmol) obtained in step A and according to the method of Example 1, step C, the title compound (0.17 g, yield 82%) was obtained as a colorless solid.

$^1$H-NMR (300 MHz, DMSO-d$_6$); δ (ppm) 1.16 (t, J=6.9, 3H), 1.30 (t, J=7.2, 3H), 2.32 (s, 3H), 2.88 (s, 3H), 3.37-3.40

(m, 2H), 3.56-3.79 (m, 4H), 3.90 (s, 2H), 4.10-4.33 (m, 8H), 7.22-7.27 (m, 5H), 7.46-7.50 (m, 1H), 7.68 (s, 1H), 8.34 (m, 1H), 8.84 (brs, 2H).

Example 98

$N^2$-{2-[1,3-dihydro-2H-isoindol-2-yl(methyl)amino]-2-oxoethyl}-$N^2$-[2-methyl-5-(5-methyl-1,3-oxazol-2-yl)phenyl]-$N^1$-[2-(isopropylamino)ethyl]glycinamide dihydrochloride Step A N-{2-[1,3-dihydro-2H-isoindol-2-yl(methyl)amino]-2-oxoethyl}-N-[2-methyl-5-(5-methyl-1,3-oxazol-2-yl)phenyl]glycine Using the compound (0.78 g, 2.56 mmol) of Reference Example 78 and the compound (0.71 g, 3.84 mmol) of Reference Example 17, and according to the method of Example 1, step A, the title compound (0.82 g, yield 74%) was obtained as a colorless amorphous solid.

$^1$H-NMR (300 MHz, CDCl$_3$); δ (ppm) 2.36 (s, 3H), 2.37 (s, 3H), 3.04 (s, 3H), 3.95 (s, 2H), 4.15-4.32 (m, 6H), 6.79 (s, 1H), 7.18-7.28 (m, 5H), 7.64-7.68 (m, 1H), 7.85 (s, 1H).

Step B $N^2$-{2-[1,3-dihydro-2H-isoindol-2-yl(methyl)amino]-2-oxoethyl}-$N^2$-[2-methyl-5-(5-methyl-1,3-oxazol-2-yl)phenyl]-$N^1$-{2-[(tert-butoxycarbonyl)(isopropyl)amino]ethyl}glycinamide Using the compound (0.82 g, 1.89 mmol) obtained in step A and the compound (592 mg, 2.93 mmol) of Reference Example 3, and according to the method of Example 1, step B, the title compound (0.93 g, yield 79%) was obtained as a colorless amorphous solid.

$^1$H-NMR (300 MHz, CDCl$_3$); δ (ppm) 1.10-1.16 (m, 6H), 1.47 (s, 9H), 2.36 (s, 3H), 2.39 (s, 3H), 2.94 (s, 3H), 3.17 (brs, 2H), 3.28-3.45 (m, 2H), 3.85 (s, 2H), 4.11-4.28 (m, 7H), 6.78 (s, 1H), 7.17-7.32 (m, 5H), 7.64 (d, J=7.8, 1H), 7.89 (s, 1H), 8.30-8.59 (broad, 1H).

Step C $N^2$-{2-[1,3-dihydro-2H-isoindol-2-yl(methyl)amino]-2-oxoethyl}-$N^2$-[2-methyl-5-(5-methyl-1,3-oxazol-2-yl)phenyl]-$N^1$-[2-(isopropylamino)ethyl]glycinamide dihydrochloride Using the compound (0.93 g, 1.50 mmol) obtained in step B and according to the method of Example 1, step C, the title compound (0.87 g, yield 98%) was obtained as a colorless solid.

$^1$H-NMR (300 MHz, DMSO-d$_6$); δ (ppm) 1.19 (d, J=6.5, 6H), 2.32 (s, 3H), 2.38 (s, 3H), 2.88-2.94 (m, 5H), 3.20-3.25 (m, 1H), 3.35-3.45 (m, 2H), 3.93 (s, 2H), 4.14 (d, J=11.7, 2H), 4.27 (d, J=11.7, 2H), 4.37 (s, 2H), 6.96 (s, 1H), 7.04-7.30 (m, 5H), 7.45 (dd, J=1.1, 7.6, 1H), 7.68 (d, J=1.1, 1H), 8.3-8.44 (m, 1H), 9.02 (broad, 2H).

Example 99

$N^2$-{2-[1,3-dihydro-2H-isoindol-2-yl(methyl)amino]-2-oxoethyl}-$N^2$-[2-methyl-5-(5-methyl-1,3-thiazol-2-yl)phenyl]-$N^1$-[2-(isopropylamino)ethyl]glycinamide dihydrochloride Step A N-{2-[1,3-dihydro-2H-isoindol-2-yl(methyl)amino]-2-oxoethyl}-N-[2-methyl-5-(5-methyl-1,3-thiazol-2-yl)phenyl]glycine Using the compound (0.50 g, 1.56 mmol) of Reference Example 80 and the compound (0.43 g, 2.33 mmol) of Reference Example 17, and according to the method of Example 1, step A, the title compound (0.40 g, yield 57%) was obtained as a colorless amorphous solid.

$^1$H-NMR (300 MHz, DMSO-d$_6$); δ (ppm) 2.34 (s, 3H), 2.47 (s, 3H), 3.03 (s, 3H), 3.96 (s, 2H), 4.16 (d, J=11.7, 2H), 4.26 (d, J=11.7, 2H), 4.32 (s, 2H), 7.12-7.27 (m, 5H), 7.44-7.52 (m, 2H), 7.78 (s, 1H).

Step B $N^2$-{2-[1,3-dihydro-2H-isoindol-2-yl(methyl)amino]-2-oxoethyl}-$N^2$-[2-methyl-5-(5-methyl-1,3-thiazol-2-yl)phenyl]-$N^1$-{2-[(tert-butoxycarbonyl)(isopropyl)amino]ethyl}glycinamide Using the compound (0.40 g, 0.89 mmol) obtained in step A and the compound (0.28 g, 1.38 mmol) of Reference Example 3, and according to the method of Example 1, step B, the title compound (0.56 g, yield 99%) was obtained as a colorless amorphous solid.

$^1$H-NMR (300 MHz, CDCl$_3$); δ (ppm) 1.11 (d, J=6.6, 6H), 1.47 (s, 9H), 2.38 (s, 3H), 2.48 (s, 3H), 2.94 (s, 3H), 3.15-3.18 (brs, 2H), 3.28-3.45 (m, 2H), 3.83 (s, 2H), 3.9-4.3 (broad, 1H), 4.14 (d, J=12.0, 2H), 4.22 (d, J=12.0, 2H), 4.28 (s, 2H), 6.90-7.30 (m, 5H), 7.43-7.52 (m, 2H), 7.81 (s, 1H), 8.35-8.66 (broad, 1H).

Step C $N^2$-{2-[1,3-dihydro-2H-isoindol-2-yl(methyl)amino]-2-oxoethyl}-$N^2$-[2-methyl-5-(5-methyl-1,3-thiazol-2-yl)phenyl]-$N^1$-[2-(isopropylamino)ethyl]glycinamide dihydrochloride Using the compound (0.56 g, 0.88 mmol) obtained in step B and according to the method of Example 1, step C, the title compound (0.41 g, yield 72%) was obtained as a colorless solid.

$^1$H-NMR (300 MHz, DMSO-d$_6$); δ (ppm) 1.18 (d, J=6.3, 6H), 2.31 (s, 3H), 2.50 (s, 3H), 2.88 (m, 5H), 3.19-3.42 (m, 3H), 3.93 (s, 2H), 4.14 (d, J=11.7, 2H), 4.26 (d, J=11.7, 2H), 4.38 (s, 2H), 7.19-7.27 (m, 5H), 7.36-7.39 (m, 1H), 7.62 (d, J=16.5, 2H), 8.41-8.46 (m, 1H), 9.02 (brs, 2H).

Example 100

N²-{2-[1,3-dihydro-2H-isoindol-2-yl(methyl) amino]-2-oxoethyl}-N²-[2-methyl-5-(4-methyl-1,3-thiazol-2-yl)phenyl]-N¹-[2-(isopropylamino)ethyl] glycinamide dihydrochloride

Step A

N-{2-[1,3-dihydro-2H-isoindol-2-yl(methyl)amino]-2-oxoethyl}-N-[2-methyl-5-(4-methyl-1,3-thiazol-2-yl)phenyl]glycine Using the compound (0.86 g, 2.68 mmol) of Reference Example 79 and the compound (0.75 g, 4.06 mmol) of Reference Example 17, and according to the method of Example 1, step A, the title compound (0.87 g, yield 72%) was obtained as a colorless amorphous solid.

$^1$H-NMR (300 MHz, CDCl$_3$); δ (ppm) 2.34 (s, 3H), 2.45 (s, 3H), 3.03 (s, 3H), 3.97 (s, 2H), 4.14-4.28 (m, 4H), 4.33 (s, 2H), 6.82 (s, 1H), 7.17-7.28 (m, 5H), 7.53-7.57 (m, 1H), 7.82 (s, 1H).

Step B

N²-{2-[1,3-dihydro-2H-isoindol-2-yl(methyl) amino]-2-oxoethyl}-N²-[2-methyl-5-(4-methyl-1,3-thiazol-2-yl)phenyl]-N¹-{2-[(tert-butoxycarbonyl) (isopropyl)amino]ethyl}glycinamide Using the compound (0.87 g, 1.93 mmol) obtained in step A and the compound (0.60 g, 2.97 mmol) of Reference Example 3, and according to the method of Example 1, step B, the title compound (0.95 g, yield 78%) was obtained as a colorless amorphous solid.

$^1$H-NMR (300 MHz, CDCl$_3$); δ (ppm) 1.11 (d, J=6.8, 6H), 1.45 (s, 9H), 2.38 (s, 3H), 2.47 (s, 3H), 2.94 (s, 3H), 3.17 (brs, 2H), 3.38-3.45 (m 2H), 3.83 (s, 2H), 3.9-4.3 (m, 7H), 6.82 (s, 1H), 7.17-7.29 (m, 5H), 7.51-7.54 (m, 1H), 7.84 (s, 1H), 8.35-8.66 (broad, 1H).

Step C

N²-{2-[1,3-dihydro-2H-isoindol-2-yl(methyl) amino]-2-oxoethyl}-N²-[2-methyl-5-(4-methyl-1,3-thiazol-2-yl)phenyl]-N¹-[2-(isopropylamino)ethyl] glycinamide dihydrochloride Using the compound (0.95 g, 1.50 mmol) obtained in step B and according to the method of Example 1, step C, the title compound (0.85 g, yield 94%) was obtained as a colorless solid.

$^1$H-NMR (300 MHz, DMSO-d$_6$); δ (ppm) 1.19 (d J=6.3, 6H), 2.32 (s, 3H), 2.44 (s, 3H), 2.88 (m, 5H), 3.20-3.23 (m, 1H), 3.34-3.42 (m, 2H), 3.95 (s, 2H), 4.16 (d, J=11.7, 2H), 4.27 (d, J=11.7, 2H), 4.39 (s, 2H), 7.21-7.33 (m, 6H), 7.42-7.45 (m, 1H), 7.68 (s, 1H), 8.44 (m, 1H), 9.07 (brs, 2H).

Example 101

N²-{2-[1,3-dihydro-2H-isoindol-2-yl(methyl) amino]-2-oxoethyl}-N²-[2-methyl-5-(4-methyl-1,3-thiazol-2-yl)phenyl]-N¹-[2-(ethylamino)ethyl]glycinamide dihydrochloride

Step A

N²-{2-[1,3-dihydro-2H-isoindol-2-yl(methyl) amino]-2-oxoethyl}-N²-[2-methyl-5-(4-methyl-1,3-thiazol-2-yl)phenyl]-10-{2-[(tert-butoxycarbonyl) (ethyl)amino]ethyl}glycinamide Using the compound (0.50 g, 1.11 mmol) of Example 100, step A, and the compound (0.33 g, 1.75 mmol) of Reference Example 2, and according to the method of Example 1, step B, the title compound (0.56 g, yield 81%) was obtained as a colorless amorphous solid.

$^1$H-NMR (300 MHz, CDCl$_3$); δ (ppm) 1.04 (t, J=6.9, 3H), 1.44 (s, 9H), 2.37 (s, 3H), 2.46 (s, 3H), 2.94 (s, 3H), 3.17 (brs, 2H), 3.27-3.32 (m, 2H), 3.41-3.48 (m, 2H), 3.82 (s, 2H), 4.16 (d, J=12.3, 2H), 4.23 (d, J=12.3, 2H), 4.29 (s, 2H), 6.82 (s, 1H), 7.12-7.30 (m, 5H), 7.50-7.53 (m, 1H), 7.76-7.88 (m, 1H), 8.41-8.66 (broad, 1H).

Step B

N²-{2-[1,3-dihydro-2H-isoindol-2-yl(methyl) amino]-2-oxoethyl}-N²-[2-methyl-5-(4-methyl-1,3-thiazol-2-yl)phenyl]-N¹-[2-(ethylamino)ethyl]glycinamide dihydrochloride Using the compound (0.50 g, 0.81 mmol) obtained in step A and according to the method of Example 1, step C, the title compound (0.44 g, yield 92%) was obtained as a colorless solid.

$^1$H-NMR (300 MHz, DMSO-d$_6$); δ (ppm) 1.16 (t, J=6.9, 3H), 2.32 (s, 3H), 2.44 (s, 3H), 2.88 (m, 7H), 3.34-3.42 (m, 2H), 3.96 (s, 2H), 4.16 (d, J=12.3, 2H), 4.27 (d, J=12.3, 2H), 4.39 (s, 2H), 7.14-7.45 (m, 7H), 7.69 (s, 1H), 8.42 (m, 1H), 9.07 (brs, 2H).

Example 102

N²-{2-[1,3-dihydro-2H-isoindol-2-yl(methyl) amino]-2-oxoethyl}-N²-[5-(4-ethyl-1,3-thiazol-2-yl)-2-methylphenyl]-N¹-[2-(ethylamino)ethyl]glycinamide dihydrochloride

Step A

N-{2-[1,3-dihydro-2H-isoindol-2-yl(methyl)amino]-2-oxoethyl}-N-[5-(4-ethyl-1,3-thiazol-2-yl)-2-methylphenyl]glycine Using the compound (0.91 g, 2.72 mmol) of Reference Example 81 and the compound (0.75 g, 4.06 mmol) of Reference Example 17, and according to the method of Example 1, step A, the title compound (0.73 g, yield 58%) was obtained as a colorless amorphous solid.

Step B

N²-{2-[1,3-dihydro-2H-isoindol-2-yl(methyl)amino]-2-oxoethyl}-N²-[5-(4-ethyl-1,3-thiazol-2-yl)-2-methylphenyl]-N¹-{2-[(tert-butoxycarbonyl)(ethyl)amino]ethyl}glycinamide Using the compound (0.73 g, 1.57 mmol) obtained in step A and the compound (0.46 g, 2.44 mmol) of Reference Example 2, and according to the method of Example 1, step B, the title compound (0.60 g, yield 60%) was obtained as a colorless amorphous solid.

¹H-NMR (300 MHz, CDCl₃); δ (ppm) 1.04 (t, J=7.0, 3H), 1.32 (t, J=7.5, 3H), 1.44 (s, 9H), 2.37 (s, 3H), 2.83 (q, J=7.0, 2H), 2.94 (s, 3H), 3.17 (brs, 2H), 3.27-3.32 (m, 2H), 3.41-3.48 (m, 2H), 3.83 (s, 2H), 4.07-4.29 (m, 6H), 6.82 (s, 1H), 7.16-7.29 (m, 5H), 7.52 (dd, J=1.3, 7.9, 1H), 7.84 (d, J=1.3, 1H), 8.25-8.75 (broad, 1H).

Step C

N²-{2-[1,3-dihydro-2H-isoindol-2-yl(methyl)amino]-2-oxoethyl}-N²-[5-(4-ethyl-1,3-thiazol-2-yl)-2-methylphenyl]-N¹-[2-(ethylamino)ethyl]glycinamide dihydrochloride Using the compound (0.60 g, 0.95 mmol) obtained in step B and according to the method of Example 1, step C, the title compound (0.50 g, yield 88%) was obtained as a colorless solid.

¹H-NMR (300 MHz, DMSO-d₆); δ (ppm) 1.16 (t, J=7.2, 3H), 1.27 (t, J=7.5, 3H), 2.31 (s, 3H), 2.79 (q, J=7.8, 2H), 2.88 (s, 7H), 3.34-3.44 (m, 2H), 3.95 (s, 2H), 4.16 (d, J=11.7, 2H), 4.28 (d, J=11.7, 2H), 4.39 (s, 2H), 7.20-7.33 (m, 5H), 7.42-7.46 (dd, J=1.2, 7.5, 1H), 7.67 (s, 1H), 8.40-8.44 (m, 1H), 9.04 (brs, 2H).

Example 103

N²-[5-(4-tert-butyl-1,3-thiazol-2-yl)-2-methylphenyl]-N²-{2-[1,3-dihydro-2H-isoindol-2-yl(methyl)amino]-2-oxoethyl}-N¹-[2-(isopropylamino)ethyl]glycinamide dihydrochloride

Step A

N-[5-(4-tert-butyl-1,3-thiazol-2-yl)-2-methylphenyl]-N-{2-[1,3-dihydro-2H-isoindol-2-yl(methyl)amino]-2-oxoethyl}glycine Using the compound (0.91 g, 2.51 mmol) of Reference Example 82 and the compound (0.70 g, 3.79 mmol) of Reference Example 17, and according to the method of Example 1, step A, the title compound (0.60 g, yield 48%) was obtained as a colorless amorphous solid.

¹H-NMR (300 MHz, CDCl₃); δ (ppm) 1.36 (s, 9H), 2.33 (s, 3H), 3.03 (s, 3H), 4.01 (s, 2H), 4.17 (d, J=11.7, 2H), 4.27 (d, J=11.7, 2H), 4.34 (s, 2H), 6.83 (s, 1H), 7.17-7.27 (m, 5H), 7.57 (dd, J=1.5, 7.9, 1H), 7.78 (d, J=1.5, 1H).

Step B

N²-[5-(4-tert-butyl-1,3-thiazol-2-yl)-2-methylphenyl]-N²-{2-[1,3-dihydro-2H-isoindol-2-yl(methyl)amino]-2-oxoethyl}-N¹-{2-[(tert-butoxycarbonyl)(isopropyl)amino]ethyl}glycinamide Using the compound (0.60 g, 1.22 mmol) obtained in step A and the compound (0.38 g, 1.88 mmol) of Reference Example 3, and according to the method of Example 1, step B, the title compound (0.69 g, yield 84%) was obtained as a colorless amorphous solid.

¹H-NMR (300 MHz, CDCl₃); δ (ppm) 1.12 (d, J=6.7, 6H), 1.83 (s, 9H), 1.45 (s, 9H), 2.38 (s, 3H), 2.94 (s, 3H), 3.19 (brs, 2H), 3.40-3.44 (m, 2H), 3.85 (s, 2H), 4.09-4.27 (m, 7H), 6.83 (s, 1H), 7.17-7.31 (m, 5H), 7.54-7.57 (m, 1H), 7.82 (s, 1H), 8.61 (broad, 1H).

Step C

N²-[5-(4-tert-butyl-1,3-thiazol-2-yl)-2-methylphenyl]-N²-{2-[1,3-dihydro-2H-isoindol-2-yl(methyl)amino]-2-oxoethyl}-N¹-[2-(isopropylamino)ethyl]glycinamide dihydrochloride Using the compound (0.62 g, 0.92 mmol) obtained in step B and according to the method of Example 1, step C, the title compound (0.44 g, yield 74%) was obtained as a colorless solid.

¹H-NMR (300 MHz, DMSO-d₆); δ (ppm) 1.19 (d, J=6.3, 6H), 1.35 (s, 9H), 2.31 (s, 3H), 2.90 (m, 5H), 3.18-3.25 (m, 1H), 3.34-3.43 (m, 2H), 3.95 (s, 2H), 4.17 (d, J=11.7, 2H), 4.29 (d, J=11.7, 2H), 4.40 (s, 2H), 7.12-7.26 (m, 6H), 7.39-7.42 (m, 1H), 7.58 (s, 1H), 8.42-8.47 (m, 1H), 9.00 (brs, 2H).

Example 104

N²-{2-[1,3-dihydro-2H-isoindol-2-yl(methyl)amino]-2-oxoethyl}-N²-[2-methyl-5-(5-methyl-1,3,4-oxadiazol-2-yl)phenyl]-N¹-[2-(isopropylamino)ethyl]glycinamide dihydrochloride

Step A

N-{2-[1,3-dihydro-2H-isoindol-2-yl(methyl)amino]-2-oxoethyl}-N-[2-methyl-5-(5-methyl-1,3,4-oxadiazol-2-yl)phenyl]glycine Using the compound (0.25 g, 0.82 mmol) of Reference Example 83 and the compound (0.23 g, 1.25 mmol) of Reference Example 17, and according to the method of Example 1, step A, the title compound (0.10 g, yield 28%) was obtained as a bistered amorphous solid.

Step B

N²-{2-[1,3-dihydro-2H-isoindol-2-yl(methyl)amino]-2-oxoethyl}-N²-[2-methyl-5-(5-methyl-1,3,4-oxadiazol-2-yl)phenyl]-N¹-{2-[(tert-butoxycarbonyl)(isopropyl)amino]ethyl}glycinamide Using the compound (0.10 g, 0.23 mmol) obtained in step A and the compound (70 mg, 0.35 mmol) of Reference Example 3, and according to the method of Example 1, step B, the title compound (33 mg, yield 24%) was obtained as a pale-yellow amorphous solid ¹H-NMR (300 mHz, CDCl₃); δ (ppm) 1.10 (d, J=6.9, 6H), 1.44 (s, 9H), 2.41 (s, 3H), 2.59 (s, 3H), 2.88 (s, 3H), 3.16-3.19 (brs, 2H), 3.36-3.42 (m, 2H), 3.87 (s, 2H), 3.9-4.3 (m, 7H), 7.20-7.30 (m, 6H), 7.66-7.70 (m, 1H), 7.87 (s, 1H).

Step C

N²-{2-[1,3-dihydro-2H-isoindol-2-yl(methyl) amino]-2-oxoethyl}-N²-[2-methyl-5-(5-methyl-1,3, 4-oxadiazol-2-yl)phenyl]-N¹-[2-(isopropylamino) ethyl]glycinamide dihydrochloride Using the compound (33 mg, 0.053 mmol) obtained in step B and according to the method of Example 1, step C, the title compound (15.8 mg, yield 50%) was obtained as a pale-yellow solid.

¹H-NMR (300 MHz, DMSO-d₆); δ (ppm) 1.17 (d, J=6.6, 6H), 2.34 (s, 3H), 2.57 (s, 3H), 2.88 (m, 5H), 3.23-3.30 (m, 1H), 3.37-3.42 (m, 2H), 3.94 (s, 2H), 4.10-4.36 (m, 6H), 7.26-7.32 (m, 5H), 7.46-7.50 (m, 1H), 7.69 (s, 1H), 8.33-8.37 (m, 1H), 8.69 (brs, 2H).

Example 105

N²-{2-[1,3-dihydro-2H-isoindol-2-yl(methyl) amino]-2-oxoethyl}-N²-[2-methyl-5-(5-methyl-1,3, 4-thiadiazol-2-yl)phenyl]-N¹-[2-(isopropylamino) ethyl]glycinamide dihydrochloride

Step A

N-{2-[1,3-dihydro-2H-isoindol-2-yl(methyl)amino]- 2-oxoethyl}-N-[2-methyl-5-(5-methyl-1,3,4-thiadiazol-2-yl)phenyl]glycine Using the compound (0.23 g, 0.72 mmol) of Reference Example 84 and the compound (0.20 g, 1.08 mmol) of Reference Example 17, and according to the method of Example 1, step A, the title compound (0.28 g, yield 87%) was obtained as a colorless amorphous solid.

¹H-NMR (300 MHz, CDCl₃); δ (ppm) 2.36 (s, 3H), 1.77 (s, 3H), 3.04 (s, 3H), 3.97 (s, 2H), 4.18 (d, J=11.7, 2H), 4.28 (d, J=11.7, 2H), 4.35 (s, 2H), 7.18-7.28 (m, 5H), 7.50-7.54 (m, 1H), 7.81 (s, 1H).

Step B

N²-{2-[1,3-dihydro-2H-isoindol-2-yl(methyl) amino]-2-oxoethyl}-N²-[2-methyl-5-(5-methyl-1,3, 4-thiadiazol-2-yl)phenyl]-N¹-{2-[(tert-butoxycarbonyl)(isopropyl)amino]ethyl}glycinamide Using the compound (0.28 g, 0.62 mmol) obtained in step A and the compound (0.20 g, 0.99 mmol) of Reference Example 3, and according to the method of Example 1, step B, the title compound (0.50 g) was obtained as a colorless amorphous solid.

¹H-NMR (300 MHz, CDCl₃); δ (ppm) 1.11 (d, J=6.9, 6H), 1.44 (s, 9H), 2.40 (s, 3H), 2.78 (s, 3H), 2.94 (s, 3H), 3.16-3.46 (m, 4H), 3.84 (s, 2H), 4.0-4.4.3 (m, 7H), 7.19-7.30 (m, 5H), 7.45-7.55 (m, 1H), 7.80 (s, 1H), 8.20-8.60 (broad, 1H).

Step C

N²-{2-[1,3-dihydro-2H-isoindol-2-yl(methyl) amino]-2-oxoethyl}-N²-[2-methyl-5-(5-methyl-1,3, 4-thiadiazol-2-yl)phenyl]-N¹-[2-(isopropylamino) ethyl]glycinamide dihydrochloride Using the compound (0.50 g) obtained in step B and according to the method of Example 1, step C, the title compound (0.28 g, yield 74%) was obtained as a pale-yellow solid.

¹H-NMR (300 MHz, DMSO-d₆); δ (ppm) 1.19 1.24 (2d, J=6.4, 6H), 2.33 (s, 3H), 2.76 (s, 3H), 2.89 (m, 5H), 3.23-3.44 (m, 3H), 3.94 (s, 2H), 4.14 (d, J=11.7, 2H), 4.27 (d, J=11.7, 2H), 4.37 (s, 2H), 7.23-7.29 (m, 5H), 7.40 (dd, J=1.3, 7.7, 1H), 7.65 (d, J=1.3, 1H), 8.40-8.44 (m, 1H), 8.97 (brs, 2H).

Example 106

N²-{2-[1,3-dihydro-2H-isoindol-2-yl(methyl) amino]-2-oxoethyl}-N²-[2-methyl-5-(5-methyl-1,3, 4-thiadiazol-2-yl)phenyl]-N¹-[2-(ethylamino)ethyl] glycinamide dihydrochloride

Step A

N²-{2-[1,3-dihydro-2H-isoindol-2-yl(methyl) amino]-2-oxoethyl}-N²-[2-methyl-5-(5-methyl-1,3, 4-thiadiazol-2-yl)phenyl]-N¹-{2-[(tert-butoxycarbonyl)(ethyl)amino]ethyl}glycinamide Using the compound (0.94 g, 2.08 mmol) of Example 105, step A, and the compound (0.61 g, 3.24 mmol) of Reference Example 2, and according to the method of Example 1, step B, the title compound (0.87 g, yield 67%) was obtained as a colorless amorphous solid.

¹H-NMR (300 MHz, CDCl₃); δ (ppm) 1.04 (t, J=7.2, 3H), 1.43 (s, 9H), 2.39 (s, 3H), 2.79 (s, 3H), 2.95 (s, 3H), 3.01-3.30 (m, 4H), 3.39-3.46 (m, 2H), 3.83 (s, 2H), 4.08-4.29 (m, 6H), 7.17-7.30 (m, 5H), 7.51-7.54 (m, 1H), 7.81 (s, 1H), 8.30-8.57 (broad, 1H).

Step B

N²-{2-[1,3-dihydro-2H-isoindol-2-yl(methyl) amino]-2-oxoethyl}-N²-[2-methyl-5-(5-methyl-1,3, 4-thiadiazol-2-yl)phenyl]-N¹-[2-(ethylamino)ethyl] glycinamide dihydrochloride Using the compound (0.87 g, 1.40 mmol) obtained in step A and according to the method of Example 1, step C, the title compound (0.78 g, yield 94%) was obtained as a pale-yellow solid.

¹H-NMR (300 MHz, DMSO-d₆); δ (ppm) 1.15 (t, J=7.1, 3H), 2.32 (s, 3H), 2.76 (s, 3H), 2.892 (m, 7H), 3.37-3.41 (m, 2H), 3.94 (s, 2H), 4.14 (d, J=11.6, 2H), 4.27 (d, J=11.6, 2H), 4.37 (s, 2H), 7.26-7.30 (m, 5H), 7.39-7.42 (m, 1H), 7.65 (s, 1H), 8.38-8.42 (m, 1H), 8.96 (m, 2H).

Example 107

N²-{2-[1,3-dihydro-2H-isoindol-2-yl(methyl) amino]-2-oxoethyl}-N²-[2-methyl-5-(5-oxo-4,5-dihydro-1,3,4-oxadiazol-2-yl)phenyl]-N¹-[2-(isopropylamino)ethyl]glycinamide dihydrochloride

Step A

N-{2-[1,3-dihydro-2H-isoindol-2-yl(methyl)amino]- 2-oxoethyl}-N-[2-methyl-5-(5-oxo-4,5-dihydro-1,3, 4-oxadiazol-2-yl)phenyl]glycine Using the compound (0.94 g, 3.06 mmol) of Reference Example 85 and the compound (0.85 g, 4.60 mmol) of Reference Example 17, and according to the method of Example 1, step A, the title compound (0.31 g, yield 23%) was obtained as a colorless amorphous solid.

Step B

N²-{2-[1,3-dihydro-2H-isoindol-2-yl(methyl)amino]-2-oxoethyl}-N²-[2-methyl-5-(5-oxo-4,5-dihydro-1,3,4-oxadiazol-2-yl)phenyl]-N¹-{2-[(tert-butoxycarbonyl)(isopropyl)amino]ethyl}glycinamide Using the compound (0.31 g, 0.71 mmol) obtained in step A and the compound (0.23 g, 1.13 mmol) of Reference Example 3, and according to the method of Example 1, step B, the title compound (70 mg, yield 16%) was obtained as a colorless amorphous solid.

$^1$H-NMR (300 MHz, CDCl$_3$); δ (ppm) 1.11 (d, J=6.8, 6H), 1.44 (s, 9H), 2.39 (s, 3H), 2.95 (s, 3H), 3.18 (brs, 2H), 3.37-3.49 (m, 2H), 3.90 (s, 2H), 3.8-4.3 (m, 7H), 7.19-7.27 (m, 5H), 7.41 (d, J=7.8, 1H), 7.72 (d, J=1.1, 1H), 8.23-8.46 (broad, 1H).

Step C

N²-{2-[1,3-dihydro-2H-isoindol-2-yl(methyl)amino]-2-oxoethyl}-N²-[2-methyl-5-(5-oxo-4,5-dihydro-1,3,4-oxadiazol-2-yl)phenyl]-N¹-[2-(isopropylamino)ethyl]glycinamide dihydrochloride Using the compound (70 mg, 0.11 mmol) obtained in step B and according to the method of Example 1, step C, the title compound (53 mg, yield 79%) was obtained as a colorless solid.

$^1$H-NMR (300 MHz, DMSO-d$_6$); δ (ppm) 1.17 (d, J=6.6, 6H), 2.32 (s, 3H), 2.88 (m, 5H), 3.25-3.57 (m, 3H), 3.91 (s, 2H), 4.10-4.34 (m, 6H), 7.26 (m, 6H), 7.51 (s, 1H), 8.33 (m, 1H), 8.64 (brs, 2H).

Example 108

N²-{2-[1,3-dihydro-2H-isoindol-2-yl(methyl)amino]-2-oxoethyl}-N²-(2,6-dimethylphenyl)-N¹-[2-(isopropylamino)ethyl]glycinamide dihydrochloride

Step A

N-{2-[1,3-dihydro-2H-isoindol-2-yl(methyl)amino]-2-oxoethyl}-N-(2,6-dimethylphenyl)glycine Using the compound (1.00 g, 4.21 mmol) of Reference Example 87 and the compound (1.17 g, 6.32 mmol) of Reference Example 17, and according to the method of Example 4, step A, the title compound (1.21 g, yield 78%) was obtained as a pale-gray amorphous solid.

$^1$H-NMR (300 MHz, DMSO-d$_6$); δ (ppm) 2.31 (s, 6H), 2.92 (s, 3H), 3.82 (s, 2H), 4.03 (d, J=11.7, 2H), 4.18-4.24 (m, 4H), 6.89-6.98 (m, 3H), 7.23 (s, 4H).

Step B

N²-{2-[1,3-dihydro-2H-isoindol-2-yl(methyl)amino]-2-oxoethyl}-N²-(2,6-dimethylphenyl)-N¹-[2-(isopropylamino)ethyl]glycinamide dihydrochloride Using the compound (600 mg, 1.63 mmol) obtained in step A and the compound (495 mg, 2.45 mmol) of Reference Example 3, and according to the methods of Example 1, step B, and Example 1, step C, the title compound (284 mg, yield 33%) was obtained as a pale-bistered amorphous solid.

$^1$H-NMR (300 MHz, DMSO-d$_6$); δ (ppm) 1.24 (d, J=6.6, 6H), 2.33 (s, 6H), 2.97 (s, 3H), 2.97-3.04 (m, 2H), 3.23-3.51 (m, 3H), 3.69 (s, 2H), 3.94 (d, J=11.7, 2H), 4.18 (d, J=11.7, 2H), 4.24 (s, 2H), 6.91-7.01 (m, 3H), 7.23 (s, 4H), 8.67-9.00 (broad, 2H), 9.17 (t, J=5.6, 1H).

Example 109

N²-(4-bromo-2,6-dimethylphenyl)-N²-{2-[1,3-dihydro-2H-isoindol-2-yl(methyl)amino]-2-oxoethyl}-N¹-[2-(isopropylamino)ethyl]glycinamide dihydrochloride

Step A

N-(4-bromo-2,6-dimethylphenyl)-N-{2-[1,3-dihydro-2H-isoindol-2-yl(methyl)amino]-2-oxoethyl}glycine Using the compound (2.00 g, 6.33 mmol) of Reference Example 88 and the compound (1.75 g, 9.50 mmol) of Reference Example 17, and according to the method of Example 4, step A, the title compound (2.02 g, yield 71%) was obtained as a bistered amorphous solid.

$^1$H-NMR (300 MHz, DMSO-d$_6$); δ (ppm) 2.32 (s, 6H), 2.90 (s, 3H).
3.81 (s, 2H), 3.99-4.07 (m, 2H), 4.20 (s, 2H), 4.21 (d, J=11.4, 2H), 7.16 (s, 2H), 7.24 (s, 4H), 11.8-13.0 (broad, 1H).

Step B

N²-(4-bromo-2,6-dimethylphenyl)-N²-{2-[1,3-dihydro-2H-isoindol-2-yl(methyl)amino]-2-oxoethyl}-N¹-{2-[(tert-butoxycarbonyl)(isopropyl)amino]ethyl}glycinamide Using the compound (2.02 g, 4.53 mmol) obtained in step A and the compound (1.37 g, 6.80 mmol) of Reference Example 3, and according to the method of Example 1, step B, the title compound (2.35 g, yield 82%) was obtained as a pale-bistered amorphous solid.

$^1$H-NMR (300 MHz, CDCl$_3$); δ (ppm) 1.16 (d, J=6.6, 6H), 1.43 (s, 9H), 2.35 (s, 6H), 2.94 (s, 3H), 3.17-3.32 (m, 2H), 3.40-3.49 (m, 2H), 3.69 (s, 2H), 3.94 (d, J=11.7, 2H), 4.15 (s, 2H), 4.16 (d, J=9.3, 2H), 4.16-4.38 (m, 1H), 7.14-7.33 (m, 6H), 9.21-9.68 (broad, 1H).

Step C

N²-(4-bromo-2,6-dimethylphenyl)-N²-{2-[1,3-dihydro-2H-isoindol-2-yl(methyl)amino]-2-oxoethyl}-N¹-[2-(isopropylamino)ethyl]glycinamide dihydrochloride Using the compound (500 mg, 0.79 mmol) obtained in step B and according to the method of Example 1, step C, the title compound (365 mg, yield 77%) was obtained as a pale-bistered amorphous solid.

$^1$H-NMR (300 mHz, DMSO-d$_6$); δ (ppm) 1.23 (d, J=6.6, 6H), 2.33 (s, 6H), 2.89 (s, 3H), 2.89-3.02 (m, 2H), 3.23-3.60 (m, 3H), 3.68 (s, 2H), 3.97 (d, J=11.7, 2H), 4.19 (d, J=11.7, 2H), 4.21 (s, 2H), 7.18 (s, 2H), 7.24 (s, 4H), 8.70 (brs, 2H), 8.95 (t, J=5.7, 1H).

Example 110

N²-(4-cyano-2,6-dimethylphenyl)-N²-{2-[1,3-dihydro-2H-isoindol-2-yl(methyl)amino]-2-oxoethyl}-N¹-[2-(isopropylamino)ethyl]glycinamide dihydrochloride

Step A

N²-(4-cyano-2,6-dimethylphenyl)-N²-{2-[1,3-dihydro-2H-isoindol-2-yl(methyl)amino]-2-oxoethyl}-N¹-{2-[(tert-butoxycarbonyl)(isopropyl)amino]ethyl}glycinamide Using the compound (1.00 g, 1.59 mmol) of Example 109, step B and according to the method of Reference Example 112, step D, the title compound (550 mg, yield 60%) was obtained as a colorless amorphous solid.

¹H-NMR (300 MHz, DMSO-$d_6$); δ (ppm) 1.03 (d, J=6.0, 6H), 1.39 (s, 9H), 2.40 (s, 6H), 2.87 (s, 3H), 2.88-3.24 (m, 4H), 3.70 (s, 2H), 3.8-4.1 (broad, 1H), 4.03 (d, J=11.4, 2H), 4.21 (d, J=11.7, 2H), 4.24 (s, 2H), 7.25 (s, 4H), 7.43 (s, 2H), 8.37-8.43 (m, 1H).

Step B

N²-(4-cyano-2,6-dimethylphenyl)-N²-{2-[1,3-dihydro-2H-isoindol-2-yl(methyl)amino]-2-oxoethyl}-N¹-[2-(isopropylamino)ethyl]glycinamide dihydrochloride Using the compound (550 mg, 0.95 mmol) obtained in step A and according to the method of Example 1, step C, the title compound (55.2 mg, yield 11%) was obtained as a pale-bistered amorphous solid.

¹H-NMR (300 MHz, DMSO-$d_6$); δ (ppm) 1.21 (d, J=6.3, 6H), 2.41 (s, 6H), 2.79-3.01 (m, 2H), 2.87 (s, 3H), 3.17-3.42 (m, 3H), 3.78 (s, 2H), 4.03 (d, J=12.0, 2H), 4.21 (d, J=12.3, 2H), 4.26 (s, 2H), 7.25 (s, 4H), 7.43 (s, 2H), 8.53-8.56 (m, 1H), 8.79 (brs, 2H).

Example 111

N²-(4-bromo-2-methylphenyl)-N²-{2-[1,3-dihydro-2H-isoindol-2-yl(methyl)amino]-2-oxoethyl}-N¹-[2-(isopropylamino)ethyl]glycinamide dihydrochloride

Step A

N-(4-bromo-2-methylphenyl)-N-(2-[1,3-dihydro-2H-isoindol-2-yl(methyl)amino]-2-oxoethyl)glycine Using the compound (6.60 g, 21.8 mmol) of Reference Example 86 and the compound (6.00 g, 32.7 mmol) of Reference Example 17, and according to the method of Example 4, step A, the title compound (9.00 g, yield 95%) was obtained as a bistered oil.

¹H-NMR (300 MHz, CDCl₃); δ (ppm) 2.22 (s, 3H), 2.87 (s, 3H), 3.94 (s, 2H), 4.10 (d, J=11.7, 2H), 4.24 (d, J=11.7, 2H), 4.25 (s, 2H), 7.01 (d, J=8.7, 1H), 7.19-7.32 (m, 6H), 12.47 (brs, 1H).

Step B

N²-(4-bromo-2-methylphenyl)-N²-{2-[1,3-dihydro-2H-isoindol-2-yl(methyl)amino]-2-oxoethyl}-N¹-{2-[(tert-butoxycarbonyl)(isopropyl)amino]ethyl}glycinamide Using the compound (4.50 g, 10.41 mmol) obtained in step A and the compound (3.16 g, 15.62 mmol) of Reference Example 3, and according to the method of Example 1, step B, the title compound (5.88 g, yield 92%) was obtained as a bistered amorphous solid.

¹H-NMR (300 MHz, CDCl₃); δ (ppm) 1.02 (d, J=6.6, 6H), 1.38 (s, 9H), 2.25 (s, 3H), 2.87 (s, 3H), 2.89-3.00 (m, 2H), 3.05-3.20 (m, 2H), 3.77 (s, 2H), 3.95-4.19 (m, 1H), 4.09 (d, J=11.7, 2H), 4.23 (s, 2H), 4.25 (d, J=11.4, 2H), 7.04 (d, J=8.7, 1H), 7.16-7.29 (m, 6H), 8.01-8.08 (m, 1H).

Step C

N²-(4-bromo-2-methylphenyl)-N²-{2-[1,3-dihydro-2H-isoindol-2-yl(methyl)amino]-2-oxoethyl}-N¹-[2-(isopropylamino)ethyl]glycinamide dihydrochloride Using the compound (500 mg, 0.81 mmol) obtained in step B and according to the method of Example 1, step C, the title compound (380 mg, yield 80%) was obtained as a pale-gray amorphous solid.

¹H-NMR (300 MHz, DMSO-$d_6$); δ (ppm) 1.20 (d, J=6.6, 6H), 2.26 (s, 3H), 2.80-2.95 (m, 2H), 2.87 (s, 3H), 3.18-3.28 (m, 1H), 3.34-3.42 (m, 2H), 3.85 (s, 2H), 4.10 (d, J=11.7, 2H), 4.25 (d, J=12.0, 2H), 4.27 (s, 2H). 7.04 (d, J=8.4, 1H), 7.21-7.29 (m, 6H), 8.32 (t, J=5.7, 1H), 8.90 (brs, 2H).

Example 112

N²-(4-bromo-2-methylphenyl)-N²-{2-[1,3-dihydro-2H-isoindol-2-yl(methyl)amino]-2-oxoethyl}-N¹-[2-(ethylamino)ethyl]glycinamide dihydrochloride

Step A

N²-(4-bromo-2-methylphenyl)-N²-{2-[1,3-dihydro-2H-isoindol-2-yl(methyl)amino]-2-oxoethyl}-N¹-{2-[(tert-butoxycarbonyl)(ethyl)amino]ethyl}glycinamide Using the compound (4.50 g, 10.41 mmol) of Example 111, step A, and the compound (2.94 g, 15.62 mmol) of Reference Example 2, and according to the method of Example 1, step B, the title compound (5.43 g, yield 87%) was obtained as a bistered amorphous solid.

¹H-NMR (300 MHz, DMSO-$d_6$); δ (ppm) 0.95 (t, J=7.0, 3H), 1.36 (s, 9H), 2.24 (s, 3H), 2.87 (s, 3H), 3.01-3.19 (m, 6H), 3.76 (s, 2H), 4.0-4.3 (broad, 1H), 4.09 (d, J=11.6, 2H), 4.22 (s, 2H), 4.24 (d, J=11.6, 2H), 7.03 (d, J=8.5, 1H), 7.19-7.31 (m, 6H), 8.00-8.05 (m, 1H).

Step B

N²-(4-bromo-2-methylphenyl)-N²-{2-[1,3-dihydro-2H-isoindol-2-yl(methyl)amino]-2-oxoethyl}-N¹-[2-(ethylamino)ethyl]glycinamide dihydrochloride Using the compound (500 mg, 0.83 mmol) obtained in step A and according to the method of Example 1, step C, the title compound (422 mg, yield 88%) was obtained as a pale-gray amorphous solid.

¹H-NMR (300 MHz, DMSO-d₆); δ (ppm) 1.14-1.20 (m, 3H), 2.25 (s, 3H), 2.83-2.92 (m, 4H), 2.87 (s, 3H), 3.33-3.40 (m, 2H), 3.85 (s, 2H), 4.10 (d, J=11.6, 2H), 4.25 (d, J=11.6, 2H), 4.27 (s, 2H), 7.04 (d, J=8.6, 1H), 7.19-7.30 (m, 6H), 8.29-8.34 (m, 1H), 8.92 (brs, 2H).

Example 113

$N^2$-(5-bromo-2-methylphenyl)-$N^2$-{2-[1,3-dihydro-2H-isoindol-2-yl(methyl)amino]-2-oxoethyl}-$N^1$-[2-(isopropylamino)ethyl]glycinamide dihydrochloride

Step A

N-(5-bromo-2-methylphenyl)-N-{2-[1,3-dihydro-2H-isoindol-2-yl(methyl)amino]-2-oxoethyl}glycine Using the compound (2.34 g, 7.75 mmol) of Reference Example 89, and the compound (2.00 g, 10.9 mmol) of Reference Example 17, and according to the method of Example 1, step A, the title compound (2.91 g, yield 87%) was obtained as a colorless amorphous solid.

¹H-NMR (300 MHz, CDCl₃); δ (ppm) 2.25 (s, 3H), 3.06 (s, 3H), 3.70 (s, 2H), 4.18 (d, J=11.7, 2H), 4.27 (s, 2H), 4.29 (d, J=11.7, 2H), 7.04 (d, J=8.1, 1H), 7.15-7.30 (m, 5H), 7.35 (d, J=2.1, 1H), 13.49 (brs, 1H).

Step B $N^2$-(5-bromo-2-methylphenyl)-$N^2$-{2-[1,3-dihydro-2H-isoindol-2-yl(methyl)amino]-2-oxoethyl}-$N^1$-{2-[(tert-butoxycarbonyl)(isopropyl)amino]ethyl}glycinamide Using the compound (2.91 g, 6.73 mmol) obtained in step A and the compound (1.97 g, 9.74 mmol) of Reference Example 3, and according to the method of Example 1, step B, the title compound (3.60 g, yield 87%) was obtained as a pale-yellow amorphous solid ¹H-NMR (300 MHz, CDCl₃); δ (ppm) 1.11 (d, J=6.6, 6H), 1.45 (brs, 9H), 2.28 (s, 3H), 2.95 (s, 3H), 3.0-3.2 (m, 2H), 3.35-3.43 (m, 2H), 3.78 (s, 2H), 3.9-4.3 (broad, 1H), 4.14 (d, J=11.7, 2H), 4.20 (s, 2H), 4.25 (d, J=11.7, 2H), 7.01 (d, J=8.1, 1H), 7.11 (dd, J=1.2, 8.1, 1H), 7.2-7.3 (m, 4H), 7.37 (d, J=1.2, 1H), 7.9-8.6 (broad, 1H).

Step C $N^2$-(5-bromo-2-methylphenyl)-$N^2$-{2-[1,3-dihydro-2H-isoindol-2-yl(methyl)amino]-2-oxoethyl}-$N^1$-[2-(isopropylamino)ethyl]glycinamide dihydrochloride Using the compound (415 mg, 0.673 mmol) obtained in step B and according to the method of Example 1, step C, the title compound (382 mg, yield 96%) was obtained as a colorless solid.

¹H-NMR (300 MHz, DMSO-d₆); δ (ppm) 1.19 (d, J=6.6, 6H), 2.22 (s, 3H), 2.8-3.0 (m, 2H), 2.89 (s, 3H), 3.1-3.3 (m, 1H), 3.34-3.42 (m, 2H), 3.86 (s, 2H), 4.12 (d, J=11.6, 2H), 4.26 (d, J=11.6, 2H), 4.28 (s, 2H), 7.06 (broad, 2H), 7.2-7.3 (m, 5H), 8.30 (t, J=5.7, 1H), 8.70 (brs, 2H).

Example 114

$N^2$-{2-[1,3-dihydro-2H-isoindol-2-yl(methyl)amino]-2-oxoethyl}-$N^2$-(4-methylbiphenyl-3-yl)-$N^1$-[2-(isopropylamino)ethyl]glycinamide dihydrochloride

Step A $N^2$-{2-[1,3-dihydro-2M-isoindol-2-yl(methyl)amino]-2-oxoethyl}-$N^2$-(4-methylbiphenyl-3-yl)-$N^1$-{2-[(tert-butoxycarbonyl)(isopropyl)amino]ethyl}glycinamide To an ethanol (15 ml)-toluene (15 ml) mixed solvent were added the compound (493 mg, 0.800 mmol) of Example 113, step B, phenylboronic acid (153 mg, 1.26 mmol), tetrakistriphenylphosphinepalladium(0) (124 mg, 0.09 mmol) and sodium carbonate (300 mg, 2.83 mmol), and the mixture was heated under reflux for 23 hr. The reaction mixture was diluted with ethyl acetate, washed with water, diluted aqueous sodium hydroxide solution and saturated brine, and dried over anhydrous magnesium sulfate. The insoluble material was filtered off, and the solution was concentrated under reduced pressure, and the obtained oil was purified by silica gel column chromatography (ethyl acetate-dichloromethane) to give the title compound (337 mg, yield 69%) as a pale-yellow amorphous solid ¹H-NMR (300 MHz, CDCl₃); δ (ppm) 1.09 (d, J=6.9, 6H), 1.45 (brs, 9H), 2.38 (s, 3H), 2.95 (s, 3H), 3.0-3.2 (m, 2H), 3.35-3.43 (m, 2H), 3.88 (s, 2H), 3.9-4.3 (broad, 1H), 4.07 (d, J=11.4, 2H), 4.21 (d, J=11.4, 2H), 4.23 (s, 2H), 7.1-7.7 (m, 12H), 8.0-8.6 (broad, 1H).

Step B $N^2$-{2-[1,3-dihydro-2H-isoindol-2-yl(methyl)amino]-2-oxoethyl}-$N^2$-(4-methylbiphenyl-3-yl)-$N^1$-[2-(isopropylamino)ethyl]glycinamide dihydrochloride Using the compound (337 mg, 0.549 mmol) obtained in step A and according to the method of Example 1, step C, the title compound (275 mg, yield 85%) was obtained as a colorless solid.

¹H-NMR (300 MHz, DMSO-d₆); δ (ppm) 1.16 (d, J=6.4, 6H), 2.31 (s, 3H), 2.8-3.0 (m, 2H), 2.89 (s, 3H), 3.1-3.3 (m, 1H), 3.35-3.40 (m, 2H), 3.95 (s, 2H), 4.09 (d, J=11.7, 2H), 4.25 (d, J=11.7, 2H), 4.32 (s, 2H), 7.19 (broad, 2H), 7.25 (broad, 4H), 7.3-7.5 (m, 4H), 7.55-7.59 (m, 2H), 8.36 (t, J=5.7, 1H), 8.62 (brs, 2H).

Example 115

$N^2$-{2-[1,3-dihydro-2H-isoindol-2-yl(methyl)amino]-2-oxoethyl}$N^2$-(4'-fluoro-4-methylbiphenyl-3-yl)-$N^1$-[2-(isopropylamino)ethyl]glycinamide dihydrochloride

Step A $N^2$-{2-[1,3-dihydro-2H-isoindol-2-yl(methyl)amino]-2-oxoethyl}-$N^2$-(4'-fluoro-4-methylbiphenyl-3-yl)-$N^1$-{2-[(tert-butoxycarbonyl)(isopropyl)amino]ethyl}glycinamide Using the compound (488 mg, 0.791 mmol) of Example 113, step B, and 4-fluorophenylboronic acid (171 mg, 1.22 mmol), and according to the method of Example 114, step A, the title compound (406 mg, yield 81%) was obtained as a pale-yellow amorphous solid $^1$H-NMR (300 MHz, CDCl$_3$); δ (ppm) 1.08 (d, J=6.9, 6H), 1.44 (brs, 9H), 2.37 (s, 3H), 2.95 (s, 3H), 3.0-3.2 (m, 2H), 3.34-3.42 (m, 2H), 3.88 (s, 2H), 3.9-4.3 (broad, 1H), 4.07 (d, J=11.4, 2H), 4.22 (d, J=11.4, 2H), 4.22 (s, 2H), 7.04-7.11 (m, 2H), 7.16-7.27 (m, 3H), 7.4-7.7 (m, 6H), 7.9-8.5 (broad, 1H).

Step B $N^2$-{2-[1,3-dihydro-2H-isoindol-2-yl(methyl) amino]-2-oxoethyl}-$N^2$-(4'-fluoro-4-methylbiphenyl-3-yl)-$N^1$-[2-(isopropylamino)ethyl]glycinamide dihydrochloride Using the compound (394 mg, 0.624 mmol) obtained in step A and according to the method of Example 1, step C, the title compound (314 mg, yield 83%) was obtained as a colorless solid.

$^1$H-NMR (300 MHz, DMSO-d$_6$); δ (ppm) 1.16 (d, J=6.5, 6H), 2.30 (s, 3H), 2.8-3.0 (m, 2H), 2.88 (s, 3H), 3.1-3.3 (m, 1H), 3.3-3.5 (m, 2H), 3.94 (s, 2H), 4.09 (d, J=11.7, 2H), 4.25 (d, J=11.7, 2H), 4.31 (s, 2H), 7.1-7.4 (m, 9H), 7.57-7.63 (m, 2H), 8.34 (t, J=5.7, 1H), 8.62 (brs, 2H).

Example 116

$N^2$-{2-[1,3-dihydro-2H-isoindol-2-yl(methyl) amino]-2-oxoethyl}-$N^2$-(2'-fluoro-4-methylbiphenyl-3-yl)-$N^1$-[2-(isopropylamino)ethyl]glycinamide dihydrochloride Using the compound (500 mg, 0.81 mmol) of Example 113, step B, and 2-fluorophenylboronic acid (181 mg, 1.30 mmol), and according to the methods of Example 114, step A, and Example 1, step C, the title compound (419 mg, yield 86%) was obtained as a pale-bistered amorphous solid.

$^1$H-NMR (300 MHz, DMSO-d$_6$); δ (ppm) 1.18 (d, J=6.3, 6H), 2.33 (s, 3H), 2.88 (brs, 5H), 3.15-3.24 (m, 1H), 3.41 (q, J=6.0, 2H), 3.94 (s, 2H), 4.09 (d, J=12.6, 2H), 4.25 (d, J=12.0, 2H), 4.34 (s, 2H), 7.10 (d, J=7.5, 1H), 7.19-7.32 (m, 8H), 7.36-7.50 (m, 2H), 8.34-8.43 (m, 1H), 8.89 (brs, 2H).

Example 117

$N^2$-{2-[1,3-dihydro-2H-isoindol-2-yl(methyl) amino]-2-oxoethyl}-$N^2$-(3'-fluoro-4-methylbiphenyl-3-yl)-$N^1$-[2-(isopropylamino)ethyl]glycinamide dihydrochloride Using the compound (500 mg, 0.81 mmol) of Example 113, step B, and 3-fluorophenylboronic acid (181 mg, 1.30 mmol), and according to the methods of Example 114, step A, and Example 1, step C, the title compound (288 mg, yield 59%) was obtained as a pale-bistered amorphous solid.

$^1$H-NMR (300 MHz, DMSO-d$_6$); δ (ppm) 1.17 (d, J=6.6, 6H), 2.32 (s, 3H), 2.78-2.91 (m, 5H), 3.18-3.24 (m, 1H), 3.37-3.44 (m, 2H), 3.98 (s, 2H), 4.10 (d, J=11.7, 2H), 4.25 (d, J=11.7, 2H), 4.36 (s, 2H), 7.14-7.28 (m, 7H), 7.39-7.60 (m, 4H), 8.33-8.43 (m, 1H), 8.87 (brs, 2H).

Example 118

$N^2$-(4'-cyano-4-methylbiphenyl-3-yl)-$N^2$-{2-[1,3-dihydro-2H-isoindol-2-yl(methyl)amino]-2-oxoethyl}-$N^1$-[2-(isopropylamino)ethyl]glycinamide dihydrochloride Step A $N^2$-(4'-cyano-4-methylbiphenyl-3-yl)-$N^2$-{2-[1,3-dihydro-2H-isoindol-2-yl(methyl)amino]-2-oxoethyl}-$N^1$-{2-[(tert-butoxycarbonyl)(isopropyl)amino]ethyl}glycinamide Using the compound (483 mg, 0.783 mmol) of Example 113, step B, and 4-cyanophenylboronic acid (193 mg, 1.31 mmol), and according to the method of Example 114, step A, the title compound (399 mg, yield 80%) was obtained as a colorless amorphous solid.

$^1$H-NMR (300 MHz, CDCl$_3$); δ (ppm) 1.08 (d, J=6.6, 6H), 1.43 (brs, 9H), 2.39 (s, 3H), 2.96 (s, 3H), 3.0-3.2 (m, 2H), 3.33-3.41 (m, 2H), 3.8-4.2 (broad, 1H), 3.91 (s, 2H), 4.08 (d, J=11.4, 2H), 4.23 (s, 2H), 4.23 (d, J=11.4, 2H), 7.1-7.3 (m, 6H), 7.50 (brs, 1H), 7.62 (d, J=8.4, 2H), 7.68 (d, J=8.4, 2H), 7.9-8.4 (broad, 1H).

Step B $N^2$-(4'-cyano-4-methylbiphenyl-3-yl)-$N^2$-{2-[1,3-dihydro-2H-isoindol-2-yl(methyl)amino]-2-oxoethyl}-$N^1$-[2-(isopropylamino)ethyl]glycinamide dihydrochloride Using the compound (398 mg, 0.623 mmol) obtained in step A and according to the method of Example 1, step C, the title compound (337 mg, yield 88%) was obtained as a colorless solid.

$^1$H-NMR (300 MHz, DMSO-d$_6$); δ (ppm) 1.16 (d, J=6.4, 2H), 2.32 (s, 3H), 2.8-3.0 (m, 2H), 2.88 (s, 3H), 3.1-3.3 (m, 1H), 3.3-3.5 (m, 2H), 3.96 (s, 2H), 4.09 (d, J=11.7, 2H), 4.25 (d, J=11.7, 2H), 4.32 (s, 2H), 7.2-7.3 (m, 6H), 7.47 (s, 1H), 7.79 (d, J=8.3, 2H), 7.91 (d, J=8.3, 2H), 8.33 (t, J=5.7, 1H), 8.62 (brs, 2H).

Example 119

$N^2$-(4'-chloro-4-methylbiphenyl-3-yl)-$N^2$-{2-[1,3-dihydro-2H-isoindol-2-yl(methyl)amino]-2-oxoethyl}-$N^1$-[2-(isopropylamino)ethyl]glycinamide dihydrochloride Step A $N^2$-(4'-chloro-4-methylbiphenyl-3-yl)-$N^2$-{2-[1,3-dihydro-2H-isoindol-2-yl(methyl)amino]-2-oxoethyl}-$N^1$-{2-[(tert-butoxycarbonyl)(isopropyl)amino]ethyl}glycinamide Using the compound (467 mg, 0.76 mmol) of Example 113, step B, and 4-chlorophenylboronic acid (187 mg, 1.19 mmol), and according to the method of Example 114, step A, the title compound (490 mg, yield 100%) was obtained as a bistered oil.

$^1$H-NMR (300 MHz, CDCl$_3$); δ (ppm) 1.08 (d, J=6.9, 6H), 1.44 (s, 9H), 2.37 (s, 3H), 2.95 (s, 3H), 3.11 (brs, 2H), 3.34-3.42 (m, 2H), 3.89 (brs, 2H), 4.04-4.25 (m, 7H), 7.17-7.69 (m, 11H), 7.99-8.64 (broad, 1H).

Step B

N$^2$-(4'-chloro-4-methylbiphenyl-3-yl)-N$^2$-{2-[1,3-dihydro-2H-isoindol-2-yl(methyl)amino]-2-oxoethyl}-N$^1$-[2-(isopropylamino)ethyl]glycinamide dihydrochloride Using the compound (490 mg, 0.76 mmol) obtained in step A and according to the method of Example 1, step C, the title compound (265 mg, yield 56%) was obtained as a pale-yellow amorphous solid $^1$H-NMR (300 MHz, DMSO-d$_6$); δ (ppm) 1.17 (d, J=6.3, 6H), 2.32 (s, 3H), 2.80-2.97 (m, 5H), 3.21 (brs, 1H), 3.35-3.43 (m, 2H), 3.98 (s, 2H), 4.10 (d, J=11.4, 2H), 4.25 (d, J=12.0, 2H), 4.36 (s, 2H), 7.21 (s, 2H), 7.25 (s, 4H), 7.42 (s, 1H), 7.50 (d, J=7.2, 2H), 7.61 (d, J=8.7, 2H), 8.42 (brs, 1H), 8.93 (brs, 2H).

Example 120

N$^2$-{2-[1,3-dihydro-2H-isoindol-2-yl(methyl) amino]-2-oxoethyl}-N$^2$-[2-methyl-5-(3-thienyl)phenyl]-N$^1$-[2-(isopropylamino)ethyl]glycinamide dihydrochloride Using the compound (500 mg, 0.81 mmol) of Example 113, step B, and 3-thienylboronic acid (166 mg, 1.30 mmol), and according to the methods of Example 114, step A, and Example 1, step C, the title compound (196 mg, yield 41%) was obtained as a pale-bistered solid.

$^1$H-NMR (300 MHz, DMSO-d$_6$); δ (ppm) 1.17 (d, J=6.3, 6H), 2.29 (s, 3H), 2.78-2.95 (m, 5H), 3.15-3.24 (m, 1H), 3.26-3.43 (m, 2H), 3.95 (s, 2H), 4.10 (d, J=11.7, 2H), 4.26 (d, J=11.7, 2H), 4.33 (s, 2H), 7.15 (d, J=7.8, 1H), 7.25 (s, 5H), 7.45 (d, J=3.6, 2H), 7.62 (s, 1H), 7.73 (s, 1H), 8.41 (brs, 1H), 8.72 (brs, 2H).

The compounds of Examples 97-120 are shown below.

TABLE 11

| Example | Structural Formula | TMW | LC-MS (found) |
|---|---|---|---|
| 97 | 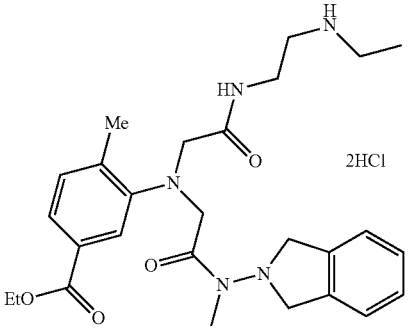 [SMILES: CCNCCNC(=O)CN(CC(=O)N(C)N1Cc2ccccc2C1)c1cc(C(=O)OCC)ccc1C ; "2HCl"] | 568.54 | 496 |
| 98 | 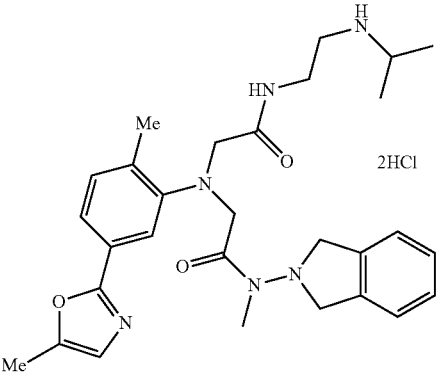 [SMILES: Cc1cnc(-c2ccc(C)c(N(CC(=O)NCCNC(C)C)CC(=O)N(C)N3Cc4ccccc4C3)c2)o1 ; "2HCl"] | 591.57 | 519 |

TABLE 11-continued

| Example | Structural Formula | TMW | LC-MS (found) |
|---|---|---|---|
| 99 | 3HCl | 644.10 | 535 |
| 100 | 2HCl | 607.64 | 535 |
| 101 | 2HCl | 593.61 | 521 |
| 102 | 2HCl | 607.64 | 535 |

TABLE 11-continued
| Example | Structural Formula | TMW | LC-MS (found) |
|---|---|---|---|
| 103 | 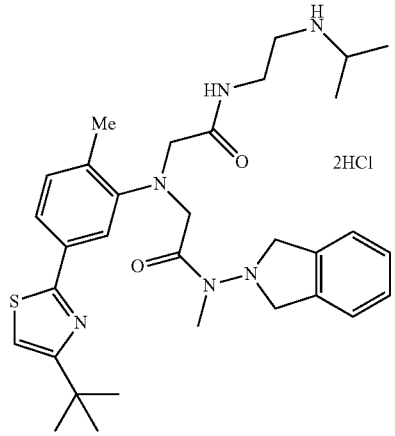 [SMILES: Cc1ccc(-c2nc(C(C)(C)C)cs2)cc1N(CC(=O)NCCNC(C)C)CC(=O)N(C)N1Cc2ccccc2C1 ; "2HCl"] | 649.72 | 577 |
| 104 | 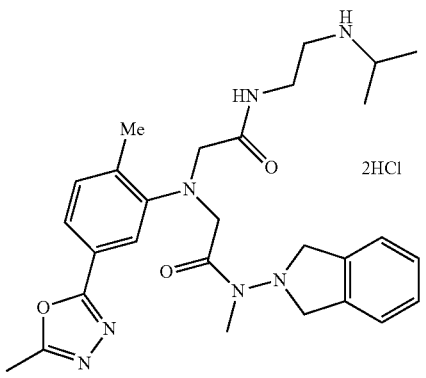 [SMILES: Cc1nnc(-c2ccc(C)c(N(CC(=O)NCCNC(C)C)CC(=O)N(C)N3Cc4ccccc4C3)c2)o1 ; "2HCl"] | 592.56 | 520 |
| 105 | 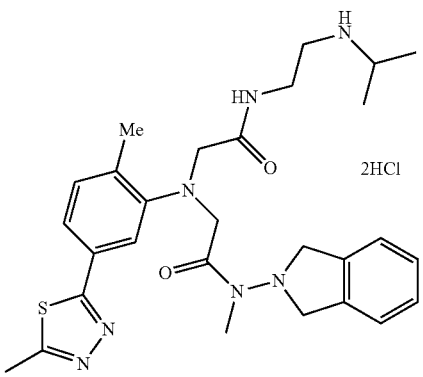 [SMILES: Cc1nnc(-c2ccc(C)c(N(CC(=O)NCCNC(C)C)CC(=O)N(C)N3Cc4ccccc4C3)c2)s1 ; "2HCl"] | 608.63 | 536 |
| 106 | 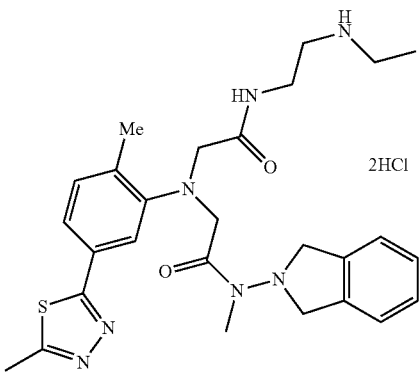 [SMILES: CCNCCNC(=O)CN(CC(=O)N(C)N1Cc2ccccc2C1)c1cc(-c2nnc(C)s2)ccc1C ; "2HCl"] | 594.60 | 522 |

TABLE 11-continued

| Example | Structural Formula | TMW | LC-MS (found) |
| --- | --- | --- | --- |
| 107 | | 594.53 | 522 |
| 108 | | 524.53 | 452 |
| 109 | | 601.16 | 530 |
| 110 | | 549.54 | 477 |

TABLE 11-continued
| Example | Structural Formula | TMW | LC-MS (found) |
|---|---|---|---|
| 111 | 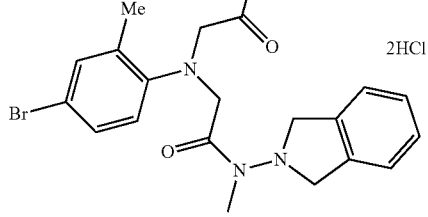 2HCl | 589.40 | 516 |
| 112 | 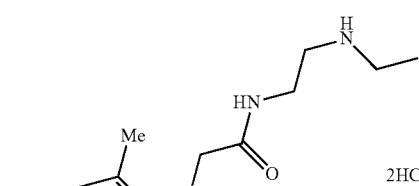 2HCl | 575.37 | 502 |
| 113 | 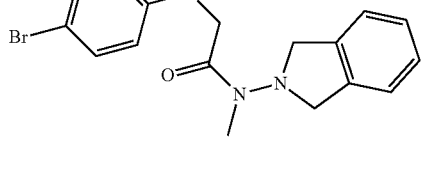 2HCl | 589.40 | 516 |
| 114 | 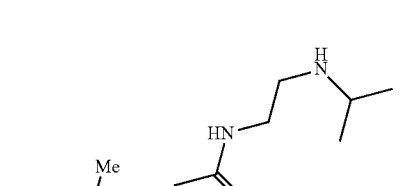 2HCl | 586.60 | 514 |

TABLE 11-continued
| Example | Structural Formula | TMW | LC-MS (found) |
|---|---|---|---|
| 115 | 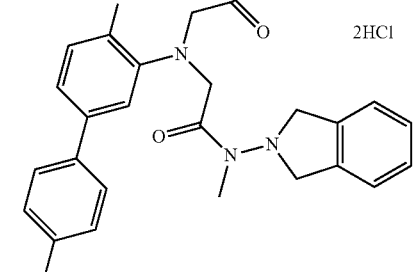 2HCl | 604.59 | 532 |
| 116 | 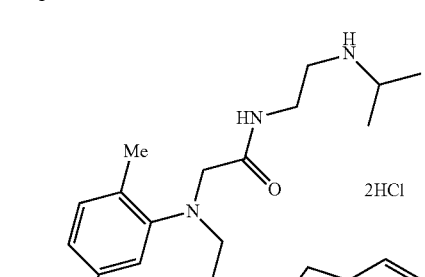 2HCl | 604.59 | 532 |
| 117 | 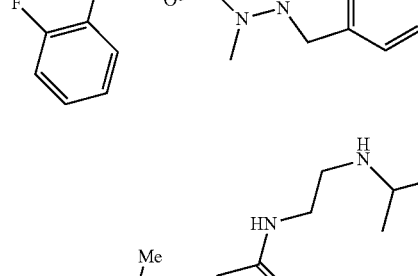 2HCl | 604.59 | 532 |
| 118 | 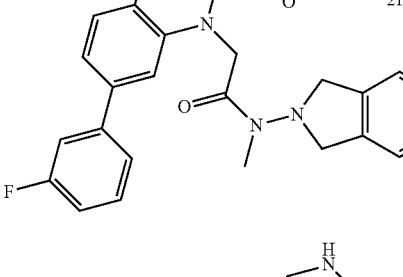 2HCl | 611.60 | 539 |

TABLE 11-continued

| Example | Structural Formula | TMW | LC-MS (found) |
|---|---|---|---|
| 119 | (structure: biphenyl with 4-Cl, 2-Me, N-substituted with glycinamide linker to isopropylaminoethyl and N-methyl-isoindoline) · 2HCl | 621.04 | 548 |
| 120 | (structure: 2-methyl-5-(3-thienyl)phenyl with glycinamide linker to isopropylaminoethyl and N-methyl-isoindoline) · 2HCl | 592.62 | 520 |

Example 121

N²-{2-[1,3-dihydro-2H-isoindol-2-yl(methyl)amino]-2-oxoethyl}-N²-[2-methyl-5-(2-thienyl)phenyl]-N¹-[2-(isopropylamino)ethyl]glycinamide dihydrochloride To toluene (15 ml) were added the compound (350 mg, 0.57 mmol) of Example 113, step B, 2-(tri-n-butylstanyl)thiophene (319 mg, 0.86 mmol) and bis(triphenylphosphine)palladium(II)dichloride (40 mg, 0.06 mmol), and the mixture was heated under reflux for 11 hr. After cooling to room temperature, the reaction mixture was diluted with water, and extracted with ethyl acetate. The organic layer was washed with saturated brine, and dried over anhydrous magnesium sulfate. The insoluble material was filtered off, and the obtained solution was concentrated under reduced pressure. The obtained oil was purified by silica gel column chromatography (methanol-chloroform) to give a bistered oil. Using this, the method of Example 1, step C, was performed to give the title compound (217 mg, yield 65%) as a pale-bistered solid.

$^1$H-NMR (300 MHz, DMSO-$d_6$); δ (ppm) 1.16 (d, J=6.4, 6H), 2.28 (s, 3H), 2.89-2.91 (m, 5H), 3.19-3.24 (m, 1H), 3.38-3.45 (m, 2H), 3.94 (s, 2H), 4.13 (d, J=11.6, 2H), 4.27 (d, J=11.6, 2H), 4.36 (s, 2H), 7.05-7.29 (m, 7H), 7.35-7.39 (m, 2H), 7.49 (d, J=5.1, 1H), 8.43 (brs, 1H), 8.95 (brs, 2H).

Example 122

N²-{2-[1,3-dihydro-2H-isoindol-2-yl(methyl)amino]-2-oxoethyl}-N²-[5-(2-furyl)-2-methylphenyl]-N¹-[2-(isopropylamino)ethyl]glycinamide dihydrochloride Using the compound (350 mg, 0.57 mmol) of Example 113, step B, and 2-(tri-n-butylstanyl)furan (305 mg, 0.86 mmol), and according to the method of Example 121, the title compound (193 mg, yield 58%) was obtained as a pale-bistered solid.

$^1$H-NMR (300 MHz, DMSO-$d_6$); δ (ppm) 1.15-1.21 (m, 6H), 2.29 (s, 3H), 2.79-2.98 (m, 5H), 3.12-3.24 (m, 1H), 3.35-3.47 (m, 2H), 3.93 (s, 2H), 4.12 (d, J=11.7, 2H), 4.26 (d, J=11.7, 2H), 4.35 (s, 2H), 6.57 (dd, J=2.1, 3.3, 1H), 6.81 (d, J=3.3, 1H), 7.05-7.30 (m, 6H), 7.46 (s, 1H), 7.71 (d, J=1.2, 1H), 8.41 (t, J=5.4, 1H), 8.92 (brs, 2H).

Example 123

N²-{2-[1,3-dihydro-2H-isoindol-2-yl(methyl)amino]-2-oxoethyl}-N²-[2-methyl-5-(1H-pyrazol-4-yl)phenyl]-N¹-[2-(isopropylamino)ethyl]glycinamide trihydrochloride Using the compound (500 mg, 0.81 mmol) of Example 113, step B, and tert-butyl 4-(4,4,5,5-tetramethyl-1,3,2-dioxaborolan-2-yl)-1H-pyrazole-1-carboxylate (381 mg, 1.30 mmol), and according to the methods of Example 114, step A, and Example 1, step C, the title compound (138 mg, yield 28%) was obtained as a pale-yellow solid.

$^1$H-NMR (300 MHz, DMSO-$d_6$); δ (ppm) 1.15-1.20 (m, 6H), 2.31 (s, 3H), 2.79-2.96 (m, 5H), 3.16-3.23 (m, 1H), 3.38-3.48 (m, 2H), 4.02 (s, 2H), 4.12 (d, J=11.7, 2H), 4.25 (d, J=11.7, 2H), 4.44 (s, 2H), 6.08 (brs, 2H), 7.13 (d, J=7.8, 1H), 7.19-7.32 (m, 5H), 7.49 (s, 1H), 8.12 (s, 2H), 8.55 (t, J=5.6, 1H), 8.97 (brs, 2H).

Example 124

$N^2$-{2-[1,3-dihydro-2H-isoindol-2-yl(methyl) amino]-2-oxoethyl}-$N^2$-[2-methyl-5-(1-methyl-1H-pyrazol-4-yl)phenyl]-$N^1$-[2-(isopropylamino)ethyl] glycinamide trihydrochloride Step A $N^2$-{2-[1,3-dihydro-2H-isoindol-2-yl(methyl) amino]-2-oxoethyl}-$N^2$-[2-methyl-5-(1-methyl-1H-pyrazol-4-yl)phenyl]-$N^1$-{2-[(tert-butoxycarbonyl) (isopropyl)amino]ethyl}glycinamide Using the compound (500 mg, 0.81 mmol) of Example 113, step B, and 1-methyl-4-(4,4,5,5-tetramethyl-1,3,2-dioxaborolan-2-yl)-1H-pyrazole (270 mg, 1.30 mmol), and according to the method of Example 114, step A, the title compound (276 mg, yield 55%) was obtained as a pale-yellow amorphous solid $^1$H-NMR (300 MHz, DMSO-$d_6$); δ (ppm) 1.01 (d, J=6.2, 6H), 1.37 (s, 9H), 2.24 (s, 3H), 2.82-3.01 (m, 5H), 3.13-3.22 (m, 2H), 3.81 (s, 2H), 3.84 (s, 3H), 3.99-4.11 (m, 3H), 4.22-4.27 (m, 4H), 7.08 (s, 2H), 7.24-7.30 (m, 5H), 7.71 (s, 1H), 7.98 (s, 1H), 8.19 (s, 1H).

Step B $N^2$-{2-[1,3-dihydro-2H-isoindol-2-yl(methyl) amino]-2-oxoethyl}-$N^2$-[2-methyl-5-(1-methyl-1H-pyrazol-4-yl)phenyl]-$N^1$-[2-(isopropylamino)ethyl] glycinamide trihydrochloride Using the compound (276 mg, 0.45 mmol) obtained in step A and according to the method of Example 1, step C, the title compound (283 mg, yield 100%) was obtained as a pale-yellow solid.

$^1$H-NMR (300 MHz, DMSO-$d_6$); δ (ppm) 1.18 (d, J=6.1, 6H), 2.30 (s, 3H), 2.81-2.89 (m, 5H), 3.16-3.24 (m, 1H), 3.39-3.46 (m, 2H), 3.85 (s, 3H), 4.02 (s, 2H), 4.12 (d, J=11.7, 2H), 4.25 (d, J=11.7, 2H), 4.42 (s, 2H), 5.21-5.84 (broad, 1H), 7.09-7.17 (m, 2H), 7.26 (s, 4H), 7.42 (s, 1H), 7.78 (s, 1H), 8.06 (s, 1H), 8.54 (brs, 1H), 8.98 (brs, 2H).

Example 125

$N^2$-{2-[1,3-dihydro-2H-isoindol-2-yl(methyl) amino]-2-oxoethyl}-$N^2$-(2-methyl-5-pyridin-4-ylphenyl)-$N^1$-[2-(isopropylamino)ethyl]glycinamide trihydrochloride Using the compound (1.12 g, 1.81 mmol) of Example 113, step B, and 4-(tri-n-butylstanyl)pyridine (1.00 g, 2.72 mmol), and according to the method of Example 121, the title compound (22.2 mg, yield 2%) was obtained as a pale-yellow solid.

$^1$H-NMR (300 MHz, DMSO-$d_6$); δ (ppm) 1.19 (d, J=6.9, 6H), 2.39 (s, 3H), 2.81-2.89 (m, 5H), 3.17-3.31 (m, 1H), 3.32-3.50 (m, 2H), 3.60-4.39 (m, 8H), 7.01-7.75 (m, 7H), 8.32-8.39 (m, 3H), 8.81-9.04 (m, 5H).

Example 126

$N^2$-{2-[1,3-dihydro-2H-isoindol-2-yl(methyl) amino]-2-oxoethyl}-$N^2$-(2-methyl-5-pyridin-2-ylphenyl)-$N^1$-[2-(isopropylamino)ethyl]glycinamide trihydrochloride Step A $N^2$-{2-[1,3-dihydro-2H-isoindol-2-yl(methyl) amino]-2-oxoethyl}-$N^2$-(2-methyl-5-pyridin-2-ylphenyl)-$N^1$-{2-[(tert-butoxycarbonyl)(isopropyl) amino]ethyl}glycinamide To toluene (15 ml) were added the compound (350 mg, 0.57 mmol) of Example 113, step B, 2-(tri-n-butylstanyl) pyridine (315 mg, 0.86 mmol), and bis(triphenylphosphine) palladium(II)dichloride (40 mg, 0.06 mmol), and the mixture was heated under reflux for 11 hr. After cooling to room temperature, the reaction mixture was diluted with water and extracted with ethyl acetate. The organic layer was washed with saturated brine, and dried over anhydrous magnesium sulfate. The insoluble material was filtered off, and the solution was concentrated under reduced pressure. The obtained oil was purified by silica gel column chromatography (methanol-chloroform) to give the title compound (298 mg, yield 85%) as a pale-yellow amorphous solid $^1$H-NMR (300 MHz, DMSO-$d_6$); δ (ppm) 0.97-1.01 (m, 6H), 1.36 (s, 9H), 2.31 (s, 3H), 2.81-3.12 (m, 5H), 3.15 (brs, 2H), 3.85 (s, 2H), 3.87-4.06 (m, 1H), 4.13 (d, J=11.9, 2H), 4.25 (d, J=11.9, 2H), 4.32 (s, 2H), 7.15-7.33 (m, 6H), 7.52-7.60 (m, 1H), 7.80-7.89 (m, 3H), 8.22 (brs, 1H), 8.62 (brs, 1H).

Step B $N^2$-{2-[1,3-dihydro-2H-isoindol-2-yl(methyl) amino]-2-oxoethyl}-$N^2$-(2-methyl-5-pyridin-2-ylphenyl)-$N^1$-[2-(isopropylamino)ethyl]glycinamide trihydrochloride Using the compound (298 mg, 0.48 mmol) obtained in step A and according to the method of Example 1, step C, the title compound (207 mg, yield 69%) was obtained as a pale-yellow solid.

$^1$H-NMR (300 MHz, DMSO-$d_6$); δ (ppm) 1.19 (d, J=6.6, 6H), 2.38 (s, 3H), 2.76-2.97 (m, 5H), 3.18-3.29 (m, 1H), 3.38-3.45 (m, 2H), 4.02 (s, 2H), 4.15 (d, J=11.7, 2H), 4.25 (d, J=11.7, 2H), 4.39 (s, 2H), 7.22-7.29 (s, 4H), 7.35 (d, J=8.4, 1H), 7.54-7.62 (m, 2H), 7.78-7.86 (m, 2H), 8.19-8.27 (m, 1H), 8.35-8.42 (m, 2H), 8.78-8.82 (m, 1H), 8.92 (brs, 2H).

Example 127

$N^2$-{2-[1,3-dihydro-2H-isoindol-2-yl(methyl) amino]-2-oxoethyl}-$N^2$-(2-methyl-5-pyridin-3-ylphenyl)-$N^1$-[2-(isopropylamino)ethyl]glycinamide trihydrochloride Step A N-{2-[1,3-dihydro-2H-isoindol-2-yl(methyl)amino]-2-oxoethyl}-N-(2-methyl-5-pyridin-3-ylphenyl)glycine Using the compound (740 mg, 2.46 mmol) of Reference Example 93 and the compound (692 mg, 3.75 mmol) of Reference Example 17, and according to the method of Example 1, step A, the title compound (968 mg, yield 91%) was obtained as a pale-yellow amorphous solid $^1$H-NMR (300 MHz, CDCl$_3$); δ (ppm) 2.36 (s, 3H), 3.06 (s, 3H), 3.97 (s, 2H), 4.17 (d, J=11.7, 2H), 4.29 (d, J=11.7, 2H), 4.33 (s, 2H), 7.19-7.38 (m, 7H), 7.44 (s, 1H), 7.81-7.85 (m, 1H), 8.56-8.58 (m, 1H), 8.78 (d, J=2.0, 1H).

Step B

N$^2$-{2-[1,3-dihydro-2H-isoindol-2-yl(methyl)amino]-2-oxoethyl}-N$^2$-(2-methyl-5-pyridin-3-ylphenyl)-N$^1$-{2-[(tert-butoxycarbonyl)(isopropyl)amino]ethyl}glycinamide Using the compound (963 mg, 2.24 mmol) obtained in step A and the compound (696 mg, 3.44 mmol) of Reference Example 3, and according to the method of Example 1, step B, the title compound (1.23 g, yield 89%) was obtained as a colorless amorphous solid.

$^1$H-NMR (300 MHz, CDCl$_3$); δ (ppm) 1.09 (d, J=6.6, 6H), 1.44 (brs, 9H), 2.39 (s, 3H), 2.96 (s, 3H), 3.0-3.2 (m, 2H), 3.34-3.42 (m, 2H), 3.8-4.3 (broad, 1H), 3.90 (s, 2H), 4.09 (d, J=11.7, 2H), 4.23 (d, J=11.7, 2H), 4.24 (s, 2H), 7.17-7.35 (m, 7H), 7.47 (d, J=1.2, 1H), 7.8-7.9 (m, 1H), 7.9-8.5 (broad, 1H), 8.56 (dd, J=1.2, 4.5, 1H), 8.79 (d, J=2.1, 1H).

Step C

N$^2$-{2-[1,3-dihydro-2H-isoindol-2-yl(methyl)amino]-2-oxoethyl}-N$^2$-(2-methyl-5-pyridin-3-ylphenyl)-N$^1$-[2-(isopropylamino)ethyl]glycinamide trihydrochloride Using the compound (1.21 g, 1.97 mmol) obtained in step B and according to the method of Example 1, step C, the title compound (1.32 g, yield>100%) was obtained as a pale-yellow solid.

$^1$H-NMR (300 MHz, DMSO-d$_6$); δ (ppm) 1.19 (d, J=6.5, 6H), 2.36 (s, 3H), 2.8-3.0 (m, 2H), 2.88 (s, 3H), 3.1-3.3 (m, 1H), 3.3-3.5 (m, 2H), 4.00 (s, 2H), 4.11 (d, J=11.7, 2H), 4.25 (d, J=11.7, 2H), 4.35 (s, 2H), 7.25 (broad, 4H), 7.31 (d, J=8.0, 1H), 7.40 (d, J=8.0, 1H), 7.60 (s, 1H), 8.0-8.1 (m, 1H), 8.38 (t, J=5.4, 1H), 8.7-8.8 (m, 1H), 8.83 (d, J=5.4, 1H), 8.92 (brs, 2H), 9.16 (s, 1H).

Example 128

N$^2$-{2-[1,3-dihydro-2H-isoindol-2-yl(methyl)amino]-2-oxoethyl}-N$^2$-(2-methyl-5-pyrimidin-2-ylphenyl)-N$^1$-[2-(isopropylamino)ethyl]glycinamide dihydrochloride Step A N-{2-[1,3-dihydro-2H-isoindol-2-yl(methyl)amino]-2-oxoethyl}-N-(2-methyl-5-pyrimidin-2-ylphenyl)glycine Using the compound (857 mg, 2.84 mmol) of Reference Example 90 and the compound (790 mg, 4.28 mmol) of Reference Example 17, and according to the method of Example 1, step A, the title compound (783 mg, yield 64%) was obtained as a gray amorphous solid.

$^1$H-NMR (300 MHz, CDCl$_3$); δ (ppm) 2.40 (s, 3H), 3.06 (s, 3H), 3.98 (s, 2H), 4.17 (d, J=11.7, 2H), 4.27 (d, J=11.7, 2H), 4.35 (s, 2H), 7.14-7.28 (m, 5H), 7.31 (d, J=7.8, 1H), 8.14 (dd, J=1.5, 7.8, 1H), 8.35 (d, J=1.5, 1H), 8.76 (d, J=4.8, 2H), 13.5 (brs, 1H).

Step B

N$^2$-{2-[1,3-dihydro-2H-isoindol-2-yl(methyl)amino]-2-oxoethyl}-N$^2$-(2-methyl-5-pyrimidin-2-ylphenyl)-N$^1$-{2-[(tert-butoxycarbonyl)(isopropyl)amino]ethyl}glycinamide Using the compound (777 mg, 1.80 mmol) obtained in step A and the compound (626 mg, 3.09 mmol) of Reference Example 3, and according to the method of Example 1, step B, the title compound (1.01 g, yield 91%) was obtained as a pale-yellow amorphous solid $^1$H-NMR (300 MHz, CDCl$_3$); δ (ppm) 1.11 (d, J=6.8, 6H), 1.46 (brs, 9H), 2.42 (s, 3H), 2.94 (s, 3H), 3.0-3.3 (m, 2H), 3.38-3.46 (m, 2H), 3.85 (s, 2H), 3.9-4.4 (broad, 1H), 4.15 (d, J=11.7, 2H), 4.22 (d, J=11.7, 2H), 4.31 (s, 2H), 7.13-7.27 (m, 5H), 7.30 (d, J=7.8, 1H), 8.09 (dd, J=1.4, 7.8, 1H), 8.3-8.8 (broad, 1H), 8.40 (d, J=1.4, 1H), 8.74 (d, J=5.2, 2H).

Step C

N$^2$-{2-[1,3-dihydro-2H-isoindol-2-yl(methyl)amino]-2-oxoethyl}-N$^2$-(2-methyl-5-pyrimidin-2-ylphenyl)-N$^1$-[2-(isopropylamino)ethyl]glycinamide dihydrochloride Using the compound (985 mg, 1.60 mmol) obtained in step B and according to the method of Example 1, step C, the title compound (910 mg, yield 97%) was obtained as a yellow solid.

$^1$H-NMR (300 MHz, DMSO-d$_6$); δ (ppm) 1.17 (d, J=6.4, 6H), 2.35 (s, 3H), 2.8-3.0 (m, 2H), 2.88 (s, 3H), 3.1-3.3 (m, 1H), 3.3-3.5 (m, 2H), 3.93 (s, 2H), 4.14 (d, J=11.7, 2H), 4.27 (d, J=11.7, 2H), 4.38 (s, 2H), 7.2-7.3 (m, 5H), 7.39-7.43 (m, 1H), 7.95 (dd, J=1.2, 8.2, 1H), 8.22 (d, J=1.2, 1H), 8.42 (t, J=5.7, 1H), 8.74 (brs, 2H), 8.88 (d, J=4.6, 2H).

Example 129

N$^2$-{2-[1,3-dihydro-2H-isoindol-2-yl(methyl)amino]-2-oxoethyl}-N$^2$-(2-methyl-5-pyrimidin-2-ylphenyl)-N$^1$-[2-(ethylamino)ethyl]glycinamide dihydrochloride Step A N$^2$-{2-[1,3-dihydro-2H-isoindol-2-yl(methyl)amino]-2-oxoethyl}-N$^2$-(2-methyl-5-pyrimidin-2-ylphenyl)-N$^1$-{2-[(tert-butoxycarbonyl)(ethyl)amino]ethyl}glycinamide Using the compound (563 mg, 1.31 mmol) of Example 128, step A, and the compound (346 mg, 1.84 mmol) of Reference Example 2, and according to the method of Example 1, step B, the title compound (615 mg, yield 78%) was obtained as a gray amorphous solid.

$^1$H-NMR (300 MHz, CDCl$_3$); δ (ppm) 1.03 (t, J=6.9, 3H), 1.45 (brs, 9H), 2.41 (s, 3H), 2.95 (s, 3H), 3.0-3.3 (m, 4H), 3.41-3.48 (m, 2H), 3.84 (s, 2H), 4.16 (d, J=11.7, 2H), 4.23 (d, J=11.7, 2H), 4.31 (s, 2H), 7.13-7.31 (m, 6H), 8.08 (d, J=8.7, 1H), 8.3-8.7 (broad, 1H), 8.39 (d, J=1.2, 1H), 8.75 (d, J=5.1, 1H).

Step B

N²-{2-[1,3-dihydro-2H-isoindol-2-yl(methyl)amino]-2-oxoethyl}-N²-(2-methyl-5-pyrimidin-2-ylphenyl)-N¹-[2-(ethylamino)ethyl]glycinamide dihydrochloride Using the compound (612 mg, 1.02 mmol) obtained in step A and according to the method of Example 1, step C, the title compound (579 mg, yield 99%) was obtained as a yellow solid.

¹H-NMR (300 MHz, DMSO-$d_6$); δ (ppm) 1.14 (t, J=7.3, 3H), 2.34 (s, 3H), 2.8-3.0 (m, 4H), 2.88 (s, 3H), 3.34-3.42 (m, 2H), 3.93 (s, 2H), 4.14 (d, J=11.7, 2H), 4.26 (d, J=11.7, 2H), 4.38 (s, 2H), 7.0-7.3 (m, 5H), 7.39-7.43 (m, 1H), 7.94 (d, J=8.0, 1H), 8.23 (s, 1H), 8.41 (t, J=5.7, 1H), 8.76 (brs, 2H), 8.88 (d, J=4.6, 2H).

Example 130

N²-{2-[1,3-dihydro-2H-isoindol-2-yl(methyl)amino]-2-oxoethyl}-N²-(2-methyl-5-pyrimidin-4-ylphenyl)-N¹-[2-(isopropylamino)ethyl]glycinamide dihydrochloride Step A N-{2-[1,3-dihydro-2H-isoindol-2-yl(methyl)amino]-2-oxoethyl}-N-(2-methyl-5-pyrimidin-4-ylphenyl)glycine Using the compound (378 mg, 1.25 mmol) of Reference Example 91 and the compound (394 mg, 2.13 mmol) of Reference Example 17, and according to the method of Example 1, step A, the title compound (388 mg, yield 72%) was obtained as a colorless amorphous solid.

¹H-NMR (300 MHz, CDCl₃); δ (ppm) 2.39 (s, 3H), 3.07 (s, 3H), 3.98 (s, 2H), 4.18 (d, J=11.7, 2H), 4.29 (d, J=11.7, 2H), 4.35 (s, 2H), 7.2-7.3 (m, 4H), 7.33 (d, J=8.1, 1H), 7.66 (dd, J=1.5, 5.4, 1H), 7.75 (dd, J=1.5, 8.1, 1H), 8.03 (d, J=1.5, 1H), 8.74 (d, J=5.4, 1H), 9.21 (d, J=1.5, 1H), 13.6 (brs, 1H).

Step B

N²-{2-[1,3-dihydro-2H-isoindol-2-yl(methyl)amino]-2-oxoethyl}N²-(2-methyl-5-pyrimidin-4-ylphenyl)-N¹-{2-[(tert-butoxycarbonyl)(isopropyl)amino]ethyl}glycinamide Using the compound (370 mg, 0.857 mmol) obtained in step A and the compound (286 mg, 1.41 mmol) of Reference Example 3, and according to the method of Example 1, step B, the title compound (440 mg, yield 83%) was obtained as a colorless amorphous solid.

¹H-NMR (300 MHz, CDCl₃); δ (ppm) 1.10 (d, J=6.8, 6H), 1.45 (brs, 9H), 2.42 (s, 3H), 2.95 (s, 3H), 3.0-3.2 (m, 2H), 3.36-3.44 (m, 2H), 3.88 (s, 2H), 3.9-4.3 (broad, 1H), 4.15 (d, J=11.7, 2H), 4.24 (d, J=11.7, 2H), 4.30 (s, 2H), 7.17-7.28 (m, 4H), 7.31 (d, J=7.8, 1H), 7.66-7.73 (m, 2H), 8.06 (d, J=1.5, 1H), 8.1-8.6 (broad, 1H), 8.72 (d, J=5.3, 1H), 9.20 (d, J=1.5, 1H).

Step C

N²-{2-[1,3-dihydro-2H-isoindol-2-yl(methyl)amino]-2-oxoethyl}-N²-(2-methyl-5-pyrimidin-4-ylphenyl)-N¹-[2-(isopropylamino)ethyl]glycinamide dihydrochloride Using the compound (437 mg, 0.710 mmol) obtained in step B and according to the method of Example 1, step C, the title compound (422 mg, yield 100%) was obtained as an orange solid.

¹H-NMR (300 MHz, DMSO-$d_6$); δ (ppm) 1.17 (d, J=6.6, 6H), 2.36 (s, 3H), 2.8-3.0 (m, 2H), 2.88 (s, 3H), 3.1-3.3 (m, 1H), 3.3-3.5 (m, 2H), 3.96 (s, 2H), 4.14 (d, J=11.7, 2H), 4.27 (d, J=11.7, 2H), 4.38 (s, 2H), 7.2-7.3 (m, 4H), 7.30 (d, J=8.1, 1H), 7.74 (dd, J=1.5, 8.1, 1H), 8.03 (s, 1H), 8.04 (d, J=5.4, 1H), 8.42 (t, J=5.7, 1H), 8.7-9.0 (broad, 2H), 8.84 (d, J=5.4, 1H), 9.24 (s, 1H).

Example 131

N²-{2-[1,3-dihydro-2H-isoindol-2-yl(methyl)amino]-2-oxoethyl}-N²-(2-methyl-5-pyrimidin-5-ylphenyl)-N¹-[2-(isopropylamino)ethyl]glycinamide dihydrochloride Step A N-{2-[1,3-dihydro-2H-isoindol-2-yl(methyl)amino]-2-oxoethyl}-N-(2-methyl-5-pyrimidin-5-ylphenyl)glycine Using the compound (270 mg, 0.896 mmol) of Reference Example 92, and the compound (259 mg, 1.40 mmol) of Reference Example 17, and according to the method of Example 1, step A, the title compound (310 mg, yield 80%) was obtained as a gray solid.

¹H-NMR (300 MHz, DMSO-$d_6$); δ (ppm) 2.30 (s, 3H), 2.88 (s, 3H), 4.06 (s, 2H), 4.13 (d, J=11.7, 2H), 4.26 (d, J=11.7, 2H), 4.33 (s, 2H), 7.22-7.33 (m, 5H), 7.43 (d, J=1.2, 1H), 8.32 (s, 1H), 9.04 (s, 2H), 9.16 (s, 1H), 12.51 (brs, 1H).

Step B

N²-{2-[1,3-dihydro-2H-isoindol-2-yl(methyl)amino]-2-oxoethyl}-N²-(2-methyl-5-pyrimidin-5-ylphenyl)-N¹-{2-[(tert-butoxycarbonyl)(isopropyl)amino]ethyl}glycinamide Using the compound (303 mg, 0.702 mmol) obtained in step A and the compound (244 mg, 1.21 mmol) of Reference Example 3, and according to the method of Example 1, step B, the title compound (313 mg, yield 72%) was obtained as a colorless amorphous solid.

¹H-NMR (300 MHz, CDCl₃); δ (ppm) 1.09 (d, J=6.8, 6H), 1.43 (brs, 9H), 2.41 (s, 3H), 2.96 (s, 3H), 3.0-3.2 (m, 2H), 3.34-3.41 (m, 2H), 3.9-4.3 (broad, 1H), 3.92 (s, 2H), 4.10 (d, J=11.4, 2H), 4.25 (d, J=11.4, 2H), 4.25 (s, 2H), 7.18-7.33 (m, 6H), 7.48 (d, J=1.2, 1H), 7.8-8.6 (broad, 1H), 8.89 (s, 2H), 9.18 (s, 1H).

Step C

N²-{2-[1,3-dihydro-2H-isoindol-2-yl(methyl)amino]-2-oxoethyl}-N²-(2-methyl-5-pyrimidin-5-ylphenyl)-N¹-[2-(isopropylamino)ethyl]glycinamide dihydrochloride Using the compound (311 mg, 0.505 mmol) obtained in step B and according to the method of Example 1, step C, the title compound (278 mg, yield 100%) was obtained as a pale-yellow solid.

$^1$H-NMR (300 MHz, DMSO-d$_6$); δ (ppm) 1.18 (d, J=6.4, 6H), 2.34 (s, 3H), 2.8-3.0 (m, 2H), 2.88 (s, 3H), 3.1-3.3 (m, 1H), 3.3-3.5 (m, 2H), 3.97 (s, 2H), 4.11 (d, J=11.7, 2H), 4.25 (d, J=11.7, 2H), 4.35 (s, 2H), 7.24-7.33 (m, 5H), 7.34 (d, J=8.0, 1H), 7.52 (d, J=1.0, 1H), 8.40 (t, J=5.7, 1H), 8.84 (brs, 2H), 9.07 (s, 2H), 9.17 (s, 1H).

Example 132

N$^2$-{2-[1,3-dihydro-2H-isoindol-2-yl(methyl) amino]-2-oxoethyl}-N$^2$-(2-methyl-5-pyrazin-2-ylphenyl)-N$^1$-[2-(isopropylamino)ethyl]glycinamide dihydrochloride

Step A

N$^2$-{2-[1,3-dihydro-2H-isoindol-2-yl(methyl) amino]-2-oxoethyl}-N$^2$-(2-methyl-5-pyrazin-2-ylphenyl)-N$^1$-{2-[(tert-butoxycarbonyl)(isopropyl) amino]ethyl}glycinamide Using the compound (789 mg, 1.28 mmol) of Example 113, step B, and 2-(tri-n-butylstanyl)pyrazine (715 mg, 1.94 mmol), and according to the method of Example 126, step A, the title compound (162 mg, yield 210) was obtained as a yellow amorphous solid.

$^1$H-NMR (300 MHz, CDCl$_3$); δ (ppm) 1.10 (d, J=6.6, 6H), 1.45 (brs, 9H), 2.42 (s, 3H), 2.95 (s, 3H), 3.0-3.2 (m, 2H), 3.36-3.44 (m, 2H), 3.89 (s, 2H), 3.9-4.3 (broad, 1H), 4.13 (d, J=11.7, 2H), 4.24 (d, J=11.7, 2H), 4.28 (s, 2H), 7.17-7.28 (m, 4H), 7.31 (d, J=8.1, 1H), 7.62 (dd, J=1.2, 8.1, 1H), 7.99 (d, J=1.2, 1H), 8.0-8.7 (broad, 1H), 8.47 (d, J=2.1, 1H), 8.57 (dd, J=1.2, 2.1, 1H), 8.98 (d, J=1.2, 1H).

Step B

N$^2$-{2-[1,3-dihydro-2H-isoindol-2-yl(methyl) amino]-2-oxoethyl}-N$^2$-(2-methyl-5-pyrazin-2-ylphenyl)-N$^1$-[2-(isopropylamino)ethyl]glycinamide dihydrochloride Using the compound (160 mg, 0.260 mmol) obtained in step A and according to the method of Example 1, step C, the title compound (121 mg, yield 79%) was obtained as a bistered solid.

$^1$H-NMR (300 MHz, DMSO-d$_6$); δ (ppm) 1.17 (d, J=6.4, 6H), 2.34 (s, 3H), 2.8-3.0 (m, 2H), 2.88 (s, 3H), 3.1-3.3 (m, 1H), 3.3-3.5 (m, 2H), 3.95 (s, 2H), 4.13 (d, J=11.7, 2H), 4.26 (d, J=11.7, 2H), 4.37 (s, 2H), 7.25-7.30 (m, 5H), 7.67 (d, J=7.8, 1H), 7.92 (s, 1H), 8.41 (broad t, 1H), 8.58 (d, J=2.4, 1H), 8.70 (dd, J=1.4, 2.4, 1H), 8.73 (brs, 2H), 9.16 (s, 1H).

Example 133

N$^2$-{2-[1,3-dihydro-2H-isoindol-2-yl(methyl) amino]-2-oxoethyl}-N$^2$-(4'-fluoro-3-methylbiphenyl-4-yl)-N$^1$-[2-(isopropylamino)ethyl]glycinamide dihydrochloride Using the compound (500 mg, 0.81 mmol) of Example 111, step B, and 4-fluorophenylboronic acid (181 mg, 1.30 mmol), and according to the method of Example 114, step A, Example 1, step C, the title compound (227 mg, yield 46%) was obtained as a pale-bistered amorphous solid.

$^1$H-NMR (300 MHz, DMSO-d$_6$); δ (ppm) 1.19 (d, J=6.5, 6H), 2.35 (s, 3H), 2.84-2.95 (m, 2H), 2.90 (s, 3H), 3.16-3.28 (m, 1H), 3.38-3.45 (m, 2H), 3.93 (s, 2H), 4.13 (d, J=11.5, 2H), 4.27 (d, J=11.7, 2H), 4.36 (s, 2H), 7.16-7.28 (m, 7H), 7.33-7.41 (m, 2H), 7.59-7.66 (m, 2H), 8.40-8.44 (m, 1H), 8.95 (brs, 2H).

Example 134

N$^2$-{2-[1,3-dihydro-2H-isoindol-2-yl(methyl) amino]-2-oxoethyl}-N$^2$-(4'-fluoro-3-methylbiphenyl-4-yl)-N$^1$-[2-(ethylamino)ethyl]glycinamide dihydrochloride Using the compound (500 mg, 0.83 mmol) of Example 112, step A, and 4-fluorophenylboronic acid (181 mg, 1.30 mmol), and according to the methods of Example 114, step A, and Example 1, step C, the title compound (262.5 mg, yield 54%) was obtained as a pale-bistered amorphous solid.

$^1$H-NMR (300 MHz, DMSO-d$_6$); δ (ppm) 1.16 (t, J=7.2, 3H), 2.34 (s, 3H), 2.80-2.99 (m, 4H), 2.90 (s, 3H), 3.36-3.43 (m, 2H), 3.92 (s, 2H), 4.13 (d, J=11.7, 2H), 4.27 (d, J=11.7, 2H), 4.35 (s, 2H), 7.15-7.28 (m, 7H), 7.33-7.41 (m, 2H), 7.60-7.68 (m, 2H), 8.36-8.41 (m, 1H), 8.88 (brs, 2H).

Example 135

N$^2$-{2-[1,3-dihydro-2H-isoindol-2-yl(methyl) amino]-2-oxoethyl}-N$^2$-[2-methyl-4-(1-methyl-1H-pyrazol-4-yl)phenyl]-N$^1$-[2-(isopropylamino)ethyl] glycinamide trihydrochloride Using the compound (1.00 g, 1.62 mmol) of Example 111, step B, and 1-methyl-4-(4,4,5,5-tetramethyl-1,3,2-dioxaborolan-2-yl)-1H-pyrazole (540 mg, 2.59 mmol), and according to the methods of Example 114, step A, and Example 1, step C, the title compound (197 mg, yield 19%) was obtained as a pale-bistered amorphous solid.

$^1$H-NMR (300 MHz, DMSO-d$_6$); δ (ppm) 1.19 (d, J=6.6, 6H), 2.33 (s, 3H), 2.76-2.94 (m, 2H), 2.89 (s, 3H), 3.18-3.29 (m, 1H), 3.37-3.50 (m, 2H), 3.85 (s, 3H), 3.94 (s, 2H), 4.11 (d, J=11.7, 2H), 4.25 (d, J=11.7, 2H), 4.39 (s, 2H), 7.17-7.35 (m, 7H), 7.79 (s, 1H), 8.05 (s, 1H), 8.47-8.52 (m, 1H), 8.99 (brs, 2H).

Example 136

N$^2$-{2-[1,3-dihydro-2H-isoindol-2-yl(methyl) amino]-2-oxoethyl}-N$^2$-[2-methyl-4-(1-methyl-1H-pyrazol-4-yl)phenyl]-N$^1$-[2-(ethylamino)ethyl]glycinamide trihydrochloride Using the compound (1.00 g, 1.66 mmol) of Example 112, step A, and 1-methyl-4-(4,4,5,5-tetramethyl-1,3,2-dioxaborolan-2-yl)-1H-pyrazole (540 mg, 2.59 mmol), and according to the methods of Example 114, step A, and Example 1, step C, the title compound (233 mg, yield 23%) was obtained as a pale-bistered amorphous solid.

$^1$H-NMR (300 MHz, DMSO-d$_6$); δ (ppm) 1.12-1.20 (m, 3H), 2.31 (s, 3H), 2.79-3.00 (m, 4H), 2.89 (s, 3H), 3.34-3.42 (m, 2H), 3.84 (s, 3H), 3.90 (s, 2H), 4.10 (d, J=11.6, 2H), 4.25 (d, J=11.7, 2H), 4.34 (s, 2H), 7.16 (d, J=8.2, 1H), 7.21-7.29 (m, 5H), 7.33 (s, 1H), 7.77 (s, 1H), 8.03 (s, 1H), 8.41-8.46 (m, 1H), 8.89 (brs, 2H).

Example 137

N²-(5-cyano-2-ethylphenyl)-N²-{2-[1,3-dihydro-2H-isoindol-2-yl(methyl)amino]-2-oxoethyl}-N¹-[2-(isopropylamino)ethyl]glycinamide dihydrochloride

Step A

N-(5-cyano-2-ethylphenyl)-N-{2-[1,3-dihydro-2H-isoindol-2-yl(methyl)amino]-2-oxoethyl}glycine Using the compound (1.98 g, 7.55 mmol) of Reference Example 94, and the compound (2.11 g, 11.4 mmol) of Reference Example 17, and according to the method of Example 1, step A, the title compound (2.42 g, yield 82%) was obtained as a pale-purple amorphous solid.

¹H-NMR (300 MHz, CDCl₃); δ (ppm) 1.24 (t, J=7.5, 3H), 2.74 (q, J=7.5, 2H), 3.07 (s, 3H), 3.91 (s, 2H), 4.17 (d, J=11.7, 2H), 4.28 (s, 2H), 4.30 (d, J=11.7, 2H), 7.2-7.3 (m, 4H), 7.33 (d, J=7.8, 1H), 7.41 (dd, J=1.5, 7.8, 1H), 7.52 (d, J=1.5, 1H), 13.4 (brs, 1H).

Step B

N²-(5-cyano-2-ethylphenyl)-N²-{2-[1,3-dihydro-2H-isoindol-2-yl(methyl)amino]-2-oxoethyl}-N¹-{2-[(tert-butoxycarbonyl)(isopropyl)amino]ethyl}glycinamide Using the compound (1.14 g, 2.91 mmol) obtained in step A and the compound (906 mg, 4.48 mmol) of Reference Example 3, and according to the method of Example 1, step B, the title compound (1.41 g, yield 84%) was obtained as a colorless solid.

¹H-NMR (300 MHz, CDCl₃); δ (ppm) 1.12 (d, J=6.8, 6H), 1.26 (t, J=7.5, 3H), 1.44 (brs, 9H), 2.78 (q, J=7.5, 2H), 2.95 (s, 3H), 3.0-3.2 (m, 2H), 3.35-3.43 (m, 2H), 3.81 (s, 2H), 3.9-4.4 (broad, 1H), 4.12 (d, J=11.7, 2H), 4.21 (s, 2H), 4.25 (d, J=11.7, 2H), 7.2-7.4 (m, 6H), 7.57 (s, 1H), 7.8-8.5 (broad, 1H).

Step C

N²-(5-cyano-2-ethylphenyl)-N²-{2-[1,3-dihydro-2H-isoindol-2-yl(methyl)amino]-2-oxoethyl}-N¹-[2-(isopropylamino)ethyl]glycinamide dihydrochloride Using the compound (476 mg, 0.825 mmol) obtained in step B and according to the method of Example 1, step C, the title compound (422 mg, yield 93%) was obtained as a colorless solid.

¹H-NMR (300 MHz, DMSO-d₆); δ (ppm) 1.1-1.3 (m, 9H), 2.73 (q, J=7.5, 2H), 2.8-3.0 (m, 2H), 2.87 (s, 3H), 3.1-3.3 (m, 1H), 3.3-3.5 (m, 2H), 3.88 (s, 2H), 4.09 (d, J=11.7, 2H), 4.25 (d, J=11.7, 2H), 4.28 (s, 2H), 7.26 (broad, 4H), 7.36 (d, J=7.8, 1H), 7.41 (d, J=7.8, 1H), 7.58 (s, 1H), 8.29 (broad t, 1H), 8.72 (brs, 2H).

Example 138

N²-(5-cyano-2-ethylphenyl)-N²-{2-[1,3-dihydro-2H-isoindol-2-yl(methyl)amino]-2-oxoethyl}-N¹-[2-(ethylamino)ethyl]glycinamide dihydrochloride

Step A

N²-(5-cyano-2-ethylphenyl)-N²-{2-[1,3-dihydro-2H-isoindol-2-yl(methyl)amino]-2-oxoethyl}-N¹-{2-[(tert-butoxycarbonyl)(ethyl)amino]ethyl}glycinamide Using the compound (1.20 g, 3.06 mmol) of Example 137, step A, and the compound (954 mg, 5.07 mmol) of Reference Example 2, and according to the method of Example 1, step B, the title compound (1.52 g, yield 88%) was obtained as a colorless amorphous solid.

¹H-NMR (300 MHz, CDCl₃); δ (ppm) 1.06 (t, J=7.2, 3H), 1.26 (t, J=7.5, 3H), 1.42 (brs, 9H), 2.77 (q, J=7.5, 2H), 2.96 (s, 3H), 3.0-3.3 (m, 4H), 3.38-3.45 (m, 2H), 3.79 (s, 2H), 4.13 (d, J=11.7, 2H), 4.21 (s, 2H), 4.25 (d, J=11.7, 2H), 7.19-7.37 (m, 6H), 7.57 (d, J=1.0, 1H), 8.0-8.5 (broad, 1H).

Step B

N²-(5-cyano-2-ethylphenyl)-N²-{2-[1,3-dihydro-2H-isoindol-2-yl(methyl)amino]-2-oxoethyl}-N¹-[2-(ethylamino)ethyl]glycinamide dihydrochloride Using the compound (520 mg, 0.924 mmol) obtained in step A and according to the method of Example 1, step C, the title compound (443 mg, yield 90%) was obtained as a colorless solid.

¹H-NMR (300 MHz, DMSO-d₆); δ (ppm) 1.16 (t, J=6.9, 3H), 1.18 (t, J=7.5, 3H), 2.75 (q, J=7.5, 2H), 2.8-3.0 (m, 4H), 2.87 (s, 3H), 3.33-3.40 (m, 2H), 3.86 (s, 2H), 4.09 (d, J=11.7, 2H), 4.24 (d, J=11.7, 2H), 4.28 (s, 2H), 7.26 (broad, 4H), 7.36 (d, J=7.8, 1H), 7.41 (d, J=7.8, 1H), 7.58 (s, 1H), 8.27 (t, J=5.7, 1H), 8.76 (brs, 2H).

Example 139

N²-{2-[1,3-dihydro-2H-isoindol-2-yl(methyl)amino]-2-oxoethyl}-N²-[2-ethyl-5-(5-methyl-1,2,4-oxadiazol-3-yl)phenyl]-N¹-[2-(isopropylamino)ethyl]glycinamide dihydrochloride

Step A

N²-{2-[1,3-dihydro-2H-isoindol-2-yl(methyl)amino]-2-oxoethyl}-N²-[2-ethyl-5-(5-methyl-1,2,4-oxadiazol-3-yl)phenyl]-N¹-{2-[(tert-butoxycarbonyl)(isopropyl)amino]ethyl}glycinamide Using the compound (922 mg, 1.60 mmol) of Example 137, step B and according to the method of Reference Example 62, step A, the title compound (677 mg, yield 67%) was obtained as a pale-yellow amorphous solid ¹H-NMR (300 MHz, CDCl₃); δ (ppm) 1.12 (d, J=6.9, 6H), 1.27 (t, J=7.5, 3H), 1.47 (brs, 9H), 2.62 (s, 3H), 2.82 (q, J=7.5, 2H), 2.94 (s, 3H), 3.0-3.2 (m, 2H), 3.3-3.5 (m, 2H), 3.79 (s, 2H), 3.9-4.4 (broad, 1H), 4.08 (d, J=11.7, 2H), 4.20 (d, J=11.7, 2H), 4.24 (s, 2H), 7.16-7.28 (m, 4H), 7.33 (d, J=8.1, 1H), 7.78 (dd, J=1.2, 8.1, 1H), 7.98 (d, J=1.2, 1H), 8.2-8.7 (broad, 1H).

Step B

N²-{2-[1,3-dihydro-2H-isoindol-2-yl(methyl)amino]-2-oxoethyl}-N²-[2-ethyl-5-(5-methyl-1,2,4-oxadiazol-3-yl)phenyl]-N¹-[2-(isopropylamino)ethyl]glycinamide dihydrochloride Using the compound (669 mg, 1.06 mmol) obtained in step A and according to the method of Example 1, step C, the title compound (588 mg, yield 91%) was obtained as a colorless solid.

$^1$H-NMR (300 MHz, DMSO-d$_6$); δ (ppm) 1.17-1.23 (m, 9H), 2.65 (s, 3H), 2.73 (q, J=7.5, 2H), 2.8-3.0 (m, 2H), 2.87 (s, 3H), 3.1-3.3 (m, 1H), 3.34-3.42 (m, 2H), 3.89 (s, 2H), 4.07 (d, J=11.7, 2H), 4.24 (d, J=11.7, 2H), 4.32 (s, 2H), 7.25 (broad, 4H), 7.35 (d, J=7.8, 1H), 7.62 (dd, J=1.2, 7.8, 1H), 7.86 (d, J=1.2, 1H), 8.36 (t, J=5.7, 1H), 8.65 (brs, 2H).

Example 140

N²-{2-[1,3-dihydro-2H-isoindol-2-yl(methyl)amino]-2-oxoethyl}-N²-[2-ethyl-5-(5-methyl-1,2,4-oxadiazol-3-yl)phenyl]-N¹-[2-(ethylamino)ethyl]glycinamide dihydrochloride

Step A

N²-{2-[1,3-dihydro-2H-isoindol-2-yl(methyl)amino]-2-oxoethyl}-N²-[2-ethyl-5-(5-methyl-1,2,4-oxadiazol-3-yl)phenyl]-N¹-{2-[(tert-butoxycarbonyl)(ethyl)amino]ethyl}glycinamide Using the compound (994 mg, 1.77 mmol) of Example 138, step A and according to the method of Reference Example 62, step A, the title compound (744 mg, yield 68%) was obtained as a pale-yellow amorphous solid $^1$H-NMR (300 MHz, CDCl$_3$); δ (ppm) 1.06 (t, J=6.9, 3H), 1.27 (t, J=7.5, 3H), 1.45 (brs, 9H), 2.62 (s, 3H), 2.80 (q, J=7.5, 2H), 2.94 (s, 3H), 3.0-3.4 (m, 4H), 3.4-3.5 (m, 2H), 3.78 (s, 2H), 4.09 (d, J=11.4, 2H), 4.20 (d, J=11.4, 2H), 4.24 (s, 2H), 7.16-7.27 (m, 4H), 7.33 (d, J=7.8, 1H), 7.77 (dd, J=1.2, 7.8, 1H), 7.98 (d, J=1.2, 1H), 8.3-8.7 (broad, 1H).

Step B

N²-{2-[1,3-dihydro-2H-isoindol-2-yl(methyl)amino]-2-oxoethyl}-N²-[2-ethyl-5-(5-methyl-1,2,4-oxadiazol-3-yl)phenyl]-N¹-[2-(ethylamino)ethyl]glycinamide dihydrochloride Using the compound (739 mg, 1.19 mmol) obtained in step A and according to the method of Example 1, step C, the title compound (679 mg, yield 96%) was obtained as a colorless solid.

$^1$H-NMR (300 MHz, DMSO-d$_6$); δ (ppm) 1.15 (t, J=7.3, 3H), 1.20 (t, J=7.5, 3H), 2.65 (s, 3H), 2.73 (q, J=7.5, 2H), 2.8-3.0 (m, 4H), 2.87 (s, 3H), 3.3-3.4 (m, 2H), 3.89 (s, 2H), 4.07 (d, J=11.7, 2H), 4.24 (d, J=11.7, 2H), 4.32 (s, 2H), 7.25 (broad, 4H), 7.35 (d, J=8.1, 1H), 7.61 (d, J=8.1, 1H), 7.86 (s, 1H), 8.34 (t, J=5.7, 1H), 8.67 (brs, 2H).

Example 141

N²-(2-benzylphenyl)-N²-{2-[1,3-dihydro-2H-isoindol-2-yl(methyl)amino]-2-oxoethyl}-N¹-(2-pyrrolidin-1-ylethyl)glycinamide

Step A

N-(2-benzylphenyl)-N-{2-[1,3-dihydro-2H-isoindol-2-yl(methyl)amino]-2-oxoethyl}glycine Using the compound (1.00 g, 3.34 mmol) of Reference Example 95, and the compound (1.23 g, 6.66 mmol of Reference Example 17), and according to the method of Example 1, step A, the title compound (1.57 g, yield>100%) was obtained as a colorless amorphous solid.

$^1$H-NMR (300 MHz, CDCl$_3$); δ (ppm) 2.89 (s, 3H), 3.71-3.76 (m, 2H), 3.88 (s, 2H), 3.92 (s, 2H), 3.98-4.02 (m, 2H), 4.07 (s, 2H), 7.08-7.32 (m, 13H).

Step B

N²-(2-benzylphenyl)-N²-{2-[1,3-dihydro-2H-isoindol-2-yl(methyl)amino]-2-oxoethyl}-N¹-(2-pyrrolidin-1-ylethyl)glycinamide Using the compound (0.50 g, 1.16 mmol) obtained in step A and 1-(2-aminoethyl)pyrrolidine (0.21 ml, 1.61 mmol), and according to the method of Example 1, step B, the title compound (0.43 g, yield 70%) was obtained as a colorless amorphous solid.

$^1$H-NMR (300 MHz, CDCl$_3$); δ (ppm) 1.65-1.70 (m, 4H), 2.39-2.48 (m, 6H), 2.87 (s, 3H), 3.30 (q, J=5.7, 2H), 3.66-3.71 (m, 2H), 3.86 (s, 2H), 3.96 (s, 2H), 3.99-4.04 (m, 2H), 4.16 (s, 2H), 7.11-7.36 (m, 13H), 7.88 (brs, 1H).

Example 142

N²-(2-benzylphenyl)-N²-{2-[1,3-dihydro-2H-isoindol-2-yl(methyl)amino]-2-oxoethyl}-N¹-[2-(methylamino)ethyl]glycinamide dihydrochloride

Step A

N²-(2-benzylphenyl)-N²-{2-[1,3-dihydro-2H-isoindol-2-yl(methyl)amino]-2-oxoethyl}-N¹-{2-[(tert-butoxycarbonyl)(methyl)amino]ethyl}glycinamide Using the compound (0.50 g, 1.16 mmol) of Example 141, step A, the compound (0.39 g, 1.85 mmol) of Reference Example 1 and triethylamine (0.26 ml, 1.89 mmol), and according to the method of Example 1, step B, the title compound (0.50 g, yield 73%) was obtained as a colorless amorphous solid.

$^1$H-NMR (300 MHz, CDCl$_3$); δ (ppm) 1.44 (s, 9H), 2.72 (s, 3H), 2.83 (s, 3H), 3.19-3.27 (m, 4H), 3.70-3.82 (m, 2H), 4.01-4.15 (m, 6H), 7.05-7.36 (m, 13H), 7.99-8.14 (broad, 1H).

Step B

N²-(2-benzylphenyl)-N²-{2-[1,3-dihydro-2H-isoindol-2-yl(methyl)amino]-2-oxoethyl}-N¹-[2-(methylamino)ethyl]glycinamide dihydrochloride Using the compound (0.50 g, 0.85 mmol) obtained in step B and according to the method of Example 1, step C, the title compound (0.39 g, yield 82%) was obtained as a colorless solid.

¹H-NMR (300 MHz, DMSO-d₆); δ (ppm) 2.49 (s, 3H), 2.84-2.90 (m, 5H), 3.30-3.37 (m, 2H), 3.74-3.79 (m, 2H), 3.86 (s, 2H), 4.08-4.14 (m, 6H), 6.96-7.32 (m, 13H), 8.24-8.29 (m, 1H), 8.81 (broad, 2H).

Example 143

N²-(2-chlorophenyl)-N²-{2-[1,3-dihydro-2H-isoindol-2-yl(methyl)amino]-2-oxoethyl}-N¹-[2-(isopropylamino)ethyl]glycinamide dihydrochloride

Step A

N-(2-chlorophenyl)-N-{2-[1,3-dihydro-2H-isoindol-2-yl(methyl)amino]-2-oxoethyl}glycine Using the compound (546 mg, 2.24 mmol) of Reference Example 96 and the compound (620 mg, 3.36 mmol) of Reference Example 17, and according to the method of Example 1, step A, the title compound (710 mg, yield 85%) was obtained as a bistered amorphous solid.

¹H-NMR (300 MHz, CDCl₃); δ (ppm) 3.04 (s, 3H), 4.00 (s, 2H), 4.20 (d, J=11.7, 2H), 4.28 (d, J=11.7, 2H), 4.38 (s, 2H), 7.04-7.10 (m, 1H), 7.20-7.29 (m, 5H), 7.33-7.39 (m, 2H).

Step B

N²-(2-chlorophenyl)-N²-{2-[1,3-dihydro-2H-isoindol-2-yl(methyl)amino]-2-oxoethyl}-N¹-[2-(isopropylamino)ethyl]glycinamide dihydrochloride Using the compound (710 mg, 1.90 mmol) obtained in step A and the compound (577 mg, 2.85 mmol) of Reference Example 3, and according to the methods of Example 1, steps B and C, the title compound (278 mg, yield 28%) was obtained as a pale-bistered amorphous solid.

¹H-NMR (300 MHz, DMSO-d₆); δ (ppm) 1.20 (d, J=6.5, 6H), 2.84-3.04 (m, 5H), 3.23-3.36 (m, 1H), 3.41 (q, J=6.0, 2H), 3.96 (s, 2H), 4.14 (d, J=11.7, 2H), 4.28 (d, J=11.7, 2H), 4.34 (s, 2H), 6.79-6.99 (m, 1H), 7.17-7.38 (m, 7H), 8.34 (t, J=5.6, 1H), 8.92 (brs, 2H).

Example 144

N²-(3-chlorophenyl)-N²-{2-[1,3-dihydro-2H-isoindol-2-yl(methyl)amino]-2-oxoethyl}-N¹-(2-pyrrolidin-1-ylethyl)glycinamide

Step A

N-(3-chlorophenyl)-N-{2-[1,3-dihydro-2H-isoindol-2-yl(methyl)amino]-2-oxoethyl}glycine Using the compound (1.00 g, 4.10 mmol) of Reference Example 97 and the compound (834 mg, 4.52 mmol) of Reference Example 17, and according to the method of Example 1, step A, the title compound (896 mg, yield 58%) was obtained as a bistered amorphous solid.

¹H-NMR (300 MHz, CDCl₃); δ (ppm) 3.10 (s, 3H), 4.14 (s, 2H), 4.41 (s, 4H), 4.61 (s, 2H), 6.45 (d, 0=8.3, 1H), 6.50 (s, 1H), 6.81 (d, J=8.3, 1H), 7.18 (t, J=8.1, 1H), 7.30-7.31 (m, 4H).

Step B

N²-(3-chlorophenyl)-N²-{2-[1,3-dihydro-2H-isoindol-2-yl(methyl)amino]-2-oxoethyl}-N¹-(2-pyrrolidin-1-ylethyl)glycinamide Using the compound (143 mg, 0.35 mmol) obtained in step A and 1-(2-aminoethyl)pyrrolidine (0.05 ml, 0.39 mmol), and according to the method of Example 1, step B, the title compound (115 mg, yield 65%) was obtained as a pale-yellow amorphous solid ¹H-NMR (300 MHz, CDCl₃); δ (ppm) 1.68 (m, 4H), 2.44 (m, 4H), 2.52-2.54 (m, 2H), 3.04 (s, 3H), 3.38-3.42 (m, 2H), 3.98 (s, 2H), 4.34 (d, J=12.0, 2H), 4.40 (d, J=12.0, 2H), 4.52 (s, 2H), 6.38-6.42 (m, 1H), 6.48 (m, 1H), 6.74 (d, J=6.3, 1H), 7.12 (t, J=8.1, 1H), 7.29 (broad, 4H), 8.94 (brs, 1H).

The compounds of Examples 121-144 are shown below.

TABLE 12

| Example | Structural Formula | TMW | LC-MS (found) |
|---|---|---|---|
| 121 | | 592.62 | 520 |

TABLE 12-continued

| Example | Structural Formula | TMW | LC-MS (found) |
|---|---|---|---|
| 122 | [structure] 2HCl | 576.56 | 504 |
| 123 | [structure] 3HCl | 613.02 | 504 |
| 124 | [structure] 3HCl | 627.05 | 518 |
| 125 | [structure] 3HCl | 624.04 | 515 |

TABLE 12-continued

| Example | Structural Formula | TMW | LC-MS (found) |
|---|---|---|---|
| 126 | (structure) 3HCl | 624.04 | 515 |
| 127 | (structure) 3HCl | 624.04 | 515 |
| 128 | (structure) 2HCl | 588.57 | 516 |
| 129 | (structure) 2HCl | 574.54 | 502 |

TABLE 12-continued
| Example | Structural Formula | TMW | LC-MS (found) |
|---|---|---|---|
| 130 | 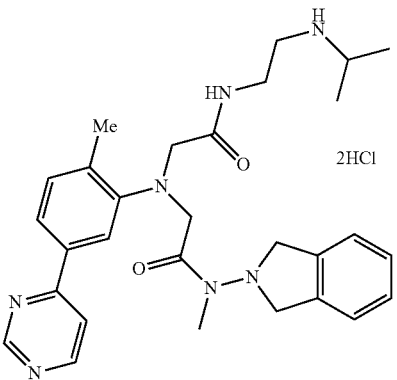 [SMILES: Cc1ccc(-c2ccncn2)cc1N(CC(=O)NCCNC(C)C)CC(=O)N(C)N1Cc2ccccc2C1 ; "2HCl"] 2HCl | 588.57 | 516 |
| 131 | 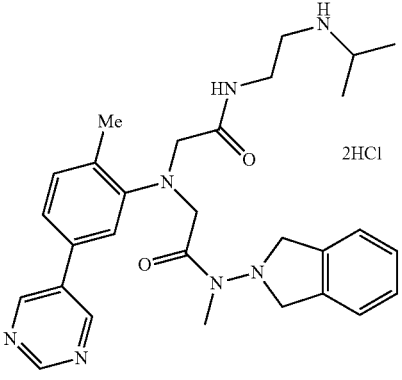 [SMILES: Cc1ccc(-c2cncnc2)cc1N(CC(=O)NCCNC(C)C)CC(=O)N(C)N1Cc2ccccc2C1 ; "2HCl"] 2HCl | 588.57 | 516 |
| 132 | 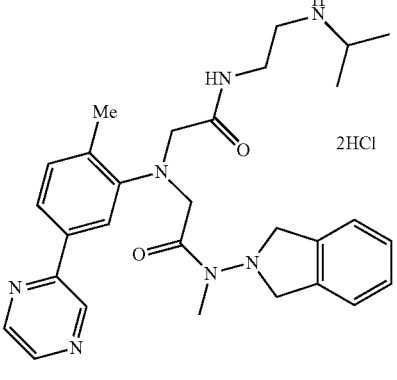 2HCl | 588.57 | 516 |
| 133 | 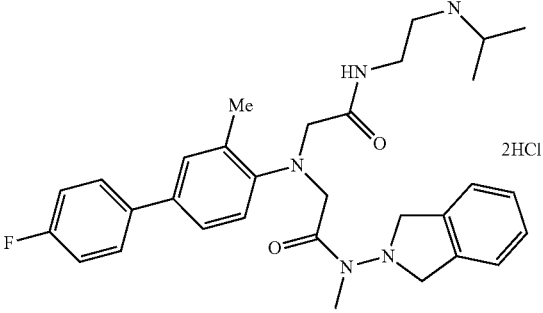 2HCl | 604.59 | 532 |

TABLE 12-continued
| Example | Structural Formula | TMW | LC-MS (found) |
|---|---|---|---|
| 134 | 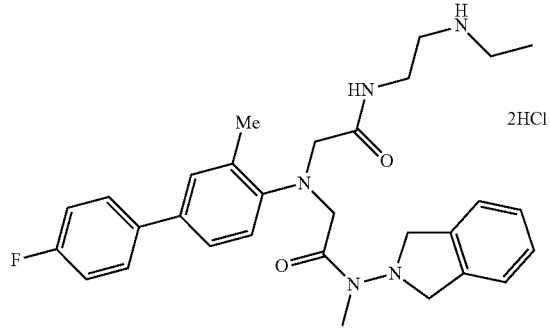 [SMILES: CCNCCNC(=O)CN(CC(=O)N(C)N1Cc2ccccc2C1)c1ccc(-c2ccc(F)cc2)cc1C] 2HCl | 590.56 | 518 |
| 135 | 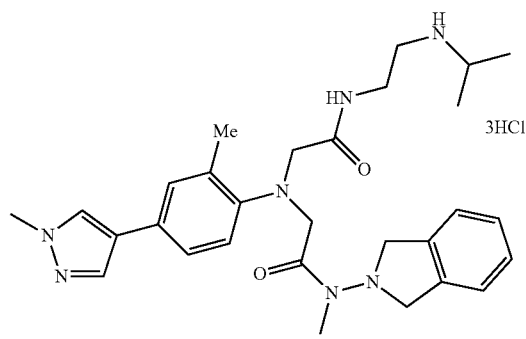 [SMILES: Cc1cc(-c2cnn(C)c2)ccc1N(CC(=O)NCCNC(C)C)CC(=O)N(C)N1Cc2ccccc2C1] 3HCl | 627.05 | 518 |
| 136 | 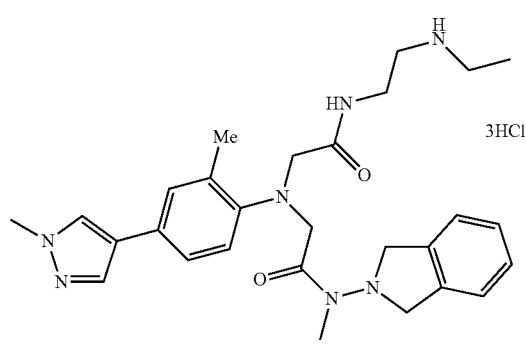 [SMILES: CCNCCNC(=O)CN(CC(=O)N(C)N1Cc2ccccc2C1)c1ccc(-c2cnn(C)c2)cc1C] 3HCl | 613.02 | 504 |
| 137 | 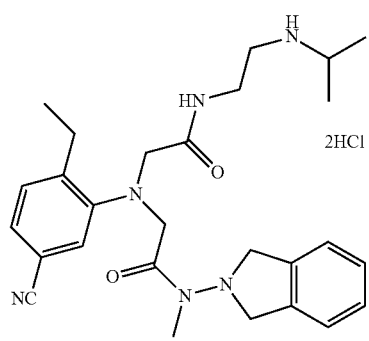 [SMILES: CCc1ccc(C#N)cc1N(CC(=O)NCCNC(C)C)CC(=O)N(C)N1Cc2ccccc2C1] 2HCl | 549.54 | 477 |

TABLE 12-continued
| Example | Structural Formula | TMW | LC-MS (found) |
|---|---|---|---|
| 138 | 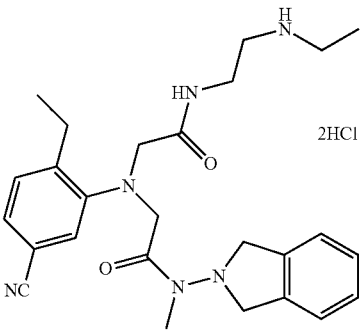 [SMILES: CCNCCNC(=O)CN(CC(=O)N(C)N1Cc2ccccc2C1)c1cc(C#N)ccc1CC] 2HCl | 535.51 | 463 |
| 139 | 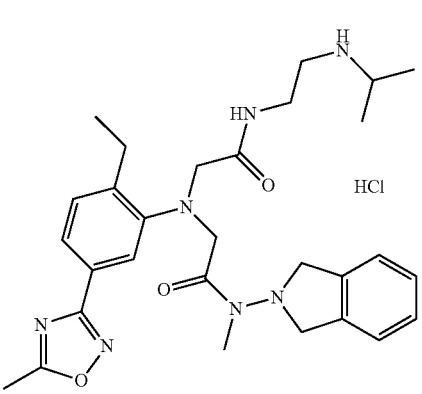 [SMILES: CCc1ccc(-c2noc(C)n2)cc1N(CC(=O)NCCNC(C)C)CC(=O)N(C)N1Cc2ccccc2C1 ; Cl] HCl | 606.59 | 534 |
| 140 | 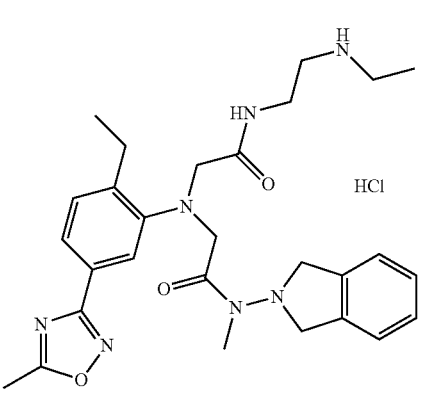 [SMILES: CCNCCNC(=O)CN(CC(=O)N(C)N1Cc2ccccc2C1)c1cc(-c2noc(C)n2)ccc1CC ; Cl] HCl | 592.56 | 520 |
| 141 | 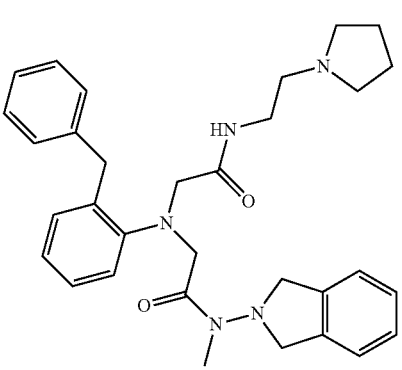 [SMILES: CN(C(=O)CN(CC(=O)NCCN1CCCC1)c1ccccc1Cc1ccccc1)N1Cc2ccccc2C1] | 525.68 | 526 |

TABLE 12-continued

| Example | Structural Formula | TMW | LC-MS (found) |
|---|---|---|---|
| 142 | (structure: benzyl-phenyl-N-CH2-C(=O)-N(CH3)-N(isoindoline); side chain -NHCH2CH2NH-CH3; 2HCl) | 558.54 | 486 |
| 143 | (structure: 2-chlorophenyl-N-CH2-C(=O)-N(CH3)-N(isoindoline); side chain -NHCH2CH2NH-iPr; 2HCl) | 530.92 | 458 |
| 144 | (structure: 3-chlorophenyl-N-CH2-C(=O)-N(CH3)-N(isoindoline); side chain -NHCH2CH2-pyrrolidine) | 470.01 | 470 |

Example 145

N$^2$-(2,5-dichlorophenyl)-N$^2$-{2-[1,3-dihydro-2H-isoindol-2-yl(methyl)amino]-2-oxoethyl}-N$^1$-(2-pyrrolidin-1-ylethyl)glycinamide

Step A

N-(2,5-dichlorophenyl)-N-{2-[1,3-dihydro-2H-isoindol-2-yl(methyl)amino]-2-oxoethyl}glycine Using the compound (470 mg, 1.69 mmol) of Reference Example 98 and the compound (343 mg, 1.86 mmol) of Reference Example 17, and according to the method of Example 1, step A, the title compound (896 mg, yield 87%) was obtained as a bistered amorphous solid.

$^1$H-NMR (300 MHz, CDCl$_3$); δ (ppm) 3.05 (s, 3H), 4.01 (s, 2H), 4.22 (d, J=11.7, 2H), 4.30 (d, J=11.7, 2H), 4.39 (s, 2H), 7.01-7.04 (m, 1H), 7.21-7.25 (m, 3H), 7.26-7.30 (m, 3H).

Step B

N$^2$-(2,5-dichlorophenyl)-N$^2$-{2-[1,3-dihydro-2H-isoindol-2-yl(methyl)amino]-2-oxoethyl}-N$^1$-(2-pyrrolidin-1-ylethyl)glycinamide Using the compound (253 mg, 0.68 mmol) obtained in step A and 1-(2-aminoethyl)pyrrolidine (0.09 ml, 0.74 mmol), and according to the method of Example 1, step B, the title compound (217 mg, yield 68%) was obtained as a colorless solid.

$^1$H-NMR (300 MHz, CDCl$_3$); δ (ppm) 1.68 (m, 4H), 2.42 (m, 4H), 2.52 (m, 2H), 2.94 (s, 3H), 3.36-3.40 (m, 2H), 3.98 (s, 2H), 4.17 (d, J=11.4, 2H), 4.26 (d, J=11.4, 2H), 4.32 (s, 2H), 6.96 (dd, J=2.4, 8.4, 1H), 7.19-7.33 (m, 5H), 7.41 (d, J=2.4, 1H), 7.83 (brs, 1H).

Example 146

N²-(2,5-dichlorophenyl)-N²-{2-[1,3-dihydro-2H-isoindol-2-yl(methyl)amino]-2-oxoethyl}-N¹-[2-(methylamino)ethyl]glycinamide dihydrochloride

Step A

N²-(2,5-dichlorophenyl)-N²-{2-[1,3-dihydro-2H-isoindol-2-yl(methyl)amino]-2-oxoethyl}-N¹-{2-[(tert-butoxycarbonyl)(methyl)amino]ethyl}glycinamide Using the compound (262 mg, 0.64 mmol) of Example 145, step A, the compound (162 mg, 0.77 mmol) of Reference Example 1 and triethylamine (0.11 ml, 0.77 mmol), and according to the method of Example 1, step B, the title compound (225 mg, yield 62%) was obtained as a pale-yellow amorphous solid ¹H-NMR (300 MHz, CDCl$_3$); δ (ppm) 1.38 (s, 9H), 2.76 (s, 3H), 2.93 (s, 3H), 3.25 (m, 2H), 3.35-3.39 (m, 2H), 3.93 (s, 2H), 4.19-4.29 (m, 6H), 6.89-6.96 (m, 1H), 7.22-7.24 (m, 5H), 7.37 (d, J=2.3, 1H).

Step B

N²-(2,5-dichlorophenyl)-N²-{2-[1,3-dihydro-2H-isoindol-2-yl(methyl)amino]-2-oxoethyl}-N¹-[2-(methylamino)ethyl]glycinamide dihydrochloride Using the compound (220 mg, 0.39 mmol) obtained in step A and according to the method of Example 1, step C, the title compound (167 mg, yield 80%) was obtained as a pale-yellow solid.

¹H-NMR (300 MHz, DMSO-d$_6$); δ (ppm) 2.54-2.55 (m, 3H), 2.90-2.97 (m, 5H), 3.38-3.41 (m, 2H), 3.98 (s, 2H), 4.15 (d, J=11.7, 2H), 4.29 (d, J=11.7, 2H), 4.45 (s, 2H), 6.99 (dd, J=2.3, 8.4, 1H), 7.15 (d, J=2.3, 1H), 7.24-7.31 (m, 4H), 7.36 (d, J=8.3, 1H), 8.27 (t, J=5.7, 1H), 8.59 (brs, 2H).

Example 147

N²-(2,5-dichlorophenyl)-N²-{2-[1,3-dihydro-2H-isoindol-2-yl(methyl)amino]-2-oxoethyl}-N¹-[2-(isopropylamino)ethyl]glycinamide dihydrochloride

Step A

N²-(2,5-dichlorophenyl)-N²-{2-[1,3-dihydro-2H-isoindol-2-yl(methyl)amino]-2-oxoethyl}-N¹-{2-[(tert-butoxycarbonyl)(isopropyl)amino]ethyl}glycinamide Using the compound (261 mg, 0.64 mmol) of Example 145, step A, and the compound (155 mg, 0.77 mmol) of Reference Example 3, and according to the method of Example 1, step B, the title compound (264 mg, yield 70%) was obtained as a pale-yellow amorphous solid.

¹H-NMR (300 MHz, CDCl$_3$); δ (ppm) 1.06 (d, J=6.7, 6H), 1.40 (s, 9H), 2.93-3.16 (m, 5H), 3.34-3.38 (m, 2H), 3.95 (s, 2H), 4.14-4.29 (m, 7H), 6.94-6.97 (m, 1H), 7.17-7.22 (m, 5H), 7.38-7.39 (m, 1H), 7.90 (brs, 1H).

Step B

N²-(2,5-dichlorophenyl)-N²-{2-[1,3-dihydro-2H-isoindol-2-yl(methyl)amino]-2-oxoethyl}-N¹-[2-(isopropylamino)ethyl]glycinamide dihydrochloride Using the compound (264 mg, 0.44 mmol) obtained in step A and according to the method of Example 1, step C, the title compound (195 mg, yield 79%) was obtained as a pale-yellow solid.

¹H-NMR (300 MHz, DMSO-d$_6$); δ (ppm) 1.19 (d, J=6.3, 6H), 2.91 (m, 5H), 3.35-3.39 (m, 3H), 3.98 (s, 2H), 4.15 (d, J=11.7, 2H), 4.29 (d, J=11.7, 2H), 4.45 (s, 2H), 7.00 (dd, J=2.4, 8.4, 1H), 7.16 (d, J=2.4, 1H), 7.24-7.30 (m, 4H), 7.36 (d, J=8.4, 1H), 8.26 (t, J=6.0, 1H), 8.46 (brs, 2H).

Example 148

N²-(2,4-dichlorophenyl)-N²-{2-[1,3-dihydro-2H-isoindol-2-yl(methyl)amino]-2-oxoethyl}-N¹-[2-(isopropylamino)ethyl]glycinamide dihydrochloride

Step A

N-(2,4-dichlorophenyl)-N-{2-[1,3-dihydro-2H-isoindol-2-yl(methyl)amino]-2-oxoethyl}glycine Using the compound (480 mg, 1.73 mmol) of Reference Example 99 and the compound (479 mg, 2.60 mmol) of Reference Example 17, and according to the method of Example 1, step A, the title compound (573 mg, yield 81%) was obtained as a colorless amorphous solid.

¹H-NMR (300 MHz, DMSO-d$_6$); δ (ppm) 2.87 (s, 3H), 4.08 (s, 2H), 4.14 (d, J=11.7, 2H), 4.26 (d, J=11.7, 2H), 4.42 (s, 2H), 7.12 (d, J=8.7, 1H), 7.22-7.30 (m, 5H), 7.42 (d, J=2.4, 1H), 12.53 (brs, 1H).

Step B

N²-(2,4-dichlorophenyl)-N²-{2-[1,3-dihydro-2H-isoindol-2-yl(methyl)amino]-2-oxoethyl}-N¹-{2-[(tert-butoxycarbonyl)(isopropyl)amino]ethyl}glycinamide Using a mixture of the compound (573 mg, 1.40 mmol) obtained in step A and the compound (425 mg, 2.10 mmol) of Reference Example 3, and according to the method of Example 1, step B, the title compound (641 mg, yield 75%) was obtained as a bistered amorphous solid.

¹H-NMR (300 MHz, CDCl$_3$); δ (ppm) 1.08 (d, J=6.6, 6H), 1.42 (s, 9H), 2.93 (s, 3H), 2.99-3.21 (m, 2H), 3.31-3.39 (m, 2H), 3.9-4.3 (broad, 1H), 3.97 (s, 2H), 4.15 (d, J=11.4, 2H), 4.24 (d, J=11.4, 2H), 4.28 (s, 2H), 7.16-7.29 (m, 5H), 7.35 (d, J=2.4, 1H), 7.40 (d, J=8.7, 1H), 7.83 (brs, 1H).

Step C

N²-(2,4-dichlorophenyl)-N²-{2-[1,3-dihydro-2H-isoindol-2-yl(methyl)amino]-2-oxoethyl}-N¹-[2-(isopropylamino)ethyl]glycinamide dihydrochloride Using the compound (641 mg, 1.06 mmol) obtained in step B and according to the method of Example 1, step C, the title compound (258 mg, yield 43%) was obtained as a pale-bistered amorphous solid.

¹H-NMR (300 MHz, DMSO-d₆); δ (ppm) 1.20 (d, J=6.6, 6H), 2.89 (brs, 5H), 3.21-3.29 (m, 3H), 3.96 (s, 2H), 4.14 (d, J=11.7, 2H), 4.28 (d, J=11.7, 2H), 4.43 (s, 2H), 7.16 (d, J=9.0, 1H), 7.21-7.27 (m, 5H), 7.45 (d, J=2.4, 1H), 8.30 (t, J=5.1, 1H), 8.81 (brs, 2H).

Example 149

N²-(2-chloro-5-cyanophenyl)-N²-{2-[1,3-dihydro-2H-isoindol-2-yl(methyl)amino]-2-oxoethyl}-N¹-[2-(isopropylamino)ethyl]glycinamide dihydrochloride

Step A

N-(2-chloro-5-cyanophenyl)-N-{2-[1,3-dihydro-2H-isoindol-2-yl(methyl)amino]-2-oxoethyl}glycine Using the compound (460 mg, 1.71 mmol) of Reference Example 100 and the compound (440 mg, 2.38 mmol) of Reference Example 17, and according to the method of Example 1, step A, the title compound (564 mg, yield 83%) was obtained as a gray amorphous solid.

¹H-NMR (300 MHz, DMSO-d₆); δ (ppm) 2.88 (s, 3H), 4.13 (s, 2H), 4.17 (d, J=11.7, 2H), 4.27 (d, J=11.7, 2H), 4.48 (s, 2H), 7.23-7.31 (m, 4H), 7.36 (dd, J=1.5, 8.1, 1H), 7.52 (d, J=1.5, 1H), 7.54 (d, J=8.1, 1H), 12.60 (brs, 1H).

Step B

N²-(2-chloro-5-cyanophenyl)-N²-{2-[1,3-dihydro-2H-isoindol-2-yl(methyl)amino]-2-oxoethyl}-N¹-{2-[(tert-butoxycarbonyl)(isopropyl)amino]ethyl}glycinamide Using the compound (558 mg, 1.40 mmol) obtained in step A and the compound (388 mg, 1.92 mmol) of Reference Example 3, and according to the method of Example 1, step B, the title compound (744 mg, yield 91%) was obtained as a colorless amorphous solid.

¹H-NMR (300 MHz, CDCl₃); δ (ppm) 1.09 (d, J=6.9, 6H), 1.41 (brs, 9H), 2.96 (s, 3H), 3.0-3.2 (m, 2H), 3.34-3.41 (m, 2H), 3.9-4.4 (broad, 1H), 4.00 (s, 2H), 4.19 (d, J=11.7, 2H), 4.28 (d, J=11.7, 2H), 4.35 (s, 2H), 7.2-7.3 (m, 5H), 7.44 (d, J=8.1, 1H), 7.64 (s, 1H), 7.7-8.0 (broad, 1H).

Step C

N²-(2-chloro-5-cyanophenyl)-N²-{2-[1,3-dihydro-2H-isoindol-2-yl(methyl)amino]-2-oxoethyl}-N¹-[2-(isopropylamino)ethyl]glycinamide dihydrochloride Using the compound (726 mg, 1.25 mmol) obtained in step B and according to the method of Example 1, step C, the title compound (610 mg, yield 88%) was obtained as a colorless solid.

¹H-NMR (300 MHz, DMSO-d₆); δ (ppm) 1.19 (d, J=6.6, 6H), 2.8-3.0 (m, 2H), 2.90 (s, 3H), 3.1-3.3 (m, 1H), 3.35-3.42 (m, 2H), 4.02 (s, 2H), 4.17 (d, J=11.7, 2H), 4.29 (d, J=11.7, 2H), 4.48 (s, 2H), 7.23-7.31 (m, 4H), 7.37 (d, J=8.1, 1H), 7.54 (s, 1H), 7.55 (d, J=8.1, 1H), 8.30 (broad t, 1H), 8.67 (brs, 2H).

Example 150

N²-[2-chloro-5-(5-methyl-1,2,4-oxadiazol-3-yl)phenyl]-N²-{2-[1,3-dihydro-2H-isoindol-2-yl(methyl)amino]-2-oxoethyl}-N¹-[2-(isopropylamino)ethyl]glycinamide dihydrochloride

Step A

N²-[2-chloro-5-(5-methyl-1,2,4-oxadiazol-3-yl)phenyl]-N²-{2-[1,3-dihydro-2H-isoindol-2-yl(methyl)amino]-2-oxoethyl}-N¹-{2-[(tert-butoxycarbonyl)(isopropyl)amino]ethyl}glycinamide Using the compound (616 mg, 1.06 mmol) of Example 149, step B and according to the method of Reference Example 62, step A, the title compound (577 mg, yield 85%) was obtained as a colorless amorphous solid.

¹H-NMR (300 MHz, CDCl₃); δ (ppm) 1.08 (d, J=6.9, 6H), 1.43 (brs, 9H), 2.64 (s, 3H), 2.94 (s, 3H), 3.0-3.2 (m, 2H), 3.34-3.42 (m, 2H), 3.9-4.4 (broad, 1H), 4.03 (s, 2H), 4.20 (d, J=12.0, 2H), 4.26 (d, J=12.0, 2H), 4.36 (s, 2H), 7.2-7.3 (m, 4H), 7.45 (d, J=8.1, 1H), 7.69 (dd, J=1.5, 8.1, 1H), 7.7-8.2 (broad, 1H), 8.10 (d, J=1.5, 1H).

Step B

N²-[2-chloro-5-(5-methyl-1,2,4-oxadiazol-3-yl)phenyl]-N²-{2-[1,3-dihydro-2H-isoindol-2-yl(methyl)amino]-2-oxoethyl}-N¹-[2-(isopropylamino)ethyl]glycinamide dihydrochloride Using the compound (569 mg, 0.889 mmol) obtained in step A and according to the method of Example 1, step C, the title compound (486 mg, yield 89%) was obtained as a colorless solid.

¹H-NMR (300 MHz, DMSO-d₆); δ (ppm) 1.17 (d, J=6.6, 6H), 2.67 (s, 3H), 2.8-3.0 (m, 2H), 2.91 (s, 3H), 3.2-3.4 (m, 3H), 4.04 (s, 2H), 4.16 (d, J=11.7, 2H), 4.31 (d, J=11.7, 2H), 4.51 (s, 2H), 7.2-7.3 (m, 4H), 7.54 (s, 2H), 7.78 (s, 1H), 8.2-8.4 (m, 3H).

Example 151

N²-[2-chloro-5-(5-methyl-1,2,4-oxadiazol-3-yl)phenyl]-N²-{2-[1,3-dihydro-2H-isoindol-2-yl(methyl)amino]-2-oxoethyl}-N¹-[2-(ethylamino)ethyl]glycinamide dihydrochloride

Step A

N²-(2-chloro-5-cyanophenyl)-N²-{2-[1,3-dihydro-2H-isoindol-2-yl(methyl)amino]-2-oxoethyl}-N¹-{2-[(tert-butoxycarbonyl)(ethyl)amino]ethyl}glycinamide Using the compound (460 mg, 1.15 mmol) of Example 149, step A, and the compound (362 mg, 1.92 mmol) of Reference Example 2, and according to the method of Example 1, step B, the title compound (624 mg, yield 95%) was obtained as a colorless amorphous solid.

¹H-NMR (300 MHz, CDCl₃); δ (ppm) 1.03 (t, J=7.2, 3H), 1.39 (brs, 9H), 2.96 (s, 3H), 3.0-3.3 (m, 4H), 3.36-3.44 (m, 2H), 3.98 (s, 2H), 4.19 (d, J=11.7, 2H), 4.28 (d, J=11.7, 2H), 4.35 (s, 2H), 7.2-7.3 (m, 5H), 7.44 (d, J=8.1, 1H), 7.63 (d, J=1.5, 1H), 7.7-8.0 (broad, 1H).

Step B

N$^2$-[2-chloro-5-(5-methyl-1,2,4-oxadiazol-3-yl)phenyl]-N$^2$-{2-[1,3-dihydro-2H-isoindol-2-yl(methyl)amino]-2-oxoethyl}-N$^1$-{2-[(tert-butoxycarbonyl)(ethyl)amino]ethyl}glycinamide Using the compound (623 mg, 1.09 mmol) obtained in step A and according to the method of Reference Example 62, step A, the title compound (555 mg, yield 81%) was obtained as a colorless amorphous solid.
$^1$H-NMR (300 MHz, CDCl$_3$); δ (ppm) 1.01 (t, J=7.2, 3H), 1.41 (brs, 9H), 2.64 (s, 3H), 2.94 (s, 3H), 3.0-3.3 (m, 4H), 3.37-3.44 (m, 2H), 4.02 (s, 2H), 4.21 (d, J=11.7, 2H), 4.26 (d, J=11.7, 2H), 4.36 (s, 2H), 7.2-7.3 (m, 4H), 7.45 (d, J=8.1, 1H), 7.68 (dd, J=1.5, 8.1, 1H), 7.8-8.3 (broad, 1H), 8.09 (d, J=1.5, 1H).

Step C

N$^2$-[2-chloro-5-(5-methyl-1,2,4-oxadiazol-3-yl)phenyl]-N$^2$-{2-[1,3-dihydro-2H-isoindol-2-yl(methyl)amino]-2-oxoethyl}-N$^1$-[2-(ethylamino)ethyl]glycinamide dihydrochloride Using the compound (552 mg, 0.882 mmol) obtained in step B and according to the method of Example 1, step C, the title compound (478 mg, yield 90%) was obtained as a colorless solid.
$^1$H-NMR (300 MHz, DMSO-d$_6$); δ (ppm) 1.14 (t, J=7.5, 3H), 2.67 (s, 3H), 2.8-3.0 (m, 4H), 2.90 (s, 3H), 3.2-3.4 (m, 2H), 4.04 (s, 2H), 4.16 (d, J=11.7, 2H), 4.30 (d, J=11.7, 2H), 4.51 (s, 2H), 7.23-7.31 (m, 4H), 7.54 (s, 2H), 7.78 (s, 1H), 8.33 (broad t, 1H), 8.52 (brs, 2H).

Example 152

N$^2$-{5-(tert-butoxycarbonyl)-2-chlorophenyl}-N$^2$-{2-[1,3-dihydro-2H-isoindol-2-yl(methyl)amino]-2-oxoethyl}-N$^1$-[2-(isopropylamino)ethyl]glycinamide Step A N-{5-(tert-butoxycarbonyl)-2-chlorophenyl}-N-{2-[1,3-dihydro-2H-isoindol-2-yl(methyl)amino]-2-oxoethyl}glycine Using the compound (1.00 g, 2.91 mmol) of Reference Example 101 and the compound (0.81 g, 4.39 mmol) of Reference Example 17, and according to the method of Example 1, step A, the title compound (1.47 g, yield>100%) was obtained as a colorless amorphous solid.
$^1$H-NMR (300 MHz, CDCl$_3$); δ (ppm) 1.57 (s, 9H), 3.04 (s, 3H), 4.08 (s, 2H), 4.22 (d, J=11.7, 2H), 4.29 (d, J=11.7, 2H), 4.44 (s, 2H), 7.19-7.29 (m, 4H), 7.39 (d, J=8.4, 1H), 7.62 (dd, J=1.8, 8.3, 1H), 7.90 (d, J=2.1, 1H).

Step B

N$^2$-{5-(tert-butoxycarbonyl)-2-chlorophenyl}-N$^2$-{2-[1,3-dihydro-2H-isoindol-2-yl(methyl)amino]-2-oxoethyl}-N$^1$-[2-{(isopropyl)[(2-nitrophenyl)sulfonyl]amino}ethyl]glycinamide Using the compound (1.47 g) obtained in step A and the compound (1.38 g, 4.80 mmol) of Reference Example 7, and according to the method of Example 1, step B, the title compound (2.00 g, yield 87%) was obtained as a colorless amorphous solid.
$^1$H-NMR (300 MHz, CDCl$_3$); δ (ppm) 1.16 (d, J=6.6, 6H), 1.57 (s, 9H), 2.95 (s, 3H), 3.32-3.37 (m, 2H), 3.44-3.49 (m, 2H), 3.98 (s, 2H), 4.0-4.2 (m, 1H), 4.2-4.4 (m, 4H), 4.41 (s, 2H), 7.22-7.28 (m, 4H), 7.38 (d, J=8.1, 1H), 7.57-7.68 (m, 4H), 7.94-8.00 (m, 2H), 8.31 (m, 1H).

Step C

N$^2$-{5-(tert-butoxycarbonyl)-2-chlorophenyl}-N$^2$-{2-[1,3-dihydro-2H-isoindol-2-yl(methyl)amino]-2-oxoethyl}-N$^1$-[2-(isopropylamino)ethyl]glycinamide Using the compound (0.50 g, 0.67 mmol) obtained in step B and according to the method of Example 50, step B, the title compound (0.32 g, yield 85%) was obtained as a colorless amorphous solid.
$^1$H-NMR (300 MHz, CDCl$_3$); δ (ppm) 0.98 (d, J=6.2, 6H), 1.57 (s, 9H), 2.67-2.75 (m, 3H), 2.95 (s, 3H), 3.35-3.42 (m, 2H), 3.97 (s, 2H), 4.19 (d, J=11.7, 2H), 4.26 (d, J=11.7, 2H), 4.33 (s, 2H), 7.20-7.29 (m, 4H), 7.39 (d, J=8.3, 1H), 7.60 (dd, J=1.8, 8.3, 1H), 7.95 (d, J=1.8, 1H), 8.19 (m, 1H).

Example 153

N$^2$-{2-chloro-5-[(methylamino)carbonyl]phenyl}-N$^2$-{2-[1,3-dihydro-2H-isoindol-2-yl(methyl)amino]-2-oxoethyl}-N$^1$-[2-(isopropylamino)ethyl]glycinamide Step A N$^2$-(5-carboxy-2-chlorophenyl)-N$^2$-{2-[1,3-dihydro-2H-isoindol-2-yl(methyl)amino]-2-oxoethyl}-N$^1$-[2-{(isopropyl)[(2-nitrophenyl)sulfonyl]amino}ethyl]glycinamide Using the compound (1.00 g, 1.35 mmol) of Example 152, step B and according to the method of Reference Example 61, step D, the title compound (1.06 g, yield>100%) was obtained as a colorless amorphous solid.
$^1$H-NMR (300 MHz, CDCl$_3$); δ (ppm) 1.14 (d, J=6.9, 6H), 2.98 (s, 3H), 3.32-3.37 (m, 2H), 3.47-3.54 (m, 2H), 4.02-4.12 (m, 3H), 4.21-4.29 (m, 4H), 4.45 (s, 2H), 7.21 (s, 4H), 7.42 (d, J=8.4, 1H), 7.53-7.71 (m, 4H), 7.94-7.98 (m, 1H), 8.12 (s, 1H), 8.52-8.55 (m, 1H), 10.10 (broad, 1H).

Step B

N$^2$-{2-chloro-5-[(methylamino)carbonyl]phenyl}-N$^2$-{2-[1,3-dihydro-2H-isoindol-2-yl(methyl)amino]-2-oxoethyl}-N$^1$-[2-{(isopropyl)[(2-nitrophenyl)sulfonyl]amino}ethyl]glycinamide Using the compound (0.35 g, 0.51 mmol) obtained in step A and according to the method of Example 77, step B, the title compound (0.37 g, yield>100%) was obtained as a colorless amorphous solid.
$^1$H-NMR (300 MHz, CDCl$_3$); δ (ppm) 1.13 (d, J=6.7, 6H), 2.92 (s, 3H), 2.93 (s, 3H), 3.28-3.34 (m, 2H), 3.41-3.49 (m, 2H), 3.99-4.10 (m, 3H), 4.17-4.27 (m, 4H), 4.39 (s, 2H), 6.88-6.91 (m, 1H), 7.21-7.23 (m, 4H), 7.35-7.47 (m, 2H), 7.57-7.59 (m, 1H), 7.64-7.68 (m, 2H), 7.80-7.81 (m, 1H), 7.93-7.95 (m, 1H), 8.37 (m, 1H).

Step C

N²-{2-chloro-5-[(methylamino)carbonyl]phenyl}-
N²-{2-[1,3-dihydro-2H-isoindol-2-yl(methyl)
amino]-2-oxoethyl}-N¹-[2-(isopropylamino)ethyl]
glycinamide Using the compound (0.37 g) obtained in step B and according to the method of Example 50, step B, the title compound (0.16 g, yield 61%) was obtained as a colorless amorphous solid.

$^1$H-NMR (300 MHz, CDCl$_3$); δ (ppm) 0.95 (d, J=6.5, 6H), 2.63-2.74 (m, 3H), 2.92 (s, 3H), 2.94 (s, 3H), 3.34 (q, J=5.9, 2H), 4.00 (s, 2H), 4.19 (d, J=11.8, 2H), 4.25 (d, J=11.8, 2H), 4.34 (s, 2H), 7.20-7.28 (m, 5H), 7.36-7.39 (m, 1H), 7.48-7.51 (m, 1H), 7.79 (s, 1H), 8.18 (m, 1H).

Example 154

N²-[5-(aminocarbonyl)-2-chlorophenyl]-N²-{2-[1,3-
dihydro-2H-isoindol-2-yl(methyl)amino]-2-oxoet-
hyl}-N¹-[2-(isopropylamino)ethyl]glycinamide

Step A

N²-[5-(aminocarbonyl)-2-chlorophenyl]-N²-{2-[1,3-
dihydro-2H-isoindol-2-yl(methyl)amino]-2-oxoet-
hyl}-N¹-[2-{(isopropyl)[(2-nitrophenyl)sulfonyl]
amino}ethyl]glycinamide Using the compound (0.35 g, 0.51 mmol) of Example 153, step A and according to the method of Example 78, step A, the title compound (0.37 g, yield>100%) was obtained as a colorless amorphous solid.

$^1$H-NMR (300 MHz, CDCl$_3$); δ (ppm) 1.12 (d, J=6.9, 6H), 2.94 (s, 3H), 3.29-3.34 (m, 2H), 3.42-3.49 (m, 2H), 4.00-4.10 (m, 3H), 4.18-4.27 (m, 4H), 4.40 (s, 2H), 6.42 (brs, 1H), 6.97 (brs, 1H), 7.20-7.23 (m, 4H), 7.39 (d, J=8.4, 1H), 7.49-7.68 (m, 4H), 7.93-7.97 (m, 2H), 8.36 (m, 1H).

Step B

N²-[5-(aminocarbonyl)-2-chlorophenyl]-N²-{2-[1,3-
dihydro-2H-isoindol-2-yl(methyl)amino]-2-oxoet-
hyl}-N¹-[2-(isopropylamino)ethyl]glycinamide Using the compound (0.37 g) obtained in step B and according to the method of Example 50, step B, the title compound (0.18 g, yield 71%) was obtained as a colorless amorphous solid.

$^1$H-NMR (300 MHz, CDCl$_3$); δ (ppm) 0.96 (d, J=6.2, 6H), 2.64-2.76 (m, 3H), 2.96 (s, 3H), 3.22-3.39 (m, 2H), 4.06 (s, 2H), 4.19 (d, J=12.3, 2H), 4.26 (d, J=12.3, 2H), 4.34 (s, 2H), 6.41 (brs, 1H), 7.00 (brs, 1H), 7.20-7.28 (m, 4H), 7.39-7.55 (m, 2H), 7.91 (s, 1H), 8.16-8.19 (m, 1H).

Example 155

N²-(5-chloro-2-fluorophenyl)-N²-{2-[1,3-dihydro-
2H-isoindol-2-yl(methyl)amino]-2-oxoethyl}-N¹-[2-
(isopropylamino)ethyl]glycinamide dihydrochloride

Step A

N-(5-chloro-2-fluorophenyl)-N-{2-[1,3-dihydro-2H-
isoindol-2-yl(methyl)amino]-2-oxoethyl}glycine Using the compound (453 mg, 1.73 mmol) of Reference Example 102 and the compound (479 mg, 2.60 mmol) of Reference Example 17, and according to the method of Example 1, step A, the title compound (543 mg, yield 80%) was obtained as a colorless solid.

$^1$H-NMR (300 MHz, DMSO-d$_6$); δ (ppm) 2.92 (s, 3H), 4.07 (s, 2H), 4.20 (d, J=11.7, 2H), 4.31 (d, J=11.7, 2H), 4.47 (s, 2H), 6.65-6.76 (m, 2H), 7.06 (dd, J=8.7, 14.1, 1H), 7.23-7.32 (m, 4H), 12.73 (brs, 1H).

Step B

N²-(5-chloro-2-fluorophenyl)-N²-{2-[1,3-dihydro-
2H-isoindol-2-yl(methyl)amino]-2-oxoethyl}-N¹-{2-
[(tert-butoxycarbonyl)(isopropyl)amino]
ethyl}glycinamide Using the compound (543 mg, 1.39 mmol) obtained in step A and the compound (422 mg, 2.09 mmol) of Reference Example 3, and according to the method of Example 1, step B, the title compound (815 mg, yield 99%) was obtained as a bistered amorphous solid.

$^1$H-NMR (300 MHz, CDCl$_3$); δ (ppm) 1.12 (d, J=6.3, 6H), 1.42 (s, 9H), 3.00 (s, 3H), 3.06-3.18 (m, 2H), 3.33-3.42 (m, 2H), 3.95 (s, 2H), 4.0-4.3 (m, 1H), 4.25 (d, J=11.7, 2H), 4.33 (d, J=11.7, 2H), 4.50 (s, 2H), 6.69-6.75 (m, 2H), 6.85-6.93 (m, 1H), 7.22-7.29 (m, 4H).

Step C

N²-(5-chloro-2-fluorophenyl)-N²-{2-[1,3-dihydro-
2H-isoindol-2-yl(methyl)amino]-2-oxoethyl}-N¹-[2-
(isopropylamino)ethyl]glycinamide dihydrochloride Using the compound (815 mg, 1.38 mmol) obtained in step B and according to the method of Example 1, step C, the title compound (395 mg, yield 52%) was obtained as a pale-bistered amorphous solid.

$^1$H-NMR (300 MHz, DMSO-d$_6$); δ (ppm) 1.19 (d, J=6.3, 6H), 2.90 (t, J=6.3, 2H), 2.94 (s, 3H), 3.21-3.31 (m, 1H), 3.34-3.47 (m, 2H), 3.95 (s, 2H), 4.21 (d, J=11.4, 2H), 4.33 (d, J=11.4, 2H), 4.57 (s, 2H), 6.62 (dd, J=2.4, 8.1, 1H), 6.70-6.75 (m, 1H), 7.07 (dd, J=8.4, 14.1, 1H), 7.24-7.33 (m, 4H), 8.66 (t, J=5.7, 1H), 8.87 (brs, 2H).

Example 156

N²-(5-cyano-2-fluorophenyl)-N²-{2-[1,3-dihydro-
2H-isoindol-2-yl(methyl)amino]-2-oxoethyl}-N¹-[2-
(isopropylamino)ethyl]glycinamide

Step A

N-(5-cyano-2-fluorophenyl)-N-{2-[1,3-dihydro-2H-
isoindol-2-yl(methyl)amino]-2-oxoethyl}glycine Using the compound (2.04 g, 8.09 mmol) of Reference Example 103 and the compound (2.30 g, 12.5 mmol) of Reference Example 17, and according to the method of Example 1, step A, the title compound (1.46 g, yield 47%) was obtained as a colorless solid.

$^1$H-NMR (300 MHz, DMSO-d$_6$); δ (ppm) 2.92 (s, 3H), 4.09 4.10 (2s, 2H), 4.22 (d, J=12.0, 2H), 4.30 (d, J=12.0, 2H), 4.49 (s, 2H), 7.12-7.32 (m, 7H), 12.71 (brs, 1H).

Step B

N²-(5-cyano-2-fluorophenyl)-N²-{2-[1,3-dihydro-2H-isoindol-2-yl(methyl)amino]-2-oxoethyl}-N¹-{2-[(tert-butoxycarbonyl)(isopropyl)amino]ethyl}glycinamide Using the compound (716 mg, 1.87 mmol) obtained in step A and the compound (588 mg, 2.91 mmol) of Reference Example 3, and according to the method of Example 1, step B, the title compound (1.11 g, yield>100%) was obtained as a pale-yellow amorphous solid ¹H-NMR (300 MHz, CDCl₃); δ (ppm) 1.11 (d, J=6.9, 6H), 1.41 1.43 (2brs, 9H), 3.0-3.2 (m, 2H), 3.02 (s, 3H), 3.34-3.41 (m, 2H), 3.9-4.4 (broad, 1H), 3.98 3.99 (2s, 2H), 4.26 (d, J=11.7, 2H), 4.34 (d, J=11.7, 2H), 4.53 (s, 2H), 6.9-7.1 (m, 3H), 7.23-7.31 (m, 4H), 8.3-8.9 (broad, 1H).

Step C

N²-(5-cyano-2-fluorophenyl)-N²-{2-[1,3-dihydro-2H-isoindol-2-yl(methyl)amino]-2-oxoethyl}-N¹-[2-(isopropylamino)ethyl]glycinamide Using the compound (450 mg, 0.794 mmol) obtained in step B and according to the method of Example 46, step B, the title compound (276 mg, yield 75%) was obtained as a colorless solid.

¹H-NMR (300 MHz, CDCl₃); δ (ppm) 0.98 (d, J=6.3, 6H), 2.66-2.76 (m, 3H), 3.03 (s, 3H), 3.34-3.41 (m, 2H), 4.00 (s, 2H), 4.26 (d, J=11.7, 2H), 4.35 (d, J=11.7, 2H), 4.56 4.57 (2s, 2H), 6.95-7.11 (m, 3H), 7.24-7.32 (m, 4H), 8.74 (broad t, 1H).

Example 157

N²-(5-cyano-2-fluorophenyl)-N²-{2-[1,3-dihydro-2H-isoindol-2-yl(methyl)amino]-2-oxoethyl}-N¹-[2-(ethylamino)ethyl]glycinamide

Step A

N²-(5-cyano-2-fluorophenyl)-N²-{2-[1,3-dihydro-2H-isoindol-2-yl(methyl)amino]-2-oxoethyl}-N¹-{2-[(tert-butoxycarbonyl)(ethyl)amino]ethyl}glycinamide Using the compound (747 mg, 1.95 mmol) of Example 156, step A, and the compound (635 mg, 3.37 mmol) of Reference Example 2, and according to the method of Example 1, step B, the title compound (1.11 g, yield>100%) was obtained as a colorless amorphous solid.

¹H-NMR (300 MHz, CDCl₃); δ (ppm 1.05 (t, J=7.2, 3H), 1.39 1.42 (2brs, 9H), 3.02 (s, 3H), 3.15 (q, J=7.2, 2H), 3.2-3.3 (m, 2H), 3.3-3.5 (m, 2H), 3.98 (s, 2H), 4.26 (d, J=11.7, 2H), 4.34 (d, J=11.7, 2H), 4.53 (s, 2H), 6.9-7.1 (m, 3H), 7.23-7.31 (m, 4H), 8.3-8.8 (broad, 1H).

Step B

N²-(5-cyano-2-fluorophenyl)-N²-{2-[1,3-dihydro-2H-isoindol-2-yl(methyl)amino]-2-oxoethyl}-N²-[2-(ethylamino)ethyl]glycinamide Using the compound (456 mg, 0.825 mmol) obtained in step A and according to the method of Example 46, step B, the title compound (280 mg, yield 75%) was obtained as a colorless solid.

¹H-NMR (300 MHz, CDCl₃); δ (ppm) 1.03 (t, J=7.1, 3H), 2.54-2.62 (m, 2H), 2.71 (t, J=6.0, 2H), 3.03 (s, 3H), 3.35-3.42 (m, 2H), 4.00 (s, 2H), 4.26 (d, J=11.7, 2H), 4.35 (d, J=11.7, 2H), 4.56 4.57 (2s, 2H), 6.9-7.1 (m, 3H), 7.26-7.32 (m, 4H), 8.73 (broad t, 1H).

Example 158

N²-{2-[1,3-dihydro-2H-isoindol-2-yl(methyl)amino]-2-oxoethyl}-N²-[2-fluoro-5-(5-methyl-1,2,4-oxadiazol-3-yl)phenyl]-N¹-[2-(isopropylamino)ethyl]glycinamide dihydrochloride

Step A

N²-{2-[1,3-dihydro-2H-isoindol-2-yl(methyl)amino]-2-oxoethyl}-N²-[2-fluoro-5-(5-methyl-1,2,4-oxadiazol-3-yl)phenyl]-N¹-{2-[(tert-butoxycarbonyl)(isopropyl)amino]ethyl}glycinamide Using the compound (653 mg, 1.15 mmol) of Example 156, step B and according to the method of Reference Example 62, step A, the title compound (523 mg, yield 73%) was obtained as a colorless amorphous solid.

¹H-NMR (300 MHz, CDCl₃); δ (ppm) 1.09 (d, J=6.6, 6H), 1.42 (brs, 9H), 2.63 (s, 3H), 3.00 (s, 3H), 3.0-3.2 (m, 2H), 3.34-3.42 (m, 2H), 3.8-4.3 (broad, 1H), 4.04 (s, 2H), 4.33 (brs, 4H), 4.56 (s, 2H), 7.07 (dd, J=8.7, 13.8, 1H), 7.23-7.31 (m, 4H), 7.46-7.53 (m, 2H), 8.4-9.0 (broad, 1H),

Step B

N²-{2-[1,3-dihydro-2H-isoindol-2-yl(methyl)amino]-2-oxoethyl}-N²-[2-fluoro-5-(5-methyl-1,2,4-oxadiazol-3-yl)phenyl]-N¹-[2-(isopropylamino)ethyl]glycinamide dihydrochloride Using the compound (521 mg, 0.835 mmol) obtained in step A and according to the method of Example 1, step C, the title compound (453 mg, yield 91%) was obtained as a colorless solid.

¹H-NMR (300 MHz, DMSO-d₆); δ (ppm) 1.17 (d, J=6.3, 6H), 2.66 (s, 3H), 2.8-3.0 (m, 2H), 2.96 (s, 3H), 3.1-3.3 (m, 1H), 3.3-3.5 (m, 2H), 4.02 (s, 2H), 4.25 (d, J=11.7, 2H), 4.36 (d, J=11.7, 2H), 4.64 (s, 2H), 7.19-7.38 (m, 7H), 8.4-8.9 (broad, 2H), 8.74 (t, J=5.7, 1H).

Example 159

N²-{2-[1,3-dihydro-2H-isoindol-2-yl(methyl)amino]-2-oxoethyl}-N²-[2-fluoro-5-(5-methyl-1,2,4-oxadiazol-3-yl)phenyl]-N¹-[2-(ethylamino)ethyl]glycinamide dihydrochloride

Step A

N²-{2-[1,3-dihydro-2H-isoindol-2-yl(methyl)amino]-2-oxoethyl}-N²-[2-fluoro-5-(5-methyl-1,2,4-oxadiazol-3-yl)phenyl]-N¹-{2-[(tert-butoxycarbonyl)(ethyl)amino]ethyl}glycinamide Using the compound (653 mg, 1.18 mmol) of Example 157, step A and according to the method of Reference Example 62, step A, the title compound (524 mg, yield 73%) was obtained as a colorless amorphous solid.

¹H-NMR (300 MHz, CDCl₃); δ (ppm) 1.01 (t, J=7.2, 3H), 1.41 (brs, 9H), 2.63 (s, 3H), 3.0-3.3 (m, 4H), 3.01 (s, 3H), 3.37-3.45 (m, 2H), 4.02 4.03 (2s, 2H), 4.33 (brs, 4H), 4.55 (s, 2H), 7.07 (dd, J=8.4, 13.8, 1H), 7.25-7.31 (m, 4H), 7.46-7.52 (m, 2H), 8.4-9.0 (broad, 1H).

Step B

N$^2$-{2-[1,3-dihydro-2H-isoindol-2-yl(methyl)amino]-2-oxoethyl}-N$^2$-[2-fluoro-5-(5-methyl-1,2,4-oxadiazol-3-yl)phenyl]-N$^1$-[2-(ethylamino)ethyl]glycinamide dihydrochloride Using the compound (520 mg, 0.853 mmol) obtained in step A and according to the method of Example 1, step C, the title compound (462 mg, yield 93%) was obtained as a colorless solid.

$^1$H-NMR (300 MHz, DMSO-d$_6$); δ (ppm) 1.14 (t, J=7.2, 3H), 2.66 (s, 3H), 2.8-3.0 (m, 4H), 2.96 (s, 3H), 3.35-3.42 (m, 2H), 4.02 (s, 2H), 4.25 (d, J=11.7, 2H), 4.36 (d, J=11.7, 2H), 4.65 (s, 2H), 7.18-7.39 (m, 7H), 8.5-8.8 (broad, 2H), 8.74 (t, J=5.7, 1H).

Example 160

N$^2$-biphenyl-3-yl-N$^2$-{2-[1,3-dihydro-2H-isoindol-2-yl(methyl)amino]-2-oxoethyl}-N$^1$-[2-(isopropylamino)ethyl]glycinamide dihydrochloride Step A N-biphenyl-3-yl-N-{2-[1,3-dihydro-2H-isoindol-2-yl(methyl)amino]-2-oxoethyl}glycine Using the compound (1.00 g, 3.51 mmol) of Reference Example 104 and the compound (0.97 g, 5.25 mmol) of Reference Example 17, and according to the method of Example 1, step A, the title compound (1.40 g, yield 96%) was obtained as a colorless amorphous solid.

$^1$H-NMR (300 MHz, CDCl$_3$); δ (ppm) 3.08 (s, 3H), 4.20 (s, 2H), 4.38-4.45 (m, 4H), 4.67 (s, 2H), 6.53 (dd, J=2.4, 8.3, 1H), 6.73 (s, 1H), 7.04 (d, J=7.5, 1H), 7.25-7.56 (m, 10H).

Step B

N$^2$-biphenyl-3-yl-N$^2$-{2-[1,3-dihydro-2H-isoindol-2-yl(methyl)amino]-2-oxoethyl}-N$^1$-{2-[(tert-butoxycarbonyl)(isopropyl)amino]ethyl}glycinamide Using the compound (0.35 g, 0.84 mmol) obtained in step A and the compound (264 mg, 1.31 mmol) of Reference Example 3, and according to the method of Example 1, step B, the title compound (0.60 g, yield>100%) was obtained as a colorless amorphous solid.

$^1$H-NMR (300 MHz, CDCl$_3$); δ (ppm) 1.05 (d, J=6.9, 6H), 1.41 (s, 9H), 3.02 (s, 3H), 3.0-3.2 (m, 2H), 3.32-3.40 (m, 2H), 4.04 (s, 2H), 4.29-4.38 (m, 5H), 4.57 (s, 2H), 6.52 (m, 1H), 6.70-6.72 (m, 1H), 6.97-7.01 (m, 1H), 7.23-7.44 (m, 8H), 7.52-7.56 (m, 2H), 9.40 (broad, 1H).

Step C

N$^2$-biphenyl-3-yl-N$^2$-{2-[1,3-dihydro-2H-isoindol-2-yl(methyl)amino]-2-oxoethyl}-N$^1$-[2-(isopropylamino)ethyl]glycinamide dihydrochloride Using the compound (0.60 g) obtained in step B and according to the method of Example 1, step C, the title compound (0.41 g, yield 85%) was obtained as a colorless solid.

$^1$H-NMR (300 MHz, DMSO-d$_6$); δ (ppm) 1.15 (d, J=6.5, 6H), 2.86-2.89 (m, 2H), 2.97 (s, 3H), 3.20-3.25 (m, 1H), 3.3.4-3.42 (m, 2H), 4.06 (s, 2H), 4.31-4.41 (m, 4H), 4.72 (s, 2H), 6.48 (m, 1H), 6.63 (s, 1H), 6.93-6.96 (m, 1H), 7.24-7.58 (m, 10H), 8.85 (brs, 2H), 9.08-9.12 (m, 1H).

Example 161

N$^2$-biphenyl-2-yl-N$^2$-{2-[1,3-dihydro-2H-isoindol-2-yl(methyl)amino]-2-oxoethyl}-N$^1$-[2-(methylamino)ethyl]glycinamide dihydrochloride Step A N-biphenyl-2-yl-N-{2-[1,3-dihydro-2H-isoindol-2-yl(methyl)amino]-2-oxoethyl}glycine Using the compound (0.72 g, 2.52 mmol) of Reference Example 105 and the compound (0.77 g, 4.17 mmol) of Reference Example 17, and according to the method of Example 1, step A, the title compound (0.93 g, yield 89%) was obtained as a colorless amorphous solid.

$^1$H-NMR (300 MHz, CDCl$_3$); δ (ppm) 2.82 (s, 3H), 3.79 (s, 2H), 3.86-3.90 (m, 2H), 4.00-4.04 (m, 2H), 4.12 (s, 2H), 7.00-7.05 (m, 1H), 7.13-7.36 (m, 12H).

Step B

N$^2$-biphenyl-2-yl-N$^2$-{2-[1,3-dihydro-2H-isoindol-2-yl(methyl)amino]-2-oxoethyl}-N$^1$-{2-[(tert-butoxycarbonyl)(methyl)amino]ethyl}glycinamide Using the compound (0.45 g, 1.08 mmol) obtained in step A, the compound (0.35 g, 1.66 mmol) of Reference Example 1, and triethylamine (0.25 ml, 1.8 mmol), and according to the method of Example 1, step B, the title compound (0.60 g, yield 97%) was obtained as a colorless amorphous solid.

$^1$H-NMR (300 MHz, CDCl$_3$); δ (ppm) 1.44 (brs, 9H), 2.74 (brs, 3H), 2.82 (s, 3H), 3.24-3.34 (m, 4H), 3.72 (s, 2H), 3.85-4.12 (m, 6H), 7.02-7.04 (m, 1H), 7.15-7.43 (m, 12H), 7.85-8.11 (broad, 1H).

Step C

N$^2$-biphenyl-2-yl-N$^2$-{2-[1,3-dihydro-2H-isoindol-2-yl(methyl)amino]-2-oxoethyl}-N$^1$-[2-(methylamino)ethyl]glycinamide dihydrochloride Using the compound (0.60 g, 1.05 mmol) obtained in step B and according to the method of Example 1, step C, the title compound (0.45 g, yield 79%) was obtained as a colorless amorphous solid.

$^1$H-NMR (300 MHz, DMSO-d$_6$); δ (ppm) 2.50 (s, 3H), 2.76 (s, 3H), 2.86-2.91 (m, 2H), 3.28-3.35 (m, 2H), 3.79-3.84 (m, 4H), 4.03-4.12 (m, 4H), 6.96-6.99 (m, 1H), 7.06-7.27 (m, 8H), 7.36 (t, J=7.2, 2H), 7.58-7.62 (m, 2H), 8.18-8.21 (m, 1H), 8.95 (brs, 2H).

Example 162

N$^2$-biphenyl-2-yl-N$^2$-{2-[1,3-dihydro-2H-isoindol-2-yl(methyl)amino]-2-oxoethyl}-N$^1$-[2-(isopropylamino)ethyl]glycinamide dihydrochloride Step A N$^2$-biphenyl-2-yl-N$^2$-{2-[1,3-dihydro-2H-isoindol-2-yl(methyl)amino]-2-oxoethyl}-N$^1$-{2-[(tert-butoxycarbonyl)(isopropyl)amino]ethyl}glycinamide Using the compound (0.45 g, 1.08 mmol) of Example 161, step A, and the compound (0.34 g, 1.68 mmol) of Reference Example 3, and according to the method of Example 1, step B, the title compound (0.65 g, yield 100%) was obtained as a colorless amorphous solid.

$^1$H-NMR (300 MHz, CDCl$_3$); δ (ppm) 1.08 (d, J=6.9, 6H), 1.46 (s, 9H), 2.80 (s, 3H), 3.07 (brs, 2H), 3.27-3.35 (m, 2H), 3.72 (s, 2H), 3.83-3.88 (m, 2H), 4.01-4.12 (m, 4H), 4.1-4.3 (broad, 1H), 7.01 (m, 1H), 7.14-7.30 (m, 8H), 7.39-7.47 (m, 4H), 8.03 (broad, 1H).

Step B

N$^2$-biphenyl-2-yl-N$^2$-{2-[1,3-dihydro-2H-isoindol-2-yl(methyl)amino]-2-oxoethyl}-N$^1$-[2-(isopropylamino)ethyl]glycinamide dihydrochloride Using the compound (0.65 g, 1.08 mmol) obtained in step A and according to the method of Example 1, step C, the title compound (0.59 g, yield 95%) was obtained as a colorless solid.

$^1$H-NMR (300 MHz, DMSO-d$_6$); δ (ppm) 1.19 (d, J=6.4, 6H), 2.77 (s, 3H), 2.84-2.87 (brs, 2H), 3.21-3.40 (m, 3H), 3.79-3.84 (m, 4H), 4.04-4.13 (m, 4H), 6.93-6.99 (m, 1H), 7.06-7.27 (m, 8H), 7.30-7.39 (m, 2H), 7.59-7.63 (m, 2H), 8.23-8.28 (m, 1H), 8.99 (brs, 2H).

Example 163

N$^2$-(4-cyanobiphenyl-2-yl)-N$^2$-{2-[1,3-dihydro-2H-isoindol-2-yl(methyl)amino]-2-oxoethyl}-N$^1$-[2-(isopropylamino)ethyl]glycinamide dihydrochloride Step A N-(4-cyanobiphenyl-2-yl)-N-{2-[1,3-dihydro-2H-isoindol-2-yl(methyl)amino]-2-oxoethyl}glycine Using the compound (305 mg, 0.983 mmol) of Reference Example 106 and the compound (267 mg, 1.45 mmol) of Reference Example 17, and according to the method of Example 1, step A, the title compound (321 mg, yield 74%) was obtained as a colorless amorphous solid.

$^1$H-NMR (300 MHz, CDCl$_3$); δ (ppm) 2.92 (s, 3H), 3.76 (s, 2H), 3.98 (d, J=11.7, 2H), 4.12 (d, J=11.7, 2H), 4.21 (s, 2H), 7.1-7.5 (m, 12H).

Step B

N$^2$-(4-cyanobiphenyl-2-yl)-N$^2$-{2-[1,3-dihydro-2H-isoindol-2-yl(methyl)amino]-2-oxoethyl}-N$^1$-{2-[(tert-butoxycarbonyl)(isopropyl)amino]ethyl}glycinamide Using the compound (295 mg, 0.670 mmol) obtained in step A and the compound (247 mg, 1.22 mmol) of Reference Example 3, and according to the method of Example 1, step B, the title compound (289 mg, yield 69%) was obtained as a colorless solid.

$^1$H-NMR (300 MHz, CDCl$_3$); δ (ppm) 1.11 (d, J=6.8, 6H), 1.46 (brs, 9H), 2.86 (s, 3H), 2.9-3.2 (m, 2H), 3.26-3.33 (m, 2H), 3.69 (s, 2H), 3.8-4.3 (broad, 1H), 3.94 (d, J=11.7, 2H), 4.13 (s, 2H), 4.15 (d, J=11.7, 2H), 7.1-7.6 (m, 12H), 7.6-8.0 (broad, 1H).

Step C

N$^2$-(4-cyanobiphenyl-2-yl)-N$^2$-{2-[1,3-dihydro-2H-isoindol-2-yl(methyl)amino]-2-oxoethyl}-N$^1$-[2-(isopropylamino)ethyl]glycinamide dihydrochloride Using the compound (282 mg, 0.451 mmol) obtained in step B and according to the method of Example 1, step C, the title compound (264 mg, yield 98%) was obtained as a colorless solid.

$^1$H-NMR (300 MHz, DMSO-d$_6$); δ (ppm) 1.19 (d, J=6.3, 2H), 2.77 (s, 3H), 2.8-3.0 (m, 2H), 3.1-3.4 (m, 3H), 3.82 (d, J=11.7, 2H), 3.86 (s, 2H), 4.04 (s, 2H), 4.10 (d, J=11.7, 2H), 7.23 (broad, 4H), 7.25-7.43 (m, 5H), 7.46 (s, 1H), 7.68 (d, J=7.5, 2H), 8.21 (t, J=5.7, 1H), 8.66 (brs, 2H).H Example 164

N$^2$-{2-[1,3-dihydro-2H-isoindol-2-yl(methyl)amino]-2-oxoethyl}-N$^2$-1-naphthyl-N$^1$-[2-(isopropylamino)ethyl]glycinamide Step A N-{2-[1,3-dihydro-2H-isoindol-2-yl(methyl)amino]-2-oxoethyl}-N-1-naphthylglycine Using the compound (1.00 g, 3.86 mmol) of Reference Example 107 and the compound (927 mg, 5.02 mmol) of Reference Example 17, and according to the method of Example 1, step A, the title compound (1.35 g, yield 90%) was obtained as a pale-bistered amorphous solid.

$^1$H-NMR (300 MHz, CDCl$_3$); δ (ppm) 3.07 (s, 3H), 4.08 (d, J=11.6, 2H), 4.10 (s, 2H), 4.24 (d, J=11.2, 2H), 4.43 (s, 2H), 7.10-7.25 (m, 4H), 7.30-7.55 (m, 4H), 7.66 (d, J=7.7, 1H), 7.86 (d, J=7.3, 1H), 8.04 (d, J=8.7, 1H).

Step B

N$^2$-{2-[1,3-dihydro-2H-isoindol-2-yl(methyl)amino]-2-oxoethyl}-N$^2$-1-naphthyl-N$^1$-{2-[(tert-butoxycarbonyl)(isopropyl)amino]ethyl}glycinamide Using the compound (600 mg, 1.54 mmol) obtained in step A and the compound (469 mg, 2.32 mmol) of Reference Example 17, and according to the method of Example 1, step B, the title compound (797 mg, yield 90%) was obtained as a pale-bistered amorphous solid.

$^1$H-NMR (300 MHz, CDCl$_3$); δ (ppm) 0.99 (d, J=6.3, 6H), 1.38 (s, 9H), 2.70-3.20 (m, 5H), 3.20-3.40 (m, 2H), 3.95-4.25 (m, 7H), 4.33 (s, 2H), 7.10-7.25 (m, 4H), 7.35-7.60 (m, 5H), 7.83 (d, J=7.5, 1H), 8.00 (broad t, 1H), 8.20 (d, J=7.8, 1H).

Step C

N$^2$-{2-[1,3-dihydro-2H-isoindol-2-yl(methyl)amino]-2-oxoethyl}-N$^2$-1-naphthyl-N$^1$-[2-(isopropylamino)ethyl]glycinamide Using the compound (797 mg, 1.39 mmol) obtained in step B and according to the method of Example 46, step B, the title compound (627 mg, yield 95%) was obtained as a bistered oil.

$^1$H-NMR (300 MHz, CDCl$_3$); δ (ppm) 0.79 (d, J=6.3, 6H), 2.45-2.55 (m, 3H), 3.00 (s, 3H), 3.30 (q, J=5.8, 2H), 4.03 (d, J=11.0, 2H), 4.04 (s, 2H), 4.21 (d, J=11.2, 2H), 4.32 (s, 2H), 7.10-7.25 (m, 4H), 7.35-7.60 (m, 5H), 7.80-7.85 (m, 1H), 8.10 (broad t, 1H), 8.19 (d, J=7.1, 1H).

Example 165

$N^2$-(4-chloro-1-naphthyl)-$N^2$-{2-[1,3-dihydro-2H-isoindol-2-yl(methyl)amino]-2-oxoethyl}-$N^1$-[2-(isopropylamino)ethyl]glycinamide dihydrochloride

Step A

N-(4-chloro-1-naphthyl)-N-{2-[1,3-dihydro-2H-isoindol-2-yl(methyl)amino]-2-oxoethyl}glycine Using the compound (500 mg, 1.70 mmol) of Reference Example 108 and the compound (408 mg, 2.21 mmol) of Reference Example 17, and according to the method of Example 1, step A, the title compound (730 mg, yield>100%) was Obtained as a yellow amorphous solid.

$^1$H-NMR (300 MHz, CDCl$_3$); δ (ppm) 3.07 (s, 3H), 4.07 (d, J=11.4, 2H), 4.08 (s, 2H), 4.23 (d, J=11.4, 2H), 4.41 (s, 2H), 7.10-7.25 (m, 4H), 7.40 (d, J=7.8, 1H), 7.48 (d, J=8.1, 1H), 7.60-7.70 (m, 2H), 8.05-8.10 (m, 1H), 8.25-8.30 (m, 1H).

Step B $N^2$-(4-chloro-1-naphthyl)-$N^2$-{2-[1,3-dihydro-2H-isoindol-2-yl(methyl)amino]-2-oxoethyl}-$N^1$-{2-[(tert-butoxycarbonyl)(isopropyl)amino]ethyl}glycinamide Using the compound (730 mg) obtained in step A and the compound (516 mg, 2.55 mmol) of Reference Example 3, and according to the method of Example 1, step B, the title compound (850 mg, yield 82%) was obtained as a yellow amorphous solid.

$^1$H-NMR (300 MHz, CDCl$_3$); δ (ppm) 1.01 (d, J=4.8, 6H), 1.38 (s, 9H), 2.70-3.20 (m, 5H), 3.20-3.40 (m, 2H), 4.00-4.20 (m, 7H), 4.32 (s, 2H), 7.10-7.25 (m, 4H), 7.35 (d, J=7.8, 1H), 7.47 (d, J=8.1, 1H), 7.50-7.65 (m, 2H), 7.95 (broad t, 1H), 8.25-8.30 (m, 2H).

Step C $N^2$-(4-chloro-1-naphthyl)-$N^2$-{2-[1,3-dihydro-2H-isoindol-2-yl(methyl)amino]-2-oxoethyl}-$N^1$-[2-(isopropylamino)ethyl]glycinamide dihydrochloride Using the compound (850 mg, 1.40 mmol) obtained in step B and according to the method of Example 1, step C, the title compound (731 mg, yield 90%) was obtained as a bistered solid.

$^1$H-NMR (300 MHz, DMSO-d$_6$); δ (ppm) 1.18 (d, J=6.3, 6H), 2.80-2.90 (m, 2H), 2.88 (s, 3H), 3.20-3.30 (m, 1H), 3.37-3.44 (m, 2H), 4.01 (d, J=11.7, 2H), 4.06 (s, 2H), 4.21 (d, J=11.7, 2H), 4.46 (s, 2H), 7.30 (d, J=8.1, 1H), 7.54-7.70 (m, 3H), 8.13 (d, J=7.8, 1H), 8.36 (d, 1H), 8.42 (broad t, 1H), 9.05 (brs, 2H).

Example 166

$N^2$-{2-[1,3-dihydro-2H-isoindol-2-yl(methyl)amino]-2-oxoethyl}-$N^2$-(3-methoxy-2-naphthyl)-$N^1$-[2-(isopropylamino)ethyl]glycinamide dihydrochloride

Step A

N-{2-[1,3-dihydro-2H-isoindol-2-yl(methyl)amino]-2-oxoethyl}-N-(3-methoxy-2-naphthyl)glycine Using the compound (480 mg, 1.66 mmol) of Reference Example 109 and the compound (435 mg, 2.36 mmol) of Reference Example 17, and according to the method of Example 1, step A, the title compound (555 mg, yield 80%) was obtained as a colorless amorphous solid.

$^1$H-NMR (300 MHz, CDCl$_3$); δ (ppm) 3.05 (s, 3H), 3.92 (s, 3H), 4.06 (s, 2H), 4.26 (d, J=11.7, 2H), 4.33 (d, J=11.7, 2H), 4.52 (s, 2H), 7.12 (s, 1H), 7.2-7.4 (m, 7H), 7.6-7.7 (m, 2H), 13.2 (brs, 1H).

Step B $N^2$-{2-[1,3-dihydro-2H-isoindol-2-yl(methyl)amino]-2-oxoethyl}-$N^2$-(3-methoxy-2-naphthyl)-$N^1$-{2-[(tert-butoxycarbonyl)(isopropyl)amino]ethyl}glycinamide Using the compound (546 mg, 1.30 mmol) obtained in step A and the compound (344 mg, 1.70 mmol) of Reference Example 3, and according to the method of Example 1, step B, the title compound (694 mg, yield 88%) was obtained as a colorless amorphous solid.

$^1$H-NMR (300 MHz, CDCl$_3$); δ (ppm) 1.05 (d, J=6.6, 6H), 1.42 (brs, 9H), 2.97 (s, 3H), 3.0-3.2 (m, 2H), 3.32-3.40 (m, 2H), 3.9-4.4 (broad, 1H), 3.91 (s, 3H), 4.01 (s, 2H), 4.19 (d, J=11.7, 2H), 4.30 (d, J=11.7, 2H), 4.40 (s, 2H), 7.09 (s, 1H), 7.22-7.33 (m, 6H), 7.36 (s, 1H), 7.62-7.67 (m, 2H), 8.2-8.7 (broad, 1H).

Step C $N^2$-{2-[1,3-dihydro-2H-isoindol-2-yl(methyl)amino]-2-oxoethyl}-$N^2$-(3-methoxy-2-naphthyl)-$N^1$-[2-(isopropylamino)ethyl]glycinamide dihydrochloride Using the compound (686 mg, 1.14 mmol) obtained in step B and according to the method of Example 1, step C, the title compound (624 mg, yield 95%) was obtained as a colorless solid.

$^1$H-NMR (300 MHz, DMSO-d$_6$); δ (ppm) 1.16 (d, J=6.3, 6H), 2.8-3.0 (m, 2H), 2.95 (s, 3H), 3.1-3.3 (m, 1H), 3.3-3.5 (m, 2H), 3.84 (s, 3H), 3.98 (s, 2H), 4.23 (d, J=11.7, 2H), 4.36 (d, J=11.7, 2H), 4.55 (s, 2H), 7.00 (s, 1H), 7.23-7.34 (m, 7H), 7.6-7.7 (m, 2H), 8.59 (t, J=5.7, 1H), 8.74 (brs, 2H).

Example 167

$N^2$-(3-methoxy-2-naphthyl)-$N^2$-[2-{methyl[4-(methylsulfonyl)piperazin-1-yl]amino}-2-oxoethyl]-$N^1$-[2-(isopropylamino)ethyl]glycinamide dihydrochloride

Step A $N^2$-(3-methoxy-2-naphthyl)-$N^2$-[2-{methyl[4-(methylsulfonyl)piperazin-1-yl]amino}-2-oxoethyl]-$N^1$-{2-[(tert-butoxycarbonyl)(isopropyl)amino]ethyl}glycinamide Using the compound (379 mg, 1.31 mmol) of Reference Example 109, the compound (253 mg, 1.31 mmol) of Reference Example 48 and compound (359 mg, 1.77 mmol) of Reference Example 3, and according to the methods of Example 4, step A, and Example 1, step B, the title compound (425 mg, yield 50%) was obtained as a colorless amorphous solid.

$^1$H-NMR (300 MHz, CDCl$_3$); δ (ppm) 1.06 (broad d, 6H), 1.42 (brs, 9H), 2.7-2.9 (m, 2H), 2.81 (s, 3H), 2.9-3.2 (m, 6H), 2.96 (s, 3H), 3.3-3.4 (m, 2H), 3.7-3.9 (m, 2H), 3.9-4.3 (broad, 1H), 3.92 (s, 3H), 4.00 (s, 2H), 4.30 (s, 2H), 7.11 (s, 1H), 7.28-7.32 (m, 3H), 7.6-7.7 (m, 2H), 7.9-8.4 (broad, 1H).

Step B

N$^2$-(3-methoxy-2-naphthyl)-N$^2$-[2-{methyl[4-(methylsulfonyl)piperazin-1-yl]amino}-2-oxoethyl]-N$^1$-[2-(isopropylamino)ethyl]glycinamide dihydrochloride Using the compound (420 mg, 0.647 mmol) obtained in step A and according to the method of Example 1, step C, the title compound (371 mg, yield 92%) was obtained as a colorless solid.

$^1$H-NMR (300 MHz, DMSO-d$_6$); δ (ppm) 1.18 (d, J=6.5, 6H), 2.8-3.0 (m, 14H), 3.1-3.3 (m, 1H), 3.3-3.5 (m, 2H), 3.5-3.6 (m, 2H), 3.83 (s, 3H), 3.98 (s, 2H), 4.53 (s, 2H), 7.01 (s, 1H), 7.2-7.3 (m, 3H), 7.5-7.7 (m, 2H), 8.62 (t, J=5.7, 1H), 8.86 (brs, 2H).

Example 168

N$^2$-{2-[1,3-dihydro-2H-isoindol-2-yl(methyl)amino]-2-oxoethyl}-N$^2$-(5,6,7,8-tetrahydronaphthalen-1-yl)-N$^1$-[2-(isopropylamino)ethyl]glycinamide dihydrochloride Step A N-{2-[1,3-dihydro-2H-isoindol-2-yl(methyl)amino]-2-oxoethyl}-N-(5,6,7,8-tetrahydronaphthalen-1-yl)glycine Using the compound (500 mg, 1.90 mmol) of Reference Example 110 and the compound (456 mg, 2.47 mmol) of Reference Example 17, and according to the method of Example 1, step A, the title compound (660 mg, yield 88%) was obtained as a pale-yellow amorphous solid $^1$H-NMR (300 MHz, CDCl$_3$); δ (ppm) 1.70-1.85 (m, 4H), 2.65-2.80 (m, 4H), 3.04 (s, 3H), 3.85 (s, 2H), 4.15 (d, J=11.6, 2H), 4.23 (s, 2H), 4.26 (d, J=11.6, 2H), 6.91 (d, J=7.2, 1H), 7.03 (d, J=7.8, 1H), 7.09 (d, J=8.1, 1H), 7.15-7.25 (m, 4H).

Step B

N$^2$-{2-[1,3-dihydro-2H-isoindol-2-yl(methyl)amino]-2-oxoethyl}-N$^2$-(5,6,7,8-tetrahydronaphthalen-1-yl)-N$^1$-{2-[(tert-butoxycarbonyl)(isopropyl)amino]ethyl}glycinamide Using the compound (660 mg, 1.68 mmol) obtained in step A and the compound (509 mg, 2.52 mmol) of Reference Example 3, and according to the method of Example 1, step B, the title compound (672 mg, yield 69%) was obtained as a yellow amorphous solid.

$^1$H-NMR (300 MHz, CDCl$_3$); δ (ppm) 1.10 (d, J=6.6, 6H), 1.39 (s, 9H), 1.65-1.85 (m, 4H), 2.65-2.80 (m, 4H), 2.94 (s, 3H), 3.00-3.20 (m, 2H), 3.33-3.41 (m, 2H), 3.78 (s, 2H), 4.04 (d, J=11.7, 2H), 4.13 (s, 2H), 4.20 (d, J=11.7, 2H), 4.20-4.30 (m, 1H), 6.85 (d, J=7.2, 1H), 7.04 (t, J=7.5, 1H), 7.12 (d, J=7.5, 1H), 7.20-7.35 (m, 4H), 8.30 (brs, 1H).

Step C

N$^2$-{2-[1,3-dihydro-2H-isoindol-2-yl(methyl)amino]-2-oxoethyl}-N$^2$-(5,6,7,8-tetrahydronaphthalen-1-yl)-N$^1$-[2-(isopropylamino)ethyl]glycinamide dihydrochloride Using the compound (650 mg, 1.13 mmol) obtained in step B and according to the method of Example 1, step C, the title compound (628 mg, yield 100%) was obtained as a pale-gray solid.

$^1$H-NMR (300 MHz, DMSO-d$_6$); δ (ppm) 1.04 (d, J=6.1, 6H), 1.60-1.70 (m, 4H), 2.65-2.75 (m, 4H), 2.80-2.90 (m, 2H), 2.87 (s, 3H), 3.20-3.30 (m, 1H), 3.39 (q, J=6.0, 2H), 3.87 (s, 2H), 4.01 (d, J=11.6, 2H), 4.21 (d, J=11.6, 2H), 4.27 (s, 2H), 6.79 (d, J=6.9, 1H), 6.95-7.10 (m, 2H), 7.25 (brs, 4H), 8.38 (t, J=5.6, 1H), 8.88 (brs, 2H).

The compounds of Examples 145-168 are shown below.

TABLE 13

| Example | Structural Formula | TMW | LC-MS (found) |
|---|---|---|---|
| 145 | 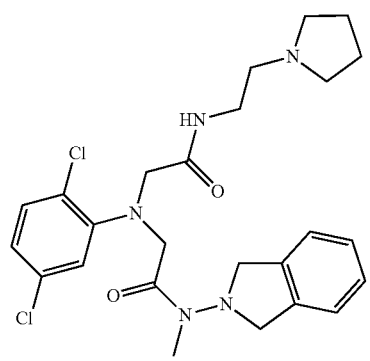 | 504.45 | 504 |

TABLE 13-continued
| Example | Structural Formula | TMW | LC-MS (found) |
|---|---|---|---|
| 146 | 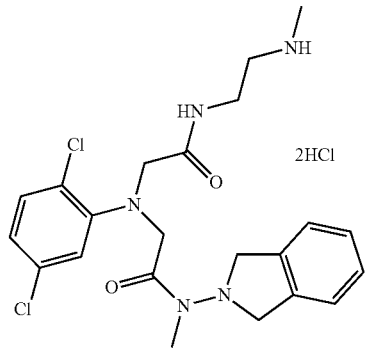 [SMILES: CNCCNC(=O)CN(CC(=O)N(C)N1Cc2ccccc2C1)c1cc(Cl)ccc1Cl] 2HCl | 537.31 | 464 |
| 147 | 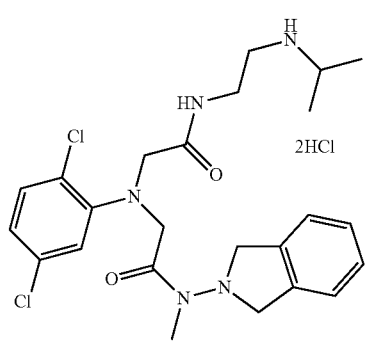 [SMILES: CC(C)NCCNC(=O)CN(CC(=O)N(C)N1Cc2ccccc2C1)c1cc(Cl)ccc1Cl] 2HCl | 565.36 | 492 |
| 148 | 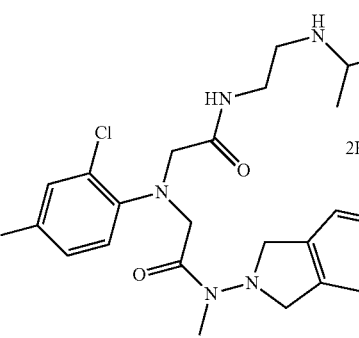 2HCl | 565.36 | 492 |
| 149 | 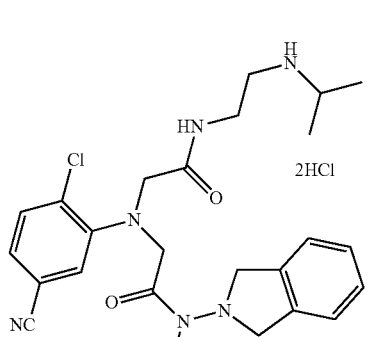 2HCl | 555.93 | 483 |

TABLE 13-continued
| Example | Structural Formula | TMW | LC-MS (found) |
|---|---|---|---|
| 150 | 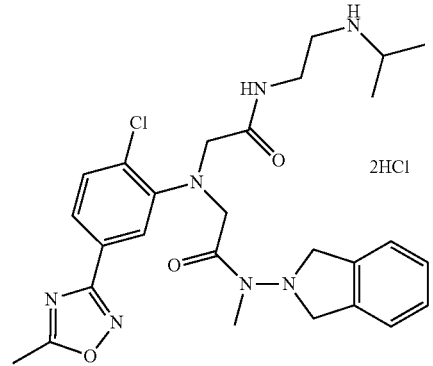 [SMILES: Cc1nc(-c2ccc(Cl)c(N(CC(=O)NCCNC(C)C)CC(=O)N(C)N3Cc4ccccc4C3)c2)no1] 2HCl | 612.98 | 540 |
| 151 | 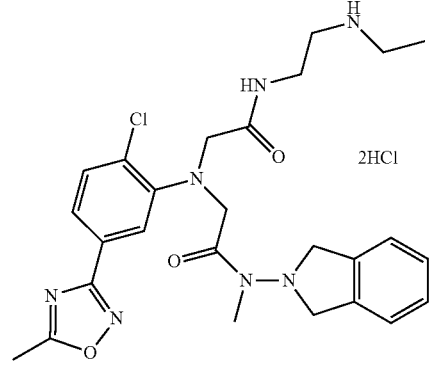 [SMILES: CCNCCNC(=O)CN(CC(=O)N(C)N1Cc2ccccc2C1)c1cc(-c2noc(C)n2)ccc1Cl] 2HCl | 598.95 | 526 |
| 152 | 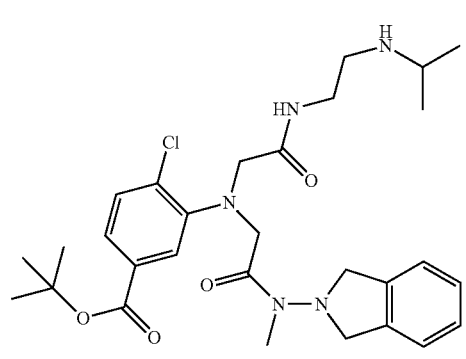 [SMILES: CC(C)NCCNC(=O)CN(CC(=O)N(C)N1Cc2ccccc2C1)c1cc(C(=O)OC(C)(C)C)ccc1Cl] | 558.11 | 558 |
| 153 | 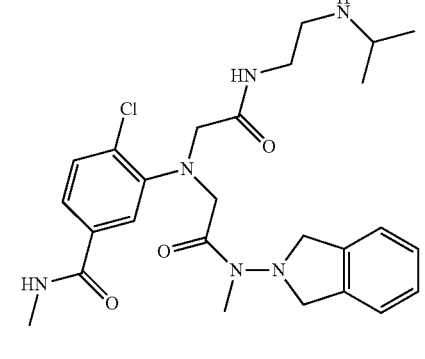 | 515.05 | 515 |

TABLE 13-continued
| Example | Structural Formula | TMW | LC-MS (found) |
|---|---|---|---|
| 154 | 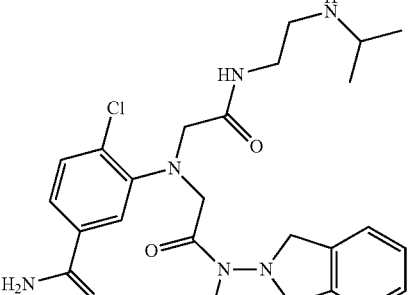 | 501.02 | 501 |
| 155 | 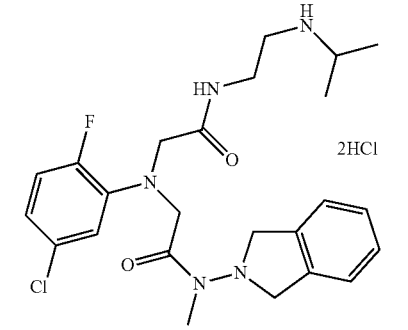 [SMILES: CC(C)NCCNC(=O)CN(CC(=O)N(C)N1Cc2ccccc2C1)c1cc(Cl)ccc1F] 2HCl | 548.91 | 476 |
| 156 | 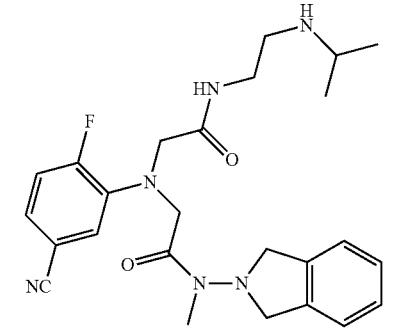 [SMILES: CC(C)NCCNC(=O)CN(CC(=O)N(C)N1Cc2ccccc2C1)c1cc(C#N)ccc1F] | 466.55 | 467 |
| 157 | 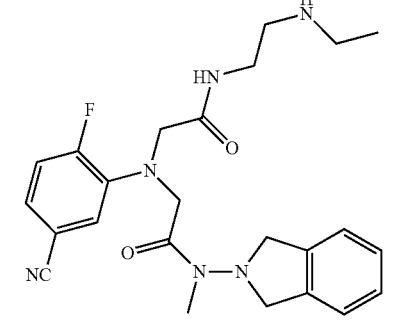 | 452.52 | 453 |

TABLE 13-continued

| Example | Structural Formula | TMW | LC-MS (found) |
|---|---|---|---|
| 158 | 2HCl | 596.52 | 524 |
| 159 | 2HCl | 582.50 | 510 |
| 160 | 2HCl | 572.57 | 500 |
| 161 | 2HCl | 544.52 | 472 |

TABLE 13-continued
| Example | Structural Formula | TMW | LC-MS (found) |
|---|---|---|---|
| 162 | 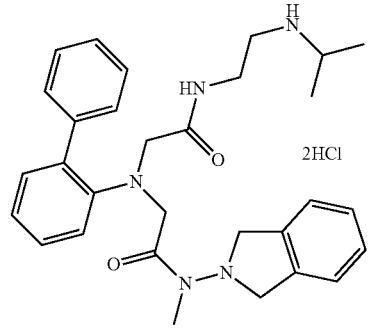 [SMILES: CC(C)NCCNC(=O)CN(CC(=O)N(C)N1Cc2ccccc2C1)c1ccccc1-c1ccccc1] | 572.57 | 500 |
| 163 | 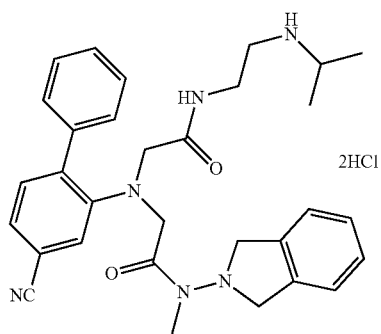 [SMILES: CC(C)NCCNC(=O)CN(CC(=O)N(C)N1Cc2ccccc2C1)c1cc(C#N)ccc1-c1ccccc1] | 597.58 | 525 |
| 164 | 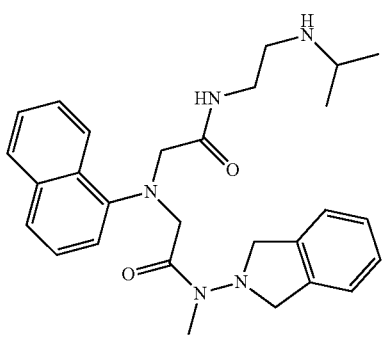 [SMILES: CC(C)NCCNC(=O)CN(CC(=O)N(C)N1Cc2ccccc2C1)c1cccc2ccccc12] | 473.61 | 474 |
| 165 | 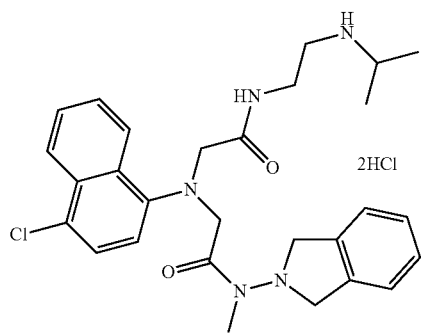 [SMILES: CC(C)NCCNC(=O)CN(CC(=O)N(C)N1Cc2ccccc2C1)c1ccc(Cl)c2ccccc12] | 580.98 | 508 |

TABLE 13-continued

| Example | Structural Formula | TMW | LC-MS (found) |
|---|---|---|---|
| 166 | 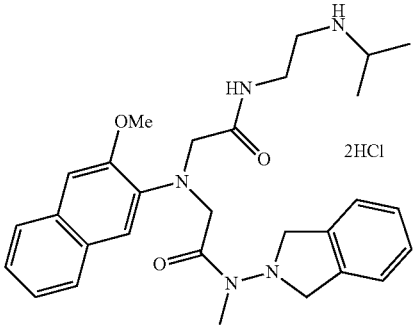 [SMILES: COc1cc2ccccc2cc1N(CC(=O)NCCNC(C)C)CC(=O)N(C)N1Cc2ccccc2C1] | 576.56 | 504 |
| 167 | 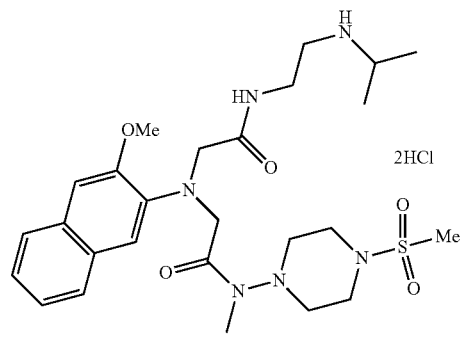 [SMILES: COc1cc2ccccc2cc1N(CC(=O)NCCNC(C)C)CC(=O)N(C)N1CCN(S(C)(=O)=O)CC1] | 621.62 | 549 |
| 168 | 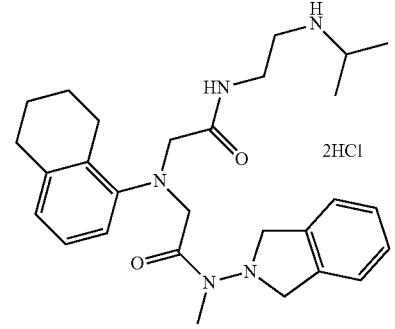 [SMILES: CC(C)NCCNC(=O)CN(CC(=O)N(C)N1Cc2ccccc2C1)c1cccc2c1CCCC2] | 550.56 | 478 |

Example 169

N²-(2,3-dihydro-1H-inden-4-yl)-N²-{2-[1,3-dihydro-2H-isoindol-2-yl(methyl)amino]-2-oxoethyl}-N¹-[2-(isopropylamino)ethyl]glycinamide dihydrochloride

Step A

N-(2,3-dihydro-1H-inden-4-yl)-N-{2-[1,3-dihydro-2H-isoindol-2-yl(methyl)amino]-2-oxoethyl}glycine Using the compound (500 mg, 2.01 mmol) of Reference Example 111 and the compound (483 mg, 2.61 mmol) of Reference Example 17, and according to the method of Example 1, step A, the title compound (680 mg, yield 89%) was obtained as a pale-yellow amorphous solid ¹H-NMR (300 MHz, CDCl₃); δ (ppm) 2.04 (quintet, J=7.5, 2H), 2.87 (t, J=7.5, 2H), 2.90 (t, J=7.5, 2H), 3.07 (s, 3H), 4.04 (s, 2H), 4.23 (d, J=11.7, 2H), 4.33 (d, J=11.7, 2H), 4.58 (s, 2H), 6.73 (d, J=7.8, 1H), 6.88 (d, J=7.2, 1H), 7.05 (d, J=7.7, 1H), 7.20-7.35 (m, 4H).

Step B

N²-(2,3-dihydro-1H-inden-4-yl)-N²-{2-[1,3-dihydro-2H-isoindol-2-yl(methyl)amino]-2-oxoethyl}-N¹-[2-(isopropylamino)ethyl]glycinamide dihydrochloride Using the compound (680 mg, 1.79 mmol) obtained in step A and the compound (544 mg, 2.69 mmol) of Reference Example 3, and according to the method of Example 1, step B, Example 1, step C, the title compound (777 mg, yield 81%) was obtained as a pale-bistered solid.

¹H-NMR (300 MHz, DMSO-d₆); δ (ppm) 1.19 (d, J=6.5, 6H), 1.91 (quintet, J=7.1, 2H), 2.76 (t, J=7.3, 2H), 2.80-2.90 (m, 4H), 2.93 (s, 3H), 3.20-3.30 (m, 1H), 3.38-3.45 (m, 2H), 3.95 (s, 2H), 4.18 (d, J=11.6, 2H), 4.31 (d, J=11.6, 2H), 4.47 (s, 2H), 6.47 (d, J=8.1, 1H), 6.72 (d, J=7.3, 1H), 6.96 (t, J=7.7, 1H), 7.25-7.35 (m, 4H), 8.58 (t, J=5.7, 1H), 8.92 (brs, 2H).

Example 170

N²-(5-cyano-2,3-dihydro-1-benzofuran-7-yl)-N²-{2-[1,3-dihydro-2H-isoindol-2-yl(methyl)amino]-2-oxoethyl}-N¹-[2-(isopropylamino)ethyl]glycinamide dihydrochloride

Step A

N-(5-cyano-2,3-dihydro-1-benzofuran-7-yl)-N-{2-[1,3-dihydro-2H-isoindol-2-yl(methyl)amino]-2-oxoethyl}glycine Using the compound (938 mg, 3.40 mmol) of Reference Example 112 and the compound (942 mg, 5.10 mmol) of Reference Example 17, and according to the method of Example 4, step A, the title compound (1.05 g, yield 76%) was obtained as a pale-bistered solid.

$^1$H-NMR (300 MHz, DMSO-$d_6$); δ (ppm) 2.91 (s, 3H), 3.13 (t, J=8.7, 2H), 4.12 (s, 2H), 4.18 (d, J=11.7, 2H), 4.30 (d, J=11.7, 2H), 4.51-4.59 (m, 2H), 4.52 (s, 2H), 6.71 (d, J=1.0, 1H), 7.08 (s, 1H), 7.22-7.32 (m, 4H), 12.66 (brs, 1H).

Step B

N²-(5-cyano-2,3-dihydro-1-benzofuran-7-yl)-N²-{2-[1,3-dihydro-2H-1-isoindol-2-yl(methyl)amino]-2-oxoethyl}-N¹-{2-[(tert-butoxycarbonyl)(isopropyl)amino]ethyl}glycinamide Using the compound (500 mg, 1.23 mmol) obtained in step A and the compound (373 mg, 1.85 mmol) of Reference Example 3, and according to the method of Example 1, step C, the title compound (726 mg, yield 100%) was obtained as a bistered solid.

$^1$H-NMR (300 MHz, CDCl$_3$); δ (ppm) 1.13 (d, J=6.0, 6H), 1.42 (brs, 9H), 3.00 (s, 3H), 3.01-3.25 (m, 2H), 3.18 (t, J=8.9, 2H), 3.34-3.41 (m, 2H), 3.60-3.69 (m, 1H), 3.99 (s, 2H), 4.25 (d, J=11.7, 2H), 4.34 (d, J=11.7, 2H), 4.53 (s, 2H), 4.57 (t, J=9.0, 2H), 6.68 (d, J=1.0, 1H), 6.99 (s, 1H), 7.22-7.32 (m, 4H), 8.21-8.84 (broad, 1H).

Step C

N²-(5-cyano-2,3-dihydro-1-benzofuran-7-yl)-N²-{2-[1,3-dihydro-2H-isoindol-2-yl(methyl)amino]-2-oxoethyl}-N¹-[2-(isopropylamino)ethyl]glycinamide dihydrochloride Using the compound (225 mg, 0.38 mmol) obtained in step B and according to the method of Example 1, step C, the title compound (200 mg, yield 94%) was obtained as a bistered solid.

$^1$H-NMR (300 MHz, DMSO-$d_6$); δ (ppm) 1.20 (d, J=6.3, 6H), 2.86-2.94 (m, 2H), 2.93 (s, 3H), 3.15 (t, J=8.7, 2H), 3.20-3.35 (m, 1H), 3.36-3.48 (m, 2H), 3.97 (s, 2H), 4.20 (d, J=11.7, 2H), 4.32 (d, J=11.7, 2H), 4.55 (t, J=8.7, 2H), 4.63 (s, 2H), 6.64 (s, 1H), 7.09 (s, 1H), 7.23-7.34 (m, 4H), 8.68 (t, J=5.7, 1H), 8.92 (brs, 2H).

Example 171

N²-(5-cyano-2,3-dihydro-1-benzofuran-7-yl)-N²-{2-[1,3-dihydro-2H-isoindol-2-yl(methyl)amino]-2-oxoethyl}-N¹-[2-(ethylamino)ethyl]glycinamide dihydrochloride

Step A

N²-(5-cyano-2,3-dihydro-1-benzofuran-7-yl)-N²-{2-[1,3-dihydro-2H-isoindol-2-yl(methyl)amino]-2-oxoethyl}-N¹-{2-[(tert-butoxycarbonyl)(ethyl)amino]ethyl}glycinamide Using the compound (550 mg, 1.35 mmol) of Example 170, step A, and the compound (382 mg, 2.03 mmol) of Reference Example 2, and according to the method of Example 1, step B, the title compound (693 mg, yield 89%) was obtained as a pale-bistered solid.

$^1$H-NMR (300 MHz, CDCl$_3$); δ (ppm) 1.05 (t, J=7.0, 3H), 1.41 (s, 9H), 3.00 (s, 3H), 3.11-3.28 (m, 6H), 3.35-3.41 (m, 2H), 3.99 (s, 2H), 4.26 (d, J=11.7, 2H), 4.34 (d, J=11.7, 2H), 4.53 (s, 2H), 4.57 (t, J=8.9, 2H), 6.67 (s, 1H), 6.99 (s, 1H), 7.22-7.32 (m, 4H), 8.40-8.89 (broad, 1H).

Step B

N²-(5-cyano-2,3-dihydro-1-benzofuran-7-yl)-N²-{2-[1,3-dihydro-2H-isoindol-2-yl(methyl)amino]-2-oxoethyl}-N¹-[2-(ethylamino)ethyl]glycinamide dihydrochloride Using the compound (192 mg, 0.33 mmol) obtained in step A and according to the method of Example 1, step C, the title compound (170 mg, yield 94%) was obtained as a bistered solid.

$^1$H-NMR (300 MHz, DMSO-$d_6$); δ (ppm) 1.17 (t, J=7.2, 3H), 2.79-3.00 (m, 4H), 2.92 (s, 3H), 3.14 (t, J=8.7, 2H), 3.34-3.47 (m, 2H), 3.97 (s, 2H), 4.20 (d, J=11.7, 2H), 4.32 (d, J=11.6, 2H), 4.55 (t, J=8.7, 2H), 4.65 (s, 2H), 6.63 (d, J=1.0, 1H), 7.09 (s, 1H), 7.23-7.33 (m, 4H), 8.68 (t, J=5.7, 1H), 8.96 (brs, 2H).

Example 172

N²-{2-[1,3-dihydro-2H-isoindol-2-yl(methyl)amino]-2-oxoethyl}-N²-[5-(5-methyl-1,2,4-oxadiazol-3-yl)-2,3-dihydro-1-benzofuran-7-yl]-N¹-[2-(isopropylamino)ethyl]glycinamide dihydrochloride Using the compound (500 mg, 0.85 mmol) of Example 170, step B and according to the methods of Reference Example 62, step A, and Example 1, step C, the title compound (266 mg, yield 51%) was obtained as a colorless solid.

$^1$H-NMR (300 MHz, DMSO-$d_6$); δ (ppm) 1.16 (d, J=6.5, 6H), 2.63 (s, 3H), 2.80-2.93 (m, 2H), 2.94 (s, 3H), 3.14-3.28 (m, 1H), 3.18 (t, J=9.1, 2H), 3.34-3.40 (m, 2H), 4.00 (s, 2H), 4.23 (d, J=11.8, 2H), 4.35 (d, J=11.8, 2H), 4.54 (t, J=8.6, 2H), 4.68 (s, 2H), 6.97 (d, J=1.1, 1H), 7.24-7.35 (m, 5H), 8.64 (brs, 2H), 8.80-8.85 (m, 1H).

Example 173

N²-{2-[1,3-dihydro-2H-isoindol-2-yl(methyl)amino]-2-oxoethyl}-N²-[5-(5-methyl-1,2,4-oxadiazol-3-yl)-2,3-dihydro-1-benzofuran-7-yl]-N¹-[2-(ethylamino)ethyl]glycinamide dihydrochloride Using the compound (500 mg, 0.87 mmol) of Example 171, step A and according to the methods of Reference Example 62, step A, and Example 1, step C, the title compound (191 mg, yield 36%) was obtained as a pale-bistered solid.

$^1$H-NMR (300 MHz, DMSO-$d_6$); δ (ppm) 1.14 (t, J=6.9, 3H), 2.63 (s, 3H), 2.79-3.00 (m, 4H), 2.94 (s, 3H), 3.18 (t, J=8.7, 2H), 3.33-3.41 (m, 2H), 4.00 (s, 2H), 4.24 (d, J=11.7, 2H), 4.36 (d, J=11.7, 2H), 4.54 (t, J=8.7, 2H), 4.69 (s, 2H), 6.98 (s, 1H), 7.24-7.35 (m, 5H), 8.61-8.85 (m, 3H).

Example 174

$N^2$-{2-[1,3-dihydro-2H-isoindol-2-yl(methyl)amino]-2-oxoethyl}-$N^2$-(1,7-dimethyl-2-oxo-1,2,3,4-tetrahydroquinolin-6-yl)-$N^1$-[2-(isopropylamino)ethyl]glycinamide dihydrochloride

Step A

N-{2-[1,3-dihydro-2H-isoindol-2-yl(methyl)amino]-2-oxoethyl}-N-(1,7-dimethyl-2-oxo-1,2,3,4-tetrahydroquinolin-6-yl)glycine Using the compound (1.05 g, 3.43 mmol) of Reference Example 113 and the compound (950 mg, 5.15 mmol) of Reference Example 17, and according to the method of Example 4, step A, the title compound (1.20 g, yield 80%) was obtained as a bistered amorphous solid.

$^1$H-NMR (300 MHz, DMSO-$d_6$); δ (ppm) 2.24 (s, 3H), 2.41-2.52 (m, 2H), 2.69-2.78 (m, 2H), 2.88 (s, 3H), 3.20 (s, 3H), 3.92 (s, 2H), 4.09 (d, J=11.7, 2H), 4.21 (s, 2H), 4.24 (d, J=11.7, 2H), 6.85 (s, 1H), 7.02 (s, 1H), 7.21-7.30 (m, 4H), 12.49 (brs, 1H).

Step B $N^2$-{2-[1,3-dihydro-2H-isoindol-2-yl(methyl)amino]-2-oxoethyl}-$N^2$-(1,7-dimethyl-2-oxo-1,2,3,4-tetrahydroquinolin-6-yl)-$N^1$-{2-[(tert-butoxycarbonyl)(isopropyl)amino]ethyl}glycinamide Using the compound (600 mg, 1.37 mmol) obtained in step A and the compound (417 mg, 2.06 mmol) of Reference Example 3, and according to the method of Example 1, step B, the title compound (723 mg, yield 85%) was obtained as a bistered amorphous solid.

$^1$H-NMR (300 MHz, DMSO-$d_6$); δ (ppm) 1.03 (d, J=6.6, 6H), 1.38 (s, 9H), 2.71 (s, 3H), 2.43-2.50 (m, 2H), 2.70-2.78 (m, 2H), 2.88 (s, 3H), 2.96-3.10 (m, 2H), 3.12-3.21 (m, 2H), 3.20 (s, 3H), 3.71 (s, 2H), 4.06 (d, J=11.7, 2H), 4.17 (s, 2H), 4.24 (d, J=11.7, 2H), 6.86 (s, 1H), 7.07 (s, 1H), 7.20-7.29 (m, 4H), 8.18-8.23 (m, 1H).

Step C $N^2$-{2-[1,3-dihydro-2H-isoindol-2-yl(methyl)amino]-2-oxoethyl}-$N^2$-(1,7-dimethyl-2-oxo-1,2,3,4-tetrahydroquinolin-6-yl)-$N^1$-[2-(isopropylamino)ethyl]glycinamide dihydrochloride Using the compound (723 mg, 1.17 mmol) obtained in step B and according to the method of Example 1, step C, the title compound (610 mg, yield 88%) was obtained as a pale-bistered amorphous solid.

$^1$H-NMR (300 MHz, DMSO-$d_6$); δ (ppm) 1.21 (d, J=6.6, 6H), 2.32 (s, 3H), 2.44-2.51 (m, 2H), 2.72-2.79 (m, 2H), 2.79-2.95 (m, 2H), 2.88 (s, 3H), 3.16-3.28 (m, 1H), 3.21 (s, 3H), 3.34-3.35 (m, 2H), 3.88 (s, 2H), 4.10 (d, J=11.7, 2H), 4.24 (d, J=11.7, 2H), 4.32 (s, 2H), 6.88 (s, 1H), 7.16 (s, 1H), 7.21-7.30 (m, 4H), 8.48-8.54 (m, 1H), 9.02 (brs, 2H).

Example 175

$N^2$-{2-[1,3-dihydro-2H-isoindol-2-yl(methyl)amino]-2-oxoethyl}-$N^2$-(1,7-dimethyl-2-oxo-1,2,3,4-tetrahydroquinolin-6-yl)-$N^1$-[2-(ethylamino)ethyl]glycinamide dihydrochloride

Step A $N^2$-{2-[1,3-dihydro-2H-isoindol-2-yl(methyl)amino]-2-oxoethyl}-$N^2$-(1,7-dimethyl-2-oxo-1,2,3,4-tetrahydroquinolin-6-yl)-$N^1$-{2-[(tert-butoxycarbonyl)(ethyl)amino]ethyl}glycinamide Using the compound (600 mg, 1.37 mmol) of Example 174, step A, and the compound (387 mg, 2.06 mmol) of Reference Example 2, and according to the method of Example 1, step B, the title compound (741 mg, yield 89%) was obtained as a bistered amorphous solid.

$^1$H-NMR (300 MHz, DMSO-$d_6$); δ (ppm) 0.96 (t, J=6.8, 3H), 1.36 (s, 9H), 2.26 (s, 3H), 2.42-2.51 (m, 2H), 2.69-2.78 (m, 2H), 2.87 (s, 3H), 3.01-3.28 (m, 6H), 3.20 (s, 3H), 3.71 (s, 2H), 4.06 (d, J=11.7, 2H), 4.16 (s, 2H), 4.24 (d, J=11.7, 2H), 6.85 (s, 1H), 7.07 (s, 1H), 7.19-7.30 (m, 4H), 8.14-8.19 (m, 1H).

Step B $N^2$-{2-[1,3-dihydro-2H-isoindol-2-yl(methyl)amino]-2-oxoethyl}-$N^2$-(1,7-dimethyl-2-oxo-1,2,3,4-tetrahydroquinolin-6-yl)-$N^1$-[2-(ethylamino)ethyl]glycinamide dihydrochloride Using the compound (741 mg, 1.22 mmol) obtained in step A and according to the method of Example 1, step C, the title compound (610 mg, yield 86%) was obtained as a pale-bistered amorphous solid.

$^1$H-NMR (300 MHz, DMSO-$d_6$); δ (ppm) 1.18 (t, J=7.2, 3H), 2.32 (s, 3H), 2.44-2.51 (m, 2H), 2.72-2.80 (m, 2H), 2.84-3.00 (m, 4H), 2.88 (s, 3H), 3.21 (s, 3H), 3.35-3.42 (m, 2H), 3.89 (s, 2H), 4.10 (d, J=11.7, 2H), 4.25 (d, J=11.7, 2H), 4.34 (s, 2H), 6.88 (s, 1H), 7.17 (s, 1H), 7.21-7.30 (m, 4H), 8.52 (t, J=5.7, 1H), 9.04 (brs, 2H).

Example 176

$N^2$-{2-[1,3-dihydro-2H-isoindol-2-yl(methyl)amino]-2-oxoethyl}-$N^2$-(1-ethyl-7-methyl-2-oxo-1,2,3,4-tetrahydroquinolin-6-yl)-$N^1$-[2-(isopropylamino)ethyl]glycinamide hydrochloride

Step A

N-{2-[1,3-dihydro-2H-isoindol-2-yl(methyl)amino]-2-oxoethyl}-N-(1-ethyl-7-methyl-2-oxo-1,2,3,4-tetrahydroquinolin-6-yl)glycine Using the compound (1.00 g, 3.12 mmol) of Reference Example 114 and the compound (864 mg, 4.68 mmol) of Reference Example 17, and according to the method of Example 4, step A, the title compound (1.14 g, yield 81%) was obtained as a pale-bistered amorphous solid.

$^1$H-NMR (300 MHz, DMSO-$d_6$); δ (ppm) 1.11 (t, J=6.9, 3H), 2.25 (s, 3H), 2.42-2.53 (m, 2H), 2.68-2.74 (m, 2H), 2.88

(s, 3H), 3.81-3.90 (m, 2H), 3.92 (s, 2H), 4.09 (d, J=11.7, 2H), 4.21 (s, 2H), 4.24 (d, J=12.0, 2H), 6.87 (s, 1H), 7.01 (s, 1H), 7.21-7.32 (m, 4H), 12.21-12.80 (broad, 1H).

Step B

N²-{2-[1,3-dihydro-2H-isoindol-2-yl(methyl) amino]-2-oxoethyl}-N²-(1-ethyl-7-methyl-2-oxo-1, 2,3,4-tetrahydroquinolin-6-yl)-N¹-{2-[(tert-butoxy-carbonyl)(isopropyl)amino]ethyl}glycinamide Using the compound (570 mg, 1.27 mmol) obtained in step A and the compound (385 mg, 1.91 mmol) of Reference Example 3, and according to the method of Example 1, step B, the title compound (724 mg, yield 90%) was obtained as a pale-yellow amorphous solid
¹H-NMR (300 MHz, DMSO-d₆); δ (ppm) 1.02 (d, J=6.0, 6H), 1.10 (t, J=6.9, 3H), 1.38 (s, 9H), 2.27 (s, 3H), 2.41-2.48 (m, 2H), 2.68-2.75 (m, 2H), 2.70 (s, 3H), 2.70-3.08 (m, 2H), 3.12-3.19 (m, 2H), 3.72 (s, 2H), 3.81-3.88 (m, 2H), 4.00-4.10 (m, 3H), 4.24 (d, J=11.7, 2H), 6.89 (s, 1H), 7.06 (s, 1H), 7.22-7.29 (m, 4H), 8.17-8.21 (m, 1H).

Step C

N²-{2-[1,3-dihydro-2H-isoindol-2-yl(methyl) amino]-2-oxoethyl}-N²-(1-ethyl-7-methyl-2-oxo-1, 2,3,4-tetrahydroquinolin-6-yl)-N¹-[2-(isopropy-lamino)ethyl]glycinamide hydrochloride Using the compound (724 mg, 1.14 mmol) obtained in step B and according to the method of Example 57, step B, the title compound (633 mg, yield 99%) was obtained as a pale-bistered amorphous solid.
¹H-NMR (300 MHz, DMSO-d₆); δ (ppm) 1.11 (t, J=6.9, 3H), 1.19 (d, J=6.6, 6H), 2.28 (s, 3H), 2.42-2.50 (m, 2H), 2.72-2.75 (m, 2H), 2.87-2.95 (m, 2H), 2.88 (s, 3H), 3.20-3.45 (m, 3H), 3.79 (s, 2H), 3.80-3.90 (m, 2H), 4.07 (d, J=11.7, 2H), 4.20 (s, 2H), 4.24 (d, J=11.7, 2H), 6.88 (s, 1H), 7.06 (s, 1H), 7.25 (s, 4H), 8.41 (t, J=5.7, 1H), 8.75 (brs, 2H).

Example 177

N²-{2-[1,3-dihydro-2H-isoindol-2-yl(methyl) amino]-2-oxoethyl}-N²-(1-ethyl-7-methyl-2-oxo-1, 2,3,4-tetrahydroquinolin-6-yl)-N¹-[2-(ethylamino) ethyl]glycinamide hydrochloride Step A N²-{2-[1,3-dihydro-2H-isoindol-2-yl(methyl) amino]-2-oxoethyl}-N²-(1-ethyl-7-methyl-2-oxo-1, 2,3,4-tetrahydroquinolin-6-yl)-N¹-{2-[(tert-butoxy-carbonyl)(ethyl)amino]ethyl}glycinamide Using the compound (570 mg, 1.27 mmol) of Example 176, step A, and the compound (359 mg, 1.91 mmol) of Reference Example 2, and according to the method of Example 1, step B, the title compound (680 mg, yield 86%) was obtained as a bistered amorphous solid.
¹H-NMR (300 MHz, DMSO-d₆); δ (ppm) 0.95 (t, J=5.8, 3H), 1.10 (t, J=7.1, 3H), 1.36 (s, 9H), 2.27 (s, 3H), 2.41-2.50 (m, 2H), 2.69-2.73 (m, 2H), 2.88 (s, 3H), 3.00-3.25 (m, 6H), 3.17 (s, 2H), 3.81-3.89 (m, 2H), 4.07 (d, J=11.7, 2H), 4.16 (s, 2H), 4.24 (d, J=11.7, 2H), 6.88 (s, 1H), 7.06 (s, 1H), 7.21-7.29 (m, 4H), 8.15-8.19 (m, 1H).

Step B

N²-{2-[1,3-dihydro-2H-isoindol-2-yl(methyl) amino]-2-oxoethyl}-N²-(1-ethyl-7-methyl-2-oxo-1, 2,3,4-tetrahydroquinolin-6-yl)-N¹-[2-(ethylamino) ethyl]glycinamide hydrochloride Using the compound (680 mg, 1.10 mmol) obtained in step A and according to the method of Example 57, step B, the title compound (602 mg, yield 100%) was obtained as a pale-bistered solid.
¹H-NMR (300 MHz, DMSO-d₆); δ (ppm) 1.08-1.20 (m, 6H), 2.28 (s, 3H), 2.41-2.50 (m, 2H), 2.69-2.76 (m, 2H), 2.84-2.93 (m, 2H), 2.88 (s, 3H), 3.21-3.42 (m, 2H), 3.79 (s, 2H), 3.81-3.87 (m, 2H), 4.07 (d, J=11.7, 2H), 4.20 (s, 2H), 4.24 (d, J=11.7, 2H), 6.88 (s, 1H), 7.06 (s, 1H), 7.21-7.30 (m, 4H), 8.40 (t, J=6.0, 1H), 8.72 (brs, 2H).

Example 178

N²-{2-[1,3-dihydro-2H-isoindol-2-yl(methyl) amino]-2-oxoethyl}-N²-phenyl-N¹-[2-(isopropy-lamino)ethyl]glycinamide hydrochloride Step A N-{2-[1,3-dihydro-2H-isoindol-2-yl(methyl)amino]-2-oxoethyl}-N-phenylglycine Using N-phenyliminodiacetic acid (1.00 g, 4.78 mmol) and the compound (1.32 g, 7.17 mmol) of Reference Example 17, and according to the method of Example 4, step A, the title compound (990 mg, yield 61%) was obtained as a pale-gray solid.
¹H-NMR (300 MHz, DMSO-d₆); δ (ppm) 2.97 (s, 3H), 4.11 (s, 2H), 4.31 (d, J=12.0, 2H), 4.37 (d, J=12.0, 2H), 4.56 (s, 2H), 6.48 (d, J=8.4, 2H), 6.67 (t, J=7.2, 1H), 7.13-7.21 (m, 2H), 7.24-7.35 (m, 4H), 13.14 (brs, 1H).

Step B

N²-{2-[1,3-dihydro-2H-isoindol-2-yl(methyl) amino]-2-oxoethyl}-N²-phenyl-N¹-{2-[(tert-butoxy-carbonyl)(isopropyl)amino]ethyl}glycinamide Using the compound (495 mg, 1.46 mmol) obtained in step A and the compound (443 mg, 2.19 mmol) of Reference Example 3, and according to the method of Example 1, step B, the title compound (744 mg, yield 97%) was obtained as a bistered amorphous solid.
¹H-NMR (300 MHz, DMSO-d₆); δ (ppm) 1.01 (d, J=6.0, 6H), 1.37 (s, 9H), 2.88-3.02 (m, 2H), 2.97 (s, 3H), 3.00-3.15 (m, 2H), 3.91 (s, 2H), 3.98-4.08 (m, 1H), 4.31 (d, J=11.7, 2H), 4.38 (d, J=11.7, 2H), 4.59 (s, 2H), 6.41 (d, J=8.4, 2H), 6.66 (t, J=7.2, 1H), 7.17 (t, J=7.8, 2H), 7.24-7.35 (m, 4H), 8.95-9.03 (broad, 1H).

Step C

N²-{2-[1,3-dihydro-2H-isoindol-2-yl(methyl) amino]-2-oxoethyl}-N²-phenyl-N¹-[2-(isopropy-lamino)ethyl]glycinamide hydrochloride Using the compound (744 mg, 1.42 mmol) obtained in step B and according to the method of Example 57, step B, the title compound (421 mg, yield 64%) was obtained as a colorless solid.

¹H-NMR (300 MHz, DMSO-d₆); δ (ppm) 1.18 (d, J=6.3, 6H), 2.87 (t, J=6.3, 2H), 2.97 (s, 3H), 3.16-3.40 (m, 3H), 3.97 (s, 2H), 4.29-4.41 (m, 4H), 4.63 (s, 2H), 6.44 (d, J=8.4, 2H), 6.67 (t, J=7.5, 1H), 7.17 (t, J=7.8, 2H), 7.24-7.35 (m, 4H), 8.72 (brs, 2H), 9.05 (t, J=5.4, 1H).

Example 179

N²-{2-[1,3-dihydro-2H-isoindol-2-yl(methyl)amino]-2-oxoethyl}-N²-phenyl-N¹-[2-(ethylamino)ethyl]glycinamide hydrochloride Step A N²-{2-[1,3-dihydro-2H-isoindol-2-yl(methyl)amino]-2-oxoethyl}-N²-phenyl-N¹-{2-[(tert-butoxycarbonyl)(ethyl)amino]ethyl}glycinamide Using the compound (495 mg, 1.46 mmol) of Example 178, step A, and the compound (412.0 mg, 2.19 mmol) of Reference Example 2, and according to the method of Example 1, step B, the title compound (724 mg, yield 97%) was obtained as a pale-bistered amorphous solid.
¹H-NMR (300 MHz, CDCl₃); δ (ppm) 0.91 (t, J=7.2, 3H), 1.36 (s, 9H), 2.88-3.24 (m, 6H), 2.98 (s, 3H), 3.91 (s, 2H), 4.31 (d, J=12.0, 2H), 4.37 (d, J=12.0, 2H), 4.59 (s, 2H), 6.39 (d, J=8.4, 2H), 6.66 (t, J=7.2, 1H), 7.16 (t, J=8.1, 2H), 7.24-7.35 (m, 4H), 8.93-9.05 (broad, 1H).

Step B

N²-{2-[1,3-dihydro-2H-isoindol-2-yl(methyl)amino]-2-oxoethyl}-N²-phenyl-N¹-[2-(ethylamino)ethyl]glycinamide hydrochloride Using the compound (724 mg, 1.42 mmol) obtained in step A and according to the method of Example 57, step B, the title compound (464 mg, yield 73%) was obtained as a colorless solid.
¹H-NMR (300 MHz, DMSO-d₆); δ (ppm) 1.14 (t, J=7.2, 3H), 2.82-2.96 (m, 4H), 2.97 (s, 3H), 3.31-3.38 (m, 2H), 3.97 (s, 2H), 4.29-4.42 (m, 4H), 4.64 (s, 2H), 6.43 (d, J=8.2, 2H), 6.67 (t, J=7.2, 1H), 7.17 (t, J=7.7, 2H), 7.24-7.36 (m, 4H), 8.70 (brs, 2H), 9.07 (t, J=5.5, 1H).

Example 180

N²-{2-[1,3-dihydro-2H-isoindol-2-yl(methyl)amino]-2-oxoethyl}-N²-(3,6-dimethyl-1,2-benzisoxazol-5-yl)-N¹-[2-(isopropylamino)ethyl]glycinamide dihydrochloride Step A N-{2-[1,3-dihydro-2H-isoindol-2-yl(methyl)amino]-2-oxoethyl}-N-(3,6-dimethyl-1,2-benzisoxazol-5-yl)glycine Using the compound (958 mg, 3.44 mmol) of Reference Example 116 and the compound (983 mg, 5.32 mmol) of Reference Example 17, and according to the method of Example 4, step A, the title compound (1.00 g, yield 71%) was obtained as a colorless solid.
¹H-NMR (300 MHz, DMSO-d₆); δ (ppm) 2.42 (s, 3H), 2.47 (s, 3H), 2.86 (s, 3H), 3.99 (s, 2H), 4.09 (d, J=11.7, 2H), 4.23 (d, J=11.7, 2H), 4.27 (s, 2H), 7.25 (broad, 4H), 7.46 (s, 1H), 7.60 (s, 1H), 12.44 (brs, 1H).

Step B

N²-{2-[1,3-dihydro-2H-isoindol-2-yl(methyl)amino]-2-oxoethyl}-N²-(3,6-dimethyl-1,2-benzisoxazol-5-yl)-N¹-{2-[(tert-butoxycarbonyl)(isopropyl)amino]ethyl}glycinamide Using the compound (0.50 g, 1.22 mmol) obtained in step A and the compound (0.38 g, 1.88 mmol) of Reference Example 3, and according to the method of Example 1, step B, the title compound (0.88 g, yield>100%) was obtained as a colorless solid.
¹H-NMR (300 MHz, CDCl₃); δ (ppm) 1.10 (d, J=6.8, 6H), 1.44-1.49 (brs, 9H), 2.49 (s, 6H), 2.96 (s, 3H), 3.16 (brs, 2H), 3.29-3.44 (m, 2H), 3.87 (s, 2H), 4.03-4.25 (m, 7H), 7.17-7.28 (m, 4H), 7.34 (s, 1H), 7.59 (s, 1H), 8.1-8.5 (broad, 1H).

Step C

N²-{2-[1,3-dihydro-2H-isoindol-2-yl(methyl)amino]-2-oxoethyl}-N²-(3,6-dimethyl-1,2-benzisoxazol-5-yl)-N¹-[2-(isopropylamino)ethyl]glycinamide dihydrochloride Using the compound (0.88 g) obtained in step B and according to the method of Example 1, step C, the title compound (0.74 g, yield 93%) was obtained as a colorless solid.
¹H-NMR (300 MHz, DMSO-d₆); δ (ppm) 1.18 (d, J=6.3, 6H), 2.45 (s, 3H), 2.47 (s, 3H), 2.8-3.0 (m, 5H), 3.20-3.42 (m, 3H), 3.87 (s, 2H), 4.08 (d, J=11.7, 2H), 4.23 (d, J=11.7, 2H), 4.30 (s, 2H), 7.25 (broad, 4H), 7.47 (s, 1H), 7.67 (s, 1H), 8.42 (t, J=5.7, 1H), 8.92 (brs, 2H).

Example 181

N²-{2-[1,3-dihydro-2H-isoindol-2-yl(methyl)amino]-2-oxoethyl}-N²-(3,6-dimethyl-1,2-benzisoxazol-5-yl)-N¹-[2-(ethylamino)ethyl]glycinamide hydrochloride Step A N²-{2-[1,3-dihydro-2H-isoindol-2-yl(methyl)amino]-2-oxoethyl}-N²-(3,6-dimethyl-1,2-benzisoxazol-5-yl)-N¹-{2-[(tert-butoxycarbonyl)(ethyl)amino]ethyl}glycinamide Using the compound (1.26 g, 3.08 mmol) of Example 180, step A, and the compound (843 mg, 4.48 mmol) of Reference Example 2, and according to the method of Example 1, step B, the title compound (1.30 g, yield 73%) was obtained as a colorless solid.
¹H-NMR (300 MHz, CDCl₃); δ (ppm) 1.03 (t, J=7.2, 3H), 1.42 (brs, 9H), 2.49 (s, 3H), 2.51 (s, 3H), 2.95 (s, 3H), 3.0-3.2 (m, 2H), 3.2-3.3 (m, 2H), 3.38-3.45 (m, 2H), 3.85 (s, 2H), 4.05 (d, J=11.4, 2H), 4.18 (s, 2H), 4.22 (d, J=11.4, 2H), 7.17-7.28 (m, 4H), 7.36 (s, 1H), 7.58 (s, 1H), 8.1-8.5 (broad, 1H).

Step B

N²-{2-[1,3-dihydro-2H-isoindol-2-yl(methyl)amino]-2-oxoethyl}-N²-(3,6-dimethyl-1,2-benzisoxazol-5-yl)-N¹-[2-(ethylamino)ethyl]glycinamide hydrochloride Using the compound (1.26 g, 2.18 mmol) obtained in step A and according to the method of Example 57, step B, the title compound (839 mg, yield 75%) was obtained as a colorless solid.
$^1$H-NMR (300 MHz, DMSO-d$_6$); δ (ppm) 1.14 (t, J=7.2, 3H), 2.45 (s, 3H), 2.47 (s, 3H), 2.8-3.0 (m, 4H), 2.87 (s, 3H), 3.0-3.4 (m, 2H), 3.86 (s, 2H), 4.07 (d, J=11.7, 2H), 4.23 (d, J=11.7, 2H), 4.27 (s, 2H), 7.25 (broad, 4H), 7.48 (s, 1H), 7.66 (s, 1H), 8.36 (t, J=5.7, 1H), 8.58 (brs, 2H).

Example 182

N²-(3,6-dimethyl-1,2-benzisoxazol-5-yl)-N²-{2-[(5-fluoro-1,3-dihydro-2H-isoindol-2-yl)(methyl)amino]-2-oxoethyl}-N¹-[2-(isopropylamino)ethyl]glycinamide dihydrochloride Step A N-(3,6-dimethyl-1,2-benzisoxazol-5-yl)-N-{2-[(5-fluoro-1,3-dihydro-2H-isoindol-2-yl)(methyl)amino]-2-oxoethyl}glycine Using the compound (893 mg, 3.21 mmol) of Reference Example 116 and the compound (743 mg, 3.67 mmol) of Reference Example 19, and according to the method of Example 4, step A, the title compound (1.21 g, yield 88%) was obtained as a pale-yellow amorphous solid
$^1$H-NMR (300 MHz, DMSO-d$_6$); δ (ppm) 2.42 (s, 3H), 2.47 (s, 3H), 2.86 (s, 3H), 3.99 (s, 2H), 4.0-4.2 (m, 4H), 4.26 (s, 2H), 7.03-7.15 (m, 2H), 7.26-7.31 (m, 1H), 7.46 (s, 1H), 7.60 (s, 1H), 12.42 (brs, 1H).

Step B

N²-(3,6-dimethyl-1,2-benzisoxazol-5-yl)-N²-{2-[(5-fluoro-1,3-dihydro-2H-isoindol-2-yl)(methyl)amino]-2-oxoethyl}-N¹-{2-[(tert-butoxycarbonyl)(isopropyl)amino]ethyl}glycinamide Using the compound (580 mg, 1.36 mmol) obtained in step A and the compound (390 mg, 1.93 mmol) of Reference Example 3, and according to the method of Example 1, step B, the title compound (746 mg, yield 90%) was obtained as a colorless solid.
$^1$H-NMR (300 MHz, CDCl$_3$); δ (ppm) 1.10 (d, J=6.6, 6H), 1.44 (brs, 9H), 2.50 (s, 3H), 2.51 (s, 3H), 2.94 (s, 3H), 3.0-3.2 (m, 2H), 3.35-3.43 (m, 2H), 3.88 (s, 2H), 3.9-4.3 (m, 5H), 4.16 (s, 2H), 6.89-6.99 (m, 2H), 7.11-7.16 (m, 1H), 7.36 (s, 1H), 7.58 (s, 1H), 7.9-8.5 (broad, 1H).

Step C

N²-(3,6-dimethyl-1,2-benzisoxazol-5-yl)-N²-{2-[(5-fluoro-1,3-dihydro-2H-isoindol-2-yl)(methyl)amino]-2-oxoethyl}-N¹-[2-(isopropylamino)ethyl]glycinamide dihydrochloride Using the compound (730 mg, 1.20 mmol) obtained in step B and according to the method of Example 1, step C, the title compound (696 mg, yield 99%) was obtained as a colorless solid.
$^1$H-NMR (300 MHz, DMSO-d$_6$); δ (ppm) 1.18 (d, J=6.6, 6H), 2.45 (s, 3H), 2.47 (s, 3H), 2.8-3.0 (m, 2H), 2.86 (s, 3H), 3.1-3.3 (m, 1H), 3.34-3.57 (m, 2H), 3.86 (s, 2H), 4.0-4.3 (m, 4H), 4.27 (s, 2H), 7.03-7.15 (m, 2H), 7.26-7.31 (m, 1H), 7.48 (s, 1H), 7.66 (s, 1H), 8.38 (t, J=5.7, 1H), 8.73 (brs, 2H).

Example 183

N²-(3,6-dimethyl-1,2-benzisoxazol-5-yl)-N²-{2-[(5-fluoro-1,3-dihydro-2H-isoindol-2-yl)(methyl)amino]-2-oxoethyl}-N¹-[2-(ethylamino)ethyl]glycinamide dihydrochloride Step A N²-(3,6-dimethyl-1,2-benzisoxazol-5-yl)-N²-{2-[(5-fluoro-1,3-dihydro-2H-isoindol-2-yl)(methyl)amino]-2-oxoethyl}-N¹-{2-[(tert-butoxycarbonyl)(ethyl)amino]ethyl}glycinamide Using the compound (585 mg, 1.37 mmol) of Example 182, step A, and the compound (371 mg, 1.97 mmol) of Reference Example 2, and according to the method of Example 1, step B, the title compound (677 mg, yield 83%) was obtained as a colorless solid.
$^1$H-NMR (300 MHz, CDCl$_3$); δ (ppm) 1.03 (t, J=7.2, 3H), 1.42 (brs, 9H), 2.49 (s, 3H), 2.51 (s, 3H), 2.94 (s, 3H), 3.0-3.2 (m, 2H), 3.2-3.3 (m, 2H), 3.38-3.45 (m, 2H), 3.86 (s, 2H), 3.9-4.3 (m, 4H), 4.16 (s, 2H), 6.88-6.99 (m, 2H), 7.11-7.16 (m, 1H), 7.36 (s, 1H), 7.58 (s, 1H), 8.0-8.5 (broad, 1H).

Step B

N²-(3,6-dimethyl-1,2-benzisoxazol-5-yl)-N²-{2-[(5-fluoro-1,3-dihydro-2H-isoindol-2-yl)(methyl)amino]-2-oxoethyl}-N¹-[2-(ethylamino)ethyl]glycinamide dihydrochloride Using the compound (655 mg, 1.10 mmol) obtained in step A and according to the method of Example 1, step C, the title compound (636 mg, yield>100%) was obtained as a colorless solid.
$^1$H-NMR (300 MHz, DMSO-d$_6$); δ (ppm) 1.15 (t, J=7.2, 3H), 2.45 (s, 3H), 2.47 (s, 3H), 2.8-3.0 (m, 4H), 2.86 (s, 3H), 3.34-3.42 (m, 2H), 3.86 (s, 2H), 4.0-4.3 (m, 4H), 4.27 (s, 2H), 7.03-7.16 (m, 2H), 7.26-7.31 (m, 1H), 7.48 (s, 1H), 7.66 (s, 1H), 8.37 (t, J=5.7, 1H), 8.74 (brs, 2H).

Example 184

N²-{2-[1,3-dihydro-2H-isoindol-2-yl(methyl)amino]-2-oxoethyl}-N²-(3,5-dimethyl-1,2-benzisoxazol-6-yl)-N¹-[2-(isopropylamino)ethyl]glycinamide dihydrochloride Step A N-{2-[1,3-dihydro-2H-isoindol-2-yl(methyl)amino]-2-oxoethyl}-N-(3,5-dimethyl-1,2-benzisoxazol-6-yl)glycine Using the compound (690 mg, 2.48 mmol) of Reference Example 117 and the compound (724 mg, 3.92 mmol) of Reference Example 17, and according to the method of Example 4, step A, the title compound (662 mg, yield 65%) was obtained as a colorless amorphous solid.

¹H-NMR (300 MHz, CDCl₃); δ (ppm) 2.40 (s, 3H), 2.51 (s, 3H), 3.08 (s, 3H), 4.02 (s, 2H), 4.19 (d, J=11.7, 2H), 4.31 (d, J=11.7, 2H), 4.38 (s, 2H), 7.2-7.3 (m, 4H), 7.36 (s, 1H), 7.40 (s, 1H), 13.3 (brs, 1H).

Step B

N²-{2-[1,3-dihydro-2H-isoindol-2-yl(methyl) amino]-2-oxoethyl}-N²-(3,5-dimethyl-1,2-benzisoxazol-6-yl)-N¹-{2-[(tert-butoxycarbonyl)(isopropyl) amino]ethyl}glycinamide Using the compound (308 mg, 0.754 mmol) obtained in step A and the compound (274 mg, 1.35 mmol) of Reference Example 3, and according to the method of Example 1, step B, the title compound (434 mg, yield 97%) was obtained as a colorless amorphous solid.

¹H-NMR (300 MHz, CDCl₃); δ (ppm) 1.09 (d, J=6.8, 6H), 1.43 (brs, 9H), 2.43 (s, 3H), 2.50 (s, 3H), 2.96 (s, 3H), 3.0-3.2 (m, 2H), 3.33-3.41 (m, 2H), 3.88 (s, 2H), 3.9-4.4 (broad, 1H), 4.17 (d, J=11.7, 2H), 4.28 (d, J=11.7, 2H), 4.30 (s, 2H), 7.2-7.3 (m, 5H), 7.37 (s, 1H), 7.8-8.4 (broad, 1H).

Step C

N²-{2-[1,3-dihydro-2H-isoindol-2-yl(methyl) amino]-2-oxoethyl}-N²-(3,5-dimethyl-1,2-benzisoxazol-6-yl)-N¹-[2-(isopropylamino)ethyl]glycinamide dihydrochloride Using the compound (432 mg, 0.729 mmol) obtained in step B and according to the method of Example 1, step C, the title compound (392 mg, yield 95%) was obtained as a colorless solid.

¹H-NMR (300 MHz, DMSO-d₆); δ (ppm) 1.18 (d, J=6.5, 6H), 2.36 (s, 3H), 2.45 (s, 3H), 2.8-3.0 (m, 2H), 2.89 (s, 3H), 3.1-3.3 (m, 1H), 3.34-3.42 (m, 2H), 3.96 (s, 2H), 4.14 (d, J=11.7, 2H), 4.27 (d, J=11.7, 2H), 4.39 (s, 2H), 7.2-7.3 (m, 4H), 7.22 (s, 1H), 7.52 (s, 1H), 8.32 (t, J=5.7, 1H), 8.74 (brs, 2H).

Example 185

N²-{2-[1,3-dihydro-2H-isoindol-2-yl(methyl) amino]-2-oxoethyl}-N²-(3,5-dimethyl-1,2-benzisoxazol-6-yl)-N¹-[2-(ethylamino)ethyl]glycinamide dihydrochloride Step A N²-{2-[1,3-dihydro-2H-isoindol-2-yl(methyl) amino]-2-oxoethyl}-N²-(3,5-dimethyl-1,2-benzisoxazol-6-yl)-N¹-{2-[(tert-butoxycarbonyl)(ethyl) amino]ethyl}glycinamide Using the compound (322 mg, 0.788 mmol) of Example 184, step A, and the compound (260 mg, 1.38 mmol) of Reference Example 2, and according to the method of Example 1, step B, the title compound (433 mg, yield 95%) was obtained as a colorless amorphous solid.

¹H-NMR (300 MHz, CDCl₃); δ (ppm) 1.00 (t, J=7.1, 3H), 1.42 (brs, 9H), 2.42 (s, 3H), 2.50 (s, 3H), 2.97 (s, 3H), 3.11 (q, J=7.1, 2H), 3.2-3.3 (m, 2H), 3.36-3.44 (m, 2H), 3.86 (s, 2H), 4.18 (d, J=11.7, 2H), 4.28 (d, J=11.7, 2H), 4.30 (s, 2H), 7.2-7.3 (s, 4H), 7.36 (s, 1H), 7.37 (s, 1H), 7.9-8.4 (broad, 1H).

Step B

N²-{2-[1,3-dihydro-2H-isoindol-2-yl(methyl) amino]-2-oxoethyl}-N²-(3,5-dimethyl-1,2-benzisoxazol-6-yl)-N¹-[2-(ethylamino)ethyl]glycinamide dihydrochloride Using the compound (428 mg, 0.740 mmol) obtained in step A and according to the method of Example 1, step C, the title compound (372 mg, yield 91%) was obtained as a pale-yellow solid.

¹H-NMR (300 MHz, DMSO-d₆); δ (ppm) 1.14 (t, J=7.0, 3H), 2.36 (s, 3H), 2.45 (s, 3H), 2.8-3.0 (m, 4H), 2.90 (s, 3H), 3.3-3.5 (m, 2H), 3.96 (s, 2H), 4.14 (d, J=11.7, 2H), 4.27 (d, J=11.7, 2H), 4.38 (s, 2H), 7.2-7.3 (m, 4H), 7.22 (s, 1H), 7.52 (s, 1H), 8.29 (broad t, 1H), 8.67 (brs, 2H).

Example 186

N²-(3,5-dimethyl-1,2-benzisoxazol-6-yl)-N²-{2-[(5-fluoro-1,3-dihydro-2H-isoindol-2-yl)(methyl) amino]-2-oxoethyl}-N¹-[2-(isopropylamino)ethyl] glycinamide hydrochloride Step A N-(3,5-dimethyl-1,2-benzisoxazol-6-yl)-N-{2-[(5-fluoro-1,3-dihydro-2H-isoindol-2-yl)(methyl) amino]-2-oxoethyl}glycine Using the compound (2.10 g, 7.60 mmol) of Reference Example 117, and the compound (2.30 g, 11.40 mmol) of Reference Example 19, and according to the method of Example 4, step A, the title compound (850 mg, yield 26%) was obtained as a bistered solid.

¹H-NMR (300 MHz, DMSO-d₆); δ (ppm) 2.33 (s, 3H), 2.45 (s, 3H), 2.88 (s, 3H), 4.05 (s, 2H), 4.06-4.29 (m, 4H), 4.36 (s, 2H), 7.02-7.17 (m, 2H), 7.19 (s, 1H), 7.30 (dd, J=5.4, 8.4, 1H), 7.51 (s, 1H), 12.52 (brs, 1H).

Step B

N²-(3,5-dimethyl-1,2-benzisoxazol-6-yl)-N²-{2-[(5-fluoro-1,3-dihydro-2H-isoindol-2-yl)(methyl) amino]-2-oxoethyl}-N¹-[2-(isopropylamino)ethyl] glycinamide hydrochloride Using the compound (425 mg, 1.00 mmol) obtained in step A and the compound (303 mg, 1.50 mmol) of Reference Example 3, and according to the methods of Example 1, step B, and Example 251, step B, the title compound (479 mg, yield 88%) was obtained as a pale-bistered amorphous solid.

¹H-NMR (300 MHz, DMSO-d₆); δ (ppm) 1.06 (d, J=6.7, 6H), 2.36 (s, 3H), 2.45 (s, 3H), 2.77 (t, J=5.9, 2H), 2.98 (s, 3H), 3.00-3.18 (m, 1H), 3.20-3.43 (m, 2H), 3.94 (s, 2H), 4.08-4.31 (m, 4H), 4.36 (s, 2H), 7.03-7.18 (m, 2H), 7.22 (s, 1H), 7.30 (dd, J=5.2, 8.2, 1H), 7.52 (s, 1H), 7.6-8.4 (broad, 2H), 8.22 (t, J=5.5, 1H).

Example 187

N²-(3,5-dimethyl-1,2-benzisoxazol-6-yl)-N²-{2-[(5-fluoro-1,3-dihydro-2H-isoindol-2-yl)(methyl) amino]-2-oxoethyl}-N¹-[2-(ethylamino)ethyl]glycinamide hydrochloride Using the compound (425 mg, 1.00 mmol) of Example 186, step A, and the compound (282 mg, 1.50 mmol) of Reference Example 2, and according to, the methods of Example 1, step B, and Example 57, step B, the title compound (472 mg, yield 89%) was obtained as a pale-bistered amorphous solid.

$^1$H-NMR (300 MHz, DMSO-d$_6$); δ (ppm) 1.11 (t, J=7.0, 3H), 2.35 (s, 3H), 2.45 (s, 3H), 2.78-2.88 (m, 4H), 2.89 (s, 3H), 3.16-3.50 (m, 2H), 3.95 (s, 2H), 4.00-4.33 (m, 4H), 4.37 (s, 2H), 7.04-7.18 (m, 2H), 7.22 (s, 1H), 7.27-7.33 (m, 1H), 7.52 (s, 1H), 7.61-8.80 (broad, 2H), 8.22-8.26 (m, 1H).

Example 188

N$^2$-{2-[1,3-dihydro-2H-isoindol-2-yl(methyl) amino]-2-oxoethyl}-N$^2$-(6-methyl-1,3-benzodioxol-5-yl)-N$^1$-[2-(isopropylamino)ethyl]glycinamide dihydrochloride Step A N-{2-[1,3-dihydro-2H-isoindol-2-yl(methyl)amino]-2-oxoethyl}-N-(6-methyl-1,3-benzodioxol-5-yl)glycine Using the compound (5.14 g, 19.23 mmol) of Reference Example 118 and the compound (5.33 g, 28.86 mmol) of Reference Example 17, and according to the method of Example 1, step A, the title compound (5.52 g, yield 72%) was obtained as a colorless amorphous solid.

$^1$H-NMR (300 MHz, CDCl$_3$); δ (ppm) 2.21 (s, 3H), 3.03 (s, 3H), 3.79 (s, 2H), 4.15 (d, J=11.6, 2H), 4.21 (s, 2H), 4.27 (d, J=11.6, 2H), 5.87 (s, 2H), 6.61 (s, 1H), 6.79 (s, 1H), 7.19-7.28 (m, 4H).

Step B

N$^2$-{2-[1,3-dihydro-2H-isoindol-2-yl(methyl) amino]-2-oxoethyl}-N$^2$-(6-methyl-1,3-benzodioxol-5-yl)-N$^1$-{2-[(tert-butoxycarbonyl)(isopropyl)amino] ethyl}glycinamide Using the compound (1.00 g, 2.52 mmol) obtained in step A and the compound (789 mg, 3.90 mmol) of Reference Example 3, and according to the method of Example 1, step B, the title compound (1.28 g, yield 88%) was obtained as a colorless amorphous solid.

$^1$H-NMR (300 MHz, CDCl$_3$); δ (ppm) 1.12 (d, J=6.8, 6H), 1.46 (s, 9H), 2.26 (s, 3H), 2.94 (s, 3H), 3.17 (brs, 2H), 3.36-3.43 (m, 2H), 3.72 (s, 2H), 4.05-4.29 (m, 7H), 5.87 (s, 2H), 6.62 (s, 1H), 6.88 (s, 1H), 7.19-7.31 (m, 4H), 8.30-8.58 (broad, 1H).

Step C

N$^2$-{2-[1,3-dihydro-2H-isoindol-2-yl(methyl) amino]-2-oxoethyl}-N$^2$-(6-methyl-1,3-benzodioxol-5-yl)-N$^1$-[2-(isopropylamino)ethyl]glycinamide dihydrochloride Using the compound (1.28 g, 2.20 mmol) obtained in step B and according to the method of Example 1, step C, the title compound (1.06 g, yield 87%) was obtained as a colorless solid.

$^1$H-NMR (300 MHz, DMSO-d$_6$); δ (ppm) 1.22 (d, J=5.9, 6H), 2.21 (s, 3H), 2.87 (m, 5H), 3.26-3.40 (m, 3H), 3.78 (s, 2H), 4.04-4.26 (m, 6H), 5.91 (s, 2H), 6.71 (s, 1H), 6.94 (s, 1H), 7.25 (m, 4H), 8.43 (brs, 1H), 8.84 (brs, 2H).

Example 189

N$^2$-{2-[1,3-dihydro-2H-isoindol-2-yl(methyl) amino]-2-oxoethyl}-N$^2$-(6-methyl-1,3-benzodioxol-5-yl)-N$^1$-[2-(ethylamino)ethyl]glycinamide dihydrochloride Step A N$^2$-{2-[1,3-dihydro-2H-isoindol-2-yl(methyl) amino]-2-oxoethyl}-N$^2$-(6-methyl-1,3-benzodioxol-5-yl)-N$^1$-{2-[(tert-butoxycarbonyl)(ethyl)amino] ethyl}glycinamide Using the compound (1.00 g, 2.52 mmol) of Example 188, step A, and the compound (0.73 g, 3.88 mmol) of Reference Example 2, and according to the method of Example 1, step B, the title compound (1.32 g, yield 92%) was obtained as a colorless amorphous solid.

$^1$H-NMR (300 MHz, CDCl$_3$); δ (ppm) 1.06 (t, J=6.9, 3H), 1.44 (s, 9H), 2.26 (s, 3H), 2.95 (s, 3H), 3.19-3.31 (m, 4H), 3.42 (q, J=6.3, 2H), 3.71 (s, 2H), 4.06-4.25 (m, 6H), 5.85 (s, 2H), 6.61 (s, 1H), 6.88 (s, 1H), 7.18-7.32 (m, 4H), 8.39-8.65 (broad, 1H).

Step B

N$^2$-{2-[1,3-dihydro-2H-isoindol-2-yl(methyl) amino]-2-oxoethyl}-N$^2$-(6-methyl-1,3-benzodioxol-5-yl)-N$^1$-[2-(ethylamino)ethyl]glycinamide dihydrochloride Using the compound (1.32 g, 2.33 mmol) obtained in step A and according to the method of Example 1, step C, the title compound (1.17 g, yield 93%) was obtained as a colorless solid.

$^1$H-NMR (300 MHz, DMSO-d$_6$); δ (ppm) 1.17 (t, J=7.2, 3H), 2.21 (s, 3H), 2.80-2.91 (m, 7H), 3.34-3.42 (m, 2H), 3.79 (s, 2H), 4.08-4.25 (m, 6H), 5.91 (s, 2H), 6.71 (s, 1H), 6.95 (s, 1H), 7.25 (m, 4H), 8.42-8.47 (m, 1H), 8.88 (brs, 2H).

Example 190

N$^2$-{2-[1,3-dihydro-2H-isoindol-2-yl(methyl) amino]-2-oxoethyl}-N$^2$-(3,6-dimethyl-1,3-benzoxazol-2 (3H)-on-5-yl)-N$^1$-[2-(isopropylamino)ethyl] glycinamide hydrochloride Step A N-{2-[1,3-dihydro-2H-isoindol-2-yl(methyl)amino]-2-oxoethyl}-N-(3,6-dimethyl-1,3-benzoxazol-2 (3H)-on-5-yl)glycine Using the compound (1.00 g, 3.40 mmol) of Reference Example 119, and the compound (942 mg, 5.10 mmol) of Reference Example 17, and according to the method of Example 4, step A, the title compound (1.04 g, yield 72%) was obtained as a pale-purple solid.

$^1$H-NMR (300 MHz, DMSO-d$_6$); δ (ppm) 2.28 (s, 3H), 2.87 (s, 3H), 3.27 (s, 3H), 3.96 (s, 2H), 4.09 (d, J=8.7, 2H), 4.23 (s, 2H), 4.24 (d, J=8.7, 2H), 7.11 (s, 1H), 7.12 (s, 1H), 7.22-7.29 (m, 4H), 12.48 (brs, 1H).

Step B

N²-{2-[1,3-dihydro-2H-isoindol-2-yl(methyl) amino]-2-oxoethyl}-N²-(3,6-dimethyl-1,3-benzoxazol-2 (3H)-on-5-yl)-N¹-[2-(isopropylamino)ethyl] glycinamide hydrochloride Using the compound (520 mg, 1.23 mmol) obtained in step A and the compound (373 mg, 1.85 mmol) of Reference Example 3, and according to the methods of Example 1, step B, and Example 57, step B, the title compound (534 mg, yield 80%) was obtained as a pale-bistered amorphous solid.

¹H-NMR (300 MHz, DMSO-d₆); δ (ppm) 1.14 (d, J=6.2, 6H), 2.31 (s, 3H), 2.81-2.89 (m, 2H), 2.87 (s, 3H), 3.08-3.20 (m, 1H), 3.26 (s, 3H), 3.31-3.37 (m, 2H), 3.81 (s, 2H), 4.02 (d, J=11.8, 2H), 4.21-4.26 (m, 2H), 4.22 (3, 2H), 7.12 (s, 1H), 7.19 (s, 1H), 7.22-7.26 (m, 4H), 7.75-8.62 (broad, 2H), 8.34 (brs, 1H).

Example 191

N²-{2-[1,3-dihydro-2H-isoindol-2-yl(methyl) amino]-2-oxoethyl}-N²-(3,6-dimethyl-1,3-benzoxazol-2 (3H)-on-5-yl)-N¹-[2-(ethylamino)ethyl]glycinamide hydrochloride Using the compound (520 mg, 1.23 mmol) of Example 190, step A, and the compound (347 mg, 1.85 mmol) of Reference Example 2, and according to the methods of Example 1, step B, and Example 57, step B, the title compound (518 mg, yield 79%) was obtained as a pale-bistered amorphous solid.

¹H-NMR (300 MHz, DMSO-d₆); δ (ppm) 1.15 (t, J=7.2, 3H), 2.31 (s, 3H), 2.85-2.93 (m, 4H), 2.87 (s, 3H), 3.26 (s, 3H), 3.31-3.41 (m, 2H), 3.81 (s, 2H), 4.05 (d, J=11.4, 2H), 4.22 (s, 2H), 4.23 (d, J=11.4, 2H), 7.12 (s, 1H), 7.18 (s, 1H), 7.21-7.25 (m, 4H), 8.37 (t, J=5.9, 1H), 8.62 (brs, 2H).

Example 192

N²-{2-[1,3-dihydro-2H-isoindol-2-yl(methyl) amino]-2-oxoethyl}-N²-(3,5-dimethyl-1,3-benzoxazol-2 (3H)-on-6-yl)-N¹-[2-(isopropylamino)ethyl] glycinamide hydrochloride Step A N-{2-[1,3-dihydro-2H-isoindol-2-yl(methyl)amino]-2-oxoethyl}-N-(3,5-dimethyl-1,3-benzoxazole-2 (3H)-on-6-yl)glycine Using the compound (678 mg, 2.30 mmol) of Reference Example 120 and the compound (637 mg, 3.45 mmol) of Reference Example 17, and according to the method of Example 4, step A, the title compound (463 mg, yield 47%) was obtained as a pale-purple solid.

¹H-NMR (300 MHz, DMSO-d₆); δ (ppm) 2.30 (s, 3H), 2.86 (s, 3H), 3.28 (s, 3H), 3.92 (s, 2H), 4.09 (d, J=11.7, 2H), 4.22 (s, 2H), 4.23 (d, J=11.7, 2H), 7.01 (s, 1H), 7.21 (s, 1H), 7.24-7.29 (m, 4H), 12.45 (brs, 1H).

Step B

N²-{2-[1,3-dihydro-2H-isoindol-2-yl(methyl) amino]-2-oxoethyl}-N²-(3,5-dimethyl-1,3-benzoxazol-2 (3H)-on-6-yl)-N¹-[2-(isopropylamino)ethyl] glycinamide hydrochloride Using the compound (231 mg, 0.54 mmol) obtained in step A and), and the compound (164 mg, 0.81 mmol) of Reference Example 3, and according to the methods of Example 1, step B, and Example 57, step B, the title compound (229 mg, yield 78%) was obtained as a pale-bistered amorphous solid.

¹H-NMR (300 MHz, DMSO-d₆); δ (ppm) 1.20 (d, J=6.4, 6H), 2.33 (s, 3H), 2.85-2.93 (m, 2H), 2.86 (s, 3H), 3.18-3.29 (m, 1H), 3.28 (s, 3H), 3.31-3.42 (m, 2H), 3.81 (s, 2H), 4.07 (d, J=11.6, 2H), 4.23 (s, 2H), 4.23 (d, J=11.6, 2H), 7.02 (s, 1H), 7.22-7.26 (m, 4H), 7.28 (s, 1H), 8.37 (t, J=5.5, 1H), 8.85 (brs, 2H).

The compounds of Examples 169-192 are shown below.

TABLE 14

| Example | Structural Formula | TMW | LC-MS (found) |
|---|---|---|---|
| 169 | | 536.54 | 464 |

TABLE 14-continued
| Example | Structural Formula | TMW | LC-MS (found) |
|---------|--------------------|-----|---------------|
| 170 | 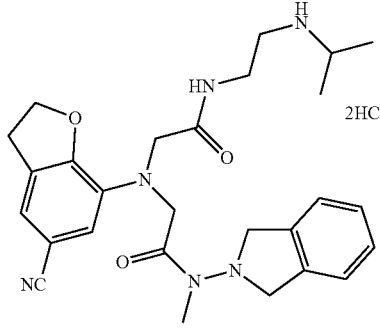 | 563.52 | 491 |
| 171 | 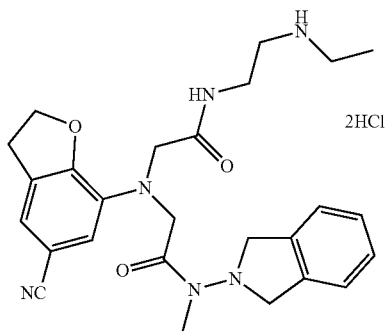 [SMILES: CCNCCNC(=O)CN(CC(=O)N(C)N1Cc2ccccc2C1)c1cc(C#N)cc2c1OCC2] | 549.49 | 477 |
| 172 | 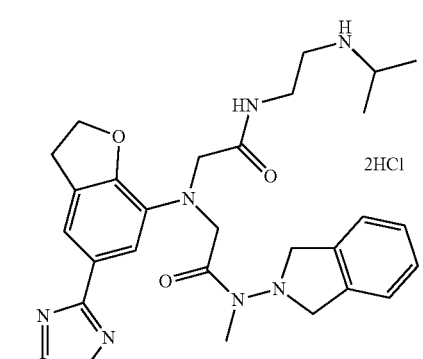 | 620.57 | 548 |
| 173 | 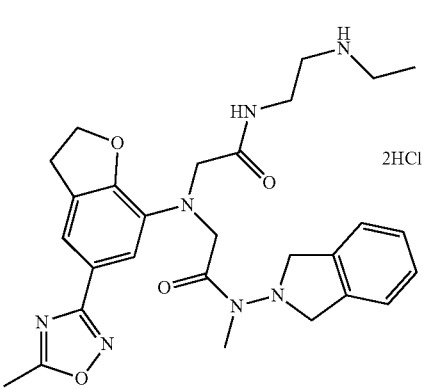 [SMILES: CCNCCNC(=O)CN(CC(=O)N(C)N1Cc2ccccc2C1)c1cc(-c2noc(C)n2)cc2c1OCC2] | 606.54 | 534 |

TABLE 14-continued
| Example | Structural Formula | | TMW | LC-MS (found) |
|---|---|---|---|---|
| 174 | 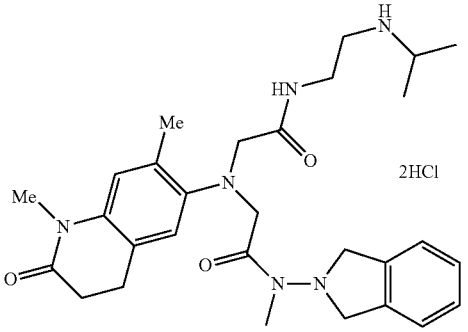 [SMILES: Cc1cc2c(cc1N(CC(=O)NCCNC(C)C)CC(=O)N(C)N1Cc3ccccc3C1)CCC(=O)N2C] | 2HCl | 593.59 | 521 |
| 175 | 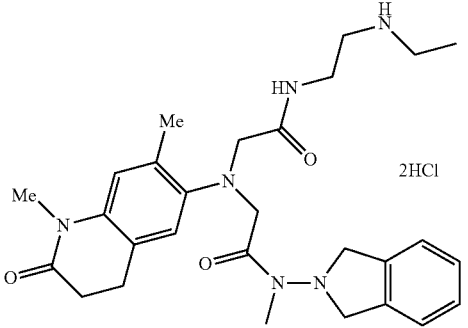 [SMILES: CCNCCNC(=O)CN(CC(=O)N(C)N1Cc2ccccc2C1)c1cc2c(cc1C)N(C)C(=O)CC2] | 2HCl | 579.56 | 507 |
| 176 | 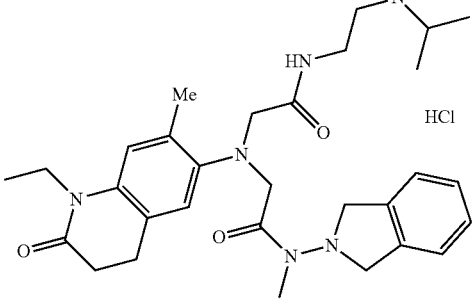 | HCl | 571.15 | 535 |
| 177 | 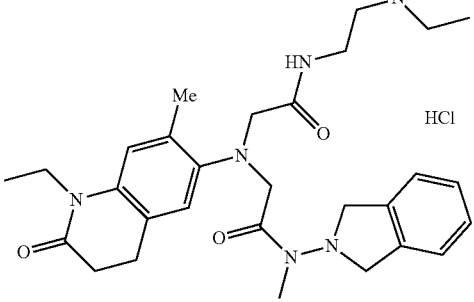 | HCl | 557.13 | 521 |

TABLE 14-continued
| Example | Structural Formula | TMW | LC-MS (found) |
|---|---|---|---|
| 178 | 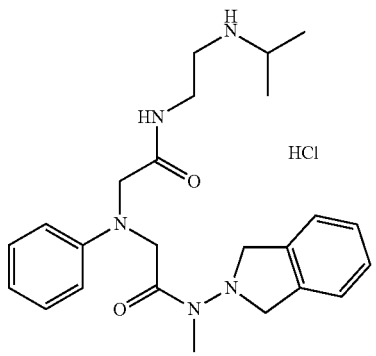 [SMILES: CC(C)NCCNC(=O)CN(CC(=O)N(C)N1Cc2ccccc2C1)c1ccccc1 ; Cl] | 460.01 | 424 |
| 179 | 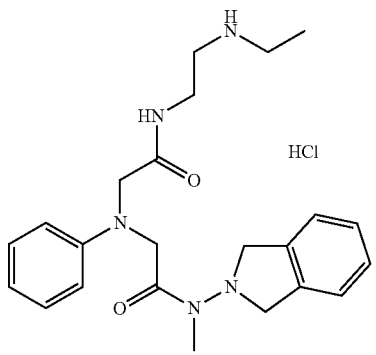 [SMILES: CCNCCNC(=O)CN(CC(=O)N(C)N1Cc2ccccc2C1)c1ccccc1 ; Cl] | 445.99 | 410 |
| 180 | 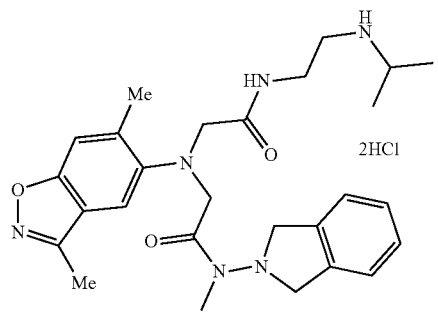 [SMILES: Cc1cc2onc(C)c2cc1N(CC(=O)NCCNC(C)C)CC(=O)N(C)N1Cc2ccccc2C1 ; "2HCl"] | 565.53 | 493 |
| 181 | 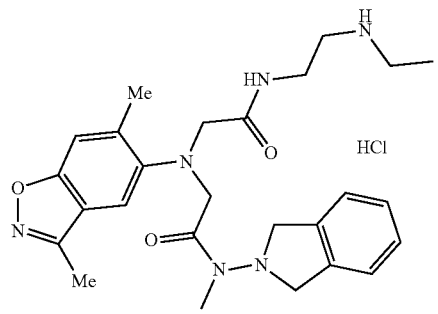 [SMILES: CCNCCNC(=O)CN(CC(=O)N(C)N1Cc2ccccc2C1)c1cc2c(C)noc2cc1C ; Cl] | 515.05 | 479 |

TABLE 14-continued

| Example | Structural Formula | TMW | LC-MS (found) |
|---------|-------------------|--------|---------------|
| 182 | (structure) 2HCl | 583.53 | 511 |
| 183 | (structure) 2HCl | 569.50 | 497 |
| 184 | (structure) 2HCl | 565.53 | 493 |
| 185 | (structure) 2HCl | 551.51 | 479 |
| 186 | (structure) HCl | 547.06 | 511 |

TABLE 14-continued
| Example | Structural Formula | TMW | LC-MS (found) |
|---|---|---|---|
| 187 | 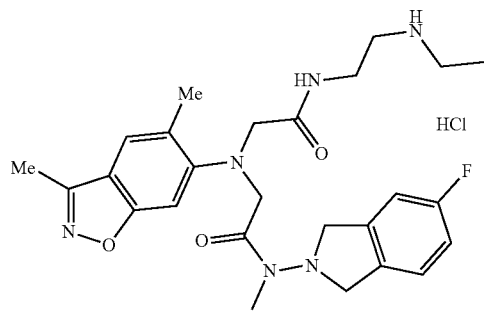 [SMILES: CCNCCNC(=O)CN(CC(=O)N(C)N1Cc2ccc(F)cc2C1)c1cc2onc(C)c2cc1C ; Cl] HCl | 533.04 | 497 |
| 188 | 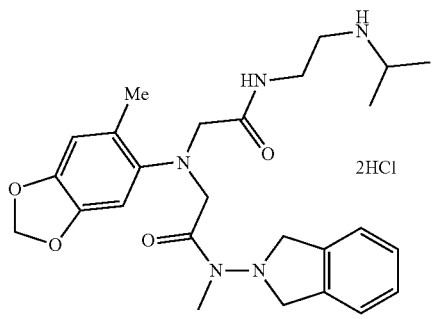 [SMILES: Cc1cc2c(cc1N(CC(=O)NCCNC(C)C)CC(=O)N(C)N1Cc3ccccc3C1)OCO2 ; "2HCl"] 2HCl | 554.51 | 482 |
| 189 | 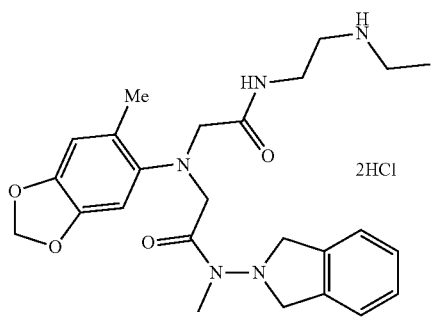 [SMILES: CCNCCNC(=O)CN(CC(=O)N(C)N1Cc2ccccc2C1)c1cc2c(cc1C)OCO2 ; "2HCl"] 2HCl | 540.48 | 468 |
| 190 | 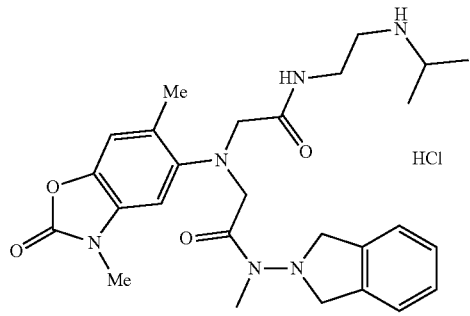 [SMILES: Cc1cc2oc(=O)n(C)c2cc1N(CC(=O)NCCNC(C)C)CC(=O)N(C)N1Cc2ccccc2C1 ; Cl] HCl | 545.07 | 509 |

TABLE 14-continued

| Example | Structural Formula | TMW | LC-MS (found) |
|---|---|---|---|
| 191 | | 531.05 | 495 |
| 192 | | 545.07 | 509 |

Example 193

N²-{2-[1,3-dihydro-2H-isoindol-2-yl(methyl)amino]-2-oxoethyl}-N²-(3,5-dimethyl-1,3-benzooxazol-2(3H)-on-6-yl)-N¹-[2-(ethylamino)ethyl]glycinamide hydrochloride Using the compound (231 mg, 0.54 mmol) of Example 192, step A, and the compound (152 mg, 0.81 mmol) of Reference Example 2, and according to the methods of Example 1, step B, and Example 57, step B, the title compound (228 mg, yield 80%) was obtained as a pale-bistered amorphous solid.

$^1$H-NMR (300 MHz, DMSO-$d_6$); (ppm) 1.06-1.17 (m, 3H), 2.33 (s, 3H), 2.82-2.91 (m, 4H), 2.86 (s, 3H), 3.28 (s, 3H), 3.28-3.42 (m, 2H), 3.79 (s, 2H), 4.07 (d, J=11.5, 2H), 4.21 (s, 2H), 4.23 (d, J=11.5, 2H), 7.03 (s, 1H), 7.25-7.26 (s, 4H), 7.27 (s, 1H), 8.32 (t, J=5.7, 1H), 8.48 (brs, 2H).

Example 194

N²-{2-[1,3-dihydro-2H-isoindol-2-yl(methyl)amino]-2-oxoethyl}-N²-(3-methoxy-8-oxo-5,6,7,8-tetrahydronaphthalen-2-yl)-N¹-[2-(isopropylamino)ethyl]glycinamide dihydrochloride

Step A

N-{2-[1,3-dihydro-2H-isoindol-2-yl(methyl)amino]-2-oxoethyl}-N-(3-methoxy-8-oxo-5,6,7,8-tetrahydronaphthalen-2-yl)glycine Using the compound (0.70 g, 2.28 mmol) of Reference Example 115 and the compound (0.63 g, 3.41 mmol) of Reference Example 17, and according to the method of Example 1, step A, the title compound (0.92 g, yield 92%) was obtained as a colorless amorphous solid.

$^1$H-NMR (300 MHz, CDCl$_3$); δ (ppm) 2.09 (quintet, J=6.3, 2H), 2.57 (t, J=6.3, 2H), 2.87 (t, J=6.3, 2H), 3.02 (s, 3H), 3.85 (s, 3H), 3.97 (s, 2H), 4.30-4.40 (m, 4H), 4.52 (s, 2H), 6.65 (s, 1H), 7.28 (s, 4H), 7.56 (s, 1H).

Step B

N²-{2-[1,3-dihydro-2H-isoindol-2-yl(methyl)amino]-2-oxoethyl}-N²-(3-methoxy-8-oxo-5,6,7,8-tetrahydronaphthalen-2-yl)-N¹-{2-[(tert-butoxycarbonyl)(isopropyl)amino]ethyl}glycinamide Using the compound (0.44 g, 1.01 mmol) obtained in step A and the compound (0.32 g, 1.58 mmol) of Reference Example 3 and according to the method of Example 1, step B, the title compound (0.76 g, yield>100%) was obtained as a colorless amorphous solid.

$^1$H-NMR (300 MHz, CDCl$_3$); δ (ppm) 1.14 (d, J=6.8, 6H), 1.46 (brs, 9H), 2.04-2.12 (m, 2H), 2.56 (t, J=6.0, 2H), 2.86 (t, J=6.0, 2H), 2.96 (s, 3H), 3.19 (brs, 2H), 3.38-3.46 (m, 2H), 3.85 (s, 5H), 4.0-4.2 (broad, 1H), 4.31-4.40 (m, 6H), 6.64 (s, 1H), 7.29 (s, 4H), 7.55 (s, 1H), 8.32-8.63 (broad, 1H).

Step C

N²-{2-[1,3-dihydro-2H-isoindol-2-yl(methyl)amino]-2-oxoethyl}-N²-(3-methoxy-8-oxo-5,6,7,8-tetrahydronaphthalen-2-yl)-N¹-[2-(isopropylamino)ethyl]glycinamide dihydrochloride Using the compound (0.76 g) obtained in step B and according to the method of Example 1, step C, the title compound (0.67 g, yield>100%) was obtained as a colorless solid.

¹H-NMR (300 MHz, DMSO-$d_6$); δ (ppm) 1.19 (d, J=6.4, 6H), 1.98 (t, J=5.5, 2H), 2.45-2.51 (m, 2H), 2.83 (t, J=5.1, 2H), 2.9-3.0 (m, 5H), 3.25-3.30 (m, 1H), 3.34-3.41 (m, 2H), 3.79 (s, 3H), 3.84 (s, 2H), 4.19 (d, J=11.7, 2H), 4.33 (d, J=11.7, 2H), 4.42 (s, 2H), 6.83 (s, 1H), 7.23-7.33 (m, 5H), 8.54 (t, J=5.6, 1H), 8.71 (brs, 2H).

Example 195

N²-{2-[1,3-dihydro-2H-isoindol-2-yl(methyl)amino]-2-oxoethyl}-N²-(3-methoxy-8-oxo-5,6,7,8-tetrahydronaphthalen-2-yl)-N¹-[2-(ethylamino)ethyl]glycinamide dihydrochloride Step A N²-{2-[1,3-dihydro-2H-isoindol-2-yl(methyl)amino]-2-oxoethyl}-N²-(3-methoxy-8-oxo-5,6,7,8-tetrahydronaphthalen-2-yl)-N¹-{2-[(tert-butoxycarbonyl)(ethyl)amino]ethyl}glycinamide Using the compound (0.44 g, 1.01 mmol) of Example 194, step A, and the compound (0.29 g, 1.54 mmol) of Reference Example 2, and according to the method of Example 1, step B, the title compound (0.74 g, yield>100%) was obtained as a colorless amorphous solid.

¹H-NMR (300 MHz, CDCl₃); δ (ppm) 1.07 (t, J=6.9, 3H), 1.43 (brs, 9H), 2.04-2.12 (m, 2H), 2.56 (t, J=6.0, 2H), 2.86 (t, J=6.0, 2H), 2.96 (s, 3H), 3.21-3.31 (m, 4H), 3.43 (q, J=6.2, 2H), 3.84 (brs, 5H), 4.35-4.39 (m, 6H), 6.63 (s, 1H), 7.27 (s, 4H), 7.54 (s, 1H), 8.39-8.65 (broad, 1H).

Step B

N²-{2-[1,3-dihydro-2H-isoindol-2-yl(methyl)amino]-2-oxoethyl}-N²-(3-methoxy-8-oxo-5,6,7,8-tetrahydronaphthalen-2-yl)-N¹-[2-(ethylamino)ethyl]glycinamide dihydrochloride Using the compound (0.74 g, 1.22 mmol) obtained in step A and according to the method of Example 1, step C, the title compound (0.57 g, yield 97%) was obtained as a colorless amorphous solid.

¹H-NMR (300 MHz, DMSO-$d_6$); δ (ppm) 1.16 (t, J=7.1, 3H), 1.98 (t, J=5.4, 2H), 2.46-2.51 (m, 2H), 2.83 (t, J=5.2, 2H), 2.91 (brs, 7H), 3.38 (q, J=6.8, 2H), 3.79 (s, 3H), 3.84 (s, 2H), 4.19 (d, J=11.7, 2H), 4.33 (d, J=11.7, 2H), 4.43 (s, 2H), 6.83 (s, 1H), 7.23-7.33 (m, 5H), 8.53 (t, J=5.6, 1H), 8.69 (brs, 2H).

Example 196

N²-{2-[4,6-dihydro-5H-thieno[2,3-c]pyrrol-5-yl(methyl)amino]-2-oxoethyl}-N²-[2-methyl-5-(5-methyl-1,2,4-oxadiazol-3-yl)phenyl]-N¹-[2-(isopropylamino)ethyl]glycinamide dihydrochloride Step A N-{2-[4,6-dihydro-5H-thieno[2,3-c]pyrrol-5-yl(methyl)amino]-2-oxoethyl}-N-[2-methyl-5-(5-methyl-1,2,4-oxadiazol-3-yl)phenyl]glycine Using the compound (490 mg, 1.61 mmol) of Reference Example 62 and the compound (409 mg, 2.14 mmol) of Reference Example 59, and according to the method of Example 4, step A, the title compound (655 mg, yield 92%) was obtained as a pale-pink amorphous solid.

¹H-NMR (300 MHz, DMSO-$d_6$); δ (ppm) 2.31 (s, 3H), 2.65 (s, 3H), 2.87 (s, 3H), 4.04 (s, 2H), 4.10 (s, 2H), 4.23 (s, 2H), 4.35 (s, 2H), 6.94 (d, J=4.5, 1H), 7.28 (d, J=7.8, 1H), 7.48-7.53 (m, 2H), 7.74 (d, J=1.5, 1H), 12.48 (s, 1H).

Step 13

N²-{2-[4,6-dihydro-5H-thieno[2,3-c]pyrrol-5-yl(methyl)amino]-2-oxoethyl}-N²-[2-methyl-5-(5-methyl-1,2,4-oxadiazol-3-yl)phenyl]-N¹-{2-[(tert-butoxycarbonyl)(isopropyl)amino]ethyl}glycinamide Using the compound (276 mg, 0.625 mmol) obtained in step A and the compound (177 mg, 0.875 mmol) of Reference Example 3, and according to the method of Example 1, step B, the title compound (329 mg, yield 84%) was obtained as a colorless amorphous solid.

¹H-NMR (300 MHz, CDCl₃); δ (ppm) 1.12 (d, J=6.9, 6H), 1.46 (brs, 9H), 2.41 (s, 3H), 2.63 (s, 3H), 2.95 (s, 3H), 3.1-3.3 (m, 2H), 3.3-3.5 (m, 2H), 3.83 (s, 2H), 4.0-4.4 (m, 7H), 6.83 (d, J=5.1, 1H), 7.2-7.3 (m, 2H), 7.69 (d, J=8.1, 1H), 7.96 (d, J=1.5, 1H), 8.2-8.8 (broad, 1H).

Step C

N²-{2-[4,6-dihydro-5H-thieno[2,3-c]pyrrol-5-yl(methyl)amino]-2-oxoethyl}-N²-[2-methyl-5-(5-methyl-1,2,4-oxadiazol-3-yl)phenyl]-N¹-[2-(isopropylamino)ethyl]glycinamide dihydrochloride Using the compound (325 mg, 0.519 mmol) obtained in step B and according to the method of Example 1, step C, the title compound (309 mg, yield 99%) was obtained as a gray solid.

¹H-NMR (300 MHz, DMSO-$d_6$); δ (ppm) 1.18 (d, J=6.3, 6H), 2.35 (s, 3H), 2.65 (s, 3H), 2.8-3.0 (m, 2H), 2.87 (s, 3H), 3.1-3.3 (m, 1H), 3.34-3.42 (m, 2H), 3.93 (s, 2H), 4.10 (s, 2H), 4.24 (s, 2H), 4.37 (s, 2H), 6.95 (d, J=5.1, 1H), 7.29 (d, J=7.8, 1H), 7.48-7.54 (m, 2H), 7.76 (d, J=1.5, 1H), 8.34 (t, J=5.7, 1H), 8.68 (brs, 2H).

Example 197

N²-{2-[4,6-dihydro-5H-thieno[2,3-c]pyrrol-5-yl(methyl)amino]-2-oxoethyl}-N²-[2-methyl-5-(5-methyl-1,2,4-oxadiazol-3-yl)phenyl]-N¹-[2-(ethylamino)ethyl]glycinamide dihydrochloride

Step A

N²-{2-[4,6-dihydro-5H-thieno[2,3-c]pyrrol-5-yl(methyl)amino]-2-oxoethyl}-N²-[2-methyl-5-(5-methyl-1,2,4-oxadiazol-3-yl)phenyl]-N¹-{2-[(tert-butoxycarbonyl)(ethyl)amino]ethyl}glycinamide Using the compound (367 mg, 0.831 mmol) of Example 196, step A, and the compound (245 mg, 1.30 mmol) of Reference Example 2, and according to the method of Example 1, step B, the title compound (423 mg, yield 83%) was obtained as a colorless amorphous solid.

$^1$H-NMR (300 MHz, CDCl$_3$); δ (ppm) 1.04 (t, J=7.2, 3H), 1.44 (brs, 9H), 2.40 (s, 3H), 2.63 (s, 3H), 2.95 (s, 3H), 3.0-3.5 (m, 6H), 3.82 (s, 2H), 4.0-4.4 (m, 6H), 6.83 (d, J=4.8, 1H), 7.2-7.3 (m, 2H), 7.69 (d, J=7.8, 1H), 7.95 (d, J=1.5, 1H), 8.2-8.8 (broad, 1H).

Step B

N²-{2-[4,6-dihydro-5H-thieno[2,3-c]pyrrol-5-yl(methyl)amino]-2-oxoethyl}-N²-[2-methyl-5-(5-methyl-1,2,4-oxadiazol-3-yl)phenyl]-N¹-[2-(ethylamino)ethyl]glycinamide dihydrochloride Using the compound (418 mg, 0.683 mmol) obtained in step A and according to the method of Example 1, step C, the title compound (376 mg, yield 94%) was obtained as a gray solid.

$^1$H-NMR (300 MHz, DMSO-d$_6$); δ (ppm) 1.16 (t, J=7.2, 3H), 2.35 (s, 3H), 2.65 (s, 3H), 2.8-3.0 (m, 4H), 2.87 (s, 3H), 3.3-3.5 (m, 2H), 3.93 (s, 2H), 4.10 (s, 2H), 4.24 (s, 2H), 4.38 (s, 2H), 6.95 (d, J=5.1, 1H), 7.28 (d, J=8.1, 1H), 7.48-7.53 (m, 2H), 7.76 (s, 1H), 8.35 (t, J=5.7, 1H), 8.85 (brs, 2H).

Example 198

N²-{2-[4,6-dihydro-5H-thieno[2,3-c]pyrrol-5-yl(methyl)amino]-2-oxoethyl}-N²-(3,6-dimethyl-1,2-benzisoxazol-5-yl)-N¹-[2-(ethylamino)ethyl]glycinamide dihydrochloride

Step A

N-{2-[4,6-dihydro-5H-thieno[2,3-c]pyrrol-5-yl(methyl)amino]-2-oxoethyl}-N-(3,6-dimethyl-1,2-benzisoxazol-5-yl)glycine Using the compound (147 mg, 0.528 mmol) of Reference Example 116 and the compound (130 mg, 0.682 mmol) of Reference Example 59, and according to the method of Example 4, step A, the title compound (196 mg, yield 90%) was obtained as a colorless amorphous solid.

$^1$H-NMR (300 MHz, DMSO-d$_6$); δ (ppm) 2.44 (s, 3H), 2.48 (s, 3H), 2.85 (s, 3H), 4.00 (s, 2H), 4.07 (s, 2H), 4.21 (s, 2H), 4.30 (s, 2H), 6.94 (d, J=5.1, 1H), 7.47 (s, 1H), 7.49 (d, J=5.1, 1H), 7.62 (s, 1H), 12.45 (s, 1H).

Step B

N²-{2-[4,6-dihydro-5H-thieno[2,3-c]pyrrol-5-yl(methyl)amino]-2-oxoethyl}-N²-(3,6-dimethyl-1,2-benzisoxazol-5-yl)-N¹-{2-[(tert-butoxycarbonyl)(ethyl)amino]ethyl}glycinamide Using the compound (195 mg, 0.470 mmol) obtained in step A and the compound (132 mg, 0.701 mmol) of Reference Example 2, and according to the method of Example 1, step B, the title compound (254 mg, yield 92%) was obtained as a colorless amorphous solid.

$^1$H-NMR (300 MHz, CDCl$_3$); δ (ppm) 1.03 (t, J=7.2, 3H), 1.42 (brs, 9H), 2.50 (s, 3H), 2.53 (s, 3H), 2.95 (s, 3H), 3.0-3.3 (m, 4H), 3.38-3.45 (m, 2H), 3.88 (s, 2H), 4.06 (s, 2H), 4.18 (s, 2H), 4.20 (s, 2H), 6.83 (d, J=5.1, 1H), 7.28 (d, J=5.1, 1H), 7.36 (s, 1H), 7.59 (s, 1H), 8.0-8.7 (broad, 1H).

Step C

N²-{2-[4,6-dihydro-5H-thieno[2,3-c]pyrrol-5-yl(methyl)amino]-2-oxoethyl}-N²-(3,6-dimethyl-1,2-benzisoxazol-5-yl)-N¹-[2-(ethylamino)ethyl]glycinamide dihydrochloride Using the compound (248 mg, 0.424 mmol) obtained in step B and according to the method of Example 1, step C, the title compound (219 mg, yield 93%) was obtained as a colorless amorphous solid.

$^1$H-NMR (300 MHz, DMSO-d$_6$); δ (ppm) 1.14 (t, J=7.2, 3H), 2.46 (s, 3H), 2.48 (s, 3H), 2.8-3.0 (m, 4H), 2.86 (s, 3H), 3.3-3.4 (m, al), 3.86 (s, 2H), 4.07 (s, 2H), 4.20 (s, 2H), 4.30 (s, 2H), 6.94 (d, J=5.1, 1H), 7.49 (s, 1H), 7.49 (d, J=5.1, 1H), 7.67 (s, 1H), 8.35 (t, J=5.7, 1H), 8.58 (brs, 2H).

Example 199

N²-{2-[methyl (5-methyl-1,3-dihydro-2H-isoindol-2-yl)amino]-2-oxoethyl}-N²-[2-methyl-4-(5-methyl-1,2,4-oxadiazol-3-yl)phenyl]-N¹-[2-(ethylamino)ethyl]glycinamide dihydrochloride

Step A

N²-{2-[methyl (5-methyl-1,3-dihydro-2H-isoindol-2-yl)amino]-2-oxoethyl}-N²-[2-methyl-4-(5-methyl-1,2,4-oxadiazol-3-yl)phenyl]-N¹-{2-[(tert-butoxycarbonyl)(ethyl)amino]ethyl}glycinamide Using the compound (305 mg, 1.00 mmol) of Reference Example 69, the compound (209 mg, 1.05 mmol) of Reference Example 60 and the compound (192 mg, 1.02 mmol) of Reference Example 2, and according to the methods of Example 4, step A, and Example 1, step B, the title compound (386 mg, yield 63%) was obtained as a brown oil.

Step B

N²-{2-[methyl (5-methyl-1,3-dihydro-2H-isoindol-2-yl)amino]-2-oxoethyl}-N²-[2-methyl-4-(5-methyl-1,2,4-oxadiazol-3-yl)phenyl]-N¹-[2-(ethylamino)ethyl]glycinamide dihydrochloride Using the compound (386 mg, 0.623 mmol) obtained in step A and according to the method of Example 1, step C, the title compound (330 mg, yield 89%) was obtained as a brown amorphous solid.

¹H-NMR (400 MHz, DMSO-d₆); δ (ppm) 1.16 (t, J=7.2, 3H), 2.29 (s, 3H), 2.32 (s, 3H), 2.63 (s, 3H), 2.86-2.92 (m, 4H), 2.89 (s, 3H), 3.36-3.41 (m, 2H), 3.95 (s, 2H), 4.09-4.12 (m, 2H), 4.20-4.25 (m, 2H), 4.38 (s, 2H), 7.05-7.10 (s, 3H), 7.14-7.16 (m, 1H), 7.66-7.68 (m, 1H), 7.71 (s, 1H), 8.35 (t, J=5.8, 1H), 8.84 (brs, 1H).

Example 200

N²-{2-[2,3-dihydro-1H-inden-2-yl(methyl)amino]-2-oxoethyl}-N²-[2-methyl-5-(5-methyl-1,2,4-oxadiazol-3-yl)phenyl]-N¹-[2-(ethylamino)ethyl]glycinamide hydrochloride Step A N²-{2-[2,3-dihydro-1H-inden-2-yl(methyl)amino]-2-oxoethyl}-N²-[2-methyl-4-(5-methyl-1,2,4-oxadiazol-3-yl)phenyl]-N¹-{2-[(tert-butoxycarbonyl)(ethyl)amino]ethyl}glycinamide Using the compound (305 mg, 1.00 mmol) of Reference Example 69, the compound (193 mg, 1.05 mmol) of Reference Example 23 and the compound (192 mg, 1.02 mmol) of Reference Example 2, and according to the methods of Example 4, step A, and Example 1, step B, the title compound (383 mg, yield 63%) was obtained as a brown oil.

Step B

N²-{2-[2,3-dihydro-1H-inden-2-yl(methyl)amino]-2-oxoethyl}-N²-[2-methyl-4-(5-methyl-1,2,4-oxadiazol-3-yl)phenyl]-N¹-[2-(ethylamino)ethyl]glycinamide hydrochloride Using the compound (383 mg, 0.633 mmol) obtained in step A and according to the method of Example 1, step C, the title compound (325 mg, yield 89%) was obtained as a colorless amorphous solid.
¹H-NMR (400 MHz, DMSO-d₆); δ (ppm) 1.07-1.23 (m, 3H), 2.34 (s, 3H), 2.63 (s, 3H), 2.70 2.78 (2s, 3H), 2.91-3.16 (m, 8H), 3.38-3.39 (m, 2H), 3.91 3.93 (2s, 2H), 4.16 4.32 (2s, 2H), 4.84 4.87 (m, 0.4H), 5.32 5.35 (m, 0.6H), 7.11-7.23 (m, 5H), 7.68 (d, J=8.3, 1H), 7.74 (s, 1H), 8.42-8.43 (m, 1H), 8.73 (brs, 2H).

Example 201

N²-{2-[2,3-dihydro-1H-inden-2-yl(methyl)amino]-2-oxoethyl}-N²-(3,5-dimethyl-1,2-benzisoxazol-6-yl)-N¹-[2-(ethylamino)ethyl]glycinamide hydrochloride Step A N²-{2-[2,3-dihydro-1H-inden-2-yl(methyl)amino]-2-oxoethyl}-N²-(3,5-dimethyl-1,2-benzisoxazol-6-yl)-N¹-{2-[(tert-butoxycarbonyl)(ethyl)amino]ethyl}glycinamide Using the compound (278 mg, 1.00 mmol) of Reference Example 117, the compound (193 mg, 1.05 mmol) of Reference Example 23 and the compound (192 mg, 1.02 mmol) of Reference Example 2, and according to the methods of Example 4, step A, and Example 1, step B, the title compound (404 mg, yield 70%) was obtained as a brown oil.

Step B

N²-{2-[2,3-dihydro-1H-inden-2-yl(methyl)amino]-2-oxoethyl}-N²-(3,5-dimethyl-1,2-benzisoxazol-6-yl)-N¹-[2-(ethylamino)ethyl]glycinamide hydrochloride Using the compound (404 mg, 0.699 mmol) obtained in step A and according to the method of Example 1, step C, the title compound (310 mg, yield 86%) was obtained as a pale-yellow amorphous solid
¹H-NMR (400 MHz, DMSO-d₆); δ (ppm) 1.14 (t, J=7.2, 3H), 2.38 (s, 3H), 2.46 (s', 3H), 2.67 2.79 (2s, 3H), 2.87-3.14 (m, 8H), 3.36-3.40 (m, 2H), 3.90 3.93 (2s, 2H), 4.17 4.33 (2s, 2H), 4.90-4.96 (m, 0.4H), 5.27-5.35 (m, 0.6H), 7.13-7.25 (m, 4H), 7.29 (s, 1H), 7.54 (s, 1H), 8.41-8.42 (m, 1H), 8.86 (brs, 2H).

Example 202

N²-{2-[2,3-dihydro-1H-inden-2-yl(methyl)amino]-2-oxoethyl}-N²-(3,6-dimethyl-1,2-benzisoxazol-5-yl)-N¹-[2-(ethylamino)ethyl]glycinamide hydrochloride Step A N²-{2-[2,3-dihydro-1H-inden-2-yl(methyl)amino]-2-oxoethyl}-N²-(3,6-dimethyl-1,2-benzisoxazol-5-yl)-N¹-{2-[(tert-butoxycarbonyl)(ethyl)amino]ethyl}glycinamide Using the compound (278 mg, 1.00 mmol) of Reference Example 116, the compound (193 mg, 1.05 mmol) of Reference Example 23 and the compound (192 mg, 1.02 mmol) of Reference Example 2, and according to the methods of Example 4, step A, and Example 1, step B, the title compound (329 mg, yield 57%) was obtained as a brown oil.

Step B

N²-{2-[2,3-dihydro-1H-inden-2-yl(methyl)amino]-2-oxoethyl}-N²-(3,6-dimethyl-1,2-benzisoxazol-5-yl)-N¹-[2-(ethylamino)ethyl]glycinamide hydrochloride Using the compound (329 mg, 0.569 mmol) obtained in step A and according to the method of Example 1, step C, the title compound (186 mg, yield 63%) was obtained as a brown amorphous solid.
¹H-NMR (400 MHz, DMSO-d₆); δ (ppm) 1.14-1.21 (m, 3H), 2.48 (s, 3H), 2.49 (s, 3H), 2.66 2.75 (2s, 3H), 2.83-3.08 (m, 8H), 3.36-3.40 (m, 2H), 3.81 3.84 (2s, 2H), 4.07 4.25 (2s, 2H), 4.88-4.92 (m, 0.4H), 5.27-5.31 (m, 0.6H), 7.13-7.20 (m, 4H), 7.50 (s, 1H), 7.69 7.72 (2s, 1H), 8.50-8.52 (m, 1H), 8.92 (brs, 2H).

Example 203

N²-{2-[methyl(5-methyl-1,3-dihydro-2H-isoindol-2-yl)amino]-2-oxoethyl}-N²-[2-methyl-5-(5-methyl-1,2,4-oxadiazol-3-yl)phenyl]-N¹-[2-(ethylamino)ethyl]glycinamide dihydrochloride Step A N²-{2-[methyl(5-methyl-1,3-dihydro-2H-isoindol-2-yl)amino]-2-oxoethyl}-N²-[2-methyl-5-(5-methyl-1,2,4-oxadiazol-3-yl)phenyl]-N¹-{2-[(tert-butoxycarbonyl)(ethyl)amino]ethyl}glycinamide Using the compound (305 mg, 1.00 mmol) of Reference Example 62, the compound (209 mg, 1.05 mmol) of Reference Example 60 and the compound (157 mg, 0.836 mmol) of Reference Example 2, and according to the methods of Example 4, step A, and Example 1, step B, the title compound (338 mg, yield 57%) was obtained as a brown oil.

Step B $N^2$-{2-[methyl(5-methyl-1,3-dihydro-2H-isoindol-2-yl)amino]-2-oxoethyl}-$N^2$-[2-methyl-5-(5-methyl-1,2,4-oxadiazol-3-yl)phenyl]-$N^1$-[2-(ethylamino)ethyl]glycinamide dihydrochloride Using the compound (338 mg, 0.545 mmol) obtained in step A and according to the method of Example 1, step C, the title compound (264 mg, yield 82%) was obtained as a brown amorphous solid.

$^1$H-NMR (400 MHz, DMSO-$d_6$); δ (ppm) 1.15 (t, J=7.2, 3H), 2.30 (s, 3H), 2.33 (s, 3H), 2.65 (s, 3H), 2.86 (s, 3H), 2.89-2.90 (m, 4H), 3.36-3.41 (m, 2H), 3.93 (s, 2H), 4.07 4.10 (2s, 2H), 4.19-4.35 (m, 4H), 7.05-7.08 (m, 2H), 7.15 (d, J=7.6, 1H), 7.28 (d, J=7.8, 1H), 7.51 (dd, J=8.0, 1.1, 1H), 7.75 (d, J=1.6, 1H), 8.37 (t, J=5.8, 1H), 8.89 (brs, 2H).

Example 204

$N^2$-{2-[(5-fluoro-1,3-dihydro-2H-isoindol-2-yl)(methyl)amino]-2-oxoethyl}-$N^2$-[2-methyl-4-(5-methyl-1,2,4-oxadiazol-3-yl)phenyl]-$N^1$-[2-(ethylamino)ethyl]glycinamide dihydrochloride Step A $N^2$-{2-[(5-fluoro-1,3-dihydro-2H-isoindol-2-yl)(methyl)amino]-2-oxoethyl}-$N^2$-[2-methyl-4-(5-methyl-1,2,4-oxadiazol-3-yl)phenyl]-$N^1$-{2-[(tert-butoxycarbonyl)(ethyl)amino]ethyl}glycinamide The compound (2.00 g, 6.55 mmol) of Reference Example 69 was dissolved in N,N-dimethylformamide (22 ml), WSC (1.27 g, 6.62 mmol) was added at room temperature, and the mixture was stirred at the same temperature for 30 min. Then, the reaction mixture was stirred under ice-cooling, and the compound (1.34 g, 6.61 mmol) of Reference Example 19 and N,N-diisopropylethylamine (1.12 ml, 6.59 mmol) were added. The mixture was stirred at room temperature for 2 hr. Then, the compound (1.35 g, 7.17 mmol) of Reference Example 2, WSC (1.38 g, 7.20 mmol) and 1-hydroxybenzotriazole (974 mg, 7.21 mmol) were added to the reaction mixture, and the mixture was stirred at room temperature for 2 hr. The reaction mixture was diluted with ethyl acetate, and the organic layer was washed with water, 10% aqueous citric acid solution, diluted aqueous sodium hydroxide solution and saturated brine, and dried over anhydrous magnesium sulfate. The insoluble material was filtered off, and the solution was concentrated under reduced pressure. The obtained oil was purified by silica gel column chromatography (ethyl acetate-methanol) to give the title compound (3.62 g, yield 89%) as a pale-yellow amorphous solid $^1$H-NMR (400 MHz, CDCl$_3$); δ (ppm) 0.94 (brs, 3H), 1.36 (s, 9H), 2.31 (s, 3H), 2.63 (s, 3H), 2.90 (s, 3H), 3.02-3.18 (m, 6H), 3.87 (s, 2H), 4.11-4.29 (m, 4H), 4.34 (s, 2H), 7.05-7.10 (m, 2H), 7.15 (dd, J=8.0, 1.9, 1H), 7.29-7.32 (m, 1H), 7.67 (dd, J=8.5, 1.7, 1H), 7.71 (d, J=1.7, 1H), 8.11 (brs, 1H).

Step B $N^2$-{2-[(5-fluoro-1,3-dihydro-2H-isoindol-2-yl)(methyl)amino]-2-oxoethyl}-$N^2$-[2-methyl-4-(5-methyl-1,2,4-oxadiazol-3-yl)phenyl]-$N^1$-[2-(ethylamino)ethyl]glycinamide dihydrochloride The compound (3.62 g, 5.80 mmol) obtained in step A was dissolved in dichloromethane (12 ml), 4N hydrochloric acid-dioxane solution (12 ml) was added, and the mixture was stirred at room temperature for 2 hr. The reaction mixture was diluted with chloroform, and the organic layer was washed with 1N aqueous sodium hydroxide solution, and dried over sodium sulfate. The insoluble material was filtered off, and the solution was concentrated under reduced pressure. The obtained oil was dissolved in diethyl ether (58 ml), and 4N hydrochloric acid-ethyl acetate (3.14 ml, 12.6 mmol) was added to allow precipitation of a solid. This was collected by filtration, washed with diethyl ether, and dried under reduced pressure to give the title compound (2.96 g, yield 86%) as a pale-yellow solid.

$^1$H-NMR (400 MHz, DMSO-$d_6$); δ (ppm) 1.14 (t, J=7.2, 3H), 2.32 (s, 3H), 2.63 (s, 3H), 2.88-2.90 (m, 4H), 2.90 (s, 3H), 3.35-3.41 (m, 2H), 3.95 (s, 3H), 4.11-4.29 (m, 4H), 4.36 (s, 2H), 7.06-7.11 (m, 2H), 7.15 (dd, J=8.8, 2.0, 1H), 7.29-7.32 (m, 1H), 7.67 (dd, J=8.4, 2.1, 1H), 7.72 (d, J=1.9, 1H), 8.30 (t, J=5.9, 1H), 8.59 (brs, 2H).

Example 205

$N^2$-{2-[(4-fluoro-1,3-dihydro-2H-isoindol-2-yl)(methyl)amino]-2-oxoethyl}-$N^2$-[2-methyl-4-(5-methyl-1,2,4-oxadiazol-3-yl)phenyl]-$N^1$-[2-(ethylamino)ethyl]glycinamide dihydrochloride Step A $N^2$-{2-[(4-fluoro-1,3-dihydro-2H-isoindol-2-yl)(methyl)amino]-2-oxoethyl}-$N^2$-[2-methyl-4-(5-methyl-1,2,4-oxadiazol-3-yl)phenyl]-$N^1$-{2-[(tert-butoxycarbonyl)(ethyl)amino]ethyl}glycinamide Using the compound (416 mg, 1.36 mmol) of Reference Example 69, the compound (280 mg, 1.38 mmol) of Reference Example 18 and the compound (282 mg, 1.47 mmol) of Reference Example 2, and according to the method of Example 204, step A, the title compound (763 mg, yield 90%) was obtained as a pale-yellow amorphous solid $^1$H-NMR (400 MHz, CDCl$_3$); δ (ppm) 1.00 (t, J=7.1, 3H), 1.41 (brs, 9H), 2.38 (s, 3H), 2.64 (s, 3H), 2.97 (s, 3H), 3.0-3.3 (m, 4H), 3.37-3.42 (m, 2H), 3.91 (s, 2H), 4.15-4.32 (m, 4H), 4.26 (s, 2H), 6.93-7.02 (m, 2H), 7.21-7.32 (m, 2H), 7.81 (dd, J=2.0, 8.4, 1H), 7.86 (s, 1H), 8.02 8.22 (2broad, 1H).

Step B $N^2$-{2-[(4-fluoro-1,3-dihydro-2H-isoindol-2-yl)(methyl)amino]-2-oxoethyl}-$N^2$-[2-methyl-4-(5-methyl-1,2,4-oxadiazol-3-yl)phenyl]-$N^1$-[2-(ethylamino)ethyl]glycinamide dihydrochloride The compound (753 mg, 1.21 mmol) obtained in step A was dissolved in dichloromethane (2 ml), trifluoroacetic acid (2 ml) was added at room temperature, and the mixture was stirred at the same temperature for 1 hr. To the reaction mixture was added aqueous ammonia, and the organic layer was extracted 55 twice with dichloromethane. The organic layer was dried over sodium sulfate, the insoluble material was filtered off, and the solution was concentrated under reduced pressure to give a pale-yellow oil. This oil was dissolved in ethyl acetate (2 ml), and 4N hydrochloric acid-ethyl acetate solution (0.75 ml, 3.0 mmol) was added at room temperature. Then, diethyl ether (20 ml) was added to allow precipitation of a solid. This was filtered, washed with diethyl ether, and dried under reduced pressure to give the title compound (655 mg, yield 91%) as a pale-yellow solid.

$^1$H-NMR (400 MHz, DMSO-$d_6$); δ (ppm) 1.15 (t, J=7.2, 3H), 2.33 (s, 3H), 2.63 (s, 3H), 2.8-3.0 (m, 4H), 2.92 (s, 3H), 3.35-3.41 (m, 2H), 3.95 (s, 2H), 4.20-4.34 (m, 4H), 4.39 (s, 2H), 7.07-7.15 (m, 3H), 7.29-7.35 (m, 1H), 7.67 (dd, J=2.0, 8.4, 1H), 7.71 (d, J=2.0, 1H), 8.31 (t, J=5.7, 1H), 8.71 (brs, 2H).

Example 206

$N^2$-{2-[1,3-dihydro-2H-isoindol-2-yl(methyl)amino]-2-oxoethyl}-$N^2$-[2-methyl-4-(3-methylisoxazol-5-yl)phenyl]-$N^1$-[2-(ethylamino)ethyl]glycinamide dihydrochloride Using the compound (194 mg, 0.638 mmol) of Reference Example 122, the compound (119 mg, 0.644 mmol) of Reference Example 17 and the compound (132 mg, 0.701 mmol) of Reference Example 2, and according to the methods of Example 204, step A, and Example 1, step C, the title compound (220 mg, yield 60%) was obtained as a brown solid.

$^1$H-NMR (400 MHz, DMSO-$d_6$); δ (ppm) 1.15 (t, J=7.1, 3H), 2.25 (s, 3H), 2.31 (s, 3H), 2.86-2.88 (m, 4H), 2.90 (s, 3H), 3.36-3.40 (m, 2H), 3.94 (s, 2H), 4.13 4.16 (2s, 2H), 4.26 4.29 (2s, 2H), 4.36 (s, 2H), 6.67 (s, 1H), 7.07 (d, J=8.4, 1H), 7.24-7.29 (m, 4H), 7.50 (dd, J=8.5, 2.0, 1H), 7.55 (d, J=1.6, 1H), 8.32 (t, J=5.8, 1H), 8.75 (brs, 2H).

Example 207

$N^2$-{2-[(4-fluoro-1,3-dihydro-2H-isoindol-2-yl)(methyl)amino]-2-oxoethyl}-$N^2$-[2-methyl-4-(3-methylisoxazol-5-yl)phenyl]-$N^1$-[2-(ethylamino)ethyl]glycinamide dihydrochloride Using the compound (194 mg, 0.638 mmol) of Reference Example 122, the compound (131 mg, 0.646 mmol) of Reference Example 19 and the compound (132 mg, 0.701 mmol) of Reference Example 2, and according to the methods of Example 204, step A, and Example 1, step C, the title compound (212 mg, yield 56%) was obtained as a colorless solid.

$^1$H-NMR (400 MHz, DMSO-$d_6$); δ (ppm) 1.15 (t, J=7.3, 3H), 2.25 (s, 3H), 2.31 (s, 3H), 2.86-2.90 (m, 4H), 2.92 (s, 3H), 3.36-3.40 (m, 2H), 3.93 (s, 2H), 4.11-4.29 (m, 4H), 4.35 (s, 2H), 6.67 (s, 1H), 7.06-7.11 (m, 2H), 7.15 (dd, J=8.8, 1.9, 1H), 7.29-7.32 (m, 1H), 7.50 (dd, J=8.4, 1.9, 1H), 7.55 (d, J=1.9, 1H), 8.32 (t, J=5.8, 1H), 8.77 (brs, 2H).

Example 208

$N^2$-{2-[1,3-dihydro-2H-isoindol-2-yl(methyl)amino]-2-oxoethyl}-$N^2$-[2-methyl-5-(3-methylisoxazol-5-yl)phenyl]-$N^1$-[2-(ethylamino)ethyl]glycinamide dihydrochloride Using the compound (153 mg, 0.504 mmol) of Reference Example 123, the compound (94 mg, 0.51 mmol) of Reference Example 17 and the compound (104 mg, 0.55 mmol) of Reference Example 2, and according to the methods of Example 204, step A, and Example 1, step C, the title compound (187 mg, yield 64%) was obtained as a colorless solid.

$^1$H-NMR (400 MHz, DMSO-$d_6$); δ (ppm) 1.15 (t, J=7.3, 3H), 2.27 (s, 3H), 2.32 (s, 3H), 2.86-2.88 (m, 4H), 2.90 (s, 3H), 3.36-3.40 (m, 2H), 3.93 (s, 2H), 4.11 4.13 (2s, 2H), 4.24 4.27 (2s, 2H), 4.33 (s, 2H), 6.75 (s, 1H), 7.24-7.29 (m, 5H), 7.34 (dd, J=7.8, 1.1, 1H), 7.55 (d, J=1.0, 1H), 8.35 (t, J=5.8, 1H), 8.79 (brs, 2H).

Example 209

$N^2$-{2-[(4-fluoro-1,3-dihydro-2H-isoindol-2-yl)(methyl)amino]-2-oxoethyl}-$N^2$-[2-methyl-5-(3-methylisoxazol-5-yl)phenyl]-$N^1$-[2-(ethylamino)ethyl]glycinamide dihydrochloride Using the compound (153 mg, 0.504 mmol) of Reference Example 123, the compound (103 mg, 0.508 mmol) of Reference Example 19 and the compound (104 mg, 0.55 mmol) of Reference Example 2, and according to the methods of Example 204, step A, and Example 1, step C, the title compound (164 mg, yield 55%) was obtained as a colorless solid.

$^1$H-NMR (400 MHz, DMSO-$d_6$); δ (ppm) 1.15 (t, J=7.2, 3H), 2.27 (s, 3H), 2.32 (s, 3H), 2.84-2.90 (m, 4H), 2.88 (s, 3H), 3.36-3.41 (m, 2H), 3.93 (s, 2H), 4.03-4.27 (m, 4H), 4.33 (s, 2H), 6.75 (s, 1H), 7.05-7.15 (m, 2H), 7.24-7.36 (m, 3H), 7.55 (d, J=1.0, 1H), 8.35 (t, J=5.8, 1H), 8.85 (brs, 2H).

Example 210

$N^2$-(4-acetyl-2-methylphenyl)-$N^2$-{2-[1,3-dihydro-2H-isoindol-2-yl(methyl)amino]-2-oxoethyl}-$N^1$-[2-(ethylamino)ethyl]glycinamide dihydrochloride Using the compound (531 mg, 2.00 mmol) of Reference Example 124, the compound (384 mg, 2.08 mmol) of Reference Example 17 and the compound (522 mg, 2.77 mmol) of Reference Example 2, and according to the methods of Example 204, step A, and Example 1, step C, the title compound (768 mg, yield 71%) was obtained as a colorless solid.

$^1$H-NMR (400 mHz, DMSO-$d_6$); δ (ppm) 1.16 (t, J=7.2, 3H), 2.30 (s, 3H), 2.47 (s, 3H), 2.8-3.0 (m, 4H), 2.91 (s, 3H), 3.35-3.41 (m, 2H), 3.98 (s, 2H), 4.17 (d, J=11.5, 2H), 4.29 (d, J=11.5, 2H), 4.42 (s, 2H), 6.93 (d, J=8.4, 1H), 7.2-7.3 (m, 4H), 7.64-7.68 (m, 2H), 8.35 (t, J=5.8, 1H), 8.81 (brs, 2H).

Example 211

$N^2$-(4-acetyl-2-methylphenyl)-$N^2$-{2-[(5-fluoro-1,3-dihydro-2H-isoindol-2-yl)(methyl)amino]-2-oxoethyl}-$N^1$-[2-(ethylamino)ethyl]glycinamide dihydrochloride Using the compound (265 mg, 1.00 mmol) of Reference Example 124, the compound (205 mg, 1.01 mmol) of Reference Example 19 and the compound (207 mg, 1.10 mmol) of Reference Example 2, and according to the methods of Example 204, step A, and Example 1, step C, the title compound (459 mg, yield 82%) was obtained as a pale-pink solid.

$^1$H-NMR (400 MHz, DMSO-$d_6$); δ (ppm) 1.15 (t, J=7.2, 3H), 2.30 (s, 3H), 2.47 (s, 3H), 2.88-2.93 (m, 4H), 2.91 (s, 3H), 3.97 (s, 2H), 4.12-4.31 (m, 4H), 4.40 (s, 2H), 6.63 (d, J=8.5, 1H), 7.06-7.11 (m, 1H), 7.15-7.27 (m, 1H), 7.29-7.33 (m, 1H), 7.64-7.68 (m, 2H), 8.32 (t, J=5.8, 1H), 8.59 (brs, 2H).

Example 212

N$^2$-(4-acetyl-2-methylphenyl)-N$^2$-{2-[(5-fluoro-1,3-dihydro-2H-isoindol-2-yl)(methyl)amino]-2-oxoethyl}-N$^1$-[2-(isopropylamino)ethyl]glycinamide dihydrochloride Using the compound (265 mg, 1.00 mmol) of Reference Example 124, the compound (205 mg, 1.01 mmol) of Reference Example 19 and the compound (222 mg, 1.10 mmol) of Reference Example 3, and according to the methods of Example 204, step A, and Example 1, step C, the title compound (334 mg, yield 58%) was obtained as a brown solid.

$^1$H-NMR (400 MHz, DMSO-d$_6$); δ (ppm) 1.19 (d, J=6.6, 6H), 2.30 (s, 3H), 2.47 (s, 3H), 2.88-2.91 (m, 5H), 3.22-3.28 (m, 1H), 3.37-3.41 (m, 2H), 3.97 (s, 2H), 4.13-4.31 (s, 4H), 4.41 (s, 2H), 6.92 (d, J=8.3, 1H), 7.06-7.11 (m, 1H), 7.16 (dd, J=9.0, 1.9, 1H), 7.29-7.33 (m, 1H), 7.64-7.67 (m, 2H), 7.36 (t, J=5.7, 1H), 8.77 (brs, 2H).

Example 213

N$^2$-(4-acetyl-2-methylphenyl)-N$^2$-{2-[(4-fluoro-1,3-dihydro-2H-isoindol-2-yl)(methyl)amino]-2-oxoethyl}-N$^1$-[2-(ethylamino)ethyl]glycinamide dihydrochloride Using the compound (297 mg, 1.12 mmol) of Reference Example 124, the compound (234 mg, 1.15 mmol) of Reference Example 18 and the compound (228 mg, 1.21 mmol) of Reference Example 2, and according to the methods of Example 204, step A, and Example 1, step C, the title compound (497 mg, yield 80%) was obtained as a colorless solid.

$^1$H-NMR (400 MHz, DMSO-d$_6$); δ (ppm) 1.15 (t, J=7.2, 3H), 2.30 (s, 3H), 2.47 (s, 3H), 2.8-3.0 (m, 4H), 2.93 (s, 3H), 3.35-3.41 (m, 2H), 3.97 (s, 2H), 4.21-4.35 (m, 4H), 4.43 (s, 2H), 6.93 (d, J=8.4, 1H), 7.07-7.16 (m, 2H), 7.29-7.36 (m, 1H), 7.64-7.68 (m, 2H), 8.34 (t, J=5.8, 1H), 8.76 (brs, 2H).

Example 214

N$^2$-{2-[1,3-dihydro-2H-isoindol-2-yl(methyl)amino]-2-oxoethyl}-N$^2$-(6-methyl-3-oxo-2,3-dihydro-1H-inden-5-yl)-N$^1$-[2-(ethylamino)ethyl]glycinamide dihydrochloride

Step A

N-{2-[1,3-dihydro-2H-isoindol-2-yl(methyl)amino]-2-oxoethyl}-N-(6-methyl-3-oxo-2,3-dihydro-1H-inden-5-yl)glycine The compound (297 mg, 1.07 mmol) of Reference Example 126 was dissolved in N,N-dimethylformamide (5 ml), WSC (213 mg, 1.11 mmol) was added at room temperature, and the mixture was stirred at the same temperature for 2 hr. Then, the reaction mixture was stirred under ice-cooling, the compound (211 mg, 1.14 mmol) of Reference Example 17 and N,N-diisopropylethylamine (0.31 ml, 1.8 mmol) were added, and the mixture was stirred at room temperature for 4 hr. To the reaction mixture was added diluted hydrochloric acid, and the precipitated solid was filtered, washed with water, and dried under reduced pressure to give the title compound (343 mg, yield 79%) as a pale-yellow solid.

$^1$H-NMR (400 MHz, DMSO-d$_6$); δ (ppm) 2.34 (s, 3H), 2.55-2.59 (m, 2H), 2.86 (s, 3H), 2.94-2.98 (m, 2H), 3.98 (s, 2H), 4.11 (d, J=11.6, 2H), 4.24 (d, J=11.6, 2H), 4.29 (s, 2H), 7.2-7.3 (m, 4H), 7.32-7.34 (m, 2H), 12.44 (brs, 1H).

Step B

N$^2$-{2-[1,3-dihydro-2H-isoindol-2-yl(methyl)amino]-2-oxoethyl}-N$^2$-(6-methyl-3-oxo-2,3-dihydro-1H-inden-5-yl)-N$^1$-{2-[(tert-butoxycarbonyl)(ethyl)amino]ethyl}glycinamide Using the compound (337 mg, 0.827 mmol) obtained in step A and the compound (224 mg, 1.19 mmol) of Reference Example 2, and according to the method of Example 1, step B, the title compound (388 mg, yield 81%) was obtained as a pale-yellow amorphous solid $^1$H-NMR (400 MHz, CDCl$_3$); δ (ppm) 1.06 (t, J=7.1, 3H), 1.44 (brs, 9H), 2.44 (s, 3H), 2.64-2.68 (m, 2H), 2.93 (s, 3H), 3.01-3.05 (m, 2H), 3.10-3.25 (m, 2H), 3.25-3.40 (m, 2H), 3.41-3.47 (m, 2H), 3.71 (s, 2H), 4.20 (d, J=11.6, 2H), 4.25 (d, J=11.6, 2H), 4.27 (s, 2H), 7.22-7.30 (m, 5H), 7.60 (s, 1H), 8.31 8.60 (2brs, 1H).

Step C

N$^2$-{2-[1,3-dihydro-2H-isoindol-2-yl(methyl)amino]-2-oxoethyl}-N$^2$-(6-methyl-3-oxo-2,3-dihydro-1H-inden-5-yl)-N$^1$-[2-(ethylamino)ethyl]glycinamide dihydrochloride Using the compound (382 mg, 0.661 mmol) obtained in step B and according to the method of Example 1, step C, the title compound (356 mg, yield 98%) was obtained as a pale-yellow solid.

$^1$H-NMR (400 MHz, DMSO-d$_6$); δ (ppm) 1.15 (t, J=7.2, 3H), 2.37 (s, 3H), 2.56-2.60 (m, 2H), 2.8-3.0 (m, 6H), 2.87 (s, 3H), 3.32-3.40 (m, 2H), 3.87 (s, 2H), 4.10 (d, J=11.5, 2H), 4.25 (d, J=11.5, 2H), 4.29 (s, 2H), 7.2-7.3 (m, 4H), 7.33 (s, 1H), 7.37 (s, 1H), 8.28 (t, J=5.9, 1H), 8.67 (brs, 2H).

Example 215

N$^2$-{2-[(5-fluoro-1,3-dihydro-2H-isoindol-2-yl)(methyl)amino]-2-oxoethyl}-N$^2$-(6-methyl-3-oxo-2,3-dihydro-1H-inden-5-yl)-N$^1$-[2-(ethylamino)ethyl]glycinamide dihydrochloride

Step A

N-{2-[(5-fluoro-1,3-dihydro-2H-isoindol-2-yl)(methyl)amino]-2-oxoethyl}-N-(6-methyl-3-oxo-2,3-dihydro-1H-inden-5-yl)glycine Using the compound (281 mg, 1.01 mmol) of Reference Example 126 and the compound (211 mg, 1.04 mmol) of Reference Example 19, and according to the method of Example 214, step A, the title compound (362 mg, yield 84%) was obtained as a colorless solid.

$^1$H-NMR (400 MHz, DMSO-d$_6$); δ (ppm) 2.34 (s, 3H), 2.55-2.59 (m, 2H), 2.85 (s, 3H), 2.95-2.99 (m, 2H), 3.98 (s, 2H), 4.06-4.26 (m, 4H), 4.28 (s, 2H), 7.04-7.10 (m, 1H), 7.12-7.16 (m, 1H), 7.27-7.32 (m, 1H), 7.32-7.33 (m, 2H), 12.44 (brs, 1H).

Step B

N²-{2-[(5-fluoro-1,3-dihydro-2H-isoindol-2-yl)(methyl)amino]-2-oxoethyl}-N²-(6-methyl-3-oxo-2,3-dihydro-1H-inden-5-yl)-N¹-{2-[(tert-butoxycarbonyl)(ethyl)amino]ethyl}glycinamide Using the compound (362 mg, 0.851 mmol) obtained in step A and the compound (231 mg, 1.23 mmol) of Reference Example 2, and according to the method of Example 1, step B, the title compound (445 mg, yield 88%) was obtained as a pale-yellow amorphous solid ¹H-NMR (400 MHz, CDCl₃); δ (ppm) 1.07 (t, J=7.1, 3H), 1.44 (brs, 9H), 2.44 (s, 3H), 2.64-2.68 (m, 2H), 2.93 (s, 3H), 3.01-3.05 (m, 2H), 3.10-3.25 (m, 2H), 3.25-3.40 (m, 2H), 3.41-3.47 (m, 2H), 3.70 (s, 2H), 4.16-4.23 (m, 4H), 4.26 (s, 2H), 6.93-7.00 (m, 2H), 7.16-7.21 (m, 1H), 7.30 (s, 1H), 7.59 (s, 1H), 8.29 8.59 (2brs, 1H).

Step C

N²-{2-[(5-fluoro-1,3-dihydro-2H-isoindol-2-yl)(methyl)amino]-2-oxoethyl}-N²-(6-methyl-3-oxo-2,3-dihydro-1H-inden-5-yl)-N¹-[2-(ethylamino)ethyl]glycinamide dihydrochloride Using the compound (442 mg, 0.742 mmol) obtained in step B and according to the method of Example 1, step C, the title compound (409 mg, yield 97%) was obtained as a pale-yellow solid.

¹H-NMR (400 MHz, DMSO-d₆); δ (ppm) 1.15 (t, J=7.2, 3H), 2.37 (s, 3H), 2.56-2.60 (m, 2H), 2.8-2.9 (m, 4H), 2.86 (s, 3H), 2.95-2.99 (m, 2H), 3.32-3.40 (m, 2H), 3.87 (s, 2H), 4.05-4.27 (m, 4H), 4.28 (s, 2H), 7.05-7.11 (m, 1H), 7.13-7.16 (m, 1H), 7.28-7.32 (m, 1H), 7.33 (s, 1H), 7.37 (s, 1H), 8.28 (brs, 1H), 8.72 (brs, 2H).

Example 216

N²-{2-[(4-fluoro-1,3-dihydro-2H-isoindol-2-yl)(methyl)amino]-2-oxoethyl}-N²-(6-methyl-3-oxo-2,3-dihydro-1H-inden-5-yl)-N¹-[2-(ethylamino)ethyl]glycinamide dihydrochloride Using the compound (308 mg, 1.11 mmol) of Reference Example 126, the compound (232 mg, 1.14 mmol) of Reference Example 18 and the compound (230 mg, 1.22 mmol) of Reference Example 2, and according to the methods of Example 204, step A, and Example 1, step C, the title compound (512 mg, yield 81%) was obtained as a colorless solid.

¹H-NMR (400 MHz, DMSO-d₆); δ (ppm) 1.15 (t, J=7.2, 3H), 2.37 (s, 3H), 2.56-2.60 (m, 2H), 2.80-2.95 (m, 4H), 2.88 (s, 3H), 2.95-2.99 (m, 2H), 3.33-3.40 (m, 2H), 3.87 (s, 2H), 4.1-4.4 (m, 4H), 4.30 (s, 2H), 7.07-7.15 (m, 2H), 7.29-7.35 (m, 1H), 7.33 (s, 1H), 7.38 (s, 1H), 8.29 (t, J=5.8, 1H), 8.76 (brs, 2H).

The compounds of Examples 193-216 are shown below.

TABLE 15

| Example | Formula | TMW | LC-MS (found) |
|---------|---------|-----|---------------|
| 193 | | 531.05 | 495 |
| 194 | | 594.57 | 522 |

TABLE 15-continued
| Example | Formula | TMW | LC-MS (found) |
|---------|---------|-----|---------------|
| 195 | 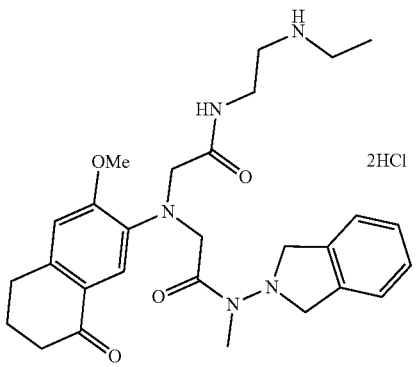 [SMILES: CCNCCNC(=O)CN(CC(=O)N(C)N1Cc2ccccc2C1)c1cc2c(cc1OC)CCCC2=O ; "2HCl"] | 580.55 | 508 |
| 196 | 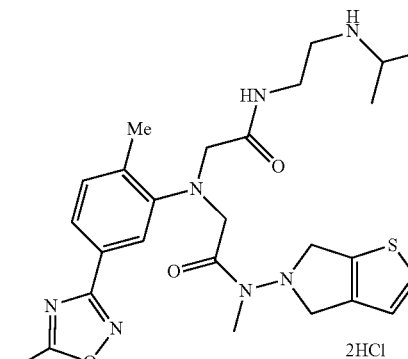 | 598.59 | 526 |
| 197 | 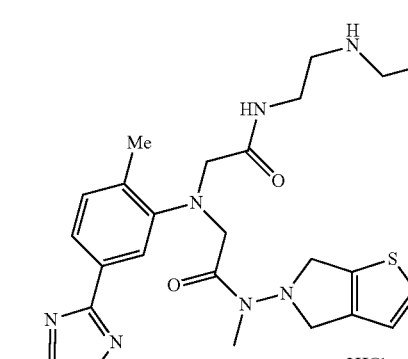 | 584.56 | 512 |
| 198 | 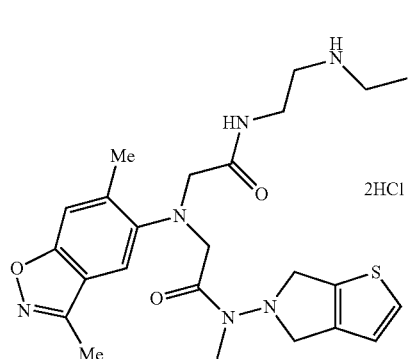 [SMILES: CCNCCNC(=O)CN(CC(=O)N(C)N1Cc2ccsc2C1)c1cc2c(C)noc2cc1C] | 557.54 | 485 |

TABLE 15-continued

| Example | Formula | TMW | LC-MS (found) |
|---------|---------|-----|---------------|
| 199 | | 592.56 | 520 |
| 200 | | 541.08 | 505 |
| 201 | | 514.06 | 478 |
| 202 | | 514.06 | 478 |

TABLE 15-continued
| Example | Formula | TMW | LC-MS (found) |
|---|---|---|---|
| 203 | 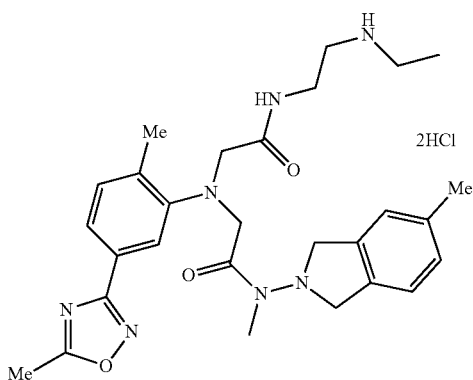 | 592.56 | 520 |
| 204 | 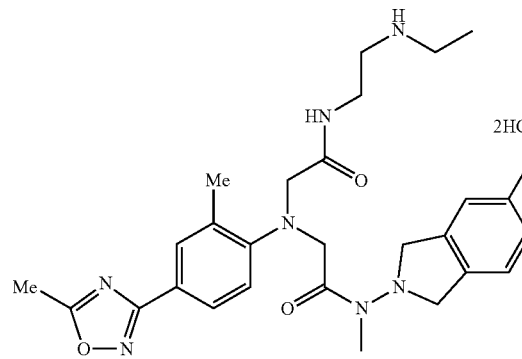 | 596.52 | 524 |
| 205 | 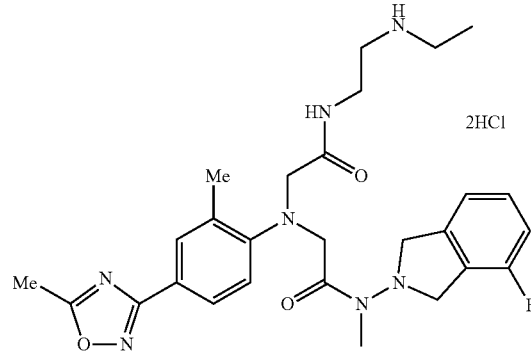 [SMILES: CCNCCNC(=O)CN(CC(=O)N(C)C1Cc2ccccc2C1)c1ccc(-c2noc(C)n2)cc1C ; Cl] | 596.52 | 524 |
| 206 | 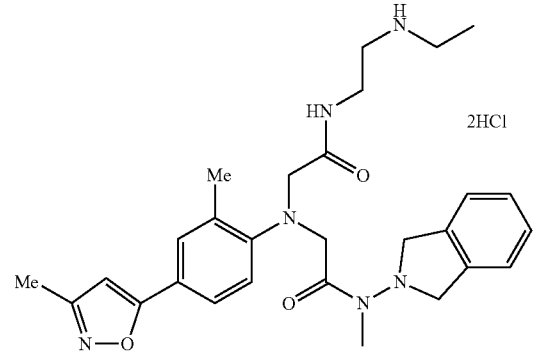 [SMILES: CCNCCNC(=O)CN(CC(=O)N(C)N1Cc2ccccc2C1)c1ccc(-c2cc(C)no2)cc1C] | 577.55 | 505 |

TABLE 15-continued
| Example | Formula | TMW | LC-MS (found) |
|---|---|---|---|
| 207 | 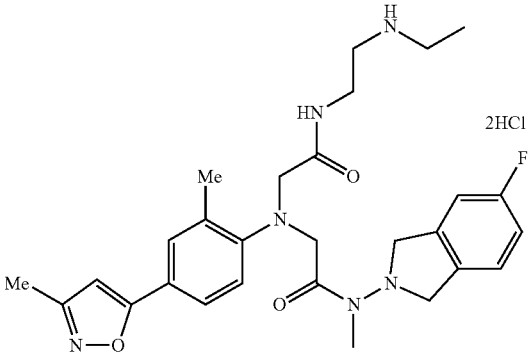 [SMILES: CCNCCNC(=O)CN(CC(=O)N(C)N1Cc2ccc(F)cc2C1)c1ccc(-c2cc(C)no2)cc1C] | 595.54 | 523 |
| 208 | 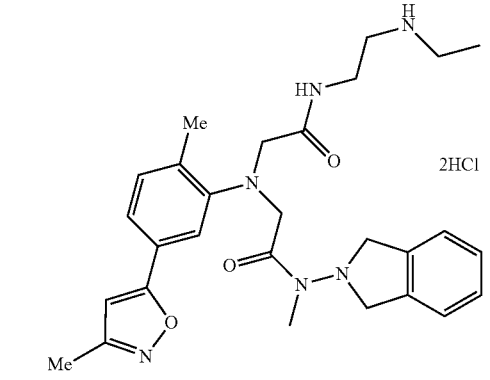 [SMILES: CCNCCNC(=O)CN(CC(=O)N(C)N1Cc2ccccc2C1)c1cc(-c2cc(C)no2)ccc1C] | 577.55 | 505 |
| 209 | 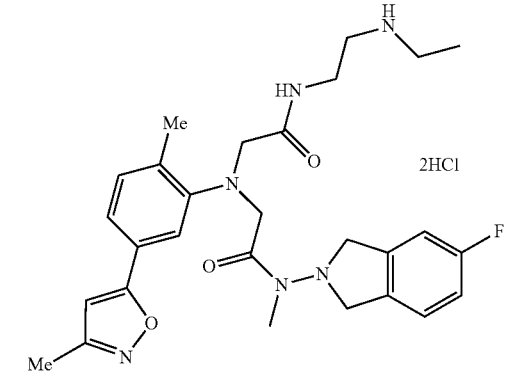 [SMILES: CCNCCNC(=O)CN(CC(=O)N(C)N1Cc2ccc(F)cc2C1)c1cc(-c2cc(C)no2)ccc1C] | 595.54 | 523 |
| 210 | 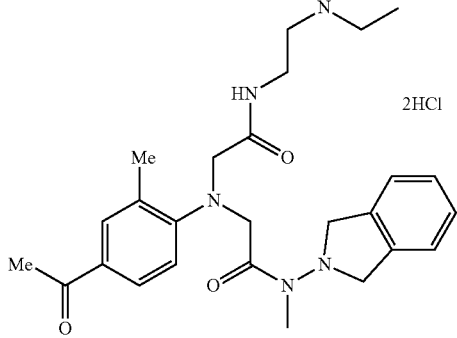 | 538.51 | 466 |

TABLE 15-continued

| Example | Formula | TMW | LC-MS (found) |
|---|---|---|---|
| 211 | | 556.50 | 484 |
| 212 | | 570.53 | 498 |
| 213 | | 556.50 | 484 |
| 214 | | 550.52 | 478 |

TABLE 15-continued

| Example | Formula | TMW | LC-MS (found) |
|---|---|---|---|
| 215 | (structure shown, 2HCl salt) | 568.51 | 496 |
| 216 | (structure shown, 2HCl salt) | 568.51 | 496 |

Example 217

N²-{2-[2,3-dihydro-1H-inden-2-yl(methyl)amino]-2-oxoethyl}-N²-(6-methyl-3-oxo-2,3-dihydro-1H-inden-5-yl)-N¹-[2-(ethylamino)ethyl]glycinamide hydrochloride Using the compound (354 mg, 1.28 mmol) of Reference Example 126, the compound (240 mg, 1.31 mmol) of Reference Example 23 and the compound (296 mg, 1.57 mmol) of Reference Example 2, and according to the methods of Example 204, step A, and Example 1, step C, the title compound (220 mg, yield 33%) was obtained as a colorless solid.

¹H-NMR (400 MHz, DMSO-$d_6$); δ (ppm) 1.16 (t, J=7.2, 3H), 2.39 (s, 3H), 2.57-2.60 (m, 2H), 2.65 2.75 (2s, 3H), 2.84-3.12 (m, 10H), 3.33-3.38 (m, 2H), 3.80 3.84 (2s, 2H), 4.06 4.22 (2s, 2H), 4.84-4.91 5.25-5.34 (2m, 1H), 7.12-7.22 (m, 4H), 7.35 (s, 1H), 7.40 7.43 (2s, 1H), 8.35-8.39 (m, 1H), 8.73 (brs, 2H).

Example 218

N²-{2-[1,3-dihydro-2H-isoindol-2-yl(methyl)amino]-2-oxoethyl}-N²-(6-methyl-3-oxo-2,3-dihydro-1H-inden-5-yl)-N¹-[2-(isopropylamino)ethyl]glycinamide dihydrochloride Using the compound (277 mg, 0.999 mmol) of Reference Example 126, the compound (187 mg, 1.01 mmol) of Reference Example 17 and the compound (223 mg, 1.10 mmol) of Reference Example 3, and according to the methods of Example 204, step A, and Example 1, step C, the title compound (295 mg, yield 52%) was obtained as a brown solid.

¹H-NMR (400 MHz, DMSO-$d_6$); δ (ppm) 1.19 (t, J=6.5, 6H), 2.38 (s, 3H), 2.56-2.59 (m, 2H), 2.86-2.88 (m, 5H), 2.96-2.98 (m, 2H), 3.20-3.27 (m, 1H), 3.36-3.39 (m, 2H), 3.88 (s, 2H), 4.09-4.30 (m, 6H), 7.24-7.29 (m, 4H), 7.33 (s, 1H), 7.37 (s, 1H), 8.33 (t, J=5.7, 1H), 8.86 (brs, 2H).

Example 219

N²-{2-[(5-fluoro-1,3-dihydro-2H-isoindol-2-yl)(methyl)amino]-2-oxoethyl}-N²-(6-methyl-3-oxo-2,3-dihydro-1H-inden-5-yl)-N¹-[2-(isopropylamino)ethyl]glycinamide dihydrochloride Using the compound (277 mg, 0.999 mmol) of Reference Example 126, the compound (205 mg, 1.01 mmol) of Reference Example 19 and the compound (223 mg, 1.10 mmol) of Reference Example 3, and according to the methods of Example 204, step A, and Example 1, step C, the title compound (415 mg, yield 71%) was obtained as a brown solid.

¹H-NMR (400 MHz, DMSO-$d_6$); δ (ppm) 1.19 (d, J=6.6, 6H), 2.37 (s, 3H), 2.56-2.59 (m, 2H), 2.86-2.88 (m, 5H), 2.96-2.98 (m, 2H), 3.20-3.27 (m, 1H), 3.36-3.39 (m, 2H), 3.88 (s, 2H), 4.06-4.26 (m, 4H), 4.29 (s, 2H), 7.05-7.10 (m, 1H), 7.15 (dd, J=8.8, 1.9, 1H), 7.28-7.32 (m, 1H), 7.33 (s, 1H), 7.36 (s, 1H), 8.32 (t, J=5.8, 1H), 8.87 (brs, 2H).

Example 220

N²-{2-[1,3-dihydro-2H-isoindol-2-yl(methyl)amino]-2-oxoethyl}-N²-(6-methyl-1-oxo-2,3-dihydro-1H-inden-5-yl)-N¹-[2-(ethylamino)ethyl]glycinamide dihydrochloride Using the compound (261 mg, 0.941 mmol) of Reference Example 125, the compound (176 mg, 1.01 mmol) of Reference Example 17 and the compound (195 mg, 1.10 mmol) of Reference Example 2, and according to the methods of Example 204, step A, and Example 1, step C, the title compound (94 mg, yield 18%) was obtained as a pale-pink solid.
$^1$H-NMR (400 MHz, DMSO-d$_6$); δ (ppm) 1.16 (d, J=7.3, 3H), 2.29 (s, 3H), 2.49-2.54 (m, 2H), 2.89-2.92 (m, 9H), 3.38-3.40 (m, 2H), 3.99 (s, 2H), 4.15 4.18 (2s, 2H), 4.28 4.31 (2s, 2H), 4.43 (s, 2H), 6.97 (s, 1H), 7.24-7.30 (m, 4H), 7.34 (s, 1H), 8.36 (t, J=5.7, 1H), 8.85 (brs, 2H).

Example 221

N$^2$-{2-[(4-fluoro-1,3-dihydro-2H-isoindol-2-yl)(methyl)amino]-2-oxoethyl}-N$^2$-(6-methyl-1-oxo-2,3-dihydro-1H-inden-5-yl)-N$^1$-[2-(ethylamino)ethyl]glycinamide dihydrochloride Using the compound (261 mg, 0.941 mmol) of Reference Example 125, the compound (193 mg, 1.01 mmol) of Reference Example 18 and the compound (195 mg, 1.10 mmol) of Reference Example 2, and according to the methods of Example 204, step A, and Example 1, step C, the title compound (98 mg, yield 18%) was obtained as a colorless solid.
$^1$H-NMR (400 MHz, DMSO-d$_6$); δ (ppm) 1.16 (t, J=7.2, 3H), 2.29 (s, 3H), 2.49-2.54 (m, 2H), 2.90-2.96 (m, 6H), 2.93 (s, 3H), 3.37-3.41 (m, 2H), 3.98 (s, 2H), 4.21 4.24 (2s, 2H), 4.31 4.35 (2s, 2H), 4.44 (s, 2H), 6.98 (s, 1H), 7.07-7.15 (m, 2H), 7.32-7.35 (m, 2H), 8.34 (t, J=5.8, 1H), 8.80 (brs, 2H).

Example 222

N$^2$-{2-[(5-fluoro-1,3-dihydro-2H-isoindol-2-yl)(methyl)amino]-2-oxoethyl}-N$^2$-(6-methyl-1-oxo-2,3-dihydro-1H-inden-5-yl)-N$^1$-[2-(ethylamino)ethyl]glycinamide dihydrochloride Using the compound (261 mg, 0.941 mmol) of Reference Example 125, the compound (193 mg, 1.01 mmol) of Reference Example 19 and the compound (195 mg, 1.10 mmol) of Reference Example 2, and according to the methods of Example 204, step A, and Example 1, step C, the title compound (98 mg, yield 19%) was obtained as a brown solid.
$^1$H-NMR (400 MHz, DMSO-d$_6$); δ (ppm) 1.16 (t, J=7.1, 3H), 2.28 (s, 3H), 2.49-2.54 (m, 2H), 2.88-2.96 (m, 6H), 2.91 (s, 3H), 3.37-3.41 (m, 2H), 3.99 (s, 2H), 4.13-4.31 (m, 4H), 4.42 (s, 2H), 6.97 (s, 1H), 7.06-7.11 (m, 1H), 7.16 (dd, J=9.0, 2.0, 1H), 7.30-7.33 (m, 1H), 7.34 (s, 1H), 8.35 (t, J=5.7, 1H), 8.83 (brs, 2H).

Example 223

N$^2$-(5-cyano-4-fluoro-2-methylphenyl)-N$^2$-{2-[1,3-dihydro-2H-isoindol-2-yl(methyl)amino]-2-oxoethyl}-N$^1$-[2-(ethylamino)ethyl]glycinamide dihydrochloride Step A N$^2$-(5-cyano-4-fluoro-2-methylphenyl)-N$^2$-{2-[1,3-dihydro-2H-isoindol-2-yl(methyl)amino]-2-oxoethyl}-N$^1$-{2-[(tert-butoxycarbonyl)(ethyl)amino]ethyl}glycinamide Using the compound (399 mg, 1.50 mmol) of Reference Example 128, the compound (280 mg, 1.52 mmol) of Reference Example 17 and the compound (311 mg, 1.65 mmol) of Reference Example 2, and according to the method of Example 204, step A, the title compound (769 mg, yield 90%) was obtained as a bistered oil.
$^1$H-NMR (400 MHz, DMSO-d$_6$); δ (ppm) 0.95 (brs, 3H), 1.35 (s, 9H), 2.35 (s, 3H), 2.87 (s, 3H), 3.04-3.16 (m, 6H), 3.77 (s, 2H), 4.11 4.14 (2s, 2H), 4.23-4.26 (m, 4H), 7.23-7.32 (m, 5H), 7.59 (d, J=6.2, 1H), 8.01 (brs, 1H).

Step B

N$^2$-(5-cyano-4-fluoro-2-methylphenyl)-N$^2$-{2-[1,3-dihydro-2H-isoindol-2-yl(methyl)amino]-2-oxoethyl}-N$^1$-[2-(ethylamino)ethyl]glycinamide dihydrochloride Using the compound (256 mg, 0.452 mmol) obtained in step A and according to the method of Example 1, step C, the title compound (219 mg, yield 90%) was obtained as a colorless amorphous solid.
$^1$H-NMR (400 MHz, DMSO-d$_6$); δ (ppm) 1.19 (t, J=7.1, 1H), 2.36 (s, 3H), 2.87 (s, 3H), 2.87-2.91 (m, 4H), 3.35-3.37 (m, 2H), 3.85 (s, 2H), 4.12 4.14 (2s, 2H), 4.23-4.26 (m, 4H), 7.24-7.33 (m, 5H), 7.60 (d, J=6.2, 1H), 8.26 (t, J=5.6, 1H), 8.76 (brs, 2H).

Example 224

N$^2$-(5-cyano-4-fluoro-2-methylphenyl)-N$^2$-{2-[(4-fluoro-1,3-dihydro-2H-isoindol-2-yl)(methyl)amino]-2-oxoethyl}-N$^1$-[2-(ethylamino)ethyl]glycinamide dihydrochloride Step A N$^2$-(5-cyano-4-fluoro-2-methylphenyl)-N$^2$-{2-[(4-fluoro-1,3-dihydro-2H-isoindol-2-yl)(methyl)amino]-2-oxoethyl}-N$^1$-{2-[(tert-butoxycarbonyl)(ethyl)amino]ethyl}glycinamide Using the compound (399 mg, 1.50 mmol) of Reference Example 128, the compound (307 mg, 1.52 mmol) of Reference Example 18 and the compound (311 mg, 1.65 mmol) of Reference Example 2, and according to the method of Example 204, step A, the title compound (760 mg, yield 87%) was obtained as a bistered oil.
$^1$H-NMR (400 MHz, DMSO-d$_6$); δ (ppm) 0.95 (brs, 3H), 1.35 (s, 9H), 2.35 (s, 3H), 2.88 (s, 3H), 3.04-3.17 (m, 6H), 3.76 (s, 2H), 4.17-4.30 (m, 6H), 7.07-7.14 (m, 2H), 7.29-7.34 (m, 2H), 7.60 (d, J=6.2, 1H), 8.00 (brs, 1H).

Step B

N$^2$-(5-cyano-4-fluoro-2-methylphenyl)-N$^2$-{2-[(4-fluoro-1,3-dihydro-2H-isoindol-2-yl)(methyl)amino]-2-oxoethyl}-N$^1$-[2-(ethylamino)ethyl]glycinamide dihydrochloride Using the compound (253 mg, 0.433 mmol) obtained in step A and according to the method of Example 1, step C, the title compound (209 mg, yield 84%) was obtained as a colorless amorphous solid.
$^1$H-NMR (400 MHz, DMSO-d$_6$); δ (ppm) 1.16 (t, J=7.1, 3H), 2.37 (s, 3H), 2.88 (brs, 7H), 3.34-3.39 (m, 2H), 3.84 (s, 2H), 4.18-4.32 (m, 6H), as 7.07-7.14 (m, 2H), 7.30-7.35 (m, 2H), 7.61 (d, J=6.2, 1H), 8.26 (t, J=5.7, 1H), 8.82 (brs, 2H).

Example 225

N$^2$-(5-cyano-4-fluoro-2-methylphenyl)-N$^2$-{2-[(5-fluoro-1,3-dihydro-2H-isoindol-2-yl)(methyl)amino]-2-oxoethyl}-N$^1$-[2-(ethylamino)ethyl]glycinamide dihydrochloride

Step A

N$^2$-(5-cyano-4-fluoro-2-methylphenyl)-N$^2$-{2-[(5-fluoro-1,3-dihydro-2H-isoindol-2-yl)(methyl)amino]-2-oxoethyl}-N$^1$-{2-[(tert-butoxycarbonyl)(ethyl)amino]ethyl}glycinamide Using the compound (399 mg, 1.50 mmol) of Reference Example 128, the compound (307 mg, 1.52 mmol) of Reference Example 19 and the compound (311 mg, 1.65 mmol) of Reference Example 2, and according to the method of Example 204, step A, the title compound (784 mg, yield 89%) was obtained as a bistered oil.

$^1$H-NMR (400 MHz, DMSO-d$_6$); δ (ppm) 0.95 (brs, 3H), 1.35 (s, 9H), 2.35 (s, 3H), 2.86 (s, 3H), 3.04-3.17 (m, 6H), 3.77 (s, 2H), 4.09-4.26 (m, 6H), 7.05-7.10 (m, 2H), 7.14 (dd, J=8.9, 1.8, 2H), 7.28-7.32 (m, 2H), 7.58 (d, J=6.2, 1H), 8.01 (brs, 1H).

Step B

N$^2$-(5-cyano-4-fluoro-2-methylphenyl)-N$^2$-{2-[(5-fluoro-1,3-dihydro-2H-isoindol-2-yl)(methyl)amino]-2-oxoethyl}-N$^1$-[2-(ethylamino)ethyl]glycinamide dihydrochloride Using the compound (261 mg, 0.447 mmol) obtained in step A and according to the method of Example 1, step C, the title compound (222 mg, yield 89%) was obtained as a colorless amorphous solid.

$^1$H-NMR (400 MHz, DMSO-d$_6$); δ (ppm) 1.16 (t, J=7.2, 3H), 2.36 (s, 3H), 2.87 (s, 3H), 2.87-2.91 (m, 4H), 3.34-3.39 (m, 2H), 3.84 (s, 2H), 4.09-4.25 (m, 6H), 7.05-7.11 (m, 2H), 7.15 (dd, J=8.8, 2.0, 1H), 7.29-7.33 (m, 2H), 7.60 (d, J=6.1, 1H), 8.27 (t, J=5.8, 1H), 8.84 (brs, 2H).

Example 226

N$^2$-{2-[1,3-dihydro-2H-isoindol-2-yl(methyl)amino]-2-oxoethyl}-N$^2$-[4-fluoro-2-methyl-5-(5-methyl-1,2,4-oxadiazol-3-yl)phenyl]-N$^1$-[2-(ethylamino)ethyl]glycinamide dihydrochloride

Step A

N$^2$-{2-[1,3-dihydro-2H-isoindol-2-yl(methyl)amino]-2-oxoethyl}-N$^2$-[4-fluoro-2-methyl-5-(5-methyl-1,2,4-oxadiazol-3-yl)phenyl]-N$^1$-{2-[(tert-butoxycarbonyl)(ethyl)amino]ethyl}glycinamide Using the compound (513 mg, 0.905 mmol) of Example 223, step A and according to the method of Reference Example 62, step A, the title compound (513 mg, yield 91%) was obtained as a yellow oil.

$^1$H-NMR (400 MHz, DMSO-d$_6$); δ (ppm) 0.92 (brs, 3H), 1.34 (s, 9H), 2.34 (s, 3H), 2.66 (s, 3H), 2.86 (s, 3H), 3.03-3.17 (m, 6H), 3.80 (s, 2H), 4.10 4.12 (2s, 2H), 4.23-4.27 (m, 4H), 7.19-7.28 (m, 5H), 7.81 (d, J=6.8, 1H), 8.07 (brs, 1H).

Step B

N$^2$-{2-[1,3-dihydro-2H-isoindol-2-yl(methyl)amino]-2-oxoethyl}-N$^2$-[4-fluoro-2-methyl-5-(5-methyl-1,2,4-oxadiazol-3-yl)phenyl]-N$^1$-[2-(ethylamino)ethyl]glycinamide dihydrochloride Using the compound (513 mg, 0.822 mmol) obtained in step A and according to the method of Example 1, step C, the title compound (458 mg, yield 93%) was obtained as a colorless amorphous solid.

$^1$H-NMR (400 MHz, DMSO-d$_6$); δ (ppm) 1.15 (t, J=7.2, 3H), 2.36 (s, 3H), 2.67 (s, 3H), 2.87 (s, 3H), 2.87-2.91 (m, 4H), 3.34-3.39 (m, 2H), 3.88 (s, 2H), 4.10 4.13 (2s, 2H), 4.23 4.26 (2s, 2H), 4.30 (s, 2H), 7.20-7.28 (m, 5H), 7.81 (d, J=6.8, 1H), 8.32 (t, J=5.8, 1H), 8.79 (brs, 2H).

Example 227

N$^2$-{2-[(4-fluoro-1,3-dihydro-2H-isoindol-2-yl)(methyl)amino]-2-oxoethyl}-N$^2$-[4-fluoro-2-methyl-5-(5-methyl-1,2,4-oxadiazol-3-yl)phenyl]-N$^1$-[2-(ethylamino)ethyl]glycinamide dihydrochloride

Step A

N$^2$-{2-[(4-fluoro-1,3-dihydro-2H-isoindol-2-yl)(methyl)amino]-2-oxoethyl}-N$^2$-[4-fluoro-2-methyl-5-(5-methyl-1,2,4-oxadiazol-3-yl)phenyl]-N$^1$-{2-[(tert-butoxycarbonyl)(ethyl)amino]ethyl}glycinamide Using the compound (507 mg, 0.867 mmol) of Example 224, step A and according to the method of Reference Example 62, step A, the title compound (487 mg, yield 88%) was obtained as a yellow oil.

$^1$H-NMR (400 MHz, DMSO-d$_6$); δ (ppm) 0.92 (brs, 3H), 1.34 (s, 9H), 2.34 (s, 3H), 2.66 (s, 3H), 2.87 (s, 3H), 3.03-3.17 (m, 6H), 3.79 (s, 2H), 4.16-4.34 (m, 6H) 7.07-7.14 (m, 2H), 7.19-7.22 (m, 1H), 7.29-7.34 (m, 1H), 7.81 (d, J=6.7, 1H), 8.06 (brs, 1H).

Step B

N$^2$-{2-[(4-fluoro-1,3-dihydro-2H-isoindol-2-yl)(methyl)amino]-2-oxoethyl}-N$^2$-[4-fluoro-2-methyl-5-(5-methyl-1,2,4-oxadiazol-3-yl)phenyl]-N$^1$-[2-(ethylamino)ethyl]glycinamide dihydrochloride Using the compound (487 mg, 0.759 mmol) obtained in step A and according to the method of Example 1, step C, the title compound (397 mg, yield 85%) was obtained as a colorless amorphous solid.

$^1$H-NMR (400 MHz, DMSO-d$_6$); δ (ppm) 1.15 (t, J=7.1, 3H), 2.36 (s, 3H), 2.67 (s, 3H), 2.87 (s, 3H), 2.87-2.91 (m, 4H), 3.35-3.39 (m, 2H), 3.87 (s, 2H), 4.16-4.38 (m, 6H), 7.07-7.14 (m, 2H), 7.20-7.23 (m, 1H), 7.30-7.35 (m, 1H), 7.81 (d, J=6.8, 1H), 8.32 (t, J=5.8, 1H), 8.83 (brs, 2H).

Example 228

N²-{2-[(5-fluoro-1,3-dihydro-2H-isoindol-2-yl)(methyl)amino]-2-oxoethyl}-N²-[4-fluoro-2-methyl-5-(5-methyl-1,2,4-oxadiazol-3-yl)phenyl]-N¹-[2-(ethylamino)ethyl]glycinamide dihydrochloride

Step A

N²-{2-[(5-fluoro-1,3-dihydro-2H-isoindol-2-yl)(methyl)amino]-2-oxoethyl}-N²-[4-fluoro-2-methyl-5-(5-methyl-1,2,4-oxadiazol-3-yl)phenyl]-N¹-{2-[(tert-butoxycarbonyl)(ethyl)amino]ethyl}glycinamide Using the compound (523 mg, 0.894 mmol) of Example 225, step A and according to the method of Reference Example 62, step A, the title compound (552 mg, yield 96%) was obtained as a yellow oil.

$^1$H-NMR (400 MHz, DMSO-$d_6$); δ (ppm) 0.92 (brs, 3H), 1.34 (s, 9H), 2.34 (s, 3H), 2.66 (s, 3H), 2.86 (s, 3H), 3.03-3.17 (m, 6H), 3.80 (s, 2H), 4.10-4.26 (m, 6H), 7.05-7.10 (m, 1H), 7.13-7.15 (m, 1H), 7.19-7.22 (m, 1H), 7.27-7.31 (m, 1H), 7.80 (d, J=6.8, 1H), 8.05 (brs, 1H).

Step B

N²-{2-[(5-fluoro-1,3-dihydro-2H-isoindol-2-yl)(methyl)amino]-2-oxoethyl}-N²-[4-fluoro-2-methyl-5-(5-methyl-1,2,4-oxadiazol-3-yl)phenyl]-N¹-[2-(ethylamino)ethyl]glycinamide dihydrochloride Using the compound (552 mg, 0.860 mmol) obtained in step A and according to the method of Example 1, step C, the title compound (452 mg, yield 85%) was obtained as a colorless amorphous solid.

$^1$H-NMR (400 MHz, DMSO-$d_6$); δ (ppm) 1.15 (t, J=7.2, 3H), 2.35 (s, 3H), 2.67 (s, 3H), 2.86 (s, 3H), 2.86-2.91 (m, 4H), 3.34-3.39 (m, 2H), 3.88 (s, 2H), 4.07-4.29 (m, 6H), 7.06-7.11 (m, 1H), 7.15 (dd, J=8.8, 1.9, 1H), 7.20-7.23 (m, 1H), 7.28-7.31 (m, 1H), 7.81 (d, J=6.9, 1H), 8.31 (t, J=5.7, 1H), 8.78 (brs, 2H).

Example 229

N²-{2-[1,3-dihydro-2H-isoindol-2-yl(methyl)amino]-2-oxoethyl}-N²-[2-methyl-4-(3-methyl-1,2,4-oxadiazol-5-yl)phenyl]-N¹-[2-(ethylamino)ethyl]glycinamide dihydrochloride Using the compound (305 mg, 1.00 mmol) of Reference Example 129, the compound (187 mg, 1.01 mmol) of Reference Example 17 and the compound (207 mg, 2.02 mmol) of Reference Example 2, and according to the methods of Example 204, step A, and Example 1, step C, the title compound (479 mg, yield 83%) was obtained as a colorless solid.

$^1$H-NMR (400 MHz, DMSO-$d_6$); δ (ppm) 1.16 (t, J=7.1, 3H), 2.34 (s, 3H), 2.37 (s, 3H), 2.89-2.90 (m, 4H), 2.92 (s, 3H), 3.37-3.42 (m, 2H), 4.00 (s, 2H), 4.17 4.20 (2s, 2H), 4.28 4.31 (2s, 2H), 4.45 (s, 2H), 7.03 (d, J=8.6, 1H), 7.24-7.30 (m, 4H), 7.75 (dd, J=8.5, 1.9, 1H), 7.79 (d, J=1.8, 1H), 8.38 (t, J=5.7, 1H), 8.89 (brs, 2H).

Example 230

N²-{2-[(4-fluoro-1,3-dihydro-2H-isoindol-2-yl)(methyl)amino]-2-oxoethyl}-N²-[2-methyl-4-(3-methyl-1,2,4-oxadiazol-5-yl)phenyl]-N¹-[2-(ethylamino)ethyl]glycinamide dihydrochloride Using the compound (401 mg, 1.31 mmol) of Reference Example 129, the compound (271 mg, 1.34 mmol) of Reference Example 18 and the compound (271 mg, 1.44 mmol) of Reference Example 2, and according to the methods of Example 204, step A, and Example 1, step C, the title compound (491 mg, yield 63%) was obtained as a colorless solid.

$^1$H-NMR (400 MHz, DMSO-$d_6$); δ (ppm) 1.15 (t, J=7.2, 3H), 2.34 (s, 3H), 2.37 (s, 3H), 2.8-3.0 (m, 4H), 2.93 (s, 3H), 3.35-3.41 (m, 2H), 3.99 (s, 2H), 4.22-4.35 (m, 4H), 4.44 (s, 2H), 7.05 (d, J=8.5, 1H), 7.07-7.16 (m, 2H), 7.29-7.36 (m, 1H), 7.76 (dd, J=2.1, 8.5, 1H), 7.79 (d, J=2.1, 1H), 8.33 (t, J=5.9, 1H), 8.67 (brs, 2H).

Example 231

N²-{2-[(5-fluoro-1,3-dihydro-2H-isoindol-2-yl)(methyl)amino]-2-oxoethyl}-N²-[2-methyl-4-(3-methyl-1,2,4-oxadiazol-5-yl)phenyl]-N¹-[2-(ethylamino)ethyl]glycinamide dihydrochloride Using the compound (305 mg, 1.00 mmol) of Reference Example 129, the compound (205 mg, 1.01 mmol) of Reference Example 19 and the compound (207 mg, 1.01 mmol) of Reference Example 2, and according to the methods of Example 204, step A, and Example 1, step C, the title compound (498 mg, yield 84%) was obtained as a colorless solid.

$^1$H-NMR (400 MHz, DMSO-$d_6$); δ (ppm) 1.16 (t, J=7.2, 1H), 2.33 (s, 3H), 2.37 (s, 3H), 2.87-2.91 (m, 4H), 2.91 (s, 3H), 3.37-3.42 (m, 2H), 3.99 (s, 2H), 4.14-4.31 (m, 4H), 4.44 (s, 2H), 7.02-7.11 (m, 2H), 7.16 (dd, J=8.9, 1.9, 1H), 7.30-7.33 (m, 1H), 7.75 (dd, J=8.5, 2.1, 1H), 7.79 (d, J=1.7, 1H), 8.38 (t, J=5.7, 1H), 8.90 (brs, 2H).

Example 232

N²-{2-[2,3-dihydro-1H-inden-2-yl(methyl)amino]-2-oxoethyl}-N²-[2-methyl-4-(3-methyl-1,2,4-oxadiazol-5-yl)phenyl]-N¹-[2-(ethylamino)ethyl]glycinamide hydrochloride Using the compound (438 mg, 1.43 mmol) of Reference Example 129, the compound (269 mg, 1.46 mmol) of Reference Example 23 and the compound (307 mg, 1.63 mmol) of Reference Example 2, and according to the methods of Example 204, step A, and Example 1, step C, the title compound (635 mg, yield 82%) was obtained as a colorless solid.

$^1$H-NMR (400 MHz, DMSO-$d_6$); δ (ppm) 1.17 (t, J=7.2, 3H), 2.35 (s, 3H), 2.37 (s, 3H), 2.71 2.79 (2s, 3H), 2.8-3.2 (m, 8H), 3.37-3.42 (m, 2H), 3.97 3.98 (2s, 2H), 4.22 4.40 (2s, 2H), 4.79-4.88 (m, 0.4H), 5.30-5.38 (m, 0.6H), 7.04-7.10 (m, 1H), 7.14-7.17 (m, 2H), 7.21-7.23 (m, 2H), 7.77 (d, J=8.6, 1H), 7.81 (s, 1H), 8.45 (t, J=5.3, 1H), 8.86 (brs, 2H).

Example 233

N²-{2-[1,3-dihydro-2H-isoindol-2-yl(methyl)amino]-2-oxoethyl}-N²-(3-methyl-8-oxo-5,6,7,8-tetrahydronaphthalen-2-yl)-N¹-[2-(ethylamino)ethyl]glycinamide dihydrochloride Using the compound (340 mg, 1.17 mmol) of Reference Example 127, the compound (222 mg, 1.20 mmol) of Reference Example 17 and the compound (246 mg, 1.31 mmol) of Reference Example 2, and according to the methods of Example 204, step A, and Example 1, step C, the title compound (477 mg, yield 72%) was obtained as a colorless solid.

¹H-NMR (400 MHz, DMSO-d₆); δ (ppm) 1.15 (t, J=7.2, 3H), 1.90-2.05 (m, 2H), 2.31 (s, 3H), 2.45-2.55 (m, 2H), 2.81 (t, J=5.8, 2H), 2.85-2.95 (m, 4H), 2.87 (s, 3H), 3.33-3.40 (m, 2H), 3.84 (s, 2H), 4.10 (d, J=11.5, 2H), 4.25 (d, J=11.5, 2H), 4.28 (s, 2H), 7.10 (s, 1H), 7.22-7.30 (m, 4H), 7.63 (s, 1H), 8.33 (t, J=5.8, 1H), 8.68 (brs, 2H).

Example 234

$N^2$-{2-[(5-fluoro-1,3-dihydro-2H-isoindol-2-yl)(methyl)amino]-2-oxoethyl}-$N^2$-(3-methyl-8-oxo-5,6,7,8-tetrahydronaphthalen-2-yl)-$N^1$-[2-(ethylamino)ethyl]glycinamide dihydrochloride Using the compound (310 mg, 1.06 mmol) of Reference Example 127, the compound (221 mg, 1.09 mmol) of Reference Example 19 and the compound (216 mg, 1.15 mmol) of Reference Example 2, and according to the methods of Example 204, step A, and Example 1, step C, the title compound (522 mg, yield 85%) was obtained as a colorless solid.
¹H-NMR (400 MHz, DMSO-d₆); δ (ppm) 1.15 (t, J=7.2, 3H), 1.90-2.05 (m, 2H), 2.30 (s, 3H), 2.45-2.55 (m, 2H), 2.81 (t, J=5.8, 2H), 2.80-2.95 (m, 4H), 2.86 (s, 3H), 3.33-3.40 (m, 2H), 3.84 (s, 2H), 4.00-4.25 (m, 4H), 4.27 (s, 2H), 7.05-7.11 (m, 1H), 7.11 (s, 1H), 7.13-7.17 (m, 1H), 7.28-7.32 (m, 1H), 7.62 (s, 1H), 8.33 (t, J=5.8, 1H), 8.70 (brs, 2H).

Example 235

$N^2$-{2-[1,3-dihydro-2H-isoindol-2-yl(methyl)amino]-2-oxoethyl}-$N^2$-[2-methyl-4-(4-methyl-1,3-thiazol-2-yl)phenyl]-$N^1$-[2-(ethylamino)ethyl]glycinamide hydrochloride Using the compound (386 mg, 1.20 mmol) of Reference Example 130, the compound (226 mg, 1.22 mmol) of Reference Example 17 and the compound (262 mg, 1.39 mmol) of Reference Example 2, and according to the methods of Example 204, step A, and Example 57, step B, the title compound (466 mg, yield 70%) was obtained as a yellow solid.
¹H-NMR (400 MHz, DMSO-d₆); δ (ppm) 1.14 (t, J=7.2, 3H), 2.32 (s, 3H), 2.39 (d, J=0.9, 3H), 2.8-3.0 (m, 4H), 2.91 (s, 3H), 3.34-3.40 (m, 2H), 3.93 (s, 2H), 4.14 (d, J=11.4, 2H), 4.28 (d, J=11.4, 2H), 4.35 (s, 2H), 7.07 (d, J=8.4, 1H), 7.21 (d, J=0.9, 1H), 7.23-7.30 (m, 4H), 7.59 (dd, J=2.1, 8.4, 1H), 7.65 (d, J=2.1, 1H), 8.31 (t, J=5.8, 1H), 8.57 (brs, 2H).

Example 236

$N^2$-{2-[1,3-dihydro-2H-isoindol-2-yl(methyl)amino]-2-oxoethyl}-$N^2$-[2-methyl-4-(5-methyl-1,3-thiazol-2-yl)phenyl]-$N^1$-[2-(ethylamino)ethyl]glycinamide hydrochloride Using the compound (290 mg, 0.905 mmol) of Reference Example 131, the compound (168 mg, 0.910 mmol) of Reference Example 17 and the compound (186 mg, 0.988 mmol) of Reference Example 2, and according to the methods of Example 204, step A, and Example 57, step B, the title compound (326 mg, yield 65%) was obtained as a yellow solid.

¹H-NMR (400 MHz, DMSO-d₆); δ (ppm) 1.14 (t, J=7.2, 3H), 2.31 (s, 3H), 2.46 (d, J=1.1, 3H), 2.8-3.0 (m, 4H), 2.90 (s, 3H), 3.34-3.40 (m, 2H), 3.93 (s, 2H), 4.14 (d, J=11.4, 2H), 4.27 (d, J=11.4, 2H), 4.35 (s, 2H), 7.07 (d, J=8.4, 1H), 7.23-7.30 (m, 4H), 7.51 (d, J=1.1, 1H), 7.55 (dd, J=2.1, 8.4, 1H), 7.60 (d, J=2.1, 1H), 8.31 (broad t, 1H), 8.67 (brs, 2H).

Example 237

$N^2$-{2-[(5-fluoro-1,3-dihydro-2H-isoindol-2-yl)(methyl)amino]-2-oxoethyl}-$N^2$-[2-methyl-4-(5-methyl-1,3-thiazol-2-yl)phenyl]-$N^1$-[2-(ethylamino)ethyl]glycinamide hydrochloride Using the compound (293 mg, 0.915 mmol) of Reference Example 131, the compound (186 mg, 0.920 mmol) of Reference Example 19 and the compound (192 mg, 1.02 mmol) of Reference Example 2, and according to the methods of Example 204, step A, and Example 57, step B, the title compound (420 mg, yield 80%) was obtained as a yellow solid.
¹H-NMR (400 MHz, DMSO-d₆); δ (ppm) 1.14 (t, J=7.2, 3H), 2.31 (s, 3H), 2.46 (d, J=1.1, 3H), 2.8-3.0 (m, 4H), 2.90 (s, 3H), 3.3-3.4 (m, 2H), 3.92 (s, 2H), 4.09-4.30 (m, 4H), 4.34 (s, 2H), 7.07 (d, J=8.4, 1H), 7.08-7.12 (m, 1H), 7.13-7.17 (m, 1H), 7.28-7.33 (m, 1H), 7.51 (d, J=1.1, 1H), 7.55 (dd, J=2.1, 8.4, 1H), 7.60 (d, J=2.1, 1H), 8.31 (t, J=5.8, 1H), 8.66 (brs, 2H).

Example 238

$N^2$-{2-[1,3-dihydro-2H-isoindol-2-yl(methyl)amino]-2-oxoethyl}-$N^2$-[2-methyl-4-(5-methyl-1,3,4-thiadiazol-2-yl)phenyl]-$N^1$-[2-(ethylamino)ethyl]glycinamide dihydrochloride Using the compound (368 mg, 1.15 mmol) of Reference Example 132, the compound (221 mg, 1.16 mmol) of Reference Example 17 and the compound (252 mg, 1.34 mmol) of Reference Example 2, and according to the methods of Example 204, step A, and Example 1, step C, the title compound (359 mg, yield 52%) was obtained as a pale-yellow solid.
¹H-NMR (400 MHz, DMSO-d₆); δ (ppm) 1.14 (t, J=7.2, 3H), 2.33 (s, 3H), 2.74 (s, 3H), 2.8-3.0 (m, 4H), 2.91 (s, 3H), 3.33-3.40 (m, 2H), 3.95 (s, 2H), 4.15 (d, J=11.5, 2H), 4.28 (d, J=11.5, 2H), 4.37 (s, 2H), 7.08 (d, J=8.4, 1H), 7.24-7.30 (m, 4H), 7.61 (dd, J=2.1, 8.4, 1H), 7.66 (d, J=2.1, 1H), 8.30 (t, J=5.6, 1H), 8.55 (brs, 2H).

Example 239

$N^2$-{2-[(5-fluoro-1,3-dihydro-2H-isoindol-2-yl)(methyl)amino]-2-oxoethyl}-$N^2$-[2-methyl-4-(5-methyl-1,3,4-thiadiazol-2-yl)phenyl]-$N^3$-[2-(ethylamino)ethyl]glycinamide dihydrochloride Using the compound (371 mg, 1.15 mmol) of Reference Example 132, the compound (242 mg, 1.20 mmol) of Reference Example 19 and the compound (252 mg, 1.34 mmol) of Reference Example 2, and according to the methods of Example 204, step A, and Example 1, step C, the title compound (389 mg, yield 55%) was obtained as a pale-yellow solid.
¹H-NMR (400 MHz, DMSO-d₆); δ (ppm) 1.14 (t, J=7.2, 3H), 2.32 (s, 3H), 2.74 (s, 3H), 2.8-3.0 (m, 4H), 2.91 (s, 3H), 3.33-3.40 (m, 2H), 3.95 (s, 2H), 4.11-4.31 (m, 4H), 4.36 (s, 2H), 7.06-7.12 (m, 1H), 7.07 (d, J=8.4, 1H), 7.15 (d, J=8.8, 1H), 7.29-7.33 (m, 1H), 7.61 (dd, J=2.1, 8.4, 1H), 7.66 (d, J=2.1, 1H), 8.29 (t, J=5.8, 1H), 8.48 (brs, 2H).

The compounds of Examples 217-239 are shown below.
TABLE 16
| Example | Structural Formula | TMW | LC-MS (found) |
|---|---|---|---|
| 217 | 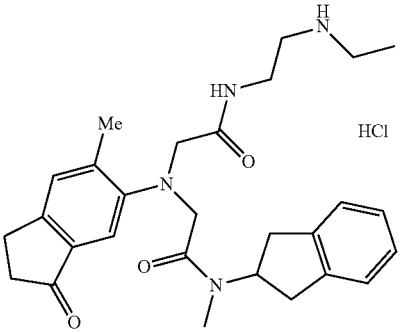 [SMILES: CCNCCNC(=O)CN(CC(=O)N(C)C1Cc2ccccc2C1)c1cc2c(cc1C)CCC2=O ; Cl] | 513.07 | 477 |
| 218 | 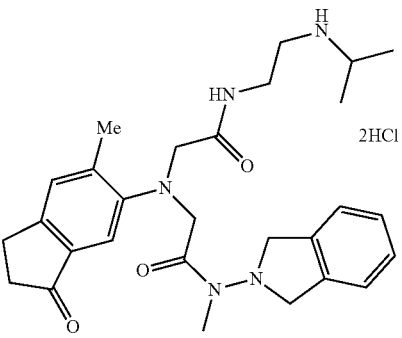 [SMILES: Cc1cc2c(cc1N(CC(=O)NCCNC(C)C)CC(=O)N(C)N1Cc3ccccc3C1)C(=O)CC2 ; "2HCl"] | 564.55 | 492 |
| 219 | 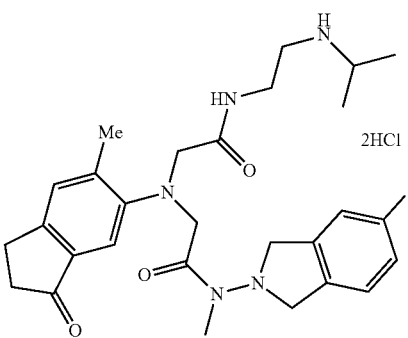 | 582.54 | 510 |
| 220 | 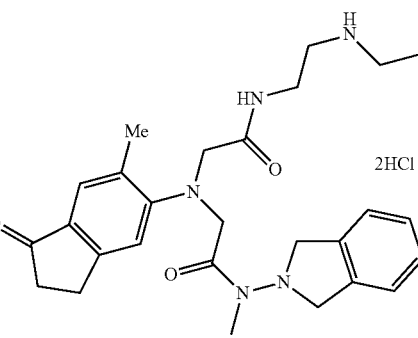 | 550.52 | 478 |

TABLE 16-continued
| Example | Structural Formula | TMW | LC-MS (found) |
|---|---|---|---|
| 221 | 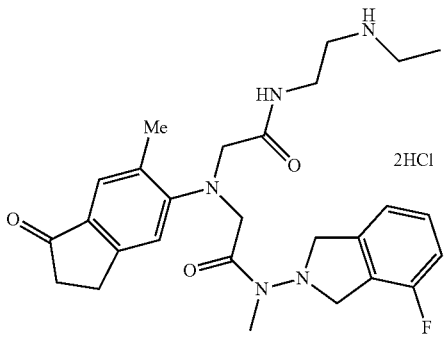 [SMILES: CCNCCNC(=O)CN(CC(=O)N(C)N1Cc2cccc(F)c2C1)c1cc2c(cc1C)C(=O)CC2 ; "2HCl"] | 568.51 | 496 |
| 222 | 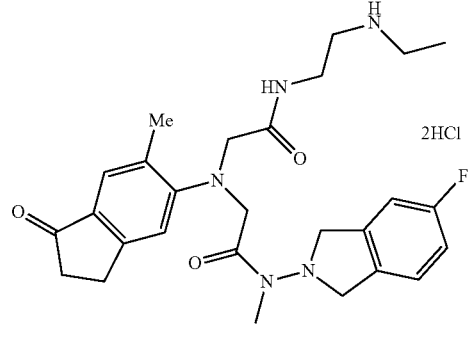 [SMILES: CCNCCNC(=O)CN(CC(=O)N(C)N1Cc2ccc(F)cc2C1)c1cc2c(cc1C)C(=O)CC2 ; "2HCl"] | 568.51 | 496 |
| 223 | 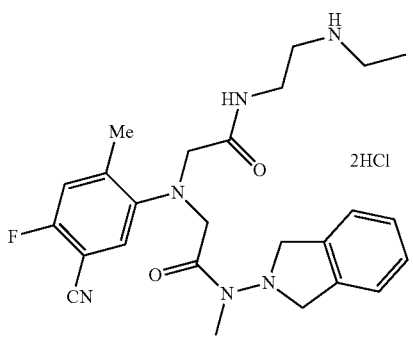 [SMILES: CCNCCNC(=O)CN(CC(=O)N(C)N1Cc2ccccc2C1)c1cc(C#N)c(F)cc1C ; "2HCl"] | 539.47 | 467 |
| 224 | 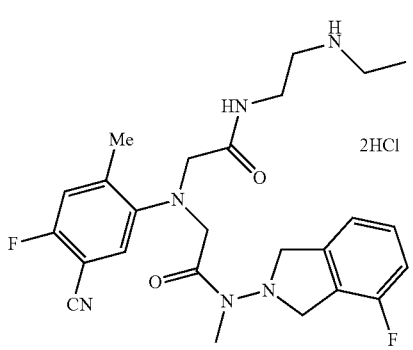 [SMILES: CCNCCNC(=O)CN(CC(=O)N(C)N1Cc2cccc(F)c2C1)c1cc(C#N)c(F)cc1C ; "2HCl"] | 557.46 | 485 |

TABLE 16-continued

| Example | Structural Formula | TMW | LC-MS (found) |
|---|---|---|---|
| 225 | | 557.46 | 485 |
| 226 | | 596.52 | 524 |
| 227 | | 614.51 | 542 |
| 228 | | 614.51 | 542 |

TABLE 16-continued

| Example | Structural Formula | TMW | LC-MS (found) |
|---|---|---|---|
| 229 | | 578.53 | 506 |
| 230 | | 596.52 | 524 |
| 231 | | 596.52 | 524 |
| 232 | | 541.08 | 505 |

TABLE 16-continued

| Example | Structural Formula | TMW | LC-MS (found) |
|---|---|---|---|
| 233 | | 564.55 | 492 |
| 234 | | 582.54 | 510 |
| 235 | | 557.15 | 521 |
| 236 | | 557.15 | 521 |
| 237 | | 575.14 | 539 |

TABLE 16-continued

| Example | Structural Formula | TMW | LC-MS (found) |
|---|---|---|---|
| 238 | | 594.60 | 522 |
| 239 | | 612.59 | 540 |

Example 241

N²-{2-[1,3-dihydro-2H-isoindol-2-yl(methyl)amino]-2-oxoethyl}-N²-(1,6-dimethyl-1H-indazol-5-yl)-N¹-[2-(ethylamino)ethyl]glycinamide hydrochloride

Step A

N-{2-[1,3-dihydro-2H-isoindol-2-yl(methyl)amino]-2-oxoethyl}-N-[6-methyl-1-(tetrahydro-2H-pyran-2-yl)-1H-indazol-5-yl]glycine To N,N-dimethylformamide (80 ml) were added the compound (6.33 g, 18.2 mmol) of Reference Example 133 and WSC₃ (3.70 g, 19.3 mmol), and the mixture was stirred at room temperature for 1 hr. The reaction mixture was ice-cooled, the compound (3.44 g, 18.6 mmol) of Reference Example 17 and N,N-diisopropylethylamine (5.0 ml, 29.4 mmol) were added, and the mixture was stirred at the same temperature for 1 hr. To the reaction mixture was added diluted hydrochloric acid, and the precipitated solid was filtered, washed with water, and dried under reduced pressure to give the title compound (7.44 g, yield 86%) as a colorless solid.

¹H-NMR (400 MHz, DMSO-d₆); δ (ppm) 1.5-1.6 (m, 2H), 1.65-1.80 (m, 1H), 1.85-2.10 (m, 2H), 2.3-2.5 (m, 1H), 2.40 (s, 3H), 2.86 (s, 3H), 3.68-3.80 (m, 1H), 3.84-3.89 (m, 1H), 3.98 (s, 2H), 4.03-4.25 (m, 4H), 4.27 (s, 2H), 5.73 (dd, J=2.4, 9.7, 1H), 7.22-7.27 (m, 4H), 7.46 (s, 1H), 7.54 (s, 1H), 7.92 (s, 1H), 12.47 (brs, 1H).

Step B

N-{2-[1,3-dihydro-2H-isoindol-2-yl(methyl)amino]-2-oxoethyl}-N-(6-methyl-1H-indazol-5-yl)glycine ethyl ester The compound (2.23 g, 4.67 mmol) of step A was dissolved in ethanol (60 ml), concentrated sulfuric acid (0.5 ml) was added at room temperature, and the mixture was heated under reflux for 80 min. The reaction mixture was concentrated under reduced pressure, and the residue was diluted with ethyl acetate. The organic layer was washed with aqueous sodium bicarbonate and saturated brine, and dried over anhydrous magnesium sulfate. The insoluble material was filtered off, and the solution was concentrated under reduced pressure. The obtained oil was purified by silica gel column chromatography (ethyl acetate-hexane) to give the title compound (1.64 g, yield 83%) as a colorless amorphous solid.

¹H-NMR (400 MHz, DMSO-d₆); δ (ppm) 1.12 (t, J=7.1, 3H), 2.39 (s, 3H), 2.84 (s, 3H), 3.99 (q, J=7.1, 2H), 4.03-4.21 (m, 4H), 4.22 (d, J=11.8, 2H), 4.25 (s, 2H), 7.25 (brs, 4H), 7.27 (s, 1H), 7.55 (s, 1H), 7.88 (s, 1H), 12.71 (brs, 1H).

Step C

N-{2-[1,3-dihydro-2H-isoindol-2-yl(methyl)amino]-2-oxoethyl}-N-(1,6-dimethyl-1H-indazol-5-yl)glycine ethyl ester The compound (871 mg, 2.07 mmol) of step B was dissolved in N,N-dimethylformamide (19 ml), 60% sodium hydride (109 mg, 2.73 mmol) was added under ice-cooling with stirring, and the mixture was stirred at the same temperature for 1 hr. Then, methyl iodide (0.44 ml) was added, and the mixture was stirred under ice-cooling for 90 min. The reaction mixture was diluted with 10% citric acid, and the mixture was extracted with ethyl acetate. The organic layer was washed with saturated aqueous sodium hydrogen carbonate and saturated brine, and dried over anhydrous magnesium sulfate. The insoluble material was filtered off, and the solution was concentrated under reduced pressure. The obtained oil was purified by silica gel column chromatography (ethyl acetate-hexane→ethyl acetate-methanol) to give the title compound (653 mg, yield 73%) as a colorless amorphous solid.

$^1$H-NMR (400 MHz, CDCl$_3$); δ (ppm) 1.19 (t, J=7.1, 3H), 2.52 (s, 3H), 2.92 (s, 3H), 3.99 (s, 3H), 4.05-4.25 (m, 6H), 4.38 (s, 2H), 7.17 (s, 1H), 7.18-7.25 (m, 4H), 7.68 (s, 1H), 7.82 (s, 1H).

In addition, N-{2-[1,3-dihydro-2H-isoindol-2-yl(methyl)amino]-2-oxoethyl}-N-(2,6-dimethyl-2H-indazol-5-yl)glycine ethyl ester (171 mg, yield 19%) was obtained as a colorless solid.

$^1$H-NMR (400 MHz, CDCl$_3$); δ (ppm) 1.18 (t, J=7.2, 3H), 2.45 (s, 3H), 2.91 (s, 3H), 4.08 (d, J=14, 2H), 4.09 (q, J=7.2, 2H), 4.16 (d, J=14, 2H), 4.21 (s, 2H), 4.37 (s, 2H), 7.17-7.30 (m, 4H), 7.45 (s, 1H), 7.51 (s, 1H), 7.70 (s, 1H).

Step D

N-{2-[1,3-dihydro-2H-isoindol-2-yl(methyl)amino]-2-oxoethyl}-N-(1,6-dimethyl-1H-indazol-5-yl)glycine The compound (631 mg, 1.45 mmol) of step C was dissolved in a methanol (5 ml)-tetrahydrofuran (2 ml) mixed solvent, 1N sodium hydroxide (5 ml) was added at room temperature, and the mixture was stirred at room temperature for 70 min. To the reaction mixture was added 1N hydrochloric acid (5 ml), and the solution was concentrated under reduced pressure. The precipitated solid was filtered, washed with water, and dried under reduced pressure to give the title compound (517 mg, yield 88%) as a colorless solid.

$^1$H-NMR (300 MHz, DMSO-d$_6$); δ (ppm) 2.41 (s, 3H), 2.86 (s, 3H), 3.95 (s, 3H), 3.97 (s, 2H), 4.07 (d, J=12, 2H), 4.23 (d, J=12, 2H), 4.27 (s, 2H), 7.21-7.28 (m, 4H), 7.37 (s, 1H), 7.53 (s, 1H), 7.85 (s, 1H), 12.49 (brs, 1H).

Step E

N$^2$-{2-[1,3-dihydro-2H-isoindol-2-yl(methyl)amino]-2-oxoethyl}-N$^2$-(1,6-dimethyl-1H-indazol-5-yl)-N$^1$-[2-(ethylamino)ethyl]glycinamide hydrochloride Using the compound (262 mg, 0.643 mmol) of step D and the compound (183 mg, 0.972 mmol) of Reference Example 2, and according to the methods of Example 1, step B, and Example 57, step B, the title compound (273 mg, yield 83%) was obtained as a colorless solid.

$^1$H-NMR (300 MHz, DMSO-d$_6$); δ (ppm) 1.13 (t, J=7.2, 3H), 2.43 (s, 3H), 2.8-3.0 (m, 4H), 2.87 (s, 3H), 3.30-3.45 (m, 2H), 3.83 (s, 2H), 3.96 (s, 3H), 4.04 (d, J=12, 2H), 4.22 (d, J=12, 2H), 4.25 (s, 2H), 7.25 (brs, 4H), 7.40 (s, 1H), 7.58 (s, 1H), 7.86 (s, 1H), 8.42 (t, J=5.7, 1H), 8.63 (brs, 2H).

Example 242

N$^2$-{2-[1,3-dihydro-2H-isoindol-2-yl(methyl)amino]-2-oxoethyl}-N$^2$-(1,6-dimethyl-1H-indazol-5-yl)-N$^1$-[2-(isopropylamino)ethyl]glycinamide hydrochloride Using the compound (248 mg, 0.609 mmol) of Example 241, step D, and the compound (182 mg, 0.900 mmol) of Reference Example 3, and according to the methods of Example 1, step B, and Example 57, step B, the title compound (197 mg, yield 61%) was obtained as a colorless solid.

$^1$H-NMR (300 MHz, DMSO-d$_6$); δ (ppm) 1.17 (d, J=6.6, 6H), 2.44 (s, 3H), 2.8-3.0 (m, 2H), 2.87 (s, 3H), 3.1-3.3 (m, 1H), 3.34-3.39 (m, 2H), 3.84 (s, 2H), 3.96 (s, 3H), 4.05 (d, J=12, 2H), 4.22 (d, J=12, 2H), 4.27 (s, 2H), 7.25 (brs, 4H), 7.40 (s, 1H), 7.58 (s, 1H), 7.86 (s, 1H), 8.43 (t, J=5.7, 1H), 8.66 (brs, 2H).

Example 243

N$^2$-{2-[1,3-dihydro-2H-isoindol-2-yl(methyl)amino]-2-oxoethyl}-N$^2$-(2,6-dimethyl-2H-indazol-5-yl)-N$^1$-[2-(ethylamino)ethyl]glycinamide hydrochloride Using N-{2-[1,3-dihydro-2H-isoindol-2-yl(methyl)amino]-2-oxoethyl}-N-(2,6-dimethyl-2H-indazol-5-yl)glycine ethyl ester (165 mg, 0.379 mmol) obtained in Example 241, step C, and according to the methods of Example 241, steps D and E, the title compound (147 mg, yield 75%) was obtained as a colorless solid.

$^1$H-NMR (300 MHz, DMSO-d$_6$); δ (ppm) 1.13 (t, J=7.2, 3H), 2.36 (s, 3H), 2.8-3.0 (m, 4H), 2.87 (s, 3H), 3.30-3.45 (m, 2H), 3.82 (s, 2H), 4.05 (d, J=12, 2H), 4.08 (s, 3H), 4.22 (d, J=12, 2H), 4.24 (s, 2H). 7.25 (brs, 4H), 7.35 (s, 1H), 7.44 (s, 1H), 8.12 (s, 1H), 8.39 (t, J=5.7, 1H), 8.63 (brs, 2H).

Example 244

N$^2$-(1,6-dimethyl-1H-indazol-5-yl)-N$^2$-{2-[(5-fluoro-1,3-dihydro-2H-isoindol-2-yl)(methyl)amino]-2-oxoethyl}-N$^1$-[2-(ethylamino)ethyl]glycinamide hydrochloride Step A N-{2-[(5-fluoro-1,3-dihydro-2H-isoindol-2-yl)(methyl)amino]-2-oxoethyl}-N-[6-methyl-1-(tetrahydro-2H-pyran-2-yl)-1H-indazol-5-yl]glycine Using the compound (601 mg, 1.73 mmol) of Reference Example 133 and the compound (360 mg, 1.78 mmol) of Reference Example 19, and according to the method of Example 241, step A, the title compound (835 mg, yield 97%) was obtained as a colorless solid.

$^1$H-NMR (400 MHz, DMSO-d$_6$); δ (ppm) 1.50-1.64 (m, 2H), 1.65-1.81 (m, 1H), 1.86-1.96 (m, 1H), 1.97-2.08 (m, 1H), 2.30-2.43 (m, 1H), 2.40 (s, 3H), 2.85 (s, 3H), 3.65-3.76 (m, 1H), 3.81-3.92 (m, 1H), 3.93-4.30 (m, 4H), 3.98 (s, 2H), 4.26 (s, 2H), 5.73 (dd, J=2.3, 9.7, 1H), 7.04-7.14 (m, 2H), 7.25-7.30 (m, 1H), 7.46 (s, 1H), 7.53 (s, 1H), 7.93 (s, 1H), 12.45 (brs, 1H).

Step B

N-{2-[(5-fluoro-1,3-dihydro-2H-isoindol-2-yl)(methyl)amino]-2-oxoethyl}-N-(6-methyl-1H-indazol-5-yl)glycine ethyl ester Using the compound (825 mg, 1.66 mg) of step A, and according to the method of Example 241, step B, the title compound (643 mg, yield 88%) was obtained as a colorless amorphous solid.

$^1$H-NMR (400 MHz, CDCl$_3$); δ (ppm) 1.19 (t, J=7.1, 3H), 2.50 (s, 3H), 2.92 (s, 3H), 4.03-4.20 (m, 4H), 4.10 (q, J=7.1, 2H), 4.17 (s, 2H), 4.38 (s, 2H), 6.86-6.98 (m, 2H), 7.06-7.18 (m, 1H), 7.27 (s, 1H), 7.71 (s, 1H), 7.92 (s, 1H), 9.88 (brs, 1H).

Step C

N-(1,6-dimethyl-1H-indazol-5-yl)-N-{2-[(5-fluoro-1,3-dihydro-2H-isoindol-2-yl)(methyl)amino]-2-oxoethyl}glycine ethyl ester Using the compound (640 mg, 1.46 mmol) of step B, and according to the method of Example 241, step C, the title compound (456 mg, yield 69%) was obtained as a colorless amorphous solid.
$^1$H-NMR (300 MHz, CDCl$_3$); δ (ppm) 1.19 (t, J=7.1, 3H), 2.52 (s, 3H), 2.91 (s, 3H), 3.99 (s, 3H), 4.03-4.23 (m, 6H), 4.16 (s, 2H), 4.37 (s, 2H), 6.87-6.98 (m, 2H), 7.10-7.16 (m, 1H), 7.18 (s, 1H), 7.67 (s, 1H), 7.82 (s, 1H).

Step D $N^2$-(1,6-dimethyl-1H-indazol-5-yl)-$N^2$-{2-[(5-fluoro-1,3-dihydro-2H-isoindol-2-yl)(methyl)amino]-2-oxoethyl}-$N^1$-[2-(ethylamino)ethyl]glycinamide hydrochloride Using the compound (456 mg, 1.01 mmol) of step C, and according to the methods of Example 241, steps D and E, the title compound (410 mg, yield 76%) was obtained as a colorless solid.
$^1$H-NMR (300 MHz, DMSO-d$_6$); δ (ppm) 1.13 (t, J=7.2, 3H), 2.43 (s, 3H), 2.8-3.0 (m, 4H), 2.86 (s, 3H), 3.30-3.43 (m, 2H), 3.83 (s, 2H), 3.96 (s, 3H), 3.97-4.22 (m, 4H), 4.24 (s, 2H), 7.04-7.14 (m, 2H), 7.25-7.31 (m, 1H), 7.39 (s, 1H), 7.57 (s, 1H), 7.86 (s, 1H), 8.41 (t, J=5.7, 1H), 8.70 (brs, 2H).

Example 245

$N^2$-(2,6-dimethyl-2H-indazol-5-yl)-$N^2$-{2-[(5-fluoro-1,3-dihydro-2H-isoindol-2-yl)(methyl)amino]-2-oxoethyl}-$N^1$-[2-(ethylamino)ethyl]glycinamide hydrochloride

Step A

N-(2,6-dimethyl-2H-indazol-5-yl)-N-{2-[(5-fluoro-1,3-dihydro-2H-isoindol-2-yl)(methyl)amino]-2-oxoethyl}glycine ethyl ester As a byproduct of Example 244, step C, the title compound (147 mg, yield 22%) was obtained as a colorless amorphous solid.
$^1$H-NMR (300 MHz, CDCl$_3$); δ (ppm) 1.19 (t, J=7.1, 3H), 2.45 (s, 3H), 2.91 (s, 3H), 3.98-4.17 (m, 6H), 4.14 (s, 3H), 4.20 (s, 2H), 4.36 (s, 2H), 6.87-6.98 (m, 2H), 7.10-7.16 (m, 1H), 7.45 (s, 1H), 7.51 (s, 1H), 7.70 (s, 1H).

Step B $N^2$-(2,6-dimethyl-2H-indazol-5-yl)-$N^2$-{2-[(5-fluoro-1,3-dihydro-2H-isoindol-2-yl)(methyl)amino]-2-oxoethyl}-$N^1$-[2-(ethylamino)ethyl]glycinamide hydrochloric acid Using the compound (147 mg, 0.324 mmol) of step A, and according to the methods of Example 241, steps D and E, the title compound (101 mg, yield 59%) was obtained as a colorless solid.
$^1$H-NMR (300 MHz, DMSO-ds); δ (ppm) 1.13 (t, J=7.2, 3H), 2.36 (s, 3H), 2.8-3.0 (m, 4H), 2.87 (s, 3H), 3.31-3.41 (m, 2H), 3.82 (s, 2H), 3.99-4.21 (m, 4H), 4.08 (s, 3H), 4.23 (s, 2H), 7.03-7.14 (m, 2H), 7.25-7.31 (m, 1H), 7.35 (s, 1H), 7.44 (s, 1H), 8.12 (s, 1H), 8.37 (t, J=5.7, 1H), 8.60 (brs, 2H).

Example 246

$N^2$-{2-[1,3-dihydro-2H-isoindol-2-yl(methyl)amino]-2-oxoethyl}-$N^2$-(1-ethyl-6-methyl-1H-indazol-5-yl)-$N^1$-[2-(ethylamino)ethyl]glycinamide hydrochloride

Step A

N-{2-[1,3-dihydro-2H-isoindol-2-yl(methyl)amino]-2-oxoethyl}-N-(1-ethyl-6-methyl-1H-indazol-5-yl) glycine ethyl ester Using the compound (746 mg, 1.77 mmol) of Example 241, step B and ethyl iodide (0.26 n2, 3.23 mmol), and according to the method of Example 241, step C, the title compound (549 mg, yield 69%) was obtained as a colorless amorphous solid.
$^1$H-NMR (400 MHz, CDCl$_3$); δ (ppm) 1.19 (t, J=7.1, 3H), 1.48 (t, J=7.2, 3H), 2.52 (s, 3H), 2.92 (s, 3H), 4.06-4.15 (m, 4H), 4.16 (s, 2H), 4.20 (d, J=11, 2H), 4.35 (q, J=7.2, 2H), 4.38 (s, 2H), 7.16-7.27 (m, 5H), 7.72 (s, 1H), 7.82 (s, 1H).

Step B $N^2$-{2-[1,3-dihydro-2H-isoindol-2-yl(methyl)amino]-2-oxoethyl}-$N^2$-(1-ethyl-6-methyl-1H-indazol-5-yl)-$N^1$-[2-(ethylamino)ethyl]glycinamide hydrochloride Using the compound (547 mg, 1.09 mmol) obtained in step A and according to the methods of Example 241, steps D and E, the title compound (536 mg, yield 93%) was obtained as a colorless solid.
$^1$H-NMR (300 MHz, DMSO-d$_6$); δ (ppm) 1.14 (t, J=7.1, 3H), 1.35 (t, J=7.2, 3H), 2.43 (s, 3H), 2.8-3.0 (m, 4H), 2.87 (s, 3H), 3.33-3.41 (m, 2H), 3.83 (s, 2H), 4.05 (d, J=12, 2H), 4.22 (d, J=12, 2H), 4.25 (s, 2H), 4.35 (q, J=7.2, 2H), 7.25 (brs, 4H), 7.43 (s, 1H), 7.58 (s, 1H), 7.87 (s, 1H), 8.44 (t, J=5.8, 1H), 8.75 (brs, 2H).

Example 247

$N^2$-{2-[1,3-dihydro-2H-isoindol-2-yl(methyl)amino]-2-oxoethyl}-$N^2$-(2-ethyl-6-methyl-2H-indazol-5-yl)-$N^1$-[2-(ethylamino)ethyl]glycinamide hydrochloride

Step A

N-{2-[1,3-dihydro-2H-isoindol-2-yl(methyl)amino]-2-oxoethyl}-N-(2-ethyl-6-methyl-2H-indazol-5-yl) glycine ethyl ester As a byproduct of Example 246, step A, the title compound (199 mg, yield 25%) was obtained as a colorless amorphous solid.
$^1$H-NMR (400 MHz, CDCl$_3$); δ (ppm) 1.19 (t, J=7.1, 3H), 1.58 (t, J=7.4, 3H), 2.46 (s, 3H), 2.91 (s, 3H), 4.05-4.15 (m, 4H), 4.19 (d, J=12, 2H), 4.21 (s, 2H), 4.37 (s, 2H), 4.40 (q, J=7.4, 2H), 7.16-7.28 (m, 4H), 7.47 (s, 1H), 7.53 (s, 1H), 7.74 (s, 1H).

Step B $N^2$-{2-[1,3-dihydro-2H-isoindol-2-yl(methyl) amino]-2-oxoethyl}-$N^2$-(2-ethyl-6-methyl-2H-indazol-5-yl)-$N^1$-[2-(ethylamino)ethyl]glycinamide hydrochloride Using the compound (198 mg, 0.440 mmol) obtained in step A and according to the methods of Example 241, steps D and E, the title compound (101 mg, yield 43%) was obtained as a colorless solid.

$^1$H-NMR (300 MHz, DMSO-$d_6$); 1.12 (t, J=7.1, 3H), 1.45 (t, J=7.3, 3H), 2.37 (s, 3H), 2.8-3.0 (m, 4H), 2.88 (s, 3H), 3.3-3.4 (m, 2H), 3.82 (s, 2H), 4.05 (d, J=11, 2H), 4.23 (d, J=11, 2H), 4.24 (s, 2H), 4.37 (q, J=7.3, 2H), 7.25 (brs, 4H), 7.36 (s, 1H), 7.44 (s, 1H), 8.17 (s, 1H), 8.39 (broad t, 1H), 8.52 (brs, 2H).

Example 248

$N^2$-(1-ethyl-6-methyl-1H-indazol-5-yl)-$N^2$-{2-[(5-fluoro-1,3-dihydro-2H-isoindol-2-yl)(methyl) amino]-2-oxoethyl}-$N^1$-[2-(ethylamino)ethyl]glycinamide hydrochloride Step A N-(1-ethyl-6-methyl-1H-indazol-5-yl)-N-{2-[(5-fluoro-1,3-dihydro-2H-isoindol-2-yl)(methyl) amino]-2-oxoethyl}glycine ethyl ester Using the compound (1.68 g, 3.82 mmol) of Example 244, step B and ethyl iodide (0.50 ml, 6.25 mmol), and according to the method of Example 241, step C, the title compound (1.22 g, yield 68%) was obtained as a colorless amorphous solid.

$^1$H-NMR (400 MHz, CDCl$_3$); δ (ppm) 1.19 (t, J=7.1, 3H), 1.47 (t, J=7.2, 3H), 2.52 (s, 3H), 2.91 (s, 3H), 4.0-4.2 (m, 6H), 4.16 (s, 2H), 4.35 (q, J=7.2, 2H), 4.37 (s, 2H), 6.87-6.97 (m, 2H), 7.10-7.15 (m, 1H), 7.19 (s, 1H), 7.67 (s, 1H), 7.82 (s, 1H).

Step B $N^2$-(1-ethyl-6-methyl-1H-indazol-5-yl)-$N^2$-{2-[(5-fluoro-1,3-dihydro-2H-isoindol-2-yl)(methyl) amino]-2-oxoethyl}-$N^1$-[2-(ethylamino)ethyl]glycinamide hydrochloride Using the compound (1.19 g, 2.55 mmol) of step A, and according to the methods of Example 241, steps D and E, the title compound (634 mg, yield 46%) was obtained as a colorless solid.

$^1$H-NMR (400 MHz, DMSO-$d_6$); δ (ppm) 1.13 (t, J=7.2, 3H)), 1.35 (t, J=7.2, 3H), 2.44 (s, 3H), 2.8-3.0 (m, 4H), 2.86 (s, 3H), 3.34-3.40 (m, 2H), 3.85 (s, 2H), 4.00-4.24 (m, 4H), 4.28 (s, 2H), 4.35 (q, J=7.2, 2H), 7.04-7.15 (m, 2H), 7.26-7.30 (m, 1H), 7.44 (s, 1H), 7.61 (s, 1H), 7.88 (s, 1H), 8.44 (broad t, 1H), 8.72 (brs, 2H).

Example 249

$N^2$-(2-ethyl-6-methyl-2H-indazol-5-yl)-$N^2$-{2-[(5-fluoro-1,3-dihydro-2H-isoindol-2-yl)(methyl) amino]-2-oxoethyl}-$N^1$-[2-(ethylamino)ethyl]glycinamide hydrochloride Step A N-(2-ethyl-6-methyl-2H-indazol-5-yl)-N-{2-[(5-fluoro-1,3-dihydro-2H-isoindol-2-yl)(methyl) amino]-2-oxoethyl}glycine ethyl ester As a byproduct of Example 248, step A, the title compound (435 mg, yield 24%) was obtained as a colorless amorphous solid.

$^1$H-NMR (400 MHz, CDCl$_3$); δ (ppm) 1.19 (t, J=7.1, 3H), 1.58 (t, J=7.3, 3H), 2.45 (s, 3H), 2.91 (s, 3H), 4.0-4.2 (m, 6H), 4.20 (s, 2H), 4.36 (s, 2H), 4.40 (q, J=7.3, 2H), 6.87-6.97 (m, 2H), 7.10-7.15 (m, 1H), 7.47 (s, 1H), 7.53 (s, 1H), 7.74 (s, 1H).

Step B $N^2$-(2-ethyl-6-methyl-2H-indazol-5-yl)-$N^2$-{2-[(5-fluoro-1,3-dihydro-2H-isoindol-2-yl)(methyl) amino]-2-oxoethyl}-$N^1$-[2-(ethylamino)ethyl]glycinamide hydrochloride Using the compound (434 mg, 0.928 mmol) of step A, and according to the methods of Example 241, steps D and E, the title compound (245 mg, yield 48%) was obtained as a colorless solid.

$^1$H-NMR (400 MHz, DMSO-$d_6$); δ (ppm) 1.13 (t, J=7.2, 3H), 1.46 (t, J=7.2, 3H), 2.36 (s, 3H), 2.8-3.0 (m, 4H), 2.87 (s, 3H), 3.34-3.42 (m, 2H), 3.82 (s, 2H), 4.01-4.21 (m, 4H), 4.23 (s, 2H), 4.37 (q, J=7.2, 2H), 7.04-7.14 (m, 2H), 7.26-7.30 (m, 1H), 7.36 (s, 1H), 7.44 (s, 1H), 8.17 (s, 1H), 8.38 (t, J=5.8, 1H), 8.70 (brs, 2H).

Example 250

$N^2$-[1-(2,2-difluoroethyl)-6-methyl-1H-indazol-5-yl]-$N^2$-{2-[1,3-dihydro-2H-isoindol-2-yl(methyl) amino]-2-oxoethyl}-$N^1$-[2-(ethylamino)ethyl]glycinamide hydrochloride Step A N-[1-(2,2-difluoroethyl)-6-methyl-1H-indazol-5-yl]-N-{2-[1,3-dihydro-2H-isoindol-2-yl(methyl)amino]-2-oxoethyl}glycine ethyl ester Using the compound (767 mg, 1.82 mmol) of Example 241, step B and 2,2-difluoroethyl trifluoromethanesulfonate (534 mg, 2.49 mmol), and according to the method of Example 241, step C, the title compound (621 mg, yield 70%) was obtained as a colorless amorphous solid.

$^1$H-NMR (400 MHz, CDCl$_3$); δ (ppm) 1.19 (t, J=7.1, 3H), 2.52 (s, 3H), 2.92 (s, 3H), 4.06-4.22 (m, 8H), 4.38 (s, 2H), 4.63 (dt, J=4.3, 14, 2H), 6.12 (tt, J=4.3, 56, 1H), 7.18-7.26 (m, 5H), 7.70 (s, 1H), 7.89 (s, 1H).

Step B

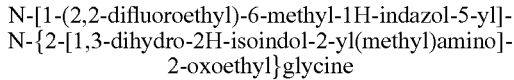

N-[1-(2,2-difluoroethyl)-6-methyl-1H-indazol-5-yl]-N-{2-[1,3-dihydro-2H-isoindol-2-yl(methyl)amino]-2-oxoethyl}glycine Using the compound (621 mg, 1.28 mmol) of step A, and according to the method of Example 241, step D, the title compound (557 mg, yield 95%) was obtained as a colorless solid.
$^1$H-NMR (400 MHz, DMSO-d$_6$); δ (ppm) 2.40 (s, 3H), 2.86 (s, 3H), 3.98 (s, 2H), 4.07 (d, J=11.5, 2H), 4.22 (d, J=11.5, 2H), 4.27 (s, 2H), 4.82 (dt; J=3.6, 15, 2H), 6.38 (tt, J=3.6, 55, 1H), 7.25 (brs, 4H), 7.48 (s, 1H), 7.56 (s, 1H), 7.98 (s, 1H), 12.47 (brs, 1H).

Step C

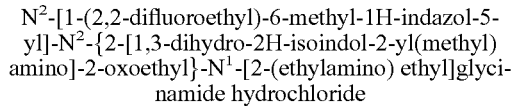

N$^2$-[1-(2,2-difluoroethyl)-6-methyl-1H-indazol-5-yl]-N$^2$-{2-[1,3-dihydro-2H-isoindol-2-yl(methyl)amino]-2-oxoethyl}-N$^1$-[2-(ethylamino)ethyl]glycinamide hydrochloride Using the compound (552 mg, 1.21 mmol) of step B and the compound (255 mg, 1.35 mmol) of Reference Example 2, and according to the methods of Example 1, step B, and Example 57, step B, the title compound (482 mg, yield 71%) was obtained as a colorless solid.
$^1$H-NMR (400 MHz, DMSO-d$_6$); δ (ppm) 1.13 (t, J=7.2, 3H), 2.43 (s, 3H), 2.8-3.0 (m, 4H), 2.86 (s, 3H), 3.34-3.41 (m, 2H), 3.84 (s, 2H), 4.05 (d, J=11.4, 2H), 4.21 (d, J=11.4, 2H), 4.26 (s, 2H), 4.83 (dt, J=3.5, 15, 2H), 6.39 (tt, J=3.5, 55, 1H), 7.25 (brs, 4H), 7.50 (s, 1H), 7.60 (s, 1H), 7.98 (s, 1H), 8.39 (t, J=5.8, 1H), 8.60 (brs, 2H).

Example 251

N$^2$-[1-(2,2-difluoroethyl)-6-methyl-1H-indazol-5-yl]-N$^2$-{2-[(4-fluoro-1,3-dihydro-2H-isoindol-2-yl)(methyl)amino]-2-oxoethyl}-N$^1$-[2-(ethylamino)ethyl]glycinamide hydrochloride Step A

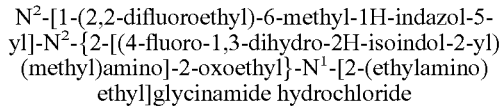

N-{2-[(4-fluoro-1,3-dihydro-2H-isoindol-2-yl)(methyl)amino]-2-oxoethyl}-N-(6-methyl-1H-indazol-5-yl)glycine ethyl ester Using the compound (875 mg, 2.52 mmol) of Reference Example 133 and the compound (519 mg, 2.56 mmol) of Reference Example 18, and according to the methods of Example 241, steps
A and B, the title compound (919 mg, yield 83%) was obtained as a pale-yellow amorphous solid
$^1$H-NMR (400 MHz, CDCl$_3$); δ (ppm) 1.20 (t, J=7.1, 3H), 2.50 (s, 3H), 2.93 (s, 3H), 4.10 (q, J=7.1, 2H), 4.13-4.23 (m, 6H), 4.39 (s, 2H), 6.91-6.99 (m, 2H), 7.20-7.26 (m, 1H), 7.28 (s, 1H), 7.71 (s, 1H), 7.93 (s, 1H), 9.85 (brs, 1H).

Step B

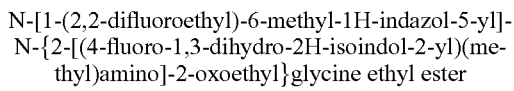

N-[1-(2,2-difluoroethyl)-6-methyl-1H-indazol-5-yl]-N-{2-[(4-fluoro-1,3-dihydro-2H-isoindol-2-yl)(methyl)amino]-2-oxoethyl}glycine ethyl ester Using the compound (909 mg, 2.07 mmol) of step A and 2,2-difluoroethyl trifluoromethanesulfonate (612 mg, 2.86 mmol), and according to the method of Example 241, step C, the title compound (732 mg, yield 70%) was obtained as a colorless amorphous solid.
$^1$H-NMR (400 MHz, CDCl$_3$); δ (ppm) 1.20 (t, J=7.1, 3H), 2.53 (s, 3H), 2.92 (s, 3H), 4.07-4.23 (m, 8H), 4.38 (s, 2H), 4.63 (dt, J=4.4, 13.6, 2H), 6.12 (tt, J=4.4, 56, 1H), 6.91-6.99 (m, 2H), 7.20-7.25 (m, 2H), 7.69 (s, 1H), 7.90 (s, 1H).

Step C

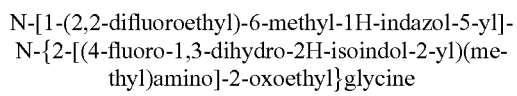

N-[1-(2,2-difluoroethyl)-6-methyl-1H-indazol-5-yl]-N-{2-[(4-fluoro-1,3-dihydro-2H-isoindol-2-yl)(methyl)amino]-2-oxoethyl}glycine Using the compound (732 mg, 1.45 mmol) of step B, and according to the method of Example 241, step D, the title compound (660 mg, yield 96%) was obtained as a colorless solid.
$^1$H-NMR (400 MHz, DMSO-d$_6$); δ (ppm) 2.41 (s, 3H), 2.87 (s, 3H), 3.97 (s, 2H), 4.12-4.25 (m, 4H), 4.28 (s, 2H), 4.82 (dt, J=3.6, 15, 2H), 6.38 (tt, J=3.6, 55, 1H), 7.05-7.13 (m, 2H), 7.28-7.34 (m, 1H), 7.48 (s, 1H), 7.57 (s, 1H), 7.98 (s, 1H), 12.45 (brs, 1H).

Step D

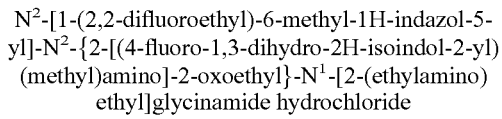

N$^2$-[1-(2,2-difluoroethyl)-6-methyl-1H-indazol-5-yl]-N$^2$-{2-[(4-fluoro-1,3-dihydro-2H-isoindol-2-yl)(methyl)amino]-2-oxoethyl}-N$^1$-[2-(ethylamino)ethyl]glycinamide hydrochloride Using the compound (654 mg, 1.38 mmol) of step C and the compound (285 mg, 1.51 mmol) of Reference Example 2, and according to the methods of Example 1, step B, and Example 57, step B, the title compound (599 mg, yield 75%) was obtained as a colorless solid.
$^1$H-NMR (400 MHz, DMSO-d$_6$); δ (ppm) 1.12 (t, J=7.2, 3H), 2.43 (s, 3H), 2.8-3.0 (m, 4H), 2.88 (s, 3H), 3.35-3.40 (m, 2H), 3.83 (s, 2H), 4.09-4.24 (m, 4H), 4.27 (s, 2H), 4.83 (dt, J=3.5, 15, 2H), 6.38 (tt, J=3.5, 55, 1H), 7.06-7.12 (m, 2H), 7.28-7.34 (m, 1H), 7.50 (s, 1H), 7.61 (s, 1H), 7.98 (s, 1H), 8.38 (t, J=5.7, 1H), 8.56 (brs, 2H).

Example 252

N$^2$-[1-(2,2-difluoroethyl)-6-methyl-1H-indazol-5-yl]-N$^2$-{2-[2,3-dihydro-1H-inden-2-yl(methyl)amino]-2-oxoethyl}-N$^1$-[2-(ethylamino)ethyl]glycinamide hydrochloride Step A

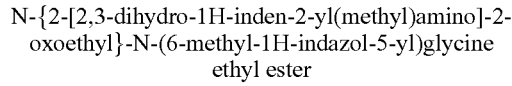

N-{2-[2,3-dihydro-1H-inden-2-yl(methyl)amino]-2-oxoethyl}-N-(6-methyl-1H-indazol-5-yl)glycine ethyl ester Using the compound (908 mg, 2.61 mmol) of Reference Example 133 and the compound (485 mg, 2.64 mmol) of Reference Example 23, and according to the methods of Example 241, steps A and B, the title compound (971 mg, yield 88%) was obtained as a colorless amorphous solid.
$^1$H-NMR (400 MHz, CDCl$_3$); δ (ppm) 1.19-1.24 (m, 3H), 2.50 (s, 3H), 2.73 2.78 (2s, 3H), 2.80-3.01 (m, 2H), 3.08-3.18 (m, 2H), 4.01 4.05 (2s, 2H), 4.08-4.16 (m, 2H), 4.13 4.25 (2s, 2H), 4.94-5.03 5.50-5.59 (m, 1H), 7.1-7.2 (m, 4H), 7.29 (s, 1H), 7.73 (s, 1H), 7.96 (s, 1H), 9.96 (brs, 1H).

Step B

N-[1-(2,2-difluoroethyl)-6-methyl-1H-indazol-5-yl]-
N-{2-[2,3-dihydro-1H-inden-2-yl(methyl)amino]-2-
oxoethyl}glycine ethyl ester Using the compound (954 mg, 2.27 mmol) of step A and 2,2-difluoroethyl trifluoromethanesulfonate (607 mg, 3.12 mmol), and according to the method of Example 241, step C, the title compound (747 mg, yield 68%) was obtained as a colorless oil.
$^1$H-NMR (400 MHz, CDCl$_3$); δ (ppm) 1.19-1.30 (m, 3H), 2.52 (s, 3H), 2.73 2.78 (2s, 3H), 2.79-3.01 (m, 2H), 3.08-3.18 (m, 2H), 4.01 4.05 (2s, 2H), 4.08-4.16 (m, 2H), 4.12 4.24 (2s, 2H), 4.64 (dt, J=4.3, 13.5, 2H), 4.9-5.0 5.4-5.6 (m, 1H), 6.12 (tt, J=4.3, 56, 1H), 7.1-7.2 (m, 4H), 7.25 (s, 1H), 7.72 (s, 1H), 7.93 (s, 1H).

Step C

N-[1-(2,2-difluoroethyl)-6-methyl-1H-indazol-5-yl]-
N-{2-[2,3-dihydro-1H-inden-2-yl(methyl)amino]-2-
oxoethyl}glycine Using the compound (747 mg, 1.54 mmol) of step B, and according to the method of Example 241, step D, the title compound (651 mg, yield 93%) was obtained as a colorless solid.
$^1$H-NMR (400 MHz, DMSO-d$_6$); δ (ppm) 2.42 (s, 3H), 2.64 2.76 (2s, 3H), 2.82-3.10 (m, 4H), 3.87 3.91 (2s, 2H), 4.06 4.19 (2s, 2H), 4.83 (dt, J=3.7, 14, 2H), 4.95-5.05 5.20-5.35 (m, 1H), 6.39 (tt, J=3.7, 55, 1H), 7.13-7.21 (m, 4H), 7.51 (s, 1H), 7.61 (s, 1H), 8.00 8.01 (2s, 1H). 12.67 (brs, 1H).

Step D

N$^2$-[1-(2,2-difluoroethyl)-6-methyl-1H-indazol-5-
yl]-N$^2$-{2-[2,3-dihydro-1H-inden-2-yl(methyl)
amino]-2-oxoethyl}-N$^1$-[2-(ethylamino)ethyl]glyci-
namide hydrochloride Using the compound (646 mg, 1.42 mmol) of step C and the compound (303 mg, 1.61 mmol) of Reference Example 2, and according to the methods of Example 1, step B, and Example 57, step B, the title compound (636 mg, yield 80%) was obtained as a colorless solid.
$^1$H-NMR (400 MHz, DMSO-d$_6$); δ (ppm) 1.10-1.16 (m, 3H), 2.45 (s, 3H), 2.65 2.74 (2s, 3H), 2.82-3.07 (m, 8H), 3.35-3.42 (m, 2H), 3.76 3.80 (2s, 2H), 4.03 4.18 (2s, 2H), 4.84 (dt, J=3.6, 15, 2H), 4.85-4.95 5.20-5.35 (m, 1H), 7.12-7.20 (m, 4H), 7.52 (s, 1H), 7.64 (s, 1H), 8.00 8.01 (2s, 1H), 8.51 (t, J=5.8, 1H), 8.54 (brs, 2H).

Example 253

N$^2$-[1-(2,2-difluoroethyl)-6-methyl-1H-indazol-5-yl]-N$^2$-
{2-[(5-fluoro-1,3-dihydro-2H-isoindol-2-yl)(methyl)
amino]-2-oxoethyl}-N$^1$-[2-(ethylamino)ethyl]glycinamide
hydrochloride

Step A

N-[1-(2,2-difluoroethyl)-6-methyl-1H-indazol-5-yl]-
N-{2-[(5-fluoro-1,3-dihydro-2H-isoindol-2-yl)(me-
thyl)amino]-2-oxoethyl}glycine ethyl ester Using the compound (1.92 g, 4.37 mmol) of Example 244, step B and 2,2-difluoroethyl trifluoromethanesulfonate (1.49 g, 6.96 mmol), and according to the method of Example 241, step C, the title compound (1.56 g, yield 71%) was obtained as a colorless amorphous solid.
$^1$H-NMR (400 MHz, CDCl$_3$); δ (ppm) 1.19 (t, J=7.1, 3H), 2.52 (s, 3H), 2.91 (s, 3H), 4.0-4.2 (m, 6H), 4.17 (s, 2H), 4.37 (s, 2H), 4.63 (dt, J=4.3, 14, 2H), 6.12 (tt, J=4.3, 56, 1H), 6.87-6.97 (m, 2H), 7.11-7.15 (m, 1H), 7.23 (s, 1H), 7.69 (s, 1H), 7.89 (s, 1H).

Step B

N$^2$-[1-(2,2-difluoroethyl)-6-methyl-1H-indazol-5-
yl]-N$^2$-{2-[(5-fluoro-1,3-dihydro-2H-isoindol-2-yl)
(methyl)amino]-2-oxoethyl}-N$^1$-[2-(ethylamino)
ethyl]glycinamide hydrochloride Using the compound (1.53 g, 3.04 mmol) of step A, and according to the methods of Example 241, steps D and E, the title compound (1.11 g, yield 63%) was obtained as a colorless solid.
$^1$H-NMR (400 MHz, DMSO-d$_6$); δ (ppm) 1.13 (t, J=7.2, 3H), 2.43 (s, 3H), 2.8-3.0 (m, 4H), 2.86 (s, 3H), 3.34-3.41 (m, 2H), 3.85 (s, 2H), 4.01-4.24 (m, 4H), 4.26 (s, 2H), 4.83 (dt, J=3.5, 15, 2H), 6.39 (tt, J=3.5, 55, 1H), 7.04-7.14 (m, 2H), 7.26-7.30 (m, 1H), 7.50 (s, 1H), 7.60 (s, 1H), 7.98 (s, 1H), 8.39 (t, J=5.8, 1H), 8.70 (brs, 2H).

Example 254

N$^2$-[2-(2,2-difluoroethyl)-6-methyl-2H-indazol-5-
yl]-N$^2$-{2-[(5-fluoro-1,3-dihydro-2H-isoindol-2-yl)
(methyl)amino]-2-oxoethyl}-N$^1$-[2-(ethylamino)
ethyl]glycinamide hydrochloride

Step A

N-[2-(2,2-difluoroethyl)-6-methyl-2H-indazol-5-yl]-
N-{2-[(5-fluoro-1,3-dihydro-2H-isoindol-2-yl)(me-
thyl)amino]-2-oxoethyl}glycine ethyl ester As a byproduct of Example 253, step A, the title compound (280 mg, yield 13%) was obtained as a colorless solid.
$^1$H-NMR (400 MHz, CDCl$_3$); δ (ppm) 1.19 (t, J=7.1, 3H), 2.46 (s, 3H), 2.92 (s, 3H), 4.0-4.2 (m, 6H), 4.19 (s, 2H), 4.36 (s, 2H), 4.67 (dt, J=4.3, 13, 2H), 6.18 (tt, J=4.3, 56, 1H), 6.88-7.00 (m, 2H), 7.11-7.15 (m, 1H), 7.46 (s, 1H), 7.52 (s, 1H), 7.81 (s, 1H).

Step B

N-[2-(2,2-difluoroethyl)-6-methyl-2H-indazol-5-yl]-
N-{2-[(5-fluoro-1,3-dihydro-2H-isoindol-2-yl)(me-
thyl)amino]-2-oxoethyl}glycine Using the compound (274 mg, 0.544 mmol) of step A, and according to the method of Example 241, step D, the title compound (238 mg, yield 92%) was obtained as a colorless solid.
$^1$H-NMR (400 MHz, DMSO-d$_6$); δ (ppm) 2.34 (s, 3H), 2.86 (s, 3H), 3.97 (s, 2H), 4.03-4.23 (m, 4H), 4.25 (s, 2H), 4.87 (dt, J=3.8, 15, 2H), 6.46 (tt, J=3.8, 55, 1H), 7.04-7.14 (m, 2H), 7.26-7.30 (m, 1H), 7.36 (s, 1H), 7.41 (s, 1H), 8.22 (s, 1H).

Step C

N²-[2-(2,2-difluoroethyl)-6-methyl-2H-indazol-5-yl]-N²-{2-[(5-fluoro-1,3-dihydro-2H-isoindol-2-yl)(methyl)amino]-2-oxoethyl}-N¹-[2-(ethylamino)ethyl]glycinamide hydrochloride Using the compound (235 mg, 0.494 mmol) of step B, the compound (111 mg, 0.590 mmol) of Reference Example 2, and according to the methods of Example 1, step B, and Example 57, step B, the title compound (237 mg, yield 82%) was obtained as a colorless solid.

$^1$H-NMR (400 MHz, DMSO-d$_6$); δ (ppm) 1.12 (t, J=7.2, 3H), 2.37 (s, 3H), 2.8-3.0 (m, 4H), 2.87 (s, 3H), 3.32-3.40 (m, 2H), 3.82 (s, 2H), 4.00-4.22 (m, 4H), 4.23 (s, 2H), 4.88 (dt, J=3.8, 11, 2H), 6.47 (tt, J=3.8, 55, 1H), 7.04-7.14 (m, 2H), 7.26-7.30 (m, 1H), 7.39 (s, 1H), 7.46 (s, 1H), 8.23 (s, 1H), 8.34 (t, J=5.8, 1H), 8.56 (brs, 2H).

Example 255

N²-{2-[1,3-dihydro-2H-isoindol-2-yl(methyl)amino]-2-oxoethyl}-N²-(1,3,6-trimethyl-1H-indazol-5-yl)-N¹-[2-(ethylamino)ethyl]glycinamide hydrochloride

Step A

N²-{2-[1,3-dihydro-2H-isoindol-2-yl(methyl)amino]-2-oxoethyl}-N²-(3-iodo-1,6-dimethyl-1H-indazol-5-yl)-N¹-{2-[(tert-butoxycarbonyl)(ethyl)amino]ethyl}glycinamide Using the compound (484 mg, 1.20 mmol) of Reference Example 136, the compound (223 mg, 1.21 mmol) of Reference Example 17 and the compound (255 mg, 1.35 mmol) of Reference Example 2, and according to the method of Example 204, step A, the title compound (743 mg, yield 88%) was obtained as a colorless amorphous solid.

$^1$H-NMR (400 MHz, CDCl$_3$); δ (ppm) 1.06 (t, J=7.0, 3H), 1.45 (s, 9H), 2.51 (s, 3H), 2.94 (s, 3H), 3.15-3.25 (m, 2H), 3.28-3.35 (m, 2H), 3.40-3.49 (m, 2H), 3.75 (s, 2H), 4.03 (s, 3H), 4.15 (d, J=11.7, 2H), 4.23 (d, J=11.7, 2H), 4.27 (s, 2H), 7.18-7.34 (m, 5H), 7.34 (s, 1H), 8.46 8.75 (2brs, 1H).

Step B

N²-{2-[1,3-dihydro-2H-isoindol-2-yl(methyl)amino]-2-oxoethyl}-N²-(1,3,6-trimethyl-1H-indazol-5-yl)-N¹-{2-[(tert-butoxycarbonyl)(ethyl)amino]ethyl}glycinamide The compound (734 mg, 1.04 mmol) of step A, trimethylboroxin (0.19 ml, 1.36 mmol), bis(tricyclohexylphosphine)palladium(II) dichloride (139 mg, 0.188 mmol), and 1.27 mol/l aqueous potassium phosphate solution (2.50 ml, 3.18 mmol) were added to 1,4-dioxane (8 ml), and the mixture was heated under reflux for 10 hr. After cooling to room temperature, the reaction mixture was diluted with ethyl acetate, washed with saturated brine, and dried over anhydrous magnesium sulfate. The insoluble material was filtered off, and the solution was concentrated under reduced pressure. The obtained oil was purified by silica gel column chromatography (ethyl acetate-methanol) to give the title compound (505 mg, yield 82%) as a colorless amorphous solid.

$^1$H-NMR (400 MHz, CDCl$_3$); δ (ppm) 1.03 (t, J=7.0, 3H), 1.45 (s, 9H), 2.48 (s, 3H), 2.49 (s, 3H), 2.94 (s, 3H), 3.10-3.20 (m, 2H), 3.25-3.35 (m, 2H), 3.40-3.46 (m, 2H), 3.80 (s, 2H), 3.93 (s, 3H), 4.04 (d, J=11.4, 2H), 4.20 (d, J=11.4, 2H), 4.21 (s, 2H), 7.13 (s, 1H), 7.16-7.25 (m, 4H), 7.57 (s, 1H), 8.44 8.72 (2brs, 1H).

Step C

N²-{2-[1,3-dihydro-2H-isoindol-2-yl(methyl)amino]-2-oxoethyl}-N²-(1,3,6-trimethyl-1H-indazol-5-yl)-N¹-[2-(ethylamino)ethyl]glycinamide hydrochloride Using the compound (496 mg, 0.838 mmol) of step B, and according to the method of Example 57, step B, the title compound (363 mg, yield 82%) was obtained as a colorless solid.

$^1$H-NMR (400 MHz, DMSO-d$_6$); δ (ppm) 1.14 (t, J=7.2, 3H), 2.38 (s, 3H), 2.42 (s, 3H), 2.8-3.0 (m, 4H), 2.87 (s, 3H), 3.35-3.41 (m, 2H), 3.81 (s, 2H), 3.87 (s, 3H), 4.03 (d, J=11.4, 2H), 4.22 (d, J=11.4, 2H), 4.25 (s, 2H), 7.24 (brs, 4H), 7.32 (s, 1H), 7.54 (s, 1H), 8.51 (t, J=5.9, 1H), 8.64 (brs, 2H).

Example 256

N²-{2-[(5-fluoro-1,3-dihydro-2H-isoindol-2-yl)(methyl)amino]-2-oxoethyl}-N²-(1,3,6-trimethyl-1H-indazol-5-yl)-N¹-[2-(ethylamino)ethyl]glycinamide hydrochloride

Step A

N²-(3-iodo-1,6-dimethyl-1H-indazol-5-yl)-N²-{2-[(5-fluoro-1,3-dihydro-2H-isoindol-2-yl)(methyl)amino]-2-oxoethyl}-N¹-{2-[(tert-butoxycarbonyl)(ethyl)amino]ethyl}glycinamide Using the compound (484 mg, 1.20 mmol) of Reference Example 136, the compound (243 mg, 1.20 mmol) of Reference Example 19 and the compound (253 mg, 1.34 mmol) of Reference Example 2, and according to the method of Example 204, step A, the title compound (798 mg, yield 92%) was obtained as a colorless amorphous solid.

$^1$H-NMR (400 MHz, CDCl$_3$); δ (ppm) 1.06 (t, J=7.0, 3H), 1.45 (s, 9H), 2.51 (s, 3H), 2.93 (s, 3H), 3.15-3.25 (m, 2H), 3.28-3.35 (m, 2H), 3.41-3.49 (m, 2H), 3.75 (s, 2H), 4.03 (s, 3H), 4.08-4.23 (m, 4H), 4.26 (s, 2H), 6.90-6.99 (m, 2H), 7.13-7.18 (m, 1H), 7.19 (s, 1H), 7.33 (s, 1H), 8.42 8.72 (2brs, 1H).

Step B

N²-{2-[(5-fluoro-1,3-dihydro-2H-isoindol-2-yl)(methyl)amino]-2-oxoethyl}-N²-(1,3,6-trimethyl-1H-indazol-5-yl)-N¹-{2-[(tert-butoxycarbonyl)(ethyl)amino]ethyl}glycinamide Using the compound (791 mg, 1.10 mmol) of step A, and according to the method of Example 255, step B, the title compound (495 mg, yield 74%) was obtained as a colorless amorphous solid.

$^1$H-NMR (400 MHz, CDCl$_3$); δ (ppm) 1.03 (t, J=7.0, 3H), 1.44 (s, 9H), 2.48 (s, 6H), 2.93 (s, 3H), 3.10-3.20 (m, 2H), 3.25-3.35 (m, 2H), 3.40-3.46 (m, 2H), 3.80 (s, 2H), 3.93 (s, 3H), 3.97-4.15 (m, 4H), 4.17 (s, 2H), 6.87-6.98 (m, 2H), 7.10-7.12 (m, 1H), 7.13 (s, 1H), 7.56 (s, 1H), 8.40 8.68 (2brs, 1H).

Step C

N²-{2-[(5-fluoro-1,3-dihydro-2H-isoindol-2-yl)(methyl)amino]-2-oxoethyl}-N²-(1,3,6-trimethyl-1H-indazol-5-yl)-N¹-[2-(ethylamino)ethyl]glycinamide hydrochloride Using the compound (486 mg, 0.797 mmol) of step B, and according to the method of Example 57, step B, the title compound (361 mg, yield 83%) was obtained as a colorless solid.
¹H-NMR (400 MHz, DMSO-$d_6$); δ (ppm) 1.13 (t, J=7.2, 3H), 2.38 (s, 3H), 2.42 (s, 3H), 2.8-3.0 (m, 4H), 2.87 (s, 3H), 3.35-3.41 (m, 2H), 3.81 (s, 2H), 3.87 (s, 3H), 3.98-4.20 (m, 4H), 4.23 (s, 2H), 7.04-7.13 (m, 2H), 7.25-7.29 (m, 1H), 7.32 (s, 1H), 7.53 (s, 1H), 8.49 (t, J=5.9, 1H), 8.56 (brs, 2H).

Example 257

N²-{2-[1,3-dihydro-2H-isoindol-2-yl(methyl)amino]-2-oxoethyl}-N²-(1,5-dimethyl-1H-indazol-6-yl)-N¹-[2-(ethylamino)ethyl]glycinamide hydrochloride Step A N-{2-[1,3-dihydro-2H-isoindol-2-yl(methyl)amino]-2-oxoethyl}N-[5-methyl-1-(tetrahydro-2H-pyran-2-yl)-1H-indazol-6-yl]glycine Using the compound (903 mg, 2.60 mmol) of Reference Example 134 and the compound (595 mg, 3.22 mmol) of Reference Example 17, and according to the method of Example 241, step A, the title compound (1.07 g, yield 86%) was obtained as a colorless solid.
¹H-NMR (400 MHz, DMSO-$d_6$); δ (ppm) 1.5-1.6 (m, 2H), 1.65-1.80 (m, 1H), 1.85-2.10 (m, 2H), 2.3-2.4 (m, 1H), 2.32 (s, 3H), 2.89 (s, 3H), 3.65-3.75 (m, 1H), 3.80-3.95 (m, 1H), 4.06 (s, 2H), 4.12 (d, J=12, 2H), 4.26 (d, J=12, 2H), 4.32 (s, 2H), 5.65-5.70 (m, 1H), 7.25 (brs, 4H), 7.32 (s, 1H), 7.46 (s, 1H), 7.87 (s, 1H), 12.52 (brs, 1H).

Step B

N-{2-[1,3-dihydro-2H-isoindol-2-yl(methyl)amino]-2-oxoethyl}-N-(5-methyl-1H-indazol-6-yl)glycine ethyl ester Using the compound (1.07 g, 2.39 mmol) of step A, and according to the method of Example 241, step B, the title compound (821 mg, yield 82%) was obtained as a colorless amorphous solid.
¹H-NMR (300 MHz, CDCl₃); δ (ppm) 1.21 (t, J=7.2, 3H), 2.43 (s, 3H), 2.94 (s, 3H), 4.07-4.16 (m, 4H), 4.22 (d, J=11.4, 2H), 4.24 (s, 2H), 4.44 (s, 2H), 7.13-7.27 (m, 4H), 7.38 (s, 1H), 7.50 (s, 1H), 7.89 (s, 1H), 9.87 (brs, 1H).

Step C

N-{2-[1,3-dihydro-2H-isoindol-2-yl(methyl)amino]-2-oxoethyl}-N-(1,5-dimethyl-1H-indazol-6-yl)glycine ethyl ester Using the compound (815 mg, 1.93 mmol) of step B, and according to the method of Example 241, step C, the title compound (530 mg, yield 63%) was obtained as a pale-yellow amorphous solid ¹H-NMR (400 MHz, CDCl₃); δ (ppm) 1.23 (t, J=7.2, 3H), 2.43 (s, 3H), 2.93 (s, 3H), 3.99 (s, 3H), 4.04-4.15 (m, 4H), 4.22 (d, J=11.3, 2H), 4.26 (s, 2H), 4.44 (s, 2H), 7.17-7.27 (m, 5H), 7.46 (s, 1H), 7.79 (s, 1H).

Step D

N²-{2-[1,3-dihydro-2H-isoindol-2-yl(methyl)amino]-2-oxoethyl}-N²-(1,5-dimethyl-1H-indazol-6-yl)-N¹-[2-(ethylamino)ethyl]glycinamide hydrochloride Using the compound (513 mg, 1.18 mmol) of step C, the compound (319 mg, 1.69 mmol) of Reference Example 2, and according to the methods of Example 241, steps D and E, the title compound (450 mg, yield 74%) was obtained as a colorless solid.
¹H-NMR (300 MHz, DMSO-$d_6$); δ (ppm) 1.13 (t, J=7.2, 3H), 2.35 (s, 3H), 2.8-3.0 (m, 4H), 2.89 (s, 3H), 3.32-3.42 (m, 2H), 3.92 (s, 5H), 4.09 (d, J=11.6, 2H), 4.25 (d, J=11.6, 2H), 4.32 (s, 2H), 7.25 (brs, 4H), 7.30 (s, 1H), 7.47 (s, 1H), 7.82 (s, 1H), 8.36 (t, J=5.7, 1H), 8.59 (brs, 2H).

Example 258

N²-{2-[1,3-dihydro-2H-isoindol-2-yl(methyl)amino]-2-oxoethyl}-N²-(2,5-dimethyl-2H-indazol-6-yl)-N¹-[2-(ethylamino)ethyl]glycinamide hydrochloride Step A N-{2-[1,3-dihydro-2H-isoindol-2-yl(methyl)amino]-2-oxoethyl}-N-(2,5-dimethyl-2H-indazol-6-yl)glycine ethyl ester As a byproduct of Example 257, step C, the title compound (191 mg, yield 23%) was obtained as a yellow-bistered amorphous solid.
¹H-NMR (400 MHz, CDCl₃); δ (ppm) 1.22 (t, J=7.2, 3H), 2.40 (s, 3H), 2.93 (s, 3H), 4.08-4.23 (m, 8H), 4.13 (s, 3H), 4.45 (s, 2H), 7.17-7.27 (m, 5H), 7.37 (s, 1H), 7.67 (s, 1H).

Step B

N²-{2-[1,3-dihydro-2H-isoindol-2-yl(methyl)amino]-2-oxoethyl}-N²-(2,5-dimethyl-2H-indazol-6-yl)-N¹-[2-(ethylamino)ethyl]glycinamide hydrochloride Using the compound (181 mg, 0.416 mmol) of step A and the compound (135 mg, 0.717 mmol) of Reference Example 2, and according to the methods of Example 241, steps D and E, the title compound (151 mg, yield 71%) was obtained as a colorless solid.
¹H-NMR (300 MHz, DMSO-$d_6$); δ (ppm) 1.12 (t, J=7.2, 3H), 2.31 (s, 3H), 2.8-3.0 (m, 4H), 2.89 (s, 3H), 3.86 (s, 2H), 4.07 (s, 3H), 4.09 (d, J=12, 2H), 4.26 (d, J=12, 2H), 4.28 (s, 2H), 7.22 (s, 1H), 7.25 (brs, 4H), 7.40 (s, 1H), 8.09 (s, 1H), 8.32 (t, J=5.8, 1H), 8.55 (brs, 2H).

Example 259

$N^2$-(1,5-dimethyl-1H-indazol-6-yl)-$N^2$-{2-[(5-fluoro-1,3-dihydro-2H-isoindol-2-yl)(methyl)amino]-2-oxoethyl}-$N^1$-[2-(ethylamino)ethyl]glycinamide hydrochloride Step A N-{2-[(5-fluoro-1,3-dihydro-2H-isoindol-2-yl)(methyl)amino]-2-oxoethyl}-N-[5-methyl-1-(tetrahydro-2H-pyran-2-yl)-1H-indazol-6-yl]glycine Using the compound (749 mg, 2.16 mmol) of Reference Example 134 and the compound (439 mg, 2.17 mmol) of Reference Example 19, and according to the method of Example 241, step A, the title compound (965 mg, yield 90%) was obtained as a colorless solid.
$^1$H-NMR (300 MHz, DMSO-$d_6$); δ (ppm) 1.5-1.6 (m, 2H), 1.6-1.8 (m, 1H), 1.8-2.1 (m, 2H), 2.3-2.4 (m, 1H), 2.32 (s, 3H), 2.88 (s, 3H), 3.6-3.8 (m, 1H), 3.8-3.9 (m, 1H), 4.06 (s, 2H), 4.06-4.25 (m, 4H), 4.31 (s, 2H), 5.68 (dd, J=2.4, 9.6, 1H), 7.0-7.2 (m, 4H), 7.23-7.30 (m, 1H), 7.32 (s, 1H), 7.46 (s, 1H), 7.87 (s, 1H), 12.51 (brs, 1H).

Step B

N-{2-[(5-fluoro-1,3-dihydro-2H-isoindol-2-yl)(methyl)amino]-2-oxoethyl}-N-(5-methyl-1H-indazol-6-yl)glycine ethyl ester Using the compound (961 mg, 1.94 mmol) of step A, and according to the method of Example 241, step B, the title compound (770 mg, yield 90%) was obtained as a colorless amorphous solid.
$^1$H-NMR (400 MHz, CDCl$_3$); δ (ppm) 1.21 (t, J=7.1, 3H), 2.43 (s, 3H), 2.93 (s, 3H), 4.05-4.22 (m, 6H), 4.23 (s, 2H), 4.43 (s, 2H), 6.88-6.98 (m, 2H), 7.11-7.16 (m, 1H), 7.38 (s, 1H), 7.50 (s, 1H), 7.89 (s, 1H), 9.93 (brs, 1H).

Step C

N-(1,5-dimethyl-1H-indazol-6-yl)-N-{2-[(5-fluoro-1,3-dihydro-2H-isoindol-2-yl)(methyl)amino]-2-oxoethyl}glycine ethyl ester Using the compound (750 mg, 1.71 mmol) of step B, and according to the method of Example 241, step C, the title compound (546 mg, yield 63%) was obtained as a colorless amorphous solid.
$^1$H-NMR (400 MHz, CDCl$_3$); δ (ppm) 1.21 (t, J=7.1, 3H), 2.43 (s, 3H), 2.92 (s, 3H), 3.99 (s, 3H), 4.04-4.21 (m, 6H), 4.25 (s, 2H), 4.42 (s, 2H), 6.86-6.98 (m, 2H), 7.10-7.18 (m, 1H), 7.25 (s, 1H), 7.46 (s, 1H), 7.79 (s, 1H).

Step D $N^2$-(1,5-dimethyl-1H-indazol-6-yl)-$N^2$-{2-[(5-fluoro-1,3-dihydro-2H-isoindol-2-yl)(methyl)amino]-2-oxoethyl}-$N^1$-[2-(ethylamino)ethyl]glycinamide hydrochloride Using the compound (536 mg, 1.18 mmol) of step C and the compound (327 mg, 1.74 mmol) of Reference Example 2, and according to the methods of Example 241, steps D and E, the title compound (557 mg, yield 89%) was obtained as a colorless solid.
$^1$H-NMR (400 MHz, DMSO-$d_6$); δ (ppm) 1.12 (t, J=7.2, 3H), 2.35 (s, 3H), 2.8-3.0 (m, 4H), 2.88 (s, 3H), 3.3-3.5 (m, 2H), 3.92 (s, 5H), 4.04-4.28 (m, 4H), 4.31 (s, 2H), 7.04-7.15 (m, 2H), 7.27-7.30 (m, 1H), 7.30 (s, 1H), 7.47 (s, 1H), 7.82 (s, 1H), 8.34 (t, J=5.8, 1H), 8.55 (brs, 2H).

Example 260

$N^2$-(2,5-dimethyl-2H-indazol-6-yl)-$N^2$-{2-[(5-fluoro-1,3-dihydro-2H-isoindol-2-yl)(methyl)amino]-2-oxoethyl}-$N^1$-[2-(ethylamino)ethyl]glycinamide hydrochloride Step A N-(2,5-dimethyl-2H-indazol-6-yl)-N-{2-[(5-fluoro-1,3-dihydro-2H-isoindol-2-yl)(methyl)amino]-2-oxoethyl}glycine ethyl ester As a byproduct of Example 259, step C, the title compound (180 mg, yield 23%) was obtained as a pale-yellow amorphous solid
$^1$H-NMR (400 MHz, CDCl$_3$); δ (ppm) 1.22 (t, J=7.1, 3H), 2.40 (s, 3H), 2.93 (s, 3H), 4.05-4.20 (m, 6H), 4.13 (s, 3H), 4.18 (s, 2H), 4.44 (s, 2H), 6.86-6.96 (m, 2H), 7.09-7.14 (m, 1H), 7.37 (s, 2H), 7.67 (s, 1H).

Step B $N^2$-(2,5-dimethyl-2H-indazol-6-yl)-$N^2$-{2-[(5-fluoro-1,3-dihydro-2H-isoindol-2-yl)(methyl)amino]-2-oxoethyl}-$N^1$-[2-(ethylamino)ethyl]glycinamide hydrochloride Using the compound (175 mg, 0.386 mmol) of step A and the compound of Reference Example 2 (122 mg, 0.648 mmol), and according to the methods of Example 241, steps D and E, the title compound (134 mg, yield 65%) was obtained as a colorless solid.
$^1$H-NMR (400 MHz, DMSO-$d_6$); δ (ppm) 1.12 (t, J=7.2, 3H), 2.31 (s, 3H), 2.8-3.0 (m, 4H), 2.88 (s, 3H), 3.34-3.42 (m, 2H), 3.86 (s, 2H), 4.03-4.32 (m, 4H), 4.07 (s, 3H), 4.27 (s, 2H), 7.04-7.15 (m, 2H), 7.21 (s, 1H), 7.27-7.31 (m, 1H), 7.40 (s, 1H), 8.09 (s, 1H), 8.31 (t, J=5.9, 1H), 8.55 (brs, 2H).

Example 261

$N^2$-{2-[1,3-dihydro-2H-isoindol-2-yl(methyl)amino]-2-oxoethyl}-$N^2$-(1,3,5-trimethyl-1H-indazol-6-yl)-$N^1$-[2-(ethylamino)ethyl]glycinamide hydrochloride Step A N-{2-[1,3-dihydro-2H-isoindol-2-yl(methyl)amino]-2-oxoethyl}-N-(3-iodo-1,5-dimethyl-1H-indazol-6-yl)glycine Using the compound (2.55 g, 6.32 mmol) of Reference Example 135 and the compound (1.37 g, 7.42 mmol) of Reference Example 17, and according to the method of Example 241, step A, the title compound (3.32 g, yield 98%) was obtained as a colorless solid.

¹H-NMR (300 MHz, DMSO-d₆); δ (ppm) 2.35 (s, 3H), 2.89 (s, 3H), 3.94 (s, 3H), 4.07 (s, 2H), 4.10 (d, J=11.7, 2H), 4.25 (d, J=11.7, 2H), 4.33 (s, 2H), 7.11 (s, 1H), 7.24 (s, 1H), 7.25 (brs, 4H), 12.4 (brs, 1H).

Step B $N^2$-{2-[1,3-dihydro-2H-isoindol-2-yl(methyl)amino]-2-oxoethyl}-$N^2$-(3-iodo-1,5-dimethyl-1H-indazol-6-yl)-$N^1$-{2-[(tert-butoxycarbonyl)(ethyl)amino]ethyl}glycinamide Using the compound (861 mg, 1.61 mmol) of step A, and according to the method of Example 1, step B, the title compound (859 mg, yield 76%) was obtained as a colorless amorphous solid.
¹H-NMR (400 MHz, CDCl₃); δ (ppm) 0.97 (t, J=7.0, 3H), 1.41 (brs, 9H), 2.43 (s, 3H), 2.96 (s, 3H), 3.00-3.22 (m, 2H), 3.22-3.30 (m, 2H), 3.33-3.39 (m, 2H), 3.93 (s, 2H), 4.00 (s, 3H), 4.09 (d, J=11.4, 2H), 4.22 (s, 2H), 4.23 (d, J=11.4, 2H), 7.18-7.27 (m, 6H), 7.98 8.15 (2brs, 1H).

Step C $N^2$-{2-[1,3-dihydro-2H-isoindol-2-yl(methyl)amino]-2-oxoethyl}-$N^2$-(1,3,5-trimethyl-1H-indazol-6-yl)-$N^1$-{2-[(tert-butoxycarbonyl)(ethyl)amino]ethyl}glycinamide Using the compound (406 mg, 0.577 mmol) of step B, and according to the method of Example 255, step B, the title compound (315 mg, yield 93%) was obtained as a colorless amorphous solid.
¹H-NMR (400 MHz, CDCl₃); δ (ppm) 0.97 (t, J=7.1, 3H), 1.42 (brs, 9H), 2.41 (s, 3H), 2.49 (s, 3H), 2.96 (s, 3H), 3.0-3.1 (m, 2H), 3.1-3.3 (m, 2H), 3.34-3.41 (m, 2H), 3.90 (s, 5H), 4.08 (d, J=12, 2H), 4.21 (s, 2H), 4.22 (d, J=12, 2H), 7.17-7.26 (m, 5H), 7.41 (s, 1H), 8.09 8.28 (2brs, 1H).

Step D $N^2$-{2-[1,3-dihydro-2H-isoindol-2-yl(methyl)amino]-2-oxoethyl}-$N^2$-(1,3,5-trimethyl-1H-indazol-6-yl)-$N^1$-[2-(ethylamino)ethyl]glycinamide hydrochloride Using the compound (313 mg, 0.838 mmol) of step C, and according to the method of Example 57, step B, the title compound (156 mg, yield 56%) was obtained as a colorless solid.
¹H-NMR (400 MHz, DMSO-d₆); δ (ppm) 1.14 (t, J=7.2, 3H), 2.35 (s, 3H), 2.38 (s, 3H), 2.8-3.0 (m, 4H), 2.88 (s, 3H), 3.35-3.41 (m, 2H), 3.83 (s, 3H), 3.92 (s, 2H), 4.09 (d, J=11.4, 2H), 4.25 (d, J=11.4, 2H), 4.32 (s, 2H), 7.22 (s, 1H), 7.25 (brs, 4H), 7.40 (s, 1H), 8.38 (t, J=5.8, 1H), 8.77 (brs, 2H).

Example 262

$N^2$-{2-[(5-fluoro-1,3-dihydro-2H-isoindol-2-yl)(methyl)amino]-2-oxoethyl}-$N^2$-(1,3,5-trimethyl-1H-indazol-6-yl)-$N^1$-[2-(ethylamino)ethyl]glycinamide hydrochloride Step A $N^2$-(3-iodo-1,5-dimethyl-1H-indazol-6-yl)-$N^2$-{2-[(5-fluoro-1,3-dihydro-2H-isoindol-2-yl)(methyl)amino]-2-oxoethyl}-$N^1$-{2-[(tert-butoxycarbonyl)(ethyl)amino]ethyl}glycinamide Using the compound (799 mg, 1.98 mmol) of Reference Example 135, the compound (418 mg, 2.06 mmol) of Reference Example 19 and the compound (433 mg, 2.30 mmol) of Reference Example 2, and according to the methods of Example 241, step A, and Example 1, step B, the title compound (1.38 g, yield 97%) was obtained as a colorless amorphous solid.
¹H-NMR (400 MHz, CDCl₃); δ (ppm) 0.97 (t, J=7.0, 3H), 1.41 (brs, 9H), 2.43 (s, 3H), 2.95 (s, 3H), 3.0-3.1 (m, 2H), 3.1-3.3 (m, 2H), 3.34-3.39 (m, 2H), 3.94 (s, 2H), 4.00 (s, 3H), 4.02-4.22 (m, 4H), 4.20 (s, 2H), 6.89-6.98 (m, 2H), 7.12-7.16 (m, 1H), 7.23 (s, 2H), 7.93 8.10 (2brs, 1H).

Step B $N^2$-{2-[(5-fluoro-1,3-dihydro-2H-isoindol-2-yl)(methyl)amino]-2-oxoethyl}-$N^2$-(1,3,5-trimethyl-1H-indazol-6-yl)-$N^1$-{2-[(tert-butoxycarbonyl)(ethyl)amino]ethyl}glycinamide Using the compound (508 mg, 0.704 mmol) of step A, and according to the method of Example 255, step B, the title compound (399 mg, yield 93%) was obtained as a colorless amorphous solid.
¹H-NMR (400 MHz, CDCl₃); δ (ppm) 0.96 (t, J=7.1, 3H), 1.42 (brs, 9H), 2.41 (s, 3H), 2.49 (s, 3H), 2.95 (s, 3H), 3.0-3.1 (m, 2H), 3.1-3.3 (m, 2H), 3.34-3.41 (m, 2H), 3.90 (s, 5H), 3.98-4.22 (m, 4H), 4.15 (s, 2H), 6.88-6.98 (m, 2H), 7.11-7.15 (m, 1H), 7.19 (s, 1H), 7.41 (s, 1H), 8.03 8.24 (2brs, 1H).

Step C $N^2$-{2-[(5-fluoro-1,3-dihydro-2H-isoindol-2-yl)(methyl)amino]-2-oxoethyl}-$N^2$-(1,3,5-trimethyl-1H-indazol-6-yl)-$N^1$-[2-(ethylamino)ethyl]glycinamide hydrochloride Using the compound (397 mg, 0.651 mmol) of step B, and according to the method of Example 57, step 13, the title compound (153 mg, yield 43%) was obtained as a colorless solid.
¹H-NMR (400 MHz, DMSO-d₆); δ (ppm) 1.14 (t, J=7.2, 3H), 2.35 (s, 3H), 2.38 (s, 3H), 2.8-3.0 (m, 4H), 2.88 (s, 3H), 3.35-3.41 (m, 2H), 3.84 (s, 3H), 3.92 (s, 2H), 4.04-4.27 (m, 4H), 4.32 (s, 2H), 7.05-7.16 (m, 2H), 7.23 (s, 1H), 7.27-7.31 (m, 1H), 7.41 (s, 1H), 8.38 (t, J=5.8, 1H), 8.78 (brs, 2H).

Example 263

$N^2$-{2-[2,3-dihydro-1H-inden-2-yl(methyl)amino]-2-oxoethyl}-$N^2$-(1,3,5-trimethyl-1H-indazol-6-yl)-$N^1$-[2-(ethylamino)ethyl]glycinamide hydrochloride Step A $N^2$-{2-[2,3-dihydro-1H-inden-2-yl(methyl)amino]-2-oxoethyl}-$N^2$-(3-iodo-1,5-dimethyl-1H-indazol-6-yl)-$N^1$-{2-[(tert-butoxycarbonyl)(ethyl)amino]ethyl}glycinamide Using the compound (587 mg, 1.46 mmol) of Reference Example 135, the compound (272 mg, 1.48 mmol) of Reference Example 23 and the compound (358 mg, 1.90 mmol) of Reference Example 2, and according to the methods of Example 241, step A, and Example 1, step B, the title compound (874 mg, yield 88%) was obtained as a colorless solid.
¹H-NMR (400 MHz, CDCl₃); δ (ppm) 0.97 (t, J=7.0, 3H), 1.42 (brs, 9H), 2.44 (s, 3H), 2.72 2.80 (2s, 3H), 2.82-2.90 (m, 1H), 3.0-3.3 (m, 7H), 3.3-3.4 (m, 2H), 3.92 3.96 4.07 (3brs, 4H), 4.03 4.04 (2s, 3H), 4.61 5.58 (2brs, 1H), 7.1-7.3 (m, 6H), 7.99 8.19 (2brs, 1H).

Step B

$N^2$-{2-[2,3-dihydro-1H-inden-2-yl(methyl)amino]-2-oxoethyl}-$N^2$-(1,3,5-trimethyl-1H-indazol-6-yl)-$N^1$-{2-[(tert-butoxycarbonyl)(ethyl)amino]ethyl}glycinamide

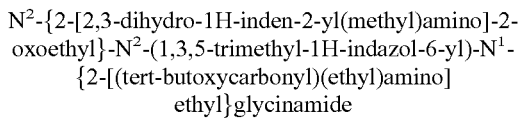

Using the compound (863 mg, 1.23 mmol) of step A, and according to the method of Example 255, step B, the title compound (664 mg, yield 91%) was obtained as a colorless amorphous solid.

$^1$H-NMR (400 MHz, CDCl$_3$); δ (ppm) 0.97 (t, J=6.9, 3H), 1.42 (brs, 9H), 2.42 (s, 3H), 2.50 (s, 3H), 2.70 2.80 (2s, 3H), 2.82-2.90 (m, 1H), 2.98-3.45 (m, 9H), 3.80-4.06 (m, 4H), 3.93 3.94 (2s, 3H), 4.61 5.59 (2brs, 1H), 7.1-7.3 (m, 5H), 7.43 (s, 1H), 8.11 8.32 (2brs, 1H).

Step C

$N^2$-{2-[2,3-dihydro-1H-inden-2-yl(methyl)amino]-2-oxoethyl}-$N^2$-(1,3,5-trimethyl-1H-indazol-6-yl)-$N^1$-[2-(ethylamino)ethyl]glycinamide hydrochloride

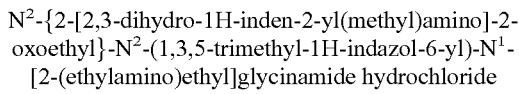

Using the compound (660 mg, 1.12 mmol) of step B, and according to the method of Example 57, step B, the title compound (425 mg, yield 72%) was obtained as a colorless solid.

$^1$H-NMR (300 MHz, DMSO-d$_6$); δ (ppm) 1.13-1.17 (m, 3H), 2.37 (s, 3H), 2.39 (s, 3H), 2.66 2.77 (2s, 3H), 2.85-3.10 (m, 8H), 3.3-3.4 (m, 2H), 3.82 3.87 (2s, 2H), 3.84 3.86 (2s, 3H), 4.09 4.25 (2s, 2H), 4.93-5.05 5.25-5.38 (2m, 1H), 7.13-7.22 (m, 4H), 7.24 7.28 (2s, 1H), 7.42 (s, 1H), 8.44-8.52 (m, 1H), 8.73 (brs, 2H).

Example 264

$N^2$-{2-[1,3-dihydro-2H-isoindol-2-yl(methyl)amino]-2-oxoethyl}-$N^2$-(3-ethyl-1,5-dimethyl-1H-indazol-6-yl)-$N^1$-[2-(ethylamino)ethyl]glycinamide hydrochloride

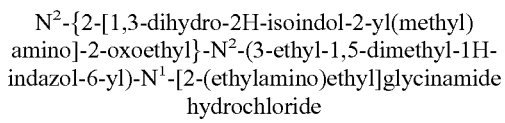

Step A

$N^2$-{2-[1,3-dihydro-2H-isoindol-2-yl(methyl)amino]-2-oxoethyl}-$N^2$-(1,5-dimethyl-3-vinyl-1H-indazol-6-yl)-$N^1$-{2-[(text-butoxycarbonyl)(ethyl)amino]ethyl}glycinamide

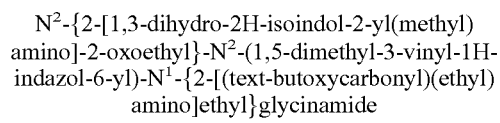

To toluene (8 ml) were added the compound (583 mg, 0.829 mmol) of Example 261, step B, tri-n-butylvinyltin (415 mg, 1.31 mmol), bis(triphenylphosphine)palladium(II) dichloride (74 mg, 0.105 mmol) and lithium chloride (94 mg, 2.22 mmol), and the mixture was heated under reflux for 100 min. The reaction mixture was cooled, diluted with ethyl acetate, washed with saturated brine, and dried over anhydrous magnesium sulfate. The insoluble material was filtered off, and the solution was concentrated under reduced pressure. The obtained oil was purified by silica gel column chromatography (ethyl acetate-methanol) to give the title compound (446 mg, yield 89%) as a yellow amorphous solid.

$^1$H-NMR (300 MHz, CDCl$_3$); δ (ppm) 0.96 (t, J=6.9, 3H), 1.41 (brs, 9H), 2.43 (s, 3H), 2.96 (s, 3H), 3.0-3.1 (m, 2H), 3.1-3.3 (m, 2H), 3.3-3.4 (m, 2H), 3.93 (s, 2H), 3.95 (s, 3H), 4.08 (d, J=11, 2H), 4.22 (s, 2H), 4.23 (d, J=11, 2H), 5.44 (dd, J=1.2, 12, 1H), 6.00 (dd, J=1.2, 18, 1H), 6.95 (dd, J=12, 18, 1H), 7.15-7.28 (m, 5H), 7.69 (s, 1H), 8.0 8.1 (2brs, 1H).

Step B

$N^2$-{2-[1,3-dihydro-2H-isoindol-2-yl(methyl)amino]-2-oxoethyl}-$N^2$-(3-ethyl-1,5-dimethyl-1H-indazol-6-yl)-$N^1$-{2-[(tert-butoxycarbonyl)(ethyl)amino]ethyl}glycinamide

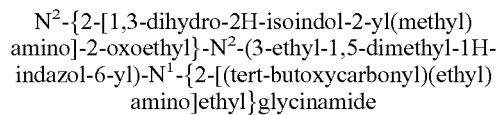

The compound (439 mg, 0.727 mmol) of step A was dissolved in an ethanol (15 ml)-tetrahydrofuran (1 ml) mixed solvent, 10% palladium carbon (containing water) (0.40 g) was added, and the mixture was stirred under a hydrogen atmosphere at room temperature for 5 hr. The reaction mixture was filtered through celite, and the solution was concentrated under reduced pressure. The obtained oil was purified by silica gel column chromatography (ethyl acetate-methanol) to give the title compound (392 mg, yield 89%) as a colorless amorphous solid.

$^1$H-NMR (400 MHz, CDCl$_3$); δ (ppm) 0.96 (t, J=7.1, 3H), 1.36 (t, J=7.5, 3H), 1.42 (brs, 9H), 2.41 (s, 3H), 2.91 (q, J=7.5, 2H), 2.96 (s, 3H), 3.0-3.1 (m, 2H), 3.1-3.3 (m, 2H), 3.35-3.41 (m, 2H), 3.91 (s, 5H), 4.08 (d, J=11.3, 2H), 4.21 (s, 2H), 4.23 (d, J=11.3, 2H), 7.17-7.26 (m, 5H), 7.45 (s, 1H), 8.08 8.28 (2brs, 1H).

Step C

$N^2$-{2-[1,3-dihydro-2H-isoindol-2-yl(methyl)amino]-2-oxoethyl}-$N^2$-(3-ethyl-1,5-dimethyl-1H-indazol-6-yl)-$N^1$-[2-(ethylamino)ethyl]glycinamide hydrochloride

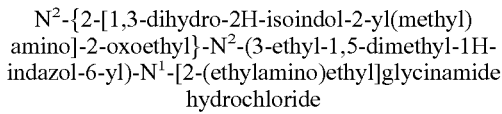

Using the compound (382 mg, 0.631 mmol) of step B, and according to the method of Example 57, step B, the title compound (265 mg, yield 77%) was obtained as a pale-yellow solid.

$^1$H-NMR (300 MHz, DMSO-d$_6$); δ (ppm) 1.13 (t, J=7.1, 3H), 1.26 (t, J=7.5, 3H), 2.35 (s, 3H), 2.8-3.0 (m, 4H), 2.82 (q, J=7.5, 2H), 2.88 (s, 3H), 3.33-3.40 (m, 2H), 3.84 (s, 3H), 3.91 (s, 2H), 4.08 (d, J=11.5, 2H), 4.25 (d, J=11.5, 2H), 4.31 (s,2H), 7.22 (s, 1H), 7.25 (brs, 4H), 7.44 (s, 1H), 8.37 (t, J=5.9, 1H), 8.70 (brs, 2H).

The compounds of Examples 241-264 are shown below.
TABLE 17
| Example | Structural Formula | TMW | LC-MS (found) |
|---|---|---|---|
| 241 | 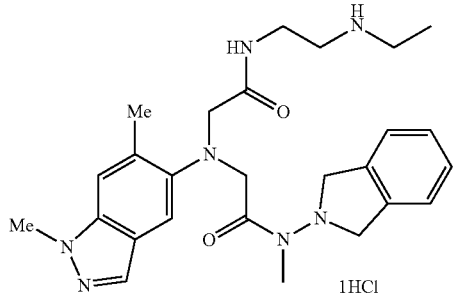 [SMILES: CCNCCNC(=O)CN(CC(=O)N(C)N1Cc2ccccc2C1)c1cc2cnn(C)c2cc1C] | 514.06 | 478 |
| 242 | 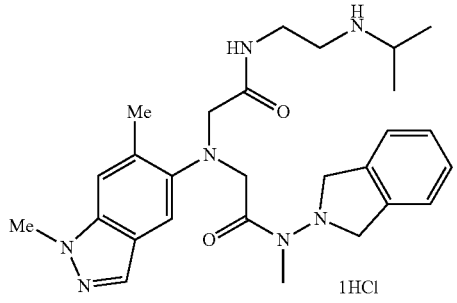 [SMILES: Cc1cc2c(cnn2C)cc1N(CC(=O)NCCNC(C)C)CC(=O)N(C)N1Cc2ccccc2C1] | 528.09 | 492 |
| 243 | 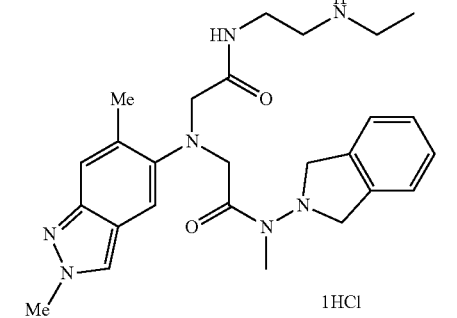 | 514.06 | 478 |
| 244 | 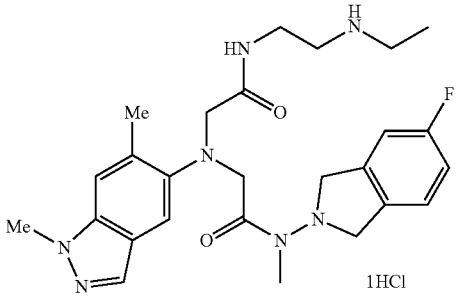 [SMILES: CCNCCNC(=O)CN(CC(=O)N(C)N1Cc2ccc(F)cc2C1)c1cc2cnn(C)c2cc1C] | 532.05 | 496 |

TABLE 17-continued

| Example | Structural Formula | TMW | LC-MS (found) |
|---|---|---|---|
| 245 | (structure) 1HCl | 532.05 | 496 |
| 246 | (structure) 1HCl | 528.09 | 492 |
| 247 | (structure) 1HCl | 528.09 | 492 |
| 248 | (structure) 1HCl | 546.08 | 510 |

TABLE 17-continued

| Example | Structural Formula | TMW | LC-MS (found) |
|---------|-------------------|-----|---------------|
| 249 | (structure) 1HCl | 546.08 | 510 |
| 250 | (structure) 1HCl | 564.07 | 528 |
| 251 | (structure) 1HCl | 582.06 | 546 |
| 252 | (structure) 1HCl | 563.08 | 527 |
| 253 | (structure) 1HCl | 582.06 | 546 |

TABLE 17-continued

| Example | Structural Formula | TMW | LC-MS (found) |
|---|---|---|---|
| 254 | (structure) 1HCl | 582.06 | 546 |
| 255 | (structure) 1HCl | 528.09 | 492 |
| 256 | (structure) 1HCl | 546.08 | 510 |
| 257 | (structure) 1HCl | 514.06 | 478 |

TABLE 17-continued
| Example | Structural Formula | TMW | LC-MS (found) |
|---|---|---|---|
| 258 | 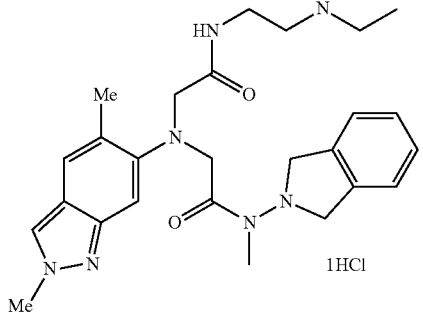 1HCl | 514.06 | 478 |
| 259 | 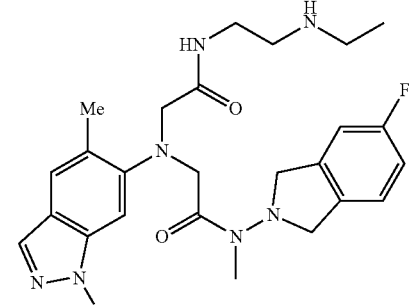 1HCl | 532.05 | 496 |
| 260 | 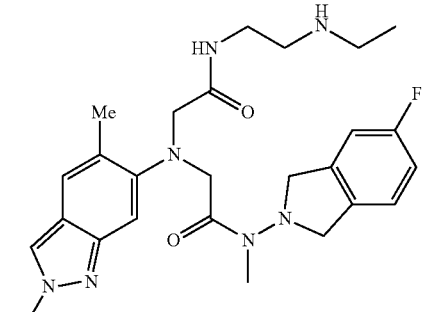 1HCl | 532.05 | 496 |
| 261 | 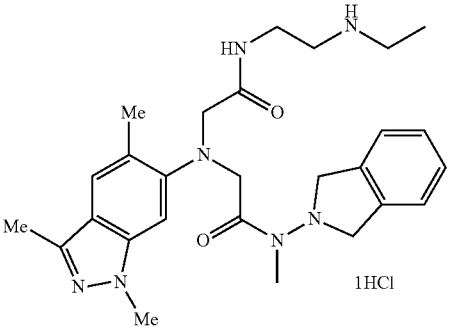 [SMILES: CCNCCNC(=O)CN(CC(=O)N(C)N1Cc2ccccc2C1)c1cc2c(cc1C)c(C)nn2C] 1HCl | 528.09 | 492 |

| Example | Structural Formula | TMW | LC-MS (found) |
|---|---|---|---|
| 262 | (structure with 1HCl) | 546.08 | 510 |
| 263 | (structure with 1HCl) | 527.10 | 491 |
| 264 | (structure with 1HCl) | 542.12 | 506 |

Example 265

$N^2$-[1-(2,2-difluoroethyl)-5-methyl-1H-indazol-6-yl]-$N^2$-{2-[1,3-dihydro-2H-isoindol-2-yl(methyl)amino]-2-oxoethyl}-$N^1$-[2-(ethylamino)ethyl]glycinamide hydrochloride Step A N-[1-(2,2-difluoroethyl)-5-methyl-1H-indazol-6-yl]-N-{2-[1,3-dihydro-2H-isoindol-2-yl(methyl)amino]-2-oxoethyl}glycine ethyl ester Using the compound (1.25 g, 2.97 mmol) of Example 257, step B and 2,2-difluoroethyl trifluoromethanesulfonate (859 mg, 4.01 mmol), and according to the method of Example 241, step C, the title compound (982 mg, yield 68%) was obtained as a colorless amorphous solid.

$^1$H-NMR (400 MHz, CDCl$_3$); δ (ppm) 1.21 (t, J=7.1, 3H), 2.43 (s, 3H), 2.93 (s, 3H), 4.10 (d, J=11.4, 2H), 4.12 (q, J=7.1, 2H), 4.22 (d, J=11.4, 2H), 4.24 (s, 2H), 4.44 (s, 2H), 4.63 (dt, J=4.3, 14, 2H), 6.10 (tt, J=4.3, 56, 1H), 7.18-7.26 (m, 5H), 7.47 (s, 1H), 7.86 (s, 1H).

Step B

N-[1-(2,2-difluoroethyl)-5-methyl-1H-indazol-6-yl]-N-{2-[1,3-dihydro-2H-isoindol-2-yl(methyl)amino]-2-oxoethyl}glycine Using the compound (975 mg, 2.01 mmol) of step A, and according to the method of Example 241, step D, the title compound (843 mg, yield 92%) was obtained as a colorless solid.

$^1$H-NMR (400 MHz, DMSO-d$_6$); δ (ppm) 2.33 (s, 3H), 2.87 (s, 3H), 4.05 (s, 2H), 4.06 (d, J=11.5, 2H), 4.24 (d, J=11.5, 2H), 4.32 (s, 2H), 4.78 (dt, J=3.6, 15, 2H), 6.35 (tt, J=3.6, 55, 1H), 7.2-7.3 (m, 4H), 7.36 (s, 1H), 7.47 (s, 1H), 7.92 (s, 1H), 12.48 (brs, 1H).

Step C

N²-[1-(2,2-difluoroethyl)-5-methyl-1H-indazol-6-yl]-N²-{2-[1,3-dihydro-2H-isoindol-2-yl(methyl)amino]-2-oxoethyl}-N¹-[2-(ethylamino)ethyl]glycinamide hydrochloride Using the compound (325 mg, 0.710 mmol) of step B and the compound (177 mg, 0.940 mmol) of Reference Example 2, and according to the methods of Example 1, step B, and Example 57, step B, the title compound (272 mg, yield 68%) was obtained as a colorless solid.

¹H-NMR (400 MHz, DMSO-d₆); δ (ppm) 1.13 (t, J=7.2, 3H), 2.36 (s, 3H).

2.8-3.0 (m, 4H), 2.88 (s, 3H), 3.35-3.39 (m, 2H), 3.92 (s, 2H), 4.09 (d, J=11.4, 2H), 4.24 (d, J=11.4, 2H), 4.33 (s, 2H), 4.80 (dt, J=3.6, 15, 2H), 6.37 (tt, J=3.6, 55, 1H), 7.25 (brs, 4H), 7.41 (s, 1H), 7.49 (s, 1H), 7.94 (s, 1H), 8.35 (t, J=5.8, 1H), 8.61 (brs. 2H).

Example 266

N²-[2-(2,2-difluoroethyl)-5-methyl-2H-indazol-6-yl]-N²-{2-[1,3-dihydro-2H-isoindol-2-yl(methyl)amino]-2-oxoethyl}-N¹-[2-(ethylamino)ethyl]glycinamide hydrochloride

Step A

N-[2-(2,2-difluoroethyl)-5-methyl-2H-indazol-6-yl]-N-{2-[1,3-dihydro-2H-isoindol-2-yl(methyl)amino]-2-oxoethyl}glycine ethyl ester As a byproduct of Example 265, step A, the title compound (346 mg, yield 24%) was obtained as a colorless amorphous solid.

¹H-NMR (400 MHz, CDCl₃); δ (ppm) 1.22 (t, J=7.1, 3H), 2.40 (s, 3H), 2.94 (s, 3H), 4.10-4.26 (m, 8H), 4.46 (s, 2H), 4.65 (dt, J=4.4, 13, 2H), 6.19 (tt, J=4.4, 56, 1H), 7.18-7.26 (m, 4H), 7.37 (s, 1H), 7.40 (s, 1H), 7.78 (s, 1H).

Step B

N-[2-(2,2-difluoroethyl)-5-methyl-2H-indazol-6-yl]-N-{2-[1,3-dihydro-2H-isoindol-2-yl(methyl)amino]-2-oxoethyl}glycine Using the compound (340 mg, 0.700 mmol) of step A, and according to the method of Example 241, step D, the title compound (267 mg, yield 83%) was obtained as a colorless solid.

¹H-NMR (400 MHz, DMSO-d₆); δ (ppm) 2.29 (s, 3H), 2.88 (s, 3H), 4.01 (s, 2H), 4.11 (d, J=11.5, 2H), 4.26 (d, J=11.5, 2H), 4.31 (s, 2H), 4.85 (dt, J=3.9, 15, 2H), 6.46 (tt, J=3.9, 55, 1H), 7.18 (s, 1H), 7.22-7.28 (m, 4H), 7.43 (s, 1H), 8.18 (s, 1H), 12.48 (brs, 1H).

Step C

N²-[1-(2,2-difluoroethyl)-5-methyl-2H-indazol-6-yl]-N²-{2-[1,3-dihydro-2H-isoindol-2-yl(methyl)amino]-2-oxoethyl}-N¹-[2-(ethylamino)ethyl]glycinamide hydrochloride Using the compound (264 mg, 0.577 mmol) of step B and the compound (152 mg, 0.807 mmol) of Reference Example 2, and according to the methods of Example 1, step B, and Example 57, step B, the title compound (220 mg, yield 68%) was obtained as a colorless solid.

¹H-NMR (400 MHz, DMSO-d₆); δ (ppm) 1.11 (t, J=7.3, 3H), 2.32 (s, 3H), 2.8-3.0 (m, 4H), 2.90 (s, 3H), 3.34-3.40 (m, 2H), 3.88 (s, 2H), 4.10 (d, J=11.4, 2H), 4.26 (d, J=11.4, 2H), 4.29 (s, 2H), 4.86 (dt, J=3.8, 15, 2H), 6.47 (tt, J=3.8, 55, 1H), 7.22 (s, 1H), 7.23-7.29 (m, 4H), 7.45 (s, 1H), 8.19 (s, 1H), 8.29 (t, J=5.8, 1H), 8.39 (brs, 2H).

Example 267

N²-[1-(2,2-difluoroethyl)-5-methyl-1H-indazol-6-yl]-N²-{2-[(5-fluoro-1,3-dihydro-2H-isoindol-2-yl)(methyl)amino]-2-oxoethyl}-N³-[2-(ethylamino)ethyl]glycinamide hydrochloride

Step A

N-[1-(2,2-difluoroethyl)-5-methyl-1H-indazol-6-yl]-N-{2-[(5-fluoro-1,3-dihydro-2H-isoindol-2-yl)(methyl)amino]-2-oxoethyl}glycine ethyl ester Using the compound (1.46 g, 3.32 mmol) of Example 259, step B, and 2,2-difluoroethyl trifluoromethanesulfonate (957 mg, 4.47 mmol), and according to the method of Example 241, step C, the title compound (1.09 g, yield 65%) was obtained as a colorless amorphous solid.

¹H-NMR (400 MHz, CDCl₃); δ (ppm) 1.21 (t, J=7.1, 3H), 2.43 (s, 3H), 2.93 (s, 3H), 4.04-4.21 (m, 6H), 4.23 (s, 2H), 4.43 (s, 2H), 4.64 (dt, J=4.3, 14, 2H), 6.10 (tt, J=4.3, 55, 1H), 6.88-6.98 (m, 2H), 7.11-7.16 (m, 1H), 7.26 (s, 1H), 7.48 (s, 1H), 7.86 (s, 1H).

Step B

N-[1-(2,2-difluoroethyl)-5-methyl-1H-indazol-6-yl]-N-{2-[(5-fluoro-1,3-dihydro-2H-isoindol-2-yl)(methyl)amino]-2-oxoethyl}glycine Using the compound (1.08 mg, 2.14 mmol) of step A, and according to the method of Example 241, step D, the title compound (925 mg, yield 91%) was obtained as a colorless solid.

¹H-NMR (400 MHz, DMSO-d₆); δ (ppm) 2.32 (s, 3H), 2.86 (s, 3H), 4.04-4.26 (m, 4H), 4.05 (s, 2H), 4.31 (s, 2H), 4.79 (dt, J=3.6, 15, 2H), 6.35 (tt, J=3.6, 55, 1H), 7.04-7.15 (m, 2H), 7.26-7.31 (m, 1H), 7.36 (s, 1H), 7.47 (s, 1H), 7.92 (s, 1H), 12.48 (brs, 1H).

Step C

N²-[1-(2,2-difluoroethyl)-5-methyl-1H-indazol-6-yl]-N²-{2-[(5-fluoro-1,3-dihydro-2H-isoindol-2-yl)(methyl)amino]-2-oxoethyl}-N¹-[2-(ethylamino)ethyl]glycinamide hydrochloride Using the compound (322 mg, 0.677 mmol) of step B, and according to the methods of Example 1, step B, and Example 57, step B, the title compound (268 mg, yield 68%) was obtained as a colorless solid.

¹H-NMR (400 MHz, DMSO-d₆); δ (ppm) 1.12 (t, J=7.2, 3H), 2.36 (s, 3H), 2.8-3.0 (m, 4H), 2.88 (s, 3H), 3.3-3.4 (m, 2H), 3.91 (s, 2H), 4.05-4.26 (m, 4H), 4.31 (s, 2H), 4.80 (dt, J=3.7, 15, 2H), 6.37 (tt, J=3.7, 55, 1H), 7.05-7.15 (m, 2H), 7.26-7.31 (m, 1H), 7.41 (s, 1H), 7.49 (s, 1H), 7.94 (s, 1H), 8.34 (broad t, 1H), 8.60 (brs, 2H).

Example 268

$N^2$-[2-(2,2-difluoroethyl)-5-methyl-2H-indazol-6-yl]-$N^2$-{2-[(5-fluoro-1,3-dihydro-2H-isoindol-2-yl)(methyl)amino]-2-oxoethyl}-$N^1$-[2-(ethylamino)ethyl]glycinamide hydrochloride

Step A

N-[2-(2,2-difluoroethyl)-5-methyl-2H-indazol-6-yl]-N-{2-[(5-fluoro-1,3-dihydro-2H-isoindol-2-yl)(methyl)amino]-2-oxoethyl}glycine ethyl ester

As a byproduct of Example 267, step A, the title compound (313 mg, yield 19%) was obtained as a colorless amorphous solid.
$^1$H-NMR (400 MHz, CDCl$_3$); δ (ppm) 1.23 (t, J=7.2, 3H), 2.40 (s, 3H), 2.94 (s, 3H), 4.08-4.22 (m, 8H), 4.45 (s, 2H), 4.65 (dt, J=4.4, 13, 2H), 6.19 (tt, J=4.4, 56, 1H), 6.87-6.97 (m, 2H), 7.11-7.15 (m, 1H), 7.36 (s, 1H), 7.40 (s, 1H), 7.78 (s, 1H).

Step B

N-[2-(2,2-difluoroethyl)-5-methyl-2H-indazol-6-yl]-N-{2-[(5-fluoro-1,3-dihydro-2H-isoindol-2-yl)(methyl)amino]-2-oxoethyl}glycine

Using the compound (308 mg, 0.612 mmol) of step A, and according to the method of Example 241, step D, the title compound (202 mg, yield 69%) was obtained as a colorless solid.
$^1$H-NMR (400 MHz, DMSO-d$_6$); δ (ppm) 2.29 (s, 3H), 2.87 (s, 3H), 4.00 (s, 2H), 4.07-4.27 (m, 4H), 4.30 (s, 2H), 4.85 (dt, J=3.9, 15, 2H), 6.46 (tt, J=3.9, 55, 1H), 7.04-7.16 (m, 2H), 7.17 (s, 1H), 7.27-7.31 (m, 1H), 7.43 (s, 1H), 8.18 (s, 1H), 12.45 (brs, 1H).

Step C

$N^2$-[2-(2,2-difluoroethyl)-5-methyl-2H-indazol-6-yl]-$N^2$-{2-[(5-fluoro-1,3-dihydro-2H-isoindol-2-yl)(methyl)amino]-2-oxoethyl}-$N^1$-[2-(ethylamino)ethyl]glycinamide hydrochloride

Using the compound (201 mg, 0.423 mmol) of step B and the compound (103 mg, 0.547 mmol) of Reference Example 2, and according to the methods of Example 1, step B, and Example 57, step B, the title compound (172 mg, yield 70%) was obtained as a colorless solid.
$^1$H-NMR (400 MHz, DMSO-d$_6$); δ (ppm) 1.12 (t, J=7.2, 3H), 2.32 (s, 3H), 2.8-3.0 (m, 4H), 2.89 (s, 3H), 3.30-3.42 (m, 2H), 3.88 (s, 2H), 4.06-4.25 (m, 4H), 4.28 (s, 2H), 4.86 (dt, J=3.8, 15, 2H), 6.47 (tt, J=3.8, 55, 1H), 7.05-7.16 (m, 2H), 7.22 (s, 1H), 7.27-7.32 (m, 1H), 7.45 (s, 1H), 8.19 (s, 1H), 8.29 (t, J=5.8, 1H), 8.55 (brs, 2H).

Example 269

$N^2$-{2-[(5-fluoro-1,3-dihydro-2H-isoindol-2-yl)(methyl)amino]-2-oxoethyl}-$N^2$-(2,3,5-trimethyl-2H-indazol-6-yl)-$N^1$-[2-(ethylamino)ethyl]glycinamide hydrochloride

Using the compound (146 mg, 0.501 mmol) of Reference Example 137, the compound (102 mg, 0.503 mmol) of Reference Example 19 and the compound (106 mg, 0.563 mmol) of Reference Example 2, and according to the methods of Example 204, step A, and Example 57, step B, the title compound (191 mg, yield 70%) was obtained as a colorless solid.
$^1$H-NMR (400 MHz, DMSO-d$_6$); δ (ppm) 1.13 (t, J=7.2, 3H), 2.31 (s, 3H), 2.52 (s, 3H), 2.8-3.0 (m, 4H), 2.88 (s, 3H), 3.31-3.43 (m, 2H), 3.87 (s, 2H), 3.97 (s, 3H), 4.01-4.24 (m, 4H), 4.27 (s, 2H), 7.05-7.15 (m, 2H), 7.10 (s, 1H), 7.27-7.31 (m, 1H), 7.38 (s, 1H), 8.32 (t, J=5.9, 1H), 8.56 (brs, 2H).

Example 270

$N^2$-(2-ethyl-3,5-dimethyl-2H-indazol-6-yl)-$N^2$-{2-[(5-fluoro-1,3-dihydro-2H-isoindol-2-yl)(methyl)amino]-2-oxoethyl}-$N^1$-[2-(ethylamino)ethyl]glycinamide hydrochloride

Using the compound (182 mg, 0.596 mmol) of Reference Example 138, the compound (124 mg, 0.612 mmol) of Reference Example 19 and the compound (132 mg, 0.701 mmol) of Reference Example 2, and according to the methods of Example 204, step A, and Example 57, step B, the title compound (236 mg, yield 71%) was obtained as a colorless solid.
$^1$H-NMR (400 MHz, DMSO-d$_6$); δ (ppm) 1.13 (t, J=7.1, 3H), 1.37 (t, J=7.2, 3H), 2.31 (s, 3H), 2.52 (s, 3H), 2.8-3.0 (m, 4H), 2.88 (s, 3H), 3.85 (s, 2H), 4.03-4.11 (m, 2H), 4.17-4.32 (m, 4H), 4.26 (s, 2H), 7.05-7.15 (m, 2H), 7.13 (s, 1H), 7.27-7.31 (m, 1H), 7.36 (s, 1H), 8.32 (t, J=5.8, 1H), 8.62 (brs, 2H).

Example 271

$N^2$-(1-ethyl-3,5-dimethyl-1H-indazol-6-yl)-$N^2$-{2-[(5-fluoro-1,3-dihydro-2H-isoindol-2-yl)(methyl)amino]-2-oxoethyl}-$N^1$-[2-(ethylamino)ethyl]glycinamide hydrochloride

Using the compound (82 mg, 0.269 mmol) of Reference Example 139, the compound (55 mg, 0.271 mmol) of Reference Example 19 and the compound (70 mg, 0.372 mmol) of Reference Example 2, and according to the methods of Example 204, step A, and Example 57, step B, the title compound (85 mg, yield 56%) was obtained as a pale-yellow solid.
$^1$H-NMR (400 MHz, DMSO-d$_6$); δ (ppm) 1.13 (t, J=7.3, 3H), 1.30 (t, J=7.2, 3H), 2.34 (s, 3H), 2.39 (s, 3H), 2.8-3.0 (m, 4H), 2.88 (s, 3H), 3.33-3.38 (m, 2H), 3.91 (s, 2H), 4.02-4.11 (m, 2H), 4.16-4.28 (m, 2H), 4.22 (q, J=7.2, 2H), 4.30 (s, 2H), 7.04-7.15 (m, 2H), 7.23 (s, 1H), 7.25-7.31 (m, 1H), 7.40 (s, 1H), 8.35 (t, J=5.8, 1H), 8.70 (brs, 2H).

Example 272

$N^2$-[2-(2,2-difluoroethyl)-3,5-dimethyl-2H-indazol-6-yl]-$N^2$-{2-[1,3-dihydro-2H-isoindol-2-yl(methyl)amino]-2-oxoethyl}-$N^1$-[2-(ethylamino)ethyl]glycinamide hydrochloride

Using the compound (185 mg, 0.542 mmol) of Reference Example 140, the compound (106 mg, 0.574 mmol) of Reference Example 17 and the compound (131 mg, 0.696 mmol) of Reference Example 2, and according to the methods of Example 204, step A, and Example 57, step B, the title compound (271 mg, yield 86%) was obtained as a colorless solid.
$^1$H-NMR (400 MHz, DMSO-d$_6$); δ (ppm) 1.13 (t, J=7.2, 3H), 2.32 (s, 3H), 2.55 (s, 3H), 2.8-3.0 (m, 4H), 2.89 (s, 3H), 3.32-3.45 (m, 2H), 3.87 (s, 2H), 4.10 (d, J=11.4, 2H), 4.26 (d, J=11.4, 2H), 4.29 (s, 2H), 4.80 (dt, J=3.8, 15, 2H), 6.45 (dt, J=3.8, 55, 1H), 7.12 (s, 1H), 7.23-7.29 (m, 4H), 7.39 (s, H), 8.31 (t, J=5.9, 1H), 8.64 (brs, 2H).

Example 273

$N^2$-[2-(2,2-difluoroethyl)-3,5-dimethyl-2H-indazol-6-yl]-$N^2$-{2-[(5-fluoro-1,3-dihydro-2H-isoindol-2-yl)(methyl)amino]-2-oxoethyl}-$N^1$-[2-(ethylamino)ethyl]glycinamide hydrochloride Using the compound (192 mg, 0.563 mmol) of Reference Example 140, the compound (118 mg, 0.582 mmol) of Reference Example 19 and the compound (147 mg, 0.563 mmol) of Reference Example 2, and according to the methods of Example 204, step A, and Example 57, step B, the title compound (264 mg, yield 79%) was obtained as a pale-yellow solid.

$^1$H-NMR (400 MHz, DMSO-$d_6$); δ (ppm) 1.13 (t, J=7.2, 3H), 2.31 (s, 3H), 2.55 (s, 3H), 2.8-3.0 (m, 4H), 2.89 (s, 3H), 3.30-3.45 (m, 2H), 3.87 (s, 2H), 4.04-4.25 (m, 4H), 4.27 (s, 2H), 4.79 (dt, J=3.7, 15, 2H), 6.44 (dt, J=3.7, 55, 1H), 7.05-7.16 (m, 2H), 7.12 (s, 1H), 7.26-7.32 (m, 1H), 7.39 (s, H), 8.29 (t, J=6.0, 1H), 8.56 (brs, 2H).

Example 274

$N^2$-(3-ethyl-2,5-dimethyl-2H-indazol-6-yl)-$N^2$-{2-[(5-fluoro-1,3-dihydro-2H-isoindol-2-yl)(methyl)amino]-2-oxoethyl}-$N^1$-[2-(ethylamino)ethyl]glycinamide hydrochloride Using the compound (123 mg, 0.403 mmol) of Reference Example 141, the compound (82 mg, 0.405 mmol) of Reference Example 19 and the compound (94 mg, 0.499 mmol) of Reference Example 2, and according to the methods of Example 204, step A, and Example 57, step B, the title compound (150 mg, yield 66%) was obtained as a colorless solid.

$^1$H-NMR (400 MHz, DMSO-$d_6$); δ (ppm) 1.12 (t, J=7.2, 3H), 1.22 (t, J=7.6, 3H), 2.31 (s, 3H), 2.8-3.0 (m, 4H), 2.88 (s, 3H), 2.98 (q, J=7.6, 2H), 3.34-3.42 (m, 2H), 3.86 (s, 2H), 3.99 (s, 3H), 4.02-4.11 (m, 2H), 4.17-4.25 (m, 2H), 4.26 (s, 2H), 7.05-7.15 (m, 2H), 7.12 (s, 1H), 7.27-7.31 (m, 1H), 7.41 (s, 1H), 8.32 (t, J=5.8, 1H), 8.54 (brs, 2H).

Example 275

$N^2$-(2,3-diethyl-5-methyl-2H-indazol-6-yl)-$N^2$-{2-[1,3-dihydro-2H-isoindol-2-yl(methyl)amino]-2-oxoethyl}-$N^1$-[2-(ethylamino)ethyl]glycinamide hydrochloride Using the compound (129 mg, 0.404 mmol) of Reference Example 142, the compound (76 mg, 0.412 mmol) of Reference Example 17 and the compound (104 mg, 0.552 mmol) of Reference Example 2, and according to the methods of Example 204, step A, and Example 57, step B, the title compound (170 mg, yield 76%) was obtained as a pale-yellow solid.

$^1$H-NMR (400 MHz, DMSO-$d_6$); δ (ppm) 1.13 (t, J=7.2, 3H), 1.23 (t, J=7.5, 3H), 1.41 (t, J=7.2, 3H), 2.32 (s, 3H), 2.8-3.0 (m, 4H), 2.89 (s, 3H), 2.99 (q, J=7.5, 2H), 3.34-3.40 (m, 2H), 3.86 (s, 2H), 4.10 (d, J=11.6, 2H), 4.26 (d, J=11.6, 2H), 4.29 (s, 2H), 4.30 (q, J=7.2, 2H), 7.15 (s, 1H), 7.2-7.3 (m, 4H), 7.42 (s, 1H), 8.35 (t, J=5.8, 1H), 8.78 (brs, 2H).

Example 276

$N^2$-(2,3-diethyl-5-methyl-2H-indazol-6-yl)-$N^2$-{2-[(5-fluoro-1,3-dihydro-2H-isoindol-2-yl)(methyl)amino]-2-oxoethyl}-$N^1$-[2-(ethylamino)ethyl]glycinamide hydrochloride Using the compound (131 mg, 0.410 mmol) of Reference Example 142, the compound (86 mg, 0.424 mmol) of Reference Example 19 and the compound (104 mg, 0.552 mmol) of Reference Example 2, and according to the methods of Example 204, step A, and Example 57, step B, the title compound (160 mg, yield 68%) was obtained as a pale-yellow solid.

$^1$H-NMR (400 MHz, DMSO-$d_6$); δ (ppm) 1.13 (t, J=7.2, 3H), 1.23 (t, J=7.5, 3H), 1.40 (t, J=7.2, 3H), 2.32 (s, 3H), 2.8-3.0 (m, 4H), 2.88 (s, 3H), 2.99 (q, J=7.5, 2H), 3.34-3.41 (m, 2H), 3.86 (s, 2H), 4.05-4.24 (m, 4H), 4.27 (s, 2H), 4.30 (q, J=7.2, 2H), 7.05-7.13 (m, 2H), 7.15 (s, 1H), 7.27-7.31 (m, 1H), 7.40 (s, 1H), 8.34 (t, J=5.8, 1H), 8.76 (brs, 2H).

Example 277

$N^2$-[2-(2,2-difluoroethyl)-3-ethyl-5-methyl-2H-indazol-6-yl]-$N^2$-{2-[1,3-dihydro-2H-isoindol-2-yl(methyl)amino]-2-oxoethyl}-$N^1$-[2-(ethylamino)ethyl]glycinamide hydrochloride Using the compound (206 mg, 0.580 mmol) of Reference Example 143, the compound (110 mg, 0.596 mmol) of Reference Example 17 and the compound (138 mg, 0.733 mmol) of Reference Example 2, and according to the methods of Example 204, step A, and Example 57, step B, the title compound (286 mg, yield 83%) was obtained as a colorless solid.

$^1$H-NMR (400 MHz, DMSO-$d_6$); δ (ppm) 1.12 (t, J=7.2, 3H), 1.23 (t, J=7.5, 3H), 2.32 (s, 3H), 2.8-3.0 (m, 4H), 2.89 (s, 3H), 3.02 (q, J=7.5, 2H), 3.34-3.40 (m, 2H), 3.87 (s, 2H), 4.10 (d, J=11.4, 2H), 4.26 (d, J=11.4, 2H), 4.29 (s, 2H), 4.80 (dt, J=3.9, 15, 2H), 6.48 (tt, J=3.9, 55, 1H), 7.14 (s, 1H), 7.24-7.27 (m, 4H), 7.44 (s, 1H), 8.31 (t, J=5.8, 1H), 8.69 (brs, 2H).

Example 278

$N^2$-[2-(2,2-difluoroethyl)-3-ethyl-5-methyl-2H-indazol-6-yl]-$N^2$-{2-[(5-fluoro-1,3-dihydro-2H-isoindol-2-yl)(methyl)amino]-2-oxoethyl}-$N^1$-[2-(ethylamino)ethyl]glycinamide hydrochloride Using the compound (196 mg, 0.552 mmol) of Reference Example 143, the compound (113 mg, 0.558 mmol) of Reference Example 19 and the compound (130 mg, 0.563 mmol) of Reference Example 2, and according to the methods of Example 204, step A, and Example 57, step B, the title compound (259 mg, yield 77%) was obtained as a pale-yellow solid.

$^1$H-NMR (400 MHz, DMSO-$d_6$); δ (ppm) 1.12 (t, J=7.2, 3H), 1.23 (t, J=7.5, 3H), 2.32 (s, 3H), 2.8-3.0 (m, 4H), 2.89 (s, 3H), 3.02 (q, J=7.5, 2H), 3.3-3.5 (m, 2H), 3.87 (s, 2H), 4.06-4.24 (m, 4H), 4.28 (s, 2H), 4.80 (dt, J=3.9, 15, 2H), 6.47 (tt, J=3.9, 55, 1H), 7.05-7.16 (m, 2H), 7.13 (s, 1H), 7.27-7.31 (m, 1H), 7.43 (s, 1H), 8.30 (t, J=5.6, 1H), 8.64 (brs, 2H).

Example 279

N$^2$-[1-(2,2-difluoroethyl)-3-ethyl-5-methyl-1H-indazol-6-yl]-N$^2$-{2-[(5-fluoro-1,3-dihydro-2H-isoindol-2-yl)(methyl)amino]-2-oxoethyl}-N$^1$-[2-(ethylamino)ethyl]glycinamide hydrochloride Using the compound (178 mg, 0.501 mmol) of Reference Example 144, the compound (106 mg, 0.523 mmol) of Reference Example 19 and the compound (114 mg, 0.606 mmol) of Reference Example 2, and according to the methods of Example 204, step A, and Example 57, step B, the title compound (124 mg, yield 41%) was obtained as a yellow-bistered solid.

$^1$H-NMR (400 MHz, DMSO-d$_6$); δ (ppm) 1.13 (t, J=7.2, 3H), 1.27 (t, J=7.6, 3H), 2.36 (s, 3H), 2.8-3.0 (m, 4H), 2.84 (q, J=7.6, 2H), 2.87 (s, 3H), 3.34-3.41 (m, 2H), 3.90 (s, 2H), 4.04-4.26 (m, 4H), 4.31 (s, 2H), 4.70 (dt, J=3.6, 15, 2H), 6.33 (tt, J=3.6, 55, 1H), 7.04-7.14 (m, 2H), 7.24-7.30 (m, 1H), 7.33 (s, 1H), 7.47 (s, 1H), 8.35 (t, J=5.6, 1H), 8.67 (brs, 2H).

Example 280

N$^2$-[1-(2,2-difluoroethyl)-7-methyl-2-oxo-1,2,3,4-tetrahydroquinolin-6-yl]-N$^2$-{2-[1,3-dihydro-2H-isoindol-2-yl(methyl)amino]-2-oxoethyl}-N$^1$-[2-(ethylamino)ethyl]glycinamide dihydrochloride Using the compound (391 mg, 1.10 mmol) of Reference Example 145, the compound (207 mg, 1.12 mmol) of Reference Example 17 and the compound (227 mg, 1.21 mmol) of Reference Example 2, and according to the methods of Example 204, step A, and Example 205, step B, the title compound (536 mg, yield 77%) was obtained as a colorless solid.

$^1$H-NMR (400 MHz, DMSO-d$_6$); δ (ppm) 1.16 (t, J=7.2, 3H), 2.27 (s, 3H), 2.50-2.56 (m, 2H), 2.74-2.79 (m, 2H), 2.8-3.0 (m, 4H), 2.88 (s, 3H), 3.34-3.42 (m, 2H), 3.81 (s, 2H), 4.08 (d, J=11.4, 2H), 4.23 (s, 2H), 4.24 (d, J=11.4, 2H), 4.31 (dt, J=4.1, 15, 2H), 6.20 (tt, J=4.1, 56, 1H), 7.02 (s, 1H), 7.08 (s, 1H), 7.23-7.29 (m, 4H), 8.40 (t, J=5.7, 1H), 8.82 (brs, 2H).

Example 281

N$^2$-[1-(2,2-difluoroethyl)-7-methyl-2-oxo-1,2,3,4-tetrahydroquinolin-6-yl]-N$^2$-{2-[(5-fluoro-1,3-dihydro-2H-isoindol-2-yl)(methyl)amino]-2-oxoethyl}-N$^1$-[2-(ethylamino)ethyl]glycinamide dihydrochloride Using the compound (395 mg, 1.11 mmol) of Reference Example 145, the compound (228 mg, 1.13 mmol) of Reference Example 19 and the compound (229 mg, 1.22 mmol) of Reference Example 2, and according to the methods of Example 204, step A, and Example 205, step B, the title compound (549 mg, yield 76%) was obtained as a colorless solid.

$^1$H-NMR (400 MHz, DMSO-d$_6$); δ (ppm) 1.16 (t, J=7.2, 3H), 2.27 (s, 3H), 2.50-2.57 (m, 2H), 2.74-2.79 (m, 2H), 2.8-3.0 (m, 4H), 2.87 (s, 3H), 3.34-3.42 (m, 2H), 3.81 (s, 2H), 4.03-4.28 (m, 4H), 4.21 (s, 2H), 4.31 (dt, J=4.1, 14, 2H), 6.20 (tt, J=4.1, 56, 1H), 7.02 (s, 1H), 7.05-7.16 (m, 2H), 7.07 (s, 1H), 7.27-7.32 (m, 1H), 8.38 (t, J=5.8, 1H), 8.75 (brs, 2H).

Example 282

N$^2$-[2-(2,2-difluoroethyl)-6-methyl-3-oxo-2,3-dihydro-1H-isoindol-5-yl]-N$^2$-{2-[1,3-dihydro-2H-isoindol-2-yl(methyl)amino]-2-oxoethyl}-N$^1$-[2-(ethylamino)ethyl]glycinamide dihydrochloride Using the compound (297 mg, 0.868 mmol) of Reference Example 146, the compound (163 mg, 0.883 mmol) of Reference Example 17 and the compound (180 mg, 0.956 mmol) of Reference Example 2, and according to the methods of Example 204, step A, and Example 205, step B, the title compound (453 mg, yield 85%) was obtained as a colorless solid.

$^1$H-NMR (400 MHz, DMSO-d$_6$); δ (ppm) 1.14 (t, J=7.2, 3H), 2.37 (s, 3H), 2.8-3.0 (m, 4H), 2.87 (s, 3H), 3.32-3.40 (m, 2H), 3.90 (s, 2H), 3.93 (dt, J=3.5, 16, 2H), 4.10 (d, J=11.4, 2H), 4.25 (d, J=11.4, 2H), 4.31 (s, 2H), 4.46 (s, 2H), 6.27 (tt, J=3.5, 15, 1H), 7.24-7.28 (m, 4H), 7.36 (s, 1H), 7.47 (s, 1H), 8.28 (t, J=5.8, 1H), 8.64 (brs, 2H).

Example 283

N$^2$-[2-(2,2-difluoroethyl)-6-methyl-3-oxo-2,3-dihydro-1H-isoindol-5-yl]-N$^2$-{2-[(5-fluoro-1,3-dihydro-2H-isoindol-2-yl)(methyl)amino]-2-oxoethyl}-N$^1$-[2-(ethylamino)ethyl]glycinamide dihydrochloride Using the compound (306 mg, 0.894 mmol) of Reference Example 146, the compound (190 mg, 0.938 mmol) of Reference Example 19 and the compound (213 mg, 1.13 mmol) of Reference Example 2, and according to the methods of Example 204, step A, and Example 205, step B, the title compound (426 mg, yield 75%) was obtained as a colorless solid.

$^1$H-NMR (400 MHz, DMSO-d$_6$); δ (ppm) 1.14 (t, J=7.2, 3H), 2.37 (s, 3H), 2.8-3.0 (m, 4H), 2.86 (s, 3H), 3.90 (s, 2H), 3.93 (dt, J=3.6, 16, 2H), 4.04-4.27 (m, 4H), 4.30 (s, 2H), 4.46 (s, 2H), 6.27 (tt, J=3.6, 55, 1H), 7.05-7.16 (m, 2H), 7.27-7.32 (m, 1H), 7.36 (s, 1H), 7.47 (s, 1H), 8.27 (t, J=5.7, 1H), 8.57 (brs, 2H).

Example 284

N$^2$-{2-[1,3-dihydro-2H-isoindol-2-yl(methyl)amino]-2-oxoethyl}-N$^2$-(2-ethyl-6-methyl-3-oxo-2,3-dihydro-1H-isoindol-5-yl)-N$^1$-[2-(ethylamino)ethyl]glycinamide dihydrochloride Using the compound (237 mg, 0.774 mmol) of Reference Example 147, the compound (145 mg, 0.785 mmol) of Reference Example 17 and the compound (161 mg, 0.855 mmol) of Reference Example 2, and according to the methods of Example 204, step A, and Example 205, step B, the title compound (366 mg, yield 82%) was obtained as a colorless solid.

$^1$H-NMR (400 MHz, DMSO-d$_6$); δ (ppm) 1.12-1.17 (m, 6H), 2.36 (s, 3H), 2.8-3.0 (m, 4H), 2.87 (s, 3H), 3.32-3.39 (m, 2H), 3.50 (q, J=7.2, 2H), 3.89 (s, 2H), 4.10 (d, J=11.4, 2H), 4.25 (d, J=11.4, 2H), 4.30 (s, 2H), 4.34 (s, 2H), 7.23-7.29 (m, 4H), 7.32 (s, 1H), 7.43 (s, 1H), 8.29 (t, J=5.7, 1H), 8.65 (brs, 2H).

Example 285

N$^2$-(2-ethyl-6-methyl-3-oxo-2,3-dihydro-1H-isoindol-5-yl)-N$^2$-{2-[(5-fluoro-1,3-dihydro-2H-isoindol-2-yl)(methyl)amino]-2-oxoethyl}-N$^1$-[2-(ethylamino)ethyl]glycinamide dihydrochloride Using the compound (251 mg, 0.819 mmol) of Reference Example 147, the compound (171 mg, 0.844 mmol) of Reference Example 19 and the compound (201 mg, 1.07 mmol) of Reference Example 2, and according to the methods of Example 204, step A, and Example 205, step B, the title compound (350 mg, yield 72%) was obtained as a colorless solid.

$^1$H-NMR (400 MHz, DMSO-d$_6$); δ (ppm) 1.11-1.17 (m, 6H), 2.36 (s, 3H), 2.8-3.0 (m, 4H), 2.86 (s, 3H), 3.32-3.40 (m, 2H), 3.50 (q, J=7.2, 2H), 3.89 (s, 2H), 4.04-4.26 (m, 4H), 4.29 (s, 2H), 4.34 (s, 2H), 7.05-7.16 (m, 2H), 7.27-7.33 (m, 1H), 7.32 (s, 1H), 7.43 (s, 1H), 8.28 (t, J=5.7, 1H), 8.63 (brs, 2H).

Example 286

N$^2$-{5-[5-(difluoromethyl)-1,2,4-oxadiazol-3-yl]-2-methylphenyl}-N$^2$-{2-[1,3-dihydro-2H-isoindol-2-yl(methyl)amino]-2-oxoethyl}-N$^1$-[2-(ethylamino)ethyl]glycinamide dihydrochloride Step A N$^2$-{5-[amino(hydroxyimino)methyl]-2-methylphenyl}-N$^2$-{2-[1,3-dihydro-2H-isoindol-2-yl(methyl)amino]-2-oxoethyl}-N$^1$-{2-[(tert-butoxycarbonyl)(ethyl)amino]ethyl}glycinamide To ethanol (20 ml) were added the compound (1.10 g, 2.00 mmol) of Example 2, step A, sodium acetate (347 mg, 4.23 mmol) and hydroxylammonium chloride (292 mg, 4.20 mmol) and the mixture was heated under reflux for 210 min. The reaction mixture was cooled, diluted with an ethyl acetate-hexane=1:1 mixed solvent, washed with saturated aqueous sodium hydrogen carbonate and saturated brine, and dried over anhydrous magnesium sulfate. The insoluble material was filtered off, and the solution was concentrated under reduced pressure to give a colorless amorphous solid (1.19 g).

$^1$H-NMR (400 MHz, CDCl$_3$); δ (ppm) 1.03 (t, J=7.1, 3H), 1.40 (brs, 9H), 1.80 (brs, 1H), 2.33 (s, 3H), 2.94 (s, 3H), 3.05-3.20 (m, 2H), 3.20-3.35 (m, 2H), 3.37-3.43 (m, 2H), 3.81 (s, 2H), 4.12 (d, J=11.4, 2H), 4.20 (s, 2H), 4.22 (d, J=11.4, 2H), 4.95 (brs, 2H), 7.16-7.28 (m, 6H), 7.56 (brs, 1H), 8.36 8.59 (2brs, 1H).

Step B

N$^2$-{5-[5-(difluoromethyl)-1,2,4-oxadiazol-3-yl]-2-methylphenyl}-N$^2$-{2-[1,3-dihydro-2H-isoindol-2-yl(methyl)amino]-2-oxoethyl}-N$^1$-{2-[(tert-butoxycarbonyl)(ethyl)amino]ethyl}glycinamide The compound (406 mg, 0.698 mmol) of step A, difluoroacetic acid (0.12 ml, 1.90 mmol) and WSC (530 mg, 2.76 mmol) were dissolved in 1,4-dioxane (5 ml) and the mixture was heated under reflux for 5 hr. The reaction mixture was diluted with an ethyl acetate-hexane=1:1 mixed solvent, and the organic layer was washed with water, 10% aqueous citric acid solution, diluted aqueous sodium hydroxide solution and saturated brine, and dried over anhydrous magnesium sulfate. The insoluble material was filtered off, and the residue was purified by silica gel column chromatography (ethyl acetate-hexane→ethyl acetate-methanol) to give the title compound (97 mg, yield 22%) as a pale-yellow amorphous solid $^1$H-NMR (400 MHz, CDCl$_3$); δ (ppm) 1.05 (t, J=7.0, 3H), 1.43 (brs, 9H), 2.41 (s, 3H), 2.95 (s, 3H), 3.10-3.25 (m, 2H), 3.25-3.40 (m, 2H), 3.41-3.47 (m, 2H), 3.83 (s, 2H), 4.18 (d, J=11.4, 2H), 4.25 (d, J=11.4, 2H), 4.30 (s, 2H), 6.84 (t, J=52, 1H), 7.19-7.32 (m, 5H), 7.72 (d, J=7.5, 1H), 7.96 (d, J=1.5, 1H), 8.33 8.60 (2brs, 1H).

Step C

N$^2$-{5-[5-(difluoromethyl)-1,2,4-oxadiazol-3-yl]-2-methylphenyl}-N$^2$-{2-[1,3-dihydro-2H-isoindol-2-yl(methyl)amino]-2-oxoethyl}-N$^1$-[2-(ethylamino)ethyl]glycinamide dihydrochloride Using the compound (96 mg, 0.150 mmol) of step B, and according to the method of Example 1, step C, the title compound (86 mg, yield 93%) was obtained as a colorless solid.

$^1$H-NMR (400 MHz, DMSO-d$_6$); δ (ppm) 1.14 (t, J=7.2, 3H), 2.35 (s, 3H), 2.8-3.0 (m, 4H), 2.88 (s, 3H), 3.35-3.40 (m, 2H), 3.95 (s, 2H), 4.14 (d, J=11.5, 2H), 4.27 (d, J=11.5, 2H), 4.37 (s, 2H), 7.26 (brs, 4H), 7.33 (d, J=7.9, 1H), 7.55 (t, J=52, 1H), 7.57 (dd, J=1.4, 7.9, 1H), 7.78 (d, J=1.4, 1H), 8.33 (broad t, 1H), 8.68 (brs, 2H).

Example 287

N$^2$-{2-[1,3-dihydro-2H-isoindol-2-yl(methyl)amino]-2-oxoethyl}-N$^2$-{2-methyl-5-[5-(trifluoromethyl)-1,2,4-oxadiazol-3-yl]phenyl}-N$^1$-[2-(ethylamino)ethyl]glycinamide dihydrochloride Step A N$^2$-{2-[1,3-dihydro-2H-isoindol-2-yl(methyl)amino]-2-oxoethyl}-N$^2$-{2-methyl-5-[5-(trifluoromethyl)-1,2,4-oxadiazol-3-yl]phenyl}-N$^1$-{2-[(tert-butoxycarbonyl)(ethyl)amino]ethyl}glycinamide To N,N-dimethylformamide (5 ml) were added the compound (350 mg, 0.602 mmol) of Example 286, step A, triethylamine (0.12 ml, 0.86 mmol) and trifluoroacetic acid anhydride (0.090 ml, 0.64 mmol), and the mixture was stirred with heating at 100° C. for 90 min. The reaction mixture was cooled, and diluted with an ethyl acetate-hexane=1:1 mixed solvent. The organic layer was washed with water, 10% aqueous citric acid solution, saturated aqueous sodium hydrogen carbonate and saturated brine, and dried over anhydrous magnesium sulfate. The insoluble material was filtered off, and the residue was purified by silica gel column chromatography (ethyl acetate-hexane→ethyl acetate-methanol) to give the title compound (235 mg, yield 59%) as a pale-yellow amorphous solid $^1$H-NMR (400 MHz, CDCl$_3$); δ (ppm) 1.05 (t, J=7.0, 3H), 1.43 (brs, 9H), 2.42 (s, 3H), 2.96 (s, 3H), 3.10-3.25 (m, 2H), 3.25-3.35 (m, 2H), 3.41-3.47 (m, 2H), 3.83 (s, 2H), 4.19 (d, J=11.7, 2H), 4.26 (d, J=11.7, 2H), 4.32 (s, 2H), 7.19-7.28 (m, 4H), 7.31 (d, J=7.8, 1H), 7.72 (d, J=7.8, 1H), 7.94 (d, J=1.6, 1H), 8.30 8.60 (2brs, 1H).

Step B

N$^2$-{2-[1,3-dihydro-2H-isoindol-2-yl(methyl)amino]-2-oxoethyl}-N$^2$-{2-methyl-5-[5-(trifluoromethyl)-1,2,4-oxadiazol-3-yl]phenyl}-N$^1$-[2-(ethylamino)ethyl]glycinamide dihydrochloride Using the compound (233 mg, 0.353 mmol) of step B, and according to the method of Example 1, step C, the title compound (197 mg, yield 88%) was obtained as a colorless solid.

¹H-NMR (400 MHz, DMSO-d₆); δ (ppm) 1.15 (t, J=7.2, 3H), 2.36 (s, 3H), 2.8-3.0 (m, 4H), 2.88 (s, 3H), 3.35-3.40 (m, 2H), 3.96 (s, 2H), 4.14 (d, J=11.4, 2H), 4.27 (d, J=11.4, 2H), 4.37 (s, 2H), 7.26 (brs, 4H), 7.35 (d, J=7.8, 1H), 7.58 (dd, J=1.4, 7.8, 1H), 7.77 (d, J=1.4, 1H), 8.34 (t, J=6.0, 1H), 8.66 (brs, 2H).

Example 288

N²-{4-[5-(difluoromethyl)-1,2,4-oxadiazol-3-yl]-2-methylphenyl}-N²-{2-[1,3-dihydro-2H-isoindol-2-yl(methyl)amino]-2-oxoethyl}-N¹-[2-(ethylamino)ethyl]glycinamide dihydrochloride

Step A

N²-{4-[amino(hydroxyimino)methyl]-2-methylphenyl}-N²-{2-[1,3-dihydro-2H-isoindol-2-yl(methyl)amino]-2-oxoethyl}-N¹-{2-[(tert-butoxycarbonyl)(ethyl)amino]ethyl}glycinamide Using the compound (1.18 g, 2.15 mmol) of Example 62, step A, and according to the method of Example 286, step A, the title compound (1.30 g) was obtained as a colorless amorphous solid.

¹H-NMR (400 MHz, CDCl₃); δ (ppm) 1.01 (t, J=7.1, 3H), 1.42 (brs, 9H), 1.72 (brs, 1H), 2.33 (s, 3H), 2.95 (s, 3H), 3.09-3.13 (m, 2H), 3.15-3.30 (m, 2H), 3.35-3.41 (m, 2H), 3.86 (s, 2H), 4.15 (d, J=11.4, 2H), 4.21 (s, 2H), 4.25 (d, J=11.4, 2H), 4.82 (brs, 2H), 7.20-7.28 (m, 6H), 7.43 (s, 1H), 8.09 8.30 (2brs, 1H).

Step B

N²-{4-[5-(difluoromethyl)-1,2,4-oxadiazol-3-yl]-2-methylphenyl}-N²-{2-[1,3-dihydro-2H-isoindol-2-yl(methyl)amino]-2-oxoethyl}-N¹-[2-(ethylamino)ethyl]glycinamide dihydrochloride Using the compound (406 mg, 0.698 mmol) of step A, and according to the methods of Example 286, step B, and Example 1, step C, the title compound (78 mg, yield 18%) was obtained as a colorless solid.

¹H-NMR (400 MHz, DMSO-d₆); δ (ppm) 1.15 (t, J=7.2, 3H), 2.34 (s, 3H), 2.8-3.0 (m, 4H), 2.92 (s, 3H), 3.36-3.41 (m, 2H), 3.98 (s, 2H), 4.16 (d, J=11.5, 2H), 4.29 (d, J=11.5, 2H), 4.41 (s, 2H), 7.10 (d, J=8.4, 1H), 7.24-7.30 (m, 4H), 7.52 (t, J=52, 1H), 7.73 (dd, J=2.0, 8.4, 1H), 7.77 (d, J=2.0, 1H), 8.33 (broad t, 1H), 8.68 (brs, 2H).

The compounds of Examples 265-288 are shown below.

TABLE 18

| Example | Structural Formula | TMW | LC-MS (found) |
|---|---|---|---|
| 265 | | 564.07 | 528 |
| 266 | | 564.07 | 528 |

TABLE 18-continued

| Example | Structural Formula | TMW | LC-MS (found) |
|---|---|---|---|
| 267 | | 582.06 | 546 |
| 268 | | 582.06 | 546 |
| 269 | | 546.08 | 510 |
| 270 | | 560.11 | 524 |

TABLE 18-continued

| Example | Structural Formula | TMW | LC-MS (found) |
|---|---|---|---|
| 271 | | 560.11 | 524 |
| 272 | | 578.10 | 542 |
| 273 | | 596.09 | 560 |
| 274 | | 560.11 | 524 |

TABLE 18-continued

| Example | Structural Formula | TMW | LC-MS (found) |
|---|---|---|---|
| 275 | | 556.14 | 520 |
| 276 | | 574.13 | 538 |
| 277 | | 592.12 | 556 |
| 278 | | 610.11 | 574 |

TABLE 18-continued
| Example | Structural Formula | TMW | LC-MS (found) |
|---|---|---|---|
| 279 | 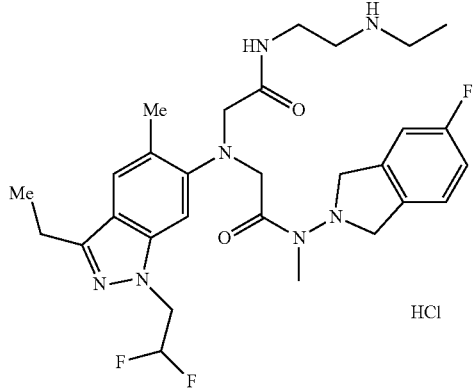 [SMILES: CCNCCNC(=O)CN(CC(=O)N(C)N1Cc2ccc(F)cc2C1)c1cc2c(cc1C)c(CC)nn2CC(F)F ; Cl] HCl | 610.11 | 574 |
| 280 | 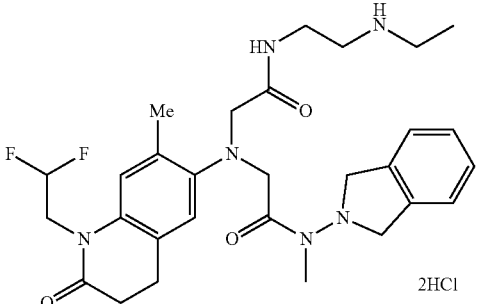 2HCl | 629.57 | 557 |
| 281 | 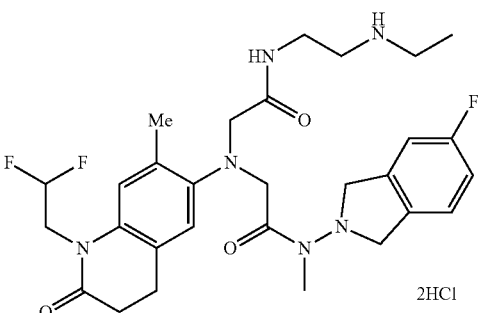 2HCl | 647.56 | 575 |
| 282 | 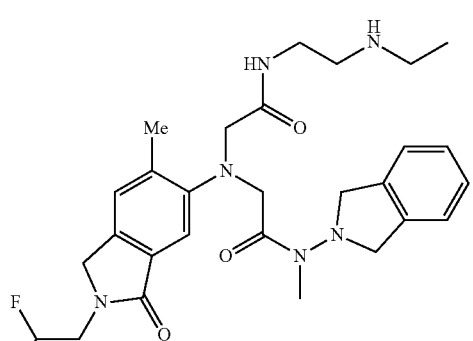 2HCl | 615.54 | 543 |

TABLE 18-continued

| Example | Structural Formula | TMW | LC-MS (found) |
|---|---|---|---|
| 283 | | 633.53 | 561 |
| 284 | | 579.56 | 507 |
| 285 | | 597.55 | 525 |
| 286 | | 614.51 | 542 |

TABLE 18-continued

| Example | Structural Formula | TMW | LC-MS (found) |
|---|---|---|---|
| 287 | | 632.51 | 560 |
| 288 | | 614.51 | 542 |

Example 289

N²-{2-[1,3-dihydro-2H-isoindol-2-yl(methyl)amino]-2-oxoethyl}-N²-{2-methyl-4-[5-(trifluoromethyl)-1,2,4-oxadiazol-3-yl]phenyl}-N¹-[2-(ethylamino)ethyl]glycinamide dihydrochloride Using the compound (355 mg, 0.610 mmol) of Example 288, step A, and according to the methods of Example 287, step A, and Example 1, step C, the title compound (83 mg, yield 22%) was obtained as a colorless solid.
¹H-NMR (400 MHz, DMSO-d₆); δ (ppm) 1.15 (t, J=7.2, 3H), 2.34 (s, 3H), 2.8-3.0 (m, 4H), 2.92 (s, 3H), 3.3-3.4 (m, 2H), 3.99 (s, 2H), 4.17 (d, J=11.6, 2H), 4.29 (d, J=11.6, 2H), 4.42 (s, 2H), 7.09 (d, J=8.4, 1H), 7.2-7.3 (m, 4H), 7.75 (d, J=8.4, 1H), 7.77 (s, 1H), 8.34 (t, J=5.7, 1H), 8.65 (brs, 2H).

Example 290

N²-{5-[5-(difluoromethyl)-1,2,4-oxadiazol-3-yl]-2-methylphenyl}-N²-{2-[(5-fluoro-1,3-dihydro-2H-isoindol-2-yl)(methyl)amino]-2-oxoethyl}-N¹-[2-(ethylamino)ethyl]glycinamide dihydrochloride Step A N²-(5-cyano-2-methylphenyl)-N²-{2-[(5-fluoro-1,3-dihydro-2H-isoindol-2-yl)(methyl)amino]-2-oxoethyl}-N¹-{2-[(tert-butoxycarbonyl)(ethyl)amino]ethyl}glycinamide Using the compound (534 mg, 2.15 mmol) of Reference Example 61, the compound (442 mg, 2.18 mmol) of Reference Example 19 and the compound (452 mg, 2.40 mmol) of Reference Example 2, and according to the method of Example 204, step A, the title compound (1.07 g, yield 88%) was obtained as a pale-yellow amorphous solid.

¹H-NMR (400 MHz, CDCl₃); δ (ppm) 1.05 (t, J=7.1, 3H), 1.41 (brs, 9H), 2.39 (s, 3H), 2.96 (s, 3H), 3.13-3.19 (m, 2H), 3.20-3.35 (m, 2H), 3.38-3.44 (m, 2H), 3.82 (s, 2H), 4.14-4.28 (m, 4H), 4.24 (s, 2H), 6.92-7.00 (m, 2H), 7.16-7.20 (m, 1H), 7.22-7.25 (m, 2H), 7.48 (s, 1H), 8.02 8.36 (2brs, 1H).

Step B

N²-{5-[amino(hydroxyimino)methyl]-2-methylphenyl}-N²-{2-[(5-fluoro-1,3-dihydro-2H-isoindol-2-yl)(methyl)amino]-2-oxoethyl}-N¹-{2-[(tert-butoxycarbonyl)(ethyl)amino]ethyl}glycinamide Using the compound (1.04 g, 1.84 mmol) of step A, and according to the method of Example 286, step A, the title compound (1.08 g, yield 98%) was obtained as a colorless amorphous solid.

¹H-NMR (400 MHz, CDCl₃); δ (ppm) 1.04 (t, J=7.1, 3H), 1.40 (brs, 9H), 1.75 (brs, 1H), 2.33 (s, 3H), 2.94 (s, 3H), 3.1-3.2 (m, 2H), 3.2-3.3 (m, 2H), 3.38-3.43 (m, 2H), 3.80 (s, 2H), 4.06-4.23 (m, 4H), 4.19 (s, 2H), 4.95 (brs, 2H), 6.90-6.98 (m, 2H), 7.13-7.19 (m, 2H), 7.24-7.26 (m, 1H), 7.56 (brs, 1H), 8.34 8.57 (2brs, 1H).

Step C

N²-{5-[5-(difluoromethyl)-1,2,4-oxadiazol-3-yl]-2-methylphenyl}-N²-{2-[(5-fluoro-1,3-dihydro-2H-isoindol-2-yl)(methyl)amino]-2-oxoethyl}-N¹-{2-[(tert-butoxycarbonyl)(ethyl)amino]ethyl}glycinamide Using the compound (1.06 g, 1.77 mmol) of step B, difluoroacetic anhydride (463 mg, 2.66 mmol), and according to the method of Example 287, step A, the title compound (838 mg, yield 72%) was obtained as a colorless amorphous solid.
¹H-NMR (400 MHz, CDCl₃); δ (ppm) 1.05 (t, J=7.1, 3H), 1.43 (brs, 9H), 2.41 (s, 3H), 2.95 (s, 3H), 3.10-3.25 (m, 2H), 3.25-3.35 (m, 2H), 3.41-3.47 (m, 2H), 3.82 (s, 2H), 4.12-4.26 (m, 4H), 4.30 (s, 2H), 6.85 (t, J=52, 1H), 6.90-6.98 (m, 2H), 7.13-7.18 (m, 1H), 7.30 (d, J=7.9, 1H), 7.72 (d, J=7.5, 1H), 7.95 (d, J=1.4, 1H), 8.30 8.58 (2brs, 1H).

Step D

N²-{5-[5-(difluoromethyl)-1,2,4-oxadiazol-3-yl]-2-methylphenyl}-N²-{2-[(5-fluoro-1,3-dihydro-2H-isoindol-2-yl)(methyl)amino]-2-oxoethyl}-N¹-[2-(ethylamino)ethyl]glycinamide dihydrochloride Using the compound (821 mg, 1.24 mmol) of step C, and according to the method of Example 205, step B, the title compound (670 mg, yield 85%) was obtained as a colorless solid.
¹H-NMR (400 MHz, DMSO-d₆); δ (ppm) 1.15 (t, J=7.2, 3H), 2.35 (s, 3H), 2.8-3.0 (m, 4H), 2.88 (s, 3H), 3.35-3.40 (m, 2H), 3.95 (s, 2H), 4.08-4.29 (m, 4H), 4.36 (s, 2H), 7.05-7.16 (m, 2H), 7.28-7.32 (m, 1H), 7.33 (d, J=8.0, 1H), 7.55 (t, J=52, 1H), 7.57 (dd, J=1.6, 8.0, 1H), 7.78 (d, J=1.6, 1H), 8.34 (t, J=5.8, 1H), 8.75 (brs, 2H).

Example 291

N²-{4-[5-(difluoromethyl)-1,2,4-oxadiazol-3-yl]-2-methylphenyl}-N²-{2-[(5-fluoro-1,3-dihydro-2H-isoindol-2-yl)(methyl)amino]-2-oxoethyl}-N¹-[2-(ethylamino)ethyl]glycinamide dihydrochloride Step A N²-(4-cyano-2-methylphenyl)-N²-{2-[(5-fluoro-1,3-dihydro-2H-isoindol-2-yl)(methyl)amino]-2-oxoethyl}-N¹-{2-[(tert-butoxycarbonyl)(ethyl)amino]ethyl}glycinamide Using the compound (524 mg, 2.11 mmol) of Reference Example 68, the compound (434 mg, 2.14 mmol) of Reference Example 19 and the compound (445 mg, 2.36 mmol) of Reference Example 2, and according to the method of Example 204, step A, the title compound (1.04 g, yield 87%) was obtained as a pale-yellow solid.
¹H-NMR (400 MHz, CDCl₃); δ (ppm) 1.01 (t, J=7.1, 3H), 1.39 (brs, 9H), 2.33 (s, 3H), 2.98 (s, 3H), 3.06-3.12 (m, 2H), 3.15-3.30 (m, 2H), 3.34-3.40 (m, 2H), 3.92 (s, 2H), 4.09-4.26 (m, 4H), 4.29 (s, 2H), 6.92-7.00 (m, 2H), 7.14-7.20 (m, 2H), 7.39 (d, J=1.8, 1H), 7.41 (s, 1H), 7.87 8.08 (2brs, 1H).

Step B

N²-{4-[5-(difluoromethyl)-1,2,4-oxadiazol-3-yl]-2-methylphenyl}-N²-{2-[(5-fluoro-1,3-dihydro-2H-isoindol-2-yl)(methyl)amino]-2-oxoethyl}-N¹-[2-(ethylamino)ethyl]glycinamide dihydrochloride Using the compound (982 mg, 1.73 mmol) of step A, and according to the methods of Example 286, step A, Example 290, step C, and Example 205, step B, the title compound (451 mg, yield 41%) was obtained as a colorless solid.
¹H-NMR (400 MHz, DMSO-d₆); δ (ppm) 1.15 (t, J=7.2, 3H), 2.34 (s, 3H), 2.8-3.0 (m, 4H), 2.91 (s, 3H), 3.35-3.41 (m, 2H), 3.97 (s, 2H), 4.12-4.31 (m, 4H), 4.40 (s, 2H), 7.05-7.11 (m, 1H), 7.10 (d, J=8.6, 1H), 7.14-7.18 (m, 1H), 7.29-7.33 (m, 1H), 7.52 (t, J=52, 1H), 7.73 (dd, J=1.8, 8.6, 1H), 7.76 (d, J=1.8, 1H), 8.33 (t, J=5.8, 1H), 8.72 (brs, 2H).

Example 292

N²-{2-[(5-fluoro-1,3-dihydro-2H-isoindol-2-yl)(methyl)amino]-2-oxoethyl}-N²-{5-[5-(hydroxymethyl)-1,2,4-oxadiazol-3-yl]-2-methylphenyl}-N¹-[2-(ethylamino)ethyl]glycinamide hydrochloride Step A N²-{5-[5-(chloromethyl)-1,2,4-oxadiazol-3-yl]-2-methylphenyl}-N²-{2-[(5-fluoro-1,3-dihydro-2H-isoindol-2-yl)(methyl)amino]-2-oxoethyl}-N¹-{2-[(tert-butoxycarbonyl)(ethyl)amino]ethyl}glycinamide The compound (4.82 g, 8.04 mmol) of Example 290, step B was dissolved in 1,4-dioxane (70 ml), magnesium oxide (355 mg, 8.81 mmol) and chloroacetyl chloride (0.67 ml, 8.42 mmol) were added at room temperature, and the mixture was stirred at 100° C. for 1 hr. After cooling to room temperature, the reaction mixture was diluted with ethyl acetate, and the organic layer was washed with saturated brine, and dried over anhydrous magnesium sulfate. The insoluble material was filtered off, and the solution was concentrated under reduced pressure. The obtained oil was purified by silica gel column chromatography (ethyl acetate-hexane) to give the title compound (3.40 g, yield 64%) as a pale-yellow amorphous solid
¹H-NMR (400 MHz, CDCl₃); δ (ppm) 1.05 (t, J=7.2, 3H), 1.43 (brs, 9H), 2.40 (s, 3H), 2.95 (s, 3H), 3.10-3.24 (m, 2H), 3.24-3.36 (m, 2H), 3.41-3.47 (m, 2H), 3.81 (s, 2H), 4.09-4.25 (m, 4H), 4.28 (s, 2H), 4.72 (s, 2H), 6.90-7.01 (m, 2H), 7.13-7.18 (m, 1H), 7.29 (d, J=7.7, 1H), 7.70 (d, J=8.2, 1H), 7.93 (s, 1H), 8.32 8.60 (2brs, 1H).

Step B

N²-[5-{5-[(acetoxy)methyl]-1,2,4-oxadiazol-3-yl}-2-methylphenyl]-N²-{2-[(5-fluoro-1,3-dihydro-2H-isoindol-2-yl)(methyl)amino]-2-oxoethyl}-N¹-{2-[(tert-butoxycarbonyl)(ethyl)amino]ethyl}glycinamide To N,N-dimethylformamide (40 ml) were added the compound (3.39 g, 5.15 mmol) of step A and sodium acetate (1.37 g, 16.7 mmol), and the mixture was stirred at 60° C. for 5 hr. After cooling to room temperature, ethyl acetate-hexane=1:1 mixed solvent and water were added to the reaction mixture, and the organic layer was extracted. The organic layer was washed with saturated brine, and dried over anhydrous magnesium sulfate. The insoluble material was filtered off, and the solution was concentrated under reduced pressure. The obtained oil was purified by silica gel column chromatography (ethyl acetate-hexane) to give the title compound (3.15 g, yield 90%) as a pale-yellow amorphous solid $^1$H-NMR (400 MHz, CDCl$_3$); δ (ppm) 1.05 (t, J=7.2, 3H), 1.43 (brs, 9H), 2.22 (s, 3H), 2.40 (s, 3H), 2.94 (s, 3H), 3.10-3.24 (m, 2H), 3.24-3.35 (m, 2H), 3.41-3.47 (m, 2H), 3.81 (s, 2H), 4.09-4.32 (m, 4H), 4.28 (s, 2H), 5.33 (s, 2H), 6.89-6.99 (m, 2H), 7.13-7.18 (m, 1H), 7.28 (d, J=8.2, 1H), 7.70 (d, J=7.7, 1H), 7.94 (s, 1H), 8.32 8.61 (2brs, 1H).

Step C

N$^2$-{2-[(5-fluoro-1,3-dihydro-2H-isoindol-2-yl)(methyl)amino]-2-oxoethyl}-N$^2$-{5-[5-(hydroxymethyl)-1,2,4-oxadiazol-3-yl]-2-methylphenyl}-N$^1$-[2-(ethylamino)ethyl]glycinamide hydrochloride The compound (535 mg, 0.785 mmol) of step B was dissolved in a 2N hydrochloric acid-ethanol solution (8 ml) at room temperature, and the mixture was stirred at the same temperature for 24 hr. To the reaction mixture was added diluted aqueous ammonia to alkalify the solution, and the organic layer was extracted with dichloromethane, and dried over sodium sulfate. The insoluble material was filtered off, and the solution was concentrated under reduced pressure. The obtained oil was purified by silica gel column chromatography (NH silica gel use, ethyl acetate-methanol) to give a colorless amorphous solid (363 mg). This was dissolved in ethanol (1 ml), and 2N hydrochloric acid-ethanol (0.34 ml) was added. To the solution was added diethyl ether, and the precipitated solid was filtered, washed with diethyl ether, and dried under reduced pressure to give the title compound (357 mg, yield 79%) as a colorless solid.

$^1$H-NMR (400 MHz, DMSO-d$_6$); δ (ppm) 1.14 (t, J=7.2, 3H), 2.34 (s, 3H), 2.8-3.0 (m, 4H), 2.88 (s, 3H), 3.30-3.41 (m, 2H), 3.93 (s, 2H), 4.09-4.29 (m, 4H), 4.34 (s, 2H), 4.79 (s, 2H), 6.09 (brs, 1H), 7.05-7.18 (m, 2H), 7.28-7.33 (m, 2H), 7.54 (d, J=9.2, 1H), 7.77 (s, 1H), 8.32 (t, J=5.7, 1H), 8.65 (brs, 2H).

Example 293

N$^2$-{2-[1,3-dihydro-2H-isoindol-2-yl(methyl)amino]-2-oxoethyl}-N$^2$-(2-methyl-4-pyrimidin-5-ylphenyl)-N$^1$-[2-(ethylamino)ethyl]glycinamide dihydrochloride Step A N$^2$-{2-[1,3-dihydro-2H-isoindol-2-yl(methyl)amino]-2-oxoethyl}-N$^2$-(4-iodo-2-methylphenyl)-N$^1$-{2-[(tert-butoxycarbonyl)(ethyl)amino]ethyl}glycinamide Using the compound (6.33 g, 18.1 mmol) of Reference Example 121, the compound (3.51 g, 19.0 mmol) of Reference Example 17 and the compound (3.47 g, 19.0 mmol) of Reference Example 2, and according to the method of Example 204, step A, the title compound (11.24 g, yield 96%) was obtained as a brown oil.

$^1$H-NMR (400 MHz, DMSO-d$_6$); δ (ppm) 0.94 (brs, 3H), 1.36 1.39 (2s, 11H), 2.20 (s, 3H), 2.87 (s, 3H), 3.02-3.15 (m, 4H), 3.76 (s, 2H), 4.08-4.26 (m, 6H), 6.87 (d, J=8.4, 1H), 7.23-7.28 (m, 4H), 7.35-7.38 (m, 1H), 7.43 (s, 1H).

Step B

N$^2$-{2-[1,3-dihydro-2H-isoindol-2-yl(methyl)amino]-2-oxoethyl}-N$^2$-(2-methyl-4-pyrimidin-5-ylphenyl)-N$^1$-[2-(ethylamino)ethyl]glycinamide dihydrochloride Using the compound (325 mg, 0.500 mmol) of step A and pyrimidine-5-boronic acid (74 mg, 0.600 mmol), and according to the methods of Example 255, step B, and Example 1, step C, the title compound (167 mg, yield 58%) was obtained as a yellow solid.

$^1$H-NMR (400 MHz, DMSO-d$_6$); δ (ppm) 1.16 (t, J=7.3, 3H), 2.35 (s, 3H), 2.87-2.90 (m, 2H), 3.36-3.41 (m, 3H), 3.84 (brs, 4H), 3.94 (s, 2H), 4.13-4.16 (m, 2H), 4.26-4.29 (m, 2H), 4.36 (s, 2H), 7.17 (d, J=8.4, 1H), 7.24-7.30 (m, 4H), 7.52-7.54 (m, 1H), 7.58 (s, 1H), 8.33-8.37 (m, 1H), 8.82 (brs, 2H), 9.09 (s, 2H), 9.12 (s, 1H).

Example 294

N$^2$-[4-(6-aminopyridin-3-yl)-2-methylphenyl]-N$^2$-{2-[1,3-dihydro-2H-isoindol-2-yl(methyl)amino]-2-oxoethyl}-N$^1$-[2-(ethylamino)ethyl]glycinamide trihydrochloride Using the compound (325 mg, 0.500 mmol) of Example 293, step A and 2-amino-5-(4,4,5,5-tetramethyl-1,3,2-dioxaborolan-2-yl)pyridine (132 mg, 0.600 mmol), and according to the methods of Example 255, step B, and Example 1, step C, the title compound (197 mg, yield 63%) was obtained as a brown solid.

$^1$H-NMR (400 MHz, DMSO-d$_6$); δ (ppm) 1.16 (t, J=7.2, 3H), 2.32 (s, 3H), 2.89 (brs, 3H), 3.90 (s, 2H), 4.11-4.14 (m, 2H), 4.26-4.32 (m, 4H), 7.07 (d, J=9.2, 1H), 7.14 (d, J=8.4, 1H), 7.24-7.29 (m, 4H), 7.35-7.38 (m, 1H), 7.42 (s, 1H), 8.07 (brs, 1H), 8.20-8.26 (m, 2H), 8.33-8.35 (m, 1H), 8.79 (brs, 2H).

Example 295

N$^2$-{2-[1,3-dihydro-2H-isoindol-2-yl(methyl)amino]-2-oxoethyl}-N$^2$-{4-[5-(methyloxycarbonyl)pyridin-2-yl]-2-methylphenyl}-N$^1$-[2-(ethylamino)ethyl]glycinamide dihydrochloride Step A N$^2$-{2-[1,3-dihydro-2H-isoindol-2-yl(methyl)amino]-2-oxoethyl}-N$^2$-[4-(5,5-dimethyl-1,3,2-dioxaborinan-2-yl)-2-methylphenyl]-N$^1$-{2-[(tert-butoxycarbonyl)(ethyl)amino]ethyl}glycinamide The compound (2.16 g, 3.33 mmol) of Example 293, step A, bis(neopentylglycolate)diboron (827 mg, 3.66 mmol), bis(tricyclohexylphosphine)palladium(II)dichloride (123 mg, 0.167 mmol) and potassium acetate (490 mg, 5.00 mmol) were dissolved in 1,4-dioxane (7 ml), and the mixture was heated under reflux for 5 hr. The reaction mixture was diluted with ethyl acetate, and the organic layer was washed with water and saturated brine, and dried over sodium sulfate. The insoluble material was filtered off, and the solution was concentrated under reduced pressure. The obtained oil was purified by silica gel column chromatography (ethyl acetate-hexane) to give the title compound (2.04 g, yield 97%) as a crude brown oil.

Step B

N²-{2-[1,3-dihydro-2H-isoindol-2-yl(methyl)amino]-2-oxoethyl}-N²-{4-[5-(methoxycarbonyl)pyridin-2-yl]-2-methylphenyl}-N¹-{2-[(tert-butoxycarbonyl)(ethyl)amino]ethyl}glycinamide The compound (510 mg, 0.802 mmol) obtained in step A, 6-bromonicotinic acid methyl ester (208 mg, 0.962 mmol), bis(tricyclohexylphosphine)palladium(II)dichloride (59 mg, 0.080 mmol) and 1.27 mol/l aqueous potassium phosphate solution (0.95 ml) were dissolved in 1,4-dioxane (4 ml), and the mixture was heated under reflux for 8 hr. The reaction mixture was diluted with ethyl acetate, and the organic layer was washed with water and saturated brine, and dried over sodium sulfate. The insoluble material was filtered off, and the solution was concentrated under reduced pressure. The obtained oil was purified by silica gel column chromatography (ethyl acetate-methanol) to give the title compound (375 mg, yield 71%) as a brown oil.

Step C

N²-{2-[1,3-dihydro-2H-isoindol-2-yl(methyl)amino]-2-oxoethyl}-N²-{4-[5-(methyloxycarbonyl)pyridin-2-yl]-2-methylphenyl}-N¹-[2-(ethylamino)ethyl]glycinamide dihydrochloride Using the compound (78 mg, 0.118 mmol) of step B, and according to the method of Example 1, step C, the title compound (25 mg, yield 33%) was obtained as a yellow solid.
¹H-NMR (400 MHz, DMSO-d₆); δ (ppm) 1.16 (t, J=7.3, 3H), 2.36 (s, 3H), 2.86-2.91 (m, 7H), 3.37-3.42 (m, 2H), 3.90 (s, 3H), 3.98-4.23 (m, 4H), 4.27-4.42 (m, 4H), 7.09 (d, J=8.6, 1H), 7.24-7.30 (m, 4H), 7.89-7.91 (m, 1H), 7.97 (s, 1H), 8.08 (d, J=8.4, 1H), 8.33-8.41 (m, 2H), 8.89 (brs, 2H), 9.08 (s, 1H).

Example 296

N²-{2-[1,3-dihydro-2H-isoindol-2-yl(methyl)amino]-2-oxoethyl}-N²-{4-[4-(ethoxycarbonyl)-1,3-thiazol-2-yl]-2-methylphenyl}-N¹-[2-(ethylamino)ethyl]glycinamide dihydrochloride Step A N²-{2-[1,3-dihydro-2H-isoindol-2-yl(methyl)amino]-2-oxoethyl}-N²-{4-[4-(ethoxycarbonyl)-1,3-thiazol-2-yl]-2-methylphenyl}-N¹-{2-[(tert-butoxycarbonyl)(ethyl)amino]ethyl}glycinamide Using the compound (510 mg, 0.802 mmol) of Example 295, step A and ethyl 2-bromothiazole-4-carboxylate (227 mg, 0.962 mmol), and according to the method of Example 295, step B, the title compound (282 mg, yield 52%) was obtained as a brown oil.

Step B

N²-{2-[1,3-dihydro-2H-isoindol-2-yl(methyl)amino]-2-oxoethyl}-N²-{4-[4-(ethoxycarbonyl)-1,3-thiazol-2-yl]-2-methylphenyl}-N¹-[2-(ethylamino)ethyl]glycinamide dihydrochloride Using the compound (36 mg, 0.053 mmol) of step A, and according to the method of Example 1, step C, the title compound (14 mg, yield 40%) was obtained as a yellow solid.
¹H-NMR (400 MHz, DMSO-d₆); δ (ppm) 1.16 (t, J=7.2, 3H), 1.33 (t, J=7.4, 3H), 2.34 (s, 3H), 2.87-2.91 (m, 7H), 3.37-3.41 (m, 2H), 3.91-3.96 (m, 2H), 4.14-4.17 (m, 2H), 4.27-4.39 (m, 6H), 7.07 (d, J=8.4, 1H), 7.24-7.30 (m, 4H), 7.64-7.71 (m, 2H), 8.36 (t, J=5.7, 1H), 8.47 (s, 1H), 8.81 (brs, 2H).

Example 297

N²-{2-[1,3-dihydro-2H-isoindol-2-yl(methyl)amino]-2-oxoethyl}-N²-[2-methyl-4-(6-oxo-1,6-dihydropyridazin-3-yl)phenyl]-N¹-[2-(ethylamino)ethyl]glycinamide Using the compound (510 mg, 0.802 mmol) of Example 295, step A and 3-chloro-6-methoxypyridazine (139 mg, 0.962 mmol), and according to the method of Example 295, step B, N²-{2-[1,3-dihydro-2H-isoindol-2-yl(methyl)amino]-2-oxoethyl}-N²-[4-(6-methoxypyridazin-3-yl)-2-methylphenyl]-N¹-{2-[(tert-butoxycarbonyl)(ethyl)amino]ethyl}glycinamide (250 mg) was obtained as a brown oil. Using this oil (210 mg, 0.332 mmol), and according to the method of Example 46, step B, the title compound (92 mg, yield 53%) was obtained as a pale-yellow solid.
¹H-NMR (400 MHz, DMSO-d₆); δ (ppm) 0.91 (t, J=7.1, 3H), 2.31 (s, 3H), 2.40-2.48 (m, 4H), 2.89 (s, 3H), 3.10-3.15 (m, 2H), 3.84 (s, 2H), 4.11-4.14 (m, 2H), 4.25-4.30 (m, 4H), 6.95 (d, J=9.7, 1H), 7.11 (d, J=8.5, 1H), 7.23-7.29 (m, 4H), 7.54-7.57 (m, 1H), 7.62 (s, 1H), 7.96-8.02 (m, 2H).

Example 298

N²-{2-[1,3-dihydro-2H-isoindol-2-yl(methyl)amino]-2-oxoethyl}-N²-[2-methyl-4-(2-oxopyrrolidin-1-yl)phenyl]-N¹-[2-(ethylamino)ethyl]glycinamide dihydrochloride Step A N²-{2-[1,3-dihydro-2H-isoindol-2-yl(methyl)amino]-2-oxoethyl}-N²-[2-methyl-4-(2-oxopyrrolidin-1-yl)phenyl]-N¹-{2-[(tert-butoxycarbonyl)(ethyl)amino]ethyl}glycinamide The compound (650 mg, 1.00 mmol) of Example 293, step A, 2-pyrrolidone (128 mg, 1.50 mmol), copper iodide(I) (19 mg, 0.10 mmol), N,N'-dimethylethylenediamine (0.022 ml, 0.20 mmol) and potassium phosphate (425 mg, 2.00 mmol) were dissolved in toluene (4.0 ml), and the mixture was heated under reflux for 7 hr. The reaction mixture was diluted with ethyl acetate and water, and the organic layer was extracted. The organic layer was washed with saturated brine and dried over sodium sulfate. The insoluble material was filtered off, and the solution was concentrated under reduced pressure. The obtained oil was purified by silica gel column chromatography (ethyl acetate-hexane) to give the title compound (542 mg, yield 89%) as a brown oil.

Step B

N²-{2-[1,3-dihydro-2H-isoindol-2-yl(methyl)amino]-2-oxoethyl}-N²-[2-methyl-4-(2-oxopyrrolidin-1-yl)phenyl]-N¹-[2-(ethylamino)ethyl]glycinamide dihydrochloride Using the compound (542 mg, 0.893 mmol) of step A, and according to the method of Example 1, step C, the title compound (391 mg, yield 40%) was obtained as a brown solid.

¹H-NMR (400 MHz, DMSO-d₆); δ (ppm) 1.16-1.19 (m, 3H), 2.01-2.07 (m, 2H), 2.29 (s, 3H), 2.45 (t, J=8.0, 2H), 2.87-2.92 (m, 9H), 3.32-3.41 (m, 2H), 3.86 (brs, 2H), 4.07-4.10 (m, 2H), 4.23-4.29 (m, 4H), 7.17 (d, J=8.7, 1H), 7.23-7.28 (m, 4H), 7.31-7.33 (m, 1H), 7.39 (s, 1H), 8.40 (t, J=5.7, 1H), 8.82 (brs, 3H).

Example 299

N²-{2-[1,3-dihydro-2H-isoindol-2-yl(methyl)amino]-2-oxoethyl}-N²-[2-methyl-4-(2-oxoimidazolidin-1-yl)phenyl]-N¹-[2-(ethylamino)ethyl]glycinamide dihydrochloride Using the compound (650 mg, 1.00 mmol) of Example 293, step A and ethyleneurea (129 mg, 1.50 mmol), and according to the methods of Example 298, step A, and Example 1, step C, the title compound (150 mg, yield 26%) was obtained as a pale-yellow solid.

¹H-NMR (400 MHz, DMSO-d₆); δ (ppm) 1.16 (t, J=7.1, 3H), 2.30 (s, 3H).
2.88-2.91 (m, 7H), 3.35-3.39 (m, 4H), 3.57 (s, 2H), 3.88 (s, 2H), 4.07-4.10 (m, 2H), 4.22-4.33 (m, 4H), 7.21-7.40 (m, 7H), 8.44-6.51 (m, 1H), 8.82 (brs, 2H).

Example 300

N²-{4-[4-(aminocarbonyl)-2-oxopyrrolidin-1-yl]-2-methylphenyl}-N²-{2-[1,3-dihydro-2H-isoindol-2-yl(methyl)amino]-2-oxoethyl}-N¹-[2-(ethylamino)ethyl]glycine amide 2 hydrochloride

Step A

N²-{2-[1,3-dihydro-2H-isoindol-2-yl(methyl)amino]-2-oxoethyl}-N²-{4-[4-(methoxycarbonyl)-2-oxopyrrolidin-1-yl]-2-methylphenyl}-N¹-{2-[(tert-butoxycarbonyl)(ethyl)amino]ethyl}glycinamide Using the compound (650 mg, 1.00 mmol) of Example 293, step A and methyl 5-oxopyrrolidine-3-carboxylate (215 mg, 1.50 mmol), and according to the method of Example 298, step A, the title compound (480 mg, yield 72%) was obtained as a brown oil (480 mg).

Step B

N²-{4-[4-(aminocarbonyl)-2-oxopyrrolidin-1-yl]-2-methylphenyl}-N²-{2-[1,3-dihydro-2H-isoindol-2-yl(methyl)amino]-2-oxoethyl}-N¹-{2-[(tert-butoxycarbonyl)(ethyl)amino]ethyl}glycinamide The compound (480 mg, 0.722 mmol) of step A was dissolved in a methanol (1.5 ml)-tetrahydrofuran (1.5 ml) mixed solvent. Then, 1N aqueous sodium hydroxide solution (3.0 ml) was added, and the mixture was stirred at room temperature for 1 hr. To the reaction mixture was added 10% aqueous citric acid solution, and the mixture was extracted with ethyl acetate. The organic layer was washed with saturated brine, and dried over sodium sulfate. The insoluble material was filtered off, and the solution was concentrated under reduced pressure to give a crude pale-yellow oil (497 mg). This oil was dissolved in N,N-dimethylformamide (7 ml), 3H-[1,2,3]triazolo[4,5-b]pyridin-3-ol (147 mg, 1.08 mmol) and WSC (208 mg, 1.08 mmol) were added at room temperature, and the mixture was stirred at the same temperature for 30 min. Then, to the reaction mixture was added 28% aqueous ammonia (0.72 ml), and the mixture was successively stirred at room temperature for 3 hr. The reaction mixture was diluted with ethyl acetate and water, and the organic layer was extracted. The organic layer was washed with saturated brine and dried over sodium sulfate. The insoluble material was filtered off, and the solution was concentrated under reduced pressure. The obtained oil was purified by silica gel column chromatography (ethyl acetate-hexane→ethyl acetate-methanol) to give the title compound (312 mg, yield 67%) as a colorless amorphous solid.

Step C

N²-{4-[4-(aminocarbonyl)-2-oxopyrrolidin-1-yl]-2-methylphenyl}-N²-{2-[1,3-dihydro-2H-isoindol-2-yl(methyl)amino]-2-oxoethyl}-N¹-[2-(ethylamino)ethyl]glycinamide dihydrochloride Using the compound (312 mg, 0.480 mmol) of step B, and according to the method of Example 1, step C, the title compound (274 mg, yield 92%) was obtained as a colorless solid.

¹H-NMR (400 MHz, DMSO-d₆); δ (ppm) 1.15 (t, J=7.0, 3H), 2.28 (s, 3H), 2.56-2.70 (m, 2H), 2.87 (brs, 7H), 3.17-3.18 (m, 1H), 3.36-3.40 (m, 2H), 3.55-3.57 (m, 2H), 3.79-3.85 (m, 2H), 4.06-4.09 (m, 2H), 4.22-4.26 (m, 4H), 7.11-7.16 (m, 2H), 7.25-7.32 (m, 5H), 7.38 (s, 1H), 7.61 (s, 1H), 8.36 (brs, 1H), 8.72 (brs, 2H).

Example 301

N²-{4-[5-(aminocarbonyl)pyridin-2-yl]-2-methylphenyl}-N²-{2-[1,3-dihydro-2H-isoindol-2-yl(methyl)amino]-2-oxoethyl}-N¹-[2-(ethylamino)ethyl]glycinamide dihydrochloride Using the compound (238 mg, 0.361 mmol) of Example 295, step B, and according to the methods of Example 300, step B, and Example 1, step C, the title compound (138 mg, yield 62%) was obtained as a yellow solid.

¹H-NMR (400 MHz, DMSO-d₆); δ (ppm) 1.17 (t, J=6.4, 3H), 2.36 (s, 3H), 2.87-2.93 (m, 7H), 3.36-3.42 (m, 2H), 3.98 (s, 2H), 4.15-4.18 (m, 2H), 4.28-4.31 (m, 2H), 4.41 (m, 2H), 7.09 (d, J=8.6, 1H), 7.24-7.30 (m, 4H), 7.69 (s, 1H), 7.87-7.90 (m, 1H), 7.95 (s, 1H), 8.10 (d, J=8.5, 1H), 8.29 (s, 1H), 8.37-8.41 (m, 2H), 8.81 (brs, 2H), 9.05 (s, 1H).

Example 302

N²-{4-[4-(aminocarbonyl)-1,3-thiazol-2-yl]-2-methylphenyl}-N²-{2-[1,3-dihydro-2H-isoindol-2-yl(methyl)amino]-2-oxoethyl}-N¹-[2-(ethylamino)ethyl]glycinamide dihydrochloride Using the compound (181 mg, 0.267 mmol) of Example 296, step A, and according to the methods of Example 300, step B, and Example 1, step C, the title compound (65 mg, yield 39%) was obtained as a colorless solid.

¹H-NMR (400 MHz, DMSO-d₆); δ (ppm) 1.15 (t, J=7.1, 3H), 2.34 (s, 3H), 2.87-2.91 (m, 7H), 3.36-3.41 (m, 2H), 3.96 (s, 2H), 4.14-4.17 (m, 2H), 4.27-4.30 (m, 2H), 4.38 (s, 2H), 7.06 (d, J=8.5, 1H), 7.24-7.30 (m, 4H), 7.65 (s, 2H), 7.69-7.72 (m, 2H), 7.78-7.84 (m, 2H), 8.17 (s, 1H), 8.35 (t, J=5.8, 1H), 8.75 (brs, 2H).

Example 303

N²-{4-[4-(aminocarbonyl)-1H-pyrazol-1-yl]-2-methylphenyl}-N²-{2-[1,3-dihydro-2H-isoindol-2-yl(methyl)amino]-2-oxoethyl}-N¹-[2-(ethylamino)ethyl] glycinamide dihydrochloride Using the compound (650 mg, 1.00 mmol) of Example 293, step A and ethyl 4-pyrazolecarboxylate (210 mg, 1.50 mmol), and according to the methods of Example 298, step A, Example 300, step B, and Example 1, step C, the title compound (79 mg, yield 13%) was obtained as a colorless solid.
¹H-NMR (400 MHz, DMSO-d₆); δ (ppm) 1.15 (t, J=7.1, 3H), 2.34 (s, 3H), 2.87-2.89 (m, 7H), 3.34-3.41 (m, 2H), 3.90 (s, 2H), 4.11-4.14 (m, 2H), 4.25-4.31 (m, 4H), 7.17-7.29 (m, 6H), 7.49-7.52 (m, 1H), 7.59 (s, 1H), 7.70 (brs, 1H), 8.07 (s, 1H), 8.33 (t, J=5.8, 1H), 8.76-8.79 (m, 3H).

Example 304

N²-{2-[1,3-dihydro-2H-isoindol-2-yl(methyl)amino]-2-oxoethyl}-N²-[4-{4-[(dimethylamino)carbonyl]-1,3-thiazol-2-yl}-2-methylphenyl]-N¹-[2-(ethylamino)ethyl]glycinamide dihydrochloride Using the compound (247 mg, 0.364 mmol) of Example 296, step A and 50% aqueous dimethylamine solution (0.36 ml), and according to the methods of Example 300, step B, and Example 1, step C, the title compound (111 mg, yield 47%) was obtained as a yellow solid.
¹H-NMR (400 MHz, DMSO-d₆); δ (ppm) 1.15 (t, J=7.3, 3H), 2.33 (s, 3H), 2.88-2.91 (m, 7H), 3.01 (s, 3H), 3.16 (s, 3H), 3.36-3.40 (m, 2H), 3.95 (s, 2H), 4.13-4.16 (m, 2H), 4.27-4.29 (m, 2H), 4.38 (s, 2H), 7.08 (d, J=8.5, 1H), 7.24-7.29 (m, 4H), 7.63-7.69 (m, 2H), 7.99 (s, 1H), 8.33 (t, J=5.8, 1H), 8.76 (brs, 2H).

Example 305

N²-{4-[5-(aminocarbonyl)-1,3-thiazol-2-yl]-2-methylphenyl}-N²-{2-[1,3-dihydro-2H-isoindol-2-yl(methyl)amino]-2-oxoethyl}-N¹-[2-(ethylamino)ethyl] glycinamide dihydrochloride

Step A

N²-{2-[1,3-dihydro-2H-isoindol-2-yl(methyl)amino]-2-oxoethyl}-N²-{4-[5-(ethoxycarbonyl)-1,3-thiazol-2-yl]-2-methylphenyl}-N¹-{2-[(tert-butoxycarbonyl)(ethyl)amino]ethyl}glycinamide Using the compound (1.69 g, 2.66 mmol) of Example 295, step A and ethyl 2-bromothiazole-5-carboxylate (754 mg, 3.19 mmol), and according to the method of Example 295, step B, the title compound (246 mg, yield 14%) was obtained.

Step B

N²-{4-[5-(aminocarbonyl)-1,3-thiazol-2-yl]-2-methylphenyl}-N²-{2-[1,3-dihydro-2H-isoindol-2-yl(methyl)amino]-2-oxoethyl}-N¹-[2-(ethylamino)ethyl] glycinamide dihydrochloride Using the compound (246 mg, 0.362 mmol) of step A, and according to the methods of Example 300, step B, and Example 1, step C, the title compound (202 mg, yield 90%) was obtained as a yellow solid.
¹H-NMR (400 MHz, DMSO-d₆); δ (ppm) 1.16 (t, J=7.2, 3H), 2.33 (s, 3H), 2.86-2.91 (m, 5H), 3.37-3.41 (m, 2H), 3.96 (s, 2H), 4.15-4.18 (m, 2H), 4.27-4.30 (m, 2H), 4.40 (s, 2H), 7.05 (d, J=8.5, 1H), 7.24-7.30 (m, 4H), 7.59-7.70 (m, 3H), 8.16 (brs, 1H), 8.34-8.38 (m, 2H), 8.87 (brs, 2H).

Example 306

N²-{2-[1,3-dihydro-2H-isoindol-2-yl(methyl)amino]-2-oxoethyl}-N²-[2-methyl-4-{5-[(methylamino)carbonyl]-1,3-thiazol-2-yl}phenyl]-N¹-[2-(ethylamino)ethyl]glycinamide dihydrochloride Using the compound (120 mg, 0.177 mmol) of Example 305, step A, and 50% aqueous methylamine solution (0.195 ml), and according to the methods of Example 300, step B, and Example 1, step C, the title compound (105 mg, yield 93%) was obtained as a yellow solid.
¹H-NMR (400 MHz, DMSO-d₆); δ (ppm) 1.16 (t, J=7.1, 3H), 2.32 (s, 3H), 2.78 (s, 3H), 2.88-2.91 (m, 7H), 3.37-3.41 (m, 2H), 3.96 (s, 2H), 4.15-4.17 (m, 2H), 4.27-4.30 (m, 2H), 4.39 (s, 2H), 7.04 (d, J=8.5, 1H), 7.24-7.30 (m, 4H), 7.64-7.67 (m, 1H), 7.70 (s, 1H), 8.35-8.37 (m, 2H), 8.70-8.73 (m, 1H), 8.88 (brs, 2H).

Example 307

N²-{2-[1,3-dihydro-2H-isoindol-2-yl(methyl)amino]-2-oxoethyl}-N²-[4-{5-[(dimethylamino)carbonyl]-1,3-thiazol-2-yl}-2-methylphenyl]-N¹-[2-(ethylamino)ethyl]glycinamide dihydrochloride Using the compound (120 mg, 0.177 mmol) of Example 305, step A and 50% aqueous dimethylamine solution (0.195 ml), and according to the methods of Example 300, step B, and Example 1, step C, the title compound (106 mg, yield 92%) was obtained as a yellow solid.
¹H-NMR (400 MHz, DMSO-d₆); δ (ppm) 1.16 (t, J=7.3, 3H), 2.33 (s, 3H), 2.88-2.91 (m, 7H), 3.38-3.41 (m, 2H), 3.96 (s, 2H), 4.15-4.18 (m, 2H), 4.27-4.30 (m, 2H), 4.40 (s, 2H), 7.05 (d, J=8.5, 1H), 7.24-7.30 (m, 4H), 7.66-7.71 (m, 2H), 8.17 (s, 1H), 8.36 (t, J=5.8, 1H), 8.90 (brs, 2H).

Example 308

N²-{4-[4-(aminocarbonyl)-1,3-thiazol-2-yl]-2-methylphenyl}-N²-{2-[(5-fluoro-1,3-dihydro-2H-isoindol-2-yl)(methyl)amino]-2-oxoethyl}-N¹-[2-(ethylamino)ethyl]glycinamide dihydrochloride

Step A

N²-[4-(5,5-dimethyl-1,3,2-dioxaborinan-2-yl)-2-methylphenyl]-N²-{2-[(5-fluoro-1,3-dihydro-2H-isoindol-2-yl)(methyl)amino]-2-oxoethyl}-N¹-{2-[(tert-butoxycarbonyl)(ethyl)amino]ethyl}glycinamide Using the compound (887 mg, 2.54 mmol) of Reference Example 121, the compound (520 mg, 2.57 mmol) of Reference Example 19 and the compound (526 mg, 2.79 mmol) of Reference Example 2, and according to the methods of Example 204, step A, and Example 295, step A, the title compound (1.24 g, yield 75%) was obtained as a brown oil.

Step B

N²-{4-[4-(aminocarbonyl)-1,3-thiazol-2-yl]-2-methylphenyl}-N²-{2-[(5-fluoro-1,3-dihydro-2H-isoindol-2-yl)(methyl)amino]-2-oxoethyl}-N¹-[2-(ethylamino)ethyl]glycinamide dihydrochloride Using the compound (611 mg, 0.935 mmol) of step A and ethyl 2-bromothiazole-4-carboxylate (265 mg, 1.12 mmol), and according to the methods of Example 295, step B, Example 300, step B, and Example 1, step C, the title compound (85 mg, yield 14%) was obtained as a yellow solid.

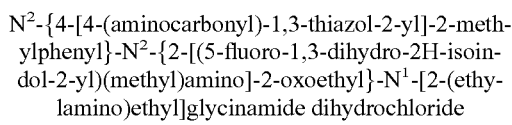

¹H-NMR (400 MHz, DMSO-d₆); δ (ppm) 1.16 (t, J=7.3, 3H), 2.34 (s, 3H), 2.89-2.90 (m, 7H), 3.37-3.41 (m, 2H), 3.96 (s, 2H), 4.12-4.30 (m, 4H), 4.38 (s, 2H), 7.05-7.11 (m, 2H), 7.15-7.17 (m, 1H), 7.29-7.33 (m, 1H), 7.65 (s, 1H), 7.69-7.72 (m, 1H), 7.78 (s, 1H), 7.83 (s, 1H), 8.18 (s, 1H), 8.35 (t, J=5.8, 1H), 8.85 (brs, 2H).

Example 309

N²-{4-[4-(aminocarbonyl)-1,3-oxazol-2-yl]-2-methylphenyl}-N²-{2-[1,3-dihydro-2H-isoindol-2-yl(methyl)amino]-2-oxoethyl}-N¹-[2-(ethylamino)ethyl]glycinamide dihydrochloride Using the compound (547 mg, 0.836 mmol) of Example 295, step A, and methyl 2-chlorooxazole-4-carboxylate (176 mg, 1.00 mmol), and according to the methods of Example 295, step B, Example 300, step B, and Example 1, step C, the title compound (208 mg, yield 41%) was obtained as a colorless solid.

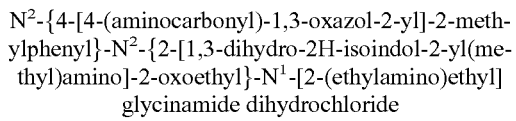

¹H-NMR (400 MHz, DMSO-d₆); δ (ppm) 1.16 (t, J=7.2, 3H), 2.33 (s, 3H), 2.88-2.91 (m, 7H), 3.37-3.41 (m, 2H), 3.96 (s, 2H), 4.15-4.17 (m, 2H), 4.27-4.30 (m, 2H), 4.40 (s, 2H), 7.09 (d, J=8.6, 1H), 7.24-7.30 (m, 4H), 7.54 (s, 1H), 7.64-7.70 (m, 2H), 7.75 (s, 1H), 8.36 (t, J=5.8, 1H), 8.59 (s, 1H), 8.87 (brs, 2H).

Example 310

N²-{4-[4-(aminocarbonyl)-1,3-oxazol-2-yl]-2-methylphenyl}-N²-{2-[(5-fluoro-1,3-dihydro-2H-isoindol-2-yl)(methyl)amino]-2-oxoethyl}-N¹-[2-(ethylamino)ethyl]glycinamide dihydrochloride Using the compound (559 mg, 0.855 mmol) of Example 308, step A and methyl-2-chlorooxazole-4-carboxylate (180 mg, 1.03 mmol), and according to the methods of Example 295, step B, Example 300, step B, and Example 1, step C, the title compound (223 mg, yield 42%) was obtained as a pale-yellow solid.

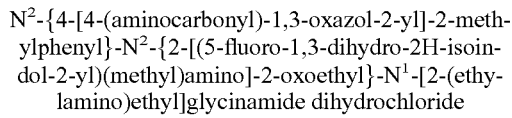

¹H-NMR (400 MHz, DMSO-d₆); δ (ppm) 1.16 (t, J=7.3, 3H), 2.33 (s, 3H), 2.89-2.91 (m, 7H), 3.36-3.41 (m, 2H), 3.96 (s, 2H), 4.12-4.30 (m, 6H), 7.06-7.11 (m, 2H), 7.15-7.17 (m, 1H), 7.29-7.33 (m, 1H), 7.54 (s, 1H), 7.64-7.74 (m, 2H), 7.75 (s, 1H), 8.34 (t, J=5.5, 1H), 8.59 (s, 1H), 8.83 (brs, 2H).

Example 311

N²-{2-[1,3-dihydro-2H-isoindol-2-yl(methyl)amino]-2-oxoethyl}-N²-(3,5-dimethyl-1,2-benzisoxazol-6-yl)-N¹-{2-[(2-fluoroethyl)amino]ethyl}glycinamide hydrochloride Step A N²-{2-[1,3-dihydro-2H-isoindol-2-yl(methyl)amino]-2-oxoethyl}-N²-(3,5-dimethyl-1,2-benzisoxazol-6-yl)-N¹-[2-{[(2-nitrophenyl)sulfonyl]amino}ethyl]glycinamide Using the compound (278 mg, 1.00 mmol) of Reference Example 117, the compound (186 mg, 1.01 mmol) of Reference Example 17 and N-(2-aminoethyl)-2-nitrobenzenesulfonamide (270 mg, 1.10 mmol), and according to the method of Example 204, step A, a yellow solid (557 mg, yield 88%) was obtained.

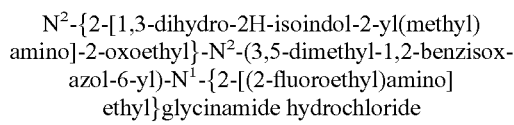

Step B

N²-{2-[1,3-dihydro-2H-isoindol-2-yl(methyl)amino]-2-oxoethyl}-N²-(3,5-dimethyl-1,2-benzisoxazol-6-yl)-N¹-[2-{(2-fluoroethyl)[(2-nitrophenyl)sulfonyl]amino}ethyl]glycinamide The compound (557 mg, 0.876 mmol) of step A, 2-fluoroethanol (84 mg, 1.31 mmol) and triphenylphosphine (345 mg, 1.31 mmol) were dissolved in tetrahydrofuran (4.4 ml), and the mixture was stirred at room temperature. Thereto was slowly added a 40% diisopropyl azodicarboxylate-toluene solution (0.70 ml), and the mixture was stirred at the same temperature for 12 hr. The reaction mixture was diluted with ethyl acetate, and the organic layer was washed with water and saturated brine, and dried over sodium sulfate. The insoluble material was filtered off, and the solution was concentrated under reduced pressure. The obtained oil was purified by silica gel column chromatography (ethyl acetate-hexane) to give the title compound (561 mg, yield 94%) as a yellow solid.

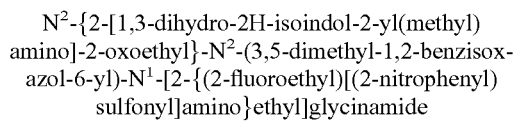

Step C

Example 312

N²-{2-[1,3-dihydro-2H-isoindol-2-yl(methyl)amino]-2-oxoethyl}-N²-(3,5-dimethyl-1,2-benzisoxazol-6-yl)-N¹-{2-[(2-fluoroethyl)amino]ethyl}glycinamide hydrochloride Using the compound (561 mg, 0.823 mmol) of step B, and according to the methods of Example 40, step E, and Example 57, step B, the title compound (304 mg, yield 69%) was obtained as a pale-yellow solid.

¹H-NMR (400 MHz, DMSO-d₆); δ (ppm) 2.35 (s, 3H), 2.45 (s, 3H), 2.90 (s, 3H), 3.24-3.39 (m, 2H), 3.40-3.42 (m, 2H), 3.96 (s, 4H), 4.12-4.15 (m, 2H), 4.26-4.29 (m, 2H), 4.38 (s, 2H), 4.64-4.78 (m, 2H), 7.22-7.28 (m, 5H), 7.52 (s, 1H), 8.30 (t, J=5.8, 1H), 9.08 (brs, 2H).

Example 312

N²-{2-[1,3-dihydro-2H-isoindol-2-yl(methyl)amino]-2-oxoethyl}-N²-(3,5-dimethyl-1,2-benzisoxazol-6-yl)-N¹-{2-[(2,2-difluoroethyl)amino]ethyl}glycinamide hydrochloride Using the compound (533 mg, 0.838 mmol) of Example 311, step A and 2,2-difluoroethanol (103 mg, 1.26 mmol), and according to the methods of Example 311, step B, Example 40, step E, and Example 57, step B, the title compound (53 mg, yield 11%) was obtained as a pale-yellow solid.

¹H-NMR (400 MHz, DMSO-d₆); δ (ppm) 2.35 (s, 3H), 2.45 (s, 3H), 2.90 (s, 3H), 3.04 (brs, 2H), 3.96 (s, 2H), 4.12-4.15 (m, 2H), 4.26-4.29 (m, 2H), 4.38 (s, 2H), 6.28-6.57 (m, 1H), 7.21-7.29 (m, 5H), 7.52 (s, 1H), 8.32 (t, J=5.8, 1H), 9.46 (brs, 2H).

The compounds of Examples 289-312 are shown below.

TABLE 19

| Example | Structural Formula | TMW | LC-MS (found) |
|---|---|---|---|
| 289 | 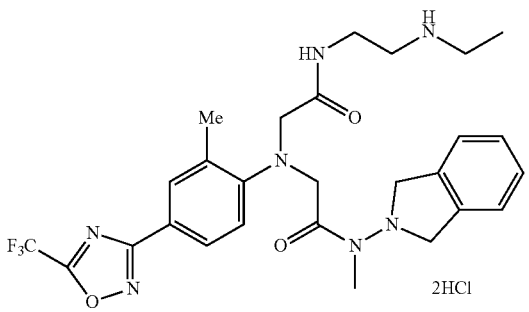 [SMILES: CCNCCNC(=O)CN(CC(=O)N(C)N1Cc2ccccc2C1)c1ccc(-c2noc(C(F)(F)F)n2)cc1C] | 632.51 | 560 |
| 290 | 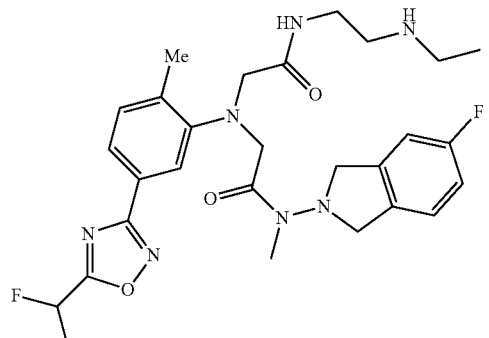 | 632.51 | 560 |
| 291 | 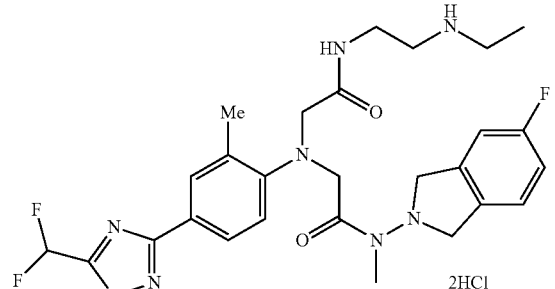 | 632.51 | 560 |

TABLE 19-continued
| Example | Structural Formula | TMW | LC-MS (found) |
|---|---|---|---|
| 292 | 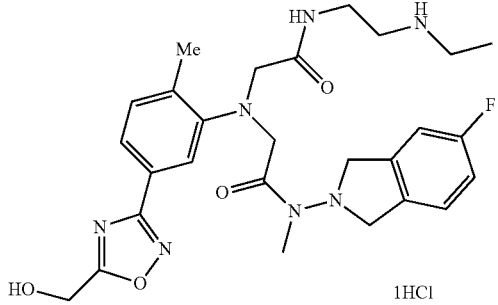 [SMILES: CCNCCNC(=O)CN(CC(=O)N(C)N1Cc2ccc(F)cc2C1)c1cc(-c2noc(CO)n2)ccc1C] 1HCl | 576.06 | 540 |
| 293 | 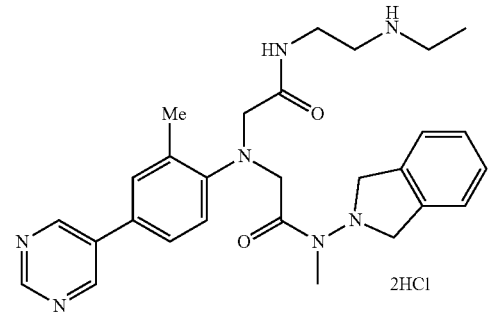 [SMILES: CCNCCNC(=O)CN(CC(=O)N(C)N1Cc2ccccc2C1)c1ccc(-c2cncnc2)cc1C] 2HCl | 574.55 | 502 |
| 294 | 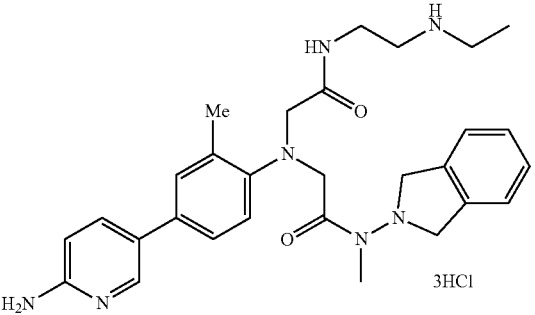 [SMILES: CCNCCNC(=O)CN(CC(=O)N(C)N1Cc2ccccc2C1)c1ccc(-c2ccc(N)nc2)cc1C] 3HCl | 625.03 | 516 |
| 295 | 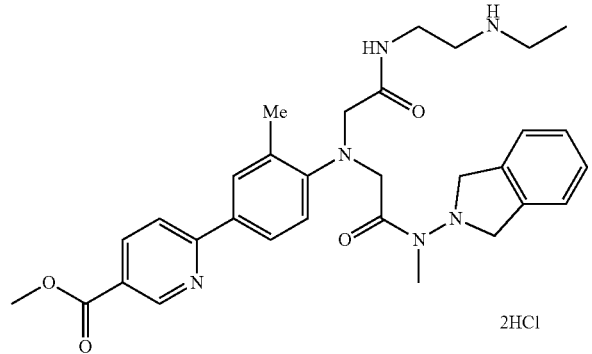 [SMILES: CCNCCNC(=O)CN(CC(=O)N(C)N1Cc2ccccc2C1)c1ccc(-c2ccc(C(=O)OC)cn2)cc1C] 2HCl | 631.59 | 559 |

TABLE 19-continued

| Example | Structural Formula | TMW | LC-MS (found) |
|---|---|---|---|
| 296 | (structure) 2HCl | 651.65 | 579 |
| 297 | (structure) | 517.62 | 518 |
| 298 | (structure) 2HCl | 579.56 | 507 |
| 299 | (structure) 2HCl | 580.55 | 508 |

TABLE 19-continued
| Example | Structural Formula | TMW | LC-MS (found) |
|---|---|---|---|
| 300 | 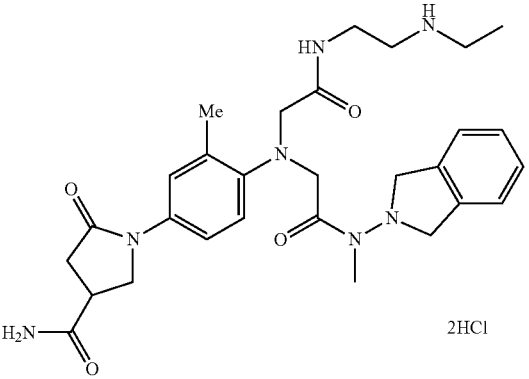 [SMILES: CCNCCNC(=O)CN(CC(=O)N(C)N1Cc2ccccc2C1)c1ccc(N2CC(C(N)=O)CC2=O)cc1C] 2HCl | 622.59 | 550 |
| 301 | 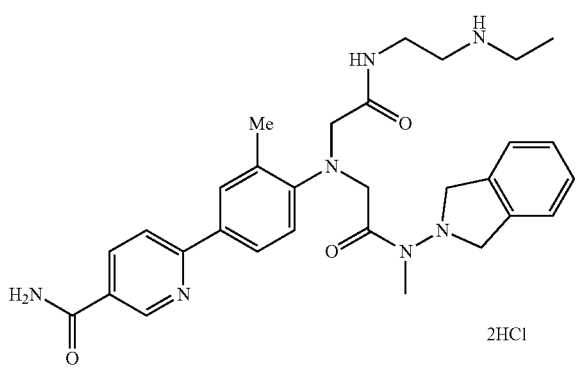 [SMILES: CCNCCNC(=O)CN(CC(=O)N(C)N1Cc2ccccc2C1)c1ccc(-c2ccc(C(N)=O)cn2)cc1C] 2HCl | 616.58 | 544 |
| 302 | 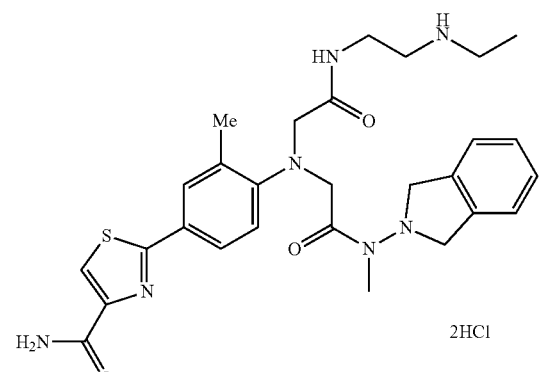 2HCl | 622.61 | 550 |
| 303 | 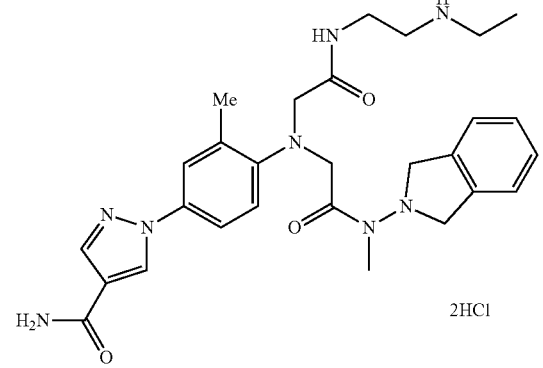 2HCl | 605.56 | 533 |

TABLE 19-continued
| Example | Structural Formula | TMW | LC-MS (found) |
|---|---|---|---|
| 304 | 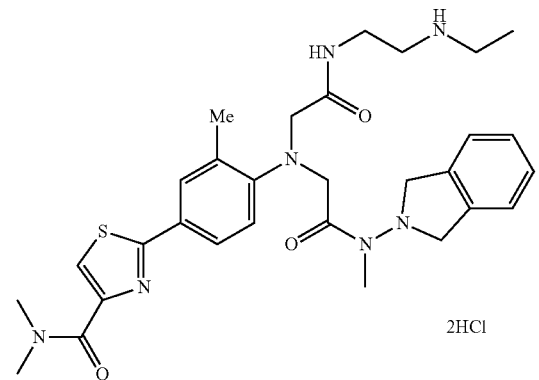 [SMILES: CCNCCNC(=O)CN(CC(=O)N(C)N1Cc2ccccc2C1)c1ccc(-c2nc(C(=O)N(C)C)cs2)cc1C] 2HCl | 650.66 | 578 |
| 305 | 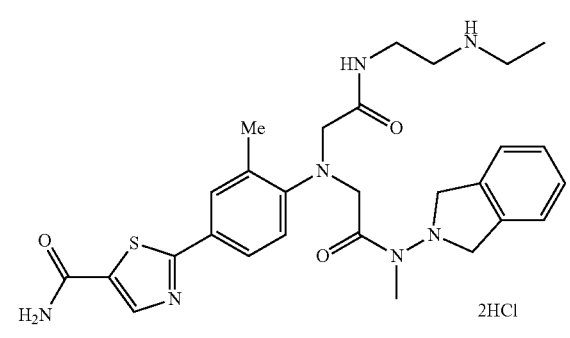 [SMILES: CCNCCNC(=O)CN(CC(=O)N(C)N1Cc2ccccc2C1)c1ccc(-c2ncc(C(N)=O)s2)cc1C] 2HCl | 622.61 | 550 |
| 306 | 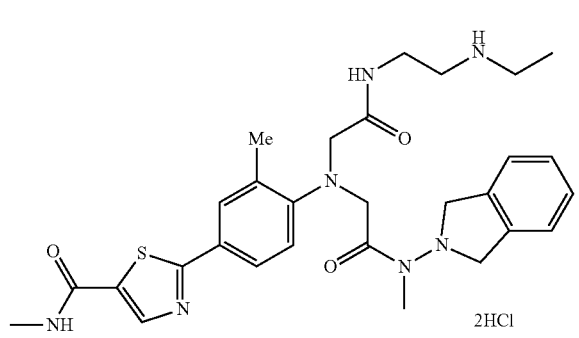 [SMILES: CCNCCNC(=O)CN(CC(=O)N(C)N1Cc2ccccc2C1)c1ccc(-c2ncc(C(=O)NC)s2)cc1C] 2HCl | 636.64 | 564 |
| 307 | 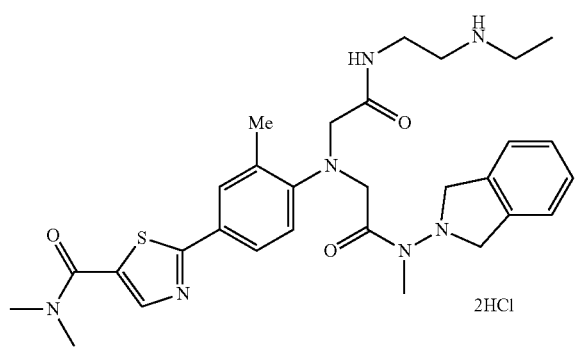 [SMILES: CCNCCNC(=O)CN(CC(=O)N(C)N1Cc2ccccc2C1)c1ccc(-c2ncc(C(=O)N(C)C)s2)cc1C] 2HCl | 650.66 | 578 |

TABLE 19-continued

| Example | Structural Formula | TMW | LC-MS (found) |
|---|---|---|---|
| 308 | 2HCl | 640.60 | 568 |
| 309 | 2HCl | 606.54 | 534 |
| 310 | 2HCl | 624.53 | 552 |
| 311 | 1HCl | 533.04 | 497 |

TABLE 19-continued

| Example | Structural Formula | TMW | LC-MS (found) |
|---|---|---|---|
| 312 | | 551.03 | 515 |

Example 313

N²-{2-[(5-fluoro-1,3-dihydro-2H-isoindol-2-yl)(methyl)amino]-2-oxoethyl}-N²-[2-methyl-5-(5-methyl-1,2,4-oxadiazol-3-yl)phenyl]-N¹-(2-aminoethyl)glycinamide hydrochloride Using the compound (963 mg, 3.15 mmol) of Reference Example 62, the compound (653 mg, 3.22 mmol) of Reference Example 19 and tert-butyl (2-aminoethyl)carbamate (635 mg, 3.96 mmol), and according to the methods of Example 204, step A, and Example 57, step B, the title compound (1.28 g, yield 76%) was obtained as a colorless solid.
$^1$H-NMR (400 MHz, DMSO-d$_6$); δ (ppm) 2.33 (s, 3H), 2.65 (s, 3H), 2.78-2.83 (m, 2H), 2.88 (s, 3H), 3.29-3.37 (m, 2H), 3.91 (s, 2H), 4.07-4.28 (m, 4H), 4.33 (s, 2H), 7.05-7.17 (m, 2H), 7.26-7.32 (m, 2H), 7.51 (dd, J=1.4, 7.8, 1H), 7.75 (d, J=1.4, 1H), 7.89 (brs, 3H), 8.28 (t, J=5.8, 1H).

Example 314

N²-{2-[1,3-dihydro-2H-isoindol-2-yl(methyl)amino]-2-oxoethyl}-N²-(2-methyl-8,9,10,11-tetrahydro-7H-azepino[1,2-b]indazol-3-yl)-N¹-[2-(ethylamino)ethyl]glycinamide Using the compound (277 mg, 0.836 mmol) of Reference Example 148, the compound (156 mg, 0.845 mmol) of Reference Example 17 and the compound (175 mg, 0.930 mmol) of Reference Example 2, and according to the methods of Example 204, step A, and Example 46, step B, the title compound (287 mg, yield 65%) was obtained as a colorless solid.
$^1$H-NMR (400 MHz, CDCl$_3$); δ (ppm) 0.99 (t, J=7.2, 3H), 1.50 (brs, 1H), 1.68-1.78 (m, 2H), 1.80-1.89 (m, 2H), 1.89-2.00 (m, 2H), 2.42 (s, 3H), 2.56 (q, J=7.2, 2H), 2.72 (t, J=5.9, 2H), 2.94 (s, 3H), 3.01-3.05 (m, 2H), 3.38-3.44 (m, 2H), 3.78 (s, 2H), 4.16 (d, J=11.3, 2H), 4.23 (d, J=11.3, 2H), 4.24 (s, 2H), 4.47-4.51 (m, 2H), 7.19-7.28 (m, 4H), 7.32 (s, 1H), 7.42 (s, 1H), 8.43 (t, J=5.6, 1H).

Example 315

N²-{2-[(5-fluoro-1,3-dihydro-2H-isoindol-2-yl)(methyl)amino]-2-oxoethyl}-N²-(2-methyl-8,9,10,11-tetrahydro-7H-azepino[1,2-b]indazol-3-yl)-N¹-[2-(ethylamino)ethyl]glycinamide Using the compound (256 mg, 0.773 mmol) of Reference Example 148, the compound (166 mg, 0.819 mmol) of Reference Example 19 and the compound (169 mg, 0.898 mmol) of Reference Example 2, and according to the methods of Example 204, step A, and Example 46, step B, the title compound (299 mg, yield 70%) was obtained as a colorless solid.
$^1$H-NMR (400 MHz, CDCl$_3$); δ (ppm) 0.99 (t, J=7.2, 3H), 1.39 (brs, 1H), 1.69-1.78 (m, 2H), 1.80-1.89 (m, 2H), 1.89-1.99 (m, 2H), 2.42 (s, 3H), 2.56 (q, J=7.2, 2H), 2.72 (t, J=5.9, 2H), 2.93 (s, 3H), 3.01-3.05 (m, 2H), 3.38-3.43 (m, 2H), 3.78 (s, 2H), 4.09-4.21 (m, 4H), 4.23 (s, 2H), 4.47-4.51 (m, 2H), 6.88-6.99 (m, 2H), 7.13-7.17 (m, 1H), 7.33 (s, 1H), 7.41 (s, 1H), 8.40 (t, J=5.7, 1H).

Example 316

N²-{2-[2,3-dihydro-1H-inden-2-yl(methyl)amino]-2-oxoethyl}-N²-(2-methyl-8,9,10,11-tetrahydro-7H-azepino[1,2-b]indazol-3-yl)-N¹-[2-(ethylamino)ethyl]glycinamide hydrochloride Using the compound (298 mg, 0.899 mmol) of Reference Example 148, the compound (167 mg, 0.909 mmol) of Reference Example 23 and the compound (188 mg, 0.999 mmol) of Reference Example 2, and according to the methods of Example 204, step A, and Example 57, step B, the title compound (294 mg, yield 58%) was obtained as a colorless solid.
$^1$H-NMR (400 MHz, DMSO-d$_6$); δ (ppm) 1.09-1.19 (m, 3H), 1.57-1.67 (m, 2H), 1.67-1.78 (m, 2H), 1.82-1.93 (m, 2H), 2.34 (s, 3H), 2.65 2.77 (2s, 3H), 2.6-3.2 (m, 10H), 3.34-3.42 (m, 2H), 3.76 3.81 (2s, 2H), 4.06 4.21 (2s, 2H), 4.41-4.50 (m, 2H), 4.96-5.06 5.26-5.36 (2m, 1H), 7.11-7.23 (m, 5H), 7.41 (s, 1H), 8.46 (t, J=5.6, 1H), 8.76 (brs, 2H).

Example 317

N²-{2-[1,3-dihydro-2H-isoindol-2-yl(methyl)amino]-2-oxoethyl}-N²-(2-methyl-7,8,9,10-tetrahydropyrido[1,2-b]indazol-3-yl)-N¹-[2-(ethylamino)ethyl]glycinamide Using the compound (300 mg, 0.945 mmol) of Reference Example 149, the compound (183 mg, 0.991 mmol) of Reference Example 17 and the compound (200 mg, 1.06 mmol) of Reference Example 2, and according to the methods of Example 204, step A, and Example 46, step B, the title compound (335 mg, yield 68%) was obtained as a colorless solid.
$^1$H-NMR (400 MHz, CDCl$_3$); δ (ppm) 1.00 (t, J=7.2, 3H), 1.2-1.7 (broad, 1H), 1.94-2.03 (m, 2H), 2.09-2.18 (m, 2H), 2.42 (s, 3H), 2.56 (q, J=7.2, 2H), 2.72 (t, J=5.9, 2H), 2.94 (s, 3H), 3.04 (t, J=6.2, 2H), 3.38-3.43 (m, 2H), 3.78 (s, 2H), 4.16 (d, J=11.3, 2H), 4.24 (d, J=11.3, 2H), 4.25 (s, 2H), 4.39 (t, J=5.9, 2H), 7.19-7.27 (m, 4H), 7.35 (s, 1H), 7.42 (s, 1H), 8.44 (t, J=5.6, 1H).

Example 318

$N^2$-{2-[(5-fluoro-1,3-dihydro-2H-isoindol-2-yl)(methyl)amino]-2-oxoethyl}-$N^2$-(2-methyl-7,8,9,10-tetrahydropyrido[1,2-b]indazol-3-yl)-$N^1$-[2-(ethylamino)ethyl]glycinamide Using the compound (285 mg, 0.898 mmol) of Reference Example 149, the compound (190 mg, 0.938 mmol) of Reference Example 19 and the compound (190 mg, 1.01 mmol) of Reference Example 2, and according to the methods of Example 204, step A, and Example 46, step B, the title compound (352 mg, yield 73%) was obtained as a colorless solid.
$^1$H-NMR (400 MHz, CDCl$_3$); δ (ppm) 1.00 (t, J=7.2, 3H), 1.2-1.7 (broad, 1H), 1.95-2.03 (m, 2H), 2.10-2.18 (m, 2H), 2.42 (s, 3H), 2.57 (q, J=7.2, 2H), 2.72 (t, J=6.1, 2H), 2.93 (s, 3H), 3.04 (t, J=6.4, 2H), 3.38-3.44 (m, 2H), 3.78 (s, 2H), 4.10-4.23 (m, 4H), 4.24 (s, 2H), 4.39 (t, J=6.2, 2H), 6.88-6.98 (m, 2H), 7.13-7.17 (m, 1H), 7.35 (s, 1H), 7.42 (s, 1H), 8.41 (t, J=5.7, 1H).

Example 319

$N^2$-{2-[2,3-dihydro-1H-inden-2-yl(methyl)amino]-2-oxoethyl}-$N^2$-(2-methyl-7,8,9,10-tetrahydropyrido[1,2-b]indazol-3-yl)-$N^1$-[2-(ethylamino)ethyl]glycinamide hydrochloride Using the compound (324 mg, 1.02 mmol) of Reference Example 149, the compound (190 mg, 1.03 mmol) of Reference Example 23 and the compound (214 mg, 1.14 mmol) of Reference Example 2, and according to the methods of Example 204, step A, and Example 57, step B, the title compound (390 mg, yield 69%) was obtained as a colorless solid.
$^1$H-NMR (400 MHz, DMSO-d$_6$); δ (ppm) 1.11-1.17 (m, 3H), 1.86-1.95 (m, 2H), 2.01-2.10 (m, 2H), 2.34 (s, 3H), 2.65 2.77 (2s, 3H), 2.84-3.11 (m, 10H), 3.34-3.42 (m, 2H), 3.79 3.83 (2s, 2H), 4.08 4.23 (2s, 2H), 4.30 (t, J=5.7, 2H), 4.97-5.07 5.26-5.36 (2m, 1H), 7.11-7.23 (m, 5H), 7.41 (s, 1H), 8.44 (t, J=5.4, 1H), 8.74 (brs, 2H).

Example 320

$N^2$-{2-[1,3-dihydro-2H-isoindol-2-yl(methyl)amino]-2-oxoethyl}-$N^2$-(8-methyl-2,3-dihydro-1H-pyrrolo[1,2-b]indazol-7-yl)-$N^1$-[2-(ethylamino)ethyl]glycinamide Using the compound (120 mg, 0.396 mmol) of Reference Example 150, the compound (76 mg, 0.412 mmol) of Reference Example 17 and the compound (87 mg, 0.462 mmol) of Reference Example 2; and according to the methods of Example 204, step A, and Example 46, step B, the title compound (132 mg, yield 66%) was obtained as a colorless solid.
$^1$H-NMR (400 MHz, CDCl$_3$); δ (ppm) 1.01 (t, J=7.2, 3H), 1.69 (brs, 1H), 2.42 (s, 3H), 2.57 (q, J=7.2, 2H), 2.68-2.78 (m, 4H), 2.94 (s, 3H), 3.13 (t, J=7.2, 2H), 3.38-3.44 (m, 2H), 3.79 (s, 2H), 4.17 (d, J=11.8, 2H), 4.24 (d, J=11.8, 2H), 4.26 (s, 2H), 4.39 (t, J=7.2, 2H), 7.18-7.27 (m, 4H), 7.37 (s, 1H), 7.46 (s, 1H), 8.46 (t, J=5.9, 1H).

Example 321

$N^2$-{2-[(5-fluoro-1,3-dihydro-2H-isoindol-2-yl)(methyl)amino]-2-oxoethyl}-$N^2$-(8-methyl-2,3-dihydro-1H-pyrrolo[1,2-b]indazol-7-yl)-$N^1$-[2-(ethylamino)ethyl]glycinamide Using the compound (113 mg, 0.373 mmol) of Reference Example 150, the compound (79 mg, 0.390 mmol) of Reference Example 19 and the compound (85 mg, 0.451 mmol) of Reference Example 2, and according to the methods of Example 204, step A, and Example 46, step B, the title compound (112 mg, yield 58%) was obtained as a colorless solid.
$^1$H-NMR (400 MHz, CDCl$_3$); δ (ppm) 1.01 (t, J=7.2, 3H), 1.64 (brs, 1H).
2.42 (s, 3H), 2.57 (q, J=7.2, 2H), 2.67-2.78 (m, 4H), 2.94 (s, 3H), 3.13 (t, J=7.4, 2H), 3.38-3.44 (m, 2H), 3.78 (s, 2H), 4.10-4.24 (m, 4H), 4.25 (s, 2H), 4.39 (t, J=7.4, 2H), 6.88-6.99 (m, 2H), 7.13-7.17 (m, 1H), 7.37 (s, 1H), 7.45 (s, 1H), 8.44 (t, J=5.6, 1H).

Example 322

$N^2$-{5-[4-(aminocarbonyl)-1,3-thiazol-2-yl]-2-methylphenyl}-$N^2$-{2-[1,3-dihydro-2H-isoindol-2-yl(methyl)amino]-2-oxoethyl}-$N^1$-[2-(ethylamino)ethyl]glycinamide hydrochloride Using the compound (309 mg, 0.884 mmol) of Reference Example 151, the compound (171 mg, 0.926 mmol) of Reference Example 17 and the compound (190 mg, 1.01 mmol) of Reference Example 2, and according to the methods of Example 204, step A, and Example 57, step B, the title compound (323 mg, yield 62%) was obtained as a colorless solid.
$^1$H-NMR (400 MHz, DMSO-d$_6$); δ (ppm) 1.13 (t, J=7.2, 3H), 2.33 (s, 3H), 2.8-3.0 (m, 4H), 2.89 (s, 3H), 3.96 (s, 2H), 4.14 (d, J=11.6, 2H), 4.27 (d, J=11.6, 2H), 4.35 (s, 2H), 7.23-7.29 (m, 5H), 7.56 (d, J=7.7, 1H), 7.70 (brs, 1H), 7.71 (s, 1H), 7.84 (brs, 1H), 8.24 (s, 1H), 8.36 (t, J=5.6, 1H), 8.52 (brs, 2H).

Example 323

$N^2$-{5-[4-(aminocarbonyl)-1,3-thiazol-2-yl]-2-methylphenyl}-$N^2$-{2-[(5-fluoro-1,3-dihydro-2H-isoindol-2-yl)(methyl)amino]-2-oxoethyl}-$N^1$-[2-(ethylamino)ethyl]glycinamide hydrochloride Using the compound (323 mg, 0.925 mmol) of Reference Example 151, the compound (193 mg, 0.952 mmol) of Reference Example 19 and the compound (195 mg, 1.04 mmol) of Reference Example 2, and according to the methods of Example 204, step A, and Example 57, step B, the title compound (377 mg, yield 67%) was obtained as a colorless solid.
$^1$H-NMR (400 MHz, DMSO-d$_6$); δ (ppm) 1.14 (t, J=7.2, 3H), 2.32 (s, 3H), 2.8-3.0 (m, 4H), 2.89 (s, 3H), 3.35-3.42 (m, 2H), 3.95 (s, 2H), 4.09-4.30 (m, 4H), 4.34 (s, 2H), 7.04-7.17 (m, 2H), 7.26 (d, J=8.2, 1H), 7.28-7.32 (m, 1H), 7.55 (d, J=8.2, 1H), 7.70 (brs, 2H), 7.84 (brs, 1H), 8.24 (s, 1H), 8.37 (t, J=5.7, 1H), 8.65 (brs, 2H).

Example 324

$N^2$-{2-[1,3-dihydro-2H-isoindol-2-yl(methyl)amino]-2-oxoethyl}-$N^2$-[2-methyl-5-{4-[(methylamino)carbonyl]-1,3-thiazol-2-yl}phenyl]-$N^1$-[2-(ethylamino)ethyl]glycinamide hydrochloride Using the compound (364 mg, 1.00 mmol) of Reference Example 152, the compound (193 mg, 1.01 mmol) of Reference Example 17 and the compound (210 mg, 1.12 mmol) of Reference Example 2, and according to the methods of Example 204, step A, and Example 57, step B, the title compound (508 mg, yield 85%) was obtained as a colorless solid.

$^1$H-NMR (400 MHz, DMSO-d$_6$); δ (ppm) 1.15 (t, J=7.2, 3H), 2.33 (s, 3H), 2.83 (d, J=4.6, 3H), 2.84-2.97 (m, 4H), 2.89 (s, 3H), 3.35-3.42 (m, 2H), 3.97 (s, 2H), 4.14 (d, J=11.3, 2H), 4.27 (d, J=11.3, 2H), 4.36 (s, 2H), 7.22-7.29 (m, 5H), 7.58 (d, J=7.7, 1H), 7.70 (s, 1H), 8.22 (s, 1H), 8.38-8.48 (m, 2H), 8.81 (brs, 2H).

Example 325

N$^2$-{2-[(5-fluoro-1,3-dihydro-2H-isoindol-2-yl)(methyl)amino]-2-oxoethyl}-N$^2$-[2-methyl-5-{4-[(methylamino)carbonyl]-1,3-thiazol-2-yl}phenyl]-N$^1$-[2-(ethylamino)ethyl]glycinamide hydrochloride Using the compound (363 mg, 0.999 mmol) of Reference Example 152, the compound (209 mg, 1.03 mmol) of Reference Example 19 and the compound (211 mg, 1.12 mmol) of Reference Example 2, and according to the methods of Example 204, step A, and Example 57, step B, the title compound (480 mg, yield 78%) was obtained as a colorless solid.

$^1$H-NMR (400 MHz, DMSO-d$_6$); δ (ppm) 1.14 (t, J=7.2, 3H), 2.33 (s, 3H), 2.83 (d, J=4.6, 3H), 2.84-2.98 (m, 4H), 2.89 (s, 3H), 3.35-3.42 (m, 2H), 3.96 (s, 2H), 4.08-4.30 (m, 4H), 4.34 (s, 2H), 7.05-7.18 (m, 2H), 7.27 (d, J=7.7, 1H), 7.28-7.31 (m, 1H), 7.58 (d, J=7.7, 1H), 7.70 (s, 1H), 8.22 (s, 1H), 8.38 (t, J=5.4, 1H), 8.43 (q, J=4.6, 1H), 8.64 (brs, 2H).

Example 326

N$^2$-{2-[1,3-dihydro-2H-isoindol-2-yl(methyl)amino]-2-oxoethyl}-N$^2$-[5-{4-[(dimethylamino)carbonyl]-1,3-thiazol-2-yl}-2-methylphenyl]-N$^1$-[2-(ethylamino)ethyl]glycinamide hydrochloride Using the compound (378 mg, 1.00 mmol) of Reference Example 153, the compound (194 mg, 1.01 mmol) of Reference Example 17 and the compound (214 mg, 1.14 mmol) of Reference Example 2, and according to the methods of Example 204, step A, and Example 57, step B, the title compound (447 mg, yield 73%) was obtained as a colorless solid.

$^1$H-NMR (400 MHz, DMSO-d$_6$); δ (ppm) 1.14 (t, J=7.2, 3H), 2.32 (s, 3H), 2.8-3.0 (m, 4H), 2.90 (s, 3H), 3.02 (s, 3H), 3.15 (s, 3H), 3.35-3.41 (m, 2H), 3.94 (s, 2H), 4.14 (d, J=11.3, 2H), 4.27 (d, J=11.3, 2H), 4.37 (s, 2H), 7.22-7.29 (m, 5H), 7.46 (d, J=7.7, 1H), 7.66 (s, 1H), 8.05 (s, 1H), 8.37 (t, J=5.7, 1H), 8.66 (brs, 2H).

Example 327

N$^2$-[5-{4-[(dimethylamino)carbonyl]-1,3-thiazol-2-yl}-2-methylphenyl]-N$^2$-{2-[(5-fluoro-1,3-dihydro-2H-isoindol-2-yl)(methyl)amino]-2-oxoethyl}-N$^1$-[2-(ethylamino)ethyl]glycinamide hydrochloride Using the compound (378 mg, 1.00 mmol) of Reference Example 153, the compound (207 mg, 1.02 mmol) of Reference Example 19 and the compound (216 mg, 1.15 mmol) of Reference Example 2, and according to the methods of Example 204, step A, and Example 57, step B, the title compound (409 mg, yield 65%) was obtained as a colorless solid.

$^1$H-NMR (400 MHz, DMSO-d$_6$); δ (ppm) 1.14 (t, J=7.2, 3H), 2.31 (s, 3H), 2.8-3.0 (m, 4H), 2.89 (s, 3H), 3.02 (s, 3H), 3.15 (s, 3H), 3.34-3.42 (m, 2H), 3.94 (s, 2H), 4.08-4.30 (m, 4H), 4.36 (s, 2H), 7.05-7.17 (m, 2H), 7.25 (d, J=7.7, 1H), 7.27-7.32 (m, 1H), 7.46 (d, J=7.7, 1H), 7.66 (s, 1H), 8.05 (s, 1H), 8.36 (t, J=5.6, 1H), 8.66 (brs, 2H).

Example 328

N$^2$-{2-[1,3-dihydro-2H-isoindol-2-yl(methyl)amino]-2-oxoethyl}-N$^2$-(3,6-dimethyl-1,2-benzisoxazol-5-yl)-N$^1$-[(2S)-pyrrolidin-2-ylmethyl]glycinamide dihydrochloride Using the compound (357 mg, 0.874 mmol) of Example 180, step A, and the compound (304 mg, 1.28 mmol) of Reference Example 12, and according to the methods of Example 1, steps B and C, the title compound (389 mg, yield 79%) was obtained as a colorless solid.

$^1$H-NMR (400 MHz, DMSO-d$_6$); δ (ppm) 1.4-1.5 (m, 1H), 1.70-1.85 (m, 3H), 2.46 (s, 3H), 2.47 (s, 3H), 2.87 (s, 3H), 3.01-3.08 (m, 2H), 3.30-3.55 (m, 3H), 3.88 (s, 2H), 4.08 (d, J=11.4, 2H), 4.23 (d, J=11.4, 2H), 4.27 (s, 2H), 7.25 (brs, 4H), 7.49 (s, 1H), 7.66 (s, 1H), 8.46 (t, J=6.1, 1H), 8.56 (brs, 1H), 9.14 (brs, 1H).

The compounds of Examples 313-328 are shown below.

TABLE 20

| Example | Structural Formula | TMW | LC-MS (found) |
|---|---|---|---|
| 313 | | 532.01 | 496 |

TABLE 20-continued
| Example | Structural Formula | TMW | LC-MS (found) |
|---|---|---|---|
| 314 | 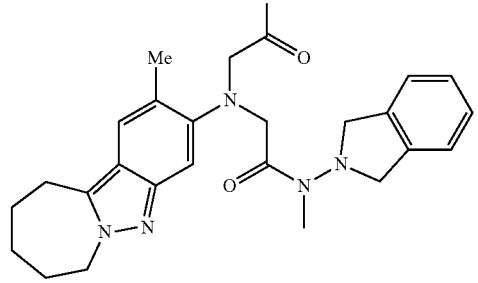 | 531.69 | 532 |
| 315 | 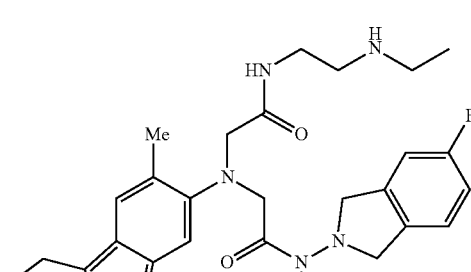 | 549.68 | 550 |
| 316 | 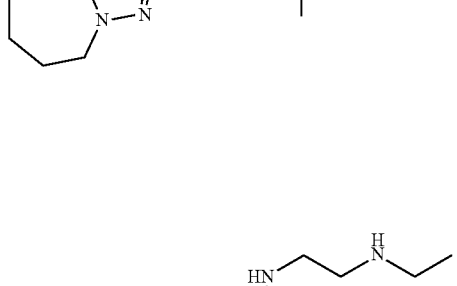 HCl | 567.17 | 531 |
| 317 | 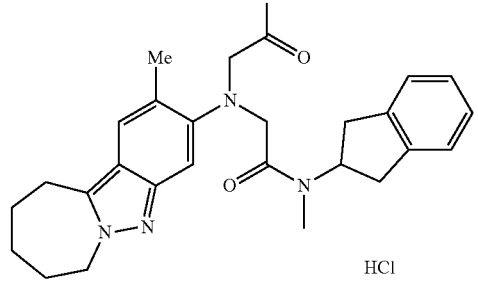 | 517.67 | 518 |

TABLE 20-continued

| Example | Structural Formula | TMW | LC-MS (found) |
|---|---|---|---|
| 318 | | 535.66 | 536 |
| 319 | HCl | 553.14 | 517 |
| 320 | | 503.64 | 504 |
| 321 | | 521.63 | 522 |

TABLE 20-continued

| Example | Structural Formula | TMW | LC-MS (found) |
|---|---|---|---|
| 322 | | 586.15 | 550 |
| 323 | | 604.14 | 568 |
| 324 | | 600.18 | 564 |
| 325 | | 618.17 | 582 |

TABLE 20-continued

| Example | Structural Formula | TMW | LC-MS (found) |
|---|---|---|---|
| 326 | (structure with Me-thiazole-N(Me)(Me)carboxamide, methylphenyl, N-glycinamide linker to N-methyl-isoindoline-N, and HN-CH2CH2-NH-Et side chain; HCl salt) | 614.20 | 578 |
| 327 | (structure as 326 with fluoro-isoindoline; HCl salt) | 632.19 | 596 |
| 328 | (Me, Me-benzisoxazole with N-glycinamide linker to N-methyl-isoindoline-N, and HN-CH2-pyrrolidine (NH) side chain; 2HCl salt) | 563.52 | 491 |

The pharmacological test results of the compounds of the Examples are shown below.

Experimental Example 1

Measurement of Enzyme Inhibitory Activity

The enzyme inhibitory activity of the compounds of the Examples was measured using the hydrolysis activity of S-Adenosyl-L-Homocysteine as an index. The measurement method was modification of the method of Henry H. Richards et al. (J. Biol. Chem. 253, 4476-4480, 1978). That is, S-Adenosyl-L-Homocysteine (10 μM) and Adenosine Deaminase (Roche) (4 units) were added to 50 mM phosphate buffer (pH 7.2, containing 1 mM EDTA) with the total amount being 200 μl, and to the solution were added a test substance and then Human-recombinant-S-Adenosyl-L-Homocysteine Hydrolase (50 ng, Diazyme Laboratories) to start the reaction, and the mixture was incubated at 37° C. for 15 min. The reaction was quenched by the addition of 1N aqueous perchloric solution (20 μl), and the mixture was centrifuged under the conditions of 10000 rpm, 5 min, 4° C. The supernatant was collected, and the amount of S-Adenosyl-L-Homocysteine after the reaction was quantified by HPLC. The column used was a reversed-phase column. The detailed conditions of HPLC were as follows.

column used: Wakopak® HandyODS 150*4.6 mm (Wako Pure Chemical Industries, Ltd.)

elution condition: 1.0 ml/min elution solvent: 0.1M acetate buffer (pH 4.0) containing 10 mM 1-heptanesulfonic acid containing 4% acetonitrile wavelength: 258 nm (UV)

The inhibitory rate was determined with the amount of decrease in S-Adenosyl-L-Homocysteine before and after the reaction without using the test substance as 100%.

Inhibitory rate (%)={(amount of decrease of S-Adenosyl-L-Homocysteine in the presence of test substance)/(amount of decrease of S-Adenosyl-L-Homocysteine in the absence of test substance)}×100

The results are shown in the following Table.

TABLE 21

| Example | IC50 (nM) | Example | IC50 (nM) | Example | IC50 (nM) |
|---|---|---|---|---|---|
| 1 | 68 | 176 | 63 | 242 | 6 |
| 2 | 92 | 177 | 46 | 243 | 7 |
| 15 | 17 | 180 | 15 | 247 | 15 |
| 16 | 19 | 181 | 16 | 253 | 20 |
| 19 | 33 | 184 | 37 | 256 | 47 |
| 20 | 39 | 185 | 8 | 259 | 30 |
| 21 | 89 | 190 | 88 | 279 | 66 |
| 24 | 46 | 191 | 51 | 284 | 33 |
| 26 | 56 | 192 | 46 | 287 | 58 |
| 56 | 52 | 193 | 29 | 289 | 76 |
| 57 | 42 | 204 | 65 | 298 | 50 |
| 64 | 103 | 205 | 48 | 301 | 37 |
| 65 | 47 | 210 | 34 | 303 | 41 |
| 84 | 34 | 211 | 51 | 308 | 26 |
| 85 | 17 | 214 | 23 | 309 | 23 |
| 87 | 18 | 215 | 47 | 328 | 150 |
| 88 | 43 | 216 | 33 | | |
| 89 | 53 | 229 | 35 | | |
| 92 | 48 | 231 | 46 | | |
| 129 | 10 | 241 | 9 | | |

Experimental Example 2

Measurement of Homocysteine Synthesis Inhibitory Activity In Vivo

A sample was orally administered to BALB/c mouse and, 1 hr later, methionine water (50 g/L) was orally administered at a proportion of 10 ml/kg. 30 min later, blood samples were collected with heparin from the abdominal vein and plasma was obtained. The plasma homocysteine concentration was measured by treating the plasma with tributylphosphine, removing protein with 10% trichloroacetic acid (TCA), fluorescent labeling the supernatant with 4-fluoro-7-sulfobenzofurazan ammonium salt (SBD-F) under alkali conditions, and quantifying by HPLC. The homocysteine synthesis inhibitory rate of the sample was determined with the difference in the homocysteine value between methionine water-loaded animal and methionine water-unloaded animal as 100%. The detailed conditions of HPLC were as follows.

column used: Wakopak® HandyODS 150*4.6 mm (Wako Pure Chemical Industries, Ltd.)

elution condition: 1.0 ml/min elution solvent: 0.1M phosphate buffer (pH 6.0) 2% methanol wavelength: ex 385 nm em 515 nm The results at a dose of 10 mg/kg are shown in the following Table.

TABLE 22

| Example | activity | Example | activity | Example | activity |
|---|---|---|---|---|---|
| 1 | A | 89 | B | 241 | A |
| 2 | A | 92 | A | 244 | A |
| 20 | A | 105 | B | 245 | B |
| 21 | A | 136 | A | 253 | A |
| 24 | B | 176 | A | 254 | B |
| 57 | A | 184 | A | 268 | C |

TABLE 22-continued

| Example | activity | Example | activity | Example | activity |
|---|---|---|---|---|---|
| (2HCl salt) | | 185 | A | 292 | B |
| 64 | A | 215 | A | 304 | A |
| 65 | A | 229 | A | | |
| 88 | B | | | | |

Activity: A: homocysteine synthesis inhibitory rate ≧ 40%
B: 40% > homocysteine synthesis inhibitory rate ≧ 20%
C: 20% > homocysteine synthesis inhibitory rate

INDUSTRIAL APPLICABILITY

The amide derivative of the present invention or a pharmacologically acceptable salt thereof, or a solvate thereof shows a homocysteine synthase inhibitory action, and can be a medicament effective for the prophylaxis or treatment of diseases involving the enzyme.

This application is based on Japanese patent application No. 2008-102924 filed in Japan, the contents of which are incorporated in full herein.

The invention claimed is:

1. An amide derivative represented by the following formula (I)

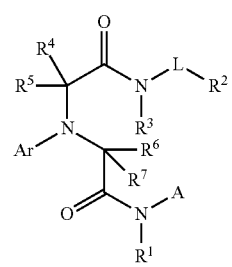

(I)

wherein $R^1$ is a hydrogen atom or a $C_1$-$C_3$ alkyl group, $R^2$ is an optionally substituted heterocyclic group (said heterocyclic group contains at least one nitrogen atom in the ring), or —$N(R^{2a})(R^{2b})$, $R^{2a}$ and $R^{2b}$ are independently selected and each is a hydrogen atom, a $C_1$-$C_6$ alkyl group, a haloalkyl group or an optionally substituted aryl group, $R^3$ is a hydrogen atom, $R^4$, $R^5$, $R^6$, $R^7$ are independently selected and each is a hydrogen atom or a $C_1$-$C_4$ alkyl group, L is a linker represented by the following formula

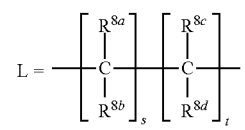

wherein s is an integer of 0-2, t is an integer of 0-2, $R^{8a}$, $R^{8b}$, $R^{8c}$ and $R^{8d}$ are independently selected and each is a hydrogen atom or a $C_1$-$C_3$ alkyl group, Ar is a substituent represented by any of the following formulas (II)-(IV),

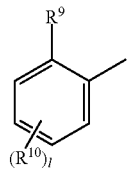

(II)

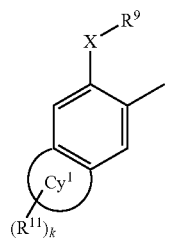

(III)

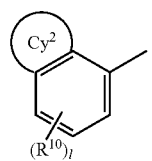

(IV)

wherein
l is an integer of 0-4,
k is an integer of 0-4,
$Cy^1$ and $Cy^2$ are independently selected and each is a carbocyclic group, a heterocyclic group or a heteroaryl group,
X is a bond, an oxygen atom or a sulfur atom,
$R^9$ is a halogen atom or $R^{12}$,
wherein
$R^{12}$ is
a hydrogen atom,
an optionally substituted $C_1$-$C_6$ alkyl group,
an optionally substituted $C_2$-$C_6$ alkenyl group,
an optionally substituted $C_2$-$C_6$ alkynyl group,
an optionally substituted $C_3$-$C_8$ cycloalkyl group,
an optionally substituted heterocyclic group,
an optionally substituted aryl group,
an optionally substituted heteroaryl group, or
an optionally substituted arylalkyl group,
$R^{10}$ is
a halogen atom,
a cyano group,
an optionally substituted $C_1$-$C_6$ alkyl group,
—$CF_3$,
—O—$R^{13}$,
—CO—$R^{14}$,
an optionally substituted amino group,
an optionally substituted aryl group,
an optionally substituted heteroaryl group,
an optionally substituted heterocyclic group, or
an —S(O)$_m$—$C_1$-$C_6$ alkyl group wherein m is an integer of 0-2,
$R^{11}$ is a halogen atom, an optionally substituted $C_1$-$C_4$ alkyl group or $CF_3$, $R^{13}$ is a hydrogen atom, a $C_1$-$C_4$ alkyl group, or —$CF_3$,
$R^{14}$ is a hydroxy group, a $C_1$-$C_6$ alkyl group, a $C_1$-$C_6$ alkoxy group, or an optionally substituted amino group,
A is
an optionally substituted aryl group,
an optionally substituted aryl-$C_1$-$C_4$ alkyl group,
an optionally substituted heteroaryl-$C_1$-$C_4$ alkyl group,
a $C_3$-$C_6$ alkynyl group,
an optionally substituted $C_3$-$C_8$ cycloalkyl group, or
a group represented by any of the following formulas (V)-(VIII)

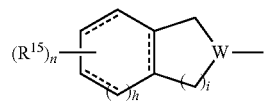

(V)

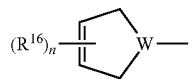

(VI)

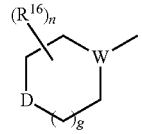

(VII)

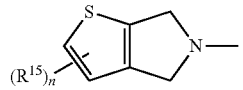

(VIII)

wherein
----- is a single bond or a double bond,
n is an integer of 0-2,
g is an integer of 0-2,
h is an integer of 0-1,
i is an integer of 1-2,
$R^{15}$ is a $C_1$-$C_4$ alkyl group, a $C_1$-$C_4$ alkoxy group, a cyano group or a halogen atom,
$R^{16}$ is a $C_1$-$C_4$ alkyl group,
W is =CH— or =N—, and
D is an oxygen atom, a sulfur atom, =N-(E)u-$R^{17}$ or =CH—$R^{17}$, u is an integer of 0-1, E is —$SO_2$— or —CO—, $R^{17}$ is a hydrogen atom, a $C_1$-$C_4$ alkyl group, an aryl group, a $C_1$-$C_4$ alkylamino group, a $C_1$-$C_6$ alkoxy group, an arylamino group or an aryloxy group, or a pharmacologically acceptable salt thereof.

2. The amide derivative according to claim 1, which is represented by the following formula (IX)

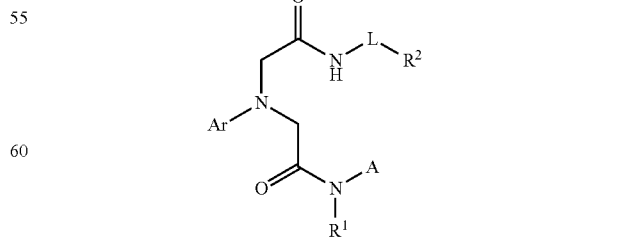

(IX)

the formula (IX) shows that $R^3$ is a hydrogen atom, and $R^4$, $R^5$, $R^6$ and $R^7$ are each a hydrogen atom in the formula (I), and other symbols are the same as defined in claim 1, or a pharmacologically acceptable salt thereof.

3. The amide derivative according to claim 1 wherein $R^1$ is a $C_1$-$C_3$ alkyl group, or a pharmacologically acceptable salt thereof.

4. The amide derivative according to claim 1, wherein A is selected from the groups represented by the following formulas (V)-(VIII)

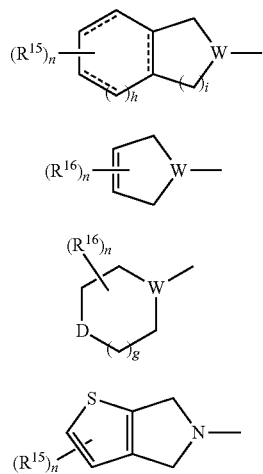

wherein
----- is a single bond or a double bond,
n is an integer of 0-2,
g is an integer of 0-2,
h is an integer of 0-1,
i is an integer of 1-2,
$R^{15}$ is a $C_1$-$C_4$ alkyl group, a $C_1$-$C_4$ alkoxy group, a cyano group or a halogen atom,
$R^{16}$ is a $C_1$-$C_4$ alkyl group,
W is =CH— or =N—,
D is an oxygen atom, a sulfur atom, =N-(E)u-$R^{17}$ or =CH—$R^{17}$, u is an integer of 0-1, E is —$SO_2$— or —CO—, $R^{17}$ is a hydrogen atom, a $C_1$-$C_4$ alkyl group, an aryl group, a $C_1$-$C_4$ alkylamino group, a $C_1$-$C_6$ alkoxy group, an arylamino group or an aryloxy group, or a pharmacologically acceptable salt thereof.

5. The amide derivative according to claim 1, wherein A is a group represented by the following formula (V)

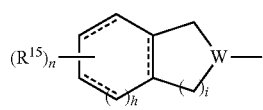

wherein
----- is a single bond or a double bond,
n is an integer of 0-2,
h is an integer of 0-1,
i is an integer of 1-2,
$R^{15}$ is a $C_1$-$C_4$ alkyl group, a $C_1$-$C_4$ alkoxy group, a cyano group or a halogen atom,
W is =CH— or =N—,
or a pharmacologically acceptable salt thereof.

6. The amide derivative according to claim 1, wherein L is a linker represented by the following formula

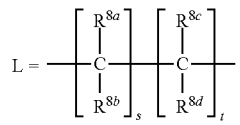

wherein $R^{8a}$, $R^{8b}$, $R^{8c}$ and $R^{8d}$ are each a hydrogen atom, or a pharmacologically acceptable salt thereof.

7. The amide derivative according to claim 1, wherein $R^{10}$ is
a halogen atom,
a cyano group,
—CO—$R^{14}$,
an optionally substituted aryl group,
an optionally substituted heteroaryl group, or
an optionally substituted heterocyclic group,
or a pharmacologically acceptable salt thereof.

8. The amide derivative according to claim 1, wherein $R^{10}$ is a heteroaryl group having a substituent, or a heterocyclic group having a substituent, or a pharmacologically acceptable salt thereof.

9. The amide derivative according to claim 1, wherein the heteroaryl group for $R^{10}$ is selected from a furyl group, a thienyl group, a pyrazolyl group, a 1,2,4-triazolyl group, a tetrazolyl group, an oxazolyl group, a thiazolyl group, an isoxazolyl group, a 1,2,4-oxadiazolyl group, a 1,3,4-oxadiazolyl group, a 1,3,4-thiadiazolyl group, a pyridyl group, a pyrazinyl group and a pyrimidyl group, or a pharmacologically acceptable salt thereof.

10. The amide derivative according to claim 1, wherein $R^{10}$ is a heteroaryl group having a substituent, and the substituent is a group selected from a halogen atom, a cyano group, a $C_1$-$C_4$ alkyl group, a $C_1$-$C_4$ alkoxy group, a —$CH_2OH$ group, a —$CF_3$ group, a —$CHF_2$ group, a —$CH_2F$ group, a —$OCF_3$ group, a —$OCHF_2$ group, a —$OCH_2F$ group, a —$CONH_2$ group, a —$CONHCH_3$ group and a —$CON(CH_3)_2$ group, or a pharmacologically acceptable salt thereof.

11. The amide derivative according to claim 1, wherein $R^{12}$ is
an optionally substituted $C_1$-$C_6$ alkyl group,
an optionally substituted $C_2$-$C_6$ alkenyl group,
an optionally substituted $C_2$-$C_6$ alkynyl group,
an optionally substituted $C_3$-$C_8$ cycloalkyl group,
an optionally substituted aryl group, or
an optionally substituted heteroaryl group,
or a pharmacologically acceptable salt thereof.

12. An amide derivative selected from the following compounds, or a pharmacologically acceptable salt thereof:
$N^2$-(5-acetyl-2-methylphenyl)-$N^2$-{2-[1,3-dihydro-2H-isoindol-2-yl(methyl)amino]-2-oxoethyl}-$N^1$-[2-(isopropylamino)ethyl]glycinamide,
$N^2$-(5-acetyl-2-methylphenyl)-$N^2$-{2-[1,3-dihydro-2H-isoindol-2-yl(methyl)amino]-2-oxoethyl}-$N^1$-[2-(ethylamino)ethyl]glycinamide,
$N^2$-{2-[1,3-dihydro-2H-isoindol-2-yl(methyl)amino]-2-oxoethyl}-$N^2$-[2-methyl-4-(5-methyl-1,2,4-oxadiazol-3-yl)phenyl]-$N^1$-[2-(isopropylamino)ethyl]glycinamide,
$N^2$-{2-[1,3-dihydro-2H-isoindol-2-yl(methyl)amino]-2-oxoethyl}-$N^2$-[2-methyl-4-(5-methyl-1,2,4-oxadiazol-3-yl)phenyl]-$N^1$-[2-(ethylamino)ethyl]glycinamide, $N^2$-{2-[(5-fluoro-1,3-dihydro-2H-isoindol-2-yl)(methyl)amino]-2-oxoethyl}-$N^2$-[2-methyl-4-(5-methyl-1,2,4-oxadiazol-3-yl)phenyl]-$N^1$-[2-(ethylamino)ethyl]glycinamide, $N^2$-(5-cyano-2-methylphenyl)-$N^2$-{2-[1,3-dihydro-2H-isoindol-2-yl(methyl)amino]-2-oxoethyl}-$N^1$-[2-(isopropylamino)ethyl]glycinamide, $N^2$-(5-cyano-2-methylphenyl)-$N^2$-{2-[1,3-dihydro-2H-isoindol-2-yl(methyl)amino]-2-oxoethyl}-$N^1$-[2-(ethylamino)ethyl]glycinamide, $N^2$-{2-[1,3-dihydro-2H-isoindol-2-yl(methyl)amino]-2-oxoethyl}-$N^2$-[2-methyl-5-(5-methyl-1,2,4-oxadiazol-3-yl)phenyl]-$N^1$-[2-(isopropylamino)ethyl]glycinamide, $N^2$-{2-[1,3-dihydro-2H-isoindol-2-yl(methyl)amino]-2-oxoethyl}-$N^2$-[2-methyl-5-(5-methyl-1,2,4-oxadiazol-3-yl)phenyl]-$N^1$-[2-(ethylamino)ethyl]glycinamide, $N^2$-{2-[(4-fluoro-1,3-dihydro-2H-isoindol-2-yl)(methyl)amino]-2-oxoethyl}-$N^2$-[2-methyl-5-(5-methyl-1,2,4-oxadiazol-3-yl)phenyl]-$N^1$-[2-(ethylamino)ethyl]glycinamide, $N^2$-{2-[(5-fluoro-1,3-dihydro-2H-isoindol-2-yl)(methyl)amino]-2-oxoethyl}-$N^2$-[2-methyl-5-(5-methyl-1,2,4-oxadiazol-3-yl)phenyl]-$N^1$-[2-(ethylamino)ethyl]glycinamide, $N^2$-{2-[(5-fluoro-1,3-dihydro-2H-isoindol-2-yl)(methyl)amino]-2-oxoethyl}-$N^2$-[2-methyl-5-(5-methyl-1,2,4-oxadiazol-3-yl)phenyl]-$N^1$-[2-(isopropylamino)ethyl]glycinamide, $N^2$-{2-[(5-methoxy-1,3-dihydro-2H-isoindol-2-yl)(methyl)amino]-2-oxoethyl}-$N^2$-[2-methyl-5-(5-methyl-1,2,4-oxadiazol-3-yl)phenyl]-$N^1$-[2-(ethylamino)ethyl]glycinamide, $N^2$-{2-[2,3-dihydro-1H-inden-2-yl(methyl)amino]-2-oxoethyl}-$N^2$-[2-methyl-5-(5-methyl-1,2,4-oxadiazol-3-yl)phenyl]-$N^1$-[2-(ethylamino)ethyl]glycinamide, $N^2$-{2-[1,3-dihydro-2H-isoindol-2-yl(methyl)amino]-2-oxoethyl}-$N^2$-[2-methyl-5-(3-methyl-1,2,4-oxadiazol-5-yl)phenyl]-$N^1$-[2-(isopropylamino)ethyl]glycinamide, $N^2$-{2-[1,3-dihydro-2H-isoindol-2-yl(methyl)amino]-2-oxoethyl}-$N^2$-[2-methyl-5-(3-methyl-1,2,4-oxadiazol-5-yl)phenyl]-$N^1$-[2-(ethylamino)ethyl]glycinamide, $N^2$-{2-[(5-fluoro-1,3-dihydro-2H-isoindol-2-yl)(methyl)amino]-2-oxoethyl}-$N^2$-[2-methyl-5-(3-methyl-1,2,4-oxadiazol-5-yl)phenyl]-$N^1$-[2-(ethylamino)ethyl]glycinamide, $N^2$-{2-[1,3-dihydro-2H-isoindol-2-yl(methyl)amino]-2-oxoethyl}-$N^2$-[2-methyl-5-(4-methyl-5-oxo-4,5-dihydro-1,3,4-oxadiazol-2-yl)phenyl]-$N^1$-[2-(isopropylamino)ethyl]glycinamide, $N^2$-{2-[1,3-dihydro-2H-isoindol-2-yl(methyl)amino]-2-oxoethyl}-$N^2$-[2-methyl-5-(4-methyl-5-oxo-4,5-dihydro-1,3,4-oxadiazol-2-yl)phenyl]-$N^1$-[2-(ethylamino)ethyl]glycinamide, $N^2$-{2-[1,3-dihydro-2H-isoindol-2-yl(methyl)amino]-2-oxoethyl}-$N^2$-[5-(4-ethyl-5-oxo-4,5-dihydro-1,3,4-oxadiazol-2-yl)-2-methylphenyl]-$N^1$-[2-(ethylamino)ethyl]glycinamide, $N^2$-{2-[1,3-dihydro-2H-isoindol-2-yl(methyl)amino]-2-oxoethyl}-$N^2$-(2-methyl-5-pyrimidin-2-ylphenyl)-$N^1$-[2-(ethylamino)ethyl]glycinamide, $N^2$-{2-[1,3-dihydro-2H-isoindol-2-yl(methyl)amino]-2-oxoethyl}-$N^2$-(1-ethyl-7-methyl-2-oxo-1,2,3,4-tetrahydroquinolin-6-yl)-$N^1$-[2-(isopropylamino)ethyl]glycinamide, $N^2$-{2-[1,3-dihydro-2H-isoindol-2-yl(methyl)amino]-2-oxoethyl}-$N^2$-(1-ethyl-7-methyl-2-oxo-1,2,3,4-tetrahydroquinolin-6-yl)-$N^1$-[2-(ethylamino)ethyl]glycinamide, $N^2$-{2-[1,3-dihydro-2H-isoindol-2-yl(methyl)amino]-2-oxoethyl}-$N^2$-(3,6-dimethyl-1,2-benzisoxazol-5-yl)-$N^1$-[2-(isopropylamino)ethyl]glycinamide, $N^2$-{2-[1,3-dihydro-2H-isoindol-2-yl(methyl)amino]-2-oxoethyl}-$N^2$-(3,6-dimethyl-1,2-benzisoxazol-5-yl)-$N^1$-[2-(ethylamino)ethyl]glycinamide, $N^2$-{2-[1,3-dihydro-2H-isoindol-2-yl(methyl)amino]-2-oxoethyl}-$N^2$-(3,5-dimethyl-1,2-benzisoxazol-6-yl)-$N^1$-[2-(isopropylamino)ethyl]glycinamide, $N^2$-{2-[1,3-dihydro-2H-isoindol-2-yl(methyl)amino]-2-oxoethyl}-$N^2$-(3,5-dimethyl-1,2-benzisoxazol-6-yl)-$N^1$-[2-(ethylamino)ethyl]glycinamide, $N^2$-{2-[1,3-dihydro-2H-isoindol-2-yl(methyl)amino]-2-oxoethyl}-$N^2$-(3,6-dimethyl-1,3-benzoxazol-2(3H)-on-5-yl)-$N^1$-[2-(isopropylamino)ethyl]glycinamide, $N^2$-{2-[1,3-dihydro-2H-isoindol-2-yl(methyl)amino]-2-oxoethyl}-$N^2$-(3,6-dimethyl-1,3-benzoxazol-2(3H)-on-5-yl)-$N^2$-[2-(ethylamino)ethyl]glycinamide, $N^2$-{2-[1,3-dihydro-2H-isoindol-2-yl(methyl)amino]-2-oxoethyl}-$N^2$-(3,5-dimethyl-1,3-benzoxazol-2(3H)-on-6-yl)-$N^1$-[2-(isopropylamino)ethyl]glycinamide, $N^2$-{2-[1,3-dihydro-2H-isoindol-2-yl(methyl)amino]-2-oxoethyl}-$N^2$-(3,5-dimethyl-1,3-benzoxazol-2(3H)-on-6-yl)-$N^1$-[2-(ethylamino)ethyl]glycinamide, $N^2$-{2-[(4-fluoro-1,3-dihydro-2H-isoindol-2-yl)(methyl)amino]-2-oxoethyl}-$N^2$-[2-methyl-4-(5-methyl-1,2,4-oxadiazol-3-yl)phenyl]-$N^1$-[2-(ethylamino)ethyl]glycinamide, $N^2$-(4-acetyl-2-methylphenyl)-$N^2$-{2-[1,3-dihydro-2H-isoindol-2-yl(methyl)amino]-2-oxoethyl}-$N^1$-[2-(ethylamino)ethyl]glycinamide, $N^2$-(4-acetyl-2-methylphenyl)-$N^2$-{2-[(5-fluoro-1,3-dihydro-2H-isoindol-2-yl)(methyl)amino]-2-oxoethyl}-$N^1$-[2-(ethylamino)ethyl]glycinamide, $N^2$-{2-[1,3-dihydro-2H-isoindol-2-yl(methyl)amino]-2-oxoethyl}-$N^2$-(6-methyl-3-oxo-2,3-dihydro-1H-inden-5-yl)-$N^1$-[2-(ethylamino)ethyl]glycinamide, $N^2$-{2-[(5-fluoro-1,3-dihydro-2H-isoindol-2-yl)(methyl)amino]-2-oxoethyl}-$N^2$-(6-methyl-3-oxo-2,3-dihydro-1H-inden-5-yl)-$N^1$-[2-(ethylamino)ethyl]glycinamide, $N^2$-{2-[(4-fluoro-1,3-dihydro-2H-isoindol-2-yl)(methyl)amino]-2-oxoethyl}-$N^2$-(6-methyl-3-oxo-2,3-dihydro-1H-inden-5-yl)-$N^1$-[2-(ethylamino)ethyl]glycinamide, $N^2$-{2-[1,3-dihydro-2H-isoindol-2-yl(methyl)amino]-2-oxoethyl}-$N^2$-[2-methyl-4-(3-methyl-1,2,4-oxadiazol-5-yl)phenyl]-$N^1$-[2-(ethylamino)ethyl]glycinamide, and $N^2$-{2-[(5-fluoro-1,3-dihydro-2H-isoindol-2-yl)(methyl)amino]-2-oxoethyl}-$N^2$-[2-methyl-4-(3-methyl-1,2,4-oxadiazol-5-yl)phenyl]-$N^1$-[2-(ethylamino)ethyl]glycinamide.

13. A pharmaceutical composition comprising the amide derivative according to claim 1, or a pharmacologically acceptable salt thereof, as an active ingredient.

14. A pharmaceutical composition comprising the amide derivative according to claim 12, or a pharmacologically acceptable salt thereof, as an active ingredient.

* * * * *

UNITED STATES PATENT AND TRADEMARK OFFICE
CERTIFICATE OF CORRECTION

PATENT NO. : 8,513,235 B2  
APPLICATION NO. : 12/937187  
DATED : August 20, 2013  
INVENTOR(S) : Nakao et al.

Page 1 of 1

It is certified that error appears in the above-identified patent and that said Letters Patent is hereby corrected as shown below:

IN THE CLAIMS

Claim 12, column 607, lines 3-4, "oxadiazol-3-yl)phenyl]-$N^2$-[2-(ethylamino)ethyl]glycinamide," should read "oxadiazol-3-yl)phenyl]-$N^1$-[2-(ethylamino)ethyl]glycinamide,"

Claim 12, column 608, line 23, "on-5-yl)-$N^2$-[2-(ethylamino)ethyl]glycinamide," should read "on-5-yl)-$N^1$-[2-(ethylamino)ethyl]glycinamide,"

Signed and Sealed this  
Twenty-second Day of April, 2014

Michelle K. Lee  
*Deputy Director of the United States Patent and Trademark Office*